(12) United States Patent
Chen et al.

(10) Patent No.: US 7,247,717 B2
(45) Date of Patent: Jul. 24, 2007

(54) POLYNUCLEOTIDE ENCODING A NOVEL HUMAN SERPIN SECRETED FROM LYMPHOID CELLS, LSI-01

(75) Inventors: Jian Chen, Princeton, NJ (US); Thomas Nelson, Lawrenceville, NJ (US); Daniel L. Cheney, Flemington, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 809 days.

(21) Appl. No.: 09/993,180

(22) Filed: Nov. 14, 2001

(65) Prior Publication Data

US 2003/0054445 A1 Mar. 20, 2003

Related U.S. Application Data

(60) Provisional application No. 60/248,434, filed on Nov. 14, 2000, provisional application No. 60/257,610, filed on Dec. 21, 2000, provisional application No. 60/282,745, filed on Apr. 10, 2001.

(51) Int. Cl.
 *C12N 15/15* (2006.01)
 *C12N 15/62* (2006.01)
 *C12N 15/70* (2006.01)
 *C12N 15/74* (2006.01)
 *C12N 15/79* (2006.01)

(52) U.S. Cl. ............... 536/23.5; 435/69.2; 435/69.7; 435/252.3; 435/320.1; 536/23.4

(58) Field of Classification Search ............ 536/23.5, 536/25.5, 24.31; 435/69.1, 69.7, 252.3, 320.1, 435/471, 69.2; 530/350
See application file for complete search history.

(56) References Cited

U.S. PATENT DOCUMENTS

| 5,955,284 A | 9/1999 | Braxton et al. ............ 435/6 |
| 6,008,020 A | 12/1999 | Hastings et al. .......... 435/69.2 |
| 6,753,164 B2* | 6/2004 | Ni et al. ................. 435/69.1 |
| 2002/0160491 A1* | 10/2002 | Ni et al. ................. 435/226 |

(Continued)

FOREIGN PATENT DOCUMENTS

WO WO9811134 3/1998

(Continued)

OTHER PUBLICATIONS

Frazer, J.K., et al., 2000, "Identification of centerin: a novel human germinal center B cell-restricted serpin", European Journal of Immunology, vol. 30, pp. 3039-2048.*

(Continued)

*Primary Examiner*—Nashaat Nashed
*Assistant Examiner*—William W. Moore
(74) *Attorney, Agent, or Firm*—Stephen C. D'Amico; Karen Mangasarian; Denise L. Loring

(57) ABSTRACT

The present invention provides novel polynucleotides encoding LSI-01 polypeptides, fragments and homologues thereof. Also provided are vectors, host cells, antibodies, and recombinant and synthetic methods for producing said polypeptides. The invention further relates to diagnostic and therapeutic methods for applying these novel LSI-01 polypeptides to the diagnosis, treatment, and/or prevention of various diseases and/or disorders related to these polypeptides. The invention further relates to screening methods for identifying agonists and antagonists of the polynucleotides and polypeptides of the present invention.

15 Claims, 8 Drawing Sheets

U.S. PATENT DOCUMENTS

Figure 4:
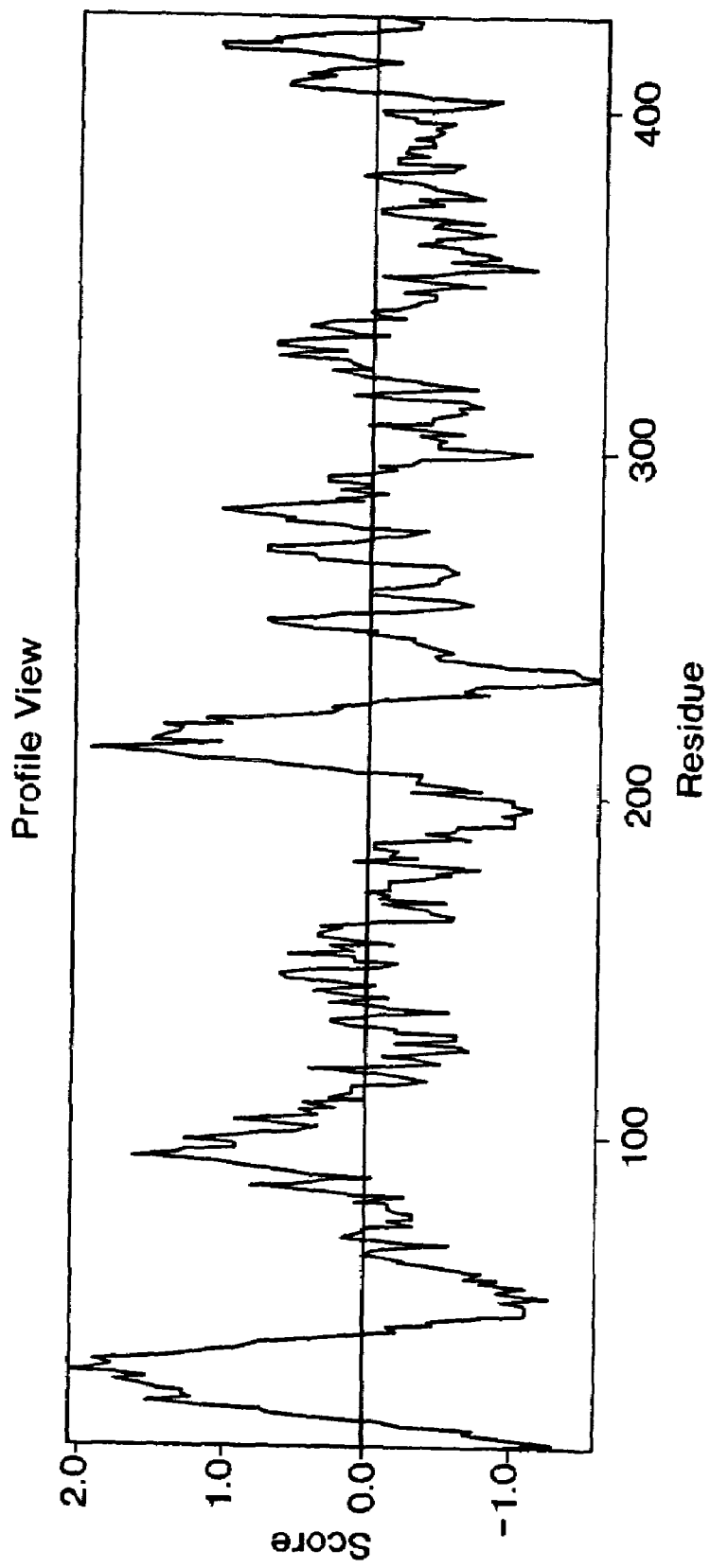

| | | | |
|---|---|---|---|
| 2003/0027272 A1 | 2/2003 | Baker, et al. | 435/69.1 |
| 2003/0032102 A1 | 2/2003 | Baker, et al. | 435/69.1 |
| 2003/0036143 A1 | 2/2003 | Baker, et al. | 435/69.1 |
| 2003/0036156 A1 | 2/2003 | Baker, et al. | 435/69.1 |
| 2003/0036157 A1 | 2/2003 | Baker, et al. | 435/69.1 |
| 2003/0036162 A1 | 2/2003 | Baker, et al. | 435/69.1 |

FOREIGN PATENT DOCUMENTS

| | | |
|---|---|---|
| WO | WO0012708 | 3/2000 |
| WO | WO0078961 | 12/2000 |
| WO | WO0132874 | 5/2001 |
| WO | WO0149715 A2 | 7/2001 |
| WO | WO 2001/55390 A1 * | 8/2001 |
| WO | WO0155390 A1 | 8/2001 |
| WO | WO0166690 | 9/2001 |
| WO | WO0168848 | 9/2001 |
| WO | WO0200690 A2 | 1/2002 |
| WO | WO0202603 | 1/2002 |
| WO | WO0208284 A2 | 1/2002 |
| WO | WO0214358 A2 | 2/2002 |
| WO | WO02072769AW | 9/2002 |

OTHER PUBLICATIONS

NCBI Entrez Accession No: gi118583071.

Frazer, et al. (2000) European Journal of Immunology 30:3039-3048.

Database EMBL Online, Aug. 8, 2000, Baker, et al. "Human PR01337 (UNQ692)" retrieved from EBI, Database Accession No. AAY99407, XP002229973.

Altschul, et al., "Basic Alignment Search Tool", J. Mol. Biol, vol. 215, pp. 403-410 (1990).

Backes, et al., "Synthesis of positional-scanning libraries of fluorogenic peptide substrates to define the extended substrate specificity of plasmin and thrombin", Nature Biotechnology, vol. 18, pp. 187-193 (2000).

Balasubramanian, et al., "Active Site-Directed Synthetic Thrombin Inhibitors: Synthesis, in Vitro and in Vivo Activity Profile of BMY 44621 and Analogs. An Examination of the Role of the Amino Group in the D-Phe-Pro-Arg-H Series", J. Med. Chem., vol. 36, pp. 300-303 (1993).

Bateman, et al., "The Pfam Protein Families Database", Nucleic Acids Research, vol. 28(1), pp. 263-266 (2000).

Baumann, et al., "Crystal Structure of Cleaved Human $\alpha_{1}$-Antichymotrypsin at 27 A Resolution and its comparison with Other Serpins", J. Mol. Biol., vol. 218, pp. 595-606 (1991).

Blinder, et al., "Site-directed Mutagenesis of Arginine 103 and Lysine 185 in the Proposed Glycosaminoglycan-binding Site of Herparin Cofactor II", J. Biol. Chem., vol. 265(1), pp. 286-291 (1990).

Blinder, et al., "Heparin Cofactor $II_{Oslo}$, Mutation of ARG-189 To His Decreases The Affinity for Dermatan Sulfate", J. Biol. Chem., vol. 264(9), pp. 5128-5133 (1989).

Bohm, Hans-Joachim, "The computer program LUDI: A new method for the de novo design of enzyme inhibitors", J. Computer-Aided Molecular Design, vol. 6, pp. 61-78 (1992).

Cajot, et al., "Plasminogen-activator inhibitor type 1 is a potent natural inhibitor of extracellular matrix degradation by fibrosarcoma and colon carcinoma cells", PNAS, vol. 87, pp. 6939-6943 (1990).

Cardozo, et al., "Homology Modeling by the ICM Method", Proteins, vol. 23, pp. 403-414 (1995).

Carrell, et al., "The Serpins: Evolution and Adaptation in a Family of Protease Inhibitors", Cold Spring Harbor Symposia on Quantitative Biology, vol. LII, pp. 527-535 (1987).

Carrell, et al., "$\alpha_{1}$- Antitrypsin and the serpins: variation and countervariation", TIBS, pp. 20-24 (1985).

Chai, et al., "Molecular Cloning, Sequence Analysis, and Chromosomal Localization of the Human Protease Inhibitor 4 (Kallistatin) Gene (P14)", Genomics, vol. 23, pp. 370-378 (1994).

Chai, et al., "Kallistatin: A Novel Human Serine Proteinase Inhibitor", J. Biol. Chem., vol. 268 (32), pp. 24498-24505 (1993).

Chandra, et al., "Sequence Homology between Human"$\alpha$1-Antichymotrypsin, $\alpha$1-Antitrypsin, and Antithrombin III, Biochem., vol. 22(22), pp. 5055-5061 (1983).

Chen, Wen-Tien, "Membrance proteases:roles in tissue remodeling and tumour invasion", Curr. Opin. Cell Biol., vol. 4, pp. 802-809 (1992).

Clarke, et al., "Cloning of a human collagen-binding protein, and its homology with rat gp46, chick hsp47 and mouse J6 proteins", Biochemica Biophysica Acta, vol. 1129, pp. 246-248 (1992).

Clark, et al., "The Secreted Protein Discovery Initiative (SPDI), a Large-Scale Effort to Identify Novel Human Secreted and Transmembrane Proteins: A Bioinformatics Assessment", Genome Res., vol. 13, pp. 2265-2270 (2003).

Combrink, et al., "1,2-Benzisothiazol-3-one 1,1-Dioxide Inhibitors of Human Mast Cell Tryptase", J. Med. Chem., vol. 41, pp. 4854-4860 (1998).

Cooper, et al., "Phosphorylation Sites in Enolase and Lactate Dehydrogenase Utilized by Tyrosine Protein Kinases in Vivo and in Vitro", J. Biol. Chem., vol. 259(12), pp. 7835-7841 (1984).

Dano, et al., "Plasminogen Activators, Tissue Degradation, and Cancer", Advances in Cancer Research, vol. 44, pp. 139-266 (1985).

Feramisco, et al., "Optimal Spatial Requirements for the Location of Basic Residues in Peptide Substrates for the Cyclic AMP-dependent Protein Kinase", J. Biol. Chem., vol. 255(9), pp. 4240-4245 (1980).

Foekens, et al., "Prognostic Value of Urokinase-type Plasminogen Activator in 671 Primary Breast Cancer Patients", Cancer Res., vol. 52, pp. 6101-6105 (1992).

Flink, et al., "Complete amino acid sequence of human thyroxine-binding globulin deduced from cloned DNA: Close homology to the serine antiproteases", PNAC, vol. 83, pp. 708-7712 (1986).

Forgue-Lafitte, "Effects of Ketoconazole on the Proliferation and Cell Cycle of Human Cancer Cell Lines", Cancer Res., pp. 6827-6831 (1992).

Foucre', et al., "Relationship between cathepsin D, urokinase, and plasminogen activator inhibitors in malignant vs. benign breast tumours", Br. J. Cancer, vol. 64, pp. 926-932 (1991).

Gils, et al., "Structure-function Relationships in Serpins: Current Concepts and Controversies", Thromb. Haemost., vol. 80, pp. 531-541 (1998).

Glass, et al., "Phosphorylation by Cyclic GMP-dependent Protein Kinase of a Synthetic Peptide Corresponding to the Autophosphorylation Site in the Enzyme", J. Biol. Chem., vol. 258(24), pp. 14797-14803 (1983).

Glass, et al., "Synthetic Peptides Corresponding to the Site Phosphorylated in 6-Phosphofructo-2-kinase/Fructose-2,6-bisphosphatase as Substrates of Cyclic Nucleotide-dependent Protein Kinases", J. Biol. Chem., vol. 261(6), pp. 2987-2993 (1986).

Goodford, P.J., "A Computational Procedure for Determining Energetically Favorable Binding Sites on Biologically Important Macromolecules", J. Med. Chem., vol. 28, pp. 849-857 (1985).

Goodsell, et al., "Automated Docketing of Substrates to Proteins by Simulated Annealing", Proteins, vol. 8, pp. 195-202 (1990).

Grand, Roger, J.A., "Acylation of viral and eukaryotic proteins", Biochem. J., vol. 258, pp. 625-638 (1989).

Heidtmann, et al., "Synthesis and Secretion of Plasminogen Activators and Plasminogen Activator Inhibitors in Cell Lines of Different Groups of Human Lung Tumors", Cancer Res, vol 49, pp. 6960-6965 (1989).

Hendlich, et al., "Identification of Native Protein Folds Amongst a Large Number of Incorrect Models", J. Mol. Biol., vol. 216, pp. 167-180 (1990).

Hocini, et al., "Secretory Leukocyte Protease Inhibitor Inhibits Infection of Monocytes and Lymphocytes with Human Immunodeficiency Virus Type 1 but Does Not Interfere with Transcytosis of Cell-Associated Virus across Tight Epithelial Barriers", Clin. Lab. Diagnostic Lab. Immonol., vol. 7(3), pp. 515-518 (2000).

Memorec, et al., "The Prosite Database, its Status in 1999", Nucleic Acid Res., vol. 27(1), pp. 215-219 (1999).

Holland, et al., "A Major Estrogen-regulated Protein Secreted from the Liver of Xenopus laevis is a Member of the Serpin Superfamily", J. Biol. Chem., vol. 267(10), pp. 7053-7059 (1992).

Huber, et al., "Implications of the Three-Dimensional Structure of $\alpha_1$-Antitrypsin for Structure and Function of Serpins", Biochem., vol. 28(23), pp. 8951-8966 (1989).

Hunter, Tony, "Synthetic Peptide Substrates for a Tyrosine Protein Kinase", J. Biol. Chem., vol. 257(9), pp. 4843-4848 (1982).

Huntington, et al., "Structure of a serpin-protease complex shows inhibition by deformation", Nature, vol. 407, pp. 923-926 (2000).

Janicke, et al., "Urokinase (uPA) and its inhibitor PAI-1 are strong and independent prognostic factors in node-negative breast cancer", Breast Cancer Res. Treatment, vol. 24, pp. 195-208 (1993).

Kalaria, et al., "Molecular Aspects of Inflammatory and Immune Responses in Alzheimer's Disease", Neurobiology of Aging, vol. 17(5), pp. 687-693 (1996).

Kam, et al., "Granzymes (lymphocyte serine proteases): characterization with natural and synthetic substrates and inhibitors", Biochimica Biophysica Acta, vol. 1477, pp. 307-323 (2000).

Kishimoto, et al., "Studies on the Phosphorylation of Myelin Basic Protein by Protein Kinase C and Adenosine 3':5'-Monophosphate-dependent Protein Kinase", J. Biol. Chem., vol. 260(23), pp. 12492-12499 (1985).

Komiyama, et al., "Inhibition of Interleukin-1$\beta$ Converting Enzyme by the Cowpox Virus Serpin CrmA", J. Biol. Chem., vol. 269(30), pp. 19331-19337 (1994).

Kreil, Gunther, "Occurrence, Detection, and Biosynthesis of Carboxy-Terminal Amides", Methods Enzymology, vol. 106, pp. 218-223 (1984).

Kuntz, et al., "A Geometric Approach to Macromolecule-Ligand Interactions", J. Mol. Biol., vol. 161, pp. 269-288 (1982).

Lane, et al., "Antithrombin and its deficiency states", Blood Coagulation Fibrinolysis, vol. 3, pp. 315-341 (1992).

Lindmark, et al., "The microheterogeneity of desialylated $\alpha_1$-antichymotrypsis: the occurrence of two amino-terminal isoforms, one lacking a His-Pro dipeptide", Biochimica Biophysica Acta, vol. 997, pp. 90-95 (1989).

Lukacs, et al., "Arginine substitutions in the hinge region of antichymotrypsin affect serpin $\beta$-sheet rearrangement", Nature, vol. 3(10), pp. 888-893 (1996).

Lukacs, et al., "Engineering an Anion-Binding Cavity in Antichymotrypsin Modulates the 'Spring-Loaded' Serpin-Protease Interaction", Biochem., vol. 37, pp. 3297-3304 (1998).

Martin, et al., "Calphotin: A Drosophila photoreceptor cell calcium-binding protein", PNAS, vol. 90, pp. 1531-1535 (1993).

Meissauer, et al., "Urokinase-Type and Tissue-Type Plasminogen Activators Are Essential for in Vitro Invasion of Human Melanoma Cells", vol. 192, pp. 453-459 (1991).

Miller, Andrew, "The European Synchrotron Radiation Facility and Angiography", Curr. Op. Struct. Biol., vol. 2, pp. 242-247 (1992).

Ngan, et al., "Expression in Non-Hodgkin's Lymphoma of the bcl-2 Protein Associated with the t(14;18) Chromosomal Translocation", New England J. Med., vol. 318(25), pp. 1638-1644 (1988).

Nguyen, et al., "The Specific Variable Domain of Camel Heavy-chain Antibodies is Encoded in the Germline", J. Mol. Biol., vol. 275, pp. 413-418 (1998).

Martin, Yvonne, C., "3D Database Searching in Drug Design", J. Med. Chem., vol. 35(12), pp. 2145-2154 (1992).

Morii, et al., "Amino Acid Sequence at the Reactive Site of Human $\alpha_1$-Antichymotrypsin", J. of Biol. Chem., vol. 258(21), pp. 12749-12752 (1983).

Novotny, et al., "Criteria That Discriminate Between Native Proteins and Incorrectly Folded Models", Proteins, vol. 4, pp. 19-30 (1988).

Opal, Steven, M., "Therapeutic rationale for antithrombin III in sepsis", Crit. Care Med., vol. 28(9), pp. S34-S37 (2000).

O'Reilly, et al., "Antiangiogenic Activity of the Cleaved Conformation of the Serpin Antithrobin", Science, vol. 285, pp. 1926-1928 (1999).

Ossowski, Liliana, "Invasion of Connective Tissue by Human Carcinoma Cell Lines: Requirement for Urokinase, Urokinase Receptor, and Interstitial Collagenase", Cancer Res., vol. 52, pp. 6754-6760 (1992).

Osterwalder, et al., "Neuroserpin, an axonally secreted serine protease inhibitor", EMBO J., vol. 15(12), pp. 2944-2953 (1996).

Pan, et al., "Two Newly Characterized Germinal Center B-Cell-Associated Genes, GCET1 and GCET2, Have Differential Expression in Normal and Neoplastic B cells", Amer. J. Path., vol. 163(1), pp. 135-144 (2003).

Patschinsky, et al., "Analysis of the sequence of amino acids surrounding sites of tyrosine phosphorylation", PNAS, vol. 79, pp. 973-977 (1982).

Pearson, William, R., "Rapid and Sensitive Sequence Comparison with FASTP and FASTA", Methods Enzymology, vol. 183, pp. 63-98 (1990).

Peltier, et al., "Regulation of Lymphocyte Proliferation by Uterine Serpin: Interleukin-2 mRNA Production, CD25 Expression and Responsiveness to Interleukin-2", vol. 223, pp. 75-81 (2000).

Pinna, Lorenzo, A., "Casein kinase 2: an 'eminence grise' in cellular regulation?", Biochimica Biophysica Acta, vol. 1054, pp. 267-284 (1990).

Poller, et al., "A Leucine-to-Proline Substitution Causes a Defective $\alpha^1$-Antichymotrypsin Allele Associated with Familial Obstructive Lung Disease", Genomics, vol. 17, pp. 740-743 (1993).

Pratt, et al., "Antithrombin: Structure and Function", Seminars in Hematology, vol. 28(1), pp. 3-9 (1991).

Ragg, et al., "Glycosaminoglycan-mediated Leuserpin-2/Thrombin Interaction", J. Biol. Chem., vol. 265(36), pp. 22386-22391 (1990).

Reed, et al., "Synergistic fibrinolysis: Combined effects of plasminogen activators and an antibody that inhibits $\alpha_2$-antiplasmin", PNAS, vol. 87, pp. 1114-1118 (1990).

Reilly, et al., "Type-1 Plasminogen Activator Inhibitor in Human Breast Carcinomas", Int. J. Cancer, vol. 50, pp. 208-214 (1992).

Remold-O'Donnell, Eileen, "The ovalbumin family of serpin proteins", FEBS, vol. 315(2), pp. 105-108 (1993).

Rubin, et al., "Cloning, Expression, Purification, and Biological Activity of Recombinant Native and Variant Human $\alpha$1-Antichymotrypsins", J. Biol. Chem., vol. 265(2), pp. 1199-1207 (1990).

Saitou, et al., "Identification of the TCL6 genes within the breakpoint cluster region on chromosome 14q32 in T-cell leukemia", Oncogene, vol. 19, pp. 2796-2802 (2000).

Sali, et al., "Evaluation of Comparative Protein Modeling by Modeller", Proteins, vol. 23, pp. 318-326 (1995).

Shirasuna, et al., "Extracellular Matrix Production and Degradation by Adenoid Cystic Carcinoma Cells: Participation of Plasminogen Activator and Its Inhibitor in Matrix Degradation", Cancer Res., vol. 53, pp. 147-152 (1993).

Shirk, et al., "Role of the H Helix in Heparin Binding to Protein C Inhibitor", J. Biol. Chem., vol. 269(46), pp. 28690-28695 (1994).

Sumiyoshi, et al., "Plasminogen Activator System in Human Breast Cancer", Int. J. Cancer, vol. 50, pp. 345-348 (1992).

Sumiyoshi, et al., "Increase in Levels of Plasminogen Activator and Type-1 Plasminogen Activator Inhibitor in Human Breast Cancer: Possible roles in tumor progression and metastasis", Thromb. Res., vol. 63, pp. 59-71 (1991).

Testa, et al., "The role of urokinase-type plasminogen activator in aggressive tumor cell behavior", Cancer Metastasis Reviews, vol. 9, pp. 353-367 (1990).

Towler, et al., "The Biology and Enzymology of Eukaryotic Protein Acylation", Ann Rev. Biochem., vol. 57, pp. 69-99 (1988).

Tsuda, et al., "Detection of a new mutant $\alpha$-1-antichymotrypsin in patients with occlusive-cerebrovascular disease", FEBS, vol. 304(1), pp. 66-68 (1992).

Whinna, et al., "Role of Lysine 173 in Heparin Binding to Heparin Cofactor II", J. Biol. Chem., vol. 266(13), pp. 8129-8135 (1991).

Whisstock, et al., "An atlas of serpin conformations", TIBS, vol. 23, pp. 63-67 (1998).

Woodgett, et al., "Substrate specificity of protein kinase C", J. Biochem., vol. 161, pp. 177-184 (1986).

Zou, et al., "Maspin, a Serpin with Tumor-Suppressing Activity in Human Mammary Epithelial Cells", Science, vol. 263, pp. 526-529 (1994).

NCBI Entrez Accession No. AL132708 (gi:7009592), Heilig, et al., May 4, 2001.

NCBI Entrez Accession No. AL132990 (gi:15796543), Heilig, et al., Sep. 26. 2001.
NCBI Entrez Accession No. CAA45509 (gi:37142), Akbari, et al., Jun. 26, 1997.
NCBI Entrez Accession No. CAD29031 (gi:19701015), Edmonds, et al., Mar. 23, 2002.
NCBI Entrez Accession No. NM_175739 (gi:31343337), Namciu, et al., Sep. 3, 2004.
NCBI Entrez Accession No. NP_000345 (gi:4507377), Grasberger, et al., Aug. 23, 2004.
NCBI Entrez Accession No. NP_006206 (gi:5453888), Chai, et al., Nov. 3, 2000.
NCBI Entrez Accession No. NP_783866 (gi:28376637), Namciu, et al., Sep. 3, 2004.
NCBI Entrez Accession No. P01011 (gi:112874), Chandra, et al., Oct. 25, 2004.
NCBI Entrez Accession No. 1QLPA (gi:6137432), Elliott, et al., Sep. 10, 1999.

* cited by examiner

FIG. 1A

```
  1  CCCACGCGTCCGATTAAAGTGAGGAGAGAGCTACAACCAAGTAAGCAAGTGTCAGGGCTC    60

61  ACCAACCATGCAAGGACAGGGCAGGAGAAGAGGAACCTGCAAAGACATATTTTGTTCCAA   120
  1        M  Q  G  Q  G  R  R  R  G  T  C  K  D  I  F  C  S  K    18

121  AATGGCATCTTACCTTTATGGAGTACTCTTTGCTGTTGGCCTCTGTGCTCCAATCTACTG   180
 19   M  A  S  Y  L  Y  G  V  L  F  A  V  G  L  C  A  P  I  Y  C   38

181  TGTGTCCCCGGCCAATGCCCCCAGTGCATACCCCCGCCCTTCCTCCACAAAGAGCACCCC   240
 39   V  S  P  A  N  A  P  S  A  Y  P  R  P  S  S  T  K  S  T  P   58

241  TGCCTCACAGGTGTATTCCCTCAACACCGACTTTGCCTTCCGCCTATACCGCAGGCTGGT   300
 59   A  S  Q  V  Y  S  L  N  T  D  F  A  F  R  L  Y  R  R  L  V   78

301  TTTGGAGACCCCGAGTCAGAACATCTTCTTCTCCCCTGTGAGTGTCTCCACTTCCCTGGC   360
 79   L  E  T  P  S  Q  N  I  F  F  S  P  V  S  V  S  T  S  L  A   98

361  CATGCTCTCCCTTGGGGCCCACTCAGTCACCAAGACCCAGATTCTCCAGGGCCTGGGCTT   420
 99   M  L  S  L  G  A  H  S  V  T  K  T  Q  I  L  Q  G  L  G  F  118

421  CAACCTCACACACACACACCAGAGTCTGCCATCCACCAGGGCTTCCAGCACCTGGTTCACTC   480
119   N  L  T  H  T  P  E  S  A  I  H  Q  G  F  Q  H  L  V  H  S   138

481  ACTGACTGTTCCCAGCAAAGACCTGACCTTGAAGATGGGAAGTGCCCTCTTCGTCAAGAA   540
139   L  T  V  P  S  K  D  L  T  L  K  M  G  S  A  L  F  V  K  K   158

541  GGAGCTGCAGCTGCAGGCAAATTTCTTGGGCAATGTCAAGAGGCTGTATGAAGCAGAAGT   600
159   E  L  Q  L  Q  A  N  F  L  G  N  V  K  R  L  Y  E  A  E  V   178

601  CTTTTCTACAGATTTCTCCAACCCCTCCATTGCCCAGGCGAGGATCAACAGCCATGTGAA   660
179   F  S  T  D  F  S  N  P  S  I  A  Q  A  R  I  N  S  H  V  K   198

661  AAAGAAGACCCAAGGGAAGGTTGTAGACATAATCCAAGGCCTTGACCTTCTGACGGCCAT   720
199   K  K  T  Q  G  K  V  V  D  I  I  Q  G  L  D  L  L  T  A  M   218

721  GGTTCTGGTGAATCACATTTTCTTTAAAGCCAAGTGGGAGAAGCCCTTTCACCTTGAATA   780
219   V  L  V  N  H  I  F  F  K  A  K  W  E  K  P  F  H  L  E  Y   238

781  TACAAGAAAGAACTTCCCATTCCTGGTGGGCGAGCAGGTCACTGTGCAAGTCCCCATGAT   840
239   T  R  K  N  F  P  F  L  V  G  E  Q  V  T  V  Q  V  P  M  M   258

841  GCACCAGAAAGAGCAGTTCGCTTTTGGGGTGGATACAGAGCTGAACTGCTTTGTGCTGCA   900
259   H  Q  K  E  Q  F  A  F  G  V  D  T  E  L  N  C  F  V  L  Q   278
```

FIG. 1B

```
 901  GATGGATTACAAGGGAGATGCCGTGGCCTTCTTTGTCCTCCCTAGCAAGGGCAAGATGAG   960
 279   M  D  Y  K  G  D  A  V  A  F  F  V  L  P  S  K  G  K  M  R   298

961  GCAACTGGAACAGGCCTTGTCAGCCAGAACACTGATAAAGTGGAGCCACTCACTCCAGAA  1020
 299   Q  L  E  Q  A  L  S  A  R  T  L  I  K  W  S  H  S  L  Q  K   318

1021  AAGGTGGATAGAGGTGTTCATCCCCAGATTTTCCATTTCTGCCTCCTACAATCTGGAAAC  1080
 319   R  W  I  E  V  F  I  P  R  F  S  I  S  A  S  Y  N  L  E  T   338

1081  CATCCTCCCGAAGATGGGCATCCAAAATGCCTTTGACAAAAATGCTGATTTTTCTGGAAT  1140
 339   I  L  P  K  M  G  I  Q  N  A  F  D  K  N  A  D  F  S  G  I   358

1141  TGCAAAGAGAGACTCCCTGCAGGTTTCTAAAGCAACCCACAAGGCTGTGCTGGATGTCAG  1200
 359   A  K  R  D  S  L  Q  V  S  K  A  T  H  K  A  V  L  D  V  S   378

1201  TGAAGAGGGCACTGAGGCCACAGCAGCTACCACCACCAAGTTCATAGTCCGATCGAAGGA  1260
 379   E  E  G  T  E  A  T  A  A  T  T  T  K  F  I  V  R  S  K  D   398

1261  TGGTCCCTCTTACTTCACTGTCTCCTTCAATAGGACCTTCCTGATGATGATTACAAATAA  1320
 399   G  P  S  Y  F  T  V  S  F  N  R  T  F  L  M  M  I  T  N  K   418

1321  AGCCACAGACGGTATTCTCTTTCTAGGGAAAGTGGAAAATCCCACTAAATCCTAGGTGGG  1380
 419   A  T  D  G  I  L  F  L  G  K  V  E  N  P  T  K  S  *         436

1381  AAATGGCCTGTTAACTGATGGCACATTGCTAATGCACAAGAAATAACAAACCACATCCCT  1440

1441  CTTTCTGTTCTGAGGGTGCATTTGACCCCAGTGGAGCTGGATTCGCTGGCAGGGATGCCA  1500

1501  CTTCCAAGGCTCAATCACCAAACCATCAACAGGGACCCCAGTCACAAGCCAACACCCATT  1560

1561  AACCCCAGTCAGTGCCCTTTTCCACAAATTCTCCCAGGTAACTAGCTTCATGGGATGTTG  1620

1621  CTGGGTTACCATATTTCCATTCCTTGGGGCTCCCAGGAATGGAAATACGCCAACCCAGGT  1680

1681  TAGGCACCTCTATTGCAGAATTACAATAACACATTCAATAAAACTAAATATGAAAAAAA   1740

1741  AAAAAAAAAAAAAAAAAAAAAAAAAA  1766
```

FIG. 2

```
                       1                                                  50
AL132708_FL     (1)    MQGQGRRRGTCKDIFCSKMASYLYGVEFAVGLCAPIYCVSPANAPSAYPR
AACT_HUMAN      (1)    ------------------MERMLPLLALGLLAAGFCPAVLCHPNSPLD
KAIN_HUMAN      (1)    ------------------MHLIDYLLLLLVGLLALSHGQLHVEHDGESCS
THBG_HUMAN      (1)    -----------------MSPFLYLVLLVLGLHATIHCASPEGKVTACHS 51                                                 100
AL132708_FL     (51)   PS-------STKSTPASQVYSLNTDFAFRLYRRLVLETPSQNIFFSPVSV
AACT_HUMAN      (31)   EENLTQENQDRGTHVDLGLASANVDFAFSLYKQLVLKAPDKNVIFSPLSI
KAIN_HUMAN      (33)   NSSHQQILETGEGSPSLKIAPANADFAFRFYYLIASETPGKNIFFSPLSI
THBG_HUMAN      (33)   ---------SQPNATLYKMSSINADFAFNLYRRFTVETPDKNIFFSPVSI 101                                                150
AL132708_FL     (94)   STSLAMLSLGAHSVTKTQILQGLGFNLTHTPESAIHQGFQHLVHSETVPS
AACT_HUMAN      (81)   STALAFLSLGAHNTTLTEILKGLKFNLTETSEAEIHQSFQHLLRTLNQSS
KAIN_HUMAN      (83)   SAAYAMLSLGACSHSRSQILEGLGFNLTELSESDVHRGFQHLLHTLNLPG
THBG_HUMAN      (74)   SAALVMLSFGACCSTQTEIVETLGFNLTDTPMVEIQHGFQHLICSLNFPK 151                                                200
AL132708_FL     (144)  KDLTLKMGSALFVKKELQLQANFLGNVKRLYEAEVFSTDFSNPSIAQART
AACT_HUMAN      (131)  DELQLSMGNAMFVKEQLSLLDRFTEDAKRLYGSEAFATDFQDSAAAKKLI
KAIN_HUMAN      (133)  HGLETRVGSALFLSHNLKFLAKFLNDTMAVYEAKLFHTNFYDTVGTIQLI
THBG_HUMAN      (124)  KELELQIGNALFIGKHLKPLAKFLNDVKTLYETEVFSTDFSNISAAKQEI 201                                                250
AL132708_FL     (194)  NSHVKKKTQGKVVDIIQGLDLLTAMVLVNHIFFRKAKWEKPFHLEYPRKNF
AACT_HUMAN      (181)  NDYVKNGTRGKITDLIKDLDSQTMMVLVNYIFFKAKWEMPFDPQDTHQSR
KAIN_HUMAN      (183)  NDHVKKETRGKIVDLVSELKKDVLMVLVNYIYFKALWEKPFISSRTTPKD
THBG_HUMAN      (174)  NSHVEMQTKGKVVGLIQDLKPNTIMVLVNYIHFKAQWANPFDPSKTEDSS 251                                                300
AL132708_FL     (244)  PFLVGEQVTVQVPMMHQKEQFAFGVDTELNCFVLQMDYKGDAVAFFVLPS
AACT_HUMAN      (231)  FYLSKKKWVMVPMMSLHHLTIPYFRDEELSCTVVELKYTGNASALFILPD
KAIN_HUMAN      (233)  FYVDENTTVRVPMMLQDQEHHWYLHDRYLPCSVLRMDYKGDATVFFILPN
THBG_HUMAN      (224)  SFLIDKTTTVQVPMMHQMEQYYHLVDMELNCTVLQMDYSKNALALFVLPK 301                                                350
AL132708_FL     (294)  KGKMRQLEQALSARTLIKWSHSLQKR----WIEVFIPRFSISASYNLETI
AACT_HUMAN      (281)  QDKMEEVEAMLLPETLKRWRDSLEFR---EIGELYLPKFSISRDYNLNDI
KAIN_HUMAN      (283)  QGKMREIEEVLTPEMLMRWNNLLRKRNFYKKLELHLPKFSISGSYVLDQI
THBG_HUMAN      (274)  EGQMESVEAAMSSKTLKKWNRLLQKG----WVDLFVPKFSISATYDLGAT 351                                                400
AL132708_FL     (340)  LPKMGIQNAFDKNADFSGIAKRDSLQVSKATHKAVLDVSEEGTEATAATT
AACT_HUMAN      (328)  LLQLGIEEAFTSKADLSGITGARNLAVSQVVHKAVLDVFEEGTEASAATA
KAIN_HUMAN      (333)  LPRLGFTDLFSKWADLSGITKQQKLEASKSFHKATLDVDEAGTEAAAATT
THBG_HUMAN      (320)  LLKMGIQHAYSENADFSGLTEDNGLKLSNAAHKAVLHIGEKGTEAAAVPE

401          ↓↓↓↓↓↓↓↓↓↓                           446
AL132708_FL     (390)  TKFIVRSKDGPSYFTVSFNRTFLMMITNKATDGILFLGKVENPTKS
AACT_HUMAN      (378)  VKITLLSALVETRTIVRFNRPFLMIIVPTDTQNIFFMSKVTNPKQA
KAIN_HUMAN      (383)  FAIKFFSAQTN-RHILRFNRPFLVVIFSTSTQSVLFLGKVVDPTKP
THBG_HUMAN      (370)  VELSDQPENTFLHPIIQIDRSFMLLILERSTRSILFLGKVVNPTEA
```

FIG. 3

```
LSI-01    MQGQGRRRGT CKDIFCSKMA SYLYGVLFAV GLCAPIYCVS PANEPSAYPR
pdb1q1p   .......... .......... .......... ......MDPQ GDAAQKTDTS LSI-01    PSSTKSTPAS QVYSLNTDFA FRLVRREVLE TPSQNEEFSP VSVSTSLAME
pdb1q1p   HHDQDHPTFN KITPNLAERA RSLVRQEAHQ SNSTNEEFSP VSIAEAFANL LSI-01    SLGAHSVEKT QELQSHGFNL THTRESAEHQ GEQHEVHSET VPSKDETEKM
pdb1q1p   SLGTKADTHD EELEGENFNL TEIPEAQEHE GEQELLRTEN QPDSQEQETT LSI-01    GSALFVKKEL QLQANELGNV KRLYEAEVFS TDFSNPSIAQ ARENSHVKKK
pdb1q1p   GNGLFLSEGL KLVDKELEDV KELYHSEAFT VNEGDTEEAK KQENDYVEKG LSI-01    TQGKVVDIIQ GLDLLTAMVL VNHIFFKAKW EKPFHLEYTR KNFPELVGEQ
pdb1q1p   TQGKIVDLVK ELDRDTVFAL VNYFFFRGKW ERPFEVKDT. EEEDFHVDQV LSI-01    VTVQVPMMHQ KEQFAFGVDT ELNCFVEQMD YKGDAVAFFV LPSKGEMRQL
pdb1q1p   TTVKVPMMKR LGMFNIQHCK KLSSWVLLMK YLGNATAIFF LPDEGKLQHL LSI-01    EQALSARTLI KWSHSLQKRW IEVFIPRFSI SASYNEETIL PKMGEQNAFD
pdb1q1p   ENELTHDIIT KFLENEDRRS ASLHLPKLSI TGTYDEKSVL GQLGETKVFS LSI-01    KNADFSGIAK RDSLQVSKAT HKAVEDVSEE GTEATAATTT KFIVRSKDGP
pdb1q1p   NGADLSGVTE EAPEKLSEAV HKAVLTIDEK GTEAAGAMFL EAIPMSI..P LSI-01    S.YFTVSFNR TFLMMITNKA TDGIDFLGKV ENPTKS
pdb1q1p   PE...VKFNK PFVFLMIEQN TKSPLFMGKV VNPTQK
```

FIG. 6

| Protein | Genbank ID | Identities | Similarities |
|---|---|---|---|
| human $\alpha_1$-antichymotrypsin | gi\|112874 | 46% | 52% |
| human Kallistatin | gi\|5453888 | 48% | 56% |
| human thyroxin-binding globulin | gi\|37142 | 51% | 57% |
| human $\alpha_1$-antithrypsin | gi\|6137432 | 43% | 50% |

SEQUENCE LISTING

<160> NUMBER OF SEQ ID NOS: 46

<210> SEQ ID NO 1
<211> LENGTH: 1766
<212> TYPE: DNA
<213> ORGANISM: Homo sapiens
<220> FEATURE:
<221> NAME/KEY: CDS
<222> LOCATION: (68)..(1372)

<400> SEQUENCE: 1

```
cccacgcgtc cgattaaagt gaggagagag ctacaaccaa gtaagcaagt gtcagggctc        60 accaacc atg caa gga cag ggc agg aga aga gga acc tgc aaa gac ata        109
        Met Gln Gly Gln Gly Arg Arg Arg Gly Thr Cys Lys Asp Ile
        1               5                   10 ttt tgt tcc aaa atg gca tct tac ctt tat gga gta ctc ttt gct gtt        157
Phe Cys Ser Lys Met Ala Ser Tyr Leu Tyr Gly Val Leu Phe Ala Val
15                  20                  25                  30 ggc ctc tgt gct cca atc tac tgt gtg tcc ccg gcc aat gcc ccc agt        205
Gly Leu Cys Ala Pro Ile Tyr Cys Val Ser Pro Ala Asn Ala Pro Ser
                35                  40                  45 gca tac ccc cgc cct tcc tcc aca aag agc acc cct gcc tca cag gtg        253
Ala Tyr Pro Arg Pro Ser Ser Thr Lys Ser Thr Pro Ala Ser Gln Val
            50                  55                  60 tat tcc ctc aac acc gac ttt gcc ttc gcc cta tac cgc agg ctg gtt        301
Tyr Ser Leu Asn Thr Asp Phe Ala Phe Arg Leu Tyr Arg Arg Leu Val
        65                  70                  75 ttg gag acc ccg agt cag aac atc ttc ttc tcc cct gtg agt gtc tcc        349
Leu Glu Thr Pro Ser Gln Asn Ile Phe Phe Ser Pro Val Ser Val Ser
80                  85                  90 act tcc ctg gcc atg ctc tcc ctt ggg gcc cac tca gtc acc aag acc        397
Thr Ser Leu Ala Met Leu Ser Leu Gly Ala His Ser Val Thr Lys Thr
95                  100                 105                 110 cag att ctc cag ggc ctg ggc ttc aac ctc aca cac aca cca gag tct        445
Gln Ile Leu Gln Gly Leu Gly Phe Asn Leu Thr His Thr Pro Glu Ser
                115                 120                 125 gcc atc cac cag ggc ttc cag cac ctg gtt cac tca ctg act gtt ccc        493
Ala Ile His Gln Gly Phe Gln His Leu Val His Ser Leu Thr Val Pro
            130                 135                 140 agc aaa gac ctg acc ttg aag atg gga agt gcc ctc ttc gtc aag aag        541
Ser Lys Asp Leu Thr Leu Lys Met Gly Ser Ala Leu Phe Val Lys Lys
        145                 150                 155 gag ctg cag ctg cag gca aat ttc ttg ggc aat gtc aag agg ctg tat        589
Glu Leu Gln Leu Gln Ala Asn Phe Leu Gly Asn Val Lys Arg Leu Tyr
160                 165                 170 gaa gca gaa gtc ttt tct aca gat ttc tcc aac ccc tcc att gcc cag        637
Glu Ala Glu Val Phe Ser Thr Asp Phe Ser Asn Pro Ser Ile Ala Gln
175                 180                 185                 190 gcg agg atc aac agc cat gtg aaa aag aag acc caa ggg aag gtt gta        685
Ala Arg Ile Asn Ser His Val Lys Lys Lys Thr Gln Gly Lys Val Val
                195                 200                 205 gac ata atc caa ggc ctt gac ctt ctg acg gcc atg gtt ctg gtg aat        733
Asp Ile Ile Gln Gly Leu Asp Leu Leu Thr Ala Met Val Leu Val Asn
            210                 215                 220 cac att ttc ttt aaa gcc aag tgg gag aag ccc ttt cac ctt gaa tat        781
His Ile Phe Phe Lys Ala Lys Trp Glu Lys Pro Phe His Leu Glu Tyr
        225                 230                 235 aca aga aag aac ttc cca ttc ctg gtg ggc gag cag gtc act gtg caa        829
Thr Arg Lys Asn Phe Pro Phe Leu Val Gly Glu Gln Val Thr Val Gln
```

|     |     |     |
| --- | --- | --- |
| 240 | 245 | 250 |

| | | |
|---|---|---|
| gtc ccc atg atg cac cag aaa gag cag ttc gct ttt ggg gtg gat aca<br>Val Pro Met Met His Gln Lys Glu Gln Phe Ala Phe Gly Val Asp Thr<br>255              260              265              270 | | 877 |
| gag ctg aac tgc ttt gtg ctg cag atg gat tac aag gga gat gcc gtg<br>Glu Leu Asn Cys Phe Val Leu Gln Met Asp Tyr Lys Gly Asp Ala Val<br>              275              280              285 | | 925 |
| gcc ttc ttt gtc ctc cct agc aag ggc aag atg agg caa ctg gaa cag<br>Ala Phe Phe Val Leu Pro Ser Lys Gly Lys Met Arg Gln Leu Glu Gln<br>              290              295              300 | | 973 |
| gcc ttg tca gcc aga aca ctg ata aag tgg agc cac tca ctc cag aaa<br>Ala Leu Ser Ala Arg Thr Leu Ile Lys Trp Ser His Ser Leu Gln Lys<br>           305               310              315 | | 1021 |
| agg tgg ata gag gtg ttc atc ccc aga ttt tcc att tct gcc tcc tac<br>Arg Trp Ile Glu Val Phe Ile Pro Arg Phe Ser Ile Ser Ala Ser Tyr<br>      320              325              330 | | 1069 |
| aat ctg gaa acc atc ctc ccg aag atg ggc atc caa aat gcc ttt gac<br>Asn Leu Glu Thr Ile Leu Pro Lys Met Gly Ile Gln Asn Ala Phe Asp<br>335              340              345              350 | | 1117 |
| aaa aat gct gat ttt tct gga att gca aag aga gac tcc ctg cag gtt<br>Lys Asn Ala Asp Phe Ser Gly Ile Ala Lys Arg Asp Ser Leu Gln Val<br>              355              360              365 | | 1165 |
| tct aaa gca acc cac aag gct gtg ctg gat gtc agt gaa gag ggc act<br>Ser Lys Ala Thr His Lys Ala Val Leu Asp Val Ser Glu Glu Gly Thr<br>           370               375              380 | | 1213 |
| gag gcc aca gca gct acc acc acc aag ttc ata gtc cga tcg aag gat<br>Glu Ala Thr Ala Ala Thr Thr Thr Lys Phe Ile Val Arg Ser Lys Asp<br>385              390              395 | | 1261 |
| ggt ccc tct tac ttc act gtc tcc ttc aat agg acc ttc ctg atg atg<br>Gly Pro Ser Tyr Phe Thr Val Ser Phe Asn Arg Thr Phe Leu Met Met<br>400              405              410 | | 1309 |
| att aca aat aaa gcc aca gac ggt att ctc ttt cta ggg aaa gtg gaa<br>Ile Thr Asn Lys Ala Thr Asp Gly Ile Leu Phe Leu Gly Lys Val Glu<br>415              420              425              430 | | 1357 |
| aat ccc act aaa tcc taggtgggaa atggcctgtt aactgatggc acattgctaa<br>Asn Pro Thr Lys Ser<br>              435 | | 1412 |
| tgcacaagaa ataacaaacc acatccctct ttctgttctg agggtgcatt tgaccccagt | | 1472 |
| ggagctggat tcgctggcag ggatgccact tccaaggctc aatcaccaaa ccatcaacag | | 1532 |
| ggacccccagt cacaagccaa cacccattaa ccccagtcag tgcccttttc cacaaattct | | 1592 |
| cccaggtaac tagcttcatg ggatgttgct gggttaccat atttccattc cttggggctc | | 1652 |
| ccaggaatgg aaatacgcca acccaggtta ggcacctcta ttgcagaatt acaataacac | | 1712 |
| attcaataaa actaaaatat gaaaaaaaaa aaaaaaaaa aaaaaaaaa aaaa | | 1766 |

<210> SEQ ID NO 2
<211> LENGTH: 435
<212> TYPE: PRT
<213> ORGANISM: Homo sapiens

<400> SEQUENCE: 2

Met Gln Gly Gln Gly Arg Arg Gly Thr Cys Lys Asp Ile Phe Cys
1                 5                        10                    15

Ser Lys Met Ala Ser Tyr Leu Tyr Gly Val Leu Phe Ala Val Gly Leu
              20                     25                     30

Cys Ala Pro Ile Tyr Cys Val Ser Pro Ala Asn Ala Pro Ser Ala Tyr
        35                     40                     45

```
Pro Arg Pro Ser Ser Thr Lys Ser Thr Pro Ala Ser Gln Val Tyr Ser
 50                  55                  60

Leu Asn Thr Asp Phe Ala Phe Arg Leu Tyr Arg Arg Leu Val Leu Glu
 65                  70                  75                  80

Thr Pro Ser Gln Asn Ile Phe Phe Ser Pro Val Ser Val Ser Thr Ser
                 85                  90                  95

Leu Ala Met Leu Ser Leu Gly Ala His Ser Val Thr Lys Thr Gln Ile
            100                 105                 110

Leu Gln Gly Leu Gly Phe Asn Leu Thr His Thr Pro Glu Ser Ala Ile
            115                 120                 125

His Gln Gly Phe Gln His Leu Val His Ser Leu Thr Val Pro Ser Lys
            130                 135                 140

Asp Leu Thr Leu Lys Met Gly Ser Ala Leu Phe Val Lys Lys Glu Leu
145                 150                 155                 160

Gln Leu Gln Ala Asn Phe Leu Gly Asn Val Lys Arg Leu Tyr Glu Ala
                165                 170                 175

Glu Val Phe Ser Thr Asp Phe Ser Asn Pro Ser Ile Ala Gln Ala Arg
            180                 185                 190

Ile Asn Ser His Val Lys Lys Thr Gln Gly Lys Val Val Asp Ile
            195                 200                 205

Ile Gln Gly Leu Asp Leu Leu Thr Ala Met Val Leu Val Asn His Ile
210                 215                 220

Phe Phe Lys Ala Lys Trp Glu Lys Pro Phe His Leu Glu Tyr Thr Arg
225                 230                 235                 240

Lys Asn Phe Pro Phe Leu Val Gly Glu Gln Val Thr Val Gln Val Pro
                245                 250                 255

Met Met His Gln Lys Glu Gln Phe Ala Phe Gly Val Asp Thr Glu Leu
            260                 265                 270

Asn Cys Phe Val Leu Gln Met Asp Tyr Lys Gly Asp Ala Val Ala Phe
            275                 280                 285

Phe Val Leu Pro Ser Lys Gly Lys Met Arg Gln Leu Glu Gln Ala Leu
            290                 295                 300

Ser Ala Arg Thr Leu Ile Lys Trp Ser His Ser Leu Gln Lys Arg Trp
305                 310                 315                 320

Ile Glu Val Phe Ile Pro Arg Phe Ser Ile Ser Ala Ser Tyr Asn Leu
                325                 330                 335

Glu Thr Ile Leu Pro Lys Met Gly Ile Gln Asn Ala Phe Asp Lys Asn
            340                 345                 350

Ala Asp Phe Ser Gly Ile Ala Lys Arg Asp Ser Leu Gln Val Ser Lys
            355                 360                 365

Ala Thr His Lys Ala Val Leu Asp Val Ser Glu Glu Gly Thr Glu Ala
            370                 375                 380

Thr Ala Ala Thr Thr Thr Lys Phe Ile Val Arg Ser Lys Asp Gly Pro
385                 390                 395                 400

Ser Tyr Phe Thr Val Ser Phe Asn Arg Thr Phe Leu Met Met Ile Thr
                405                 410                 415

Asn Lys Ala Thr Asp Gly Ile Leu Phe Leu Gly Lys Val Glu Asn Pro
            420                 425                 430

Thr Lys Ser
       435

<210> SEQ ID NO 3
<211> LENGTH: 423
<212> TYPE: PRT
```

-continued

<213> ORGANISM: Homo sapiens

<400> SEQUENCE: 3

```
Met Glu Arg Met Leu Pro Leu Ala Leu Gly Leu Leu Ala Ala Gly
1               5                   10                  15

Phe Cys Pro Ala Val Leu Cys His Pro Asn Ser Pro Leu Asp Glu
                20                  25                  30

Asn Leu Thr Gln Glu Asn Gln Asp Arg Gly Thr His Val Asp Leu Gly
            35                  40                  45

Leu Ala Ser Ala Asn Val Asp Phe Ala Phe Ser Leu Tyr Lys Gln Leu
        50                  55                  60

Val Leu Lys Ala Pro Asp Lys Asn Val Ile Phe Ser Pro Leu Ser Ile
65                  70                  75                  80

Ser Thr Ala Leu Ala Phe Leu Ser Leu Gly Ala His Asn Thr Thr Leu
                85                  90                  95

Thr Glu Ile Leu Lys Gly Leu Lys Phe Asn Leu Thr Glu Thr Ser Glu
                100                 105                 110

Ala Glu Ile His Gln Ser Phe Gln His Leu Leu Arg Thr Leu Asn Gln
            115                 120                 125

Ser Ser Asp Glu Leu Gln Leu Ser Met Gly Asn Ala Met Phe Val Lys
130                 135                 140

Glu Gln Leu Ser Leu Leu Asp Arg Phe Thr Glu Asp Ala Lys Arg Leu
145                 150                 155                 160

Tyr Gly Ser Glu Ala Phe Ala Thr Asp Phe Gln Asp Ser Ala Ala Ala
                165                 170                 175

Lys Lys Leu Ile Asn Asp Tyr Val Lys Asn Gly Thr Arg Gly Lys Ile
                180                 185                 190

Thr Asp Leu Ile Lys Asp Leu Asp Ser Gln Thr Met Met Val Leu Val
            195                 200                 205

Asn Tyr Ile Phe Phe Lys Ala Lys Trp Glu Met Pro Phe Asp Pro Gln
210                 215                 220

Asp Thr His Gln Ser Arg Phe Tyr Leu Ser Lys Lys Trp Val Met
225                 230                 235                 240

Val Pro Met Met Ser Leu His His Leu Thr Ile Pro Tyr Phe Arg Asp
                245                 250                 255

Glu Glu Leu Ser Cys Thr Val Val Glu Leu Lys Tyr Thr Gly Asn Ala
                260                 265                 270

Ser Ala Leu Phe Ile Leu Pro Asp Gln Asp Lys Met Glu Glu Val Glu
            275                 280                 285

Ala Met Leu Leu Pro Glu Thr Leu Lys Arg Trp Arg Asp Ser Leu Glu
290                 295                 300

Phe Arg Glu Ile Gly Glu Leu Tyr Leu Pro Lys Phe Ser Ile Ser Arg
305                 310                 315                 320

Asp Tyr Asn Leu Asn Asp Ile Leu Leu Gln Leu Gly Ile Glu Glu Ala
                325                 330                 335

Phe Thr Ser Lys Ala Asp Leu Ser Gly Ile Thr Gly Ala Arg Asn Leu
            340                 345                 350

Ala Val Ser Gln Val Val His Lys Ala Val Leu Asp Val Phe Glu Glu
        355                 360                 365

Gly Thr Glu Ala Ser Ala Ala Thr Ala Val Lys Ile Thr Leu Leu Ser
    370                 375                 380

Ala Leu Val Glu Thr Arg Thr Ile Val Arg Phe Asn Arg Pro Phe Leu
385                 390                 395                 400
```

```
Met Ile Ile Val Pro Thr Asp Thr Gln Asn Ile Phe Phe Met Ser Lys
            405                 410                 415
Val Thr Asn Pro Lys Gln Ala
            420
```

<210> SEQ ID NO 4
<211> LENGTH: 427
<212> TYPE: PRT
<213> ORGANISM: Homo sapiens

<400> SEQUENCE: 4

```
Met His Leu Ile Asp Tyr Leu Leu Leu Leu Val Gly Leu Leu Ala
1               5                   10                  15
Leu Ser His Gly Gln Leu His Val Glu His Asp Gly Glu Ser Cys Ser
                20                  25                  30
Asn Ser Ser His Gln Gln Ile Leu Glu Thr Gly Glu Gly Ser Pro Ser
                35                  40                  45
Leu Lys Ile Ala Pro Ala Asn Ala Asp Phe Ala Phe Arg Phe Tyr Tyr
    50                  55                  60
Leu Ile Ala Ser Glu Thr Pro Gly Lys Asn Ile Phe Phe Ser Pro Leu
65                  70                  75                  80
Ser Ile Ser Ala Ala Tyr Ala Met Leu Ser Leu Gly Ala Cys Ser His
                85                  90                  95
Ser Arg Ser Gln Ile Leu Glu Gly Leu Gly Phe Asn Leu Thr Glu Leu
                100                 105                 110
Ser Glu Ser Asp Val His Arg Gly Phe Gln His Leu Leu His Thr Leu
                115                 120                 125
Asn Leu Pro Gly His Gly Leu Glu Thr Arg Val Gly Ser Ala Leu Phe
    130                 135                 140
Leu Ser His Asn Leu Lys Phe Leu Ala Lys Phe Leu Asn Asp Thr Met
145                 150                 155                 160
Ala Val Tyr Glu Ala Lys Leu Phe His Thr Asn Phe Tyr Asp Thr Val
                165                 170                 175
Gly Thr Ile Gln Leu Ile Asn Asp His Val Lys Lys Glu Thr Arg Gly
                180                 185                 190
Lys Ile Val Asp Leu Val Ser Glu Leu Lys Lys Asp Val Leu Met Val
                195                 200                 205
Leu Val Asn Tyr Ile Tyr Phe Lys Ala Leu Trp Glu Lys Pro Phe Ile
    210                 215                 220
Ser Ser Arg Thr Thr Pro Lys Asp Phe Tyr Val Asp Glu Asn Thr Thr
225                 230                 235                 240
Val Arg Val Pro Met Met Leu Gln Asp Gln Glu His His Trp Tyr Leu
                245                 250                 255
His Asp Arg Tyr Leu Pro Cys Ser Val Leu Arg Met Asp Tyr Lys Gly
                260                 265                 270
Asp Ala Thr Val Phe Phe Ile Leu Pro Asn Gln Gly Lys Met Arg Glu
                275                 280                 285
Ile Glu Glu Val Leu Thr Pro Glu Met Leu Met Arg Trp Asn Asn Leu
    290                 295                 300
Leu Arg Lys Arg Asn Phe Tyr Lys Lys Leu Glu Leu His Leu Pro Lys
305                 310                 315                 320
Phe Ser Ile Ser Gly Ser Tyr Val Leu Asp Gln Ile Leu Pro Arg Leu
                325                 330                 335
Gly Phe Thr Asp Leu Phe Ser Lys Trp Ala Asp Leu Ser Gly Ile Thr
                340                 345                 350
```

-continued

```
Lys Gln Gln Lys Leu Glu Ala Ser Lys Ser Phe His Lys Ala Thr Leu
            355                 360                 365

Asp Val Asp Glu Ala Gly Thr Glu Ala Ala Ala Thr Thr Phe Ala
    370                 375                 380

Ile Lys Phe Phe Ser Ala Gln Thr Asn Arg His Ile Leu Arg Phe Asn
385                 390                 395                 400

Arg Pro Phe Leu Val Val Ile Phe Ser Thr Ser Thr Gln Ser Val Leu
                405                 410                 415

Phe Leu Gly Lys Val Val Asp Pro Thr Lys Pro
            420                 425

<210> SEQ ID NO 5
<211> LENGTH: 415
<212> TYPE: PRT
<213> ORGANISM: Homo sapiens

<400> SEQUENCE: 5

Met Ser Pro Phe Leu Tyr Leu Val Leu Leu Val Leu Gly Leu His Ala
1               5                   10                  15

Thr Ile His Cys Ala Ser Pro Glu Gly Lys Val Thr Ala Cys His Ser
            20                  25                  30

Ser Gln Pro Asn Ala Thr Leu Tyr Lys Met Ser Ser Ile Asn Ala Asp
        35                  40                  45

Phe Ala Phe Asn Leu Tyr Arg Arg Phe Thr Val Glu Thr Pro Asp Lys
    50                  55                  60

Asn Ile Phe Phe Ser Pro Val Ser Ile Ser Ala Ala Leu Val Met Leu
65                  70                  75                  80

Ser Phe Gly Ala Cys Cys Ser Thr Gln Thr Glu Ile Val Glu Thr Leu
                85                  90                  95

Gly Phe Asn Leu Thr Asp Thr Pro Met Val Glu Ile Gln His Gly Phe
            100                 105                 110

Gln His Leu Ile Cys Ser Leu Asn Phe Pro Lys Lys Glu Leu Glu Leu
        115                 120                 125

Gln Ile Gly Asn Ala Leu Phe Ile Gly Lys His Leu Lys Pro Leu Ala
    130                 135                 140

Lys Phe Leu Asn Asp Val Lys Thr Leu Tyr Glu Thr Glu Val Phe Ser
145                 150                 155                 160

Thr Asp Phe Ser Asn Ile Ser Ala Ala Lys Gln Glu Ile Asn Ser His
                165                 170                 175

Val Glu Met Gln Thr Lys Gly Lys Val Val Gly Leu Ile Gln Asp Leu
            180                 185                 190

Lys Pro Asn Thr Ile Met Val Leu Val Asn Tyr Ile His Phe Lys Ala
        195                 200                 205

Gln Trp Ala Asn Pro Phe Asp Pro Ser Lys Thr Glu Asp Ser Ser Ser
    210                 215                 220

Phe Leu Ile Asp Lys Thr Thr Thr Val Gln Val Pro Met Met His Gln
225                 230                 235                 240

Met Glu Gln Tyr Tyr His Leu Val Asp Met Glu Leu Asn Cys Thr Val
                245                 250                 255

Leu Gln Met Asp Tyr Ser Lys Asn Ala Leu Ala Leu Phe Val Leu Pro
            260                 265                 270

Lys Glu Gly Gln Met Glu Ser Val Glu Ala Ala Met Ser Ser Lys Thr
        275                 280                 285

Leu Lys Lys Trp Asn Arg Leu Leu Gln Lys Gly Trp Val Asp Leu Phe
```

-continued

```
                290                 295                 300
Val Pro Lys Phe Ser Ile Ser Ala Thr Tyr Asp Leu Gly Ala Thr Leu
305                 310                 315                 320

Leu Lys Met Gly Ile Gln His Ala Tyr Ser Glu Asn Ala Asp Phe Ser
                325                 330                 335

Gly Leu Thr Glu Asp Asn Gly Leu Lys Leu Ser Asn Ala Ala His Lys
                340                 345                 350

Ala Val Leu His Ile Gly Glu Lys Gly Thr Glu Ala Ala Ala Val Pro
                355                 360                 365

Glu Val Glu Leu Ser Asp Gln Pro Glu Asn Thr Phe Leu His Pro Ile
370                 375                 380

Ile Gln Ile Asp Arg Ser Phe Met Leu Leu Ile Leu Glu Arg Ser Thr
385                 390                 395                 400

Arg Ser Ile Leu Phe Leu Gly Lys Val Val Asn Pro Thr Glu Ala
                405                 410                 415

<210> SEQ ID NO 6
<211> LENGTH: 394
<212> TYPE: PRT
<213> ORGANISM: Homo sapiens

<400> SEQUENCE: 6

Met Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
                20                  25                  30

Phe Ala Phe Ser Leu Tyr Arg Gln Leu Ala His Gln Ser Asn Ser Thr
            35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
                100                 105                 110

Thr Thr Gly Asn Gly Leu Phe Leu Ser Glu Gly Leu Lys Leu Val Asp
            115                 120                 125

Lys Phe Leu Glu Asp Val Lys Lys Leu Tyr His Ser Glu Ala Phe Thr
130                 135                 140

Val Asn Phe Gly Asp Thr Glu Glu Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
            195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255
```

```
Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300

Gln Leu Gly Ile Thr Lys Val Phe Ser Asn Gly Ala Asp Leu Ser Gly
305                 310                 315                 320

Val Thr Glu Glu Ala Pro Leu Lys Leu Ser Lys Ala Val His Lys Ala
                325                 330                 335

Val Leu Thr Ile Asp Glu Lys Gly Thr Glu Ala Ala Gly Ala Met Phe
            340                 345                 350

Leu Glu Ala Ile Pro Met Ser Ile Pro Pro Glu Val Lys Phe Asn Lys
        355                 360                 365

Pro Phe Val Phe Leu Met Ile Glu Gln Asn Thr Lys Ser Pro Leu Phe
    370                 375                 380

Met Gly Lys Val Val Asn Pro Thr Gln Lys
385                 390

<210> SEQ ID NO 7
<211> LENGTH: 14
<212> TYPE: PRT
<213> ORGANISM: homo sapiens

<400> SEQUENCE: 7

Gln Gly Leu Gly Phe Asn Leu Thr His Thr Pro Glu Ser Ala
1               5                   10

<210> SEQ ID NO 8
<211> LENGTH: 14
<212> TYPE: PRT
<213> ORGANISM: homo sapiens

<400> SEQUENCE: 8

Phe Thr Val Ser Phe Asn Arg Thr Phe Leu Met Met Ile Thr
1               5                   10

<210> SEQ ID NO 9
<211> LENGTH: 13
<212> TYPE: PRT
<213> ORGANISM: homo sapiens

<400> SEQUENCE: 9

Gly Arg Arg Arg Gly Thr Cys Lys Asp Ile Phe Cys Ser
1               5                   10

<210> SEQ ID NO 10
<211> LENGTH: 13
<212> TYPE: PRT
<213> ORGANISM: homo sapiens

<400> SEQUENCE: 10

Tyr Pro Arg Pro Ser Ser Thr Lys Ser Thr Pro Ala Ser
1               5                   10

<210> SEQ ID NO 11
<211> LENGTH: 13
<212> TYPE: PRT
<213> ORGANISM: homo sapiens

<400> SEQUENCE: 11
```

Pro Ser Lys Asp Leu Thr Leu Lys Met Gly Ser Ala Leu
1               5                   10

<210> SEQ ID NO 12
<211> LENGTH: 13
<212> TYPE: PRT
<213> ORGANISM: homo sapiens

<400> SEQUENCE: 12

Phe His Leu Glu Tyr Thr Arg Lys Asn Phe Pro Phe Leu
1               5                   10

<210> SEQ ID NO 13
<211> LENGTH: 13
<212> TYPE: PRT
<213> ORGANISM: homo sapiens

<400> SEQUENCE: 13

Leu Glu Gln Ala Leu Ser Ala Arg Thr Leu Ile Lys Trp
1               5                   10

<210> SEQ ID NO 14
<211> LENGTH: 13
<212> TYPE: PRT
<213> ORGANISM: homo sapiens

<400> SEQUENCE: 14

Gln Val Ser Lys Ala Thr His Lys Ala Val Leu Asp Val
1               5                   10

<210> SEQ ID NO 15
<211> LENGTH: 13
<212> TYPE: PRT
<213> ORGANISM: homo sapiens

<400> SEQUENCE: 15

Ala Thr Ala Ala Thr Thr Thr Lys Phe Ile Val Arg Ser
1               5                   10

<210> SEQ ID NO 16
<211> LENGTH: 13
<212> TYPE: PRT
<213> ORGANISM: homo sapiens

<400> SEQUENCE: 16

Phe Leu Met Met Ile Thr Asn Lys Ala Thr Asp Gly Ile
1               5                   10

<210> SEQ ID NO 17
<211> LENGTH: 18
<212> TYPE: PRT
<213> ORGANISM: homo sapiens

<400> SEQUENCE: 17

Thr Lys Phe Ile Val Arg Ser Lys Asp Gly Pro Ser Tyr Phe Thr Val
1               5                   10                  15

<210> SEQ ID NO 18
<211> LENGTH: 72
<212> TYPE: DNA
<213> ORGANISM: homo sapiens

<400> SEQUENCE: 18
ggcacttccc atcttcaagg tcaggtcttt gctgggaaca gtcagtgagt gaaccaggtg    60

```
ctggaagccc tg                                                          72
```

<210> SEQ ID NO 19
<211> LENGTH: 21
<212> TYPE: DNA
<213> ORGANISM: homo sapiens

<400> SEQUENCE: 19

```
gcctctgtgc tccaatctac t                                                21
```

<210> SEQ ID NO 20
<211> LENGTH: 19
<212> TYPE: DNA
<213> ORGANISM: homo sapiens

<400> SEQUENCE: 20

```
gctgcagctc cttcttgac                                                   19
```

<210> SEQ ID NO 21
<211> LENGTH: 11
<212> TYPE: PRT
<213> ORGANISM: homo sapiens

<400> SEQUENCE: 21

```
Val Ser Phe Asn Arg Thr Phe Leu Met Met Ile
1               5                   10
```

<210> SEQ ID NO 22
<211> LENGTH: 16
<212> TYPE: PRT
<213> ORGANISM: homo sapiens

<400> SEQUENCE: 22

```
Gly Thr Glu Ala Thr Ala Ala Thr Thr Thr Lys Phe Ile Val Arg Ser
1               5                   10                  15
```

<210> SEQ ID NO 23
<211> LENGTH: 21
<212> TYPE: PRT
<213> ORGANISM: homo sapiens

<400> SEQUENCE: 23

```
Pro Ser Tyr Phe Thr Val Ser Phe Asn Arg Thr Phe Leu Met Met Ile
1               5                   10                  15

Thr Asn Lys Ala Thr
            20
```

<210> SEQ ID NO 24
<211> LENGTH: 18
<212> TYPE: PRT
<213> ORGANISM: homo sapiens

<400> SEQUENCE: 24

```
Tyr Ser Leu Asn Thr Asp Phe Ala Phe Arg Leu Tyr Arg Arg Leu Val
1               5                   10                  15

Leu Glu
```

<210> SEQ ID NO 25
<211> LENGTH: 16
<212> TYPE: PRT
<213> ORGANISM: homo sapiens

<400> SEQUENCE: 25

```
Glu Ser Ala Ile His Gln Gly Phe Gln His Leu Val His Ser Leu Thr
1               5                   10                  15
```

<210> SEQ ID NO 26
<211> LENGTH: 10
<212> TYPE: PRT
<213> ORGANISM: homo sapiens

<400> SEQUENCE: 26

```
Ala Arg Thr Leu Ile Lys Trp Ser His Ser
1               5                   10
```

<210> SEQ ID NO 27
<211> LENGTH: 17
<212> TYPE: PRT
<213> ORGANISM: homo sapiens

<400> SEQUENCE: 27

```
Asn Pro Ser Ile Ala Gln Ala Arg Ile Asn Ser His Val Lys Lys Lys
1               5                   10                  15

Thr
```

<210> SEQ ID NO 28
<211> LENGTH: 8
<212> TYPE: PRT
<213> ORGANISM: homo sapiens

<400> SEQUENCE: 28

```
Gln Gly Lys Val Val Asp Ile Ile
1               5
```

<210> SEQ ID NO 29
<211> LENGTH: 11
<212> TYPE: PRT
<213> ORGANISM: homo sapiens

<400> SEQUENCE: 29

```
Ala Met Val Leu Val Asn His Ile Phe Phe Lys
1               5                   10
```

<210> SEQ ID NO 30
<211> LENGTH: 10
<212> TYPE: PRT
<213> ORGANISM: homo sapiens

<400> SEQUENCE: 30

```
Lys Ala Thr His Lys Ala Val Leu Asp Val
1               5                   10
```

<210> SEQ ID NO 31
<211> LENGTH: 21
<212> TYPE: PRT
<213> ORGANISM: homo sapiens

<400> SEQUENCE: 31

```
Ala Thr Ala Ala Thr Thr Thr Lys Phe Ile Val Arg Ser Lys Asp Gly
1               5                   10                  15

Pro Ser Tyr Phe Thr
            20
```

<210> SEQ ID NO 32
<211> LENGTH: 733
<212> TYPE: DNA
<213> ORGANISM: homo sapiens

<400> SEQUENCE: 32

```
gggatccgga gcccaaatct tctgacaaaa ctcacacatg cccaccgtgc ccagcacctg    60
aattcgaggg tgcaccgtca gtcttcctct tccccccaaa acccaaggac accctcatga   120
tctcccggac tcctgaggtc acatgcgtgg tggtggacgt aagccacgaa gaccctgagg   180
tcaagttcaa ctggtacgtg gacggcgtgg aggtgcataa tgccaagaca aagccgcggg   240
aggagcagta caacagcacg taccgtgtgg tcagcgtcct caccgtcctg caccaggact   300
ggctgaatgg caaggagtac aagtgcaagg tctccaacaa agcccctccca accccccatcg   360
agaaaaccat ctccaaagcc aaagggcagc ccgagaacc acaggtgtac accctgcccc   420
catcccggga tgagctgacc aagaaccagg tcagcctgac ctgcctggtc aaaggcttct   480
atccaagcga catcgccgtg gagtgggaga gcaatgggca gccggagaac aactacaaga   540
ccacgcctcc cgtgctggac tccgacggct ccttcttcct ctacagcaag ctcaccgtgg   600
acaagagcag gtggcagcag gggaacgtct tctcatgctc cgtgatgcat gaggctctgc   660
acaaccacta cacgcagaag agcctctccc tgtctccggg taaatgagtg cgacggccgc   720
gactctagag gat                                                      733
```

<210> SEQ ID NO 33
<211> LENGTH: 8
<212> TYPE: PRT
<213> ORGANISM: Bacteriophage T7

<400> SEQUENCE: 33

Asp Tyr Lys Asp Asp Asp Asp Lys
1               5

<210> SEQ ID NO 34
<211> LENGTH: 39
<212> TYPE: DNA
<213> ORGANISM: Homo sapiens

<400> SEQUENCE: 34

```
gcagcagcgg ccgcgtgtcc ccggccaatg cccccagtg                           39
```

<210> SEQ ID NO 35
<211> LENGTH: 37
<212> TYPE: DNA
<213> ORGANISM: Homo sapiens

<400> SEQUENCE: 35

```
gcagcagtcg acggatttag tgggattttc cactttc                             37
```

<210> SEQ ID NO 36
<211> LENGTH: 39
<212> TYPE: DNA
<213> ORGANISM: Homo sapiens

<400> SEQUENCE: 36

```
gcagcagcgg ccgcatgcaa ggacagggca ggagaagag                           39
```

<210> SEQ ID NO 37
<211> LENGTH: 36
<212> TYPE: DNA
<213> ORGANISM: Homo sapiens

<400> SEQUENCE: 37

```
gcagcagtcg actgacatcc agcacagcct tgtggg                              36
```

<210> SEQ ID NO 38
<211> LENGTH: 12
<212> TYPE: PRT
<213> ORGANISM: Homo sapiens

<400> SEQUENCE: 38

Met Gln Gly Gln Gly Arg Arg Arg Gly Thr Cys Lys
1               5                   10

<210> SEQ ID NO 39
<211> LENGTH: 14
<212> TYPE: PRT
<213> ORGANISM: Homo sapiens

<400> SEQUENCE: 39

Gln Gly Gln Gly Arg Arg Arg Gly Thr Cys Lys Asp Ile Phe
1               5                   10

<210> SEQ ID NO 40
<211> LENGTH: 14
<212> TYPE: PRT
<213> ORGANISM: Homo sapiens

<400> SEQUENCE: 40

Ile Asn Ser His Val Lys Lys Lys Thr Gln Gly Lys Val Val
1               5                   10

<210> SEQ ID NO 41
<211> LENGTH: 14
<212> TYPE: PRT
<213> ORGANISM: Homo sapiens

<400> SEQUENCE: 41

Phe Ser Gly Ile Ala Lys Arg Asp Ser Leu Gln Val Ser Lys
1               5                   10

<210> SEQ ID NO 42
<211> LENGTH: 16
<212> TYPE: PRT
<213> ORGANISM: Homo sapiens

<400> SEQUENCE: 42

Ala Ser Tyr Leu Tyr Gly Val Leu Phe Ala Val Gly Leu Cys Ala Pro
1               5                   10                  15

<210> SEQ ID NO 43
<211> LENGTH: 16
<212> TYPE: PRT
<213> ORGANISM: Homo sapiens

<400> SEQUENCE: 43

Thr Gln Ile Leu Gln Gly Leu Gly Phe Asn Leu Thr His Thr Pro Glu
1               5                   10                  15

<210> SEQ ID NO 44
<211> LENGTH: 16
<212> TYPE: PRT
<213> ORGANISM: Homo sapiens

<400> SEQUENCE: 44

Ile Leu Pro Lys Met Gly Ile Gln Asn Ala Phe Asp Lys Asn Ala Asp
1               5                   10                  15

```
<210> SEQ ID NO 45
<211> LENGTH: 16
<212> TYPE: PRT
<213> ORGANISM: Homo sapiens

<400> SEQUENCE: 45

Asp Val Ser Glu Glu Gly Thr Glu Ala Thr Ala Ala Thr Thr Thr Lys
1               5                   10                  15

<210> SEQ ID NO 46
<211> LENGTH: 14
<212> TYPE: PRT
<213> ORGANISM: Homo sapiens

<400> SEQUENCE: 46

Gly Arg Arg Arg Gly Thr Cys Lys Asp Ile Phe Cys Ser Lys
1               5                   10
```

POLYNUCLEOTIDE ENCODING A NOVEL HUMAN SERPIN SECRETED FROM LYMPHOID CELLS, LSI-01

This application claims benefit to provisional application U.S. Ser. No. 60/248,434, filed Nov. 14, 2000; to provisional application U.S. Ser. No. 60/257,610, filed Dec. 21, 2000; and to provisional application U.S. Ser. No. 60/282,745, filed Apr. 10, 2001.

FIELD OF THE INVENTION

The present invention provides novel polynucleotides encoding LSI-01 polypeptides, fragments and homologues thereof. Also provided are vectors, host cells, antibodies, and recombinant and synthetic methods for producing said polypeptides. The invention further relates to diagnostic and therapeutic methods for applying these novel LSI-01 polypeptides to the diagnosis, treatment, and/or prevention of various diseases and/or disorders related to these polypeptides. The invention further relates to screening methods for identifying agonists and antagonists of the polynucleotides and polypeptides of the present invention.

BACKGROUND OF THE INVENTION

Limited-proteolysis by serine and cysteine proteases plays a central regulatory role in many physiological and pathophysiological processes including coagulation, fibrinolysis, complement fixation, apoptosis, angiogenesis, tumor cell attachment and growth. Serpins (Serine Protease Inhibitors) are the principle protease inhibitors in human plasma (serpins make up 10% of plasma proteins on a molar basis), and have been shown to regulate these physiological processes. Well known examples include antithrombin which regulates the blood coagulation cascade; $C_1$-inhibitor which controls complement activation; plasminogen activator inhibitors (PAI-1 and $\alpha_2$-antiplasmin) which regulate fibrinolysis; and alpha$_1$-antitrypsin, also called alpha$_1$ proteinase inhibitor, which modulates connective tissue remodeling (see Gils & Declerck, 1998 and Whisstock et al. 1998 for reviews on these and other serpins).

Serpins regulate proteases through a suicide-substrate inhibition mechanism forming a covalent complex between the protease active site serine and the bait P1 amino acid (Huntington et al., 2000). This results in a 1:1, SDS-resistant complex. In addition to the inhibitory serpins, there are also serpin family members that function as hormone transport or growth factor proteins (examples include the thyroxin and corticosteroid binding globulins and the vasopressor peptide source angiotensinogen). In addition, serpins have demonstrated involvement in angiogenesis and tumor growth (see for example O'Reilly et al., 1999).

As a class, serpins contain conserved residues located internal to the protein or on surface niches, therefore the serpin family has remarkably-conserved 3-dimentional structure despite less dramatic overall homology elsewhere (see Huber & Carrell,1989 and Whisstock et al., 1998 for reviews). Protease inhibitory serpins (of which the present invention relates) contain a mobile reactive site loop (P16–P10') that is subject to proteolytic cleavage. This loop cleavage site (sometimes referred to as the "bait region") is cleaved by a cognate protease. The loop region is flexible and has the ability to profoundly change its conformation (alanine-rich regions in the loop P13–P9 allow increased flexibility (Gils & Declerck, 1998)). Once cleaved, the P14–P1 portion of the loop has high affinity for insertion into a P-sheet domain ( Whisstock et al., 1998; Huntington et al., 2000). In general, peptides corresponding to the P14–P1 or P14–P7 or P14–P10 loop regions and small molecule mimics of the loop region prevent protease inhibitory activity.

The serpin proteolytic cleavage site is designated P1P1'. It is generally accepted that the P1 residue is the major determinant of the protease specificity of the serpin (Gills & Declerck, 1998). Typically the bait region (especially the P1 site) mimics the natural substrate of the cognate protease. While each inhibitory serpin shows some preference for selected proteases, most serpins recognize several proteases with varying degrees of specificity (for example antithrombin will inhibit Factors IXa, Xa, XIa, as well as thrombin; α1-antitrypsin will inhibit trypsin and neutrophil elastase; PAI-1 inhibits tPA, uPA and trypsin etc.). Furthermore, relatively minor amino acid changes in the bait region, especially at the P1 position, can dramatically change the specificity of the serpin (Gils and Declerck, 1998).

In addition to the bait region, domains away from the cleavage site also confer selectivity. For some serpins, non-enzymatic cofactors activate the serpin and modulate the rate of protease inactivation. For example antithrombin, PAI-1, protease nexin 1, protein C inhibitor and heparin cofactor II are stimulated by heparin. Furthermore, the specificity of a serpin may depend on the cofactor composition and concentration. For example the specificity of antithrombin depends on the size of the heparin molecule. Large molecular weight heparins stimulate inhibition of thrombin where as low molecular heparin has more FXa selectivity. Another example is vitronectin, which binds to PAI-1 and increases its affinity for thrombin. Studies (Shirk, et al, 1994, Lane et al, 1994, Pratt et al 1991, Blinder, et al, 1989, Blinder et al 1991, Whinna et al, 1991, Ragg et al, 1991) have implicated one or more of the A, D and H helices of serpins (for example, the helices in antithrombin, protein C inhibitor and heparin cofactor II) which are rich in basic residues and bind heparin, and, 3-dimensional structures and models have been useful in the design of low molecular weight molecules which modulate serpin reactivity.

Recently, the crystal structure of a serpin-protease complex was reported (Huntington, et al, 2000) in which the reactive loop has been cleaved at the bait position. The tethered protease moves 70 angstroms, with the tether sequence (P10–P1) inserted in the "A" beta sheet of alpha anti-trypsin. This shallow groove, which we call the cleaved reactive loop-binding region, represents a potential target for small molecule inhibition.

Serpins in Disease and Therapy

Members of the serpin family play a variety of roles in physiology, disease and in therapy. Deficiencies in some serpins can cause well-characterized diseases. Alpha-1-antitrypsin deficiency, which is a common autosomal recessive disorder, is associated with development of emphysema, liver cirrhosis and hepatocellular carcinoma. Patients deficient in antithrombin are prone to sever thrombotic consequences.

Serpins are useful as therapeutics. Antithrombin is a potent inhibitor of thrombin-mediated vascular injury in the microcirculation in severe sepsis. This endogenous anticoagulant is rapidly depleted in the early phases of sepsis as a result of decreased synthesis, increased destruction, and enhanced clearance by thrombin-antithrombin complex formation. The therapeutic efficacy of antithrombin in experimental sepsis is readily demonstrable in numerous animal systems (Opal 2000).

In addition to the therapeutic activity of the serpins, modulators of serpin activity have well documented utility in antithrombotic therapy. The anticoagulant efficacy of heparin and low molecular weight heparin is mediated by antithrombin inhibition of proteases (i.e. thrombin and FXa). Indeed antithrombin is required for the anti-coagulant efficacy of heparin and low molecular weight heparins which are useful in the treatment of arterial thrombosis (for example myocardial infarction, unstable angina & stroke) and venous thrombosis (for example deep vein thrombosis and pulmonary embolism).

Inhibitors of serpins have also shown utility. Antibodies or small molecule inhibitors can inhibit serpin activity and prolong cognate protease function. Examples of serpin inhibition with therapeutic value that preserve fibrinolytic function include antibodies to alpha 2-antiplasmin (Reed et al., 1990) and plasminogen activator inhibitor-1 (Biemond et al., 1995). Both have been shown to improve thrombolysis under thrombotic conditions in animal models of disease.

Serpins are also useful in measurement of cognate protease activation and are useful in diagnosis of disease states. In general, proteolytic enzymes form stable complexes with serpins that can be followed by measuring the cognate protease-serpin complex using ELISA or other techniques. As such, measurement of the serpin-protease complex is useful as a reporter of cognate protease activation. An example is thrombin-antithrombin complex (TAT) which is a reporter of thrombin activation in vivo. TAT levels are elevated in thrombotic disease states and measurement of thrombin-antithrombin complexes is useful in the diagnosis of arterial and venous thrombotic diseases as well as a biomarker of disease and therapy. In general, serpin inhibition of proteolytic activities are measured by following the inhibition of cognate protease in vitro or in vivo.

Using the above examples, it is clear the availability of a novel cloned serpin provides opportunity for adjunct or replacement therapy, and are useful for the identification of serpin agonists, or stimulators (which might stimulate and/or bias serpin action), as well as, in the identification of serpin inhibitors. All of which might be therapeutically useful under different circumstances. The serpin of the present invention can also be used as a scaffold to tailor-make specific protease inhibitors and prevent angiogenesis. In addition detection of the serpin-cognate protease complex can be a useful diagnostic tool.

Polynucleotides and polypeptides corresponding to a portion of the full-length LSI-01 polypeptide of the present invention, in addition to its encoding polynucleotides, have been described by Baker et. al., International Publication Number WO 00/12708, gene UNQ692. Baker et al. did not appreciate the fact that their UNQ692 gene was not representative of the entire coding region, nor the fact that the UNQ692 translation product was deficient in the N-terminal domain. Baker et al., have termed their peptide fragment, encoded by their UNQ692 polynucleotide fragment, as PRO1337. Baker et al. teach the PRO1337 peptide as representing a homologue of a human thyroxin-binding globulin (TBG; Genbank Accession No. gil4507377), and did not appreciate the fact that the protein shares higher identity to Arg/lys protease inhibitor serpins in domains essential for serpin activity and specificity, as opposed to the hormone-binding serpins.

The inventors of the present invention describe herein, the polynucleotides corresponding to the full-length LSI-01 gene and its encoded polypeptide. Also provided are polypeptide alignments illustrating the strong conservation of the LSI-01 polypeptide to known protease inhibitor serpins, and the dissimilarity of the protein in key amino acid domains to TBG. As inferred above, the dissimilarity is particularly evident in the 'bait' region, and the flexible loop region, which are essential for determining serpin function and specificity, as shown in FIG. 2. Based on this strong conservation, the inventors have ascribed the LSI-01 polypeptide as having at least some serpin protease inhibitory activities, particularly inhibition of proteases exhibiting Arg/lys specificity. Data is also provided illustrating the unique tissue expression profile of the LSI-01 polypeptide in lymphoid tissues, which has not been appreciated heretofore.

The present invention also relates to recombinant vectors, which include the isolated nucleic acid molecules of the present invention, and to host cells containing the recombinant vectors, as well as to methods of making such vectors and host cells, in addition to their use in the production of LSI-01 polypeptides or peptides using recombinant techniques. Synthetic methods for producing the polypeptides and polynucleotides of the present invention are provided. Also provided are diagnostic methods for detecting diseases, disorders, and/or conditions related to the LSI-01 polypeptides and polynucleotides, and therapeutic methods for treating such diseases, disorders, and/or conditions. The invention further relates to screening methods for identifying binding partners of the polypeptides.

BRIEF SUMMARY OF THE INVENTION

The present invention provides isolated nucleic acid molecules, that comprise, or alternatively consist of, a polynucleotide encoding the LSI-01 protein having the amino acid sequence shown in FIGS. 1A–B (SEQ ID NO:2) or the amino acid sequence encoded by the cDNA clone, LSI-01 (bac708.clone 24; AL132708_FL, BA-14448, protease 6; and/or protease inhibitor 6), deposited as ATCC Deposit Number PTA-2766 on Dec. 8, 2000.

The present invention also relates to recombinant vectors, which include the isolated nucleic acid molecules of the present invention, and to host cells containing the recombinant vectors, as well as to methods of making such vectors and host cells, in addition to their use in the production of LSI-01 polypeptides or peptides using recombinant techniques. Synthetic methods for producing the polypeptides and polynucleotides of the present invention are provided. Also provided are diagnostic methods for detecting diseases, disorders, and/or conditions related to the LSI-01 polypeptides and polynucleotides, and therapeutic methods for treating such diseases, disorders, and/or conditions. The invention further relates to screening methods for identifying binding partners of the polypeptides.

The invention further provides an isolated LSI-01 polypeptide having an amino acid sequence encoded by a polynucleotide described herein.

The invention also provides a machine readable storage medium which comprises the structure coordinates of LSI-01, including all or any parts of the heparin binding region, the cleaved reactive loop binding region, and reactive loop region. Such storage medium encoded with these data are capable of displaying on a computer screen or similar viewing device, a three-dimensional graphical representation of a molecule or molecular complex which comprises said regions or similarly shaped homologous regions.

The invention also provides methods for designing, evaluating and identifying compounds which bind to all or parts of the aforementioned regions. Such compounds are potential inhibitors of LSI-01 or its homologues.

The invention also provides novel classes of compounds, and pharmaceutical compositions thereof, that are useful as inhibitors of LSI-01 or its homologues.

The invention further relates to a method of identifying a compound that modulates the biological activity of LSI-01, comprising the steps of, (a) combining a candidate modulator compound with LSI-01 having the sequence set forth in one or more of SEQ ID NO:2; and measuring an effect of the candidate modulator compound on the activity of LSI-01.

The invention further relates to a method of identifying a compound that modulates the biological activity of a serpin, comprising the steps of, (a) combining a candidate modulator compound with a host cell expressing LSI-01 having the sequence as set forth in SEQ ID NO:2; and, (b) measuring an effect of the candidate modulator compound on the activity of the expressed LSI-01.

The invention further relates to a method of identifying a compound that modulates the biological activity of LSI-01, comprising the steps of, (a) combining a candidate modulator compound with a host cell containing a vector described herein, wherein LSI-01 is expressed by the cell; and, (b) measuring an effect of the candidate modulator compound on the activity of the expressed LSI-01.

The invention further relates to a method of screening for a compound that is capable of modulating the biological activity of LSI-01, comprising the steps of: (a) providing a host cell described herein; (b) determining the biological activity of LSI-01 in the absence of a modulator compound; (c) contacting the cell with the modulator compound; and (d) determining the biological activity of LSI-01 in the presence of the modulator compound; wherein a difference between the activity of LSI-01 in the presence of the modulator compound and in the absence of the modulator compound indicates a modulating effect of the compound.

The invention further relates to a compound that modulates the biological activity of human LSI-01 as identified by the methods described herein.

BRIEF DESCRIPTION OF THE FIGURES/DRAWINGS

FIGS. 1A–B show the polynucleotide sequence (SEQ ID NO:1) and deduced amino acid sequence (SEQ ID NO:2) of the novel human serpin, LSI-01, of the present invention. The standard one-letter abbreviation for amino acids is used to illustrate the deduced amino acid sequence. The polynucleotide sequence contains a sequence of 1766 nucleotides (SEQ ID NO:1), encoding a polypeptide of 435 amino acids (SEQ ID NO:2). An analysis of the LSI-01 polypeptide determined that it comprised the following features: a predicted signal peptide located from about amino acid 1 to about amino acid 38 of SEQ ID NO:2 (FIGS. 1A–B) represented by double underlining; a conserved serpin domain signature from about amino acid 405 to about amino acid 415 of SEQ ID NO:2 (FIGS. 1A–B) represented by shading; a flexible loop region characteristic of protease inhibitor serpins from about amino acid 384 to about amino acid 387 of SEQ ID NO:2 (FIGS. 1A–B) represented by single underlining; and a protease cleaveable bait region (also referred to as a 'P1' site) characteristic of trypsin-like cognate protease from about amino acid 395 to about amino acid 396 of SEQ ID NO:2 (FIGS. 1A–B) represented by bold amino acids.

FIGS. 2 shows the regions of identity between the encoded LSI-01 protein (SEQ ID NO:2) to other serpins, specifically, the human $\alpha_1$-antichymotrypsin protein (AACT_HUMAN; Genbank Accession No:gil112874; Chandra et al., 1983; SEQ ID NO:3), the human Kallistatin protein, also known as Protease Inhibitor 4 (KAIN_HUMAN; Genbank Accession No:gil5453888; Chai et al., 1993; SEQ ID NO:4), and the human thyroxin-binding globulin protein (THBG_HUMAN; Genbank Accession No:gil37142; Flink et al., 1986; SEQ ID NO:5). The alignment was performed using the CLUSTALW algorithm described elsewhere herein. The shaded amino acids represent regions of matching identity. Lines between residues indicate gapped regions of non-identity for the aligned polypeptides. The black arrows above the alignment denote the characteristic signature peptide sequence of members of the SERPIN family of serine protease inhibitors (SEQ ID NO:21). The underlined (ATAA) sequence (SEQ ID NO:22) indicates the flexible region found in protease inhibitor serpins, which contrasts with the inflexible ATAV sequence of the thyroxin-binding globulin (Gils and Declerck, 1998).

FIG. 3 shows the regions of identity between the encoded LSI-01 protein (SEQ ID NO:2) to the human $\alpha_1$-antithrypsin protein (pdb1q1p; Genbank Accession No:gil6137432; SEQ ID NO:6). The alignment was performed using the CLUSTALW algorithm described elsewhere herein. The shaded amino acids represent regions of matching identity. Lines between residues indicate gapped regions of non-identity for the aligned polypeptides.

FIG. 4 shows a hydrophobicity plot of LSI-01 according to the BioPlot Hydrophobicity algorithm of Vector NTI (version 5.5). The hydrophilic peak at the N-terminus of the LSI-01 polypeptide is consistent with the presence of a predicted signal sequence.

Figure 5A:
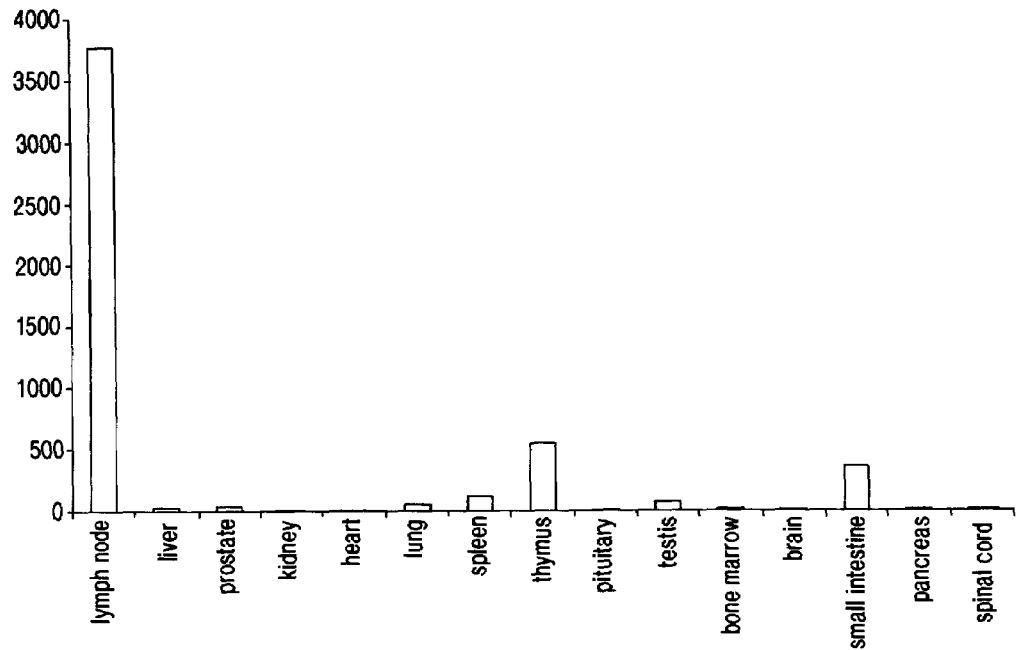
Figure 5B:
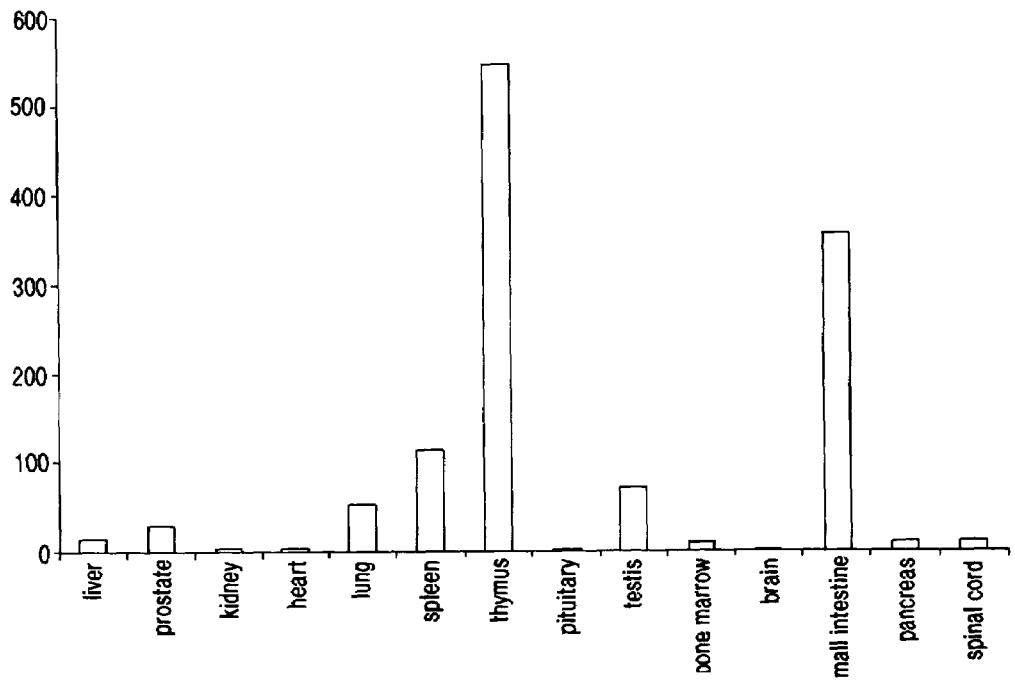

FIG. 5 shows two expression profiles of the novel human serpin, LSI-01. The top panel illustrates the relative expression level of LSI-01 amongst various mRNA tissue sources. As shown, transcripts corresponding to LSI-01 expressed highly in the lymph node—more than 7-fold higher expression was observed in lymph node compared to the next highest level of tissue expression, the thymus. The bottom panel illustrates the same relative expression data as the top panel, though in the absence of the lymph node data, to more clearly show the proportional comparison between tissues of lower LSI-01 expression levels. As shown, the LSI-01 was expressed to a lesser extent, in the thymus, small intestine, and spleen. Expression data was obtained by measuring the steady state LSI-01 mRNA levels by quantitative PCR using the same PCR primer pair used to isolate the novel LSI-01 cDNA clone (SEQ ID NO:19 and 20) as described herein.

FIG. 6 shows a table illustrating the percent identity and percent similarity between the LSI-01 polypeptide of the present invention with other serpins, specifically, the human $\alpha_1$-antichymotrypsin protein (AACT_HUMAN; Genbank Accession No:gil112874; Chandra et al., 1983; SEQ ID NO:3), the human Kallistatin protein, also known as Protease Inhibitor 4 (KAIN_HUMAN; Genbank Accession No:gil5453888; Chai et al., 1993; SEQ ID NO:4), the human thyroxin-binding globulin protein (THBG_HUMAN; Genbank Accession No:gil37142; Flink et al., 1986; SEQ ID NO:5), and the human $\alpha_1$-antithrypsin protein (pdb1q1p; Genbank Accession No:gil6137432; SEQ ID NO:6). The percent identity and percent similarity values were determined using the BestFit algorithm using default parameters (Genetics Computer Group suite of programs).

Figure 7:
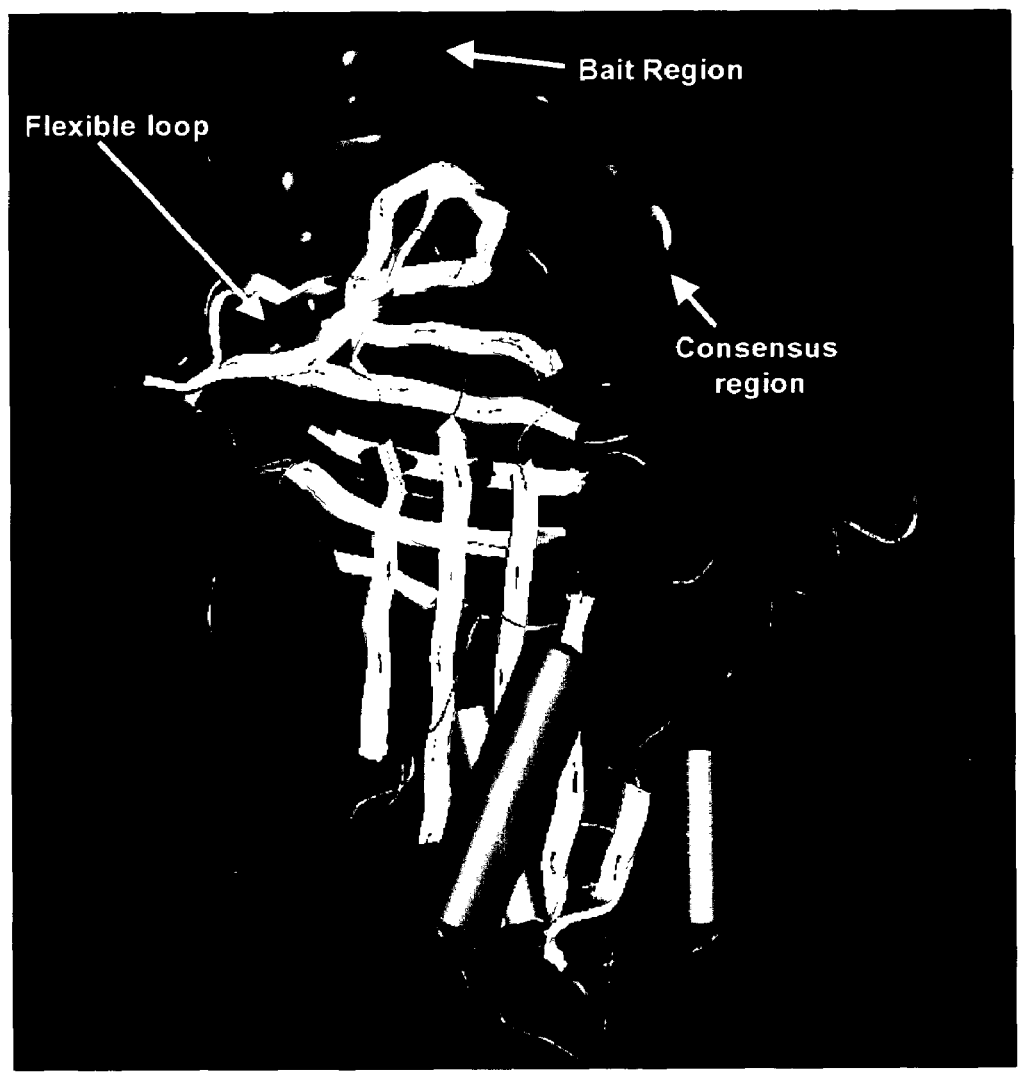

FIG. 7 shows a three-dimensional homology model of the LSI-01 polypeptide based upon the homologous structure of the human $\alpha_1$-antithrypsin protein (pdb1q1p; Genbank Accession No:; SEQ ID NO:6). The features of the human LSI-01 serpin identified in FIGS. 1A–B are labeled. Briefly, the predicted regions of beta sheet structure are represented in yellow; the predicted regions of alpha helix structure are represented in red; the predicted flexible loop region is represented in blue; the serpin bait P1 region is represented in red; and the consensus serpin region is presented in purple. Other regions of the protein structure are represented in aquamarine. The structural coordinates of the LSI-01 polypeptide are provided in Table III. The homology model of LSI-01 was derived from generating a sequence alignment with α1 anti-trypsin using the Proceryon suite of software (Proceryon Biosciences, Inc. N.Y., N.Y.), and the overall atomic model including plausible sidechain orientations using the program LOOK (V3.5.2, Molecular Applications Group).

Table III provides the structural coordinates of the homology model of the LSI-01 polypeptide provided in FIG. 7 based upon the homologous structure of the human $\alpha_1$-antithrypsin protein (pdb1q1p; Genbank Accession No:; SEQ ID NO:6). A description of the headings are as follows: "Atom" refers to the atom within the LSI-01 homology model; "Atom type" refers to the element whose coordinates are measured, the first letter in the column defines the element; "Residue" refers to the amino acid within which the atom resides; "#" refers to the amino acid number of the "residue"; "X", "Y", and "Z" structurally define the atomic position of the element measured in three dimensions; "B" is a thermal factor that measures movement of the atom around its atomic center; and "Occ" is an occupancy factor that refers to the fraction of the molecules in which each atom occupies the position specified by the coordinates. A value of "1" indicates that each atom has the same conformation, i.e., the same position, in all molecules of the model.

DETAILED DESCRIPTION OF THE INVENTION

The present invention may be understood more readily by reference to the following detailed description of the preferred embodiments of the invention and the Examples included herein.

The invention provides a novel human sequence that encodes a serine protease inhibitor (serpin) with substantial homology to the class of serpins having a protease specificity for arginine/lysine residues ("trypsin-like" serine and similarly specific cysteine proteases). Proteases of this class of serpins include members of the blood coagulation cascade (clotting factors VIIa, Xa, IXa, thrombin), anticoagulation (protein C), fibrinolysis (tissue type plasminogen activator, urokinase and plasmin), complement pathways (complement factors C1and others), proteases involved in inflammation (tryptase), and proteolytic digestion and signaling (trypsin). In addition, expression analysis indicates the LSI-01 has strong preferential expression in lymph nodes, and to a lesser extent, in thymus, small intestine, and spleen. Based on this information, we have provisionally named the gene and protein LSI-01 (Lymphocyte Specific Serine Protease Inhibitor-01.

In the present invention, "isolated" refers to material removed from its original environment (e.g., the natural environment if it is naturally occurring), and thus is altered "by the hand of man" from its natural state. For example, an isolated polynucleotide could be part of a vector or a composition of matter, or could be contained within a cell, and still be "isolated" because that vector, composition of matter, or particular cell is not the original environment of the polynucleotide. The term "isolated" does not refer to genomic or cDNA libraries, whole cell total or mRNA preparations, genomic DNA preparations (including those separated by electrophoresis and transferred onto blots), sheared whole cell genomic DNA preparations or other compositions where the art demonstrates no distinguishing features of the polynucleotide/sequences of the present invention.

In specific embodiments, the polynucleotides of the invention are at least 15, at least 30, at least 50, at least 100, at least 125, at least 500, or at least 1000 continuous nucleotides but are less than or equal to 300 kb, 200 kb, 100 kb, 50 kb, 15 kb, 10 kb, 7.5 kb, 5 kb, 2.5 kb, 2.0 kb, or 1 kb, in length. In a further embodiment, polynucleotides of the invention comprise a portion of the coding sequences, as disclosed herein, but do not comprise all or a portion of any intron. In another embodiment, the polynucleotides comprising coding sequences do not contain coding sequences of a genomic flanking gene (i.e., 5' or 3' to the gene of interest in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

As used herein, a "polynucleotide" refers to a molecule having a nucleic acid sequence contained in SEQ ID NO:1 or the cDNA contained within the clone deposited with the ATCC. For example, the polynucleotide can contain the nucleotide sequence of the full length cDNA sequence, including the 5' and 3' untranslated sequences, the coding region, with or without a signal sequence, the secreted protein coding region, as well as fragments, epitopes, domains, and variants of the nucleic acid sequence. Moreover, as used herein, a "polypeptide" refers to a molecule having the translated amino acid sequence generated from the polynucleotide as broadly defined.

In the present invention, the full length sequence identified as SEQ ID NO:1 was often generated by overlapping sequences contained in one or more clones (contig analysis). A representative clone containing all or most of the sequence for SEQ ID NO:1 was deposited with the American Type Culture Collection ("ATCC"). As shown in Table I, each clone is identified by a cDNA Clone ID (Identifier) and the ATCC Deposit Number. The ATCC is located at 10801 University Boulevard, Manassas, Va. 20110-2209, USA. The ATCC deposit was made pursuant to the terms of the Budapest Treaty on the international recognition of the deposit of microorganisms for purposes of patent procedure. The deposited clone is inserted in the pSport1 plasmid (Life Technologies) using the NotI and SalI restriction endonuclease cleavage sites.

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A–B (SEQ ID NO:1), a nucleic acid molecule of the present invention encoding the LSI-01 polypeptide may be obtained using standard cloning and screening procedures, such as those for cloning cDNAs using mRNA as starting material. Illustrative of the invention, the nucleic acid molecule described in FIGS. 1A–B (SEQ ID NO:1) was discovered in a cDNA library derived from human liver and spleen.

The determined nucleotide sequence of the LSI-01 cDNA in FIGS. 1A–B (SEQ ID NO:1) contains an open reading frame encoding a protein of about 435 amino acid residues, with a deduced molecular weight of about 48.5 kDa. The amino acid sequence of the predicted LSI-01 polypeptide is shown in FIGS. 1A–B (SEQ ID NO:2). The LSI-01 protein shown in FIGS. 1A–B is about 46% identity and 52% similarity with the human $\alpha_1$-antichymotrypsin protein (Genbank Accession No: gi|112874; SEQ ID NO: 3); 48% identity and 56% similarity to the human Kallistatin (Genbank Accession No. gi|5453888; SEQ ID NO:4); 51% identity and 57% similarity to the human thyroxin-binding globulin (Genbank Accession No: gi|37142; SEQ ID NO:5); and 43% identity and 50% similarity to the human $\alpha_1$-antithrypsin (Genbank Accession No: gi|6137432; SEQ ID NO:6), as shown in FIG. 6.

A "polynucleotide" of the present invention also includes those polynucleotides capable of hybridizing, under stringent hybridization conditions, to sequences contained in SEQ ID NO:1, the complement thereof, or the cDNA within the clone deposited with the ATCC. "Stringent hybridization conditions" refers to an overnight incubation at 42 degree C. in a solution comprising 50% formamide, 5×SSC (750 mM NaCl, 75 mM trisodium citrate), 50 mM sodium phosphate (pH 7.6), 5× Denhardt's solution, 10% dextran sulfate, and 20 µg/ml denatured, sheared salmon sperm DNA, followed by washing the filters in 0.1×SSC at about 65 degree C.

Also contemplated are nucleic acid molecules that hybridize to the polynucleotides of the present invention at lower stringency hybridization conditions. Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37 degree C. in a solution comprising 6×SSPE (20×SSPE=3M NaCl; 0.2M NaH2PO4; 0.02M EDTA, pH 7.4), 0.5% SDS, 30% formamide, 100 ug/ml salmon sperm blocking DNA; followed by washes at 50 degree C. with 1×SSPE, 0.1% SDS. In addition, to achieve even lower stringency, washes performed following stringent hybridization can be done at higher salt concentrations (e.g. 5×SSC).

Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Of course, a polynucleotide which hybridizes only to polyA+ sequences (such as any 3' terminal polyA+ tract of a cDNA shown in the sequence listing), or to a complementary stretch of T (or U) residues, would not be included in the definition of "polynucleotide," since such a polynucleotide would hybridize to any nucleic acid molecule containing a poly (A) stretch or the complement thereof (e.g., practically any double-stranded cDNA clone generated using oligo dT as a primer).

The polynucleotide of the present invention can be composed of any polyribonucleotide or polydeoxribonucleotide, which may be unmodified RNA or DNA or modified RNA or DNA. For example, polynucleotides can be composed of single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions. In addition, the polynucleotide can be composed of triple-stranded regions comprising RNA or DNA or both RNA and DNA. A polynucleotide may also contain one or more modified bases or DNA or RNA backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms.

The polypeptide of the present invention can be composed of amino acids joined to each other by peptide bonds or modified peptide bonds, i.e., peptide isosteres, and may contain amino acids other than the 20 gene-encoded amino acids. The polypeptides may be modified by either natural processes, such as posttranslational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains and the amino or carboxyl termini. It will be appreciated that the same type of modification may be present in the same or varying degrees at several sites in a given polypeptide. Also, a given polypeptide may contain many types of modifications. Polypeptides may be branched, for example, as a result of ubiquitination, and they may be cyclic, with or without branching. Cyclic, branched, and branched cyclic polypeptides may result from posttranslation natural processes or may be made by synthetic methods. Modifications include acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI anchor formation, hydroxylation, iodination, methylation, myristoylation, oxidation, pegylation, proteolytic processing, phosphorylation, prenylation, racemization, selenoylation, sulfation, transfer-RNA mediated addition of amino acids to proteins such as arginylation, and ubiquitination. (See, for instance, PROTEINS—STRUCTURE AND MOLECULAR PROPERTIES, 2nd Ed., T. E. Creighton, W. H. Freeman and Company, New York (1993); POSTTRANSLATIONAL COVALENT MODIFICATION OF PROTEINS, B. C. Johnson, Ed., Academic Press, New York, pgs. 1–12 (1983); Seifter et al., Meth Enzymol 182:626–646 (1990); Rattan et al., Ann NY Acad Sci 663:48–62 (1992).)

"SEQ ID NO:1" refers to a polynucleotide sequence while "SEQ ID NO:2" refers to a polypeptide sequence, both sequences identified by an integer specified in Table I.

"A polypeptide having biological activity" refers to polypeptides exhibiting activity similar, but not necessarily identical to, an activity of a polypeptide of the present invention, including mature forms, as measured in a particular biological assay, with or without dose dependency. In the case where dose dependency does exist, it need not be identical to that of the polypeptide, but rather substantially similar to the dose-dependence in a given activity as compared to the polypeptide of the present invention (i.e., the candidate polypeptide will exhibit greater activity or not more than about 25-fold less and, preferably, not more than about tenfold less activity, and most preferably, not more than about three-fold less activity relative to the polypeptide of the present invention.) The term "organism" as referred to herein is meant to encompass any organism referenced herein, though preferably to eukaryotic organsisms, more preferably to mammals, and most preferably to humans.

The present invention encompasses the identification of proteins, nucleic acids, or other molecules, that bind to polypeptides and polynucleotides of the present invention (for example, in a receptor-ligand interaction). The polynucleotides of the present invention can also be used in interaction trap assays (such as, for example, that described by Ozenberger and Young (Mol Endocrinol., 9(10):1321–9, (1995); and Ann. N. Y. Acad. Sci., 7;766:279–81, (1995)).

The polynucleotide and polypeptides of the present invention are useful as probes for the identification and isolation of full-length cDNAs and/or genomic DNA which correspond to the polynucleotides of the present invention, as probes to hybridize and discover novel, related DNA sequences, as probes for positional cloning of this or a related sequence, as probe to "subtract-out" known sequences in the process of discovering other novel polynucleotides, as probes to quantify gene expression, and as probes for microarrays.

In addition, polynucleotides and polypeptides of the present invention may comprise one, two, three, four, five, six, seven, eight, or more membrane domains.

Also, in preferred embodiments the present invention provides methods for further refining the biological function of the polynucleotides and/or polypeptides of the present invention.

Specifically, the invention provides methods for using the polynucleotides and polypeptides of the invention to identify orthologs, homologs, paralogs, variants, and/or allelic variants of the invention. Also provided are methods of using the polynucleotides and polypeptides of the invention to identify the entire coding region of the invention, non-coding regions of the invention, regulatory sequences of the invention, and secreted, mature, pro-, prepro-, forms of the invention (as applicable).

In preferred embodiments, the invention provides methods for identifying the glycosylation sites inherent in the polynucleotides and polypeptides of the invention, and the subsequent alteration, deletion, and/or addition of said sites for a number of desirable characteristics which include, but are not limited to, augmentation of protein folding, inhibition of protein aggregation, regulation of intracellular trafficking to organelles, increasing resistance to proteolysis, modulation of protein antigenicity, and mediation of intercellular adhesion.

In further preferred embodiments, methods are provided for evolving the polynucleotides and polypeptides of the present invention using molecular evolution techniques in an effort to create and identify novel variants with desired structural, functional, and/or physical characteristics.

The present invention further provides for other experimental methods and procedures currently available to derive functional assignments. These procedures include but are not limited to spotting of clones on arrays, micro-array technology, PCR based methods (e.g., quantitative PCR), anti-sense methodology, gene knockout experiments, and other procedures that could use sequence information from clones to build a primer or a hybrid partner.

As used herein the terms "modulate or modulates" refer to an increase or decrease in the amount, quality or effect of a particular activity, DNA, RNA, or protein.

Polynucleotides and Polypeptides of the Invention

Features of the Polypeptide Encoded by Gene No:1

The polypeptide of this gene provided as SEQ ID NO:2 (FIGS. 1A–B), encoded by the polynucleotide sequence according to SEQ ID NO:1 (FIGS. 1A–B), and/or encoded by the polynucleotide contained within the deposited clone, LSI-01, has significant homology at the nucleotide and amino acid level to a number of serpins, which include, for example, the human $\alpha_1$-antichymotrypsin protein (Genbank Accession No: gi|112874; SEQ ID NO:3); the human Kallistatin (Genbank Accession No. gi|5453888; SEQ ID NO:4); the human thyroxin-binding globulin (Genbank Accession No: gi|37142; SEQ ID NO:5); and the human $\alpha_1$-antithrypsin (Genbank Accession No: gi|6137432; SEQ ID NO:6). An alignment of the LSI-01 polypeptide with these proteins is provided in FIGS. 2.

The LSI-01 polypeptide was determined to have 46% identity and 52% similarity with the human $\alpha_1$-antichymotrypsin protein (Genbank Accession No: gi|112874; SEQ ID NO:3); 48% identity and 56% similarity to the human Kallistatin (Genbank Accession No. gi|5453888; SEQ ID NO:4); 51% identity and 57% similarity to the human thyroxin-binding globulin (Genbank Accession No: gi|37142; SEQ ID NO:5); and 43% identity and 50% similarity to the human $\alpha_1$-antithrypsin (Genbank Accession No: gi|6137432; SEQ ID NO:6).

The human $\alpha_1$-antichymotrypsin protein (Genbank Accession No: gi|112874; SEQ ID NO:3) is a member of the serpin family that is known to inhibit neutrophil cathepsin g and mast cell chymase, both of which can convert angiotensin i to the active angiotensin II. The human $\alpha_1$-antichymotrypsin protein is an extracellular protein synthesized in the liver having plasma tissue specificity. Like the related alpha-1-antitrypsin, its concentration increases in the acute phase of inflammation or infection. Deciencies in the $\alpha_1$-antichymotrypsin protein can be a cause of chronic obstructive pulmonary disease (COPD) or of occlusive cerebrovascular disease. Morever, some reports have suggested that the $\alpha_1$-antichymotrypsin protein also plays additional roles outside of its intrinsic serpin activity as it has been shown to also have DNA binding activity suggesting it may be a transcriptional modulator. Additional information relative to this protein may be found in reference to the following publications: Biochemistry 22 (22), 5055–5061 (1983); J. Biol. Chem. 265 (2), 1199–1207 (1990); Biochim. Biophys. Acta 997 (1–2), 90–95 (1989); J. Biol. Chem. 258 (21), 12749–12752 (1983); J. Mol. Biol. 218 (3), 595–606 (1991); Nat. Struct. Biol. 3 (10), 888–893 (1996); Biochemistry 37 (10), 3297–3304 (1998); Genomics 17 (3), 740–743 (1993); FEBS Lett. 304 (1), 66–68 (1992; which are hereby incorporated herein by reference in their entirety.

The human Kallistatin (Genbank Accession No. gi|5453888; SEQ ID NO:4) is a member of the serpin family which binds to tissue kallikrein and inhibits kallikrein's kininogenase and amidolytic activities. Kallistatin has a unique reactive site P1–P1' of Phe-Ser and is expressed predominately in human liver. Additional information relative to this protein may be found in reference to the following publications: J Biol Chem 1993 November 15;268 (32):24498–505; and Genomics 1994 September 15;23(2): 370–8; which are hereby incorporated herein by reference.

The human $\alpha_1$-antithrypsin (Genbank Accession No: gi|6137432; SEQ ID NO:6) is also a member of the serpin superfamily, and is often referred to as an archetypal member of the serpin superfamily. Members of the family show structural homology based on a dominant A beta-sheet and a mobile reactive centre loop. The structure of wild-type alpha 1-antitrypsin reveals a hydrophobic pocket between s2A and helices D and E that is filled on reactive loop insertion and the formation of biologically relevant loop-sheet polymers. This pocket may provide a target for rational drug design to prevent the formation of polymers and the associated plasma deficiency, liver cirrhosis and emphysema. Additional information relative to this protein may be found in reference to the following publication: J Mol Biol 1998 January 23;275(3):419–25; which is hereby incorporated herein by reference.

The LSI-01 polypeptide was determined to comprise a signal sequence from about amino acid 1 to about amino acid 38 of SEQ ID NO:2 (FIGS. 1A–B) according to the SPScan computer algorithm (Genetics Computer Group suite of programs). Based upon the predicted signal peptide cleavage site, the mature LSI-01 polypeptide is expected to be from about amino acid 39 to about amino acid 435 of SEQ ID NO:2 (FIGS. 1A–B). As this determination was based upon the prediction from a computer algorithm, the exact physiological cleavage site may vary, as discussed more particularly herein. In this context, the term "about" should be construed to mean 1, 2, 3, 4, 5, 6, 7, 8, 9, 10, 11, 12, 13, 14, 15, 16, 17, 18, 19, or 20 more amino acids in either the N- or C-terminal direction of the above referenced polypeptide. Polynucleotides encoding these polypeptides are also provided.

In addition to the mature polypeptide above, the polynucleotides encoding the mature polypeptide are also encompassed by the present invention. Specifically, from about nucleotide position 182 to about nucleotide position 1372 of SEQ ID NO:1 (FIGS. 1A–B).

In confirmation of the strong homology to known serpins, the LSI-01 polypeptide was determined to have a conserved serine protease inhibitor domain. As discussed more particularly herein, serpins a group of structurally related, high molecular weight (400 to 500 amino acids), extracellular, irreversible serine protease inhibitors with a well defined structural-functional characteristic: a reactive region that acts as a 'bait' for an appropriate serine protease. This region is found in the C-terminal part of these proteins. Non limiting examples of proteins which are known to belong to the serpin family are the following: Alpha-1 protease inhibitor (alpha-1-antitrypsin, contrapsin); Alpha-1-antichymotrypsin; Antithrombin III; Alpha-2-antiplasmin; Heparin cofactor II; Complement C1 inhibitor; Plasminogen activator inhibitors 1 (PAI-1) and 2 (PAI-2); Glia derived nexin (GDN) (Protease nexin I); Protein C inhibitor; Rat hepatocytes SPI-1, SPI-2 and SPI-3 inhibitors; Human squamous cell carcinoma antigen (SCCA) which may act in the modulation of the host immune response against tumor cells; Leukocyte elastase inhibitor which, in contrast to other serpins, is an intracellular protein; Neuroserpin, a neuronal inhibitor of plasminogen activators; and plasmin, Cowpox virus crmA, an inhibitor of the thiol protease interleukin-1B converting enzyme (ICE).

The consensus pattern for members of the serpin family is as follows: [LIVMFY]-x-[LIVMFYAC]-[DNQ]-[RKHQS]-[PST]-F-[LIVMFY]-[LIVMFYC]-x-[LIVMFAH], where 'x' represents any intervening amino acid. The consensus is centered on a well conserved Pro-Phe sequence which is found ten to fifteen residues on the C-terminal side of the reactive bond. In position 6 of the pattern, Pro is found in most serpins. However, the LSI-01 polypeptide of the present invention is an exception.

More information relating to serpins can be found elsewhere herein, or in reference to the following publications: Carrell R., Travis J., Trends Biochem. Sci. 10:20–24 (1985); Carrell R., Pemberton P. A., Boswell D. R., Cold Spring Harbor Symp. Quant. Biol. 52:527–535 (1987); Huber R., Carrell R. W., Biochemistry 28:8951–8966 (1989); Remold-O'Donneel E., FEBS Lett. 315:105–108 (1993); Osterwalder T., Contartese J., Stoeckli E. T., Kuhn T. B., Sonderegger P., EMBO J. 15:2944–2953 (1996); Komiyama T., Ray C. A., Pickup D. J., Howard A. D., Thornberry N. A., Peterson E. P., Salvesen G., J. Biol. Chem . . . 269: 19331–19337 (1994); Clarke E., Sandwal B. D., Biochim. Biophys. Acta 1129:246–248 (1992); Zou Z., Anisowicz A., Neveu M., Rafidi K., Sheng S., Sager R., Hendrix M. J., Seftor E., Thor A., Science 263:526–529 (1994); Steele F. R., Chader G. J., Johnson L. V., Tombran-Tink J., Proc. Natl. Acad. Sci. U.S.A. 90:1526–1530 (1993); and Holland L. J., Suksang C., Wall A. A., Roberts L. R., Moser D. R., Bhattacharya A., J. Biol. Chem . . . 267:7053–7059 (1992).

In preferred embodiments, the following serpin domain polypeptides are encompassed by the present invention: VSFNRTFLMMI (SEQ ID NO:21), GTEATAATTTK-FIVRS (SEQ ID NO:22), and/or PSYFTVSFNRTFLMMIT-NKAT (SEQ ID NO:23). Polynucleotides encoding these polypeptides are also provided.

In preferred embodiments, the LSI-01 polypeptide of the present invention is directed to a polypeptide having structural similarity to serpins. More preferred, is the LSI-o1 polypeptide comprising a bait region with the amino acid, arginine (Arg), located in the P1 site. Based upon this structure, the LSI-01 polypeptide is expected to recognize proteases with Arg/lys specificity ("trypsin-like" serine and similarly specific cysteine proteases). As mentioned elsewhere herein, serpins inhibit multiple proteases with varying reactivity. The serpin of the present invention may inhibit several proteases both in vitro and in vivo.

Based upon the strong homology to members of the serine protease inhibitor (serpin) proteins, the LSI-01 polypeptide is expected to share at least some biological activity with serpins, and preferable with the arg/lys specific serpins, preferably the LSI-01 polypeptide shares at least some biological activity with the serpins disclosed herein, or otherwise known in the art.

Expression profiling designed to measure the steady state mRNA levels encoding the LSI-01 polypeptide showed predominately high expression levels in lymph node tissue, and to a lesser extent, in thymus, small intestine, and spleen tissue (See FIG. 5).

Moreover, the LSI-01 polynucleotides have been mapped to chromosome 14q32.1 (See Example 54). This region has been shown to contain genes encoding 6 additional serpins (A1–A6) and a protease Z inhibitor, and is commonly involved in several chromosomal aberrations including rearrangements, inversion, and/or translocations. Such aberrations within this region of chromosome 14 have been associated with the incidence of T-cell malignancy (T-cell neoplasms, leukemias; Saitou et al,. Identification of the TCL6 genes within the breakpoint cluster region on chromosome 14q32 in T-cell leukemia. Oncogene 19: 2796–2802, 2000.), or B-cell leukemias (i.e. one of the most frequent hematologic malignancies, follicular lymphoma is associated with a reciprocal translocation t(14;18)(q32;q21) and can result in deregulated expression of a chromosome 18 gene, Bcl2, which interferes with normal apoptosis of B lymphocytes; Ngan, B.-Y. et al. Expression in non-Hodgkin's lymphoma of the BCL-2 protein associated with the t(14; 18) chromosomal translocation. New Eng. J. Med. 318:1638–1644, 1988). The oncogene activated by these different rearrangements is not always the same, and is dependent upon where the chromosomal breakpoints occur. Several candidate oncogenes responsible for malignant transformation have already been identified in chromosome 14q32 (i.e. TCL1A (T-cell leukemia/lymphoma 1a), TCL1b, TCL6, TRIP11(Thyroid Hormone Receptor Interactor 11)).

Based on its expression profile and genetic chromosome map, the LS-1 polynucleotides could be a novel specific biomarker that would be useful in pinpointing subgroups of patients with chronic lymphocytic leukemias (with a distinct prognostic). Moreover, the LS-1 polynucleotides could also be useful as a diagnostic for identifying patients with chronic lymphocytic leukemias.

The LSI-01 polynucleotides and polypeptides of the present invention, including agonists and/or fragments thereof, have uses that include modulating serine protease activity in various cells, tissues, and organisms, and particularly in mammalian lymph node, thymus, small intestine, and spleen tissue, preferably human tissue. LSI-01 polynucleotides and polypeptides of the present invention, including agonists and/or fragments thereof, may be useful in diagnosing, treating, prognosing, and/or preventing immune, gastrointestinal, metabolic, and/or proliferative diseases or disorders.

In preferred embodiments, LSI-01 polynucleotides and polypeptides including agonists and fragments thereof, have uses which include treating, diagnosing, prognosing, and/or preventing the following diseases or disorders: emphysema, liver cirrhosis, hepatocellular carcinoma, thrombosis, embolisms, thrombin-mediated vascular injury, microcirculation in sever sepsis, arterial thrombosis, myocardial infarction, unstable angina, stroke, venous thrombosis, and pulmonary embolism.

The strong homology to human serine protease inhibitors (serpins), combined with the predominate localized expression in lymph node tissue suggests the LSI-01 polynucleotides and polypeptides may be useful in treating, diagnosing, prognosing, and/or preventing immune diseases and/or disorders. Representative uses are described in the "Immune Activity" and "Infectious Disease" sections below, and elsewhere herein. Briefly, the strong expression in immune tissue indicates a role in regulating the proliferation; survival; differentiation; and/or activation of hematopoietic cell lineages, including blood stem cells. Such roles for serpins have been described. For example, the serpin described by Mueller et al., Eur-J-Immunol. 27(12): 3130–4 (1997) is believed to be involved to function as a megakaryocyte maturation factor in the presence of interleukin (IL)-3 and IL-11.

The LSI-01 polypeptide may also be useful as a preventative agent for immunological disorders including arthritis, asthma, immunodeficiency diseases such as AIDS, leukemia, rheumatoid arthritis, granulomatous disease, inflammatory bowel disease, sepsis, acne, neutropenia, neutrophilia, psoriasis, hypersensitivities, such as T-cell mediated cytotoxicity; immune reactions to transplanted organs and tissues, such as host-versus-graft and graft-versus-host diseases, or autoimmunity disorders, such as autoimmune infertility, lense tissue injury, demyelination, systemic lupus erythematosis, drug induced hemolytic anemia, rheumatoid arthritis, Sjogren's disease, and scleroderma. Moreover, the protein may represent a secreted factor that influences the differentiation or behavior of other blood cells, or that recruits hematopoietic cells to sites of injury. Thus, this gene product may be useful in the expansion of stem cells and committed progenitors of various blood lineages, and in the differentiation and/or proliferation of various cell types.

Moreover, the protein would be useful in the detection, treatment, and/or prevention of a variety of vascular disorders and conditions, which include, but are not limited to miscrovascular disease, vascular leak syndrome, aneurysm, stroke, embolism, thrombosis, coronary artery disease, arteriosclerosis, and/or atherosclerosis. Furthermore, the protein may also be used to determine biological activity, raise antibodies, as tissue markers, to isolate cognate ligands or receptors, to identify agents that modulate their interactions, in addition to its use as a nutritional supplement. Protein, as well as, antibodies directed against the protein may show utility as a tumor marker and/or immunotherapy targets for the above listed tissues.

In addition, the strong homology to human serpins, combined with the expression in small intestine tissue emphasizes the potential utility for LSI-01 polynucleotides and polypeptides in treating, diagnosing, prognosing, and/or preventing gastrointestinal disorders, such as, for example, ulcers, cancers, etc., in addition to those disorders related to aberrant function of immune cells or tissue within the small intestine (e.g., Peyer's patches, etc.).

Moreover, the LSI-01 polynucleotides and polypeptides may be useful in treating, diagnosing, prognosing, and/or preventing gastrointesinal diseases and/or disorders, which include, but are not limited to, ulcers, irritable bowel syndrome, inflammatory bowel disease, diarrhea, traveler's diarrhea, drug-related diarrhea polyps, absorption disorders, constipation, diverticulitis, vascular disease of the intestines, intestinal obstruction, intestinal infections, ulcerative colitis, Shigellosis, cholera, Crohn's Disease, amebiasis, enteric fever, Whipple's Disease, peritonitis, intrabdominal abcesses, hereditary hemochromatosis, gastroenteritis, viral gastroenteritis, food poisoning, mesenteric ischemia, mesenteric infarction, in addition to, metabolic diseases and/or disorders.

Moreover, polynucleotides and polypeptides, including fragments and/or antagonists thereof, have uses which include, directly or indirectly, treating, preventing, diagnosing, and/or prognosing susceptibility to the following, non-limiting, gastrointestinal infections: *Salmonella* infection, *E.coli* infection, *E.coli* 0157:H7 infection, Shiga Toxin-producing *E.coli* infection, *Campylobacter* infection (e.g., *Campylobacter fetus, Campylobacter upsaliensis, Campylobacter hyointestinalis, Campylobacter lari, Campylobacter jejuni, Campylobacter concisus, Campylobacter mucosalis, Campylobacter sputorum, Campylobacter rectus, Campylobacter curvus, Campylobacter sputorum*, etc.), *Heliobacter* infection (e.g., *Heliobacter cinaedi, Heliobacter fennelliae*, etc.)*Yersinia enterocolitica* infection, *Vibrio* sp. Infection (e.g., *Vibrio mimicus, Vibrio parahaemolyticus, Vibrio fluvialis, Vibrio fumissii, Vibrio hollisae, Vibrio vulnificus, Vibrio alginolyticus, Vibrio metschnikovii, Vibrio damsela, Vibrio cincinnatiensis*, etc.) *Aeromonas* infection (e.g., *Aeromonas hydrophila, Aeromo-* nas sobira, Aeromonas caviae, etc.), *Plesiomonas shigelliodes* infection, *Giardia* infection (e.g., *Giardia lamblia*, etc.), *Cryptosporidium* infection, *Listeria* infection, *Entamoeba histolytica* infection, Rotavirus infection, Norwalk virus infection, *Clostridium difficile* infection, *Clostriudium perfringens* infection, *Staphylococcus* infection, *Bacillus* infection, in addition to any other gastrointestinal disease and/or disorder implicated by the causative agents listed above or elsewhere herein.

In addition, antagonists of the LSI-01 polynucleotides and polypeptides may have uses that include diagnosing, treating, prognosing, and/or preventing diseases or disorders related to hyper serine protease activity, which may include immune and/or proliferative diseases or disorders, particularly thrombosis, embolism, and other blood disorders. Therapeutic and/or pharmaceutical compositions comprising the LSI-01 polypeptides may be formulated to comprise heparin.

Moreover, LSI-01 polynucleotides and polypeptides, including fragments and agonists thereof, may have uses which include treating, diagnosing, prognosing, and/or preventing hyperproliferative disorders, particularly of the immune and gastrointestinal systems. Such disorders may include, for example, cancers, and metastasis.

As the polypeptide of the present invention may be involved in the regulation of cytokine production, antigen presentation, T-cell maturation, or other processes, either directly or indirectly, suggests the LSI-01 polypeptide may be useful for the treatment of cancer (e.g. by boosting immune responses). A number of studies have shown a positive correlation between increased metastasis invasion to neighboring and systemic cells and tissues, to increased proteolytic activity of serine proteases (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991). The principal serine proteases known to be associated with tumor invasion mediate the plasminogen activation cascade. In this pathway, plasminogen is converted by plasminogen activators to plasmin, which is a wide-spectrum serine protease that degrades many components of the ECM directly, or indirectly via the activation of metalloproteases. The activity of the plasminogen activators is negatively regulated by plasminogen activator inhibitory proteins: PAI-1, PAI-2, and protease nexins (Chen, Current Opin. Cell Biol. 4:802, 1992).

The increased expression levels of uPA (urokinase plasminogen activator), the physiological substrate of alpha-anti-trypsin, has also been positively associated with increased incidence of cancers (Testa et al., Cancer Metastasis Rev. 9:353, 1990; Dano et al., Adv. Cancer Res. 44:139, 1985; Foekens et al., Cancer Res. 52:6101, 1992; Ossowsky, Cancer Res. 52:6754, 1992; Sumiyoshi, Int. J. Cancer 50:345, 1992; Duffy et al., Cancer Res. 50:6827, 1992; and Meissauer et al., Exp. Cell Res. 192:453, 1991; Heidtmann et al., Cancer Res. 49:6960, 1989; Sumiyoshi et al., Thromb Res. 63:59, 1991; Reilly et al., Int. J. Cancer 50:208, 1992, Cajot et al., Proc. Natl. Acad. Sci. USA 87:6939, 1990; Foucre et al., Br. J. Cancer 64:926, 1991; Shirasuna et al., Cancer Res. 53:147, 1993; and Janicke et al., Br. Can. Res. & Treat. 24:195, 1993).

The positive correlation between increased uPA expression on cancer incidence may have particular relevance to the LSI-01 polypeptide as the homology model of the present invention was based upon the structure of alpha-anti-trypsin, and may further suggest a use of the LSI-01 polypeptides, including fragments or antagonists thereof, in ameliorating or preventing metastasis, particularly in immune cells and tissues.

Moreover, based upon the chromosome mapping of LSI-01 to chromosome 14, the LSI-01 polynucleotides and polypeptides, including fragments and antagonists thereof, may have uses which include detecting, diagnosing, treating, ameliorating, and/or preventing leukemias, which include, are not limited to, T-cell malignancy (T-cell neoplasms, leukemias; Saitou et al,. Identification of the TCL6 genes within the breakpoint cluster region on chromosome 14q32 in T-cell leukemia. Oncogene 19: 2796–2802, 2000.), or B-cell leukemias (i.e. one of the most frequent hematologic malignancies, follicular lymphoma is associated with a reciprocal translocation t(14;18)(q32;q21) and can result in deregulated expression of a chromosome 18 gene, Bcl2, which interferes with normal apoptosis of B lymphocytes; Ngan, B.-Y. et al. Expression in non-Hodgkin's lymphoma of the BCL-2 protein associated with the t(14;18) chromosomal translocation. New Eng. J. Med. 318:1638–1644, 1988).

Despite the relatively specific expression in lymph node and other immune tissues, the LSI-01 polynucleotides and polypeptides, including fragments and antagonists thereof, may have uses which include detecting, diagnosing, treating, ameliorating, and/or preventing diseases and disorders of the neural system, particularly Alzheimer's disease, either directly or indirectly, in addition to other neural disorders known in the art or provided in the "Neurological Diseases" section herein. In support of this argument, Kalaria, R. N., et al. (Neurobiol-Aging,17(5): 687–93 (1996)) have reported that numerous molecular and cellular elements of the immune system are involved in the pathogenesis of Alzheimer's disease which include classical acute phase proteins of the pentraxin and serine protease inhibitor (serpin) families, as well as, a host of complement proteins and some coagulation factors.

Moreover, the LSI-01 polynucleotides and polypeptides, including fragments and /or antagonsists thereof, may have uses which include, directly or indirectly, diagnosing, prognosing, treating, preventing, and/or ameliorating cardiovascular, inflammatory diseases, particularly inflammatory diseases where proteases are known to be involved, certain cancers, diseases that result from uncontrolled complement fixation, diseases that result from uncontrolled blood coagulation, uncontrolled fibrinolysis, and uncontrolled bleeding.

The LSI-01 polynucleotides and polypeptides, including fragments and /or antagonsists thereof, may have uses which include identification of modulators of LSI-01 serpin function including antibodies (for detection or neutralization), naturally-occurring modulators and small molecule modulators. Antibodies to domains of the LSI-01 protein could be used as diagnostic agents of inflammatory conditions in patients, are useful in monitoring the activation and presence of cognate proteases, and can be used as a biomarker for the protease involvement in disease states and in the evaluation of inhibitors of the cognate protease in vivo.

Molecular genetic manipulation of the structure of the loop and of other functional domains in the serpin superfamily enables the production of serpins with tailor-made activities. Thus, the LSI-01 polypeptides, and fragments thereof, as well as any homologous product resulting from genetic manipulation of the structure, are useful for NMR-based design of modulators of LSI-01 biological activity, and serpins, in general.

LSI-01 polypeptides and polynucleotides have additional uses which include diagnosing diseases related to the over and/or under expression of LSI-01 by identifying mutations in the LSI-01 gene by using LSI-01 sequences as probes or by determining LSI-01 protein or mRNA expression levels. LSI-01 polypeptides may be useful for screening compounds that affect the activity of the protein. LSI-01 peptides can also be used for the generation of specific antibodies and as bait in yeast two hybrid screens to find proteins the specifically interact with LSI-01 (described elsewhere herein). Based on the expression pattern of this novel sequence, diseases that can be treated with agonists and/or antagonists for LSI-01 include various forms of generalized epilepsy.

Although it is believed the encoded polypeptide may share at least some biological activities with human serpin proteins (particularly serpins with Arg/Lys specificity), a number of methods of determining the exact biological function of this clone are either known in the art or are described elsewhere herein. Briefly, the function of this clone may be determined by applying microarray methodology. Nucleic acids corresponding to the LSI-01 polynucleotides, in addition to, other clones of the present invention, may be arrayed on microchips for expression profiling. Depending on which polynucleotide probe is used to hybridize to the slides, a change in expression of a specific gene may provide additional insight into the function of this gene based upon the conditions being studied. For example, an observed increase or decrease in expression levels when the polynucleotide probe used comes from diseased immune tissue, as compared to, normal tissue might indicate a function in modulating immune function, for example. In the case of LSI-01, lymph node, thymus, small intestine, and/or spleen tissue should be used to extract RNA to prepare the probe.

In addition, the function of the protein may be assessed by applying quantitative PCR methodology, for example. Real time quantitative PCR would provide the capability of following the expression of the LSI-01 gene throughout development, for example. Quantitative PCR methodology requires only a nominal amount of tissue from each developmentally important step is needed to perform such experiments. Therefore, the application of quantitative PCR methodology to refining the biological function of this polypeptide is encompassed by the present invention. In the case of LSI-01, a disease correlation related to LSI-01 may be made by comparing the mRNA expression level of LSI-01 in normal tissue, as compared to diseased tissue (particularly diseased tissue isolated from the following: lymph node, thymus, small intestine, and spleen tissue). Significantly higher or lower levels of LSI-01 expression in the diseased tissue may suggest LSI-01 plays a role in disease progression, and antagonists against LSI-01 polypeptides would be useful therapeutically in treating, preventing, and/or ameliorating the disease. Alternatively, significantly higher or lower levels of LSI-01 expression in the diseased tissue may suggest LSI-01 plays a defensive role against disease progression, and agonists of LSI-01 polypeptides may be useful therapeutically in treating, preventing, and/or ameliorating the disease. Also encompassed by the present invention are quantitative PCR probes corresponding to the polynucleotide sequence provided as SEQ ID NO:1 (FIGS. 1A–B).

The function of the protein may also be assessed through complementation assays in yeast. For example, in the case of the LSI-01, transforming yeast deficient in serpin activity, particularly Arg/Lys specificity serpin activity, and assessing their ability to grow would provide convincing evidence the LSI-01 polypeptide has serine protease inhibitor activity. Additional assay conditions and methods that may be used in assessing the function of the polynucleotides and polypeptides of the present invention are known in the art, some of which are disclosed elsewhere herein.

Alternatively, the biological function of the encoded polypeptide may be determined by disrupting a homologue of this polypeptide in Mice and/or rats and observing the resulting phenotype. Such knock-out experiments are known in the art, some of which are disclosed elsewhere herein.

Moreover, the biological function of this polypeptide may be determined by the application of antisense and/or sense methodology and the resulting generation of transgenic mice and/or rats. Expressing a particular gene in either sense or antisense orientation in a transgenic mouse or rat could lead to respectively higher or lower expression levels of that particular gene. Altering the endogenous expression levels of a gene can lead to the observation of a particular phenotype that can then be used to derive indications on the function of the gene. The gene can be either over-expressed or under expressed in every cell of the organism at all times using a strong ubiquitous promoter, or it could be expressed in one or more discrete parts of the organism using a well characterized tissue-specific promoter (e.g., a lymph node, thymus, small intestine, or spleen specific promoter), or it can be expressed at a specified time of development using an inducible and/or a developmentally regulated promoter.

In the case of LSI-01 transgenic mice or rats, if no phenotype is apparent in normal growth conditions, observing the organism under diseased conditions (immune or gastrointestinal disorders, cancers, etc.) may lead to understanding the function of the gene. Therefore, the application of antisense and/or sense methodology to the creation of transgenic mice or rats to refine the biological function of the polypeptide is encompassed by the present invention.

In preferred embodiments, the following N-terminal deletion mutants are encompassed by the present invention: M1-S435, Q2-S435, G3-S435, Q4-S435, G5-S435, R6-S435, R7-S435, R8-S435, G9-S435, T10-S435, C11-S435, K12-S435, D13-S435, I14-S435, F15-S435, C16-S435, S17-S435, K18-S435, M19-S435, A20-S435, S21-S435, Y22-S435, L23-S435, Y24-S435, G25-S435, V26-S435, L27-S435, F28-S435, A29-S435, V30-S435, G31-S435, L32-S435, C33-S435, A34-S435, P35-S435, I36-S435, Y37-S435, C38-S435, V39-S435, S40-S435, P41-S435, A42-S435, N43-S435, A44-S435, P45-S435, S46-S435, A47-S435, Y48-S435, P49-S435, R50-S435, P51-S435, S52-S435, S53-S435, T54-S435, K55-S435, S56-S435, T57-S435, P58-S435, A59-S435, S60-S435, Q61-S435, V62-S435, Y63-S435, S64-S435, L65-S435, N66-S435, T67-S435, D68-S435, F69-S435, A70-S435, F71-S435, R72-S435, L73-S435, Y74-S435, R75-S435, R76-S435, L77-S435, V78-S435, L79-S435, E80-S435, T81-S435, P82-S435, S83-S435, Q84-S435, N85-S435, I86-S435, F87-S435, F88-S435, S89-S435, P90-S435, V91-S435, S92-S435, V93-S435, S94-S435, T95-S435, S96-S435, L97-S435, A98-S435, M99-S435, L100-S435, S101-S435, L102-S435, G103-S435, A104-S435, H105-S435, S106-S435, V107-S435, T108-S435, K109-S435, T110-S435, Q111-S435, I112-S435, L113-S435, Q114-S435, G115-S435, L116-S435, G117-S435, F118-S435, N119-S435, L120-S435, T121-S435, H122-S435, T123-S435, P124-S435, E125-S435, S126-S435, A127-S435, I128-S435, H129-S435, Q130-S435, G131-S435, F132-S435, Q133-S435, H134-S435, L135-S435, V136-S435, H137-S435, S138-S435, L139-S435, T140-S435, V141-S435, P142-S435, S143-S435, K144-S435, D145-S435, L146-S435, T147-S435, L148-S435, K149-S435, M150-S435, G151-S435, S152-S435, A153-S435, L154-S435, F155-S435, V156-S435, K157-S435, K158-S435, E159-S435, L160-S435, Q161-S435, L162-S435, Q163-S435, A164-S435, N165-S435, F166-S435, L167-S435, G168-S435, N169-S435, V170-S435, K171-S435, R172-S435, L173-S435, Y174-S435, E175-S435, A176-S435, E177-S435, V178-S435, F179-S435, S180-S435, T181-S435, D182-S435, F183-S435, S184-S435, N185-S435, P186-S435, S187-S435, I188-S435, A189-S435, Q190-S435, A191-S435, R192-S435, I193-S435, N194-S435, S195-S435, H196-S435, V197-S435, K198-S435, K199-S435, K200-S435, T201-S435, Q202-S435, G203-S435, K204-S435, V205-S435, V206-S435, D207-S435, I208-S435, I209-S435, Q210-S435, G211-S435, L212-S435, D213-S435, L214-S435, L215-S435, T216-S435, A217-S435, M218-S435, V219-S435, L220-S435, V221-S435, N222-S435, H223-S435, I224-S435, F225-S435, F226-S435, K227-S435, A228-S435, K229-S435, W230-S435, E231-S435, K232-S435, P233-S435, F234-S435, H235-S435, L236-S435, E237-S435, Y238-S435, T239-S435, R240-S435, K241-S435, N242-S435, F243-S435, P244-S435, F245-S435, L246-S435, V247-S435, G248-S435, E249-S435, Q250-S435, V251-S435, T252-S435, V253-S435, Q254-S435, V255-S435, P256-S435, M257-S435, M258-S435, H259-S435, Q260-S435, K261-S435, E262-S435, Q263-S435, F264-S435, A265-S435, F266-S435, G267-S435, V268-S435, D269-S435, T270-S435, E271-S435, L272-S435, N273-S435, C274-S435, F275-S435, V276-S435, L277-S435, Q278-S435, M279-S435, D280-S435, Y281-S435, K282-S435, G283-S435, D284-S435, A285-S435, V286-S435, A287-S435, F288-S435, F289-S435, V290-S435, L291-S435, P292-S435, S293-S435, K294-S435, G295-S435, K296-S435, M297-S435, R298-S435, Q299-S435, L300-S435, E301-S435, Q302-S435, A303-S435, L304-S435, S305-S435, A306-S435, R307-S435, T308-S435, L309-S435, I310-S435, K311-S435, W312-S435, S313-S435, H314-S435, S315-S435, L316-S435, Q317-S435, K318-S435, R319-S435, W320-S435, I321-S435, E322-S435, V323-S435, F324-S435, I325-S435, P326-S435, R327-S435, F328-S435, S329-S435, I330-S435, S331-S435, A332-S435, S333-S435, Y334-S435, N335-S435, L336-S435, E337-S435, T338-S435, I339-S435, L340-S435, P341-S435, K342-S435, M343-S435, G344-S435, I345-S435, Q346-S435, N347-S435, A348-S435, F349-S435, D350-S435, K351-S435, N352-S435, A353-S435, D354-S435, F355-S435, S356-S435, G357-S435, I358-S435, A359-S435, K360-S435, R361-S435, D362-S435, S363-S435, L364-S435, Q365-S435, V366-S435, S367-S435, K368-S435, A369-S435, T370-S435, H371-S435, K372-S435, A373-S435, V374-S435, L375-S435, D376-S435, V377-S435, S378-S435, E379-S435, E380-S435, G381-S435, T382-S435, E383-S435, A384-S435, T385-S435, A386-S435, A387-S435, T388-S435, T389-S435, T390-S435, K391-S435, F392-S435, I393-S435, V394-S435, R395-S435, S396-S435, K397-S435, D398-S435, G399-S435, P400-S435, S401-S435, Y402-S435, F403-S435, T404-S435, V405-S435, S406-S435, F407-S435, N408-S435, R409-S435, T410-S435, F411-S435, L412-S435, M413-S435, M414-S435, I415-S435, T416-S435, N417-S435, K418-S435, A419-S435, T420-S435, D421-S435, G422-S435, I423-S435, L424-S435, F425-S435, L426-S435, G427-S435, K428-S435, and/or V429-S435 of SEQ ID NO:2. Polynucleotide sequences encoding these polypeptides are also provided. The present invention also encompasses the use of these LSI-01 N-terminal deletion polypeptides as immunogenic and/or antigenic epitopes as described elsewhere herein.

In preferred embodiments, the following C-terminal deletion mutants are encompassed by the present invention: M1-S435, M1-K434, M1-T433, M1-P432, M1-N431, M1-E430, M1-V429, M1-K428, M1-G427, M1-L426, M1-F425, M1-L424, M1-I423, M1-G422, M1-D421, M1-T420, M1-A419, M1-K418, M1-N417, M1-T416, M1-I415, M1-M414, M1-M413, M1-L412, M1-F411, M1-T410, M1-R409, M1-N408, M1-F407, M1-S406, M1-V405, M1-T404, M1-F403, M1-Y402, M1-S401, M1-P400, M1-G399, M1-D398, M1-K397, M1-S396, M1-R395, M1-V394, M1-I393, M1-F392, M1-K391, M1-T390, M1-T389, M1-T388, M1-A387, M1-A386, M1-T385, M1-A384, M1-E383, M1-T382, M1-G381, M1-E380, M1-E379, M1-S378, M1-V377, M1-D376, M1-L375, M1-V374, M1-A373, M1-K372, M1-H371, M1-T370, M1-A369, M1-K368, M1-S367, M1-V366, M1-Q365, M1-L364, M1-S363, M1-D362, M1-R361, M1-K360, M1-A359, M1-I358, M1-G357, M1-S356, M1-F355, M1-D354, M1-A353, M1-N352, M1-K351, M1-D350, M1-F349, M1-A348, M1-N347, M1-Q346, M1-I345, M1-G344, M1-M343, M1-K342, M1-P341, M1-L340, M1-I339, M1-T338, M1-E337, M1-L336, M1-N335, M1-Y334, M1-S333, M1-A332, M1-S331, M1-I330, M1-S329, M1-F328, M1-R327, M1-P326, M1-I325, M1-F324, M1-V323, M1-E322, M1-I321, M1-W320, M1-R319, M1-K318, M1-Q317, M1-L316, M1-S315, M1-H314, M1-S313, M1-W312, M1-K311, M1-I310, M1-L309, M1-T308, M1-R307, M1-A306, M1-S305, M1-L304, M1-A303, M1-Q302, M1-E301, M1-L300, M1-Q299, M1-R298, M1-M297, M1-K296, M1-G295, M1-K294, M1-S293, M1-P292, M1-L291, M1-V290, M1-F289, M1-F288, M1-A287, M1-V286, M1-A285, M1-D284, M1-G283, M1-K282, M1-Y281, M1-D280, M1-M279, M1-Q278, M1-L277, M1-V276, M1-F275, M1-C274, M1-N273, M1-L272, M1-E271, M1-T270, M1-D269, M1-V268, M1-G267, M1-F266, M1-A265, M1-F264, M1-Q263, M1-E262, M1-K261, M1-Q260, M1-H259, M1-M258, M1-M257, M1-P256, M1-V255, M1-Q254, M1-V253, M1-T252, M1-V251, M1-Q250, M1-E249, M1-G248, M1-V247, M1-L246, M1-F245, M1-P244, M1-F243, M1-N242, M1-K241, M1-R240, M1-T239, M1-Y238, M1-E237, M1-L236, M1-H235, M1-F234, M1-P233, M1-K232, M1-E231, M1-W230, M1-K229, M1-A228, M1-K227, M1-F226, M1-F225, M1-I224, M1-H223, M1-N222, M1-V221, M1-L220, M1-V219, M1-M218, M1-A217, M1-T216, M1-L215, M1-L214, M1-D213, M1-L212, M1-G211, M1-Q210, M1-I209, M1-I208, M1-D207, M1-V206, M1-V205, M1-K204, M1-G203, M1-Q202, M1-T201, M1-K200, M1-K199, M1-K198, M1-V197, M1-H196, M1-S195, M1-N194, M1-I193, M1-R192, M1-A191, M1-Q190, M1-A189, M1-I188, M1-S187, M1-P186, M1-N185, M1-S184, M1-F183, M1-D182, M1-T181, M1-S180, M1-F179, M1-V178, M1-E177, M1-A176, M1-E175, M1-Y174, M1-L173, M1-R172, M1-K171, M1-V170, M1-N169, M1-G168, M1-L167, M1-F166, M1-N165, M1-A164, M1-Q163, M1-L162, M1-Q161, M1-L160, M1-E159, M1-K158, M1-K157, M1-V156, M1-F155, M1-L154, M1-A153, M1-S152, M1-G151, M1-M150, M1-K149, M1-L148, M1-T147, M1-L146, M1-D145, M1-K144, M1-S143, M1-P142, M1-V141, M1-T140, M1-L139, M1-S138, M1-H137, M1-V136, M1-L135, M1-H134, M1-Q133, M1-F132, M1-G131, M1-Q130, M1-H129, M1-I128, M1-A127, M1-S126, M1-E125, M1-P124, M1-T123, M1-H122, M1-T121, M1-L120, M1-N119, M1-F118, M1-G117, M1-L116, M1-G115, M1-Q114, M1-L113, M1-I112, M1-Q111, M1-T110, M1-K109, M1-T108, M1-V107, M1-S106, M1-H105, M1-A104, M1-G103, M1-L102, M1-S101, M1-L100, M1-M99, M1-A98, M1-L97, M1-S96, M1-T95, M1-S94, M1-V93, M1-S92, M1-V91, M1-P90, M1-S89, M1-F88, M1-F87, M1-I86, M1-N85, M1-Q84, M1-S83, M1-P82, M1-T81, M1-E80, M1-L79, M1-V78, M1-L77, M1-R76, M1-R75, M1-Y74, M1-L73, M1-R72, M1-F71, M1-A70, M1-F69, M1-D68, M1-T67, M1-N66, M1-L65, M1-S64, M1-Y63, M1-V62, M1-Q61, M1-S60, M1-A59, M1-P58, M1-T57, M1-S56, M1-K55, M1-T54, M1-S53, M1-S52, M1-P51, M1-R50, M1-P49, M1-Y48, M1-A47, M1-S46, M1-P45, M1-A44, M1-N43, M1-A42, M1-P41, M1-S40, M1-V39, M1-C38, M1-Y37, M1-I36, M1-P35, M1-A34, M1-C33, M1-L32, M1-G31, M1-V30, M1-A29, M1-F28, M1-L27, M1-V26, M1-G25, M1-Y24, M1-L23, M1-Y22, M1-S21, M1-A20, M1-M19, M1-K18, M1-S17, M1-C16, M1-F15, M1-I14, M1-D13, M1-K12, M1-C11, M1-T10, M1-G9, M1-R8, and/or M1-R7 of SEQ ID NO:2. Polynucleotide sequences encoding these polypeptides are also provided. The present invention also encompasses the use of these LSI-01 C-terminal deletion polypeptides as immunogenic and/or antigenic epitopes as described elsewhere herein.

The present invention also encompasses immunogenic and/or antigenic epitopes of the LSI-01 polypeptide.

In preferred embodiments, the following immunogenic and/or antigenic epitope polypeptides are encompassed by the present invention: amino acid residues from about amino acid 133 to about amino acid 146, from about amino acid 133 to about amino acid 141, from about amino acid 138 to about amino acid 146, from about amino acid 155 to about amino acid 163, from about amino acid 193 to about amino acid 204, from about amino acid 193 to about amino acid 201, from about amino acid 196 to about amino acid 204, from about amino acid 228 to about amino acid 240, from about amino acid 228 to about amino acid 236, from about amino acid 232 to about amino acid 240, from about amino acid 302 to about amino acid 318, from about amino acid 302 to about amino acid 310, from about amino acid 310 to about amino acid 318, from about 361 to about 377, from about 361 to about 369, and/or from about 369 to about 377 of SEQ ID NO:2 (FIGS. 1A–B). In this context, the term "about" may be construed to mean 1, 2, 3, 4, 5, 6, 7, 8, 9, or 10 amino acids beyond the N-terminus and/or C-terminus of the above referenced polypeptide. Polynucleotides encoding this polypeptide are also provided.

The LSI-01 polypeptides of the present invention were determined to comprise several phosphorylation sites based upon the Motif algorithm (Genetics Computer Group, Inc.). The phosphorylation of such sites may regulate some biological activity of the LSI-01 polypeptide. For example, phosphorylation at specific sites may be involved in regulating the proteins ability to associate or bind to other molecules (e.g., proteins, ligands, substrates, DNA, etc.). In the present case, phosphorylation may modulate the ability of the LSI-01 polypeptide to associate with other polypeptides, particularly the serine protease substrate for LSI-01, or its ability to modulate serine protease function.

Specifically, the LSI-01 polypeptide was predicted to comprise one tyrosine phosphorylation site using the Motif algorithm (Genetics Computer Group, Inc.). Such sites are phosphorylated at the tyrosine amino acid residue. The consensus pattern for tyrosine phosphorylation sites are as follows: [RK]-x(2)-[DE]-x(3)-Y, or [RK]-x(3)-[DE]-x(2)-Y, where Y represents the phosphorylation site and 'x' represents an intervening amino acid residue. Additional information specific to tyrosine phosphorylation sites can be found in Patschinsky T., Hunter T., Esch F. S., Cooper J. A., Sefton B. M., Proc. Natl. Acad. Sci. U.S.A. 79:973–977 (1982); Hunter T., J. Biol. Chem . . . 257:4843–4848(1982), and Cooper J. A., Esch F. S., Taylor S. S., Hunter T., J. Biol. Chem . . . 259:7835–7841(1984), which are hereby incorporated herein by reference.

In preferred embodiments, the following tyrosine phosphorylation site polypeptides are encompassed by the present invention: TKFIVRSKDGPSYFTVSF (SEQ ID NO:17). Polynucleotides encoding these polypeptides are also provided. The present invention also encompasses the use of the LSI-01 tyrosine phosphorylation site polypeptides as immunogenic and/or antigenic epitopes as described elsewhere herein.

The LSI-01 polypeptide was predicted to comprise eight PKC phosphorylation sites using the Motif algorithm (Genetics Computer Group, Inc.). In vivo, protein kinase C exhibits a preference for the phosphorylation of serine or threonine residues. The PKC phosphorylation sites have the following consensus pattern: [ST]-x-[RK], where S or T represents the site of phosphorylation and 'x' an intervening amino acid residue. Additional information regarding PKC phosphorylation sites can be found in Woodget J. R., Gould K. L., Hunter T., Eur. J. Biochem. 161:177–184(1986), and Kishimoto A., Nishiyama K., Nakanishi H., Uratsuji Y., Nomura H., Takeyama Y., Nishizuka Y., J. Biol. Chem . . . 260:12492–12499(1985); which are hereby incorporated by reference herein.

In preferred embodiments, the following PKC phosphorylation site polypeptides are encompassed by the present invention: GRRRGTCKDIFCS (SEQ ID NO:9), YPRPSSTKSTPAS (SEQ ID NO:10), PSKDLTLKMGSAL (SEQ ID NO:1), FHLEYTRKNFPFL (SEQ ID NO:12), LEQALSARTLIKW (SEQ ID NO:13), QVSKATHKAV-LDV (SEQ ID NO:14), ATAATTTKFIVRS (SEQ ID NO:15), and/or FLMMITNKATDGI (SEQ ID NO:16). Polynucleotides encoding these polypeptides are also provided. The present invention also encompasses the use of the LSI-01 PKC phosphorylation site polypeptides as immunogenic and/or antigenic epitopes as described elsewhere herein.

The LSI-01 polypeptide was predicted to comprise one casein kinase II phosphorylation sites using the Motif algorithm (Genetics Computer Group, Inc.). Casein kinase II (CK-2) is a protein serine/threonine kinase whose activity is independent of cyclic nucleotides and calcium. CK-2 phosphorylates many different proteins. The substrate specificity [1] of this enzyme can be summarized as follows: (1) Under comparable conditions Ser is favored over Thr.; (2) An acidic residue (either Asp or Glu) must be present three residues from the C-terminal of the phosphate acceptor site; (3) Additional acidic residues in positions +1, +2, +4, and +5 increase the phosphorylation rate. Most physiological substrates have at least one acidic residue in these positions; (4) Asp is preferred to Glu as the provider of acidic determinants; and (5) A basic residue at the N-terminal of the acceptor site decreases the phosphorylation rate, while an acidic one will increase it.

A consensus pattern for casein kinase II phosphorylations site is as follows: [ST]-x(2)-[DE], wherein 'x' represents any amino acid, and S or T is the phosphorylation site.

Additional information specific to casein kinase II phosphorylation sites may be found in reference to the following publication: Pinna L. A., Biochim. Biophys. Acta 1054: 267–284(1990); which is hereby incorporated herein in its entirety.

In preferred embodiments, the following casein kinase II phosphorylation site polypeptide is encompassed by the present invention: GRRRGTCKDIFCSK (SEQ ID NO:46). Polynucleotides encoding this polypeptide are also provided. The present invention also encompasses the use of this casein kinase II phosphorylation site polypeptide as an immunogenic and/or antigenic epitope as described elsewhere herein.

The LSI-01 polypeptide was predicted to comprise three cAMP- and cGMP-dependent protein kinase phosphorylation site using the Motif algorithm (Genetics Computer Group, Inc.). There has been a number of studies relative to the specificity of cAMP- and cGMP-dependent protein kinases. Both types of kinases appear to share a preference for the phosphorylation of serine or threonine residues found close to at least two consecutive N-terminal basic residues.

A consensus pattern for cAMP- and cGMP-dependent protein kinase phosphorylation sites is as follows: [RK](2)-x-[ST], wherein "x" represents any amino acid, and S or T is the phosphorylation site.

Additional information specific to cAMP- and cGMP-dependent protein kinase phosphorylation sites may be found in reference to the following publication: Fremisco J. R., Glass D. B., Krebs E. G, J. Biol. Chem. 255:4240–4245 (1980); Glass D. B., Smith S. B., J. Biol. Chem. 258: 14797–14803(1983); and Glass D. B., E1-Maghrabi M. R., Pilkis S. J., J. Biol. Chem. 261:2987–2993(1986); which is hereby incorporated herein in its entirety.

In preferred embodiments, the following cAMP- and cGMP-dependent protein kinase phosphorylation sites polypeptide are encompassed by the present invention: QGQGRRRGTCKDIF (SEQ ID NO:39), INSHVKKK-TQGKVV (SEQ ID NO:40), and/or FSGIAKRDSLQVSK (SEQ ID NO:41). Polynucleotides encoding these polypeptides are also provided. The present invention also encompasses the use of these cAMP- and cGMP-dependent protein kinase phosphorylation site polypeptide as immunogenic and/or antigenic epitopes as described elsewhere herein.

The LSI-01 polypeptide has been shown to comprise two glycosylation sites according to the Motif algorithm (Genetics Computer Group, Inc.). As discussed more specifically herein, protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion.

In preferred embodiments, the following asparagine glycosylation site polypeptides are encompassed by the present invention: QGLGFNLTHTPESA (SEQ ID NO:7), and/or FTVSFNRTFLMMIT (SEQ ID NO:8). Polynucleotides encoding these polypeptides are also provided. The present invention also encompasses the use of the LSI-01 asparagine glycosylation site polypeptides as immunogenic and/or antigenic epitopes as described elsewhere herein.

The LSI-01 polypeptide has been shown to comprise one amidation site according to the Motif algorithm (Genetics Computer Group, Inc.). The precursor of hormones and other active peptides which are C-terminally amidated is always directly followed by a glycine residue which provides the amide group, and most often by at least two consecutive basic residues (Arg or Lys) which generally function as an active peptide precursor cleavage site. Although all amino acids can be amidated, neutral hydrophobic residues such as Val or Phe are good substrates, while charged residues such as Asp or Arg are much less reactive. A consensus pattern for amidation sites is the following: x-G-[RK]-[RK], wherein "X" represents the amidation site. Additional information relating to asparagine glycosylation may be found in reference to the following publications, which are hereby incorporated by reference herein: Kreil G., Meth. Enzymol. 106:218–223(1984); and Bradbury A. F., Smyth D. G., Biosci. Rep. 7:907–916(1987).

In preferred embodiments, the following amidation site polypeptide is encompassed by the present invention: MQGQGRRRGTCK (SEQ ID NO:38). Polynucleotides encoding these polypeptides are also provided. The present invention also encompasses the use of this LSI-01 amidation site polypeptide as an immunogenic and/or antigenic epitope as described elsewhere herein.

The LSI-01 polypeptide was predicted to comprise four N-myristoylation sites using the Motif algorithm (Genetics Computer Group, Inc.). An appreciable number of eukaryotic proteins are acylated by the covalent addition of myristate (a C14-saturated fatty acid) to their N-terminal residue via an amide linkage. The sequence specificity of the enzyme responsible for this modification, myristoyl CoA: protein N-myristoyl transferase (NMT), has been derived from the sequence of known N-myristoylated proteins and from studies using synthetic peptides. The specificity seems to be the following: i.) The N-terminal residue must be glycine; ii.) In position 2, uncharged residues are allowed; iii.) Charged residues, proline and large hydrophobic residues are not allowed; iv.) In positions 3 and 4, most, if not all, residues are allowed; v.) In position 5, small uncharged residues are allowed (Ala, Ser, Thr, Cys, Asn and Gly). Serine is favored; and vi.) In position 6, proline is not allowed.

A consensus pattern for N-myristoylation is as follows: G-{EDRKHPFYW}-x(2)-[STAGCN]-{P}, wherein 'x' represents any amino acid, and G is the N-myristoylation site.

Additional information specific to N-myristoylation sites may be found in reference to the following publication: Towler D. A., Gordon J. I., Adams S. P., Glaser L., Annu. Rev. Biochem. 57:69–99(1988); and Grand R. J. A., Biochem. J. 258:625–638(1989); which is hereby incorporated herein in its entirety.

In preferred embodiments, the following N-myristoylation site polypeptides are encompassed by the present invention: ASYLYGVLFAVGLCAP (SEQ ID NO:42), TQILQGLGFNLTHTPE (SEQ ID NO:43), ILPK-MGIQNAFDKNAD (SEQ ID NO:44), and/or DVSEE-GTEATAATTTK (SEQ ID NO:45). Polynucleotides encoding these polypeptides are also provided. The present invention also encompasses the use of these N-myristoylation site polypeptides as immunogenic and/or antigenic epitopes as described elsewhere herein.

The present invention also provides a three-dimensional homology model of the LSI-01 polypeptide (see FIG. 7). The homology model of the LSI-01 polypeptide is based upon the homologous structure of the human $\alpha_1$-antithrypsin protein (pdb1q1p; Genbank Accession No:; SEQ ID NO:6) and is defined by the set of structural coordinates set forth in Table III herein. A description of the headings in Table III are as follows: "Atom" refers to the atom within the LSI-01 homology model; "Atom type" refers to the element whose coordinates are measured, the first letter in the column defines the element; "Residue" refers to the amino acid within which the atom resides; "#" refers to the amino acid number of the "residue"; "X", "Y", and "Z" structurally define the atomic position of the element measured in three dimensions; "B" is a thermal factor that measures movement of the atom around its atomic center; and "Occ" is an occupancy factor that refers to the fraction of the molecules in which each atom occupies the position specified by the coordinates. A value of "1" indicates that each atom has the same conformation, i.e., the same position, in all molecules of the model.

The LSI-01 homology model of the present invention may provide one basis for designing rational stimulators (agonists) and/or inhibitors (antagonists) of one or more of the biological functions of LSI-01, or of LSI-01 mutants having altered specificity (e.g., molecularly evolved LSI-01 polypeptides, engineered site-specific LSI-01 mutants, LSI-01 allelic variants, etc.).

Homology models are not only useful for designing rational agonists and/or antagonists, but are also useful in predicting the function of a particular polypeptide. The functional predictions from homology models are typically more accurate than the functional attributes derived from traditional polypeptide sequence homology alignments (e.g., CLUSTALW), particularly when the three dimensional structure of a related polypeptide is known (e.g., human $\alpha_1$-antithrypsin protein). The increased prediction accuracy is based upon the fact that homology models approximate the three-dimensional structure of a protein, while homology based alignments only take into account the one dimension polypeptide sequence. Since the function of a particular polypeptide is determined not only by its primary, secondary, and tertiary structure, functional assignments derived solely upon homology alignments using the one dimensional protein sequence may be less reliable. A 3-dimensional model can be constructed on the basis of the known structure of a homologous protein (Greer et al, 1991, Lesk, et al, 1992, Cardozo, et al, 1995, Yuan, et al, 1995).

Prior to developing a homology model, those of skill in the art would appreciate that a template of a known protein, or model protein, must first be identified which will be used as a basis for constructing the homology model for the protein of unknown structure (query template). In the case of the LSI-01 polypeptide of the present invention, the model protein template used in constructing the LSI-01 homology model was the human $\alpha_1$-antithrypsin protein.

Identifying a template can be accomplished using pairwise alignment of protein sequences using such programs as FASTA (Pearson, et al 1990) and BLAST (Altschul, et al, 1990). In cases where sequence similarity is high (greater than 30%), such pairwise comparison methods may be adequate for identifying an appropriate template. Likewise, multiple sequence alignments or profile-based methods can be used to align a query sequence to an alignment of multiple (structurally and biochemically) related proteins. When the sequence similarity is low, more advanced techniques may be used. Such techniques, include, for example, protein fold recognition (protein threading; Hendlich, et al, 1990), where the compatibility of a particular polypeptide sequence with the 3-dimensional fold of a potential template protein is gauged on the basis of a knowledge-based potential.

Following the initial sequence alignment, the second step would be to optimally align the query template to the model template by manual manipulation and/or by the incorporation of features specific to the polypeptides (e.g., motifs, secondary structure predictions, and allowed conservations). Preferably, the incorporated features are found within both the model and query template.

The third step would be to identify structurally conserved regions that could be used to construct secondary core structure (Sali, et al, 1995). Loops could be added using knowledge-based techniques, and by performing forcefield calculations (Sali, et al, 1995).

The term "structure coordinates" refers to Cartesian coordinates generated from the three dimensional structure of a homology model. As referenced above, the homology model of the LSI-01 polypeptide was derived by first, generating a sequence alignment with $\alpha$1 anti-trypsin using the Proceryon suite of software (Proceryon Biosciences, Inc. N.Y., N.Y.), and secondly, generating an overall atomic model including plausible sidechain orientations using the program LOOK (V3.5.2, Molecular Applications Group).

The skilled artisan would appreciate that a set of structure coordinates for a protein represents a relative set of points that define a shape in three dimensions. Thus, it is possible that an entirely different set of coordinates could define a similar or identical shape. Moreover, slight variations in the individual coordinates, as emanate from the generation of similar homology models using different alignment templates (i.e., other than the human alphal-antitrypsin), and/or using different methods in generating the homology model, will likely have minor effects on the overall shape. Variations in coordinates may also be generated because of mathematical manipulations of the structure coordinates. For example, the structure coordinates set forth in Table III could be manipulated by fractionalization of the structure coordinates; integer additions, or integer subtractions to sets of the structure coordinates, inversion of the structure coordinates or any combination of the above.

Therefore, various computational analyses are necessary to determine whether a template molecule or a portion thereof is sufficiently similar to all or part of a query template in order to be considered the same. Such analyses may be carried out using software applications available in the art, such as, for example, INSIGHTII (Molecular Simulations Inc., San Diego, Calif.) version 2000, as described in the accompanying User's Guide.

Using the superimposition tool in the program INSIGHTII, comparisons can be made between different structures and different conformations of the same structure. The procedure used in INSIGHTII to compare structures is divided into four steps: 1) load the structures to be compared; 2) define the atom equivalencies in these structures; 3) perform a fitting operation; and 4) analyze the results. Each structure is identified by a name. One structure is identified as the target (i.e., the fixed structure); the second structure (i.e., moving structure) is identified as the source structure. The atom equivalency within INSIGHTII is defined by user input. For the purpose of this invention, we will define equivalent atoms as protein backbone atoms (N, Cα, C and O) for all conserved residues between the two structures being compared. We will also consider only rigid fitting operations. When a rigid fitting method is used, the working structure is translated and rotated to obtain an optimum fit with the target structure. The fitting operation uses an algorithm that computes the optimum translation and rotation to be applied to the moving structure, such that the root mean square difference of the fit over the specified pairs of equivalent atoms is an absolute minimum. This number, given in angstroms, is reported by the INSIGHTII program. For the purpose of the present invention, any homology model of a LSI-01 that has a root mean square deviation of conserved residue backbone atoms (N, Cα, C, O) of less than 3.0 A when superimposed on the relevant backbone atoms described by structure coordinates listed in Table III are considered identical. More preferably, the root mean square deviation for the LSI-01 polypeptide is less than 2.0 Å.

The homology model of the present invention is useful for the structure-based design of modulators of the LSI-01 biological function, as well as mutants with altered biological function and/or specificity.

In accordance with the structural coordinates provided in Table III and the three dimensional homology model of LSI-01, the LSI-01 polypeptide has been shown to comprise a heparin binding region embodied by the following amino acids: from about amino acid Y63 to about amino acid E80, from about amino acid E125 to about amino acid T140, and/or from about amino acid A306 to about amino acid S315 of SEQ ID NO:2 (FIGS. 1A–B). In this context, the term "about" may be construed to mean 1, 2, 3, 4, 5, 6, 7, 8, 9 or 10 amino acids more in either the N- or C-terminal direction of the above referenced polypeptides.

In preferred embodiments, the following LSI-01 heparin binding region polypeptides are encompassed by the present invention: YSLNTDFAFRLYRRLVLE (SEQ ID NO:24), ESAIHQGFQHLVHSLT (SEQ ID NO:25), and/or ARTLIKWSHS (SEQ ID NO:26). Polynucleotides encoding these polypeptides are also provided. The present invention also encompasses the use of the LSI-01 heparin binding polypeptides as immunogenic and/or antigenic epitopes as described elsewhere herein.

In accordance with the structural coordinates provided in Table III and the three dimensional homology model of LSI-01, the LSI-01 polypeptide has been shown to comprise a cleaved reactive loop binding region embodied by the following amino acids: from about amino acid N185 to about amino acid T201, from about amino acid Q202 to about amino acid I209, from about amino acid A217 to about amino acid K227, and/or from about amino acid K368 to about amino acid V377 of SEQ ID NO:2 (FIGS. 1A–B). In this context, the term "about" may be construed to mean 1, 2, 3, 4, 5, 6, 7, 8, 9 or 10 amino acids more in either the N- or C-terminal direction of the above referenced polypeptides.

In preferred embodiments, the following LSI-01 cleaved reactive loop binding region polypeptides are encompassed by the present invention: NPSIAQARINSHVKKKT (SEQ ID NO:27), QGKVVDII (SEQ ID NO:28), AMVLVN-HIFFK (SEQ ID NO:29), and/or KATHKAVLDV (SEQ ID NO:30). Polynucleotides encoding these polypeptides are also provided. The present invention also encompasses the use of the LSI-01 cleaved reactive loop binding region polypeptides as immunogenic and/or antigenic epitopes as described elsewhere herein.

In accordance with the structural coordinates provided in Table III and the three dimensional homology model of LSI-01, the LSI-01 polypeptide has been shown to comprise a reactive loop region specified by the following amino acids: A384, T385, A386, A387, T388, T389, T390, K391, F392, I393, V394, R395, S396, K397, D398, G399, P400, S401, Y402, F403, T404, and/or from about amino acid A384 to about amino acid T404 of SEQ ID NO:2 (FIGS. 1A–B). In this context, the term "about" may be construed to mean 1, 2, 3, 4, 5, 6, 7, 8, 9 or 10 amino acids more in either the N- or C-terminal direction of the above referenced polypeptides.

In preferred embodiments, the following LSI-01 reactive loop region polypeptide is encompassed by the present invention: ATAATTTKFIVRSKDGPSYFT (SEQ ID NO:31). Polynucleotides encoding this polypeptide are also provided. The present invention also encompasses the use of the LSI-01 reactive loop region polypeptide as an immunogenic and/or antigenic epitope as described elsewhere herein.

The present invention also encompasses polypeptides comprising at least a portion of the LSI-01 reactive loop region (SEQ ID NO: 31). Such polypeptides may correspond, for example, to the N- and/or C-terminal deletions of the reactive loop region.

In preferred embodiments, the following N-terminal reactive loop region deletions are encompassed by the present invention: A1-T21, T2-T21, A3-T21, A4-T21, T5-T21, T6-T21, T7-T21, K8-T21, F9-T21, I10-T21, V11-T21, R21-T21, S13-T21, K14-T21, and/or D15-T21 of SEQ ID NO:32. Polynucleotide sequences encoding these polypeptides are also provided. The present invention also encompasses the use of these polypeptides as an immunogenic and/or antigenic epitope as described elsewhere herein.

In preferred embodiments, the following C-terminal reactive loop region deletions are encompassed by the present invention: A1-T21, A1-F20, A1-Y19, A1-S18, A1-P17, A1-G16, A1-D15, A1-K14, A1-S13, A1-R12, A1-V11, A1-I10, A1-F9, A1-K8, and/or A1-T7 of SEQ ID NO:32. Polynucleotide sequences encoding these polypeptides are also provided. The present invention also encompasses the use of these polypeptides as an immunogenic and/or antigenic epitope as described elsewhere herein.

Alternatively, such polypeptides may comprise polypeptide sequences corresponding, for example, to internal regions of the reactive loop region (e.g., any combination of both N- and C-terminal reactive loop region deletions) of SEQ ID NO:32. For example, internal regions could be defined by the equation NX to CX, where NX refers to any N-terminal amino acid position of the reactive loop region (SEQ ID NO:31), and where CX refers to any C-terminal amino acid position of the reactive loop region (SEQ ID NO:31). Polynucleotides encoding these polypeptides are also provided. The present invention also encompasses the use of these polypeptides as an immunogenic and/or antigenic epitope as described elsewhere herein.

The present invention also encompasses polypeptides comprising at least a portion of the LSI-01 heparin binding region (SEQ ID NO: 24, 25, and/or 26). Such polypeptides may correspond, for example, to N- and/or C-terminal deletions of any one of the heparin binding regions.

In preferred embodiments, the following N-terminal heparin binding region deletions are encompassed by the present invention: Y1-E18, S2-E18, L3-E18, N4-E18, T5-E18, D6-E18, F7-E18, A8-E18, F9-E18, R10-E18, L11-E18, and/or Y12-E18 of SEQ ID NO:25. Polynucleotide sequences encoding these polypeptides are also provided. The present invention also encompasses the use of these polypeptides as an immunogenic and/or antigenic epitope as described elsewhere herein.

In preferred embodiments, the following C-terminal heparin binding region deletions are encompassed by the present invention: Y1-E18, Y1-L17, Y1-V16, Y1-L15, Y1-R14, Y1-R13, Y1-Y12, Y1-L11, Y1-R10, Y1-F9, Y1-A8, and/or Y1-F7 of SEQ ID NO:25. Polynucleotide sequences encoding these polypeptides are also provided. The present invention also encompasses the use of these polypeptides as an immunogenic and/or antigenic epitope as described elsewhere herein.

In preferred embodiments, the following N-terminal heparin binding region deletions are encompassed by the present invention: E1-T16, S2-T16, A3-T16, I4-T16, H5-T16, Q6-T16, G7-T16, F8-T16, Q9-T16, and/or H10-T16 of SEQ ID NO:26. Polynucleotide sequences encoding these polypeptides are also provided. The present invention also encompasses the use of these polypeptides as an immunogenic and/or antigenic epitope as described elsewhere herein.

In preferred embodiments, the following C-terminal heparin binding region deletions are encompassed by the present invention: E1-T16, E1-L15, E1-S14, E1-H13, E1-V12, E1-L11, E1-H10, E1-Q9, E1-F8, and/or E1-G7 of SEQ ID NO:26. Polynucleotide sequences encoding these polypeptides are also provided. The present invention also encompasses the use of these polypeptides as an immunogenic and/or antigenic epitope as described elsewhere herein.

In preferred embodiments, the following N-terminal heparin binding region deletions are encompassed by the present invention: A1-S10, R2-S10, T3-S10, and/or LA-S10 of SEQ ID NO:27. Polynucleotide sequences encoding these polypeptides are also provided. The present invention also encompasses the use of these polypeptides as an immunogenic and/or antigenic epitope as described elsewhere herein.

In preferred embodiments, the following C-terminal heparin binding region deletions are encompassed by the present invention: A1-S10, A1-H9, A1-S8, and/or A1-W7 of SEQ ID NO:27. Polynucleotide sequences encoding these polypeptides are also provided. The present invention also encompasses the use of these polypeptides as an immunogenic and/or antigenic epitope as described elsewhere herein.

Alternatively, such polypeptides may comprise polypeptide sequences corresponding, for example, to internal regions of any one of the heparin binding region polypeptides, such as any combination of both N- and C-terminal deletions for each respective region corresponding to SEQ ID NO:24, 25, or 26,. For example, internal regions could be defined by the equation NX to CX, where NX refers to any N-terminal amino acid position of any one of the heparin binding regions (SEQ ID NO:24, 25, or 26), and where CX refers to any C-terminal amino acid position of any one of the heparin binding regions (SEQ ID NO:24, 25, or 26). Polynucleotides encoding these polypeptides are also provided. The present invention also encompasses the use of these polypeptides as an immunogenic and/or antigenic epitope as described elsewhere herein.

The present invention also encompasses polypeptides comprising at least a portion of one of the LSI-01 cleaved reactive loop binding region polypeptides (SEQ ID NO: 27, 28, 29, or 30). Such polypeptides may correspond, for example, to N- and/or C-terminal deletions of any one of the cleaved reactive loop binding region polypeptides.

In preferred embodiments, the following N-terminal cleaved reactive loop binding region deletions are encompassed by the present invention: N1-T17, P2-T17, S3-T17, I4-T17, A5-T17, Q6-T17, A7-T17, R8-T17, I9-T17, N10-T17, and/or S11-T17 of SEQ ID NO:27. Polynucleotide sequences encoding these polypeptides are also provided. The present invention also encompasses the use of these polypeptides as an immunogenic and/or antigenic epitope as described elsewhere herein.

In preferred embodiments, the following C-terminal cleaved reactive loop binding region deletions are encompassed by the present invention: N1-T17, N1-K16, N1-K15, N1-K14, N1-V13, N1-H12, N1-S1, N1-N10, N1-I9, N1-R8, and/or N1-A7 of SEQ ID NO:27. Polynucleotide sequences encoding these polypeptides are also provided. The present invention also encompasses the use of these polypeptides as an immunogenic and/or antigenic epitope as described elsewhere herein.

In preferred embodiments, the following N-terminal cleaved reactive loop binding region deletions are encompassed by the present invention: Q1-I8, and/or G2-I8 of SEQ ID NO:28. Polynucleotide sequences encoding these polypeptides are also provided. The present invention also encompasses the use of these polypeptides as an immunogenic and/or antigenic epitope as described elsewhere herein.

In preferred embodiments, the following C-terminal cleaved reactive loop binding region deletions are encompassed by the present invention: Q1-I8, and/or Q1-I7 of SEQ ID NO:28. Polynucleotide sequences encoding these polypeptides are also provided. The present invention also encompasses the use of these polypeptides as an immunogenic and/or antigenic epitope as described elsewhere herein.

In preferred embodiments, the following N-terminal cleaved reactive loop binding region deletions are encompassed by the present invention: A1-K11, M2-K11, V3-K11, L4-K11, and/or V5-K11 of SEQ ID NO:29. Polynucleotide sequences encoding these polypeptides are also provided. The present invention also encompasses the use of these polypeptides as an immunogenic and/or antigenic epitope as described elsewhere herein.

In preferred embodiments, the following C-terminal cleaved reactive loop binding region deletions are encompassed by the present invention: A1-K11, A1-F10, A1-F9, A1-I8, and/or A1-H7 of SEQ ID NO:29. Polynucleotide sequences encoding these polypeptides are also provided. The present invention also encompasses the use of these polypeptides as an immunogenic and/or antigenic epitope as described elsewhere herein.

In preferred embodiments, the following N-terminal cleaved reactive loop binding region deletions are encompassed by the present invention: K1-V10, A2-V10, T3-V10, and/or H4-V10 of SEQ ID NO:30. Polynucleotide sequences encoding these polypeptides are also provided. The present invention also encompasses the use of these polypeptides as an immunogenic and/or antigenic epitope as described elsewhere herein.

In preferred embodiments, the following C-terminal cleaved reactive loop binding region deletions are encompassed by the present invention: K1-V10, K1-D9, K1-L8, and/or K1-V7 of SEQ ID NO:30. Polynucleotide sequences encoding these polypeptides are also provided. The present invention also encompasses the use of these polypeptides as an immunogenic and/or antigenic epitope as described elsewhere herein.

Alternatively, such polypeptides may comprise polypeptide sequences corresponding, for example, to internal regions of any one of the cleaved reactive loop binding region polypeptides, such as any combination of both N- and C-terminal deletions for each respective region corresponding to SEQ ID NO:27, 28, 29, or 30. For example, internal regions could be defined by the equation NX to CX, where NX refers to any N-terminal amino acid position of any one of the heparin binding regions (SEQ ID NO:27, 28, 29, or 30), and where CX refers to any C-terminal amino acid position of any one of the heparin binding regions (SEQ ID NO:27, 28, 29, or 30). Polynucleotides encoding these polypeptides are also provided. The present invention also encompasses the use of these polypeptides as an immunogenic and/or antigenic epitope as described elsewhere herein.

For purposes of the present invention, by "at least a portion of" is meant all or any part of the reactive loop region, the heparin binding regions, and the cleaved reactive loop binding region defined by the structure coordinates according to Table III (e.g., fragments thereof). More preferred are molecules comprising all or any parts of the reactive loop region, the heparin binding regions, and the cleaved reactive loop binding region, according to Table III, or a mutant or homologue of said molecule or molecular complex. By mutant or homologue of the molecule it is meant a molecule that has a root mean square deviation from the backbone atoms of said LSI-01 amino acids of not more than 3.5 Angstroms.

The term "root mean square deviation" means the square root of the arithmetic mean of the squares of the deviations from the mean. It is a term that expresses the deviation or variation from a trend or object. For the purposes of the present invention, the "root mean square deviation" defines the variation in the backbone of a protein from the relevant portion of the backbone of the AR portion of the complex as defined by the structure coordinates described herein.

A preferred embodiment is a machine-readable data storage medium that is capable of displaying a graphical three-dimensional representation of a molecule or molecular complex that is defined by the structure coordinates of all of the amino acids in Table III +/− a root mean square deviation from the backbone atoms of those amino acids of not more than 4.0 ANG, preferably 3.0 ANG.

The structure coordinates of a LSI-01 homology model, including portions thereof, is stored in a machine-readable storage medium. Such data may be used for a variety of purposes, such as drug discovery.

Accordingly, in one embodiment of this invention is provided a machine-readable data storage medium comprising a data storage material encoded with the structure coordinates set forth in Table III.

One embodiment utilizes System 10 as disclosed in WO 98/11134, the disclosure of which is incorporated herein by reference in its entirety. Briefly, one version of these embodiments comprises a computer comprising a central processing unit ("CPU"), a working memory which may be, e.g, RAM (random-access memory) or "core" memory, mass storage memory (such as one or more disk drives or CD-ROM drives), one or more cathode-ray tube ("CRT") display terminals, one or more keyboards, one or more input lines, and one or more output lines, all of which are interconnected by a conventional bidirectional system bus.

Input hardware, coupled to the computer by input lines, may be implemented in a variety of ways. Machine-readable data of this invention may be inputted via the use of a modem or modems connected by a telephone line or dedicated data line. Alternatively or additionally, the input hardware may comprise CD-ROM drives or disk drives. In conjunction with a display terminal, keyboard may also be used as an input device.

Output hardware, coupled to the computer by output lines, may similarly be implemented by conventional devices. By way of example, output hardware may include a CRT display terminal for displaying a graphical representation of a region or domain of the present invention using a program such as QUANTA as described herein. Output hardware might also include a printer, so that hard copy output may be produced, or a disk drive, to store system output for later use.

In operation, the CPU coordinates the use of the various input and output devices, coordinates data accesses from mass storage, and accesses to and from the working memory, and determines the sequence of data processing steps. A number of programs may be used to process the machine-readable data of this invention. Such programs are discussed in reference to the computational methods of drug discovery as described herein. Specific references to components of the hardware system are included as appropriate throughout the following description of the data storage medium.

For the purpose of the present invention, any magnetic data storage medium which can be encoded with machine-readable data would be sufficient for carrying out the storage requirements of the system. The medium could be a conventional floppy diskette or hard disk, having a suitable substrate, which may be conventional, and a suitable coating, which may be conventional, on one or both sides, containing magnetic domains whose polarity or orientation could be altered magnetically, for example. The medium may also have an opening for receiving the spindle of a disk drive or other data storage device.

The magnetic domains of the coating of a medium may be polarized or oriented so as to encode in a manner which may be conventional, machine readable data such as that described herein, for execution by a system such as the system described herein.

Another example of a suitable storage medium which could also be encoded with such machine-readable data, or set of instructions, which could be carried out by a system such as the system described herein, could be an optically-readable data storage medium. The medium could be a conventional compact disk read only memory (CD-ROM) or a rewritable medium such as a magneto-optical disk which is optically readable and magneto-optically writable. The medium preferably has a suitable substrate, which may be conventional, and a suitable coating, which may be conventional, usually of one side of substrate.

In the case of a CD-ROM, as is well known, the coating is reflective and is impressed with a plurality of pits to encode the machine-readable data. The arrangement of pits is read by reflecting laser light off the surface of the coating. A protective coating, which preferably is substantially transparent, is provided on top of the reflective coating.

In the case of a magneto-optical disk, as is well known, the coating has no pits, but has a plurality of magnetic domains whose polarity or orientation can be changed magnetically when heated above a certain temperature, as by a laser. The orientation of the domains can be read by measuring the polarization of laser light reflected from the coating. The arrangement of the domains encodes the data as described above.

Thus, in accordance with the present invention, data capable of displaying the three dimensional structure of the LSI-01 homology model, or portions thereof and their structurally similar homologues is stored in a machine-readable storage medium, which is capable of displaying a graphical three-dimensional representation of the structure. Such data may be used for a variety of purposes, such as drug discovery.

For the first time, the present invention permits the use of structure-based or rational drug design techniques to design, select, and synthesize chemical entities that are capable of modulating the biological function of LSI-01.

Accordingly, the present invention is also directed to the design of small molecules which imitates the structure of the LSI-01 reactive loop region (SEQ ID NO:31), or a portion thereof, in accordance with the structure coordinates provided in Table III. Alternatively, the present invention is directed to the design of small molecules which may bind to at least part of the reactive loop region (SEQ ID NO:31), or some portion thereof. For purposes of this invention, by LSI-01 reactive loop, it is also meant to include mutants or homologues thereof. In a preferred embodiment, the mutants or homologues have at least 25% identity, more preferably 50% identity, more preferably 75% identity, and most preferably 90% identity to SEQ ID NO:31. In this context, the term "small molecule" may be construed to mean any molecule described known in the art or described elsewhere herein, though may include, for example, peptides, chemicals, carbohydrates, nucleic acids, PNAs, and any derivatives thereof.

Accordingly, the present invention is also directed to the design of small molecules which imitates the structure of the cleaved reactive loop binding region polypeptides of LSI-01 (SEQ ID NO:27, 28, 29, or 30), or a portion thereof, in accordance with the structural coordinates provided in Table III. Alternatively, the present invention is directed to the design of small molecules which may bind to at least part of one of the cleaved reactive loop binding region polypeptides, or some portion thereof. For purposes of this invention, by LSI-01 cleaved reactive loop binding region, it is also meant to include mutants or homologues thereof. In a preferred embodiment, the mutants or homologues have at least 25% identity, more preferably 50% identity, more preferably 75% identity, and most preferably 90% identity to SEQ ID NO:27, 28, 29, or 30 according to Table III. In this context, the term "small molecule" may be construed to mean any molecule described known in the art or described elsewhere herein, though may include, for example, peptides, chemicals, carbohydrates, nucleic acids, PNAs, and any derivatives thereof.

The present invention is also directed to the design of small molecules which imitates the structure of one of the heparin binding region polypeptides in LSI-01 (SEQ ID NO:24, 25, or 26), or some portion thereof, in accordance with the structure coordinates provided in Table III. Alternatively, the present invention is directed to the design of small molecules which may bind to at least part of one of the heparin binding region polypeptides, or some portion thereof. For the purposes of this invention, by LSI-01 heparin binding region, it is also meant to include mutants or homologues thereof. In a preferred embodiment, the mutants or homologues have at least 25% identity, more preferably 50% identity, more preferably 75% identity, and most preferably 90% identity to (SEQ ID NO:24, 25, or 26) in accordance with the structure coordinates of Table III. In this context, the term "small molecule" may be construed to mean any molecule described known in the art or described elsewhere herein, though may include, for example, peptides, chemicals, carbohydrates, nucleic acids, PNAs, and any derivatives thereof.

The three-dimensional model structure of the LSI-01 will also provide methods for identifying modulators of biological function. Various methods or combination thereof can be used to identify these compounds.

For example, test compounds can be modeled that fit spatially into the heparin binding region in LSI-01 embodied by the sequence from about Y63 to about E80, from about E125 to about T140, from about A306 to about S315, or some portion thereof, of SEQ ID NO:2 (corresponding to SEQ ID NO:24, 25, or 26, respectively), in accordance with the structural coordinates of Table III.

For example, test compounds can be modeled that fit spatially into the cleaved reactive loop binding region in LSI-01 defined by the amino acids from about N185 to about T201, from about Q202 to about I209, from about A217 to about K227, from about K368 to about V377, or some portion thereof, of SEQ ID NO:2 (corresponding to SEQ ID NO:27, 28, 29, or 30, respectively) in accordance with the structural coordinates of Table III.

Structure coordinates of the cleaved reactive loop binding region in LSI-01 defined by the amino acids from about N185 to about T201, from about Q202 to about I209, from about A217 to about K227, and/or from about K368 to about V377 (SEQ ID NO:27, 28, 29, or 30, respectfully) and/or the heparin binding region in LSI-01 defined by the amino acids from about Y63 to about E80, from about E125 to about T140, and/or from about A306 to about S315 (SEQ ID NO:24, 25, or 26, respectfully), can also be used to identify structural and chemical features. Identified structural or chemical features can then be employed to design or select compounds as potential LSI-01 modulators. By structural and chemical features it is meant to include, but is not limited to, van der Waals interactions, hydrogen bonding interactions, charge interaction, hydrophobic bonding interaction, and dipole interaction. Alternatively, or in conjunction, the three-dimensional structural model can be employed to design or select compounds as potential LSI-01 modulators. Compounds identified as potential LSI-01 modulators can then be synthesized and screened in an assay characterized by binding of a test compound to the LSI-01, or in characterizing the ability of LSI-01 to modulate a protease target in the presence of a small molecule. Examples of assays useful in screening of potential LSI-01 modulators include, but are not limited to, screening in silico, in vitro assays and high throughput assays. Finally, these methods may also involve modifying or replacing one or more amino acids N185-T201, Q202-I209, A217-K227, K368-V377, Y63-E80, E125-T140, A306-S315, A384, T385, A386, A387, T388, T389, T390, K391, F392, I393, V394, R395, S396, K397, D398, G399, P400, S401, Y402, F403, T404 from LSI-01 (SEQ ID NO:27, 28, 29, 30, 24, 25, 26, or 31, respectfully) in accordance with the structure coordinates of Table III.

However, as will be understood by those of skill in the art based upon this disclosure, other structure based design methods can be used. Various computational structure based design methods have been disclosed in the art.

For example, a number computer modeling systems are available in which the sequence of the LSI-01 and the LSI-01 structure (i.e., atomic coordinates of LSI-01 and/or the atomic coordinates of the reactive loop, the heparin binding region, and cleaved reactive loop binding region as provided in Table III) can be input. This computer system then generates the structural details of one or more these regions in which a potential LSI-01 modulator binds so that complementary structural details of the potential modulators can be determined. Design in these modeling systems is generally based upon the compound being capable of physically and structurally associating with LSI-01. In addition, the compound must be able to assume a conformation that allows it to associate with LSI-01. Some modeling systems estimate the potential inhibitory or binding effect of a potential LSI-01 modulator prior to actual synthesis and testing.

Methods for screening chemical entities or fragments for their ability to associate with a given protein target are also well known. Often these methods begin by visual inspection of the binding site on the computer screen. Selected fragments or chemical entities are then positioned in one or more of the cleaved reactive loop binding region, the heparin binding region, or the reactive loop in LSI-01. Docking is accomplished using software such as INSIGHTII, QUANTA and SYBYL, following by energy minimization and molecular dynamics with standard molecular mechanic forcefields such as CHARMM and AMBER. Examples of computer programs which assist in the selection of chemical fragment or chemical entities useful in the present invention include, but are not limited to, GRID (Goodford, 1985), AUTODOCK (Goodsell, 1990), and DOCK (Kuntz et al. 1982).

Upon selection of preferred chemical entities or fragments, their relationship to each other and LSI-01 can be visualized and then assembled into a single potential modulator. Programs useful in assembling the individual chemical entities include, but are not limited to CAVEAT (Bartlett et al. 1989) and 3D Database systems (Martin 1992).

Alternatively, compounds may be designed de novo using either an empty active site or optionally including some portion of a known inhibitor. Methods of this type of design include, but are not limited to LUDI (Bohm 1992) and LeapFrog (Tripos Associates, St. Louis MO).

In addition, LSI-01 is overall well suited to modern methods including combinatorial chemistry.

Programs such as DOCK (Kuntz et al. 1982) can be used with the atomic coordinates from the homology model to identify potential ligands from databases or virtual databases which potentially bind the in the heparin binding regions or the cleaved reactive loop region, and which may therefore be suitable candidates for synthesis and testing.

Additionally, the three-dimensional homology model of LSI-01 will aid in the design of mutants with altered biological activity. Such mutants may comprise conservative as well as non-conservative amino acid substitutions in any of the domains referenced herein.

The following are encompassed by the present invention: a machine-readable data storage medium, comprising a data storage material encoded with machine readable data, wherein the data is defined by the structure coordinates of the model LSI-01 according to Table III or a homologue of said model, wherein said homologue comprises backbone atoms that have a root mean square deviation from the backbone atoms of the complex of not more than 4.0 Å; and a machine-readable data storage medium, wherein said molecule is defined by the set of structure coordinates of the model for LSI-01 according to Table III, or a homologue of said molecule, said homologue having a root mean square deviation from the backbone atoms of said amino acids of not more than 3.0 Å; a model comprising all or any part of the model defined by structure coordinates of LSI-01 according to Table III, or a mutant or homologue of said molecule or molecular complex.

In a further embodiment, the following are encompassed by the present invention: a method for identifying a mutant of LSI-01 with altered biological properties, function, or reactivity, the method comprising any combination of steps of: use of the model or a homologue of said model according to Table III, for the design of protein mutants with altered biological function or properties which exhibit any combination of therapeutic effects provided elsewhere herein; use of the model or a homologue of said model, for the design of a protein with mutations in the reactive loop region comprised of the amino acids A384, T385, A386, A387, T388, T389, T390, K391, F392, I393, V394, R395, S396, K397, D398, G399, P400, S401, Y402, F403, T404 according to Table III with altered biological function or properties which exhibit any combination of therapeutic effects provided elsewhere herein; use of the model or a homologue of said model, for the design of a protein with mutations in the heparin binding region comprised by the amino acids Y63-E80, E125-T140, A306-S315 according to Table III with altered biological function or properties which exhibit any combination of therapeutic effects provided elsewhere herein; and use of the model or a homologue of said model, for the design of a protein with mutations cleaved reaction loop binding region comprised by the amino acids N185-T201, Q202-I209, A217-K227, K368-V377 according to Table III, with altered biological function or properties which exhibit any combination of therapeutic effects outlined provided elsewhere herein.

In further preferred embodiments, the following are encompassed by the present invention: a method for identifying modulators of LSI-01 biological properties, function, or reactivity, the method comprising any combination of steps of: modeling test compounds that overlay spatially into the heparin bindings region defined by all or any portion of residues Y63-E80, E125-T140, A306-S315, of the three-dimensional structural model according to Table III, or using a homologue or portion thereof, modeling test compounds that overlay spatially into the regions defined by all or any portion of the cleaved reactive loop binding regions comprised of the residues N185-T201, Q202-I209, A217-K227, K368-V377 of the three-dimensional structural model according to Table III, or using a homologue or portion thereof;

The present invention encompasses using the structure coordinates as set forth herein to identify structural and chemical features of the LSI-01 polypeptide; employing identified structural or chemical features to design or select compounds as potential LSI-01 modulators; employing the three-dimensional structural model to design or select compounds as potential LSI-01 modulators; synthesizing the potential LSI-01 modulators; screening the potential LSI-01 modulators in an assay characterized by binding of a protein to the LSI-01; selecting the potential LSI-01 modulator from a database; designing the LSI-01 modulator de novo; and/or designing said LSI-01 modulator from a known modulator activity.

Many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Accordingly, preferably excluded from the present invention are one or more polynucleotides consisting of a nucleotide sequence described by the general formula of a–b, where a is any integer between 1 to 1752 of SEQ ID NO:1, b is an integer between 15 to 1766, where both a and b correspond to the positions of nucleotide residues shown in SEQ ID NO:1, and where b is greater than or equal to a+14.

TABLE I

| Gene No. | CDNA Clone ID | ATCC Deposit No. Z and Date | Vector | NT SEQ ID. No. X | Total NT Seq of Clone | 5' NT of Start Codon of ORF | 3' NT of ORF | AA Seq ID No. Y | Total AA of ORF |
|---|---|---|---|---|---|---|---|---|---|
| 1. | LSI-01 - (also referred to as bac708.clone 24; AL132708_FL; BA-14448; protease 6; and/or protease inhibitor 6) | PTA-2766 12/08/00 | PSport 1 | 1 | 1766 | 68 | 1372 | 2 | 435 |

Table I summarizes the information corresponding to each "Gene No." described above. The nucleotide sequence identified as "NT SEQ ID NO:X" was assembled from partially homologous ("overlapping") sequences obtained from the "cDNA clone ID" identified in Table I and, in some cases, from additional related DNA clones. The overlapping sequences were assembled into a single contiguous sequence of high redundancy (usually several overlapping sequences at each nucleotide position), resulting in a final sequence identified as SEQ ID NO:1.

The cDNA Clone ID was deposited on the date and given the corresponding deposit number listed in "ATCC deposit No:PTA-2766 and Date." "Vector" refers to the type of vector contained in the cDNA Clone ID.

"Total NT Seq. Of Clone" refers to the total number of nucleotides in the clone contig identified by "Gene No." The deposited clone may contain all or most of the sequence of SEQ ID NO:1. The nucleotide position of SEQ ID NO:1 of the putative start codon (methionine) is identified as "5' NT of Start Codon of ORF."

The translated amino acid sequence, beginning with the methionine, is identified as "AA SEQ ID NO:2," although other reading frames can also be easily translated using known molecular biology techniques. The polypeptides produced by these alternative open reading frames are specifically contemplated by the present invention.

The total number of amino acids within the open reading frame of SEQ ID NO:2 is identified as "Total AA of ORF".

SEQ ID NO:1 (where X may be any of the polynucleotide sequences disclosed in the sequence listing) and the translated SEQ ID NO:2 (where Y may be any of the polypeptide sequences disclosed in the sequence listing) are sufficiently accurate and otherwise suitable for a variety of uses well known in the art and described further herein. For instance, SEQ ID NO:1 is useful for designing nucleic acid hybridization probes that will detect nucleic acid sequences contained in SEQ ID NO:1 or the cDNA contained in the deposited clone. These probes will also hybridize to nucleic acid molecules in biological samples, thereby enabling a variety of forensic and diagnostic methods of the invention. Similarly, polypeptides identified from SEQ ID NO:2 may be used, for example, to generate antibodies which bind specifically to proteins containing the polypeptides and the proteins encoded by the cDNA clones identified in Table I.

Nevertheless, DNA sequences generated by sequencing reactions can contain sequencing errors. The errors exist as misidentified nucleotides, or as insertions or deletions of nucleotides in the generated DNA sequence. The erroneously inserted or deleted nucleotides may cause frame shifts in the reading frames of the predicted amino acid sequence. In these cases, the predicted amino acid sequence diverges from the actual amino acid sequence, even though the generated DNA sequence may be greater than 99.9% identical to the actual DNA sequence (for example, one base insertion or deletion in an open reading frame of over 1000 bases).

Accordingly, for those applications requiring precision in the nucleotide sequence or the amino acid sequence, the present invention provides not only the generated nucleotide sequence identified as SEQ ID NO:1 and the predicted translated amino acid sequence identified as SEQ ID NO:2, but also a sample of plasmid DNA containing a cDNA of the invention deposited with the ATCC, as set forth in Table I. The nucleotide sequence of each deposited clone can readily be determined by sequencing the deposited clone in accordance with known methods. The predicted amino acid sequence can then be verified from such deposits. Moreover, the amino acid sequence of the protein encoded by a particular clone can also be directly determined by peptide sequencing or by expressing the protein in a suitable host cell containing the deposited cDNA, collecting the protein, and determining its sequence.

The present invention also relates to the genes corresponding to SEQ ID NO:1, SEQ ID NO:2, or the deposited clone. The corresponding gene can be isolated in accordance with known methods using the sequence information disclosed herein. Such methods include preparing probes or primers from the disclosed sequence and identifying or amplifying the corresponding gene from appropriate sources of genomic material.

Also provided in the present invention are species homologs, allelic variants, and/or orthologs. The skilled artisan could, using procedures well-known in the art, obtain the polynucleotide sequence corresponding to full-length genes (including, but not limited to the full-length coding region), allelic variants, splice variants, orthologs, and/or species homologues of genes corresponding to SEQ ID NO:1, SEQ ID NO:2, or a deposited clone, relying on the sequence from the sequences disclosed herein or the clones deposited with the ATCC. For example, allelic variants and/or species homologues may be isolated and identified by making suitable probes or primers which correspond to the 5', 3', or internal regions of the sequences provided herein and screening a suitable nucleic acid source for allelic variants and/or the desired homologue.

The polypeptides of the invention can be prepared in any suitable manner. Such polypeptides include isolated naturally occurring polypeptides, recombinantly produced polypeptides, synthetically produced polypeptides, or polypeptides produced by a combination of these methods. Means for preparing such polypeptides are well understood in the art.

The polypeptides may be in the form of the protein, or may be a part of a larger protein, such as a fusion protein (see below). It is often advantageous to include an additional amino acid sequence which contains secretory or leader sequences, pro-sequences, sequences which aid in purification, such as multiple histidine residues, or an additional sequence for stability during recombinant production.

The polypeptides of the present invention are preferably provided in an isolated form, and preferably are substantially purified. A recombinantly produced version of a polypeptide, can be substantially purified using techniques described herein or otherwise known in the art, such as, for example, by the one-step method described in Smith and Johnson, Gene 67:31–40 (1988). Polypeptides of the invention also can be purified from natural, synthetic or recombinant sources using protocols described herein or otherwise known in the art, such as, for example, antibodies of the invention raised against the full-length form of the protein.

The present invention provides a polynucleotide comprising, or alternatively consisting of, the sequence identified as SEQ ID NO:1, and/or a cDNA provided in ATCC Deposit No. Z:. The present invention also provides a polypeptide comprising, or alternatively consisting of, the sequence identified as SEQ ID NO:2, and/or a polypeptide encoded by the cDNA provided in ATCC deposit No:PTA-2766. The present invention also provides polynucleotides encoding a polypeptide comprising, or alternatively consisting of the polypeptide sequence of SEQ ID NO:2, and/or a polypeptide sequence encoded by the cDNA contained in ATCC deposit No:PTA-2766.

Preferably, the present invention is directed to a polynucleotide comprising, or alternatively consisting of, the sequence identified as SEQ ID NO:1, and/or a cDNA provided in ATCC Deposit No.: that is less than, or equal to, a polynucleotide sequence that is 5 mega basepairs, 1 mega basepairs, 0.5 mega basepairs, 0.1 mega basepairs, 50,000 basepairs, 20,000 basepairs, or 10,000 basepairs in length.

The present invention encompasses polynucleotides with sequences complementary to those of the polynucleotides of the present invention disclosed herein. Such sequences may be complementary to the sequence disclosed as SEQ ID NO:1, the sequence contained in a deposit, and/or the nucleic acid sequence encoding the sequence disclosed as SEQ ID NO:2.

The present invention also encompasses polynucleotides capable of hybridizing, preferably under reduced stringency conditions, more preferably under stringent conditions, and most preferably under highly stringent conditions, to polynucleotides described herein. Examples of stringency conditions are shown in Table II below: highly stringent conditions are those that are at least as stringent as, for example, conditions A–F; stringent conditions are at least as stringent as, for example, conditions G–L; an reduced stringency conditions are at least as stringent as, for example, conditions M–R.

TABLE II

| Stringency Condition | Polynucleotide Hybrid ± | Hybrid Length (bp) ‡ | Hybridization Temperature and Buffer † | Wash Temperature and Buffer † |
|---|---|---|---|---|
| A | DNA:DNA | > or equal to 50 | 65° C.; 1xSSC – or- 42° C.; 1xSSC, 50% formamide | 65° C.; 0.3xSSC |
| B | DNA:DNA | <50 | Tb*; 1xSSC | Tb*; 1xSSC |
| C | DNA:RNA | > or equal to 50 | 67° C.; 1xSSC – or- 45° C.; 1xSSC, 50% formamide | 67° C.; 0.3xSSC |
| D | DNA:RNA | <50 | Td*; 1xSSC | Td*; 1xSSC |
| E | RNA:RNA | > or equal to 50 | 70° C.; 1xSSC – or- 50° C.; 1xSSC, 50% formamide | 70° C.; 0.3xSSC |
| F | RNA:RNA | <50 | Tf*; 1xSSC | Tf*; 1xSSC |
| G | DNA:DNA | > or equal to 50 | 65° C.; 4xSSC – or- 45° C.; 4xSSC, 50% formamide | 65° C.; 1xSSC |
| H | DNA:DNA | <50 | Th*; 4xSSC | Th*; 4xSSC |
| I | DNA:RNA | > or equal to 50 | 67° C.; 4xSSC – or- 45° C.; 4xSSC, 50% formamide | 67° C.; 1xSSC |
| J | DNA:RNA | <50 | Tj*;4xSSC | Tj*;4xSSC |
| K | RNA:RNA | > or equal to 50 | 70° C.; 4xSSC – or- 40° C.; 6xSSC, 50% formamide | 67° C.; 1xSSC |
| L | RNA:RNA | <50 | Tl*; 2xSSC | Tl*; 2xSSC |
| M | DNA:DNA | > or equal to 50 | 50° C.; 4xSSC – or- 40° C. 6xSSC, 50% formamide | 50° C.; 2xSSC |
| N | DNA:DNA | <50 | Tn*; 6xSSC | Tn*; 6xSSC |
| O | DNA:RNA | > or equal to 50 | 55° C.; 4xSSC – or- 42° C.; 6xSSC, 50% formamide | 55° C.; 2xSSC |
| P | DNA:RNA | <50 | Tp*;6xSSC | Tp*;6xSSC |

TABLE II-continued

| Stringency Condition | Polynucleotide Hybrid ± | Hybrid Length (bp) ‡ | Hybridization Temperature and Buffer † | Wash Temperature and Buffer † |
|---|---|---|---|---|
| Q | RNA:RNA | > or equal to 50 | 60° C.; 4xSSC – or- 45° C.; 6xSSC, 50% formamide | 60° C.; 2xSSC |
| R | RNA:RNA | <50 | Tr*; 4xSSC | Tr*; 4xSSC |

‡:The "hybrid length" is the anticipated length for the hybridized region(s) of the hybridizing polynucleotides. When hybridizing a polynucleotide of unknown sequence, the hybrid is assumed to be that of the hybridizing polynucleotide of the present invention. When polynucleotides of known sequence are hybridized, the hybrid length can be determined by aligning the sequences of the polynucleotides and identifying the region or regions of optimal sequence complementarity. Methods of aligning two or more polynucleotide sequences and/or determining the percent identity between two polynucleotide sequences are well known in the art (e.g., MegAlign program of the DNA*Star suite of programs, etc).
†:SSPE (1xSSPE is 0.15M NaCl, 10 mM NaH2PO4, and 1.25 mM EDTA, pH 7.4) can be substituted for SSC (1xSSC is 0.15M NaCl and 15 mM sodium citrate) in the hybridization and wash buffers; washes are performed for 15 minutes after hybridization is complete. The hydridizations and washes may additionally include 5X Denhardt's reagent, .5–1.0% SDS, 100 μg/ml denatured, fragmented salmon sperm DNA, 0.5% sodium pyrophosphate, and up to 50% formamide.*Tb–Tr: The hybridization temperature for hybrids anticipated to be less than 50 base pairs in length should be 5–10° C. less than the melting temperature Tm of the hybrids there Tm is determined according to the following equations. For hybrids less than 18 base pairs in length, Tm(° C.) = 2(# of A + T bases) + 4(# of G + C bases). For hybrids between 18 and 49 base pairs in length, Tm(° C.) = 81.5 + 16.6(log$_{10}$[Na+]) + 0.41(% G + C) – (600/N), where N is the number of bases in the hybrid, and [Na+] is the concentration of sodium ions in the hybridization buffer ([NA+] for 1xSSC = .165 M).
±:The present invention encompasses the substitution of any one, or more DNA or RNA hybrid partners with either a PNA, or a modified polynucleotide. Such modified polynucleotides are known in the art and are more particularly elsewhere herein.

Additional examples of stringency conditions for polynucleotide hybridization are provided, for example, in Sambrook, J., E. F. Fritsch, and T. Maniatis, 1989, Molecular Cloning: A Laboratory Manual, Cold Spring Harbor Laboratory Press, Cold Spring Harbor, N.Y., chapters 9 and 11, and Current Protocols in Molecular Biology, 1995, F. M., Ausubel et al., eds, John Wiley and Sons, Inc., sections 2.10 and 6.3–6.4, which are hereby incorporated by reference herein.

Preferably, such hybridizing polynucleotides have at least 70% sequence identity (more preferably, at least 80% identity; and most preferably at least 90% or 95% identity) with the polynucleotide of the present invention to which they hybridize, where sequence identity is determined by comparing the sequences of the hybridizing polynucleotides when aligned so as to maximize overlap and identity while minimizing sequence gaps. The determination of identity is well known in the art, and discussed more specifically elsewhere herein.

The invention encompasses the application of PCR methodology to the polynucleotide sequences of the present invention, the clone deposited with the ATCC, and/or the cDNA encoding the polypeptides of the present invention. PCR techniques for the amplification of nucleic acids are described in U.S. Pat. No. 4,683,195 and Saiki et al., Science, 239:487–491 (1988). PCR, for example, may include the following steps, of denaturation of template nucleic acid (if double-stranded), annealing of primer to target, and polymerization. The nucleic acid probed or used as a template in the amplification reaction may be genomic DNA, cDNA, RNA, or a PNA. PCR may be used to amplify specific sequences from genomic DNA, specific RNA sequence, and/or cDNA transcribed from mRNA. References for the general use of PCR techniques, including specific method parameters, include Mullis et al., Cold Spring Harbor Symp. Quant. Biol., 51:263, (1987), Ehrlich (ed), PCR Technology, Stockton Press, NY, 1989; Ehrlich et al., Science, 252:1643–1650, (1991); and "PCR Protocols, A Guide to Methods and Applications", Eds., Innis et al., Academic Press, New York, (1990).

Signal Sequences

The present invention also encompasses mature forms of the polypeptide comprising, or alternatively consisting of, the polypeptide sequence of SEQ ID NO:2, the polypeptide encoded by the polynucleotide described as SEQ ID NO:1, and/or the polypeptide sequence encoded by a cDNA in the deposited clone. The present invention also encompasses polynucleotides encoding mature forms of the present invention, such as, for example the polynucleotide sequence of SEQ ID NO:1, and/or the polynucleotide sequence provided in a cDNA of the deposited clone.

According to the signal hypothesis, proteins secreted by eukaryotic cells have a signal or secretary leader sequence which is cleaved from the mature protein once export of the growing protein chain across the rough endoplasmic reticulum has been initiated. Most eukaryotic cells cleave secreted proteins with the same specificity. However, in some cases, cleavage of a secreted protein is not entirely uniform, which results in two or more mature species of the protein. Further, it has long been known that cleavage specificity of a secreted protein is ultimately determined by the primary structure of the complete protein, that is, it is inherent in the amino acid sequence of the polypeptide.

Methods for predicting whether a protein has a signal sequence, as well as the cleavage point for that sequence, are available. For instance, the method of McGeoch, Virus Res. 3:271–286 (1985), uses the information from a short N-terminal charged region and a subsequent uncharged region of the complete (uncleaved) protein. The method of von Heinje, Nucleic Acids Res. 14:4683–4690 (1986) uses the information from the residues surrounding the cleavage site, typically residues –13 to +2, where +1 indicates the amino terminus of the secreted protein. The accuracy of predicting the cleavage points of known mammalian secretory proteins for each of these methods is in the range of 75–80%. (von Heinje, supra.) However, the two methods do not always produce the same predicted cleavage point(s) for a given protein.

The established method for identifying the location of signal sequences, in addition, to their cleavage sites has been the SignalP program (v1.1) developed by Henrik Nielsen et al., Protein Engineering 10:1–6 (1997). The program relies upon the algorithm developed by von Heinje, though provides additional parameters to increase the prediction accuracy.

More recently, a hidden Markov model has been developed (H. Neilson, et al., Ismb 1998;6:122–30), which has been incorporated into the more recent SignalP (v2.0). This new method increases the ability to identify the cleavage site by discriminating between signal peptides and uncleaved signal anchors. The present invention encompasses the application of the method disclosed therein to the prediction of the signal peptide location, including the cleavage site, to any of the polypeptide sequences of the present invention.

As one of ordinary skill would appreciate, however, cleavage sites sometimes vary from organism to organism and cannot be predicted with absolute certainty. Accordingly, the polypeptide of the present invention may contain a signal sequence. Polypeptides of the invention which comprise a signal sequence have an N-terminus beginning within 5 residues (i.e., + or −5 residues, or preferably at the −5, −4, −3, −2, −1, +1, +2, +3, +4, or +5 residue) of the predicted cleavage point. Similarly, it is also recognized that in some cases, cleavage of the signal sequence from a secreted protein is not entirely uniform, resulting in more than one secreted species. These polypeptides, and the polynucleotides encoding such polypeptides, are contemplated by the present invention.

Moreover, the signal sequence identified by the above analysis may not necessarily predict the naturally occurring signal sequence. For example, the naturally occurring signal sequence may be further upstream from the predicted signal sequence. However, it is likely that the predicted signal sequence will be capable of directing the secreted protein to the ER. Nonetheless, the present invention provides the mature protein produced by expression of the polynucleotide sequence of SEQ ID NO:1 and/or the polynucleotide sequence contained in the cDNA of a deposited clone, in a mammalian cell (e.g., COS cells, as described below). These polypeptides, and the polynucleotides encoding such polypeptides, are contemplated by the present invention.

Polynucleotide and Polypeptide Variants

The present invention also encompasses variants (e.g., allelic variants, orthologs, etc.) of the polynucleotide sequence disclosed herein in SEQ ID NO:1, the complementary strand thereto, and/or the cDNA sequence contained in the deposited clone.

The present invention also encompasses variants of the polypeptide sequence, and/or fragments therein, disclosed in SEQ ID NO:2, a polypeptide encoded by the polynucleotide sequence in SEQ ID NO:1, and/or a polypeptide encoded by a cDNA in the deposited clone.

"Variant" refers to a polynucleotide or polypeptide differing from the polynucleotide or polypeptide of the present invention, but retaining essential properties thereof. Generally, variants are overall closely similar, and, in many regions, identical to the polynucleotide or polypeptide of the present invention.

Thus, one aspect of the invention provides an isolated nucleic acid molecule comprising, or alternatively consisting of, a polynucleotide having a nucleotide sequence selected from the group consisting of: (a) a nucleotide sequence encoding a LSI-01 related polypeptide having an amino acid sequence as shown in the sequence listing and described in SEQ ID NO:1 or the cDNA contained in ATCC deposit No:PTA-2766; (b) a nucleotide sequence encoding a mature LSI-01 related polypeptide having the amino acid sequence as shown in the sequence listing and described in SEQ ID NO:1 or the cDNA contained in ATCC deposit No:PTA-2766; (c) a nucleotide sequence encoding a biologically active fragment of a LSI-01 related polypeptide having an amino acid sequence shown in the sequence listing and described in SEQ ID NO:1 or the cDNA contained in ATCC deposit No:PTA-2766; (d) a nucleotide sequence encoding an antigenic fragment of a LSI-01 related polypeptide having an amino acid sequence sown in the sequence listing and described in SEQ ID NO:1 or the cDNA contained in ATCC deposit No:PTA-2766; (e) a nucleotide sequence encoding a LSI-01 related polypeptide comprising the complete amino acid sequence encoded by a human cDNA plasmid contained in SEQ ID NO:1 or the cDNA contained in ATCC deposit No:PTA-2766; (f) a nucleotide sequence encoding a mature LSI-01 related polypeptide having an amino acid sequence encoded by a human cDNA plasmid contained in SEQ ID NO:1 or the cDNA contained in ATCC deposit No:PTA-2766; (g) a nucleotide sequence encoding a biologically active fragment of a LSI-01 related polypeptide having an amino acid sequence encoded by a human cDNA plasmid contained in SEQ ID NO:1 or the cDNA contained in ATCC deposit No:PTA-2766; (h) a nucleotide sequence encoding an antigenic fragment of a LSI-01 related polypeptide having an amino acid sequence encoded by a human cDNA plasmid contained in SEQ ID NO:1 or the cDNA contained in ATCC deposit No:PTA-2766; (I) a nucleotide sequence complimentary to any of the nucleotide sequences in (a), (b), (c), (d), (e), (f), (g), or (h), above.

The present invention is also directed to polynucleotide sequences which comprise, or alternatively consist of, a polynucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

Another aspect of the invention provides an isolated nucleic acid molecule comprising, or alternatively, consisting of, a polynucleotide having a nucleotide sequence selected from the group consisting of: (a) a nucleotide sequence encoding a LSI-01 related polypeptide having an amino acid sequence as shown in the sequence listing and descried in Table I; (b) a nucleotide sequence encoding a mature LSI-01 related polypeptide having the amino acid sequence as shown in the sequence listing and descried in Table I; (c) a nucleotide sequence encoding a biologically active fragment of a LSI-01 related polypeptide having an amino acid sequence as shown in the sequence listing and descried in Table I; (d) a nucleotide sequence encoding an antigenic fragment of a LSI-01 related polypeptide having an amino acid sequence as shown in the sequence listing and descried in Table I; (e) a nucleotide sequence encoding a LSI-01 related polypeptide comprising the complete amino acid sequence encoded by a human cDNA in a cDNA plasmid contained in the ATCC Deposit and described in Table I; (f) a nucleotide sequence encoding a mature LSI-01 related polypeptide having an amino acid sequence encoded by a human cDNA in a cDNA plasmid contained in the ATCC Deposit and described in Table I: (g) a nucleotide sequence encoding a biologically active fragment of a LSI-01 related polypeptide having an amino acid sequence encoded by a human cDNA in a cDNA plasmid contained in the ATCC Deposit and described in Table I; (h) a nucleotide sequence encoding an antigenic fragment of a LSI-01 related polypeptide having an amino acid sequence encoded by a human cDNA in a cDNA plasmid contained in the ATCC deposit and described in Table I; (i) a nucleotide sequence complimentary to any of the nucleotide sequences in (a), (b), (c), (d), (e), (f), (g), or (h) above.

The present invention is also directed to nucleic acid molecules which comprise, or alternatively, consist of, a nucleotide sequence which is at least 80%, 85%, 90%, 91%, 92%, 93%, 94%, 95%, 96%, 97%, 98%, or 99% identical to, for example, any of the nucleotide sequences in (a), (b), (c), (d), (e), (f), (g), or (h), above.

The present invention encompasses polypeptide sequences which comprise, or alternatively consist of, an amino acid sequence which is at least 80%, 98%, 90%, 91%, 92%, 93%, 94%, 95%, 96%, 97%, 98%, or 99% identical to, the following non-limited examples, the polypeptide sequence identified as SEQ ID NO:2, the polypeptide sequence encoded by a cDNA provided in the deposited clone, and/or polypeptide fragments of any of the polypeptides provided herein. Polynucleotides encoded by these nucleic acid molecules are also encompassed by the invention. In another embodiment, the invention encompasses nucleic acid molecules which comprise, or alternatively, consist of a polynucleotide which hybridizes under stringent conditions, or alternatively, under lower stringency conditions, to a polynucleotide in (a), (b), (c), (d), (e), (f), (g), or (h), above. Polynucleotides which hybridize to the complement of these nucleic acid molecules under stringent hybridization conditions or alternatively, under lower stringency conditions, are also encompassed by the invention, as are polypeptides encoded by these polypeptides.

The present invention is also directed to polypeptides which comprise, or alternatively consist of, an amino acid sequence which is at least 80%, 98%, 90%, 91%, 92%, 93%, 94%, 95%, 96%, 97%, 98%, or 99% identical to, for example, the polypeptide sequence shown in SEQ ID NO:2, a polypeptide sequence encoded by the nucleotide sequence in SEQ ID NO:1, a polypeptide sequence encoded by the cDNA in cDNA plasmid:Z, and/or polypeptide fragments of any of these polypeptides (e.g., those fragments described herein). Polynucleotides which hybridize to the complement of the nucleic acid molecules encoding these polypeptides under stringent hybridization conditions or alternatively, under lower stringency conditions, are also encompasses by the present invention, as are the polypeptides encoded by these polynucleotides.

By a nucleic acid having a nucleotide sequence at least, for example, 95% "identical" to a reference nucleotide sequence of the present invention, it is intended that the nucleotide sequence of the nucleic acid is identical to the reference sequence except that the nucleotide sequence may include up to five point mutations per each 100 nucleotides of the reference nucleotide sequence encoding the polypeptide. In other words, to obtain a nucleic acid having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. The query sequence may be an entire sequence referenced in Table I, the ORF (open reading frame), or any fragment specified as described herein.

As a practical matter, whether any particular nucleic acid molecule or polypeptide is at least 80%, 85%, 90%, 91%, 92%, 93%, 94%, 95%, 96%, 97%, 98%, or 99% identical to a nucleotide sequence of the present invention can be determined conventionally using known computer programs. A preferred method for determining the best overall match between a query sequence (a sequence of the present invention) and a subject sequence, also referred to as a global sequence alignment, can be determined using the CLUSTALW computer program (Thompson, J. D., et al., Nucleic Acids Research, 2(22):4673–4680, (1994)), which is based on the algorithm of Higgins, D. G., et al., Computer Applications in the Biosciences (CABIOS), 8(2):189–191, (1992). In a sequence alignment the query and subject sequences are both DNA sequences. An RNA sequence can be compared by converting U's to T's. However, the CLUSTALW algorithm automatically converts U's to T's when comparing RNA sequences to DNA sequences. The result of said global sequence alignment is in percent identity. Preferred parameters used in a CLUSTALW alignment of DNA sequences to calculate percent identity via pairwise alignments are: Matrix=IUB, k-tuple=1, Number of Top Diagonals=5, Gap Penalty=3, Gap Open Penalty 10, Gap Extension Penalty=0.1, Scoring Method=Percent, Window Size=5 or the length of the subject nucleotide sequence, whichever is shorter. For multiple alignments, the following CLUSTALW parameters are preferred: Gap Opening Penalty=10; Gap Extension Parameter=0.05; Gap Separation Penalty Range=8; End Gap Separation Penalty=Off; % Identity for Alignment Delay=40%; Residue Specific Gaps: Off; Hydrophilic Residue Gap=Off; and Transition Weighting=0. The pairwise and multple alignment parameters provided for CLUSTALW above represent the default parameters as provided with the AlignX software program (Vector NTI suite of programs, version 6.0).

The present invention encompasses the application of a manual correction to the percent identity results, in the instance where the subject sequence is shorter than the query sequence because of 5' or 3' deletions, not because of internal deletions. If only the local pairwise percent identity is required, no manual correction is needed. However, a manual correction may be applied to determine the global percent identity from a global polynucleotide alignment. Percent identity calculations based upon global polynucleotide alignments are often preferred since they reflect the percent identity between the polynucleotide molecules as a whole (i.e., including any polynucleotide overhangs, not just overlapping regions), as opposed to, only local matching polynucleotides. Manual corrections for global percent identity determinations are required since the CLUSTALW program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. Whether a nucleotide is matched/aligned is determined by results of the CLUSTALW sequence alignment. This percentage is then subtracted from the percent identity, calculated by the above CLUSTALW program using the specified parameters, to arrive at a final percent identity score. This corrected score may be used for the purposes of the present invention. Only bases outside the 5' and 3' bases of the subject sequence, as displayed by the CLUSTALW alignment, which are not matched/aligned with the query sequence, are calculated for the purposes of manually adjusting the percent identity score.

For example, a 90 base subject sequence is aligned to a 100 base query sequence to determine percent identity. The deletions occur at the 5' end of the subject sequence and therefore, the CLUSTALW alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the CLUSTALW program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by CLUSTALW is not manually corrected. Once again, only bases 5' and 3' of the subject sequence which are not matched/aligned with the query sequence are manually corrected for. No other manual corrections are required for the purposes of the present invention.

In addition to the above method of aligning two or more polynucleotide or polypeptide sequences to arrive at a percent identity value for the aligned sequences, it may be desirable in some circumstances to use a modified version of the CLUSTALW algorithm which takes into account known structural features of the sequences to be aligned, such as for example, the SWISS-PROT designations for each sequence. The result of such a modifed CLUSTALW algorithm may provide a more accurate value of the percent identity for two polynucleotide or polypeptide sequences. Support for such a modified version of CLUSTALW is provided within the CLUSTALW algorithm and would be readily appreciated to one of skill in the art of bioinformatics.

The variants may contain alterations in the coding regions, non-coding regions, or both. Especially preferred are polynucleotide variants containing alterations which produce silent substitutions, additions, or deletions, but do not alter the properties or activities of the encoded polypeptide. Nucleotide variants produced by silent substitutions due to the degeneracy of the genetic code are preferred. Moreover, variants in which 5–10, 1–5, or 1–2 amino acids are substituted, deleted, or added in any combination are also preferred. Polynucleotide variants can be produced for a variety of reasons, e.g., to optimize codon expression for a particular host (change codons in the mRNA to those preferred by a bacterial host such as *E. coli*).

Naturally occurring variants are called "allelic variants," and refer to one of several alternate forms of a gene occupying a given locus on a chromosome of an organism. (Genes II, Lewin, B., ed., John Wiley & Sons, New York (1985).) These allelic variants can vary at either the polynucleotide and/or polypeptide level and are included in the present invention. Alternatively, non-naturally occurring variants may be produced by mutagenesis techniques or by direct synthesis.

Using known methods of protein engineering and recombinant DNA technology, variants may be generated to improve or alter the characteristics of the polypeptides of the present invention. For instance, one or more amino acids can be deleted from the N-terminus or C-terminus of the protein without substantial loss of biological function. The authors of Ron et al., J. Biol. Chem . . . 268: 2984–2988 (1993), reported variant KGF proteins having heparin binding activity even after deleting 3, 8, or 27 amino-terminal amino acid residues. Similarly, Interferon gamma exhibited up to ten times higher activity after deleting 8–10 amino acid residues from the carboxy terminus of this protein (Dobeli et al., J. Biotechnology 7:199–216 (1988)).

Moreover, ample evidence demonstrates that variants often retain a biological activity similar to that of the naturally occurring protein. For example, Gayle and coworkers (J. Biol. Chem. 268:22105–22111 (1993)) conducted extensive mutational analysis of human cytokine IL-1a. They used random mutagenesis to generate over 3,500 individual IL-1a mutants that averaged 2.5 amino acid changes per variant over the entire length of the molecule. Multiple mutations were examined at every possible amino acid position. The investigators found that "[m]ost of the molecule could be altered with little effect on either [binding or biological activity]." In fact, only 23 unique amino acid sequences, out of more than 3,500 nucleotide sequences examined, produced a protein that significantly differed in activity from wild-type.

Furthermore, even if deleting one or more amino acids from the N-terminus or C-terminus of a polypeptide results in modification or loss of one or more biological functions, other biological activities may still be retained. For example, the ability of a deletion variant to induce and/or to bind antibodies which recognize the protein will likely be retained when less than the majority of the residues of the protein are removed from the N-terminus or C-terminus. Whether a particular polypeptide lacking N- or C-terminal residues of a protein retains such immunogenic activities can readily be determined by routine methods described herein and otherwise known in the art.

Alternatively, such N-terminus or C-terminus deletions of a polypeptide of the present invention may, in fact, result in a significant increase in one or more of the biological activities of the polypeptide(s). For example, biological activity of many polypeptides are governed by the presence of regulatory domains at either one or both termini. Such regulatory domains effectively inhibit the biological activity of such polypeptides in lieu of an activation event (e.g., binding to a cognate ligand or receptor, phosphorylation, proteolytic processing, etc.). Thus, by eliminating the regulatory domain of a polypeptide, the polypeptide may effectively be rendered biologically active in the absence of an activation event.

Thus, the invention further includes polypeptide variants that show substantial biological activity. Such variants include deletions, insertions, inversions, repeats, and substitutions selected according to general rules known in the art so as have little effect on activity. For example, guidance concerning how to make phenotypically silent amino acid substitutions is provided in Bowie et al., Science 247: 1306–1310 (1990), wherein the authors indicate that there are two main strategies for studying the tolerance of an amino acid sequence to change.

The first strategy exploits the tolerance of amino acid substitutions by natural selection during the process of evolution. By comparing amino acid sequences in different species, conserved amino acids can be identified. These conserved amino acids are likely important for protein function. In contrast, the amino acid positions where substitutions have been tolerated by natural selection indicates that these positions are not critical for protein function. Thus, positions tolerating amino acid substitution could be modified while still maintaining biological activity of the protein.

The second strategy uses genetic engineering to introduce amino acid changes at specific positions of a cloned gene to identify regions critical for protein function. For example, site directed mutagenesis or alanine-scanning mutagenesis (introduction of single alanine mutations at every residue in the molecule) can be used. (Cunningham and Wells, Science 244:1081–1085 (1989).) The resulting mutant molecules can then be tested for biological activity.

As the authors state, these two strategies have revealed that proteins are surprisingly tolerant of amino acid substitutions. The authors further indicate which amino acid changes are likely to be permissive at certain amino acid positions in the protein. For example, most buried (within the tertiary structure of the protein) amino acid residues require nonpolar side chains, whereas few features of surface side chains are generally conserved.

The invention encompasses polypeptides having a lower degree of identity but having sufficient similarity so as to perform one or more of the same functions performed by the polypeptide of the present invention. Similarity is determined by conserved amino acid substitution. Such substitutions are those that substitute a given amino acid in a polypeptide by another amino acid of like characteristics (e.g., chemical properties). According to Cunningham et al above, such conservative substitutions are likely to be phenotypically silent. Additional guidance concerning which amino acid changes are likely to be phenotypically silent are found in Bowie et al., Science 247:1306–1310 (1990).

Tolerated conservative amino acid substitutions of the present invention involve replacement of the aliphatic or hydrophobic amino acids Ala, Val, Leu and Ile; replacement of the hydroxyl residues Ser and Thr; replacement of the acidic residues Asp and Glu; replacement of the amide residues Asn and Gln, replacement of the basic residues Lys, Arg, and His; replacement of the aromatic residues Phe, Tyr, and Trp, and replacement of the small-sized amino acids Ala, Ser, Thr, Met, and Gly.

In addition, the present invention also encompasses the conservative substitutions provided in Table IV below.

TABLE IV

| For Amino Acid | Code | Replace with any of: |
|---|---|---|
| Alanine | A | D-Ala, Gly, beta-Ala, L-Cys, D-Cys |
| Arginine | R | D-Arg, Lys, D-Lys, homo-Arg, D-homo-Arg, Met, Ile, D-Met, D-Ile, Orn, D-Orn |
| Asparagine | N | D-Asn, Asp, D-Asp, Glu, D-Glu, Gln, D-Gln |
| Aspartic Acid | D | D-Asp, D-Asn, Asn, Glu, D-Glu, Gln, D-Gln |
| Cysteine | C | D-Cys, S-Me-Cys, Met, D-Met, Thr, D-Thr |
| Glutamine | Q | D-Gln, Asn, D-Asn, Glu, D-Glu, Asp, D-Asp |
| Glutamic Acid | E | D-Glu, D-Asp, Asp, Asn, D-Asn, Gln, D-Gln |
| Glycine | G | Ala, D-Ala, Pro, D-Pro, β-Ala, Acp |
| Isoleucine | I | D-Ile, Val, D-Val, Leu, D-Leu, Met, D-Met |
| Leucine | L | D-Leu, Val, D-Val, Met, D-Met |
| Lysine | K | D-Lys, Arg, D-Arg, homo-Arg, D-homo-Arg, Met, D-Met, Ile, D-Ile, Orn, D-Orn |
| Methionine | M | D-Met, S-Me-Cys, Ile, D-Ile, Leu, D-Leu, Val, D-Val |
| Phenylalanine | F | D-Phe, Tyr, D-Thr, L-Dopa, His, D-His, Trp, |
| Proline | P | D-Pro, L-1-thioazolidine-4-carboxylic acid, D |
| Serine | S | D-Ser, Thr, D-Thr, allo-Thr, Met, D-Met, Met(O), D-Met(O), L-Cys, D-Cys |
| Threonine | T | D-Thr, Ser, D-Ser, allo-Thr, Met, D-Met, Met(O), D-Met(O), Val, D-Val |
| Tyrosine | Y | D-Tyr, Phe, D-Phe, L-Dopa, His, D-His |
| Valine | V | D-Val, Leu, D-Leu, Ile, D-Ile, Met, D-Met |

Aside from the uses described above, such amino acid substitutions may also increase protein or peptide stability. The invention encompasses amino acid substitutions that contain, for example, one or more non-peptide bonds (which replace the peptide bonds) in the protein or peptide sequence. Also included are substitutions that include amino acid residues other than naturally occurring L-amino acids, e.g., D-amino acids or non-naturally occurring or synthetic amino acids, e.g., β or γ amino acids.

Both identity and similarity can be readily calculated by reference to the following publications: Computational Molecular Biology, Lesk, A. M., ed., Oxford University Press, New York, 1988; Biocomputing: Informatics and Genome Projects, Smith, D. W., ed., Academic Press, New York, 1993; Informatics Computer Analysis of Sequence Data, Part 1, Griffin, A. M., and Griffin, H. G., eds., Humana Press,New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991.

In addition, the present invention also encompasses substitution of amino acids based upon the probability of an amino acid substitution resulting in conservation of function. Such probabilities are determined by aligning multiple genes with related function and assessing the relative penalty of each substitution to proper gene function. Such probabilities are often described in a matrix and are used by some algorithms (e.g., BLAST, CLUSTALW, GAP, etc.) in calculating percent similarity wherein similarity refers to the degree by which one amino acid may substitute for another amino acid without lose of function. An example of such a matrix is the PAM250 or BLOSUM62 matrix.

Aside from the canonical chemically conservative substitutions referenced above, the invention also encompasses substitutions which are typically not classified as conservative, but that may be chemically conservative under certain circumstances. Analysis of enzymatic catalysis for proteases, for example, has shown that certain amino acids within the active site of some enzymes may have highly perturbed pKa's due to the unique microenvironment of the active site. Such perturbed pKa's could enable some amino acids to substitute for other amino acids while conserving enzymatic structure and function. Examples of amino acids that are known to have amino acids with perturbed pKa's are the Glu-35 residue of Lysozyme, the Ile-16 residue of Chymotrypsin, the His-159 residue of Papain, etc. The conservation of function relates to either anomalous protonation or anomalous deprotonation of such amino acids, relative to their canonical, non-perturbed pKa. The pKa perturbation may enable these amino acids to actively participate in general acid-base catalysis due to the unique ionization environment within the enzyme active site. Thus, substituting an amino acid capable of serving as either a general acid or general base within the microenvironment of an enzyme active site or cavity, as may be the case, in the same or similar capacity as the wild-type amino acid, would effectively serve as a conservative amino substitution.

Besides conservative amino acid substitution, variants of the present invention include, but are not limited to, the following: (i) substitutions with one or more of the non-conserved amino acid residues, where the substituted amino acid residues may or may not be one encoded by the genetic code, or (ii) substitution with one or more of amino acid residues having a substituent group, or (iii) fusion of the mature polypeptide with another compound, such as a compound to increase the stability and/or solubility of the polypeptide (for example, polyethylene glycol), or (iv) fusion of the polypeptide with additional amino acids, such as, for example, an IgG Fc fusion region peptide, or leader or secretory sequence, or a sequence facilitating purification. Such variant polypeptides are deemed to be within the scope of those skilled in the art from the teachings herein.

For example, polypeptide variants containing amino acid substitutions of charged amino acids with other charged or neutral amino acids may produce proteins with improved characteristics, such as less aggregation. Aggregation of pharmaceutical formulations both reduces activity and increases clearance due to the aggregate's immunogenic activity. (Pinckard et al., Clin. Exp. Immunol. 2:331–340 (1967); Robbins et al., Diabetes 36: 838–845 (1987); Cleland et al., Crit. Rev. Therapeutic Drug Carrier Systems 10:307–377 (1993).)

Moreover, the invention further includes polypeptide variants created through the application of molecular evolution ("DNA Shuffling") methodology to the polynucleotide disclosed as SEQ ID NO:1, the sequence of the clone submitted in a deposit, and/or the cDNA encoding the polypeptide disclosed as SEQ ID NO:2. Such DNA Shuffling technology is known in the art and more particularly described elsewhere herein (e.g., WPC, Stemmer, PNAS, 91:10747, (1994)), and in the Examples provided herein).

A further embodiment of the invention relates to a polypeptide which comprises the amino acid sequence of the present invention having an amino acid sequence which contains at least one amino acid substitution, but not more than 50 amino acid substitutions, even more preferably, not more than 40 amino acid substitutions, still more preferably, not more than 30 amino acid substitutions, and still even more preferably, not more than 20 amino acid substitutions. Of course, in order of ever-increasing preference, it is highly preferable for a peptide or polypeptide to have an amino acid sequence which comprises the amino acid sequence of the present invention, which contains at least one, but not more than 10, 9, 8, 7, 6, 5, 4, 3, 2 or 1 amino acid substitutions. In specific embodiments, the number of additions, substitutions, and/or deletions in the amino acid sequence of the present invention or fragments thereof (e.g., the mature form and/or other fragments described herein), is 1–5, 5–10, 5–25, 5–50, 10–50 or 50–150, conservative amino acid substitutions are preferable.

Polynucleotide and Polypeptide Fragments

The present invention is directed to polynucleotide fragments of the polynucleotides of the invention, in addition to polypeptides encoded therein by said polynucleotides and/or fragments.

In the present invention, a "polynucleotide fragment" refers to a short polynucleotide having a nucleic acid sequence which: is a portion of that contained in a deposited clone, or encoding the polypeptide encoded by the cDNA in a deposited clone; is a portion of that shown in SEQ ID NO:1 or the complementary strand thereto, or is a portion of a polynucleotide sequence encoding the polypeptide of SEQ ID NO:2. The nucleotide fragments of the invention are preferably at least about 15 nt, and more preferably at least about 20 nt, still more preferably at least about 30 nt, and even more preferably, at least about 40 nt, at least about 50 nt, at least about 75 nt, or at least about 150 nt in length. A fragment "at least 20 nt in length," for example, is intended to include 20 or more contiguous bases from the cDNA sequence contained in a deposited clone or the nucleotide sequence shown in SEQ ID NO:1. In this context "about" includes the particularly recited value, a value larger or smaller by several (5, 4, 3, 2, or 1) nucleotides, at either terminus, or at both termini. These nucleotide fragments have uses that include, but are not limited to, as diagnostic probes and primers as discussed herein. Of course, larger fragments (e.g., 50, 150, 500, 600, 2000 nucleotides) are preferred.

Moreover, representative examples of polynucleotide fragments of the invention, include, for example, fragments comprising, or alternatively consisting of, a sequence from about nucleotide number 1–50, 51–100, 101–150, 151–200, 201–250, 251–300, 301–350, 351–400, 401–450, 451–500, 501–550, 551–600, 651–700, 701–750, 751–800, 800–850, 851–900, 901–950, 951–1000, 1001–1050, 1051–1100, 1101–1150, 1151–1200, 1201–1250, 1251–1300, 1301–1350, 1351–1400, 1401–1450, 1451–1500, 1501–1550, 1551–1600, 1601–1650, 1651–1700, 1701–1750, 1751–1800, 1801–1850, 1851–1900, 1901–1950, 1951–2000, or 2001 to the end of SEQ ID NO:1, or the complementary strand thereto, or the cDNA contained in a deposited clone. In this context "about" includes the particularly recited ranges, and ranges larger or smaller by several (5, 4, 3, 2, or 1) nucleotides, at either terminus or at both termini. Preferably, these fragments encode a polypeptide which has biological activity. More preferably, these polynucleotides can be used as probes or primers as discussed herein. Also encompassed by the present invention are polynucleotides which hybridize to these nucleic acid molecules under stringent hybridization conditions or lower stringency conditions, as are the polypeptides encoded by these polynucleotides.

In the present invention, a "polypeptide fragment" refers to an amino acid sequence which is a portion of that contained in SEQ ID NO:2 or encoded by the cDNA contained in a deposited clone. Protein (polypeptide) fragments may be "free-standing," or comprised within a larger polypeptide of which the fragment forms a part or region, most preferably as a single continuous region. Representative examples of polypeptide fragments of the invention, include, for example, fragments comprising, or alternatively consisting of, from about amino acid number 1–20, 21–40, 41–60, 61–80, 81–100, 102–120, 121–140, 141–160, or 161 to the end of the coding region. Moreover, polypeptide fragments can be about 20, 30, 40, 50, 60, 70, 80, 90, 100, 110, 120, 130, 140, or 150 amino acids in length. In this context "about" includes the particularly recited ranges or values, and ranges or values larger or smaller by several (5, 4, 3, 2, or 1) amino acids, at either extreme or at both extremes. Polynucleotides encoding these polypeptides are also encompassed by the invention.

Preferred polypeptide fragments include the full-length protein. Further preferred polypeptide fragments include the full-length protein having a continuous series of deleted residues from the amino or the carboxy terminus, or both. For example, any number of amino acids, ranging from 1–60, can be deleted from the amino terminus of the full-length polypeptide. Similarly, any number of amino acids, ranging from 1–30, can be deleted from the carboxy terminus of the full-length protein. Furthermore, any combination of the above amino and carboxy terminus deletions are preferred. Similarly, polynucleotides encoding these polypeptide fragments are also preferred.

Also preferred are polypeptide and polynucleotide fragments characterized by structural or functional domains, such as fragments that comprise alpha-helix and alpha-helix forming regions, beta-sheet and beta-sheet-forming regions, turn and turn-forming regions, coil and coil-forming regions, hydrophilic regions, hydrophobic regions, alpha amphipathic regions, beta amphipathic regions, flexible regions, surface-forming regions, substrate binding region, and high antigenic index regions. Polypeptide fragments of SEQ ID NO:2 falling within conserved domains are specifically contemplated by the present invention. Moreover, polynucleotides encoding these domains are also contemplated.

Other preferred polypeptide fragments are biologically active fragments. Biologically active fragments are those exhibiting activity similar, but not necessarily identical, to an activity of the polypeptide of the present invention. The biological activity of the fragments may include an improved desired activity, or a decreased undesirable activity. Polynucleotides encoding these polypeptide fragments are also encompassed by the invention.

In a preferred embodiment, the functional activity displayed by a polypeptide encoded by a polynucleotide fragment of the invention may be one or more biological activities typically associated with the full-length polypeptide of the invention. Illustrative of these biological activities includes the fragments ability to bind to at least one of the same antibodies which bind to the full-length protein, the fragments ability to interact with at lease one of the same proteins which bind to the full-length, the fragments ability to elicit at least one of the same immune responses as the full-length protein (i.e., to cause the immune system to create antibodies specific to the same epitope, etc.), the fragments ability to bind to at least one of the same polynucleotides as the full-length protein, the fragments ability to bind to a receptor of the full-length protein, the fragments ability to bind to a ligand of the full-length protein, and the fragments ability to multimerize with the full-length protein. However, the skilled artisan would appreciate that some fragments may have biological activities which are desirable and directly inapposite to the biological activity of the full-length protein. The functional activity of polypeptides of the invention, including fragments, variants, derivatives, and analogs thereof can be determined by numerous methods available to the skilled artisan, some of which are described elsewhere herein.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. Z or encoded by a polynucleotide that hybridizes to the complement of the sequence of SEQ ID NO:1 or contained in ATCC deposit No. Z under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998–4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross- reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131–5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767–778 (1984); Sutcliffe et al., Science 219:660–666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910–914; and Bittle et al., J. Gen. Virol. 66:2347–2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347–2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl- N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 μg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394,827; Traunecker et al., Nature, 331:84–86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion disulfide bonds have also been found to be more efficient in binding and neutralizing other molecules than monomeric polypeptides or fragments thereof alone. See, e.g., Fountoulakis et al., J. Biochem., 270:3958–3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972–897). In this system, the gene of interest is subcloned into a vaccinia recombination plasmid such that the open reading frame of the gene is translationally fused to an amino-terminal tag consisting of six histidine residues. The tag serves as a matrix binding domain for the fusion protein. Extracts from cells infected with the recombinant vaccinia virus are loaded onto Ni2+ nitriloacetic acid-agarose column and histidine-tagged proteins can be selectively eluted with imidazole-containing buffers.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See, generally, U.S. Pat. Nos. 5,605,793; 5,811,238; 5,830,721; 5,834,252; and 5,837,458, and Patten et al., Curr. Opinion Biotechnol. 8:724–33 (1997); Harayama, Trends Biotechnol. 16(2):76–82 (1998); Hansson, et al., J. Mol. Biol. 287:265–76 (1999); and Lorenzo and Blasco, Biotechniques 24(2):308–13 (1998) (each of these patents and publications are hereby incorporated by reference in its entirety). In one embodiment, alteration of polynucleotides corresponding to SEQ ID NO:1 and the polypeptides encoded by these polynucleotides may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, monovalent, bispecific, heteroconjugate, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Moreover, the term "antibody" (Ab) or "monoclonal antibody" (Mab) is meant to include intact molecules, as well as, antibody fragments (such as, for example, Fab and F(ab')2 fragments) which are capable of specifically binding to protein. Fab and F(ab')2 fragments lack the Fc fragment of intact antibody, clear more rapidly from the circulation of the animal or plant, and may have less non-specific tissue binding than an intact antibody (Wahl et al., J. Nucl. Med. 24:316–325 (1983)). Thus, these fragments are preferred, as well as the products of a FAB or other immunoglobulin expression library. Moreover, antibodies of the present invention include chimeric, single chain, and humanized antibodies.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60–69 (1991); U.S.

Pat. Nos. 4,474,893; 4,714,681; 4,925,648; 5,573,920; 5,601,819; Kostelny et al., J. Immunol. 148:1547–1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homologue of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologues of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981–1988 (1998); Chen et al., Cancer Res. 58(16):3668–3678 (1998); Harrop et al., J. Immunol. 161 (4):1786–1794 (1998); Zhu et al., Cancer Res. 58(15): 3209–3214 (1998); Yoon et al., J. Immunol. 160(7):3170–3179 (1998); Prat et al., J. Cell. Sci. 111(Pt2): 237–247 (1998); Pitard et al., J. Immunol. Methods 205(2): 177–190 (1997); Liautard et al., Cytokine 9(4):233–241 (1997); Carlson et al., J. Biol. Chem . . . 272(17):11295–11301 (1997); Taryman et al., Neuron 14(4): 755–762 (1995); Muller et al., Structure 6(9):1153–1167 (1998); Bartunek et al., Cytokine 8(1):14–20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionucleotides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphorylation, amidation, derivatization by known protecting/ blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art.

The antibodies of the present invention may comprise polyclonal antibodies. Methods of preparing polyclonal antibodies are known to the skilled artisan (Harlow, et al., Antibodies: A Laboratory Manual, (Cold spring Harbor Laboratory Press, $2^{nd}$ ed. (1988), which is hereby incorporated herein by reference in its entirety). For example, a polypeptide of the invention can be administered to various host animals including, but not limited to, rabbits, mice, rats, etc. to induce the production of sera containing polyclonal antibodies specific for the antigen. The administration of the polypeptides of the present invention may entail one or more injections of an immunizing agent and, if desired, an adjuvant. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art. For the purposes of the invention, "immunizing agent" may be defined as a polypeptide of the invention, including fragments, variants, and/or derivatives thereof, in addition to fusions with heterologous polypeptides and other forms of the polypeptides described herein.

Typically, the immunizing agent and/or adjuvant will be injected in the mammal by multiple subcutaneous or intraperitoneal injections, though they may also be given intramuscularly, and/or through IV). The immunizing agent may include polypeptides of the present invention or a fusion protein or variants thereof. Depending upon the nature of the polypeptides (i.e., percent hydrophobicity, percent hydrophilicity, stability, net charge, isoelectric point etc.), it may be useful to conjugate the immunizing agent to a protein known to be immunogenic in the mammal being immunized. Such conjugation includes either chemical conjugation by derivitizing active chemical functional groups to both the polypeptide of the present invention and the immunogenic protein such that a covalent bond is formed, or through fusion-protein based methodology, or other methods known to the skilled artisan. Examples of such immunogenic proteins include, but are not limited to keyhole limpet hemocyanin, serum albumin, bovine thyroglobulin, and soybean trypsin inhibitor. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum*. Additional examples of adjuvants which may be employed includes the MPL-TDM adjuvant (monophosphoryl lipid A, synthetic trehalose dicorynomycolate). The immunization protocol may be selected by one skilled in the art without undue experimentation.

The antibodies of the present invention may comprise monoclonal antibodies. Monoclonal antibodies may be prepared using hybridoma methods, such as those described by Kohler and Milstein, Nature, 256:495 (1975) and U.S. Pat. No. 4,376,110, by Harlow, et al., Antibodies: A Laboratory Manual, (Cold spring Harbor Laboratory Press, $2^{nd}$ ed. (1988), by Hammerling, et al., Monoclonal Antibodies and T-Cell Hybridomas (Elsevier, N.Y., (1981)), or other methods known to the artisan. Other examples of methods which may be employed for producing monoclonal antibodies includes, but are not limited to, the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In a hybridoma method, a mouse, a humanized mouse, a mouse with a human immune system, hamster, or other appropriate host animal, is typically immunized with an immunizing agent to elicit lymphocytes that produce or are capable of producing antibodies that will specifically bind to the immunizing agent. Alternatively, the lymphocytes may be immunized in vitro.

The immunizing agent will typically include polypeptides of the present invention or a fusion protein thereof. Generally, either peripheral blood lymphocytes ("PBLs") are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, Monoclonal Antibodies: Principles and Practice, Academic Press, (1986), pp. 59–103). Immortalized cell lines are usually transformed mammalian cells, particularly myeloma cells of rodent, bovine and human origin. Usually, rat or mouse myeloma cell lines are employed. The hybridoma cells may be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. As inferred throughout the specification, human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, Marcel Dekker, Inc., New York, (1987) pp. 51–63).

The culture medium in which the hybridoma cells are cultured can then be assayed for the presence of monoclonal antibodies directed against the polypeptides of the present invention. Preferably, the binding specificity of monoclonal antibodies produced by the hybridoma cells is determined by immunoprecipitation or by an in vitro binding assay, such as radioimmunoassay (RIA) or enzyme-linked immunoadsorbant assay (ELISA). Such techniques are known in the art and within the skill of the artisan. The binding affinity of the monoclonal antibody can, for example, be determined by the Scatchard analysis of Munson and Pollart, Anal. Biochem., 107:220 (1980).

After the desired hybridoma cells are identified, the clones may be subcloned by limiting dilution procedures and grown by standard methods (Goding, supra). Suitable culture media for this purpose include, for example, Dulbecco's Modified Eagle's Medium and RPMI-1640. Alternatively, the hybridoma cells may be grown in vivo as ascites in a mammal.

The monoclonal antibodies secreted by the subclones may be isolated or purified from the culture medium or ascites fluid by conventional immunoglobulin purification procedures such as, for example, protein A-sepharose, hydroxyapatite chromatography, gel exclusion chromatography, gel electrophoresis, dialysis, or affinity chromatography.

The skilled artisan would acknowledge that a variety of methods exist in the art for the production of monoclonal antibodies and thus, the invention is not limited to their sole production in hydridomas. For example, the monoclonal antibodies may be made by recombinant DNA methods, such as those described in U.S. Pat. No. 4,816,567. In this context, the term "monoclonal antibody" refers to an antibody derived from a single eukaryotic, phage, or prokaryotic clone. The DNA encoding the monoclonal antibodies of the invention can be readily isolated and sequenced using conventional procedures (e.g., by using oligonucleotide probes that are capable of binding specifically to genes encoding the heavy and light chains of murine antibodies, or such chains from human, humanized, or other sources). The hydridoma cells of the invention serve as a preferred source of such DNA. Once isolated, the DNA may be placed into expression vectors, which are then transformed into host cells such as Simian COS cells, Chinese hamster ovary (CHO) cells, or myeloma cells that do not otherwise produce immunoglobulin protein, to obtain the synthesis of monoclonal antibodies in the recombinant host cells. The DNA also may be modified, for example, by substituting the coding sequence for human heavy and light chain constant domains in place of the homologous murine sequences (U.S. Pat. No. 4,816, 567; Morrison et al, supra) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

The antibodies may be monovalent antibodies. Methods for preparing monovalent antibodies are well known in the art. For example, one method involves recombinant expression of immunoglobulin light chain and modified heavy chain. The heavy chain is truncated generally at any point in the Fc region so as to prevent heavy chain crosslinking. Alternatively, the relevant cysteine residues are substituted with another amino acid residue or are deleted so as to prevent crosslinking.

In vitro methods are also suitable for preparing monovalent antibodies. Digestion of antibodies to produce fragments thereof, particularly, Fab fragments, can be accomplished using routine techniques known in the art. Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563–681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art and are discussed in detail in the Examples herein. In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182: 41–50 (1995); Ames et al., J. Immunol. Methods 184: 177–186 (1995); Kettleborough et al., Eur. J. Immunol. 24:952–958 (1994); Persic et al., Gene 187 9–18 (1997); Burton et al., Advances in Immunology 57:191–280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864–869 (1992); and Sawai et al., AJRI 34:26–34 (1995); and Better et al., Science 240:1041–1043 (1988) (said references incorporated by reference in their entireties). Examples of techniques which can be used to produce single-chain Fvs and antibodies include those described in U.S. Pat. Nos. 4,946,778 and 5,258,498; Huston et al., Methods in Enzymology 203:46–88 (1991); Shu et al., PNAS 90:7995–7999 (1993); and Skerra et al., Science 240:1038–1040 (1988).

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191–202; U.S. Pat. Nos. 5,807,715; 4,816,567; and 4,816397, which are incorporated herein by reference in their entirety. Humanized antibodies are antibody molecules from non-human species antibody that binds the desired antigen having one or more complementarity determining regions (CDRs) from the non-human species and a framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489–498 (1991); Studnicka et al., Protein Engineering 7(6):805–814 (1994); Roguska. et al., PNAS 91:969–973 (1994)), and chain shuffling (U.S. Pat. No. 5,565,332). Generally, a humanized antibody has one or more amino acid residues introduced into it from a source that is non-human. These non-human amino acid residues are often referred to as "import" residues, which are typically taken from an "import" variable domain. Humanization can be essentially performed following the methods of Winter and co-workers (Jones et al., Nature, 321:522–525 (1986); Reichmann et al., Nature, 332:323–327 (1988); Verhoeyen et al., Science, 239:1534–1536 (1988), by substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possible some FR residues are substituted from analogous sites in rodent antibodies.

In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fc), typically that of a human immunoglobulin (Jones et al., Nature, 321:522–525 (1986); Riechmann et al., Nature 332:323–329 (1988)1 and Presta, Curr. Op. Struct. Biol., 2:593–596 (1992).

Completely human antibodies are particularly desirable for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety. The techniques of cole et al., and Boerder et al., are also available for the preparation of human monoclonal antibodies (cole et al., Monoclonal Antibodies and Cancer Therapy, Alan R. Riss, (1985); and Boerner et al., J. Immunol., 147(1):86–95, (1991)).

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65–93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.), Genpharm (San Jose, Calif.), and Medarex, Inc. (Princeton, N.J.) can be engaged to provide human antibodies directed against a selected antigen using technology similar to that described above.

Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and creation of an antibody repertoire. This approach is described, for example, in U.S. Pat. Nos. 5,545,807; 5,545,806; 5,569,825; 5,625,126; 5,633,425; 5,661,106, and in the following scientific publications: Marks et al., Biotechnol., 10:779–783 (1992); Lonberg et al., Nature 368:856–859 (1994); Fishwild et al., Nature Biotechnol., 14:845–51 (1996); Neuberger, Nature Biotechnol., 14:826 (1996); Lonberg and Huszer, Intern. Rev. Immunol., 13:65–93 (1995).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899–903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437–444; (1989) and Nissinoff, J. Immunol. 147(8):2429–2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

The antibodies of the present invention may be bispecific antibodies. Bispecific antibodies are monoclonal, preferably human or humanized, antibodies that have binding specificities for at least two different antigens. In the present invention, one of the binding specificities may be directed towards a polypeptide of the present invention, the other may be for any other antigen, and preferably for a cell-surface protein, receptor, receptor subunit, tissue-specific antigen, virally derived protein, virally encoded envelope protein, bacterially derived protein, or bacterial surface protein, etc.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537–539 (1983). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published 13May 1993, and in Traunecker et al., EMBO J., 10:3655–3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transformed into a suitable host organism. For further details of generating bispecific antibodies see, for example Suresh et al., Meth. In Enzym., 121:210 (1986).

Heteroconjugate antibodies are also contemplated by the present invention. Heteroconjugate antibodies are composed of two covalently joined antibodies. Such antibodies have, for example, been proposed to target immune system cells to unwanted cells (U.S. Pat. No. 4,676,980), and for the treatment of HIV infection (WO 91/00360; WO 92/20373; and EP03089). It is contemplated that the antibodies may be prepared in vitro using known methods in synthetic protein chemistry, including those involving crosslinking agents. For example, immunotoxins may be constructed using a disulfide exchange reaction or by forming a thioester bond. Examples of suitable reagents for this purpose include iminothiolate and methyl-4-mercaptobutyrimidate and those disclosed, for example, in U.S. Pat. No. 4,676,980.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties ), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457–479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851–855 (1984); Neuberger et al., Nature 312:604–608 (1984); Takeda et al., Nature 314:452–454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423–42 (1988); Huston et al., Proc. Natl. Acad. Sci. USA 85:5879–5883 (1988); and Ward et al., Nature 334:544–54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242: 1038–1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., Saccharomyces, Pichia) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101–3109 (1985); Van Heeke & Schuster, J. Biol. Chem . . . 24:5503–5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, Autographa californica nuclear polyhedrosis virus (AcNPV) is used as a vector to express foreign genes. The virus grows in Spodoptera frugiperda cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non- essential region of the viral genome (e.g., region El or E3) will result in a recombinant virus that is viable and capable of expressing the antibody molecule in infected hosts. (e.g., see Logan & Shenk, Proc. Natl. Acad. Sci. USA 81:355–359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51–544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media.

The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk-, hgprt- or aprt- cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488–505; Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, 1993, TIB TECH 11(5): 155–215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol.3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in vitro immunoassays and purification methods using methods known in the art. See e.g., Harbor et al., supra, and PCT publication WO 93/21232; EP 439,095; Naramura et al., Immunol. Lett. 39:91–99 (1994); U.S. Pat. No. 5,474,981; Gillies et al., PNAS 89:1428–1432 (1992); Fell et al., J. Immunol. 146:2446–2452(1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535–10539 (1991); Zheng et al., J. Immunol. 154:5590–5600 (1995); and Vil et al., Proc. Natl. Acad. Sci. USA 89:11337–11341(1992) (said references incorporated by reference in their entireties).

As discussed, supra, the polypeptides corresponding to a polypeptide, polypeptide fragment, or a variant of SEQ ID NO:2 may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84–86 (1988). The polypeptides of the present invention fused or conjugated to an antibody having disulfide- linked dimeric structures (due to the IgG) may also be more efficient in binding and neutralizing other molecules, than the monomeric secreted protein or protein fragment alone. (Fountoulakis et al., J. Biochem. 270:3958–3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52–58 (1995); Johanson et al., J. Biol. Chem . . . 270:9459–9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidinibiotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include 125I, 131I, 111In or 99Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologues thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, a-interferon, B-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., Int. Immunol., 6:1567–1574 (1994)), VEGI (See, International Publication No. WO 99/23105), a thrombotic agent or an anti- angiogenic agent, e.g., angiostatin or endostatin; or, biological response modifiers such as, for example, lymphokines, interleukin-1 ("IL-1"), interleukin-2 ("L-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243–56 (Alan R. Liss, Inc. 1985); Hellstrom et al., "Antibodies For Drug Delivery", in Controlled Drug Delivery (2nd Ed.), Robinson et al. (eds.), pp. 623–53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475–506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303–16 (Academic Press 1985), and Thorpe et al., "The Preparation And Cytotoxic Properties Of Antibody-Toxin Conjugates", Immunol. Rev. 62:119–58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

The present invention also encompasses the creation of synthetic antibodies directed against the polypeptides of the present invention. One example of synthetic antibodies is described in Radrizzani, M., et al., Medicina, (Aires), 59(6): 753–8, (1999)). Recently, a new class of synthetic antibodies has been described and are referred to as molecularly imprinted polymers (MIPs) (Semorex, Inc.). Antibodies, peptides, and enzymes are often used as molecular recognition elements in chemical and biological sensors. However, their lack of stability and signal transduction mechanisms limits their use as sensing devices. Molecularly imprinted polymers (MIPs) are capable of mimicking the function of biological receptors but with less stability constraints. Such polymers provide high sensitivity and selectivity while maintaining excellent thermal and mechanical stability. MIPs have the ability to bind to small molecules and to target molecules such as organics and proteins' with equal or greater potency than that of natural antibodies. These "super" MIPs have higher affinities for their target and thus require lower concentrations for efficacious binding.

During synthesis, the MIPs are imprinted so as to have complementary size, shape, charge and functional groups of the selected target by using the target molecule itself (such as a polypeptide, antibody, etc.), or a substance having a very similar structure, as its "print" or "template." MIPs can be derivatized with the same reagents afforded to antibodies. For example, fluorescent 'super' MIPs can be coated onto beads or wells for use in highly sensitive separations or assays, or for use in high throughput screening of proteins.

Moreover, MIPs based upon the structure of the polypeptide(s) of the present invention may be useful in screening for compounds that bind to the polypeptide(s) of the invention. Such a MIP would serve the role of a synthetic "receptor" by minimicking the native architecture of the polypeptide. In fact, the ability of a MIP to serve the role of a synthetic receptor has already been demonstrated for the estrogen receptor (Ye, L., Yu, Y., Mosbach, K, Analyst., 126(6):760–5, (2001); Dickert, F, L., Hayden, O., Halikias, K, P, Analyst., 126(6):766–71, (2001)). A synthetic receptor may either be mimicked in its entirety (e.g., as the entire protein), or mimicked as a series of short peptides corresponding to the protein (Rachkov, A., Minoura, N, Biochim, Biophys, Acta., 1544(1–2):255–66, (2001)). Such a synthetic receptor MIPs may be employed in any one or more of the screening methods described elsewhere herein.

MIPs have also been shown to be useful in "sensing" the presence of its mimicked molecule (Cheng, Z., Wang, E., Yang, X, Biosens, Bioelectron., 16(3):179–85, (2001); Jenkins, A, L., Yin, R., Jensen, J. L, Analyst., 126(6):798–802, (2001); Jenkins, A, L., Yin, R., Jensen, J. L, Analyst., 126(6):798–802, (2001)). For example, a MIP designed using a polypeptide of the present invention may be used in assays designed to identify, and potentially quantitate, the level of said polypeptide in a sample. Such a MIP may be used as a substitute for any component described in the assays, or kits, provided herein (e.g., ELISA, etc.).

A number of methods may be employed to create MIPs to a specific receptor, ligand, polypeptide, peptide, organic molecule. Several preferred methods are described by Esteban et al in J. Anal, Chem., 370(7):795–802, (2001), which is hereby incorporated herein by reference in its entirety in addition to any references cited therein. Additional methods are known in the art and are encompassed by the present invention, such as for example, Hart, B, R., Shea, K, J. J. Am. Chem, Soc., 123(9):2072–3, (2001); and Quaglia, M., Chenon, K., Hall, A, J., De, Lorenzi, E., Sellergren, B, J. Am. Chem, Soc., 123(10):2146–54, (2001); which are hereby incorporated by reference in their entirety herein.

Uses for Antibodies Directed Against Polypeptides of the Invention

The antibodies of the present invention have various utilities. For example, such antibodies may be used in diagnostic assays to detect the presence or quantification of the polypeptides of the invention in a sample. Such a diagnostic assay may be comprised of at least two steps. The first, subjecting a sample with the antibody, wherein the sample is a tissue (e.g., human, animal, etc.), biological fluid (e.g., blood, urine, sputum, semen, amniotic fluid, saliva, etc.), biological extract (e.g., tissue or cellular homogenate, etc.), a protein microchip (e.g., See Arenkov P, et al., Anal Biochem., 278(2):123–131 (2000)), or a chromatography column, etc. And a second step involving the quantification of antibody bound to the substrate. Alternatively, the method may additionally involve a first step of attaching the antibody, either covalently, electrostatically, or reversibly, to a solid support, and a second step of subjecting the bound antibody to the sample, as defined above and elsewhere herein.

Various diagnostic assay techniques are known in the art, such as competitive binding assays, direct or indirect sandwich assays and immunoprecipitation assays conducted in either heterogeneous or homogenous phases (Zola, Monoclonal Antibodies: A Manual of Techniques, CRC Press, Inc., (1987), pp 147–158). The antibodies used in the diagnostic assays can be labeled with a detectable moiety. The detectable moiety should be capable of producing, either directly or indirectly, a detectable signal. For example, the detectable moiety may be a radioisotope, such as 2H, 14C, 32P, or 125I, a florescent or chemiluminescent compound, such as fluorescein isothiocyanate, rhodamine, or luciferin, or an enzyme, such as alkaline phosphatase, beta-galactosidase, green fluorescent protein, or horseradish peroxidase. Any method known in the art for conjugating the antibody to the detectable moiety may be employed, including those methods described by Hunter et al., Nature, 144:945 (1962); Dafvid et al., Biochem., 13:1014 (1974); Pain et al., J. Immunol. Metho., 40:219(1981); and Nygren, J. Histochem. And Cytochem., 30:407 (1982).

Antibodies directed against the polypeptides of the present invention are useful for the affinity purification of such polypeptides from recombinant cell culture or natural sources. In this process, the antibodies against a particular polypeptide are immobilized on a suitable support, such as a Sephadex resin or filter paper, using methods well known in the art. The immobilized antibody then is contacted with a sample containing the polypeptides to be purified, and thereafter the support is washed with a suitable solvent that will remove substantially all the material in the sample except for the desired polypeptides, which are bound to the immobilized antibody. Finally, the support is washed with another suitable solvent that will release the desired polypeptide from the antibody.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., Cell, 96:737–49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1–4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%–20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., 32P or 125I) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., 3H or 125I) in the presence of increasing amounts of an unlabeled second antibody.

Therapeutic Uses Of Antibodies

The present invention is further directed to antibody-based therapies which involve administering antibodies of the invention to an animal, preferably a mammal, and most preferably a human, patient for treating one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, inhibit or prevent diseases, disorders or conditions associated with aberrant expression and/or activity of a polypeptide of the invention, including, but not limited to, any one or more of the diseases, disorders, or conditions described herein. The treatment and/or prevention of diseases, disorders, or conditions associated with aberrant expression and/or activity of a polypeptide of the invention includes, but is not limited to, alleviating symptoms associated with those diseases, disorders or conditions. Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Antibodies directed against polypeptides of the present invention are useful for inhibiting allergic reactions in animals. For example, by administering a therapeutically acceptable dose of an antibody, or antibodies, of the present invention, or a cocktail of the present antibodies, or in combination with other antibodies of varying sources, the animal may not elicit an allergic response to antigens.

Likewise, one could envision cloning the gene encoding an antibody directed against a polypeptide of the present invention, said polypeptide having the potential to elicit an allergic and/or immune response in an organism, and transforming the organism with said antibody gene such that it is expressed (e.g., constitutively, inducibly, etc.) in the organism. Thus, the organism would effectively become resistant to an allergic response resulting from the ingestion or presence of such an immune/allergic reactive polypeptide. Moreover, such a use of the antibodies of the present invention may have particular utility in preventing and/or ameliorating autoimmune diseases and/or disorders, as such conditions are typically a result of antibodies being directed against endogenous proteins. For example, in the instance where the polypeptide of the present invention is responsible for modulating the immune response to auto-antigens, transforming the organism and/or individual with a construct comprising any of the promoters disclosed herein or otherwise known in the art, in addition, to a polynucleotide encoding the antibody directed against the polypeptide of the present invention could effective inhibit the organisms immune system from eliciting an immune response to the auto-antigen(s). Detailed descriptions of therapeutic and/or gene therapy applications of the present invention are provided elsewhere herein.

Alternatively, antibodies of the present invention could be produced in a plant (e.g., cloning the gene of the antibody directed against a polypeptide of the present invention, and transforming a plant with a suitable vector comprising said gene for constitutive expression of the antibody within the plant), and the plant subsequently ingested by an animal, thereby conferring temporary immunity to the animal for the specific antigen the antibody is directed towards (See, for example, U.S. Pat. Nos. 5,914,123 and 6,034,298).

In another embodiment, antibodies of the present invention, preferably polyclonal antibodies, more preferably monoclonal antibodies, and most preferably single-chain antibodies, can be used as a means of inhibiting gene expression of a particular gene, or genes, in a human, mammal, and/or other organism. See, for example, International Publication Number WO 00/05391, published Feb. 3, 2000, to Dow Agrosciences LLC. The application of such methods for the antibodies of the present invention are known in the art, and are more particularly described elsewhere herein.

In yet another embodiment, antibodies of the present invention may be useful for multimerizing the polypeptides of the present invention. For example, certain proteins may confer enhanced biological activity when present in a multimeric state (i.e., such enhanced activity may be due to the increased effective concentration of such proteins whereby more protein is available in a localized location).

Antibody-based Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488–505 (1993); Wu and Wu, Biotherapy 3:87–95 (1991); Tolstoshev, Ann. Rev. Pharmacol. Toxicol. 32:573–596 (1993); Mulligan, Science 260:926–932 (1993); and Morgan and Anderson, Ann. Rev. Biochem. 62:191–217 (1993); May, TIBTECH 11(5):155–215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932–8935 (1989); Zijlstra et al., Nature 342: 435–438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980, 286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem . . . 262:4429–4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932–8935 (1989); Zijlstra et al., Nature 342: 435–438 (1989)).

In a specific embodiment, viral vectors that contains nucleic acid sequences encoding an antibody of the invention are used. For example, a retroviral vector can be used (see Miller et al., Meth. Enzymol. 217:581–599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291–302 (1994), which describes the use of a retroviral vector to deliver the mdrl gene to hematopoietic stem cells in order to make the stem cells more resistant to chemotherapy. Other references illustrating the use of retroviral vectors in gene therapy are: Clowes et al., J. Clin. Invest. 93:644–651 (1994); Kiem et al., Blood 83:1467–1473 (1994); Salmons and Gunzberg, Human Gene Therapy 4:129–141 (1993); and Grossman and Wilson, Curr. Opin. in Genetics and Devel. 3:110–114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499–503 (1993) present a review of adenovirus-based gene therapy. Bout et al., Human Gene Therapy 5:3–10 (1994) demonstrated the use of adenovirus vectors to transfer genes to the respiratory epithelia of rhesus monkeys. Other instances of the use of adenoviruses in gene therapy can be found in Rosenfeld et al., Science 252:431–434 (1991); Rosenfeld et al., Cell 68:143–155 (1992); Mastrangeli et al., J. Clin. Invest. 91:225–234 (1993); PCT Publication WO94/12649; and Wang, et al., Gene Therapy 2:775–783 (1995). In a preferred embodiment, adenovirus vectors are used.

Adeno-associated virus (AAV) has also been proposed for use in gene therapy (Walsh et al., Proc. Soc. Exp. Biol. Med. 204:289–300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599–618 (1993); Cohen et al., Meth. Enzymol. 217:618–644 (1993); Cline, Pharmac. Ther. 29:69–92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as Tlymphocytes, Blymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973–985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription. Demonstration of Therapeutic or Prophylactic Activity The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Compositions

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429–4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Florida (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228:190 (1985); During et al., Ann.

Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864–1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging with Antibodies

Labeled antibodies, and derivatives and analogs thereof, which specifically bind to a polypeptide of interest can be used for diagnostic purposes to detect, diagnose, or monitor diseases, disorders, and/or conditions associated with aberrant expression and/or activity of a polypeptide of the invention. The invention provides for the detection of aberrant expression of a polypeptide of interest, comprising (a)

assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976–985 (1985); Jalkanen, et al., J. Cell . Biol. 105:3087–3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine (125I, 121I), carbon (14C), sulfur (35S), tritium (3H), indium (112In), and technetium (99Tc); luminescent labels, such as luminol; and fluorescent labels, such as fluorescein and rhodamine, and biotin.

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or colorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface- bound recombinant antigens, and a reporter-labeled anti-human antibody for detecting surface-bound anti-antigen antibody.

Fusion Proteins

Any polypeptide of the present invention can be used to generate fusion proteins. For example, the polypeptide of the present invention, when fused to a second protein, can be used as an antigenic tag. Antibodies raised against the polypeptide of the present invention can be used to indirectly detect the second protein by binding to the polypeptide. Moreover, because certain proteins target cellular locations based on trafficking signals, the polypeptides of the present invention can be used as targeting molecules once fused to other proteins.

Examples of domains that can be fused to polypeptides of the present invention include not only heterologous signal sequences, but also other heterologous functional regions. The fusion does not necessarily need to be direct, but may occur through linker sequences.

Moreover, fusion proteins may also be engineered to improve characteristics of the polypeptide of the present invention. For instance, a region of additional amino acids, particularly charged amino acids, may be added to the N-terminus of the polypeptide to improve stability and persistence during purification from the host cell or subsequent handling and storage. Peptide moieties may be added to the polypeptide to facilitate purification. Such regions may be removed prior to final preparation of the polypeptide. Similarly, peptide cleavage sites can be introduced in-between such peptide moieties, which could additionally be subjected to protease activity to remove said peptide(s) from the protein of the present invention. The addition of peptide moieties, including peptide cleavage sites, to facilitate handling of polypeptides are familiar and routine techniques in the art.

Moreover, polypeptides of the present invention, including fragments, and specifically epitopes, can be combined with parts of the constant domain of immunoglobulins (IgA, IgE, IgG, IgM) or portions thereof (CH1, CH2, CH3, and any combination thereof, including both entire domains and portions thereof), resulting in chimeric polypeptides. These fusion proteins facilitate purification and show an increased half-life in vivo. One reported example describes chimeric proteins consisting of the first two domains of the human CD4-polypeptide and various domains of the constant regions of the heavy or light chains of mammalian immunoglobulins. (EP A 394,827; Traunecker et al., Nature 331: 84–86 (1988).) Fusion proteins having disulfide-linked dimeric structures (due to the IgG) can also be more efficient in binding and neutralizing other molecules, than the monomeric secreted protein or protein fragment alone. (Fountoulakis et al., J. Biochem. 270:3958–3964 (1995).)

Similarly, EP-A-O 464 533 (Canadian counterpart 2045869) discloses fusion proteins comprising various portions of the constant region of immunoglobulin molecules together with another human protein or part thereof. In many cases, the Fc part in a fusion protein is beneficial in therapy and diagnosis, and thus can result in, for example, improved pharmacokinetic properties. (EP-A 0232 262.) Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, D. Bennett et al., J. Molecular Recognition 8:52–58 (1995); K. Johanson et al., J. Biol. Chem . . . 270:9459–9471 (1995).)

Moreover, the polypeptides of the present invention can be fused to marker sequences (also referred to as "tags"). Due to the availability of antibodies specific to such "tags", purification of the fused polypeptide of the invention, and/or its identification is significantly facilitated since antibodies specific to the polypeptides of the invention are not required. Such purification may be in the form of an affinity purification whereby an anti-tag antibody or another type of affinity matrix (e.g., anti-tag antibody attached to the matrix of a flow-thru column) that binds to the epitope tag is present. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821–824 (1989), for instance, hexa-histidine provides for convenient purification of the fusion protein. Another peptide tag useful for purification, the "HA" tag, corresponds to an epitope derived from the influenza hemagglutinin protein. (Wilson et al., Cell 37:767 (1984)).

The skilled artisan would acknowledge the existence of other "tags" which could be readily substituted for the tags referred to supra for purification and/or identification of polypeptides of the present invention (Jones C., et al., J Chromatogr A. 707(1):3–22 (1995)). For example, the c-myc tag and the 8F9, 3C7, 6E10, G4m B7 and 9E10 antibodies thereto (Evan et al., Molecular and Cellular Biology 5:3610–3616 (1985)); the Herpes Simplex virus glycoprotein D (gD) tag and its antibody (Paborsky et al., Protein Engineering, 3(6):547–553 (1990), the Flag-peptide—i.e., the octapeptide sequence DYKDDDDK (SEQ ID NO:33), (Hopp et al., Biotech. 6:1204–1210 (1988); the KT3 epitope peptide (Martin et al., Science, 255:192–194 (1992)); a-tubulin epitope peptide (Skinner et al., J. Biol. Chem . . . , 266:15136–15166, (1991)); the T7 gene 10 protein peptide tag (Lutz-Freyermuth et al., Proc. Natl. Sci. USA, 87:6363–6397 (1990)), the FITC epitope (Zymed, Inc.), the GFP epitope (Zymed, Inc.), and the Rhodamine epitope (Zymed, Inc.).

The present invention also encompasses the attachment of up to nine codons encoding a repeating series of up to nine arginine amino acids to the coding region of a polynucleotide of the present invention. The invention also encompasses chemically derivitizing a polypeptide of the present invention with a repeating series of up to nine arginine amino acids. Such a tag, when attached to a polypeptide, has recently been shown to serve as a universal pass, allowing compounds access to the interior of cells without additional derivitization or manipulation (Wender, P., et al., unpublished data).

Protein fusions involving polypeptides of the present invention, including fragments and/or variants thereof, can be used for the following, non-limiting examples, subcellular localization of proteins, determination of protein-protein interactions via immunoprecipitation, purification of proteins via affinity chromatography, functional and/or structural characterization of protein. The present invention also encompasses the application of hapten specific antibodies for any of the uses referenced above for epitope fusion proteins. For example, the polypeptides of the present invention could be chemically derivatized to attach hapten molecules (e.g., DNP, (Zymed, Inc.)). Due to the availability of monoclonal antibodies specific to such haptens, the protein could be readily purified using immunoprecipitation, for example.

Polypeptides of the present invention, including fragments and/or variants thereof, in addition to, antibodies directed against such polypeptides, fragments, and/or variants, may be fused to any of a number of known, and yet to be determined, toxins, such as ricin, saporin (Mashiba H, et al., Ann. N. Y. Acad. Sci. 1999;886:233–5), or HC toxin (Tonukari N J, et al., Plant Cell. 2000 February;12(2): 237–248), for example. Such fusions could be used to deliver the toxins to desired tissues for which a ligand or a protein capable of binding to the polypeptides of the invention exists.

The invention encompasses the fusion of antibodies directed against polypeptides of the present invention, including variants and fragments thereof, to said toxins for delivering the toxin to specific locations in a cell, to specific tissues, and/or to specific species. Such bifunctional antibodies are known in the art, though a review describing additional advantageous fusions, including citations for methods of production, can be found in P. J. Hudson, Curr. Opp. In. Imm. 11:548–557, (1999); this publication, in addition to the references cited therein, are hereby incorporated by reference in their entirety herein. In this context, the term "toxin" may be expanded to include any heterologous protein, a small molecule, radionucleotides, cytotoxic drugs, liposomes, adhesion molecules, glycoproteins, ligands, cell or tissue-specific ligands, enzymes, of bioactive agents, biological response modifiers, anti-fungal agents, hormones, steroids, vitamins, peptides, peptide analogs, anti-allergenic agents, anti-tubercular agents, anti-viral agents, antibiotics, anti-protozoan agents, chelates, radioactive particles, radioactive ions, X-ray contrast agents, monoclonal antibodies, polyclonal antibodies and genetic material. In view of the present disclosure, one skilled in the art could determine whether any particular "toxin" could be used in the compounds of the present invention. Examples of suitable "toxins" listed above are exemplary only and are not intended to limit the "toxins" that may be used in the present invention.

Thus, any of these above fusions can be engineered using the polynucleotides or the polypeptides of the present invention.

Vectors, Host Cells, and Protein Production

The present invention also relates to vectors containing the polynucleotide of the present invention, host cells, and the production of polypeptides by recombinant techniques. The vector may be, for example, a phage, plasmid, viral, or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The polynucleotide insert should be operatively linked to an appropriate promoter, such as the phage lambda PL promoter, the E. coli lac, trp, phoA and tac promoters, the SV40 early and late promoters and promoters of retroviral LTRs, to name a few. Other suitable promoters will be known to the skilled artisan. The expression constructs will further contain sites for transcription initiation, termination, and, in the transcribed region, a ribosome binding site for translation. The coding portion of the transcripts expressed by the constructs will preferably include a translation initiating codon at the beginning and a termination codon (UAA, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as *E. coli*, Streptomyces and *Salmonella typhimurium* cells; fungal cells, such as yeast cells (e.g., *Saccharomyces cerevisiae* or *Pichia pastoris* (ATCC Accession No. 201178)); insect cells such as Drosophila S2 and Spodoptera Sf9 cells; animal cells such as CHO, COS, 293, and Bowes melanoma cells; and plant cells. Appropriate culture mediums and conditions for the above-described host cells are known in the art.

Among vectors preferred for use in bacteria include pQE70, pQE60 and pQE-9, available from QIAGEN, Inc.; pBluescript vectors, Phagescript vectors, pNH8A, pNH16a, pNH18A, pNH46A, available from Stratagene Cloning Systems, Inc.; and ptrc99a, pKK223-3, pKK233-3, pDR540, pRIT5 available from Pharmacia Biotech, Inc. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to pYES2, pYD1, pTEF1/Zeo, pYES2/GS, pPICZ, pGAPZ, pGAPZalph, pPIC9, pPIC3.5, pHIL-D2, pHIL-S1, pPIC3.5K, pPIC9K, and PA0815 (all available from Invitrogen, Carlsbad, Calif.). Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection, or other methods. Such methods are described in many standard laboratory manuals, such as Davis et al., Basic Methods In Molecular Biology (1986). It is specifically contemplated that the polypeptides of the present invention may in fact be expressed by a host cell lacking a recombinant vector.

A polypeptide of this invention can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

Polypeptides of the present invention, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In one embodiment, the yeast *Pichia pastoris* is used to express the polypeptide of the present invention in a eukaryotic system. *Pichia pastoris* is a methylotrophic yeast which can metabolize methanol as its sole carbon source. A main step in the methanol metabolization pathway is the oxidation of methanol to formaldehyde using O2. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for O2. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 30% of the total soluble protein in *Pichia pastoris*. See, Ellis, S. B., et al., Mol. Cell. Biol. 5:1111–21 (1985); Koutz, P. J, et al., Yeast 5:167–77 (1989); Tschopp, J. F., et al., Nucl. Acids Res. 15:3859–76 (1987). Thus, a heterologous coding sequence, such as, for example, a polynucleotide of the present invention, under the transcriptional regulation of all or part of the AOX1 regulatory sequence is expressed at exceptionally high levels in Pichia yeast grown in the presence of methanol.

In one example, the plasmid vector pPIC9K is used to express DNA encoding a polypeptide of the invention, as set forth herein, in a Pichea yeast system essentially as described in "Pichia Protocols: Methods in Molecular Biology," D. R. Higgins and J. Cregg, eds. The Humana Press, Totowa, N.J., 1998. This expression vector allows expression and secretion of a protein of the invention by virtue of the strong AOX1 promoter linked to the Pichia pastoris alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG, as required.

In another embodiment, high-level expression of a heterologous coding sequence, such as, for example, a polynucleotide of the present invention, may be achieved by cloning the heterologous polynucleotide of the invention into an expression vector such as, for example, pGAPZ or pGAPZalpha, and growing the yeast culture in the absence of methanol.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., coding sequence), and/or to include genetic material (e.g., heterologous polynucleotide sequences) that is operably associated with the polynucleotides of the invention, and which activates, alters, and/or amplifies endogenous polynucleotides. For example, techniques known in the art may be used to operably associate heterologous control regions (e.g., promoter and/or enhancer) and endogenous polynucleotide sequences via homologous recombination, resulting in the formation of a new transcription unit (see, e.g., U.S. Pat. No. 5,641,670, issued Jun. 24, 1997; U.S. Pat. No. 5,733,761, issued Mar. 31, 1998; International Publication No. WO 96/29411, published Sep. 26, 1996; International Publication No. WO 94/12650, published Aug. 4, 1994; Koller et al., Proc. Natl. Acad. Sci. USA 86:8932–8935 (1989); and Zijlstra et al., Nature 342:435–438 (1989), the disclosures of each of which are incorporated by reference in their entireties).

In addition, polypeptides of the invention can be chemically synthesized using techniques known in the art (e.g., see Creighton, 1983, Proteins: Structures and Molecular Principles, W.H. Freeman & Co., N.Y., and Hunkapiller et al., Nature, 310:105–111 (1984)). For example, a polypeptide corresponding to a fragment of a polypeptide sequence of the invention can be synthesized by use of a peptide synthesizer. Furthermore, if desired, nonclassical amino acids or chemical amino acid analogs can be introduced as a substitution or addition into the polypeptide sequence. Nonclassical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

The invention encompasses polypeptides which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited, to specific chemical cleavage by cyanogen bromide, trypsin, chymotrypsin, papain, V8 protease, NaBH4; acetylation, formylation, oxidation, reduction; metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of prokaryotic host cell expression. The polypeptides may also be modified with a detectable label, such as an enzymatic, fluorescent, isotopic or affinity label to allow for detection and isolation of the protein, the addition of epitope tagged peptide fragments (e.g., FLAG, HA, GST, thioredoxin, maltose binding protein, etc.), attachment of affinity tags such as biotin and/or streptavidin, the covalent attachment of chemical moieties to the amino acid backbone, N- or C-terminal processing of the polypeptides ends (e.g., proteolytic processing), deletion of the N-terminal methionine residue, etc.

Also provided by the invention are chemically modified derivatives of the polypeptides of the invention which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The invention further encompasses chemical derivitization of the polypeptides of the present invention, preferably where the chemical is a hydrophilic polymer residue. Exemplary hydrophilic polymers, including derivatives, may be those that include polymers in which the repeating units contain one or more hydroxy groups (polyhydroxy polymers), including, for example, poly(vinyl alcohol); polymers in which the repeating units contain one or more amino groups (polyamine polymers), including, for example, peptides, polypeptides, proteins and lipoproteins, such as albumin and natural lipoproteins; polymers in which the repeating units contain one or more carboxy groups (polycarboxy polymers), including, for example, carboxymethylcellulose, alginic acid and salts thereof, such as sodium and calcium alginate, glycosaminoglycans and salts thereof, including salts of hyaluronic acid, phosphorylated and sulfonated derivatives of carbohydrates, genetic material, such as interleukin-2 and interferon, and phosphorothioate oligomers; and polymers in which the repeating units contain one or more saccharide moieties (polysaccharide polymers), including, for example, carbohydrates.

The molecular weight of the hydrophilic polymers may vary, and is generally about 50 to about 5,000,000, with polymers having a molecular weight of about 100 to about 50,000 being preferred. The polymers may be branched or unbranched. More preferred polymers have a molecular weight of about 150 to about 10,000, with molecular weights of 200 to about 8,000 being even more preferred.

For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog).

Additional preferred polymers which may be used to derivatize polypeptides of the invention, include, for example, poly(ethylene glycol) (PEG), poly(vinylpyrrolidine), polyoxomers, polysorbate and poly(vinyl alcohol), with PEG polymers being particularly preferred. Preferred among the PEG polymers are PEG polymers having a molecular weight of from about 100 to about 10,000. More preferably, the PEG polymers have a molecular weight of from about 200 to about 8,000, with PEG 2,000, PEG 5,000 and PEG 8,000, which have molecular weights of 2,000, 5,000 and 8,000, respectively, being even more preferred. Other suitable hydrophilic polymers, in addition to those exemplified above, will be readily apparent to one skilled in the art based on the present disclosure. Generally, the polymers used may include polymers that can be attached to the polypeptides of the invention via alkylation or acylation reactions.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028–1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

One may specifically desire proteins chemically modified at the N-terminus. Using polyethylene glycol as an illustration of the present composition, one may select from a variety of polyethylene glycol molecules (by molecular weight, branching, etc.), the proportion of polyethylene glycol molecules to protein (polypeptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective proteins chemically modified at the N-terminus modification may be accomplished by reductive alkylation which exploits differential reactivity of different types of primary amino groups (lysine versus the N-terminus) available for derivatization in a particular protein. Under the appropriate reaction conditions, substantially selective derivatization of the protein at the N-terminus with a carbonyl group containing polymer is achieved.

As with the various polymers exemplified above, it is contemplated that the polymeric residues may contain functional groups in addition, for example, to those typically involved in linking the polymeric residues to the polypeptides of the present invention. Such functionalities include, for example, carboxyl, amine, hydroxy and thiol groups. These functional groups on the polymeric residues can be further reacted, if desired, with materials that are generally reactive with such functional groups and which can assist in targeting specific tissues in the body including, for example, diseased tissue. Exemplary materials which can be reacted with the additional functional groups include, for example, proteins, including antibodies, carbohydrates, peptides, glycopeptides, glycolipids, lectins, and nucleosides.

In addition to residues of hydrophilic polymers, the chemical used to derivatize the polypeptides of the present invention can be a saccharide residue. Exemplary saccharides which can be derived include, for example, monosaccharides or sugar alcohols, such as erythrose, threose, ribose, arabinose, xylose, lyxose, fructose, sorbitol, mannitol and sedoheptulose, with preferred monosaccharides being fructose, mannose, xylose, arabinose, mannitol and sorbitol; and disaccharides, such as lactose, sucrose, maltose and cellobiose. Other saccharides include, for example, inositol and ganglioside head groups. Other suitable saccharides, in addition to those exemplified above, will be readily apparent to one skilled in the art based on the present disclosure. Generally, saccharides which may be used for derivitization include saccharides that can be attached to the polypeptides of the invention via alkylation or acylation reactions.

Moreover, the invention also encompasses derivitization of the polypeptides of the present invention, for example, with lipids (including cationic, anionic, polymerized, charged, synthetic, saturated, unsaturated, and any combination of the above, etc.). stabilizing agents.

The invention encompasses derivitization of the polypeptides of the present invention, for example, with compounds that may serve a stabilizing function (e.g., to increase the polypeptides half-life in solution, to make the polypeptides more water soluble, to increase the polypeptides hydrophilic or hydrophobic character, etc.). Polymers useful as stabilizing materials may be of natural, semi-synthetic (modified natural) or synthetic origin. Exemplary natural polymers include naturally occurring polysaccharides, such as, for example, arabinans, fructans, fucans, galactans, galacturonans, glucans, mannans, xylans (such as, for example, inulin), levan, fucoidan, carrageenan, galatocarolose, pectic acid, pectins, including amylose, pullulan, glycogen, amylopectin, cellulose, dextran, dextrin, dextrose, glucose, polyglucose, polydextrose, pustulan, chitin, agarose, keratin, chondroitin, dermatan, hyaluronic acid, alginic acid, xanthin gum, starch and various other natural homopolymer or heteropolymers, such as those containing one or more of the following aldoses, ketoses, acids or amines: erythose, threose, ribose, arabinose, xylose, lyxose, allose, altrose, glucose, dextrose, mannose, gulose, idose, galactose, talose, erythrulose, ribulose, xylulose, psicose, fructose, sorbose, tagatose, mannitol, sorbitol, lactose, sucrose, trehalose, maltose, cellobiose, glycine, serine, threonine, cysteine, tyrosine, asparagine, glutamine, aspartic acid, glutamic acid, lysine, arginine, histidine, glucuronic acid, gluconic acid, glucaric acid, galacturonic acid, mannuronic acid, glucosamine, galactosamine, and neuraminic acid, and naturally occurring derivatives thereof Accordingly, suitable polymers include, for example, proteins, such as albumin, polyalginates, and polylactide-coglycolide polymers. Exemplary semi-synthetic polymers include carboxymethylcellulose, hydroxymethylcellulose, hydroxypropylmethylcellulose, methylcellulose, and methoxycellulose. Exemplary synthetic polymers include polyphosphazenes, hydroxyapatites, fluoroapatite polymers, polyethylenes (such as, for example, polyethylene glycol (including for example, the class of compounds referred to as Pluronics.RTM., commercially available from BASF, Parsippany, N.J.), polyoxyethylene and polyethylene terephthlate), polypropylenes (such as, for example, polypropylene glycol), polyurethanes (such as, for example, polyvinyl alcohol (PVA), polyvinyl chloride and polyvinylpyrrolidone), polyamides including nylon, polystyrene, polylactic acids, fluorinated hydrocarbon polymers, fluorinated carbon polymers (such as, for example, polytetrafluoroethylene), acrylate, methacrylate, and polymethylmethacrylate, and derivatives thereof. Methods for the preparation of derivatized polypeptides of the invention which employ polymers as stabilizing compounds will be readily apparent to one skilled in the art, in view of the present disclosure, when coupled with information known in the art, such as that described and referred to in Unger, U.S. Pat. No. 5,205,290, the disclosure of which is hereby incorporated by reference herein in its entirety.

Moreover, the invention encompasses additional modifications of the polypeptides of the present invention. Such additional modifications are known in the art, and are specifically provided, in addition to methods of derivitization, etc., in U.S. Pat. No. 6,028,066, which is hereby incorporated in its entirety herein.

The polypeptides of the invention may be in monomers or multimers (i.e., dimers, trimers, tetramers and higher multimers). Accordingly, the present invention relates to monomers and multimers of the polypeptides of the invention, their preparation, and compositions (preferably, Therapeutics) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only polypeptides corresponding to the amino acid sequence of SEQ ID NO:2 or encoded by the cDNA contained in a deposited clone (including fragments, variants, splice variants, and fusion proteins, corresponding to these polypeptides as described herein). These homomers may contain polypeptides having identical or different amino acid sequences. In a specific embodiment, a homomer of the invention is a multimer containing only polypeptides having an identical amino acid sequence. In another specific embodiment, a homomer of the invention is a multimer containing polypeptides having different amino acid sequences. In specific embodiments, the multimer of the invention is a homodimer (e.g., containing polypeptides having identical or different amino acid sequences) or a homotrimer (e.g., containing polypeptides having identical and/or different amino acid sequences). In additional embodiments, the homomeric multimer of the invention is at least a homodimer, at least a homotrimer, or at least a homotetramer.

As used herein, the term heteromer refers to a multimer containing one or more heterologous polypeptides (i.e., polypeptides of different proteins) in addition to the polypeptides of the invention. In a specific embodiment, the multimer of the invention is a heterodimer, a heterotrimer, or a heterotetramer. In additional embodiments, the heteromeric multimer of the invention is at least a heterodimer, at least a heterotrimer, or at least a heterotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when polypeptides of the invention contact one another in solution. In another embodiment, heteromultimers of the invention, such as, for example, heterotrimers or heterotetramers, are formed when polypeptides of the invention contact antibodies to the polypeptides of the invention (including antibodies to the heterologous polypeptide sequence in a fusion protein of the invention) in solution. In other embodiments, multimers of the invention are formed by covalent associations with and/or between the polypeptides of the invention. Such covalent associations may involve one or more amino acid residues contained in the polypeptide sequence (e.g., that recited in the sequence listing, or contained in the polypeptide encoded by a deposited clone). In one instance, the covalent associations are cross-linking between cysteine residues located within the polypeptide sequences which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a fusion protein of the invention.

In one example, covalent associations are between the heterologous sequence contained in a fusion protein of the invention (see, e.g., U.S. Pat. No. 5,478,925). In a specific example, the covalent associations are between the heterologous sequence contained in an Fc fusion protein of the invention (as described herein). In another specific example, covalent associations of fusion proteins of the invention are between heterologous polypeptide sequence from another protein that is capable of forming covalently associated multimers, such as for example, osteoprotegerin (see, e.g., International Publication NO: WO 98/49305, the contents of which are herein incorporated by reference in its entirety). In another embodiment, two or more polypeptides of the invention are joined through peptide linkers. Examples include those peptide linkers described in U.S. Pat. No. 5,073,627 (hereby incorporated by reference). Proteins comprising multiple polypeptides of the invention separated by peptide linkers may be produced using conventional recombinant DNA technology.

Another method for preparing multimer polypeptides of the invention involves use of polypeptides of the invention fused to a leucine zipper or isoleucine zipper polypeptide sequence. Leucine zipper and isoleucine zipper domains are polypeptides that promote multimerization of the proteins in which they are found. Leucine zippers were originally identified in several DNA-binding proteins (Landschulz et al., Science 240:1759, (1988)), and have since been found in a variety of different proteins. Among the known leucine zippers are naturally occurring peptides and derivatives thereof that dimerize or trimerize. Examples of leucine zipper domains suitable for producing soluble multimeric proteins of the invention are those described in PCT application WO 94/10308, hereby incorporated by reference. Recombinant fusion proteins comprising a polypeptide of the invention fused to a polypeptide sequence that dimerizes or trimerizes in solution are expressed in suitable host cells, and the resulting soluble multimeric fusion protein is recovered from the culture supernatant using techniques known in the art.

Trimeric polypeptides of the invention may offer the advantage of enhanced biological activity. Preferred leucine zipper moieties and isoleucine moieties are those that preferentially form trimers. One example is a leucine zipper derived from lung surfactant protein D (SPD), as described in Hoppe et al. (FEBS Letters 344:191, (1994)) and in U.S. patent application Ser. No. 08/446,922, hereby incorporated by reference. Other peptides derived from naturally occurring trimeric proteins may be employed in preparing trimeric polypeptides of the invention.

In another example, proteins of the invention are associated by interactions between Flag® polypeptide sequence contained in fusion proteins of the invention containing Flag® polypeptide sequence. In a further embodiment, associations proteins of the invention are associated by interactions between heterologous polypeptide sequence contained in Flag® fusion proteins of the invention and anti-Flag® antibody.

The multimers of the invention may be generated using chemical techniques known in the art. For example, polypeptides desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more intermolecule cross-links between the cysteine residues located within the sequence of the polypeptides desired to be contained in the multimer (see, e.g., U.S. Pat. No. 5,478,925, which is herein incorporated by reference in its entirety). Further, polypeptides of the invention may be routinely modified by the addition of cysteine or biotin to the C terminus or N-terminus of the polypeptide and techniques known in the art may be applied to generate multimers containing one or more of these modified polypeptides (see, e.g., U.S. Pat. No. 5,478,925, which is herein incorporated by reference in its entirety). Additionally, techniques known in the art may be applied to generate liposomes containing the polypeptide components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, polypeptides contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain (or hydrophobic or signal peptide) and which can be incorporated by membrane reconstitution techniques into liposomes (see, e.g., U.S. Pat. No. 5,478,925, which is herein incorporated by reference in its entirety).

In addition, the polynucleotide insert of the present invention could be operatively linked to "artificial" or chimeric promoters and transcription factors. Specifically, the artificial promoter could comprise, or alternatively consist, of any combination of cis-acting DNA sequence elements that are recognized by trans-acting transcription factors. Preferably, the cis acting DNA sequence elements and trans-acting transcription factors are operable in mammals. Further, the trans-acting transcription factors of such "artificial" promoters could also be "artificial" or chimeric in design themselves and could act as activators or repressors to said "artificial" promoter.

Uses of the Polynucleotides

Each of the polynucleotides identified herein can be used in numerous ways as reagents. The following description should be considered exemplary and utilizes known techniques.

The polynucleotides of the present invention are useful for chromosome identification. There exists an ongoing need to identify new chromosome markers, since few chromosome marking reagents, based on actual sequence data (repeat polymorphisms), are presently available. Each polynucleotide of the present invention can be used as a chromosome marker.

Briefly, sequences can be mapped to chromosomes by preparing PCR primers (preferably 15–25 bp) from the sequences shown in SEQ ID NO:1. Primers can be selected using computer analysis so that primers do not span more than one predicted exon in the genomic DNA. These primers are then used for PCR screening of somatic cell hybrids containing individual human chromosomes. Only those hybrids containing the human gene corresponding to the SEQ ID NO:1 will yield an amplified fragment.

Similarly, somatic hybrids provide a rapid method of PCR mapping the polynucleotides to particular chromosomes. Three or more clones can be assigned per day using a single thermal cycler. Moreover, sublocalization of the polynucleotides can be achieved with panels of specific chromosome fragments. Other gene mapping strategies that can be used include in situ hybridization, prescreening with labeled flow-sorted chromosomes, and preselection by hybridization to construct chromosome specific-cDNA libraries.

Precise chromosomal location of the polynucleotides can also be achieved using fluorescence in situ hybridization (FISH) of a metaphase chromosomal spread. This technique uses polynucleotides as short as 500 or 600 bases; however, polynucleotides 2,000–4,000 bp are preferred. For a review of this technique, see Verma et al., "Human Chromosomes: a Manual of Basic Techniques," Pergamon Press, New York (1988).

For chromosome mapping, the polynucleotides can be used individually (to mark a single chromosome or a single site on that chromosome) or in panels (for marking multiple sites and/or multiple chromosomes). Preferred polynucleotides correspond to the noncoding regions of the cDNAs because the coding sequences are more likely conserved within gene families, thus increasing the chance of cross hybridization during chromosomal mapping.

Once a polynucleotide has been mapped to a precise chromosomal location, the physical position of the polynucleotide can be used in linkage analysis. Linkage analysis establishes coinheritance between a chromosomal location and presentation of a particular disease. Disease mapping data are known in the art. Assuming 1 megabase mapping resolution and one gene per 20 kb, a cDNA precisely localized to a chromosomal region associated with the disease could be one of 50–500 potential causative genes.

Thus, once coinheritance is established, differences in the polynucleotide and the corresponding gene between affected and unaffected organisms can be examined. First, visible structural alterations in the chromosomes, such as deletions or translocations, are examined in chromosome spreads or by PCR. If no structural alterations exist, the presence of point mutations are ascertained. Mutations observed in some or all affected organisms, but not in normal organisms, indicates that the mutation may cause the disease. However, complete sequencing of the polypeptide and the corresponding gene from several normal organisms is required to distinguish the mutation from a polymorphism. If a new polymorphism is identified, this polymorphic polypeptide can be used for further linkage analysis.

Furthermore, increased or decreased expression of the gene in affected organisms as compared to unaffected organisms can be assessed using polynucleotides of the present invention. Any of these alterations (altered expression, chromosomal rearrangement, or mutation) can be used as a diagnostic or prognostic marker.

Thus, the invention also provides a diagnostic method useful during diagnosis of a disorder, involving measuring the expression level of polynucleotides of the present invention in cells or body fluid from an organism and comparing the measured gene expression level with a standard level of polynucleotide expression level, whereby an increase or decrease in the gene expression level compared to the standard is indicative of a disorder.

By "measuring the expression level of a polynucleotide of the present invention" is intended qualitatively or quantitatively measuring or estimating the level of the polypeptide of the present invention or the level of the mRNA encoding the polypeptide in a first biological sample either directly (e.g., by determining or estimating absolute protein level or mRNA level) or relatively (e.g., by comparing to the polypeptide level or mRNA level in a second biological sample). Preferably, the polypeptide level or mRNA level in the first biological sample is measured or estimated and compared to a standard polypeptide level or mRNA level, the standard being taken from a second biological sample obtained from an individual not having the disorder or being determined by averaging levels from a population of organisms not having a disorder. As will be appreciated in the art, once a standard polypeptide level or mRNA level is known, it can be used repeatedly as a standard for comparison.

By "biological sample" is intended any biological sample obtained from an organism, body fluids, cell line, tissue culture, or other source which contains the polypeptide of the present invention or mRNA. As indicated, biological samples include body fluids (such as the following non-limiting examples, sputum, amniotic fluid, urine, saliva, breast milk, secretions, interstitial fluid, blood, serum, spinal fluid, etc.) which contain the polypeptide of the present invention, and other tissue sources found to express the polypeptide of the present invention. Methods for obtaining tissue biopsies and body fluids from organisms are well known in the art. Where the biological sample is to include mRNA, a tissue biopsy is the preferred source.

The method(s) provided above may Preferably be applied in a diagnostic method and/or kits in which polynucleotides and/or polypeptides are attached to a solid support. In one exemplary method, the support may be a "gene chip" or a "biological chip" as described in U.S. Pat. Nos. 5,837,832, 5,874,219, and 5,856,174. Further, such a gene chip with polynucleotides of the present invention attached may be used to identify polymorphisms between the polynucleotide sequences, with polynucleotides isolated from a test subject. The knowledge of such polymorphisms (i.e. their location, as well as, their existence) would be beneficial in identifying disease loci for many disorders, including proliferative diseases and conditions. Such a method is described in U.S. Pat. Nos. 5,858,659 and 5,856,104. The U.S. Patents referenced supra are hereby incorporated by reference in their entirety herein.

The present invention encompasses polynucleotides of the present invention that are chemically synthesized, or reproduced as peptide nucleic acids (PNA), or according to other methods known in the art. The use of PNAs would serve as the preferred form if the polynucleotides are incorporated onto a solid support, or gene chip. For the purposes of the present invention, a peptide nucleic acid (PNA) is a polyamide type of DNA analog and the monomeric units for adenine, guanine, thymine and cytosine are available commercially (Perceptive Biosystems). Certain components of DNA, such as phosphorus, phosphorus oxides, or deoxyribose derivatives, are not present in PNAs. As disclosed by P. E. Nielsen, M. Egholm, R. H. Berg and O. Buchardt, Science 254, 1497 (1991); and M. Egholm, O. Buchardt, L. Christensen, C. Behrens, S. M. Freier, D. A. Driver, R. H. Berg, S. K. Kim, B. Norden, and P. E. Nielsen, Nature 365, 666 (1993), PNAs bind specifically and tightly to complementary DNA strands and are not degraded by nucleases. In fact, PNA binds more strongly to DNA than DNA itself does. This is probably because there is no electrostatic repulsion between the two strands, and also the polyamide backbone is more flexible. Because of this, PNA/DNA duplexes bind under a wider range of stringency conditions than DNA/DNA duplexes, making it easier to perform multiplex hybridization. Smaller probes can be used than with DNA due to the stronger binding characteristics of PNA:DNA hybrids. In addition, it is more likely that single base mismatches can be determined with PNA/DNA hybridization because a single mismatch in a PNA/DNA 15-mer lowers the melting point (T.sub.m) by 8°–20° C., vs. 4°–16° C. for the DNA/DNA 15-mer duplex. Also, the absence of charge groups in PNA means that hybridization can be done at low ionic strengths and reduce possible interference by salt during the analysis.

In addition to the foregoing, a polynucleotide can be used to control gene expression through triple helix formation or antisense DNA or RNA. Antisense techniques are discussed, for example, in Okano, J. Neurochem. 56: 560 (1991); "Oligodeoxynucleotides as Antisense Inhibitors of Gene Expression", CRC Press, Boca Raton, Fla. (1988). Triple helix formation is discussed in, for instance Lee et al., Nucleic Acids Research 6: 3073 (1979); Cooney et al., Science 241: 456 (1988); and Dervan et al., Science 251: 1360 (1991). Both methods rely on binding of the polynucleotide to a complementary DNA or RNA. For these techniques, preferred polynucleotides are usually oligonucleotides 20 to 40 bases in length and complementary to either the region of the gene involved in transcription (triple helix—see Lee et al., Nucl. Acids Res. 6:3073 (1979); Cooney et al., Science 241:456 (1988); and Dervan et al., Science 251:1360 (1991) ) or to the mRNA itself (antisense—Okano, J. Neurochem. 56:560 (1991); Oligodeoxynucleotides as Antisense Inhibitors of Gene Expression, CRC Press, Boca Raton, Fla. (1988).) Triple helix formation optimally results in a shut-off of RNA transcription from DNA, while antisense RNA hybridization blocks translation of an mRNA molecule into polypeptide. Both techniques are effective in model systems, and the information disclosed herein can be used to design antisense or triple helix polynucleotides in an effort to treat or prevent disease.

The present invention encompasses the addition of a nuclear localization signal, operably linked to the 5' end, 3' end, or any location therein, to any of the oligonucleotides, antisense oligonucleotides, triple helix oligonucleotides, ribozymes, PNA oligonucleotides, and/or polynucleotides, of the present invention. See, for example, G. Cutrona, et al., Nat. Biotech., 18:300–303, (2000); which is hereby incorporated herein by reference.

Polynucleotides of the present invention are also useful in gene therapy. One goal of gene therapy is to insert a normal gene into an organism having a defective gene, in an effort to correct the genetic defect. The polynucleotides disclosed in the present invention offer a means of targeting such genetic defects in a highly accurate manner. Another goal is to insert a new gene that was not present in the host genome, thereby producing a new trait in the host cell. In one example, polynucleotide sequences of the present invention may be used to construct chimeric RNA/DNA oligonucleotides corresponding to said sequences, specifically designed to induce host cell mismatch repair mechanisms in an organism upon systemic injection, for example (Bartlett, R. J., et al., Nat. Biotech, 18:615–622 (2000), which is hereby incorporated by reference herein in its entirety). Such RNA/DNA oligonucleotides could be designed to correct genetic defects in certain host strains, and/or to introduce desired phenotypes in the host (e.g., introduction of a specific polymorphism within an endogenous gene corresponding to a polynucleotide of the present invention that may ameliorate and/or prevent a disease symptom and/or disorder, etc.). Alternatively, the polynucleotide sequence of the present invention may be used to construct duplex oligonucleotides corresponding to said sequence, specifically designed to correct genetic defects in certain host strains, and/or to introduce desired phenotypes into the host (e.g., introduction of a specific polymorphism within an endogenous gene corresponding to a polynucleotide of the present invention that may ameliorate and/or prevent a disease symptom and/or disorder, etc). Such methods of using duplex oligonucleotides are known in the art and are encompassed by the present invention (see EP 1007712, which is hereby incorporated by reference herein in its entirety).

The polynucleotides are also useful for identifying organisms from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identifying personnel. This method does not suffer from the current limitations of "Dog Tags" which can be lost, switched, or stolen, making positive identification difficult. The polynucleotides of the present invention can be used as additional DNA markers for RFLP.

The polynucleotides of the present invention can also be used as an alternative to RFLP, by determining the actual base-by-base DNA sequence of selected portions of an organisms genome. These sequences can be used to prepare PCR primers for amplifying and isolating such selected DNA, which can then be sequenced. Using this technique, organisms can be identified because each organism will have a unique set of DNA sequences. Once an unique ID database is established for an organism, positive identification of that organism, living or dead, can be made from extremely small tissue samples. Similarly, polynucleotides of the present invention can be used as polymorphic markers, in addition to, the identification of transformed or non-transformed cells and/or tissues.

There is also a need for reagents capable of identifying the source of a particular tissue. Such need arises, for example, when presented with tissue of unknown origin. Appropriate reagents can comprise, for example, DNA probes or primers specific to particular tissue prepared from the sequences of the present invention. Panels of such reagents can identify tissue by species and/or by organ type. In a similar fashion, these reagents can be used to screen tissue cultures for contamination. Moreover, as mentioned above, such reagents can be used to screen and/or identify transformed and non-transformed cells and/or tissues.

In the very least, the polynucleotides of the present invention can be used as molecular weight markers on Southern gels, as diagnostic probes for the presence of a specific mRNA in a particular cell type, as a probe to "subtract-out" known sequences in the process of discovering novel polynucleotides, for selecting and making oligomers for attachment to a "gene chip" or other support, to raise anti-DNA antibodies using DNA immunization techniques, and as an antigen to elicit an immune response.

Uses of the Polypeptides

Each of the polypeptides identified herein can be used in numerous ways. The following description should be considered exemplary and utilizes known techniques.

A polypeptide of the present invention can be used to assay protein levels in a biological sample using antibody-based techniques. For example, protein expression in tissues can be studied with classical immunohistological methods. (Jalkanen, M., et al., J. Cell. Biol. 101:976–985 (1985); Jalkanen, M., et al., J. Cell . Biol. 105:3087–3096 (1987).) Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase, and radioisotopes, such as iodine (125I, 121I), carbon (14C), sulfur (35S), tritium (3H), indium (112In), and technetium (99mTc), and fluorescent labels, such as fluorescein and rhodamine, and biotin.

In addition to assaying protein levels in a biological sample, proteins can also be detected in vivo by imaging. Antibody labels or markers for in vivo imaging of protein include those detectable by X-radiography, NMR or ESR. For X-radiography, suitable labels include radioisotopes such as barium or cesium, which emit detectable radiation but are not overtly harmful to the subject. Suitable markers for NMR and ESR include those with a detectable characteristic spin, such as deuterium, which may be incorporated into the antibody by labeling of nutrients for the relevant hybridoma.

A protein-specific antibody or antibody fragment which has been labeled with an appropriate detectable imaging moiety, such as a radioisotope (for example, 131I, 112In, 99mTc), a radio-opaque substance, or a material detectable by nuclear magnetic resonance, is introduced (for example, parenterally, subcutaneously, or intraperitoneally) into the mammal. It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of 99mTc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).)

Thus, the invention provides a diagnostic method of a disorder, which involves (a) assaying the expression of a polypeptide of the present invention in cells or body fluid of an individual; (b) comparing the level of gene expression with a standard gene expression level, whereby an increase or decrease in the assayed polypeptide gene expression level compared to the standard expression level is indicative of a disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Moreover, polypeptides of the present invention can be used to treat, prevent, and/or diagnose disease. For example, patients can be administered a polypeptide of the present invention in an effort to replace absent or decreased levels of the polypeptide (e.g., insulin), to supplement absent or decreased levels of a different polypeptide (e.g., hemoglobin S for hemoglobin B, SOD, catalase, DNA repair proteins), to inhibit the activity of a polypeptide (e.g., an oncogene or tumor suppressor), to activate the activity of a polypeptide (e.g., by binding to a receptor), to reduce the activity of a membrane bound receptor by competing with it for free ligand (e.g., soluble TNF receptors used in reducing inflammation), or to bring about a desired response (e.g., blood vessel growth inhibition, enhancement of the immune response to proliferative cells or tissues).

Similarly, antibodies directed to a polypeptide of the present invention can also be used to treat, prevent, and/or diagnose disease. For example, administration of an antibody directed to a polypeptide of the present invention can bind and reduce overproduction of the polypeptide. Similarly, administration of an antibody can activate the polypeptide, such as by binding to a polypeptide bound to a membrane (receptor).

At the very least, the polypeptides of the present invention can be used as molecular weight markers on SDS-PAGE gels or on molecular sieve gel filtration columns using methods well known to those of skill in the art. Polypeptides can also be used to raise antibodies, which in turn are used to measure protein expression from a recombinant cell, as a way of assessing transformation of the host cell. Moreover, the polypeptides of the present invention can be used to test the following biological activities.

Gene Therapy Methods

Another aspect of the present invention is to gene therapy methods for treating or preventing disorders, diseases and conditions. The gene therapy methods relate to the introduction of nucleic acid (DNA, RNA and antisense DNA or RNA) sequences into an animal to achieve expression of a polypeptide of the present invention. This method requires a polynucleotide which codes for a polypeptide of the invention that operatively linked to a promoter and any other genetic elements necessary for the expression of the polypeptide by the target tissue. Such gene therapy and delivery techniques are known in the art, see, for example, WO90/11092, which is herein incorporated by reference.

Thus, for example, cells from a patient may be engineered with a polynucleotide (DNA or RNA) comprising a promoter operably linked to a polynucleotide of the invention ex vivo, with the engineered cells then being provided to a patient to be treated with the polypeptide. Such methods are well-known in the art. For example, see Belldegrun et al., J. Natl. Cancer Inst., 85:207–216 (1993); Ferrantini et al., Cancer Research, 53:107–1112 (1993); Ferrantini et al., J. Immunology 153: 4604–4615 (1994); Kaido, T., et al., Int. J. Cancer 60: 221–229 (1995); Ogura et al., Cancer Research 50: 5102–5106 (1990); Santodonato, et al., Human Gene Therapy 7:1–10 (1996); Santodonato, et al., Gene Therapy 4:1246–1255 (1997); and Zhang, et al., Cancer Gene Therapy 3: 31–38 (1996)), which are herein incorporated by reference. In one embodiment, the cells which are engineered are arterial cells. The arterial cells may be reintroduced into the patient through direct injection to the artery, the tissues surrounding the artery, or through catheter injection.

As discussed in more detail below, the polynucleotide constructs can be delivered by any method that delivers injectable materials to the cells of an animal, such as, injection into the interstitial space of tissues (heart, muscle, skin, lung, liver, and the like). The polynucleotide constructs may be delivered in a pharmaceutically acceptable liquid or aqueous carrier.

In one embodiment, the polynucleotide of the invention is delivered as a naked polynucleotide. The term "naked" polynucleotide, DNA or RNA refers to sequences that are free from any delivery vehicle that acts to assist, promote or facilitate entry into the cell, including viral sequences, viral particles, liposome formulations, lipofectin or precipitating agents and the like. However, the polynucleotides of the invention can also be delivered in liposome formulations and lipofectin formulations and the like can be prepared by methods well known to those skilled in the art. Such methods are described, for example, in U.S. Pat. Nos. 5,593,972, 5,589,466, and 5,580,859, which are herein incorporated by reference.

The polynucleotide vector constructs of the invention used in the gene therapy method are preferably constructs that will not integrate into the host genome nor will they contain sequences that allow for replication. Appropriate vectors include pWLNEO, pSV2CAT, pOG44, pXT1 and pSG available from Stratagene; pSVK3, pBPV, pMSG and pSVL available from Pharmacia; and pEF1/V5, pcDNA3.1, and pRc/CMV2 available from Invitrogen. Other suitable vectors will be readily apparent to the skilled artisan.

Any strong promoter known to those skilled in the art can be used for driving the expression of polynucleotide sequence of the invention. Suitable promoters include adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs; the b-actin promoter; and human growth hormone promoters. The promoter also may be the native promoter for the polynucleotides of the invention.

Unlike other gene therapy techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct of the invention can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular, fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked nucleic acid sequence injection, an effective dosage amount of DNA or RNA will be in the range of from about 0.05 mg/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration.

The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked DNA constructs can be delivered to arteries during angioplasty by the catheter used in the procedure.

The naked polynucleotides are delivered by any method known in the art, including, but not limited to, direct needle injection at the delivery site, intravenous injection, topical administration, catheter infusion, and so-called "gene guns". These delivery methods are known in the art.

The constructs may also be delivered with delivery vehicles such as viral sequences, viral particles, liposome formulations, lipofectin, precipitating agents, etc. Such methods of delivery are known in the art.

In certain embodiments, the polynucleotide constructs of the invention are complexed in a liposome preparation. Liposomal preparations for use in the instant invention include cationic (positively charged), anionic (negatively charged) and neutral preparations. However, cationic liposomes are particularly preferred because a tight charge complex can be formed between the cationic liposome and the polyanionic nucleic acid. Cationic liposomes have been shown to mediate intracellular delivery of plasmid DNA (Felgner et al., Proc. Natl. Acad. Sci. USA , 84:7413–7416 (1987), which is herein incorporated by reference); mRNA (Malone et al., Proc. Natl. Acad. Sci. USA , 86:6077–6081 (1989), which is herein incorporated by reference); and purified transcription factors (Debs et al., J. Biol. Chem . . . , 265:10189–10192 (1990), which is herein incorporated by reference), in functional form.

Cationic liposomes are readily available. For example, N[1-2,3-dioleyloxy)propyl]-N,N,N-triethylammonium (DOTMA) liposomes are particularly useful and are available under the trademark Lipofectin, from GIBCO BRL, Grand Island, N.Y. (See, also, Felgner et al., Proc. Natl. Acad. Sci. USA , 84:7413–7416 (1987), which is herein incorporated by reference). Other commercially available liposomes include transfectace (DDAB/DOPE) and DOTAP/DOPE (Boehringer).

Other cationic liposomes can be prepared from readily available materials using techniques well known in the art. See, e.g. PCT Publication NO: WO 90/11092 (which is herein incorporated by reference) for a description of the synthesis of DOTAP (1,2-bis(oleoyloxy)-3-(trimethylammonio)propane) liposomes. Preparation of DOTMA liposomes is explained in the literature, see, e.g., Feigner et al., Proc. Natl. Acad. Sci. USA, 84:7413–7417, which is herein incorporated by reference. Similar methods can be used to prepare liposomes from other cationic lipid materials.

Similarly, anionic and neutral liposomes are readily available, such as from Avanti Polar Lipids (Birmingham, Ala.), or can be easily prepared using readily available materials. Such materials include phosphatidyl, choline, cholesterol, phosphatidyl ethanolamine, dioleoylphosphatidyl choline (DOPC), dioleoylphosphatidyl glycerol (DOPG), dioleoylphoshatidyl ethanolamine (DOPE), among others. These materials can also be mixed with the DOTMA and DOTAP starting materials in appropriate ratios. Methods for making liposomes using these materials are well known in the art.

For example, commercially dioleoylphosphatidyl choline (DOPC), dioleoylphosphatidyl glycerol (DOPG), and dioleoylphosphatidyl ethanolamine (DOPE) can be used in various combinations to make conventional liposomes, with or without the addition of cholesterol. Thus, for example, DOPG/DOPC vesicles can be prepared by drying 50 mg each of DOPG and DOPC under a stream of nitrogen gas into a sonication vial. The sample is placed under a vacuum pump overnight and is hydrated the following day with deionized water. The sample is then sonicated for 2 hours in a capped vial, using a Heat Systems model 350 sonicator equipped with an inverted cup (bath type) probe at the maximum setting while the bath is circulated at 15EC. Alternatively, negatively charged vesicles can be prepared without sonication to produce multilamellar vesicles or by extrusion through nucleopore membranes to produce unilamellar vesicles of discrete size. Other methods are known and available to those of skill in the art.

The liposomes can comprise multilamellar vesicles (MLVs), small unilamellar vesicles (SUVs), or large unilamellar vesicles (LUVs), with SUVs being preferred. The various liposome-nucleic acid complexes are prepared using methods well known in the art. See, e.g., Straubinger et al., Methods of Immunology, 101:512–527 (1983), which is herein incorporated by reference. For example, MLVs containing nucleic acid can be prepared by depositing a thin film of phospholipid on the walls of a glass tube and subsequently hydrating with a solution of the material to be encapsulated. SUVs are prepared by extended sonication of MLVs to produce a homogeneous population of unilamellar liposomes. The material to be entrapped is added to a suspension of preformed MLVs and then sonicated. When using liposomes containing cationic lipids, the dried lipid film is resuspended in an appropriate solution such as sterile water or an isotonic buffer solution such as 10 mM Tris/NaCl, sonicated, and then the preformed liposomes are mixed directly with the DNA. The liposome and DNA form a very stable complex due to binding of the positively charged liposomes to the cationic DNA. SUVs find use with small nucleic acid fragments. LUVs are prepared by a number of methods, well known in the art. Commonly used methods include $Ca^{2+}$-EDTA chelation (Papahadjopoulos et al., Biochim. Biophys. Acta, 394:483 (1975); Wilson et al., Cell , 17:77 (1979)); ether injection (Deamer et al., Biochim. Biophys. Acta, 443:629 (1976); Ostro et al., Biochem. Biophys. Res. Commun., 76:836 (1977); Fraley et al., Proc. Natl. Acad. Sci. USA, 76:3348 (1979)); detergent dialysis (Enoch et al., Proc. Natl. Acad. Sci. USA , 76:145 (1979)); and reverse-phase evaporation (REV) (Fraley et al., J. Biol. Chem . . . , 255:10431 (1980); Szoka et al., Proc. Natl. Acad. Sci. USA , 75:145 (1978); Schaefer-Ridder et al., Science, 215:166 (1982)), which are herein incorporated by reference.

Generally, the ratio of DNA to liposomes will be from about 10:1 to about 1:10. Preferably, the ration will be from about 5:1 to about 1:5. More preferably, the ration will be about 3:1 to about 1:3. Still more preferably, the ratio will be about 1:1.

U.S. Pat. No. 5,676,954 (which is herein incorporated by reference) reports on the injection of genetic material, complexed with cationic liposomes carriers, into mice. U.S. Pat. Nos. 4,897,355, 4,946,787, 5,049,386, 5,459,127, 5,589,466, 5,693,622, 5,580,859, 5,703,055, and international publication NO: WO 94/9469 (which are herein incorporated by reference) provide cationic lipids for use in transfecting DNA into cells and mammals. U.S. Pat. Nos. 5,589,466, 5,693,622, 5,580,859, 5,703,055, and international publication NO: WO 94/9469 (which are herein incorporated by reference) provide methods for delivering DNA-cationic lipid complexes to mammals.

In certain embodiments, cells are engineered, ex vivo or in vivo, using a retroviral particle containing RNA which comprises a sequence encoding polypeptides of the invention. Retroviruses from which the retroviral plasmid vectors may be derived include, but are not limited to, Moloney Murine Leukemia Virus, spleen necrosis virus, Rous sarcoma Virus, Harvey Sarcoma Virus, avian leukosis virus, gibbon ape leukemia virus, human immunodeficiency virus, Myeloproliferative Sarcoma Virus, and mammary tumor virus.

The retroviral plasmid vector is employed to transduce packaging cell lines to form producer cell lines. Examples of packaging cells which may be transfected include, but are not limited to, the PE501, PA317, R-2, R-AM, PA12, T19-14X, VT-19-17-H2, RCRE, RCRIP, GP+E-86, GP+en-vAm12, and DAN cell lines as described in Miller, Human Gene Therapy, 1:5–14 (1990), which is incorporated herein by reference in its entirety. The vector may transduce the packaging cells through any means known in the art. Such means include, but are not limited to, electroporation, the use of liposomes, and CaPO4 precipitation. In one alternative, the retroviral plasmid vector may be encapsulated into a liposome, or coupled to a lipid, and then administered to a host.

The producer cell line generates infectious retroviral vector particles which include polynucleotide encoding polypeptides of the invention. Such retroviral vector particles then may be employed, to transduce eukaryotic cells, either in vitro or in vivo. The transduced eukaryotic cells will express polypeptides of the invention.

In certain other embodiments, cells are engineered, ex vivo or in vivo, with polynucleotides of the invention contained in an adenovirus vector. Adenovirus can be manipulated such that it encodes and expresses polypeptides of the invention, and at the same time is inactivated in terms of its ability to replicate in a normal lytic viral life cycle. Adenovirus expression is achieved without integration of the viral DNA into the host cell chromosome, thereby alleviating concerns about insertional mutagenesis. Furthermore, adenoviruses have been used as live enteric vaccines for many years with an excellent safety profile (Schwartzet al., Am. Rev. Respir. Dis., 109:233–238 (1974)). Finally, adenovirus mediated gene transfer has been demonstrated in a number of instances including transfer of alpha-1-antitrypsin and CFTR to the lungs of cotton rats (Rosenfeld et al., Science, 252:431–434 (1991); Rosenfeld et al., Cell, 68:143–155 (1992)). Furthermore, extensive studies to attempt to establish adenovirus as a causative agent in human cancer were uniformly negative (Green et al. Proc. Natl. Acad. Sci. USA, 76:6606 (1979)).

Suitable adenoviral vectors useful in the present invention are described, for example, in Kozarsky and Wilson, Curr. Opin. Genet. Devel., 3:499–503 (1993); Rosenfeld et al., Cell, 68:143–155 (1992); Engelhardt et al., Human Genet. Ther., 4:759–769 (1993); Yang et al., Nature Genet., 7:362–369 (1994); Wilson et al., Nature, 365:691–692 (1993); and U.S. Pat. No. 5,652,224, which are herein incorporated by reference. For example, the adenovirus vector Ad2 is useful and can be grown in human 293 cells. These cells contain the E1 region of adenovirus and constitutively express E1a and E1b, which complement the defective adenoviruses by providing the products of the genes deleted from the vector. In addition to Ad2, other varieties of adenovirus (e.g., Ad3, Ad5, and Ad7) are also useful in the present invention.

Preferably, the adenoviruses used in the present invention are replication deficient. Replication deficient adenoviruses require the aid of a helper virus and/or packaging cell line to form infectious particles. The resulting virus is capable of infecting cells and can express a polynucleotide of interest which is operably linked to a promoter, but cannot replicate in most cells. Replication deficient adenoviruses may be deleted in one or more of all or a portion of the following genes: E1a, E1b, E3, E4, E2a, or L1 through L5.

In certain other embodiments, the cells are engineered, ex vivo or in vivo, using an adeno-associated virus (AAV). AAVs are naturally occurring defective viruses that require helper viruses to produce infectious particles (Muzyczka, Curr. Topics in Microbiol. Immunol., 158:97 (1992)). It is also one of the few viruses that may integrate its DNA into non-dividing cells. Vectors containing as little as 300 base pairs of AAV can be packaged and can integrate, but space for exogenous DNA is limited to about 4.5 kb. Methods for producing and using such AAVs are known in the art. See, for example, U.S. Pat. Nos. 5,139,941, 5,173,414, 5,354,678, 5,436,146, 5,474,935, 5,478,745, and 5,589,377.

For example, an appropriate AAV vector for use in the present invention will include all the sequences necessary for DNA replication, encapsidation, and host-cell integration. The polynucleotide construct containing polynucleotides of the invention is inserted into the AAV vector using standard cloning methods, such as those found in Sambrook et al., Molecular Cloning: A Laboratory Manual, Cold Spring Harbor Press (1989). The recombinant AAV vector is then transfected into packaging cells which are infected with a helper virus, using any standard technique, including lipofection, electroporation, calcium phosphate precipitation, etc. Appropriate helper viruses include adenoviruses, cytomegaloviruses, vaccinia viruses, or herpes viruses. Once the packaging cells are transfected and infected, they will produce infectious AAV viral particles which contain the polynucleotide construct of the invention. These viral particles are then used to transduce eukaryotic cells, either ex vivo or in vivo. The transduced cells will contain the polynucleotide construct integrated into its genome, and will express the desired gene product.

Another method of gene therapy involves operably associating heterologous control regions and endogenous polynucleotide sequences (e.g. encoding the polypeptide sequence of interest) via homologous recombination (see, e.g., U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not normally expressed in the cells, or is expressed at a lower level than desired.

Polynucleotide constructs are made, using standard techniques known in the art, which contain the promoter with targeting sequences flanking the promoter. Suitable promoters are described herein. The targeting sequence is sufficiently complementary to an endogenous sequence to permit homologous recombination of the promoter-targeting sequence with the endogenous sequence. The targeting sequence will be sufficiently near the 5' end of the desired endogenous polynucleotide sequence so the promoter will be operably linked to the endogenous sequence upon homologous recombination.

The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter. The amplified promoter and targeting sequences are digested and ligated together.

The promoter-targeting sequence construct is delivered to the cells, either as naked polynucleotide, or in conjunction with transfection-facilitating agents, such as liposomes, viral sequences, viral particles, whole viruses, lipofection, precipitating agents, etc., described in more detail above. The P promoter-targeting sequence can be delivered by any method, included direct needle injection, intravenous injection, topical administration, catheter infusion, particle accelerators, etc. The methods are described in more detail below.

The promoter-targeting sequence construct is taken up by cells. Homologous recombination between the construct and the endogenous sequence takes place, such that an endogenous sequence is placed under the control of the promoter. The promoter then drives the expression of the endogenous sequence.

The polynucleotides encoding polypeptides of the present invention may be administered along with other polynucleotides encoding angiogenic proteins. Angiogenic proteins include, but are not limited to, acidic and basic fibroblast growth factors, VEGF-1, VEGF-2 (VEGF-C), VEGF-3 (VEGF-B), epidermal growth factor alpha and beta, platelet-derived endothelial cell growth factor, platelet-derived growth factor, tumor necrosis factor alpha, hepatocyte growth factor, insulin like growth factor, colony stimulating factor, macrophage colony stimulating factor, granulocyte/macrophage colony stimulating factor, and nitric oxide synthase.

Preferably, the polynucleotide encoding a polypeptide of the invention contains a secretory signal sequence that facilitates secretion of the protein. Typically, the signal sequence is positioned in the coding region of the polynucleotide to be expressed towards or at the 5' end of the coding region. The signal sequence may be homologous or heterologous to the polynucleotide of interest and may be homologous or heterologous to the cells to be transfected. Additionally, the signal sequence may be chemically synthesized using methods known in the art.

Any mode of administration of any of the above-described polynucleotides constructs can be used so long as the mode results in the expression of one or more molecules in an amount sufficient to provide a therapeutic effect. This includes direct needle injection, systemic injection, catheter infusion, biolistic injectors, particle accelerators (i.e., "gene guns"), gelfoam sponge depots, other commercially available depot materials, osmotic pumps (e.g., Alza minipumps), oral or suppositorial solid (tablet or pill) pharmaceutical formulations, and decanting or topical applications during surgery. For example, direct injection of naked calcium phosphate-precipitated plasmid into rat liver and rat spleen or a protein-coated plasmid into the portal vein has resulted in gene expression of the foreign gene in the rat livers. (Kaneda et al., Science, 243:375 (1989)).

A preferred method of local administration is by direct injection. Preferably, a recombinant molecule of the present invention complexed with a delivery vehicle is administered by direct injection into or locally within the area of arteries. Administration of a composition locally within the area of arteries refers to injecting the composition centimeters and preferably, millimeters within arteries.

Another method of local administration is to contact a polynucleotide construct of the present invention in or around a surgical wound. For example, a patient can undergo surgery and the polynucleotide construct can be coated on the surface of tissue inside the wound or the construct can be injected into areas of tissue inside the wound.

Therapeutic compositions useful in systemic administration, include recombinant molecules of the present invention complexed to a targeted delivery vehicle of the present invention. Suitable delivery vehicles for use with systemic administration comprise liposomes comprising ligands for targeting the vehicle to a particular site.

Preferred methods of systemic administration, include intravenous injection, aerosol, oral and percutaneous (topical) delivery. Intravenous injections can be performed using methods standard in the art. Aerosol delivery can also be performed using methods standard in the art (see, for example, Stribling et al., Proc. Natl. Acad. Sci. USA, 189:11277–11281(1992), which is incorporated herein by reference). Oral delivery can be performed by complexing a polynucleotide construct of the present invention to a carrier capable of withstanding degradation by digestive enzymes in the gut of an animal. Examples of such carriers, include plastic capsules or tablets, such as those known in the art. Topical delivery can be performed by mixing a polynucleotide construct of the present invention with a lipophilic reagent (e.g., DMSO) that is capable of passing into the skin.

Determining an effective amount of substance to be delivered can depend upon a number of factors including, for example, the chemical structure and biological activity of the substance, the age and weight of the animal, the precise condition requiring treatment and its severity, and the route of administration. The frequency of treatments depends upon a number of factors, such as the amount of polynucleotide constructs administered per dose, as well as the health and history of the subject. The precise amount, number of doses, and timing of doses will be determined by the attending physician or veterinarian. Therapeutic compositions of the present invention can be administered to any animal, preferably to mammals and birds. Preferred mammals include humans, dogs, cats, mice, rats, rabbits sheep, cattle, horses and pigs, with humans being particularly preferred.

Biological Activities

The polynucleotides or polypeptides, or agonists or antagonists of the present invention can be used in assays to test for one or more biological activities. If these polynucleotides and polypeptides do exhibit activity in a particular assay, it is likely that these molecules may be involved in the diseases associated with the biological activity. Thus, the polynucleotides or polypeptides, or agonists or antagonists could be used to treat the associated disease.

Immune Activity

The polynucleotides or polypeptides, or agonists or antagonists of the present invention may be useful in treating, preventing, and/or diagnosing diseases, disorders, and/or conditions of the immune system, by activating or inhibiting the proliferation, differentiation, or mobilization (chemotaxis) of immune cells. Immune cells develop through a process called hematopoiesis, producing myeloid (platelets, red blood cells, neutrophils, and macrophages) and lymphoid (B and T lymphocytes) cells from pluripotent stem cells. The etiology of these immune diseases, disorders, and/or conditions may be genetic, somatic, such as cancer or some autoimmune diseases, disorders, and/or conditions, acquired (e.g., by chemotherapy or toxins), or infectious. Moreover, a polynucleotides or polypeptides, or agonists or antagonists of the present invention can be used as a marker or detector of a particular immune system disease or disorder.

A polynucleotides or polypeptides, or agonists or antagonists of the present invention may be useful in treating, preventing, and/or diagnosing diseases, disorders, and/or conditions of hematopoietic cells. A polynucleotides or polypeptides, or agonists or antagonists of the present invention could be used to increase differentiation and proliferation of hematopoietic cells, including the pluripotent stem cells, in an effort to treat or prevent those diseases, disorders, and/or conditions associated with a decrease in certain (or many) types hematopoietic cells. Examples of immunologic deficiency syndromes include, but are not limited to: blood protein diseases, disorders, and/or conditions (e.g. agammaglobulinemia, dysgammaglobulinemia), ataxia telangiectasia, common variable immunodeficiency, Digeorge Syndrome, HIV infection, HTLV-BLV infection, leukocyte adhesion deficiency syndrome, lymphopenia, phagocyte bactericidal dysfunction, severe combined immunodeficiency (SCIDs), Wiskott-Aldrich Disorder, anemia, thrombocytopenia, or hemoglobinuria.

Moreover, a polynucleotides or polypeptides, or agonists or antagonists of the present invention could also be used to modulate hemostatic (the stopping of bleeding) or thrombolytic activity (clot formation). For example, by increasing hemostatic or thrombolytic activity, a polynucleotides or polypeptides, or agonists or antagonists of the present invention could be used to treat or prevent blood coagulation diseases, disorders, and/or conditions (e.g., afibrinogenemia, factor deficiencies, arterial thrombosis, venous thrombosis, etc.), blood platelet diseases, disorders, and/or conditions (e.g. thrombocytopenia), or wounds resulting from trauma, surgery, or other causes. Alternatively, a polynucleotides or polypeptides, or agonists or antagonists of the present invention that can decrease hemostatic or thrombolytic activity could be used to inhibit or dissolve clotting. Polynucleotides or polypeptides, or agonists or antagonists of the present invention are may also be useful for the detection, prognosis, treatment, and/or prevention of heart attacks (infarction), strokes, scarring, fibrinolysis, uncontrolled bleeding, uncontrolled coagulation, uncontrolled complement fixation, and/or inflammation.

A polynucleotides or polypeptides, or agonists or antagonists of the present invention may also be useful in treating, preventing, and/or diagnosing autoimmune diseases, disorders, and/or conditions. Many autoimmune diseases, disorders, and/or conditions result from inappropriate recognition of self as foreign material by immune cells. This inappropriate recognition results in an immune response leading to the destruction of the host tissue. Therefore, the administration of a polynucleotides or polypeptides, or agonists or antagonists of the present invention that inhibits an immune response, particularly the proliferation, differentiation, or chemotaxis of T-cells, may be an effective therapy in preventing autoimmune diseases, disorders, and/or conditions.

Examples of autoimmune diseases, disorders, and/or conditions that can be treated, prevented, and/or diagnosed or detected by the present invention include, but are not limited to: Addison's Disease, hemolytic anemia, antiphospholipid syndrome, rheumatoid arthritis, dermatitis, allergic encephalomyelitis, glomerulonephritis, Goodpasture's Syndrome, Graves' Disease, Multiple Sclerosis, Myasthenia Gravis, Neuritis, Ophthalmia, Bullous Pemphigoid, Pemphigus, Polyendocrinopathies, Purpura, Reiter's Disease, Stiff-Man Syndrome, Autoimmune Thyroiditis, Systemic Lupus Erythematosus, Autoimmune Pulmonary Inflammation, Guillain-Barre Syndrome, insulin dependent diabetes mellitus, and autoimmune inflammatory eye disease.

Similarly, allergic reactions and conditions, such as asthma (particularly allergic asthma) or other respiratory problems, may also be treated, prevented, and/or diagnosed by polynucleotides or polypeptides, or agonists or antagonists of the present invention. Moreover, these molecules can be used to treat anaphylaxis, hypersensitivity to an antigenic molecule, or blood group incompatibility.

A polynucleotides or polypeptides, or agonists or antagonists of the present invention may also be used to treat, prevent, and/or diagnose organ rejection or graft-versus-host disease (GVHD). Organ rejection occurs by host immune cell destruction of the transplanted tissue through an immune response. Similarly, an immune response is also involved in GVHD, but, in this case, the foreign transplanted immune cells destroy the host tissues. The administration of a polynucleotides or polypeptides, or agonists or antagonists of the present invention that inhibits an immune response, particularly the proliferation, differentiation, or chemotaxis of T-cells, may be an effective therapy in preventing organ rejection or GVHD.

Similarly, a polynucleotides or polypeptides, or agonists or antagonists of the present invention may also be used to modulate inflammation. For example, the polypeptide or polynucleotide or agonists or antagonist may inhibit the proliferation and differentiation of cells involved in an inflammatory response. These molecules can be used to treat, prevent, and/or diagnose inflammatory conditions, both chronic and acute conditions, including chronic prostatitis, granulomatous prostatitis and malacoplakia, inflammation associated with infection (e.g., septic shock, sepsis, or systemic inflammatory response syndrome (SIRS)), ischemia-reperfusion injury, endotoxin lethality, arthritis, complement-mediated hyperacute rejection, nephritis, cytokine or chemokine induced lung injury, inflammatory bowel disease, Crohn's disease, or resulting from over production of cytokines (e.g., TNF or IL-1.)

Hyperproliferative Disorders

A polynucleotides or polypeptides, or agonists or antagonists of the invention can be used to treat, prevent, and/or diagnose hyperproliferative diseases, disorders, and/or conditions, including neoplasms. A polynucleotides or polypeptides, or agonists or antagonists of the present invention may inhibit the proliferation of the disorder through direct or indirect interactions. Alternatively, a polynucleotides or polypeptides, or agonists or antagonists of the present invention may proliferate other cells which can inhibit the hyperproliferative disorder.

For example, by increasing an immune response, particularly increasing antigenic qualities of the hyperproliferative disorder or by proliferating, differentiating, or mobilizing T-cells, hyperproliferative diseases, disorders, and/or conditions can be treated, prevented, and/or diagnosed. This immune response may be increased by either enhancing an existing immune response, or by initiating a new immune response. Alternatively, decreasing an immune response may also be a method of treating, preventing, and/or diagnosing hyperproliferative diseases, disorders, and/or conditions, such as a chemotherapeutic agent.

Examples of hyperproliferative diseases, disorders, and/or conditions that can be treated, prevented, and/or diagnosed by polynucleotides or polypeptides, or agonists or antagonists of the present invention include, but are not limited to neoplasms located in the: colon, abdomen, bone, breast, digestive system, liver, pancreas, peritoneum, endocrine glands (adrenal, parathyroid, pituitary, testicles, ovary, thymus, thyroid), eye, head and neck, nervous (central and peripheral), lymphatic system, pelvic, skin, soft tissue, spleen, thoracic, and urogenital.

Similarly, other hyperproliferative diseases, disorders, and/or conditions can also be treated, prevented, and/or diagnosed by a polynucleotides or polypeptides, or agonists or antagonists of the present invention. Examples of such hyperproliferative diseases, disorders, and/or conditions include, but are not limited to: hypergammaglobulinemia, lymphoproliferative diseases, disorders, and/or conditions, paraproteinernias, purpura, sarcoidosis, Sezary Syndrome, Waldenstron's Macroglobulinemia, Gaucher's Disease, histiocytosis, and any other hyperproliferative disease, besides neoplasia, located in an organ system listed above.

One preferred embodiment utilizes polynucleotides of the present invention to inhibit aberrant cellular division, by gene therapy using the present invention, and/or protein fusions or fragments thereof.

Thus, the present invention provides a method for treating or preventing cell proliferative diseases, disorders, and/or conditions by inserting into an abnormally proliferating cell a polynucleotide of the present invention, wherein said polynucleotide represses said expression.

Another embodiment of the present invention provides a method of treating or preventing cell-proliferative diseases, disorders, and/or conditions in individuals comprising administration of one or more active gene copies of the present invention to an abnormally proliferating cell or cells. In a preferred embodiment, polynucleotides of the present invention is a DNA construct comprising a recombinant expression vector effective in expressing a DNA sequence encoding said polynucleotides. In another preferred embodiment of the present invention, the DNA construct encoding the polynucleotides of the present invention is inserted into cells to be treated utilizing a retrovirus, or more Preferably an adenoviral vector (See G J. Nabel, et. al., PNAS 1999 96: 324–326, which is hereby incorporated by reference). In a most preferred embodiment, the viral vector is defective and will not transform non-proliferating cells, only proliferating cells. Moreover, in a preferred embodiment, the polynucleotides of the present invention inserted into proliferating cells either alone, or in combination with or fused to other polynucleotides, can then be modulated via an external stimulus (i.e. magnetic, specific small molecule, chemical, or drug administration, etc.), which acts upon the promoter upstream of said polynucleotides to induce expression of the encoded protein product. As such the beneficial therapeutic affect of the present invention may be expressly modulated (i.e. to increase, decrease, or inhibit expression of the present invention) based upon said external stimulus.

Polynucleotides of the present invention may be useful in repressing expression of oncogenic genes or antigens. By "repressing expression of the oncogenic genes" is intended the suppression of the transcription of the gene, the degradation of the gene transcript (pre-message RNA), the inhibition of splicing, the destruction of the messenger RNA, the prevention of the post-translational modifications of the protein, the destruction of the protein, or the inhibition of the normal function of the protein.

For local administration to abnormally proliferating cells, polynucleotides of the present invention may be administered by any method known to those of skill in the art including, but not limited to transfection, electroporation, microinjection of cells, or in vehicles such as liposomes, lipofectin, or as naked polynucleotides, or any other method described throughout the specification. The polynucleotide of the present invention may be delivered by known gene delivery systems such as, but not limited to, retroviral vectors (Gilboa, J. Virology 44:845 (1982); Hocke, Nature 320:275 (1986); Wilson, et al., Proc. Natl. Acad. Sci. U.S.A. 85:3014), vaccinia virus system (Chakrabarty et al., Mol. Cell Biol. 5:3403 (1985) or other efficient DNA delivery systems (Yates et al., Nature 313:812 (1985)) known to those skilled in the art. These references are exemplary only and are hereby incorporated by reference. In order to specifically deliver or transfect cells which are abnormally proliferating and spare non-dividing cells, it is preferable to utilize a retrovirus, or adenoviral (as described in the art and elsewhere herein) delivery system known to those of skill in the art. Since host DNA replication is required for retroviral DNA to integrate and the retrovirus will be unable to self replicate due to the lack of the retrovirus genes needed for its life cycle. Utilizing such a retroviral delivery system for polynucleotides of the present invention will target said gene and constructs to abnormally proliferating cells and will spare the non-dividing normal cells.

The polynucleotides of the present invention may be delivered directly to cell proliferative disorder/disease sites in internal organs, body cavities and the like by use of imaging devices used to guide an injecting needle directly to the disease site. The polynucleotides of the present invention may also be administered to disease sites at the time of surgical intervention.

By "cell proliferative disease" is meant any human or animal disease or disorder, affecting any one or any combination of organs, cavities, or body parts, which is characterized by single or multiple local abnormal proliferations of cells, groups of cells, or tissues, whether benign or malignant.

Any amount of the polynucleotides of the present invention may be administered as long as it has a biologically inhibiting effect on the proliferation of the treated cells. Moreover, it is possible to administer more than one of the polynucleotide of the present invention simultaneously to the same site. By "biologically inhibiting" is meant partial or total growth inhibition as well as decreases in the rate of proliferation or growth of the cells. The biologically inhibitory dose may be determined by assessing the effects of the polynucleotides of the present invention on target malignant or abnormally proliferating cell growth in tissue culture, tumor growth in animals and cell cultures, or any other method known to one of ordinary skill in the art.

The present invention is further directed to antibody-based therapies which involve administering of anti-polypeptides and anti-polynucleotide antibodies to a mammalian, preferably human, patient for treating, preventing, and/or diagnosing one or more of the described diseases, disorders, and/or conditions. Methods for producing anti-polypeptides and anti-polynucleotide antibodies polyclonal and monoclonal antibodies are described in detail elsewhere herein. Such antibodies may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

In particular, the antibodies, fragments and derivatives of the present invention are useful for treating, preventing, and/or diagnosing a subject having or developing cell proliferative and/or differentiation diseases, disorders, and/or conditions as described herein. Such treatment comprises administering a single or multiple doses of the antibody, or a fragment, derivative, or a conjugate thereof.

The antibodies of this invention may be advantageously utilized in combination with other monoclonal or chimeric antibodies, or with lymphokines or hematopoietic growth factors, for example, which serve to increase the number or activity of effector cells which interact with the antibodies.

It is preferred to use high affinity and/or potent in vivo inhibiting and/or neutralizing antibodies against polypeptides or polynucleotides of the present invention, fragments or regions thereof, for both immunoassays directed to and therapy of diseases, disorders, and/or conditions related to polynucleotides or polypeptides, including fragments thereof, of the present invention. Such antibodies, fragments, or regions, will preferably have an affinity for polynucleotides or polypeptides, including fragments thereof. Preferred binding affinities include those with a dissociation constant or Kd less than $5 \times 10^{-6}$M, $10^{-6}$M, $5 \times 10^{-7}$M, $10^{-7}$M, $5 \times 10^{-8}$M, $10^{-8}$M, $5 \times 10^{-9}$M, $10^{-9}$M, $5 \times 10^{-10}$M, $10^{-10}$M, $5 \times 10^{-11}$M, $10^{-11}$M, $5 \times 10^{-12}$M, $10^{-12}$M, $5 \times 10^{-13}$M, $10^{-13}$M, $5 \times 10^{-14}$M, $10^{-14}$M, $5 \times 10^{-15}$M, and $10^{-15}$M.

Moreover, polypeptides of the present invention may be useful in inhibiting the angiogenesis of proliferative cells or tissues, either alone, as a protein fusion, or in combination with other polypeptides directly or indirectly, as described elsewhere herein. In a most preferred embodiment, said anti-angiogenesis effect may be achieved indirectly, for example, through the inhibition of hematopoietic, tumor-specific cells, such as tumor-associated macrophages (See Joseph I B, et al. J Natl Cancer Inst, 90(21):1648–53 (1998), which is hereby incorporated by reference). Antibodies directed to polypeptides or polynucleotides of the present invention may also result in inhibition of angiogenesis directly, or indirectly (See Witte L, et al., Cancer Metastasis Rev. 17(2):155–61 (1998), which is hereby incorporated by reference)).

Polypeptides, including protein fusions, of the present invention, or fragments thereof may be useful in inhibiting proliferative cells or tissues through the induction of apoptosis. Said polypeptides may act either directly, or indirectly to induce apoptosis of proliferative cells and tissues, for example in the activation of a death-domain receptor, such as tumor necrosis factor (TNF) receptor-1, CD95 (Fas/APO-1), TNF-receptor-related apoptosis-mediated protein (TRAMP) and TNF-related apoptosis-inducing ligand (TRAIL) receptor-1 and -2 (See Schulze-Osthoff K, et al., Eur J Biochem 254(3):439–59 (1998), which is hereby incorporated by reference). Moreover, in another preferred embodiment of the present invention, said polypeptides may induce apoptosis through other mechanisms, such as in the activation of other proteins which will activate apoptosis, or through stimulating the expression of said proteins, either alone or in combination with small molecule drugs or adjuvants, such as apoptonin, galectins, thioredoxins, anti-inflammatory proteins (See for example, Mutat. Res. 400 (1–2):447–55 (1998), Med Hypotheses.50(5):423–33 (1998), Chem. Biol. Interact. April 24;111–112:23–34 (1998), J Mol Med.76(6):402–12 (1998), Int. J. Tissue React. 20(1):3–15 (1998), which are all hereby incorporated by reference).

Polypeptides, including protein fusions to, or fragments thereof, of the present invention are useful in inhibiting the metastasis of proliferative cells or tissues. Inhibition may occur as a direct result of administering polypeptides, or antibodies directed to said polypeptides as described elsewhere herein, or indirectly, such as activating the expression of proteins known to inhibit metastasis, for example alpha 4 integrins, (See, e.g., Curr Top Microbiol Immunol 1998;231: 125–41, which is hereby incorporated by reference). Such therapeutic affects of the present invention may be achieved either alone, or in combination with small molecule drugs or adjuvants.

In another embodiment, the invention provides a method of delivering compositions containing the polypeptides of the invention (e.g., compositions containing polypeptides or polypeptide antibodies associated with heterologous polypeptides, heterologous nucleic acids, toxins, or prodrugs) to targeted cells expressing the polypeptide of the present invention. Polypeptides or polypeptide antibodies of the invention may be associated with heterologous polypeptides, heterologous nucleic acids, toxins, or prodrugs via hydrophobic, hydrophilic, ionic and/or covalent interactions.

Polypeptides, protein fusions to, or fragments thereof, of the present invention are useful in enhancing the immunogenicity and/or antigenicity of proliferating cells or tissues, either directly, such as would occur if the polypeptides of the present invention 'vaccinated' the immune response to respond to proliferative antigens and immunogens, or indirectly, such as in activating the expression of proteins known to enhance the immune response (e.g. chemokines), to said antigens and immunogens.

Cardiovascular Disorders

Polynucleotides or polypeptides, or agonists or antagonists of the invention may be used to treat, prevent, and/or diagnose cardiovascular diseases, disorders, and/or conditions, including peripheral artery disease, such as limb ischemia.

Cardiovascular diseases, disorders, and/or conditions include cardiovascular abnormalities, such as arterio-arterial fistula, arteriovenous fistula, cerebral arteriovenous malformations, congenital heart defects, pulmonary atresia, and Scimitar Syndrome. Congenital heart defects include aortic coarctation, cor triatriatum, coronary vessel anomalies, crisscross heart, dextrocardia, patent ductus arteriosus, Ebstein's anomaly, Eisenmenger complex, hypoplastic left heart syndrome, levocardia, tetralogy of fallot, transposition of great vessels, double outlet right ventricle, tricuspid atresia, persistent truncus arteriosus, and heart septal defects, such as aortopulmonary septal defect, endocardial cushion defects, Lutembacher's Syndrome, trilogy of Fallot, ventricular heart septal defects.

Cardiovascular diseases, disorders, and/or conditions also include heart disease, such as arrhythmias, carcinoid heart disease, high cardiac output, low cardiac output, cardiac tamponade, endocarditis (including bacterial), heart aneurysm, cardiac arrest, congestive heart failure, congestive cardiomyopathy, paroxysmal dyspnea, cardiac edema, heart hypertrophy, congestive cardiomyopathy, left ventricular hypertrophy, right ventricular hypertrophy, post-infarction heart rupture, ventricular septal rupture, heart valve diseases, myocardial diseases, myocardial ischemia, pericardial effusion, pericarditis (including constrictive and tuberculous), pneumopericardium, postpericardiotomy syndrome, pulmonary heart disease, rheumatic heart disease, ventricular dysfunction, hyperemia, cardiovascular pregnancy complications, Scimitar Syndrome, cardiovascular syphilis, and cardiovascular tuberculosis.

Arrhythmias include sinus arrhythmia, atrial fibrillation, atrial flutter, bradycardia, extrasystole, Adams-Stokes Syndrome, bundle-branch block, sinoatrial block, long QT syndrome, parasystole, Lown-Ganong-Levine Syndrome, Mahaim-type pre-excitation syndrome, Wolff-Parkinson-White syndrome, sick sinus syndrome, tachycardias, and ventricular fibrillation. Tachycardias include paroxysmal tachycardia, supraventricular tachycardia, accelerated idioventricular rhythm, atrioventricular nodal reentry tachycardia, ectopic atrial tachycardia, ectopic junctional tachycardia, sinoatrial nodal reentry tachycardia, sinus tachycardia, Torsades de Pointes, and ventricular tachycardia.

Heart valve disease include aortic valve insufficiency, aortic valve stenosis, hear murmurs, aortic valve prolapse, mitral valve prolapse, tricuspid valve prolapse, mitral valve insufficiency, mitral valve stenosis, pulmonary atresia, pulmonary valve insufficiency, pulmonary valve stenosis, tricuspid atresia, tricuspid valve insufficiency, and tricuspid valve stenosis.

Myocardial diseases include alcoholic cardiomyopathy, congestive cardiomyopathy, hypertrophic cardiomyopathy, aortic subvalvular stenosis, pulmonary subvalvular stenosis, restrictive cardiomyopathy, Chagas cardiomyopathy, endocardial fibroelastosis, endomyocardial fibrosis, Kearns Syndrome, myocardial reperfusion injury, and myocarditis.

Myocardial ischemias include coronary disease, such as angina pectoris, coronary aneurysm, coronary arteriosclerosis, coronary thrombosis, coronary vasospasm, myocardial infarction and myocardial stunning.

Cardiovascular diseases also include vascular diseases such as aneurysms, angiodysplasia, angiomatosis, bacillary angiomatosis, Hippel-Lindau Disease, Klippel-Trenaunay-Weber Syndrome, Sturge-Weber Syndrome, angioneurotic edema, aortic diseases, Takayasu's Arteritis, aortitis, Leriche's Syndrome, arterial occlusive diseases, arteritis, enarteritis, polyarteritis nodosa, cerebrovascular diseases, disorders, and/or conditions, diabetic angiopathies, diabetic retinopathy, embolisms, thrombosis, erythromelalgia, hemorrhoids, hepatic veno-occlusive disease, hypertension, hypotension, ischemia, peripheral vascular diseases, phlebitis, pulmonary veno-occlusive disease, Raynaud's disease, CREST syndrome, retinal vein occlusion, Scimitar syndrome, superior vena cava syndrome, telangiectasia, atacia telangiectasia, hereditary hemorrhagic telangiectasia, varicocele, varicose veins, varicose ulcer, vasculitis, and venous insufficiency.

Aneurysms include dissecting aneurysms, false aneurysms, infected aneurysms, ruptured aneurysms, aortic aneurysms, cerebral aneurysms, coronary aneurysms, heart aneurysms, and iliac aneurysms.

Arterial occlusive diseases include arteriosclerosis, intermittent claudication, carotid stenosis, fibromuscular dysplasias, mesenteric vascular occlusion, Moyamoya disease, renal artery obstruction, retinal artery occlusion, and thromboangiitis obliterans.

Cerebrovascular diseases, disorders, and/or conditions include carotid artery diseases, cerebral amyloid angiopathy, cerebral aneurysm, cerebral anoxia, cerebral arteriosclerosis, cerebral arteriovenous malformation, cerebral artery diseases, cerebral embolism and thrombosis, carotid artery thrombosis, sinus thrombosis, Wallenberg's syndrome, cerebral hemorrhage, epidural hematoma, subdural hematoma, subaraxhnoid hemorrhage, cerebral infarction, cerebral ischemia (including transient), subclavian steal syndrome, periventricular leukomalacia, vascular headache, cluster headache, migraine, and vertebrobasilar insufficiency.

Embolisms include air embolisms, amniotic fluid embolisms, cholesterol embolisms, blue toe syndrome, fat embolisms, pulmonary embolisms, and thromoboembolisms. Thrombosis include coronary thrombosis, hepatic vein thrombosis, retinal vein occlusion, carotid artery thrombosis, sinus thrombosis, Wallenberg's syndrome, and thrombophlebitis.

Ischemia includes cerebral ischemia, ischemic colitis, compartment syndromes, anterior compartment syndrome, myocardial ischemia, reperfusion injuries, and peripheral limb ischemia. Vasculitis includes aortitis, arteritis, Behcet's Syndrome, Churg-Strauss Syndrome, mucocutaneous lymph node syndrome, thromboangiitis obliterans, hypersensitivity vasculitis, Schoenlein-Henoch purpura, allergic cutaneous vasculitis, and Wegener's granulomatosis.

Polynucleotides or polypeptides, or agonists or antagonists of the invention, are especially effective for the treatment of critical limb ischemia and coronary disease.

Polypeptides may be administered using any method known in the art, including, but not limited to, direct needle injection at the delivery site, intravenous injection, topical administration, catheter infusion, biolistic injectors, particle accelerators, gelfoam sponge depots, other commercially available depot materials, osmotic pumps, oral or suppositorial solid pharmaceutical formulations, decanting or topical applications during surgery, aerosol delivery. Such methods are known in the art. Polypeptides of the invention may be administered as part of a Therapeutic, described in more detail below. Methods of delivering polynucleotides of the invention are described in more detail herein.

Anti-Angiogenesis Activity

The naturally occurring balance between endogenous stimulators and inhibitors of angiogenesis is one in which inhibitory influences predominate. Rastinejad et al., Cell 56:345–355 (1989). In those rare instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail. Unregulated angiogenesis becomes pathologic and sustains progression of many neoplastic and non-neoplastic diseases. A number of serious diseases are dominated by abnormal neovascularization including solid tumor growth and metastases, arthritis, some types of eye diseases, disorders, and/or conditions, and psoriasis. See, e.g., reviews by Moses et al., Biotech. 9:630–634 (1991); Folkman et al., N. Engl. J. Med., 333:1757–1763 (1995); Auerbach et al., J. Microvasc. Res. 29:401–411 (1985); Folkman, Advances in Cancer Research, eds. Klein and Weinhouse, Academic Press, New York, pp. 175–203 (1985); Patz, Am. J. Opthalmol. 94:715–743 (1982); and Folkman et al., Science 221:719–725 (1983). In a number of pathological conditions, the process of angiogenesis contributes to the disease state. For example, significant data have accumulated which suggest that the growth of solid tumors is dependent on angiogenesis. Folkman and Klagsbrun, Science 235:442–447 (1987).

The present invention provides for treatment of diseases, disorders, and/or conditions associated with neovascularization by administration of the polynucleotides and/or polypeptides of the invention, as well as agonists or antagonists of the present invention. Malignant and metastatic conditions which can be treated with the polynucleotides and polypeptides, or agonists or antagonists of the invention include, but are not limited to, malignancies, solid tumors, and cancers described herein and otherwise known in the art (for a review of such disorders, see Fishman et al., Medicine, 2d Ed., J. B. Lippincott Co., Philadelphia (1985)).Thus, the present invention provides a method of treating, preventing, and/or diagnosing an angiogenesis-related disease and/or disorder, comprising administering to an individual in need thereof a therapeutically effective amount of a polynucleotide, polypeptide, antagonist and/or agonist of the invention. For example, polynucleotides, polypeptides, antagonists and/or agonists may be utilized in a variety of additional methods in order to therapeutically treat or prevent a cancer or tumor. Cancers which may be treated, prevented, and/or diagnosed with polynucleotides, polypeptides, antagonists and/or agonists include, but are not limited to solid tumors, including prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases; melanomas; glioblastoma; Kaposi's sarcoma; leiomyosarcoma; non- small cell lung cancer; colorectal cancer; advanced malignancies; and blood born tumors such as leukemias. For example, polynucleotides, polypeptides, antagonists and/or agonists may be delivered topically, in order to treat or prevent cancers such as skin cancer, head and neck tumors, breast tumors, and Kaposi's sarcoma.

Within yet other aspects, polynucleotides, polypeptides, antagonists and/or agonists may be utilized to treat superficial forms of bladder cancer by, for example, intravesical administration. Polynucleotides, polypeptides, antagonists and/or agonists may be delivered directly into the tumor, or near the tumor site, via injection or a catheter. Of course, as the artisan of ordinary skill will appreciate, the appropriate mode of administration will vary according to the cancer to be treated. Other modes of delivery are discussed herein.

Polynucleotides, polypeptides, antagonists and/or agonists may be useful in treating, preventing, and/or diagnosing other diseases, disorders, and/or conditions, besides cancers, which involve angiogenesis. These diseases, disorders, and/or conditions include, but are not limited to: benign tumors, for example hemangiomas, acoustic neuromas, neurofibromas, trachomas, and pyogenic granulomas; artheroscleric plaques; ocular angiogenic diseases, for example, diabetic retinopathy, retinopathy of prematurity, macular degeneration, corneal graft rejection, neovascular glaucoma, retrolental fibroplasia, rubeosis, retinoblastoma, uvietis and Pterygia (abnormal blood vessel growth) of the eye; rheumatoid arthritis; psoriasis; delayed wound healing; endometriosis; vasculogenesis; granulations; hypertrophic scars (keloids); nonunion fractures; scleroderma; trachoma; vascular adhesions; myocardial angiogenesis; coronary collaterals; cerebral collaterals; arteriovenous malformations; ischemic limb angiogenesis; Osler-Webber Syndrome; plaque neovascularization; telangiectasia; hemophiliac joints; angiofibroma; fibromuscular dysplasia; wound granulation; Crohn's disease; and atherosclerosis.

For example, within one aspect of the present invention methods are provided for treating, preventing, and/or diagnosing hypertrophic scars and keloids, comprising the step of administering a polynucleotide, polypeptide, antagonist and/or agonist of the invention to a hypertrophic scar or keloid.

Within one embodiment of the present invention polynucleotides, polypeptides, antagonists and/or agonists are directly injected into a hypertrophic scar or keloid, in order to prevent the progression of these lesions. This therapy is of particular value in the prophylactic treatment of conditions which are known to result in the development of hypertrophic scars and keloids (e.g., burns), and is preferably initiated after the proliferative phase has had time to progress (approximately 14 days after the initial injury), but before hypertrophic scar or keloid development. As noted above, the present invention also provides methods for treating, preventing, and/or diagnosing neovascular diseases of the eye, including for example, corneal neovascularization, neovascular glaucoma, proliferative diabetic retinopathy, retrolental fibroplasia and macular degeneration.

Moreover, Ocular diseases, disorders, and/or conditions associated with neovascularization which can be treated, prevented, and/or diagnosed with the polynucleotides and polypeptides of the present invention (including agonists and/or antagonists) include, but are not limited to: neovascular glaucoma, diabetic retinopathy, retinoblastoma, retrolental fibroplasia, uveitis, retinopathy of prematurity macular degeneration, corneal graft neovascularization, as well as other eye inflammatory diseases, ocular tumors and diseases associated with choroidal or iris neovascularization. See, e.g., reviews by Waltman et al., Am. J. Ophthal. 85:704–710 (1978) and Gartner et al., Surv. Ophthal. 22:291–312 (1978).

Thus, within one aspect of the present invention methods are provided for treating or preventing neovascular diseases of the eye such as corneal neovascularization (including corneal graft neovascularization), comprising the step of administering to a patient a therapeutically effective amount of a compound (as described above) to the cornea, such that the formation of blood vessels is inhibited. Briefly, the cornea is a tissue which normally lacks blood vessels. In certain pathological conditions however, capillaries may extend into the cornea from the pericorneal vascular plexus of the limbus. When the cornea becomes vascularized, it also becomes clouded, resulting in a decline in the patient's visual acuity. Visual loss may become complete if the cornea completely opacitates. A wide variety of diseases, disorders, and/or conditions can result in corneal neovascularization, including for example, corneal infections (e.g., trachoma, herpes simplex keratitis, leishmaniasis and onchocerciasis), immunological processes (e.g., graft rejection and Stevens-Johnson's syndrome), alkali burns, trauma, inflammation (of any cause), toxic and nutritional deficiency states, and as a complication of wearing contact lenses.

Within particularly preferred embodiments of the invention, may be prepared for topical administration in saline (combined with any of the preservatives and antimicrobial agents commonly used in ocular preparations), and administered in eyedrop form. The solution or suspension may be prepared in its pure form and administered several times daily. Alternatively, anti-angiogenic compositions, prepared as described above, may also be administered directly to the cornea. Within preferred embodiments, the anti-angiogenic composition is prepared with a muco-adhesive polymer which binds to cornea. Within further embodiments, the anti-angiogenic factors or anti-angiogenic compositions may be utilized as an adjunct to conventional steroid therapy. Topical therapy may also be useful prophylactically in corneal lesions which are known to have a high probability of inducing an angiogenic response (such as chemical burns). In these instances the treatment, likely in combination with steroids, may be instituted immediately to help prevent subsequent complications.

Within other embodiments, the compounds described above may be injected directly into the corneal stroma by an ophthalmologist under microscopic guidance. The preferred site of injection may vary with the morphology of the individual lesion, but the goal of the administration would be to place the composition at the advancing front of the vasculature (i.e., interspersed between the blood vessels and the normal cornea). In most cases this would involve perilimbic corneal injection to "protect" the cornea from the advancing blood vessels. This method may also be utilized shortly after a corneal insult in order to prophylactically prevent corneal neovascularization. In this situation the material could be injected in the perilimbic cornea interspersed between the corneal lesion and its undesired potential limbic blood supply. Such methods may also be utilized in a similar fashion to prevent capillary invasion of transplanted corneas. In a sustained-release form injections might only be required 2–3 times per year. A steroid could also be added to the injection solution to reduce inflammation resulting from the injection itself.

Within another aspect of the present invention, methods are provided for treating or preventing neovascular glaucoma, comprising the step of administering to a patient a therapeutically effective amount of a polynucleotide, polypeptide, antagonist and/or agonist to the eye, such that the formation of blood vessels is inhibited. In one embodiment, the compound may be administered topically to the eye in order to treat or prevent early forms of neovascular glaucoma. Within other embodiments, the compound may be implanted by injection into the region of the anterior chamber angle. Within other embodiments, the compound may also be placed in any location such that the compound is continuously released into the aqueous humor. Within another aspect of the present invention, methods are provided for treating or preventing proliferative diabetic retinopathy, comprising the step of administering to a patient a therapeutically effective amount of a polynucleotide, polypeptide, antagonist and/or agonist to the eyes, such that the formation of blood vessels is inhibited.

Within particularly preferred embodiments of the invention, proliferative diabetic retinopathy may be treated by injection into the aqueous humor or the vitreous, in order to increase the local concentration of the polynucleotide, polypeptide, antagonist and/or agonist in the retina. Preferably, this treatment should be initiated prior to the acquisition of severe disease requiring photocoagulation.

Within another aspect of the present invention, methods are provided for treating or preventing retrolental fibroplasia, comprising the step of administering to a patient a therapeutically effective amount of a polynucleotide, polypeptide, antagonist and/or agonist to the eye, such that the formation of blood vessels is inhibited. The compound may be administered topically, via intravitreous injection and/or via intraocular implants.

Additionally, diseases, disorders, and/or conditions which can be treated, prevented, and/or diagnosed with the polynucleotides, polypeptides, agonists and/or agonists include, but are not limited to, hemangioma, arthritis, psoriasis, angiofibroma, atherosclerotic plaques, delayed wound healing, granulations, hemophilic joints, hypertrophic scars, nonunion fractures, Osler-Weber syndrome, pyogenic granuloma, scleroderma, trachoma, and vascular adhesions.

Moreover, diseases, disorders, and/or conditions and/or states, which can be treated, prevented, and/or diagnosed with the polynucleotides, polypeptides, agonists and/or agonists include, but are not limited to, solid tumors, blood born tumors such as leukemias, tumor metastasis, Kaposi's sarcoma, benign tumors, for example hemangiomas, acoustic neuromas, neurofibromas, trachomas, and pyogenic granulomas, rheumatoid arthritis, psoriasis, ocular angiogenic diseases, for example, diabetic retinopathy, retinopathy of prematurity, macular degeneration, corneal graft rejection, neovascular glaucoma, retrolental fibroplasia, rubeosis, retinoblastoma, and uvietis, delayed wound healing, endometriosis, vascluogenesis, granulations, hypertrophic scars (keloids), nonunion fractures, scleroderma, trachoma, vascular adhesions, myocardial angiogenesis, coronary collaterals, cerebral collaterals, arteriovenous malformations, ischemic limb angiogenesis, Osler-Webber Syndrome, plaque neovascularization, telangiectasia, hemophiliac joints, angiofibroma fibromuscular dysplasia, wound granulation, Crohn's disease, atherosclerosis, birth control agent by preventing vascularization required for embryo implantation controlling menstruation, diseases that have angiogenesis as a pathologic consequence such as cat scratch disease (Rochele minalia quintosa), ulcers (Helicobacter pylori), Bartonellosis and bacillary angiomatosis.

In one aspect of the birth control method, an amount of the compound sufficient to block embryo implantation is administered before or after intercourse and fertilization have occurred, thus providing an effective method of birth control, possibly a "morning after" method. Polynucleotides, polypeptides, agonists and/or agonists may also be used in controlling menstruation or administered as either a peritoneal lavage fluid or for peritoneal implantation in the treatment of endometriosis.

Polynucleotides, polypeptides, agonists and/or agonists of the present invention may be incorporated into surgical sutures in order to prevent stitch granulomas.

Polynucleotides, polypeptides, agonists and/or agonists may be utilized in a wide variety of surgical procedures. For example, within one aspect of the present invention a compositions (in the form of, for example, a spray or film) may be utilized to coat or spray an area prior to removal of a tumor, in order to isolate normal surrounding tissues from malignant tissue, and/or to prevent the spread of disease to surrounding tissues. Within other aspects of the present invention, compositions (e.g., in the form of a spray) may be delivered via endoscopic procedures in order to coat tumors, or inhibit angiogenesis in a desired locale. Within yet other aspects of the present invention, surgical meshes which have been coated with anti-angiogenic compositions of the present invention may be utilized in any procedure wherein a surgical mesh might be utilized. For example, within one embodiment of the invention a surgical mesh laden with an anti-angiogenic composition may be utilized during abdominal cancer resection surgery (e.g., subsequent to colon resection) in order to provide support to the structure, and to release an amount of the anti-angiogenic factor.

Within further aspects of the present invention, methods are provided for treating tumor excision sites, comprising administering a polynucleotide, polypeptide, agonist and/or agonist to the resection margins of a tumor subsequent to excision, such that the local recurrence of cancer and the formation of new blood vessels at the site is inhibited. Within one embodiment of the invention, the anti-angiogenic compound is administered directly to the tumor excision site (e.g., applied by swabbing, brushing or otherwise coating the resection margins of the tumor with the anti-angiogenic compound). Alternatively, the anti-angiogenic compounds may be incorporated into known surgical pastes prior to administration. Within particularly preferred embodiments of the invention, the anti-angiogenic compounds are applied after hepatic resections for malignancy, and after neurosurgical operations.

Within one aspect of the present invention, polynucleotides, polypeptides, agonists and/or agonists may be administered to the resection margin of a wide variety of tumors, including for example, breast, colon, brain and hepatic tumors. For example, within one embodiment of the invention, anti-angiogenic compounds may be administered to the site of a neurological tumor subsequent to excision, such that the formation of new blood vessels at the site are inhibited.

The polynucleotides, polypeptides, agonists and/or agonists of the present invention may also be administered along with other anti-angiogenic factors. Representative examples of other anti-angiogenic factors include: Anti-Invasive Factor, retinoic acid and derivatives thereof, paclitaxel, Suramin, Tissue Inhibitor of Metalloproteinase-1, Tissue Inhibitor of Metalloproteinase-2, Plasminogen Activator Inhibitor-1, Plasminogen Activator Inhibitor-2, and various forms of the lighter "d group" transition metals.

Lighter "d group" transition metals include, for example, vanadium, molybdenum, tungsten, titanium, niobium, and tantalum species. Such transition metal species may form transition metal complexes. Suitable complexes of the above-mentioned transition metal species include oxo transition metal complexes.

Representative examples of vanadium complexes include oxo vanadium complexes such as vanadate and vanadyl complexes. Suitable vanadate complexes include metavanadate and orthovanadate complexes such as, for example, ammonium metavanadate, sodium metavanadate, and sodium orthovanadate. Suitable vanadyl complexes include, for example, vanadyl acetylacetonate and vanadyl sulfate including vanadyl sulfate hydrates such as vanadyl sulfate mono- and trihydrates.

Representative examples of tungsten and molybdenum complexes also include oxo complexes. Suitable oxo tungsten complexes include tungstate and tungsten oxide complexes. Suitable tungstate complexes include ammonium tungstate, calcium tungstate, sodium tungstate dihydrate, and tungstic acid. Suitable tungsten oxides include tungsten (IV) oxide and tungsten (VI) oxide. Suitable oxo molybdenum complexes include molybdate, molybdenum oxide, and molybdenyl complexes. Suitable molybdate complexes include ammonium molybdate and its hydrates, sodium molybdate and its hydrates, and potassium molybdate and its hydrates. Suitable molybdenum oxides include molybdenum (VI) oxide, molybdenum (VI) oxide, and molybdic acid. Suitable molybdenyl complexes include, for example, molybdenyl acetylacetonate. Other suitable tungsten and molybdenum complexes include hydroxo derivatives derived from, for example, glycerol, tartaric acid, and sugars.

A wide variety of other anti-angiogenic factors may also be utilized within the context of the present invention. Representative examples include platelet factor 4; protamine sulphate; sulphated chitin derivatives (prepared from queen crab shells), (Murata et al., Cancer Res. 51:22–26, 1991); Sulphated Polysaccharide Peptidoglycan Complex (SP-PG) (the function of this compound may be enhanced by the presence of steroids such as estrogen, and tamoxifen citrate); Staurosporine; modulators of matrix metabolism, including for example, proline analogs, cishydroxyproline, d,L-3,4-dehydroproline, Thiaproline, alpha,alpha-dipyridyl, aminopropionitrile fumarate; 4-propyl-5-(4-pyridinyl)-2(3H)-oxazolone; Methotrexate; Mitoxantrone; Heparin; Interferons; 2 Macroglobulin-serum; ChIMP-3 (Pavloff et al., J. Bio. Chem. 267:17321–17326, 1992); Chymostatin (Tomkinson et al., Biochem J. 286:475–480, 1992); Cyclodextrin Tetradecasulfate; Eponemycin; Camptothecin; Fumagillin (Ingber et al., Nature 348:555–557, 1990); Gold Sodium Thiomalate ("GST"; Matsubara and Ziff, J. Clin. Invest. 79:1440–1446, 1987); anticollagenase-serum; alpha2-antiplasmin (Holmes et al., J. Biol. Chem . . . 262(4):1659–1664, 1987); Bisantrene (National Cancer Institute); Lobenzarit disodium (N-(2)-carboxyphenyl-4-chloroanthronilic acid disodium or "CCA"; Takeuchi et al., Agents Actions 36:312–316, 1992); Thalidomide; Angostatic steroid; AGM-1470; carboxynaminolmidazole; and metalloproteinase inhibitors such as BB94.

Diseases at the Cellular Level

Diseases associated with increased cell survival or the inhibition of apoptosis that could be treated, prevented, and/or diagnosed by the polynucleotides or polypeptides and/or antagonists or agonists of the invention, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostate cancer, Kaposi's sarcoma and ovarian cancer); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) and viral infections (such as herpes viruses, pox viruses and adenoviruses), inflammation, graft v. host disease, acute graft rejection, and chronic graft rejection. In preferred embodiments, the polynucleotides or polypeptides, and/or agonists or antagonists of the invention are used to inhibit growth, progression, and/or metastasis of cancers, in particular those listed above.

Additional diseases or conditions associated with increased cell survival that could be treated, prevented or diagnosed by the polynucleotides or polypeptides, or agonists or antagonists of the invention, include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis that could be treated, prevented, and/or diagnosed by the polynucleotides or polypeptides, and/or agonists or antagonists of the invention, include AIDS; neurodegenerative diseases, disorders, and/or conditions (such as Alzheimer's disease, Parkinson's disease, Amyotrophic lateral sclerosis, Retinitis pigmentosa, Cerebellar degeneration and brain tumor or prior associated disease); autoimmune diseases, disorders, and/or conditions (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia.

Wound Healing and Epithelial Cell Proliferation

In accordance with yet a further aspect of the present invention, there is provided a process for utilizing the polynucleotides or polypeptides, and/or agonists or antagonists of the invention, for therapeutic purposes, for example, to stimulate epithelial cell proliferation and basal keratinocytes for the purpose of wound healing, and to stimulate hair follicle production and healing of dermal wounds. Polynucleotides or polypeptides, as well as agonists or antagonists of the invention, may be clinically useful in stimulating wound healing including surgical wounds, excisional wounds, deep wounds involving damage of the dermis and epidermis, eye tissue wounds, dental tissue wounds, oral cavity wounds, diabetic ulcers, dermal ulcers, cubitus ulcers, arterial ulcers, venous stasis ulcers, burns resulting from heat exposure or chemicals, and other abnormal wound healing conditions such as uremia, malnutrition, vitamin deficiencies and complications associated with systemic treatment with steroids, radiation therapy and antineoplastic drugs and antimetabolites. Polynucleotides or polypeptides, and/or agonists or antagonists of the invention, could be used to promote dermal reestablishment subsequent to dermal loss.

The polynucleotides or polypeptides, and/or agonists or antagonists of the invention, could be used to increase the adherence of skin grafts to a wound bed and to stimulate re-epithelialization from the wound bed. The following are a non-exhaustive list of grafts that polynucleotides or polypeptides, agonists or antagonists of the invention, could be used to increase adherence to a wound bed: autografts, artificial skin, allografts, autodermic graft, autoepidermic grafts, avacular grafts, Blair-Brown grafts, bone graft, brephoplastic grafts, cutis graft, delayed graft, dermic graft, epidermic graft, fascia graft, full thickness graft, heterologous graft, xenograft, homologous graft, hyperplastic graft, lamellar graft, mesh graft, mucosal graft, Ollier-Thiersch graft, omenpal graft, patch graft, pedicle graft, penetrating graft, split skin graft, thick split graft. The polynucleotides or polypeptides, and/or agonists or antagonists of the invention, can be used to promote skin strength and to improve the appearance of aged skin.

It is believed that the polynucleotides or polypeptides, and/or agonists or antagonists of the invention, will also produce changes in hepatocyte proliferation, and epithelial cell proliferation in the lung, breast, pancreas, stomach, small intestine, and large intestine. The polynucleotides or polypeptides, and/or agonists or antagonists of the invention, could promote proliferation of epithelial cells such as sebocytes, hair follicles, hepatocytes, type II pneumocytes, mucin-producing goblet cells, and other epithelial cells and their progenitors contained within the skin, lung, liver, and gastrointestinal tract. The polynucleotides or polypeptides, and/or agonists or antagonists of the invention, may promote proliferation of endothelial cells, keratinocytes, and basal keratinocytes.

The polynucleotides or polypeptides, and/or agonists or antagonists of the invention, could also be used to reduce the side effects of gut toxicity that result from radiation, chemotherapy treatments or viral infections. The polynucleotides or polypeptides, and/or agonists or antagonists of the invention, may have a cytoprotective effect on the small intestine mucosa. The polynucleotides or polypeptides, and/or agonists or antagonists of the invention, may also stimulate healing of mucositis (mouth ulcers) that result from chemotherapy and viral infections.

The polynucleotides or polypeptides, and/or agonists or antagonists of the invention, could further be used in full regeneration of skin in full and partial thickness skin defects, including burns, (i.e., repopulation of hair follicles, sweat glands, and sebaceous glands), treatment of other skin defects such as psoriasis. The polynucleotides or polypeptides, and/or agonists or antagonists of the invention, could be used to treat epidermolysis bullosa, a defect in adherence of the epidermis to the underlying dermis which results in frequent, open and painful blisters by accelerating reepithelialization of these lesions. The polynucleotides or polypeptides, and/or agonists or antagonists of the invention, could also be used to treat gastric and doudenal ulcers and help heal by scar formation of the mucosal lining and regeneration of glandular mucosa and duodenal mucosal lining more rapidly. Inflamamatory bowel diseases, such as Crohn's disease and ulcerative colitis, are diseases which result in destruction of the mucosal surface of the small or large intestine, respectively. Thus, the polynucleotides or polypeptides, and/or agonists or antagonists of the invention, could be used to promote the resurfacing of the mucosal surface to aid more rapid healing and to prevent progression of inflammatory bowel disease. Treatment with the polynucleotides or polypeptides, and/or agonists or antagonists of the invention, is expected to have a significant effect on the production of mucus throughout the gastrointestinal tract and could be used to protect the intestinal mucosa from injurious substances that are ingested or following surgery. The polynucleotides or polypeptides, and/or agonists or antagonists of the invention, could be used to treat diseases associate with the under expression of the polynucleotides of the invention.

Moreover, the polynucleotides or polypeptides, and/or agonists or antagonists of the invention, could be used to prevent and heal damage to the lungs due to various pathological states. A growth factor such as the polynucleotides or polypeptides, and/or agonists or antagonists of the invention, which could stimulate proliferation and differentiation and promote the repair of alveoli and brochiolar epithelium to prevent or treat acute or chronic lung damage. For example, emphysema, which results in the progressive loss of aveoli, and inhalation injuries, i.e., resulting from smoke inhalation and bums, that cause necrosis of the bronchiolar epithelium and alveoli could be effectively treated, prevented, and/or diagnosed using the polynucleotides or polypeptides, and/or agonists or antagonists of the invention. Also, the polynucleotides or polypeptides, and/or agonists or antagonists of the invention, could be used to stimulate the proliferation of and differentiation of type II pneumocytes, which may help treat or prevent disease such as hyaline membrane diseases, such as infant respiratory distress syndrome and bronchopulmonary displasia, in premature infants.

The polynucleotides or polypeptides, and/or agonists or antagonists of the invention, could stimulate the proliferation and differentiation of hepatocytes and, thus, could be used to alleviate or treat liver diseases and pathologies such as fulminant liver failure caused by cirrhosis, liver damage caused by viral hepatitis and toxic substances (i.e., acetaminophen, carbon tetraholoride and other hepatotoxins known in the art).

In addition, the polynucleotides or polypeptides, and/or agonists or antagonists of the invention, could be used treat or prevent the onset of diabetes mellitus. In patients with newly diagnosed Types I and II diabetes, where some islet cell function remains, the polynucleotides or polypeptides, and/or agonists or antagonists of the invention, could be used to maintain the islet function so as to alleviate, delay or prevent permanent manifestation of the disease. Also, the polynucleotides or polypeptides, and/or agonists or antagonists of the invention, could be used as an auxiliary in islet cell transplantation to improve or promote islet cell function.

Neurological Diseases

Nervous system diseases, disorders, and/or conditions, which can be treated, prevented, and/or diagnosed with the compositions of the invention (e.g., polypeptides, polynucleotides, and/or agonists or antagonists), include, but are not limited to, nervous system injuries, and diseases, disorders, and/or conditions which result in either a disconnection of axons, a diminution or degeneration of neurons, or demyelination. Nervous system lesions which may be treated, prevented, and/or diagnosed in a patient (including human and non-human mammalian patients) according to the invention, include but are not limited to, the following lesions of either the central (including spinal cord, brain) or peripheral nervous systems: (1) ischemic lesions, in which a lack of oxygen in a portion of the nervous system results in neuronal injury or death, including cerebral infarction or ischemia, or spinal cord infarction or ischemia; (2) traumatic lesions, including lesions caused by physical injury or associated with surgery, for example, lesions which sever a portion of the nervous system, or compression injuries; (3) malignant lesions, in which a portion of the nervous system is destroyed or injured by malignant tissue which is either a nervous system associated malignancy or a malignancy derived from non-nervous system tissue; (4) infectious lesions, in which a portion of the nervous system is destroyed or injured as a result of infection, for example, by an abscess or associated with infection by human immunodeficiency virus, herpes zoster, or herpes simplex virus or with Lyme disease, tuberculosis, syphilis; (5) degenerative lesions, in which a portion of the nervous system is destroyed or injured as a result of a degenerative process including but not limited to degeneration associated with Parkinson's disease, Alzheimer's disease, Huntington's chorea, or amyotrophic lateral sclerosis (ALS); (6) lesions associated with nutritional diseases, disorders, and/or conditions, in which a portion of the nervous system is destroyed or injured by a nutritional disorder or disorder of metabolism including but not limited to, vitamin B12 deficiency, folic acid deficiency, Wernicke disease, tobacco-alcohol amblyopia, Marchiafava-Bignami disease (primary degeneration of the corpus callosum), and alcoholic cerebellar degeneration; (7) neurological lesions associated with systemic diseases including, but not limited to, diabetes (diabetic neuropathy, Bell's palsy), systemic lupus erythematosus, carcinoma, or sarcoidosis; (8) lesions caused by toxic substances including alcohol, lead, or particular neurotoxins; and (9) demyelinated lesions in which a portion of the nervous system is destroyed or injured by a demyelinating disease including, but not limited to, multiple sclerosis, human immunodeficiency virus-associated myelopathy, transverse myelopathy or various etiologies, progressive multifocal leukoencephalopathy, and central pontine myelinolysis.

In a preferred embodiment, the polypeptides, polynucleotides, or agonists or antagonists of the invention are used to protect neural cells from the damaging effects of cerebral hypoxia. According to this embodiment, the compositions of the invention are used to treat, prevent, and/or diagnose neural cell injury associated with cerebral hypoxia. In one aspect of this embodiment, the polypeptides, polynucleotides, or agonists or antagonists of the invention are used to treat, prevent, and/or diagnose neural cell injury associated with cerebral ischemia. In another aspect of this embodiment, the polypeptides, polynucleotides, or agonists or antagonists of the invention are used to treat, prevent, and/or diagnose neural cell injury associated with cerebral infarction. In another aspect of this embodiment, the polypeptides, polynucleotides, or agonists or antagonists of the invention are used to treat, prevent, and/or diagnose or prevent neural cell injury associated with a stroke. In a further aspect of this embodiment, the polypeptides, polynucleotides, or agonists or antagonists of the invention are used to treat, prevent, and/or diagnose neural cell injury associated with a heart attack.

The compositions of the invention which are useful for treating or preventing a nervous system disorder may be selected by testing for biological activity in promoting the survival or differentiation of neurons. For example, and not by way of limitation, compositions of the invention which elicit any of the following effects may be useful according to the invention: (1) increased survival time of neurons in culture; (2) increased sprouting of neurons in culture or in vivo; (3) increased production of a neuron-associated molecule in culture or in vivo, e.g., choline acetyltransferase or acetylcholinesterase with respect to motor neurons; or (4) decreased symptoms of neuron dysfunction in vivo. Such effects may be measured by any method known in the art. In preferred, non-limiting embodiments, increased survival of neurons may routinely be measured using a method set forth herein or otherwise known in the art, such as, for example, the method set forth in Arakawa et al. (J. Neurosci. 10:3507–3515 (1990)); increased sprouting of neurons may be detected by methods known in the art, such as, for example, the methods set forth in Pestronk et al. (Exp. Neurol. 70:65–82 (1980)) or Brown et al. (Ann. Rev. Neurosci. 4:17–42 (1981)); increased production of neuron-associated molecules may be measured by bioassay, enzymatic assay, antibody binding, Northern blot assay, etc., using techniques known in the art and depending on the molecule to be measured; and motor neuron dysfunction may be measured by assessing the physical manifestation of motor neuron disorder, e.g., weakness, motor neuron conduction velocity, or functional disability.

In specific embodiments, motor neuron diseases, disorders, and/or conditions that may be treated, prevented, and/or diagnosed according to the invention include, but are not limited to, diseases, disorders, and/or conditions such as infarction, infection, exposure to toxin, trauma, surgical damage, degenerative disease or malignancy that may affect motor neurons as well as other components of the nervous system, as well as diseases, disorders, and/or conditions that selectively affect neurons such as amyotrophic lateral sclerosis, and including, but not limited to, progressive spinal muscular atrophy, progressive bulbar palsy, primary lateral sclerosis, infantile and juvenile muscular atrophy, progressive bulbar paralysis of childhood (Fazio-Londe syndrome), poliomyelitis and the post polio syndrome, and Hereditary Motorsensory Neuropathy (Charcot-Marie-Tooth Disease).

Infectious Disease

A polypeptide or polynucleotide and/or agonist or antagonist of the present invention can be used to treat, prevent, and/or diagnose infectious agents. For example, by increasing the immune response, particularly increasing the proliferation and differentiation of B and/or T cells, infectious diseases may be treated, prevented, and/or diagnosed. The immune response may be increased by either enhancing an existing immune response, or by initiating a new immune response. Alternatively, polypeptide or polynucleotide and/or agonist or antagonist of the present invention may also directly inhibit the infectious agent, without necessarily eliciting an immune response.

Viruses are one example of an infectious agent that can cause disease or symptoms that can be treated, prevented, and/or diagnosed by a polynucleotide or polypeptide and/or agonist or antagonist of the present invention. Examples of viruses, include, but are not limited to Examples of viruses, include, but are not limited to the following DNA and RNA viruses and viral families: Arbovirus, Adenoviridae, Arenaviridae, Arterivirus, Birnaviridae, Bunyaviridae, Caliciviridae, Circoviridae, Coronaviridae, Dengue, EBV, HIV, Flaviviridae, Hepadnaviridae (Hepatitis), Herpesviridae (such as, Cytomegalovirus, Herpes Simplex, Herpes Zoster), Mononegavirus (e.g., Paramyxoviridae, Morbillivirus, Rhabdoviridae), Orthomyxoviridae (e.g., Influenza A, Influenza B, and parainfluenza), Papiloma virus, Papovaviridae, Paivoviridae, Picornaviridae, Poxviridae (such as Smallpox or Vaccinia), Reoviridae (e.g., Rotavirus), Retroviridae (HTLV-I, HTLV-II, Lentivirus), and Togaviridae (e.g., Rubivirus). Viruses falling within these families can cause a variety of diseases or symptoms, including, but not limited to: arthritis, bronchiollitis, respiratory syncytial virus, encephalitis, eye infections (e.g., conjunctivitis, keratitis), chronic fatigue syndrome, hepatitis (A, B, C, E, Chronic Active, Delta), Japanese B encephalitis, Junin, Chikungunya, Rift Valley fever, yellow fever, meningitis, opportunistic infections (e.g., AIDS), pneumonia, Burkitt's Lymphoma, chickenpox, hemorrhagic fever, Measles, Mumps, Parainfluenza, Rabies, the common cold, Polio, leukemia, Rubella, sexually transmitted diseases, skin diseases (e.g., Kaposi's, warts), and viremia, polynucleotides or polypeptides, or agonists or antagonists of the invention, can be used to treat, prevent, and/or diagnose any of these symptoms or diseases. In specific embodiments, polynucleotides, polypeptides, or agonists or antagonists of the invention are used to treat, prevent, and/or diagnose: meningitis, Dengue, EBV, and/or hepatitis (e.g., hepatitis B). In an additional specific embodiment polynucleotides, polypeptides, or agonists or antagonists of the invention are used to treat patients nonresponsive to one or more other commercially available hepatitis vaccines. In a further specific embodiment polynucleotides, polypeptides, or agonists or antagonists of the invention are used to treat, prevent, and/or diagnose AIDS.

Similarly, bacterial or fungal agents that can cause disease or symptoms and that can be treated, prevented, and/or diagnosed by a polynucleotide or polypeptide and/or agonist or antagonist of the present invention include, but not limited to, include, but not limited to, the following Gram-Negative and Gram-positive bacteria and bacterial families and fungi: Actinomycetales (e.g., *Corynebacterium, Mycobacterium, Norcardia*), *Cryptococcus neoformans*, Aspergillosis, Bacillaceae (e.g., Anthrax, *Clostridium*), Bacteroidaceae, Blastomycosis, *Bordetella, Borrelia* (e.g., *Borrelia burgdorferi*), Brucellosis, Candidiasis, *Campylobacter*, Coccidioidomycosis, *Cryptococcosis*, Dermatocycoses, *E. coli* (e.g., Enterotoxigenic *E. coli* and Enterohemorrhagic *E. coli*), Enterobacteriaceae (*Klebsiella, Salmonella* (e.g., *Salmonella typhi*, and *Salmonella paratyphi*), *Serratia, Yersinia*), Erysipelothrix, *Helicobacter*, Legionellosis, Leptospirosis, *Listeria*, Mycoplasmatales, *Mycobacterium leprae, Vibrio cholerae*, Neisseriaceae (e.g., Acinetobacter, Gonorrhea, Menigococcal), *Meisseria meningitidis*, Pasteurellacea Infections (e.g., *Actinobacillus, Heamophilus* (e.g., *Heamophilus* influenza type B), *Pasteurella*), *Pseudomonas*, Rickettsiaceae, Chlamydiaceae, Syphilis, *Shigella* spp., Staphylococcal, Meningiococcal, Pneumococcal and Streptococcal (e.g., *Streptococcus pneumoniae* and Group B *Streptococcus*). These bacterial or fungal families can cause the following diseases or symptoms, including, but not limited to: bacteremia, endocarditis, eye infections (conjunctivitis, tuberculosis, uveitis), gingivitis, opportunistic infections (e.g., AIDS related infections), paronychia, prosthesis-related infections, Reiter's Disease, respiratory tract infections, such as Whooping Cough or Empyema, sepsis, Lyme Disease, Cat-Scratch Disease, Dysentery, Paratyphoid Fever, food poisoning, Typhoid, pneumonia, Gonorrhea, meningitis (e.g., mengitis types A and B), Chlamydia, Syphilis, Diphtheria, Leprosy, Paratuberculosis, Tuberculosis, Lupus, Botulism, gangrene, tetanus, impetigo, Rheumatic Fever, Scarlet Fever, sexually transmitted diseases, skin diseases (e.g., cellulitis, dermatocycoses), toxemia, urinary tract infections, wound infections. Polynucleotides or polypeptides, agonists or antagonists of the invention, can be used to treat, prevent, and/or diagnose any of these symptoms or diseases. In specific embodiments, polynucleotides, polypeptides, agonists or antagonists of the invention are used to treat, prevent, and/or diagnose: tetanus, Diptheria, botulism, and/or meningitis type B.

Moreover, parasitic agents causing disease or symptoms that can be treated, prevented, and/or diagnosed by a polynucleotide or polypeptide and/or agonist or antagonist of the present invention include, but not limited to, the following families or class: Amebiasis, Babesiosis, Coccidiosis, Cryptosporidiosis, Dientamoebiasis, Dourine, Ectoparasitic, Giardiasis, Helminthiasis, Leishmaniasis, Theileriasis, Toxoplasmosis, Trypanosomiasis, and Trichomonas and Sporozoans (e.g., Plasmodium virax, Plasmodium falciparium, Plasmodium malariae and Plasmodium ovale). These parasites can cause a variety of diseases or symptoms, including, but not limited to: Scabies, Trombiculiasis, eye infections, intestinal disease (e.g., dysentery, giardiasis), liver disease, lung disease, opportunistic infections (e.g., AIDS related), malaria, pregnancy complications, and toxoplasmosis. polynucleotides or polypeptides, or agonists or antagonists of the invention, can be used totreat, prevent, and/or diagnose any of these symptoms or diseases. In specific embodiments, polynucleotides, polypeptides, or agonists or antagonists of the invention are used to treat, prevent, and/or diagnose malaria.

Preferably, treatment or prevention using a polypeptide or polynucleotide and/or agonist or antagonist of the present invention could either be by administering an effective amount of a polypeptide to the patient, or by removing cells from the patient, supplying the cells with a polynucleotide of the present invention, and returning the engineered cells to the patient (ex vivo therapy). Moreover, the polypeptide or polynucleotide of the present invention can be used as an antigen in a vaccine to raise an immune response against infectious disease.

Regeneration

A polynucleotide or polypeptide and/or agonist or antagonist of the present invention can be used to differentiate, proliferate, and attract cells, leading to the regeneration of tissues. (See, Science 276:59–87 (1997).) The regeneration of tissues could be used to repair, replace, or protect tissue damaged by congenital defects, trauma (wounds, burns, incisions, or ulcers), age, disease (e.g. osteoporosis, osteocarthritis, periodontal disease, liver failure), surgery, including cosmetic plastic surgery, fibrosis, reperfusion injury, or systemic cytokine damage.

Tissues that could be regenerated using the present invention include organs (e.g., pancreas, liver, intestine, kidney, skin, endothelium), muscle (smooth, skeletal or cardiac), vasculature (including vascular and lymphatics), nervous, hematopoietic, and skeletal (bone, cartilage, tendon, and ligament) tissue. Preferably, regeneration occurs without or decreased scarring. Regeneration also may include angiogenesis.

Moreover, a polynucleotide or polypeptide and/or agonist or antagonist of the present invention may increase regeneration of tissues difficult to heal. For example, increased tendon/ligament regeneration would quicken recovery time after damage. A polynucleotide or polypeptide and/or agonist or antagonist of the present invention could also be used prophylactically in an effort to avoid damage. Specific diseases that could be treated, prevented, and/or diagnosed include of tendinitis, carpal tunnel syndrome, and other tendon or ligament defects. A further example of tissue regeneration of non-healing wounds includes pressure ulcers, ulcers associated with vascular insufficiency, surgical, and traumatic wounds.

Similarly, nerve and brain tissue could also be regenerated by using a polynucleotide or polypeptide and/or agonist or antagonist of the present invention to proliferate and differentiate nerve cells. Diseases that could be treated, prevented, and/or diagnosed using this method include central and peripheral nervous system diseases, neuropathies, or mechanical and traumatic diseases, disorders, and/or conditions (e.g., spinal cord disorders, head trauma, cerebrovascular disease, and stoke). Specifically, diseases associated with peripheral nerve injuries, peripheral neuropathy (e.g., resulting from chemotherapy or other medical therapies), localized neuropathies, and central nervous system diseases (e.g., Alzheimer's disease, Parkinson's disease, Huntington's disease, amyotrophic lateral sclerosis, and Shy-Drager syndrome), could all be treated, prevented, and/or diagnosed using the polynucleotide or polypeptide and/or agonist or antagonist of the present invention.

Chemotaxis

A polynucleotide or polypeptide and/or agonist or antagonist of the present invention may have chemotaxis activity. A chemotaxic molecule attracts or mobilizes cells (e.g., monocytes, fibroblasts, neutrophils, T-cells, mast cells, eosinophils, epithelial and/or endothelial cells) to a particular site in the body, such as inflammation, infection, or site of hyperproliferation. The mobilized cells can then fight off and/or heal the particular trauma or abnormality.

A polynucleotide or polypeptide and/or agonist or antagonist of the present invention may increase chemotaxic activity of particular cells. These chemotactic molecules can then be used to treat, prevent, and/or diagnose inflammation, infection, hyperproliferative diseases, disorders, and/or conditions, or any immune system disorder by increasing the number of cells targeted to a particular location in the body. For example, chemotaxic molecules can be used to treat, prevent, and/or diagnose wounds and other trauma to tissues by attracting immune cells to the injured location. Chemotactic molecules of the present invention can also attract fibroblasts, which can be used to treat, prevent, and/or diagnose wounds.

It is also contemplated that a polynucleotide or polypeptide and/or agonist or antagonist of the present invention may inhibit chemotactic activity. These molecules could also be used to treat, prevent, and/or diagnose diseases, disorders, and/or conditions. Thus, a polynucleotide or polypeptide and/or agonist or antagonist of the present invention could be used as an inhibitor of chemotaxis.

Binding Activity

A polypeptide of the present invention may be used to screen for molecules that bind to the polypeptide or for molecules to which the polypeptide binds. The binding of the polypeptide and the molecule may activate (agonist), increase, inhibit (antagonist), or decrease activity of the polypeptide or the molecule bound. Examples of such molecules include antibodies, oligonucleotides, proteins (e.g., receptors),or small molecules.

Preferably, the molecule is closely related to the natural ligand of the polypeptide, e.g., a fragment of the ligand, or a natural substrate, a ligand, a structural or functional mimetic. (See, Coligan et al., Current Protocols in Immunology 1(2):Chapter 5 (1991).) Similarly, the molecule can be closely related to the natural receptor to which the polypeptide binds, or at least, a fragment of the receptor capable of being bound by the polypeptide (e.g., active site). In either case, the molecule can be rationally designed using known techniques.

Preferably, the screening for these molecules involves producing appropriate cells which express the polypeptide, either as a secreted protein or on the cell membrane. Preferred cells include cells from mammals, yeast, Drosophila, or E. coli. Cells expressing the polypeptide (or cell membrane containing the expressed polypeptide) are then preferably contacted with a test compound potentially containing the molecule to observe binding, stimulation, or inhibition of activity of either the polypeptide or the molecule.

The assay may simply test binding of a candidate compound to the polypeptide, wherein binding is detected by a label, or in an assay involving competition with a labeled competitor. Further, the assay may test whether the candidate compound results in a signal generated by binding to the polypeptide.

Alternatively, the assay can be carried out using cell-free preparations, polypeptide/molecule affixed to a solid support, chemical libraries, or natural product mixtures. The assay may also simply comprise the steps of mixing a candidate compound with a solution containing a polypeptide, measuring polypeptide/molecule activity or binding, and comparing the polypeptide/molecule activity or binding to a standard.

Preferably, an ELISA assay can measure polypeptide level or activity in a sample (e.g., biological sample) using a monoclonal or polyclonal antibody. The antibody can measure polypeptide level or activity by either binding, directly or indirectly, to the polypeptide or by competing with the polypeptide for a substrate.

Additionally, the receptor to which a polypeptide of the invention binds can be identified by numerous methods known to those of skill in the art, for example, ligand panning and FACS sorting (Coligan, et al., Current Protocols in Immun., 1(2), Chapter 5, (1991)). For example, expression cloning is employed wherein polyadenylated RNA is prepared from a cell responsive to the polypeptides, for example, NIH3T3 cells which are known to contain multiple receptors for the FGF family proteins, and SC-3 cells, and a cDNA library created from this RNA is divided into pools and used to transfect COS cells or other cells that are not responsive to the polypeptides. Transfected cells which are grown on glass slides are exposed to the polypeptide of the present invention, after they have been labeled. The polypeptides can be labeled by a variety of means including iodination or inclusion of a recognition site for a site-specific protein kinase.

Following fixation and incubation, the slides are subjected to auto-radiographic analysis. Positive pools are identified and sub-pools are prepared and re-transfected using an iterative sub-pooling and re-screening process, eventually yielding a single clones that encodes the putative receptor.

As an alternative approach for receptor identification, the labeled polypeptides can be photoaffinity linked with cell membrane or extract preparations that express the receptor molecule. Cross-linked material is resolved by PAGE analysis and exposed to X-ray film. The labeled complex containing the receptors of the polypeptides can be excised, resolved into peptide fragments, and subjected to protein microsequencing. The amino acid sequence obtained from microsequencing would be used to design a set of degenerate oligonucleotide probes to screen a cDNA library to identify the genes encoding the putative receptors.

Moreover, the techniques of gene-shuffling, motif-shuffling, exon-shuffling, and/or codon-shuffling (collectively referred to as "DNA shuffling") may be employed to modulate the activities of polypeptides of the invention thereby effectively generating agonists and antagonists of polypeptides of the invention. See generally, U.S. Pat. Nos. 5,605, 793, 5,811,238, 5,830,721, 5,834,252, and 5,837,458, and Patten, P. A., et al., Curr. Opinion Biotechnol. 8:724–33 (1997); Harayama, S. Trends Biotechnol. 16(2):76–82 (1998); Hansson, L. O., et al., J. Mol. Biol. 287:265–76 (1999); and Lorenzo, M. M. and Blasco, R. Biotechniques 24(2):308–13 (1998) (each of these patents and publications are hereby incorporated by reference). In one embodiment, alteration of polynucleotides and corresponding polypeptides of the invention may be achieved by DNA shuffling. DNA shuffling involves the assembly of two or more DNA segments into a desired polynucleotide sequence of the invention molecule by homologous, or site-specific, recombination. In another embodiment, polynucleotides and corresponding polypeptides of the invention may be altered by being subjected to random mutagenesis by error-prone PCR, random nucleotide insertion or other methods prior to recombination. In another embodiment, one or more components, motifs, sections, parts, domains, fragments, etc., of the polypeptides of the invention may be recombined with one or more components, motifs, sections, parts, domains, fragments, etc. of one or more heterologous molecules. In preferred embodiments, the heterologous molecules are family members. In further preferred embodiments, the heterologous molecule is a growth factor such as, for example, platelet-derived growth factor (PDGF), insulin-like growth factor (IGF-I), transforming growth factor (TGF)-alpha, epidermal growth factor (EGF), fibroblast growth factor (FGF), TGF-beta, bone morphogenetic protein (BMP)-2, BMP-4, BMP-5, BMP-6, BMP-7, activins A and B, decapentaplegic(dpp), 60A, OP-2, dorsalin, growth differentiation factors (GDFs), nodal, MIS, inhibin-alpha, TGF-beta1, TGF-beta2, TGF-beta3, TGF-beta5, and glial-derived neurotrophic factor (GDNF).

Other preferred fragments are biologically active fragments of the polypeptides of the invention. Biologically active fragments are those exhibiting activity similar, but not necessarily identical, to an activity of the polypeptide. The biological activity of the fragments may include an improved desired activity, or a decreased undesirable activity.

Additionally, this invention provides a method of screening compounds to identify those which modulate the action of the polypeptide of the present invention. An example of such an assay comprises combining a mammalian fibroblast cell, a the polypeptide of the present invention, the compound to be screened and 3 [H] thymidine under cell culture conditions where the fibroblast cell would normally proliferate. A control assay may be performed in the absence of the compound to be screened and compared to the amount of fibroblast proliferation in the presence of the compound to determine if the compound stimulates proliferation by determining the uptake of 3[H] thymidine in each case. The amount of fibroblast cell proliferation is measured by liquid scintillation chromatography which measures the incorporation of 3[H] thymidine. Both agonist and antagonist compounds may be identified by this procedure.

In another method, a mammalian cell or membrane preparation expressing a receptor for a polypeptide of the present invention is incubated with a labeled polypeptide of the present invention in the presence of the compound. The ability of the compound to enhance or block this interaction could then be measured. Alternatively, the response of a known second messenger system following interaction of a compound to be screened and the receptor is measured and the ability of the compound to bind to the receptor and elicit a second messenger response is measured to determine if the compound is a potential agonist or antagonist. Such second messenger systems include but are not limited to, cAMP guanylate cyclase, ion channels or phosphoinositide hydrolysis.

All of these above assays can be used as diagnostic or prognostic markers. The molecules discovered using these assays can be used to treat, prevent, and/or diagnose disease or to bring about a particular result in a patient (e.g., blood vessel growth) by activating or inhibiting the polypeptide/molecule. Moreover, the assays can discover agents which may inhibit or enhance the production of the polypeptides of the invention from suitably manipulated cells or tissues. Therefore, the invention includes a method of identifying compounds which bind to the polypeptides of the invention comprising the steps of: (a) incubating a candidate binding compound with the polypeptide; and (b) determining if binding has occurred. Moreover, the invention includes a method of identifying agonists/antagonists comprising the steps of: (a) incubating a candidate compound with the polypeptide, (b) assaying a biological activity, and (b) determining if a biological activity of the polypeptide has been altered.

Also, one could identify molecules bind a polypeptide of the invention experimentally by using the beta-pleated sheet regions contained in the polypeptide sequence of the protein. Accordingly, specific embodiments of the invention are directed to polynucleotides encoding polypeptides which comprise, or alternatively consist of, the amino acid sequence of each beta pleated sheet regions in a disclosed polypeptide sequence. Additional embodiments of the invention are directed to polynucleotides encoding polypeptides which comprise, or alternatively consist of, any combination or all of contained in the polypeptide sequences of the invention. Additional preferred embodiments of the invention are directed to polypeptides which comprise, or alternatively consist of, the amino acid sequence of each of the beta pleated sheet regions in one of the polypeptide sequences of the invention. Additional embodiments of the invention are directed to polypeptides which comprise, or alternatively consist of, any combination or all of the beta pleated sheet regions in one of the polypeptide sequences of the invention.

Targeted Delivery

In another embodiment, the invention provides a method of delivering compositions to targeted cells expressing a receptor for a polypeptide of the invention, or cells expressing a cell bound form of a polypeptide of the invention.

As discussed herein, polypeptides or antibodies of the invention may be associated with heterologous polypeptides, heterologous nucleic acids, toxins, or prodrugs via hydrophobic, hydrophilic, ionic and/or covalent interactions. In one embodiment, the invention provides a method for the specific delivery of compositions of the invention to cells by administering polypeptides of the invention (including antibodies) that are associated with heterologous polypeptides or nucleic acids. In one example, the invention provides a method for delivering a therapeutic protein into the targeted cell. In another example, the invention provides a method for delivering a single stranded nucleic acid (e.g., antisense or ribozymes) or double stranded nucleic acid (e.g., DNA that can integrate into the cell's genome or replicate episomally and that can be transcribed) into the targeted cell.

In another embodiment, the invention provides a method for the specific destruction of cells (e.g., the destruction of tumor cells) by administering polypeptides of the invention (e.g., polypeptides of the invention or antibodies of the invention) in association with toxins or cytotoxic prodrugs.

By "toxin" is meant compounds that bind and activate endogenous cytotoxic effector systems, radioisotopes, holotoxins, modified toxins, catalytic subunits of toxins, or any molecules or enzymes not normally present in or on the surface of a cell that under defined conditions cause the cell's death. Toxins that may be used according to the methods of the invention include, but are not limited to, radioisotopes known in the art, compounds such as, for example, antibodies (or complement fixing containing portions thereof) that bind an inherent or induced endogenous cytotoxic effector system, thymidine kinase, endonuclease, RNAse, alpha toxin, ricin, abrin, Pseudomonas exotoxin A, diphtheria toxin, saporin, momordin, gelonin, pokeweed antiviral protein, alpha-sarcin and cholera toxin. By "cytotoxic prodrug" is meant a non-toxic compound that is converted by an enzyme, normally present in the cell, into a cytotoxic compound. Cytotoxic prodrugs that may be used according to the methods of the invention include, but are not limited to, glutamyl derivatives of benzoic acid mustard alkylating agent, phosphate derivatives of etoposide or mitomycin C, cytosine arabinoside, daunorubisin, and phenoxyacetamide derivatives of doxorubicin.

Drug Screening

Further contemplated is the use of the polypeptides of the present invention, or the polynucleotides encoding these polypeptides, to screen for molecules which modify the activities of the polypeptides of the present invention. Such a method would include contacting the polypeptide of the present invention with a selected compound(s) suspected of having antagonist or agonist activity, and assaying the activity of these polypeptides following binding.

This invention is particularly useful for screening therapeutic compounds by using the polypeptides of the present invention, or binding fragments thereof, in any of a variety of drug screening techniques. The polypeptide or fragment employed in such a test may be affixed to a solid support, expressed on a cell surface, free in solution, or located intracellularly. One method of drug screening utilizes eukaryotic or prokaryotic host cells which are stably transformed with recombinant nucleic acids expressing the polypeptide or fragment. Drugs are screened against such transformed cells in competitive binding assays. One may measure, for example, the formulation of complexes between the agent being tested and a polypeptide of the present invention.

Thus, the present invention provides methods of screening for drugs or any other agents which affect activities mediated by the polypeptides of the present invention. These methods comprise contacting such an agent with a polypeptide of the present invention or a fragment thereof and assaying for the presence of a complex between the agent and the polypeptide or a fragment thereof, by methods well known in the art. In such a competitive binding assay, the agents to screen are typically labeled. Following incubation, free agent is separated from that present in bound form, and the amount of free or uncomplexed label is a measure of the ability of a particular agent to bind to the polypeptides of the present invention.

Another technique for drug screening provides high throughput screening for compounds having suitable binding affinity to the polypeptides of the present invention, and is described in great detail in European Patent Application 84/03564, published on Sep. 13, 1984, which is incorporated herein by reference herein. Briefly stated, large numbers of different small peptide test compounds are synthesized on a solid substrate, such as plastic pins or some other surface. The peptide test compounds are reacted with polypeptides of the present invention and washed. Bound polypeptides are then detected by methods well known in the art. Purified polypeptides are coated directly onto plates for use in the aforementioned drug screening techniques. In addition, non-neutralizing antibodies may be used to capture the peptide and immobilize it on the solid support.

This invention also contemplates the use of competitive drug screening assays in which neutralizing antibodies capable of binding polypeptides of the present invention specifically compete with a test compound for binding to the polypeptides or fragments thereof. In this manner, the antibodies are used to detect the presence of any peptide which shares one or more antigenic epitopes with a polypeptide of the invention.

The human LSI-1 polypeptides and/or peptides of the present invention, or immunogenic fragments or oligopeptides thereof, can be used for screening therapeutic drugs or compounds in a variety of drug screening techniques. The fragment employed in such a screening assay may be free in solution, affixed to a solid support, borne on a cell surface, or located intracellularly. The reduction or abolition of activity of the formation of binding complexes between the ion channel protein and the agent being tested can be measured. Thus, the present invention provides a method for screening or assessing a plurality of compounds for their specific binding affinity with a LSI-1 polypeptide, or a bindable peptide fragment, of this invention, comprising providing a plurality of compounds, combining the LSI-1 polypeptide, or a bindable peptide fragment, with each of a plurality of compounds for a time sufficient to allow binding under suitable conditions and detecting binding of the LSI-1 polypeptide or peptide to each of the plurality of test compounds, thereby identifying the compounds that specifically bind to the LSI-1 polypeptide or peptide.

Methods of identifying compounds that modulate the activity of the novel human LSI-1 polypeptides and/or peptides are provided by the present invention and comprise combining a potential or candidate compound or drug modulator of calpain biological activity with an LSI-1 polypeptide or peptide, for example, the LSI-1 amino acid sequence as set forth in SEQ ID NOS:2, and measuring an effect of the candidate compound or drug modulator on the biological activity of the LSI-1 polypeptide or peptide. Such measurable effects include, for example, physical binding interaction; the ability to cleave a suitable calpain substrate; effects on native and cloned LSI-1-expressing cell line; and effects of modulators or other calpain-mediated physiological measures.

Another method of identifying compounds that modulate the biological activity of the novel LSI-1 polypeptides of the present invention comprises combining a potential or candidate compound or drug modulator of a calpain biological activity with a host cell that expresses the LSI-1 polypeptide and measuring an effect of the candidate compound or drug modulator on the biological activity of the LSI-1 polypeptide. The host cell can also be capable of being induced to express the LSI-1 polypeptide, e.g., via inducible expression. Physiological effects of a given modulator candidate on the LSI-1 polypeptide can also be measured. Thus, cellular assays for particular calpain modulators may be either direct measurement or quantification of the physical biological activity of the LSI-1 polypeptide, or they may be measurement or quantification of a physiological effect. Such methods preferably employ a LSI-1 polypeptide as described herein, or an overexpressed recombinant LSI-1 polypeptide in suitable host cells containing an expression vector as described herein, wherein the LSI-1 polypeptide is expressed, overexpressed, or undergoes upregulated expression.

Another aspect of the present invention embraces a method of screening for a compound that is capable of modulating the biological activity of a LSI-1 polypeptide, comprising providing a host cell containing an expression vector harboring a nucleic acid sequence encoding a LSI-1 polypeptide, or a functional peptide or portion thereof (e.g., SEQ ID NOS:2); determining the biological activity of the expressed LSI-1 polypeptide in the absence of a modulator compound; contacting the cell with the modulator compound and determining the biological activity of the expressed LSI-1 polypeptide in the presence of the modulator compound. In such a method, a difference between the activity of the LSI-1 polypeptide in the presence of the modulator compound and in the absence of the modulator compound indicates a modulating effect of the compound.

Essentially any chemical compound can be employed as a potential modulator or ligand in the assays according to the present invention. Compounds tested as calpain modulators can be any small chemical compound, or biological entity (e.g., protein, sugar, nucleic acid, lipid). Test compounds will typically be small chemical molecules and peptides. Generally, the compounds used as potential modulators can be dissolved in aqueous or organic (e.g., DMSO-based) solutions. The assays are designed to screen large chemical libraries by automating the assay steps and providing compounds from any convenient source. Assays are typically run in parallel, for example, in microtiter formats on microtiter plates in robotic assays. There are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs, Switzerland), for example. Also, compounds may be synthesized by methods known in the art.

High throughput screening methodologies are particularly envisioned for the detection of modulators of the novel LSI-1 polynucleotides and polypeptides described herein. Such high throughput screening methods typically involve providing a combinatorial chemical or peptide library containing a large number of potential therapeutic compounds (e.g., ligand or modulator compounds). Such combinatorial chemical libraries or ligand libraries are then screened in one or more assays to identify those library members (e.g., particular chemical species or subclasses) that display a desired characteristic activity. The compounds so identified can serve as conventional lead compounds, or can themselves be used as potential or actual therapeutics.

A combinatorial chemical library is a collection of diverse chemical compounds generated either by chemical synthesis or biological synthesis, by combining a number of chemical building blocks (i.e., reagents such as amino acids). As an example, a linear combinatorial library, e.g., a polypeptide or peptide library, is formed by combining a set of chemical building blocks in every possible way for a given compound length (i.e., the number of amino acids in a polypeptide or peptide compound). Millions of chemical compounds can be synthesized through such combinatorial mixing of chemical building blocks.

The preparation and screening of combinatorial chemical libraries is well known to those having skill in the pertinent art. Combinatorial libraries include, without limitation, peptide libraries (e.g. U.S. Pat. No. 5,010,175; Furka, 1991, *Int. J. Pept. Prot. Res.*, 37:487–493; and Houghton et al., 1991, *Nature*, 354:84–88). Other chemistries for generating chemical diversity libraries can also be used. Nonlimiting examples of chemical diversity library chemistries include, peptoids (PCT Publication No. WO 91/019735), encoded peptides (PCT Publication No. WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., 1993, *Proc. Natl. Acad. Sci. USA*, 90:6909–6913), vinylogous polypeptides (Hagihara et al., 1992, *J. Amer. Chem. Soc.*, 114:6568), nonpeptidal peptidomimetics with glucose scaffolding (Hirschmann et al., 1992, *J. Amer. Chem. Soc.*, 114:9217–9218), analogous organic synthesis of small compound libraries (Chen et al., 1994, *J. Amer. Chem. Soc.*, 116:2661), oligocarbamates (Cho et al., 1993, *Science*, 261: 1303), and/or peptidyl phosphonates (Campbell et al., 1994, *J. Org. Chem.*, 59:658), nucleic acid libraries (see Ausubel, Berger and Sambrook, all supra), peptide nucleic acid libraries (U.S. Pat. No. 5,539,083), antibody libraries (e.g., Vaughn et al., 1996, *Nature Biotechnology*, 14(3):309–314) and PCT/US96/10287), carbohydrate libraries (e.g., Liang et al., 1996, Science, 274–1520–1522) and U.S. Pat. No. 5,593,853), small organic molecule libraries (e.g., benzodiazepines, Baum C&EN, Jan. 18, 1993, page 33; and U.S. Pat. No. 5,288,514; isoprenoids, U.S. Pat. No. 5,569,588; thiazolidinones and metathiazanones, U.S. Pat. No. 5,549, 974; pyrrolidines, U.S. Pat. Nos. 5,525,735 and 5,519,134; morpholino compounds, U.S. Pat. No. 5,506,337; and the like).

Devices for the preparation of combinatorial libraries are commercially available (e.g., 357 MPS, 390 MPS, Advanced Chem Tech, Louisville Ky.; Symphony, Rainin, Woburn, Mass.; 433A Applied Biosystems, Foster City, Calif.; 9050 Plus, Millipore, Bedford, Mass.). In addition, a large number of combinatorial libraries are commercially available (e.g., ComGenex, Princeton, N.J.; Asinex, Moscow, Russia; Tripos, Inc., St. Louis, Mo.; ChemStar, Ltd., Moscow, Russia; 3D Pharmaceuticals, Exton, Pa.; Martek Biosciences, Columbia, Md., and the like).

In one embodiment, the invention provides solid phase based in vitro assays in a high throughput format, where the cell or tissue expressing an ion channel is attached to a solid phase substrate. In such high throughput assays, it is possible to screen up to several thousand different modulators or ligands in a single day. In particular, each well of a microtiter plate can be used to perform a separate assay against a selected potential modulator, or, if concentration or incubation time effects are to be observed, every 5–10 wells can test a single modulator. Thus, a single standard microtiter plate can assay about 96 modulators. If 1536 well plates are used, then a single plate can easily assay from about 100 to about 1500 different compounds. It is possible to assay several different plates per day; thus, for example, assay screens for up to about 6,000–20,000 different compounds are possible using the described integrated systems.

In another of its aspects, the present invention encompasses screening and small molecule (e.g., drug) detection assays which involve the detection or identification of small molecules that can bind to a given protein, i.e., a LSI-1 polypeptide or peptide. Particularly preferred are assays suitable for high throughput screening methodologies.

In such binding-based detection, identification, or screening assays, a functional assay is not typically required. All that is needed is a target protein, preferably substantially purified, and a library or panel of compounds (e.g., ligands, drugs, small molecules) or biological entities to be screened or assayed for binding to the protein target. Preferably, most small molecules that bind to the target protein will modulate activity in some manner, due to preferential, higher affinity binding to functional areas or sites on the protein.

An example of such an assay is the fluorescence based thermal shift assay (3-Dimensional Pharmaceuticals, Inc., 3DP, Exton, Pa.) as described in U.S. Pat. Nos. 6,020,141 and 6,036,920 to Pantoliano et al.; see also, J. Zimmerman, 2000, Gen. Eng. News, 20(8)). The assay allows the detection of small molecules (e.g., drugs, ligands) that bind to expressed, and preferably purified, ion channel polypeptide based on affinity of binding determinations by analyzing thermal unfolding curves of protein-drug or ligand complexes. The drugs or binding molecules determined by this technique can be further assayed, if desired, by methods, such as those described herein, to determine if the molecules affect or modulate function or activity of the target protein.

To purify a LSI-1 polypeptide or peptide to measure a biological binding or ligand binding activity, the source may be a whole cell lysate that can be prepared by successive freeze-thaw cycles (e.g., one to three) in the presence of standard protease inhibitors. The LSI-1 polypeptide may be partially or completely purified by standard protein purification methods, e.g., affinity chromatography using specific antibody described infra, or by ligands specific for an epitope tag engineered into the recombinant LSI-1 polypeptide molecule, also as described herein. Binding activity can then be measured as described.

Compounds which are identified according to the methods provided herein, and which modulate or regulate the biological activity or physiology of the LSI-1 polypeptides according to the present invention are a preferred embodiment of this invention. It is contemplated that such modulatory compounds may be employed in treatment and therapeutic methods for treating a condition that is mediated by the novel LSI-1 polypeptides by administering to an individual in need of such treatment a therapeutically effective amount of the compound identified by the methods described herein.

In addition, the present invention provides methods for treating an individual in need of such treatment for a disease, disorder, or condition that is mediated by the LSI-1 polypeptides of the invention, comprising administering to the individual a therapeutically effective amount of the LSI-1-modulating compound identified by a method provided herein.

Antisense and Ribozyme (Antagonists)

In specific embodiments, antagonists according to the present invention are nucleic acids corresponding to the sequences contained in SEQ ID NO:1, or the complementary strand thereof, and/or to nucleotide sequences contained a deposited clone. In one embodiment, antisense sequence is generated internally by the organism, in another embodiment, the antisense sequence is separately administered (see, for example, O'Connor, Neurochem., 56:560 (1991). Oligodeoxynucleotides as Antisense Inhibitors of Gene Expression, CRC Press, Boca Raton, Fla. (1988). Antisense technology can be used to control gene expression through antisense DNA or RNA, or through triple-helix formation. Antisense techniques are discussed for example, in Okano, Neurochem., 56:560 (1991); Oligodeoxynucleotides as Antisense Inhibitors of Gene Expression, CRC Press, Boca Raton, Fla. (1988). Triple helix formation is discussed in, for instance, Lee et al., Nucleic Acids Research, 6:3073 (1979); Cooney et al., Science, 241:456 (1988); and Dervan et al., Science, 251:1300 (1991). The methods are based on binding of a polynucleotide to a complementary DNA or RNA.

For example, the use of c-myc and c-myb antisense RNA constructs to inhibit the growth of the non-lymphocytic leukemia cell line HL-60 and other cell lines was previously described. (Wickstrom et al. (1988); Anfossi et al. (1989)). These experiments were performed in vitro by incubating cells with the oligoribonucleotide. A similar procedure for in vivo use is described in WO 91/15580. Briefly, a pair of oligonucleotides for a given antisense RNA is produced as follows: A sequence complimentary to the first 15 bases of the open reading frame is flanked by an EcoR1 site on the 5 end and a HindIII site on the 3 end. Next, the pair of oligonucleotides is heated at 90° C. for one minute and then annealed in 2× ligation buffer (20 mM TRIS HCl pH 7.5, 10 mM MgCl2, 10 MM dithiothreitol (DTT) and 0.2 mM ATP) and then ligated to the EcoR1/Hind III site of the retroviral vector PMV7 (WO 91/15580).

For example, the 5' coding portion of a polynucleotide that encodes the mature polypeptide of the present invention may be used to design an antisense RNA oligonucleotide of from about 10 to 40 base pairs in length. A DNA oligonucleotide is designed to be complementary to a region of the gene involved in transcription thereby preventing transcription and the production of the receptor. The antisense RNA oligonucleotide hybridizes to the mRNA in vivo and blocks translation of the mRNA molecule into receptor polypeptide.

In one embodiment, the antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the antisense nucleic acid of the invention. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in vertebrate cells. Expression of the sequence encoding a polypeptide of the invention, or fragments thereof, can be by any promoter known in the art to act in vertebrate, preferably human cells. Such promoters can be inducible or constitutive. Such promoters include, but are not limited to, the SV40 early promoter region (Bernoist and Chambon, Nature, 29:304–310 (1981), the promoter contained in the 3' long terminal repeat of Rous sarcoma virus (Yamamoto et al., Cell, 22:787–797 (1980), the herpes thymidine promoter (Wagner et al., Proc. Natl. Acad. Sci. U.S.A., 78:1441–1445 (1981), the regulatory sequences of the metallothionein gene (Brinster et al., Nature, 296:39–42 (1982)), etc.

The antisense nucleic acids of the invention comprise a sequence complementary to at least a portion of an RNA transcript of a gene of interest. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded antisense nucleic acids of the invention, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a RNA sequence of the invention it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., Nature, 372: 333–335 (1994). Thus, oligonucleotides complementary to either the 5'- or 3'-non-translated, non-coding regions of a polynucleotide sequence of the invention could be used in an antisense approach to inhibit translation of endogenous mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., Proc. Natl. Acad. Sci. U.S.A. 86:6553–6556 (1989); Lemaitre et al., Proc. Natl. Acad. Sci., 84:648–652 (1987); PCT Publication NO: WO88/09810, published Dec. 15, 1988) or the blood-brain barrier (see, e.g., PCT Publication NO: WO89/10134, published Apr. 25, 1988), hybridization-triggered cleavage agents. (See, e.g., Krol et al., BioTechniques, 6:958–976 (1988)) or intercalating agents. (See, e.g., Zon, Pharm. Res., 5:539–549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an a-anomeric oligonucleotide. An a-anomeric oligonucleotide forms specific double-stranded hybrids with complementary RNA in which, contrary to the usual b-units, the strands run parallel to each other (Gautier et al., Nucl. Acids Res., 15:6625–6641 (1987)). The oligonucleotide is a 2-0-methylribonucleotide (Inoue et al., Nucl. Acids Res., 15:6131–6148 (1987)), or a chimeric RNA-DNA analogue (Inoue et al., FEBS Lett. 215:327–330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res., 16:3209 (1988)), methylphosphonate oligonucleotides can be prepared by use of controlled pore glass polymer supports (Sarin et al., Proc. Natl. Acad. Sci. U.S.A., 85:7448–7451 (1988)), etc.

While antisense nucleotides complementary to the coding region sequence of the invention could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, Science, 247:1222–1225 (1990). While ribozymes that cleave mRNA at site specific recognition sequences can be used to destroy mRNAs corresponding to the polynucleotides of the invention, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, Nature, 334:585–591 (1988). There are numerous potential hammerhead ribozyme cleavage sites within each nucleotide sequence disclosed in the sequence listing. Preferably, the ribozyme is engineered so that the cleavage recognition site is located near the 5' end of the mRNA corresponding to the polynucleotides of the invention; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express the polynucleotides of the invention in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous messages and inhibit translation. Since ribozymes unlike antisense molecules, are catalytic, a lower intracellular concentration is required for efficiency.

Antagonist/agonist compounds may be employed to inhibit the cell growth and proliferation effects of the polypeptides of the present invention on neoplastic cells and tissues, i.e. stimulation of angiogenesis of tumors, and, therefore, retard or prevent abnormal cellular growth and proliferation, for example, in tumor formation or growth.

The antagonist/agonist may also be employed to prevent hyper-vascular diseases, and prevent the proliferation of epithelial lens cells after extracapsular cataract surgery. Prevention of the mitogenic activity of the polypeptides of the present invention may also be desirous in cases such as restenosis after balloon angioplasty.

The antagonist/agonist may also be employed to prevent the growth of scar tissue during wound healing.

The antagonist/agonist may also be employed to treat, prevent, and/or diagnose the diseases described herein.

Thus, the invention provides a method of treating or preventing diseases, disorders, and/or conditions, including but not limited to the diseases, disorders, and/or conditions listed throughout this application, associated with overexpression of a polynucleotide of the present invention by administering to a patient (a) an antisense molecule directed to the polynucleotide of the present invention, and/or (b) a ribozyme directed to the polynucleotide of the present invention. invention, and/or (b) a ribozyme directed to the polynucleotide of the present invention.

Biotic Associations

A polynucleotide or polypeptide and/or agonist or antagonist of the present invention may increase the organisms ability, either directly or indirectly, to initiate and/or maintain biotic associations with other organisms. Such associations may be symbiotic, nonsymbiotic, endosymbiotic, macrosymbiotic, and/or microsymbiotic in nature. In general, a polynucleotide or polypeptide and/or agonist or antagonist of the present invention may increase the organisms ability to form biotic associations with any member of the fungal, bacterial, lichen, mycorrhizal, cyanobacterial, dinoflaggellate, and/or algal, kingdom, phylums, families, classes, genuses, and/or species.

The mechanism by which a polynucleotide or polypeptide and/or agonist or antagonist of the present invention may increase the host organisms ability, either directly or indirectly, to initiate and/or maintain biotic associations is variable, though may include, modulating osmolarity to desirable levels for the symbiont, modulating pH to desirable levels for the symbiont, modulating secretions of organic acids, modulating the secretion of specific proteins, phenolic compounds, nutrients, or the increased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

In an alternative embodiment, a polynucleotide or polypeptide and/or agonist or antagonist of the present invention may decrease the host organisms ability to form biotic associations with another organism, either directly or indirectly. The mechanism by which a polynucleotide or polypeptide and/or agonist or antagonist of the present invention may decrease the host organisms ability, either directly or indirectly, to initiate and/or maintain biotic associations with another organism is variable, though may include, modulating osmolarity to undesirable levels, modulating pH to undesirable levels, modulating secretions of organic acids, modulating the secretion of specific proteins, phenolic compounds, nutrients, or the decreased expression of a protein required for host-biotic organisms interactions (e.g., a receptor, ligand, etc.). Additional mechanisms are known in the art and are encompassed by the invention (see, for example, "Microbial Signalling and Communication", eds., R. England, G. Hobbs, N. Bainton, and D. McL. Roberts, Cambridge University Press, Cambridge, (1999); which is hereby incorporated herein by reference).

The hosts ability to maintain biotic associations with a particular pathogen has significant implications for the overall health and fitness of the host. For example, human hosts have symbiosis with enteric bacteria in their gastrointestinal tracts, particularly in the small and large intestine. In fact, bacteria counts in feces of the distal colon often approach $10^{12}$ per milliliter of feces. Examples of bowel flora in the gastrointestinal tract are members of the Enterobacteriaceae, Bacteriodes, in addition to a-hemolytic streptococci, *E. coli*, Bifobacteria, *Anaerobic cocci*, Eubacteria, *Costridia, lactobacilli*, and yeasts. Such bacteria, among other things, assist the host in the assimilation of nutrients by breaking down food stuffs not typically broken down by the hosts digestive system, particularly in the hosts bowel. Therefore, increasing the hosts ability to maintain such a biotic association would help assure proper nutrition for the host.

Aberrations in the enteric bacterial population of mammals, particularly humans, has been associated with the following disorders: diarrhea, ileus, chronic inflammatory disease, bowel obstruction, duodenal diverticula, biliary calculous disease, and malnutrition. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant enteric flora population.

The composition of the intestinal flora, for example, is based upon a variety of factors, which include, but are not limited to, the age, race, diet, malnutrition, gastric acidity, bile salt excretion, gut motility, and immune mechanisms. As a result, the polynucleotides and polypeptides, including agonists, antagonists, and fragments thereof, may modulate the ability of a host to form biotic associations by affecting, directly or indirectly, at least one or more of these factors.

Although the predominate intestinal flora comprises anaerobic organisms, an underlying percentage represents aerobes (e.g., *E. coli*). This is significant as such aerobes rapidly become the predominate organisms in intraabdominal infections—effectively becoming opportunistic early in infection pathogenesis. As a result, there is an intrinsic need to control aerobe populations, particularly for immune compromised individuals.

In a preferred embodiment, a polynucleotides and polypeptides, including agonists, antagonists, and fragments thereof, are useful for inhibiting biotic associations with specific enteric symbiont organisms in an effort to control the population of such organisms.

Biotic associations occur not only in the gastrointestinal tract, but also on an in the integument. As opposed to the gastrointestinal flora, the cutaneous flora is comprised almost equally with aerobic and anaerobic organisms. Examples of cutaneous flora are members of the gram-positive cocci (e.g., *S. aureus*, coagulase-negative staphylococci, micrococcus, *M.sedentarius*), gram-positive bacilli (e.g., *Corynebacterium* species, *C. minutissimum*, Brevibacterium species, Propoionibacterium species, *P.acnes*), gram-negative bacilli (e.g., Acinebacter species), and fungi (*Pityrosporum orbiculare*). The relatively low number of flora associated with the integument is based upon the inability of many organisms to adhere to the skin. The organisms referenced above have acquired this unique ability. Therefore, the polynucleotides and polypeptides of the present invention may have uses which include modulating the population of the cutaneous flora, either directly or indirectly.

Aberrations in the cutaneous flora are associated with a number of significant diseases and/or disorders, which include, but are not limited to the following: impetigo, ecthyma, blistering distal dactulitis, pustules, folliculitis, cutaneous abscesses, pitted keratolysis, trichomycosis axcillaris, dermatophytosis complex, axillary odor, erthyrasma, cheesy foot odor, acne, tinea versicolor, seborrheic dermititis, and Pityrosporum folliculitis, to name a few. A polynucleotide or polypeptide and/or agonist or antagonist of the present invention are useful for treating, detecting, diagnosing, prognosing, and/or ameliorating, either directly or indirectly, and of the above mentioned diseases and/or disorders associated with aberrant cutaneous flora population.

Additional biotic associations, including diseases and disorders associated with the aberrant growth of such associations, are known in the art and are encompassed by the invention. See, for example, "Infectious Disease", Second Edition, Eds., S. L., Gorbach, J. G., Bartlett, and N. R., Blacklow, W. B. Saunders Company, Philadelphia, (1998); which is hereby incorporated herein by reference).

Pheromones

In another embodiment, a polynucleotide or polypeptide and/or agonist or antagonist of the present invention may increase the organisms ability to synthesize and/or release a pheromone. Such a pheromone may, for example, alter the organisms behavior and/or metabolism.

A polynucleotide or polypeptide and/or agonist or antagonist of the present invention may modulate the biosynthesis and/or release of pheromones, the organisms ability to respond to pheromones (e.g., behaviorally, and/or metabolically), and/or the organisms ability to detect pheromones. Preferably, any of the pheromones, and/or volatiles released from the organism, or induced, by a polynucleotide or polypeptide and/or agonist or antagonist of the invention have behavioral effects the organism.

Other Activities

The polypeptide of the present invention, as a result of the ability to stimulate vascular endothelial cell growth, may be employed in treatment for stimulating re-vascularization of ischemic tissues due to various disease conditions such as thrombosis, arteriosclerosis, and other cardiovascular conditions. These polypeptide may also be employed to stimulate angiogenesis and limb regeneration, as discussed above.

The polypeptide may also be employed for treating wounds due to injuries, burns, post-operative tissue repair, and ulcers since they are mitogenic to various cells of different origins, such as fibroblast cells and skeletal muscle cells, and therefore, facilitate the repair or replacement of damaged or diseased tissue.

The polypeptide of the present invention may also be employed stimulate neuronal growth and to treat, prevent, and/or diagnose neuronal damage which occurs in certain neuronal disorders or neuro-degenerative conditions such as Alzheimer's disease, Parkinson's disease, and AIDS-related complex. The polypeptide of the invention may have the ability to stimulate chondrocyte growth, therefore, they may be employed to enhance bone and periodontal regeneration and aid in tissue transplants or bone grafts.

The polypeptide of the present invention may be also be employed to prevent skin aging due to sunburn by stimulating keratinocyte growth.

The polypeptide of the invention may also be employed for preventing hair loss, since FGF family members activate hair-forming cells and promotes melanocyte growth. Along the same lines, the polypeptides of the present invention may be employed to stimulate growth and differentiation of hematopoietic cells and bone marrow cells when used in combination with other cytokines.

The polypeptide of the invention may also be employed to maintain organs before transplantation or for supporting cell culture of primary tissues.

The polypeptide of the present invention may also be employed for inducing tissue of mesodermal origin to differentiate in early embryos.

The polypeptide or polynucleotides and/or agonist or antagonists of the present invention may also increase or decrease the differentiation or proliferation of embryonic stem cells, besides, as discussed above, hematopoietic lineage.

The polypeptide or polynucleotides and/or agonist or antagonists of the present invention may also be used to modulate mammalian characteristics, such as body height, weight, hair color, eye color, skin, percentage of adipose tissue, pigmentation, size, and shape (e.g., cosmetic surgery). Similarly, polypeptides or polynucleotides and/or agonist or antagonists of the present invention may be used to modulate mammalian metabolism affecting catabolism, anabolism, processing, utilization, and storage of energy.

Polypeptide or polynucleotides and/or agonist or antagonists of the present invention may be used to change a mammal's mental state or physical state by influencing biorhythms, caricadic rhythms, depression (including depressive diseases, disorders, and/or conditions), tendency for violence, tolerance for pain, reproductive capabilities (preferably by Activin or Inhibin-like activity), hormonal or endocrine levels, appetite, libido, memory, stress, or other cognitive qualities.

Polypeptide or polynucleotides and/or agonist or antagonists of the present invention may also be used as a food additive or preservative, such as to increase or decrease storage capabilities, fat content, lipid, protein, carbohydrate, vitamins, minerals, cofactors or other nutritional components.

Polypeptide or polynucleotides and/or agonist or antagonists of the present invention may also be used to increase the efficacy of a pharmaceutical composition, either directly or indirectly. Such a use may be administered in simultaneous conjunction with said pharmaceutical, or separately through either the same or different route of administration (e.g., intravenous for the polynucleotide or polypeptide of the present invention, and orally for the pharmaceutical, among others described herein.).

Polypeptide or polynucleotides and/or agonist or antagonists of the present invention may also be used to prepare individuals for extraterrestrial travel, low gravity environments, prolonged exposure to extraterrestrial radiation levels, low oxygen levels, reduction of metabolic activity, exposure to extraterrestrial pathogens, etc. Such a use may be administered either prior to an extraterrestrial event, during an extraterrestrial event, or both. Moreover, such a use may result in a number of beneficial changes in the recipient, such as, for example, any one of the following, non-limiting, effects: an increased level of hematopoietic cells, particularly red blood cells which would aid the recipient in coping with low oxygen levels; an increased level of B-cells, T-cells, antigen presenting cells, and/or macrophages, which would aid the recipient in coping with exposure to extraterrestrial pathogens, for example; a temporary (i.e., reversible) inhibition of hematopoietic cell production which would aid the recipient in coping with exposure to extraterrestrial radiation levels; increase and/or stability of bone mass which would aid the recipient in coping with low gravity environments; and/or decreased metabolism which would effectively facilitate the recipients ability to prolong their extraterrestrial travel by any one of the following, non-limiting means: (i) aid the recipient by decreasing their basal daily energy requirements; (ii) effectively lower the level of oxidative and/or metabolic stress in recipient (i.e., to enable recipient to cope with increased extraterrestial radiation levels by decreasing the level of internal oxidative/metabolic damage acquired during normal basal energy requirements; and/or (iii) enabling recipient to subsist at a lower metabolic temperature (i.e., cryogenic, and/or sub-cryogenic environment).

Other Preferred Embodiments

Other preferred embodiments of the claimed invention include an isolated nucleic acid molecule comprising a nucleotide sequence which is at least 95% identical to a sequence of at least about 50 contiguous nucleotides in the nucleotide sequence of SEQ ID NO:1 wherein X is any integer as defined in Table I.

Also preferred is a nucleic acid molecule wherein said sequence of contiguous nucleotides is included in the nucleotide sequence of SEQ ID NO:1 in the range of positions beginning with the nucleotide at about the position of the "5' NT of Start Codon of ORF" and ending with the nucleotide at about the position of the "3' NT of ORF" as defined for SEQ ID NO:1 in Table I.

Also preferred is an isolated nucleic acid molecule comprising a nucleotide sequence which is at least 95% identical to a sequence of at least about 150 contiguous nucleotides in the nucleotide sequence of SEQ ID NO:1.

Further preferred is an isolated nucleic acid molecule comprising a nucleotide sequence which is at least 95% identical to a sequence of at least about 500 contiguous nucleotides in the nucleotide sequence of SEQ ID NO:1.

A further preferred embodiment is a nucleic acid molecule comprising a nucleotide sequence which is at least 95% identical to the nucleotide sequence of SEQ ID NO:1 beginning with the nucleotide at about the position of the "5' NT of ORF" and ending with the nucleotide at about the position of the "3' NT of ORF" as defined for SEQ ID NO:1 in Table I.

A further preferred embodiment is an isolated nucleic acid molecule comprising a nucleotide sequence which is at least 95% identical to the complete nucleotide sequence of SEQ ID NO:1.

Also preferred is an isolated nucleic acid molecule which hybridizes under stringent hybridization conditions to a nucleic acid molecule, wherein said nucleic acid molecule which hybridizes does not hybridize under stringent hybridization conditions to a nucleic acid molecule having a nucleotide sequence consisting of only A residues or of only T residues.

Also preferred is a composition of matter comprising a DNA molecule which comprises a cDNA clone identified by a cDNA Clone Identifier in Table I, which DNA molecule is contained in the material deposited with the American Type Culture Collection and given the ATCC Deposit Number shown in Table I for said cDNA Clone Identifier.

Also preferred is an isolated nucleic acid molecule comprising a nucleotide sequence which is at least 95% identical to a sequence of at least 50 contiguous nucleotides in the nucleotide sequence of a cDNA clone identified by a cDNA Clone Identifier in Table I, which DNA molecule is contained in the deposit given the ATCC Deposit Number shown in Table I.

Also preferred is an isolated nucleic acid molecule, wherein said sequence of at least 50 contiguous nucleotides is included in the nucleotide sequence of the complete open reading frame sequence encoded by said cDNA clone.

Also preferred is an isolated nucleic acid molecule comprising a nucleotide sequence which is at least 95% identical to sequence of at least 150 contiguous nucleotides in the nucleotide sequence encoded by said cDNA clone.

A further preferred embodiment is an isolated nucleic acid molecule comprising a nucleotide sequence which is at least 95% identical to sequence of at least 500 contiguous nucleotides in the nucleotide sequence encoded by said cDNA clone.

A further preferred embodiment is an isolated nucleic acid molecule comprising a nucleotide sequence which is at least 95% identical to the complete nucleotide sequence encoded by said cDNA clone.

A further preferred embodiment is a method for detecting in a biological sample a nucleic acid molecule comprising a nucleotide sequence which is at least 95% identical to a sequence of at least 50 contiguous nucleotides in a sequence selected from the group consisting of: a nucleotide sequence of SEQ ID NO:1 wherein X is any integer as defined in Table I; and a nucleotide sequence encoded by a cDNA clone identified by a cDNA Clone Identifier in Table I and contained in the deposit with the ATCC Deposit Number shown for said cDNA clone in Table I; which method comprises a step of comparing a nucleotide sequence of at least one nucleic acid molecule in said sample with a sequence selected from said group and determining whether the sequence of said nucleic acid molecule in said sample is at least 95% identical to said selected sequence.

Also preferred is the above method wherein said step of comparing sequences comprises determining the extent of nucleic acid hybridization between nucleic acid molecules in said sample and a nucleic acid molecule comprising said sequence selected from said group. Similarly, also preferred is the above method wherein said step of comparing sequences is performed by comparing the nucleotide sequence determined from a nucleic acid molecule in said sample with said sequence selected from said group. The nucleic acid molecules can comprise DNA molecules or RNA molecules.

A further preferred embodiment is a method for identifying the species, tissue or cell type of a biological sample which method comprises a step of detecting nucleic acid molecules in said sample, if any, comprising a nucleotide sequence that is at least 95% identical to a sequence of at least 50 contiguous nucleotides in a sequence selected from the group consisting of: a nucleotide sequence of SEQ ID NO:1 wherein X is any integer as defined in Table I; and a nucleotide sequence encoded by a cDNA clone identified by a cDNA Clone Identifier in Table I and contained in the deposit with the ATCC Deposit Number shown for said cDNA clone in Table I.

The method for identifying the species, tissue or cell type of a biological sample can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a method for diagnosing in a subject a pathological condition associated with abnormal structure or expression of a gene encoding a protein identified in Table I, which method comprises a step of detecting in a biological sample obtained from said subject nucleic acid molecules, if any, comprising a nucleotide sequence that is at least 95% identical to a sequence of at least 50 contiguous nucleotides in a sequence selected from the group consisting of: a nucleotide sequence of SEQ ID NO:1 wherein X is any integer as defined in Table I; and a nucleotide sequence encoded by a cDNA clone identified by a cDNA Clone Identifier in Table I and contained in the deposit with the ATCC Deposit Number shown for said cDNA clone in Table I.

The method for diagnosing a pathological condition can comprise a step of detecting nucleic acid molecules comprising a nucleotide sequence in a panel of at least two nucleotide sequences, wherein at least one sequence in said panel is at least 95% identical to a sequence of at least 50 contiguous nucleotides in a sequence selected from said group.

Also preferred is a composition of matter comprising isolated nucleic acid molecules wherein the nucleotide sequences of said nucleic acid molecules comprise a panel of at least two nucleotide sequences, wherein at least one sequence in said panel is at least 95% identical to a sequence of at least 50 contiguous nucleotides in a sequence selected from the group consisting of: a nucleotide sequence of SEQ ID NO:1 wherein X is any integer as defined in Table I; and a nucleotide sequence encoded by a cDNA clone identified by a cDNA Clone Identifier in Table I and contained in the deposit with the ATCC Deposit Number shown for said cDNA clone in Table I. The nucleic acid molecules can comprise DNA molecules or RNA molecules.

Also preferred is an isolated polypeptide comprising an amino acid sequence at least 90% identical to a sequence of at least about 10 contiguous amino acids in the amino acid sequence of SEQ ID NO:2 wherein Y is any integer as defined in Table I.

Also preferred is a polypeptide, wherein said sequence of contiguous amino acids is included in the amino acid sequence of SEQ ID NO:2 in the range of positions "Total AA of the Open Reading Frame (ORF)" as set forth for SEQ ID NO:2 in Table I.

Also preferred is an isolated polypeptide comprising an amino acid sequence at least 95% identical to a sequence of at least about 30 contiguous amino acids in the amino acid sequence of SEQ ID NO:2.

Further preferred is an isolated polypeptide comprising an amino acid sequence at least 95% identical to a sequence of at least about 100 contiguous amino acids in the amino acid sequence of SEQ ID NO:2.

Further preferred is an isolated polypeptide comprising an amino acid sequence at least 95% identical to the complete amino acid sequence of SEQ ID NO:2.

Further preferred is an isolated polypeptide comprising an amino acid sequence at least 90% identical to a sequence of at least about 10 contiguous amino acids in the complete amino acid sequence of a protein encoded by a cDNA clone identified by a cDNA Clone Identifier in Table I and contained in the deposit with the ATCC Deposit Number shown for said cDNA clone in Table I.

Also preferred is a polypeptide wherein said sequence of contiguous amino acids is included in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to a sequence of at least about 30 contiguous amino acids in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to a sequence of at least about 100 contiguous amino acids in the amino acid sequence of the protein encoded by a cDNA clone identified by a cDNA Clone Identifier in Table I and contained in the deposit with the ATCC Deposit Number shown for said cDNA clone in Table I.

Also preferred is an isolated polypeptide comprising an amino acid sequence at least 95% identical to the amino acid sequence of the protein encoded by a cDNA clone identified by a cDNA Clone Identifier in Table I and contained in the deposit with the ATCC Deposit Number shown for said cDNA clone in Table I.

Further preferred is an isolated antibody which binds specifically to a polypeptide comprising an amino acid sequence that is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

Further preferred is a method for detecting in a biological sample a polypeptide comprising an amino acid sequence which is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I; which method comprises a step of comparing an amino acid sequence of at least one polypeptide molecule in said sample with a sequence selected from said group and determining whether the sequence of said polypeptide molecule in said sample is at least 90% identical to said sequence of at least 10 contiguous amino acids.

Also preferred is the above method wherein said step of comparing an amino acid sequence of at least one polypeptide molecule in said sample with a sequence selected from said group comprises determining the extent of specific binding of polypeptides in said sample to an antibody which binds specifically to a polypeptide comprising an amino acid sequence that is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

Also preferred is the above method wherein said step of comparing sequences is performed by comparing the amino acid sequence determined from a polypeptide molecule in said sample with said sequence selected from said group.

Also preferred is a method for identifying the species, tissue or cell type of a biological sample which method comprises a step of detecting polypeptide molecules in said sample, if any, comprising an amino acid sequence that is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

Also preferred is the above method for identifying the species, tissue or cell type of a biological sample, which method comprises a step of detecting polypeptide molecules comprising an amino acid sequence in a panel of at least two amino acid sequences, wherein at least one sequence in said panel is at least 90% identical to a sequence of at least 10 contiguous amino acids in a sequence selected from the above group.

Also preferred is a method for diagnosing a pathological condition associated with an organism with abnormal structure or expression of a gene encoding a protein identified in Table I, which method comprises a step of detecting in a biological sample obtained from said subject polypeptide molecules comprising an amino acid sequence in a panel of at least two amino acid sequences, wherein at least one sequence in said panel is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

In any of these methods, the step of detecting said polypeptide molecules includes using an antibody.

Also preferred is an isolated nucleic acid molecule comprising a nucleotide sequence which is at least 95% identical to a nucleotide sequence encoding a polypeptide wherein said polypeptide comprises an amino acid sequence that is at least 90% identical to a sequence of at least 10 contiguous amino acids in a sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

Also preferred is an isolated nucleic acid molecule, wherein said nucleotide sequence encoding a polypeptide has been optimized for expression of said polypeptide in a prokaryotic host.

Also preferred is an isolated nucleic acid molecule, wherein said polypeptide comprises an amino acid sequence selected from the group consisting of: an amino acid sequence of SEQ ID NO:2 wherein Y is any integer as defined in Table I; and a complete amino acid sequence of a protein encoded by a cDNA clone identified by a cDNA Clone Identifier in Table I and contained in the deposit with the ATCC Deposit Number shown for said cDNA clone in Table I.

Further preferred is a method of making a recombinant vector comprising inserting any of the above isolated nucleic acid molecule(s) into a vector. Also preferred is the recombinant vector produced by this method. Also preferred is a method of making a recombinant host cell comprising introducing the vector into a host cell, as well as the recombinant host cell produced by this method.

Also preferred is a method of making an isolated polypeptide comprising culturing this recombinant host cell under conditions such that said polypeptide is expressed and recovering said polypeptide. Also preferred is this method of making an isolated polypeptide, wherein said recombinant host cell is a eukaryotic cell and said polypeptide is a protein comprising an amino acid sequence selected from the group consisting of: an amino acid sequence of SEQ ID NO:2 wherein Y is an integer set forth in Table I and said position of the "Total AA of ORF" of SEQ ID NO:2 is defined in Table I; and an amino acid sequence of a protein encoded by a cDNA clone identified by a cDNA Clone Identifier in Table I and contained in the deposit with the ATCC Deposit Number shown for said cDNA clone in Table I. The isolated polypeptide produced by this method is also preferred.

Also preferred is a method of treatment of an individual in need of an increased level of a protein activity, which method comprises administering to such an individual a pharmaceutical composition comprising an amount of an isolated polypeptide, polynucleotide, or antibody of the claimed invention effective to increase the level of said protein activity in said individual.

Having generally described the invention, the same will be more readily understood by reference to the following examples, which are provided by way of illustration and are not intended as limiting.

REFERENCES

Altschul S F; Gish W; Miller W; Myers E W; Lipman D J. Basic local alignment search tool. J. Mol. Biol. 215: 403–10 (1990).

Baker K; Goddard A; Gurney A L; Smith V; Watanabe C K; Wood W I; International Publication Number: WO200012708-A2. New mammalian DNA sequences encoding transmembrane, receptor or secreted PRO polypeptides, useful for screening of potential peptide or small molecule inhibitors of the relevant receptor/ligand interactions. Pub. Date: 09-MAR-2000 File. Date:01-SEP-1999.

Bartlett et al. Molecular Recognition in Chemical and Biological Problems Special Publication, Royal Chem. Soc. 78:182–196 (1989).

Bateman A, Birney E, Durbin R, Eddy S R, Howe K L, Sonnhammer E L. The Pfam protein families database. Nucleic Acids Res. 28:263–6 (2000).

Biemond B J, Levi M, Coronel R, Janse M J, ten Cate J W, Pannekoek H. Thrombolysis and reocclusion in experimental jugular vein and coronary artery thrombosis. Effects of a plasminogen activator inhibitor type 1-neutralizing monoclonal antibody. Circulation. 91:1175–81 (1995).

Birney E, Durbin R. Using GeneWise in the Drosophila annotation experiment. Genome Res. 10:547–8 (2000).

Blinder M A; Andersson T R; Abildgaard U; Tollefsen D M. Heparin cofactor IIOslo. Mutation Of Arg-189 To His Decreases The Affinity For Dermatan Sulfate. J. Biol. Chem . . . 264:5128–33 (1989).

Blinder M A; Tollefsen D M. Site-directed mutagenesis of arginine 103 and lysine 185 in the proposed glycosaminoglycan-binding site of heparin cofactor II. J. Biol. Chem . . . 265:286–91 (1990).

Bohm H-J, LUDI: rule-based automatic design of new substituents for enzyme inhibitor leads. J. Comp. Aid. Molec. Design 6:61–78 (1992)

Cardozo T; Totrov M; Abagyan R. Homology modeling by the ICM method. Proteins 23:403–14 (1995).

Chandra T., Stackhouse R., Kidd V. J., Robson K. J. H., Woo S. L. C. Sequence homology between human alpha 1-antichymotrypsin, alpha 1-antitrypsin, and antithrombin III. Biochemistry 22:5055–5061 (1983).

Chai K. X., Chen L. -M., Chao J., Chao L. Kallistatin: a novel human serine proteinase inhibitor. Molecular cloning, tissue distribution, and expression in *Escherichia coli*. J. Biol. Chem . . . 268:24498–24505 (1993).

Flink I. L., Bayley T. J., Gustafson T. A., Markham B. E., Morkin E. Complete amino acid sequence of human thyroxine-binding globulin deduced from cloned DNA: close homology to the serine antiproteases. Proc. Natl. Acad. Sci. U.S.A. 83:7708–7712 (1986).

Gils A, Declerck P J. Structure-function Relationships in Serpins: Current Concepts and Controversies Thromb Haemost. 80:531–541 (1998).

Goodford, P. J. A computational procedure for determining energetically favorable binding sites on biologically important macromolecules. J. Med. Chem. 28:849–857 (1985)

Goodsell, D. S. and Olsen, A. J. Automated docking of substrates to proteins by simulated annealing. Proteins 8:195–202 (1990)

Greer J. Comparative modeling of homologous proteins. Methods Enzymol 202:239–52 (1991).

Huber R, Carrell R W. Implications of the three-dimensional structure of alpha 1-antitrypsin for structure and function of serpins. Biochemistry 28:8951–8966 (1989)

Hendlich M; Lackner P; Weitckus S; Floeckner H; Froschauer R; Gottsbacher K; Casari G; Sippl M J. Identification of native protein folds amongst a large number of incorrect models. The calculation of low energy conformations from potentials of mean force. J. Mol. Biol. 216:167–80 (1990).

Hocini H, Bacquart P, Bouhlal H, Adle-Biassette H, Kazatchkine M D, Belec L. Secretory leukocyte inhibitor inhibits infection of monocytes and lymphocytes with human immunodeficiency virus type 1 but does not intrefere with transcytosis of cell-associated virus across tight epithelial barriers. Clin Diagn Lab Immunol. 7:515–518 (2000).

Hofmann K., Bucher P., Falquet L., Bairoch A. The PROSITE database, its status in 1999. Nucleic Acids Res. 27:215–219 (1999).

Huntington, J., Read, R. J., Carrell, R. W. Structure of a Serpin-Protease Complex Shows Inhibition by Deformation. Nature 407:923–926 (2000)

Kam C M, Hudig D, Powers J C. Granzymes (lymphocyte serine proteases): characterization with natural and synthetic substrates and inhibitors. Biochim Biophys Acta. 1477:307–23 (2000)

Kuntz I D, Blaney J M, Oatley S J, Langridge R, Ferrin T E. A geometric approach to macromolecule-ligand interactions. J. Mol. Biol. 161:269–288 (1982)

Lane, D A.; Olds, R R.; Thein, S L Antithrombin and its deficiency states. Blood Coagulation Fibrinolysis 3:315–41 (1992).

Lesk, A. M., Boswell, D. R., Homology Modeling: Inferences from Tables of Aligned Sequences. Curr. Op. Struc. Biol. 2:242–247 (1992)

Martin, Y. C. 3D database searching in drug design. J. Med. Chem. 35:2145–2154 (1992)

Novotny J; Rashin A A; Bruccoleri R E. Criteria that discriminate between native proteins and incorrectly folded models. Proteins, 4:19–30 (1988).

Opal S M. Therapeutic rationale for antithrombin III in sepsis. Crit Care Med 28(9 Suppl):S34–7 (2000).

O'Reilly M S, Pirie-Shepherd S, Lane W S, Folkman J. Antiangiogenic activity of the cleaved conformation of the serpin antithrombin. Science. 285:1926–8 (1999)

Pearson W R. Rapid and sensitive sequence comparison with FASTP and FASTA. Methods Enzymol 183:63–98 (1990).

Pelteir M R, Liu W J, Hansen P J. Regulation of lymphocyte proliferation by uterine serpin: interleukin -2 mRNA production, CD25 expression and responsiveness to interleukin-2. Proc Soc Exp Biol Med. 223: 75–81 (2000)

Pratt C W; Church F C. Antithrombin: structure and function. Sem Hematol 28:3–9 (1991).

Ragg H; Ulshofer T; Gerewitz J. Glycosaminoglycan-mediated leuserpin-2/thrombin interaction. Structure-function relationships. J. Biol. Chem . . . 265:22386–91 (1990).

Reed G L 3d, Matsueda G R, Haber E. Synergistic fibrinolysis: combined effects of plasminogen activators and an antibody that inhibits alpha 2-antiplasmin. Proc Natl Acad Sci U S A. 87:1114–8 (1990).

Sali A; Potterton L; Yuan F; van Vlijmen H; Karplus M. Evaluation of comparative protein modeling by MODELLER. PROTEINS 23:318–26 (1995).

Shirk, R. A., Elisen, M. G. L. M., Meijers, J. C. M., Church, Frank C. Role Of The H Helix In Heparin Binding To Protein C Inhibitor. J. Biol. Chem . . . 269:28690–5 (1994).

Whinna H C, Blinder M A, Szewczyk M, Tollefsen D M; Church F C. Role of lysine 173 in heparin binding to heparin cofactor II. J. Biol. Chem . . . 266:8129–35 (1991).

Whisstock J, Skinner R, Lesk AM. An atlas of serpin conformations. Trends Biochem Sci. 23:63–7 (1998)

EXAMPLES

DESCRIPTION OF THE PREFERRED EMBODIMENTS

Example 1

Bioinformatics Analysis

To search for novel protease inhibitors, a Hidden-Markov Model (HMM) of serine protease inhibitors SERPIN (obtained from the Pfam database in Sanger center) (Bateman et. al., 2000) was used to search against human genomic sequence database using the computer program GENEWISEDB. Genomic sequences that were found to have a GENEWISEDB matching score of more than 15 against SERPIN HMM model were selected for further analysis. Genomic sequence contained in BAC (bacteria artificial chromosome) AL132708 was found to contain putative exon sequences that are similar to serpins. The portion of sequence from AL132708 that matched Peptidase_M22 HMM profile was extracted and back-searched against non-redundant protein database using BLASTX program (Altschul et. al., 1990). The most similar protein sequence was used as a template to predict more exons from AL132708 using GENEWISEDB program (Birney and Durbin, 2000).

The final predicted exons were assembled and a full-length clone of gene LSI-01 was obtained using the predicted exon sequences. The complete protein sequence of LSI-01 was found to have significant sequence homology with a family of known protease inhibitors. A peptide sequence VSFNRT-FLMMI fitting the conserved peptide signature pattern of serpins [LIVMFY]-x-[LIVMFYAC]-[DNQ]-[RKHQS]-[PST]-F-[LIVMFY]-[LIVMFYC]-x-[LIVMFAH] is found in the protein sequence of LSI-01 (Hofmann et. al., 1999).

Proteins in the SERPIN family are secreted proteins. AL132708 contains a strong signal sequence at the $NH_2$ terminal (see FIGS. 1A–B), suggesting that LSI-01 is also a secreted protein. Protein threading and molecular modeling of LSI-01 suggest that LSI-01 have a structure folding of serine protease inhibitor, with RS as putative bait sequence. Based on sequence, structure and known SERPIN signature sequences, the novel LSI-01 is a novel human serine protease inhibitor.

Example 2

Method for Constructing a Size Fractionated Brain cDNA Library

Brain poly A+RNA was purchased from Clontech and converted into double stranded cDNA using the SuperScript™ Plasmid System for cDNA Synthesis and Plasmid Cloning (Life Technologies) except that no radioisotope was incorporated in either of the cDNA synthesis steps and that the cDNA was fractionated by HPLC. This was accomplished on a TransGenomics HPLC system equipped with a size exclusion column (TosoHass) with dimensions of 7.8 mm×30 cm and a particle size of 10□m. Tris buffered saline was used as the mobile phase and the column was run at a flow rate of 0.5 mL/min.

The resulting chromatograms were analyzed to determine which fractions should be pooled to obtain the largest cDNA's; generally fractions that eluted in the range of 12 to 15 minutes were pooled. The cDNA was precipitated prior to ligation into the Sal I/Not I sites in the pSport vector supplied with the kit. Using a combination of PCR with primers to the ends of the vector and Sal I/Not I restriction enzyme digestion of mini-prep DNA, it was determined that the average insert size of the library was greater the 3.5 Kb. The overall complexity of the library was greater that $10^7$ independent clones. The library was amplified in semi-solid agar for 2 days at 30° C. An aliquot (200 microliters) of the amplified library was inoculated into a 200 ml culture for single-stranded DNA isolation by super-infection with a f1 helper phage. After overnight growth, the released phage particles with precipitated with PEG and the DNA isolated with proteinase K, SDS and phenol extractions. The single stranded circular DNA was concentrated by ethanol precipitation and used for the cDNA capture experiments.

Example 3

Cloning of the Novel Human LSI-01 Serpin

Using the predict exon genomic sequence from bac AL132708, an antisense 80 bp oligonucleotide with biotin on the 5' end was designed with the following sequence;

```
5'bGGCACTTCCCATCTTCAAGGTCAGGTCTTTGCTGGGAACAGTCAGTGAGTGAACCAGGTGCTGGAAGCCCTG-3'     (SEQ ID NO: 18)
```

One microliter (one hundred and fifty nanograms) of the biotinylated oligonucleotide was added to six microliters (six micrograms) of a mixture of single-stranded covalently closed circular liver and spleen cDNA libraries (These libraries are commercially available from Life Technologies, Rockville, Maryland) and seven microliters of 100% formamide in a 0.5 ml PCR tube. The mixture was heated in a thermal cycler to 95° C. for 2 mins. Fourteen microliters of 2× hybridization buffer (50% formamide, 1.5 M NaCl, 0.04 M $NaPO_4$, pH 7.2, 5 mM EDTA, 0.2% SDS) was added to the heated probe/cDNA library mixture and incubated at 42° C. for 26 hours. Hybrids between the biotinylated oligonucleotide and the circular cDNA were isolated by diluting the hybridization mixture to 220 microliters in a solution containing 1 M NaCl, 10 mM Tris-HCl pH 7.5, 1 mM EDTA, pH 8.0 and adding 125 microliters of streptavidin magnetic beads. This solution was incubated at 42° C. for 60 mins, mixing every 5 mins to resuspend the beads. The beads were separated from the solution with a magnet and the beads washed three times in 200 microliters of 0.1× SSPE, 0.1% SDS at 45° C.

The single stranded cDNAs were released from the biotinlyated oligonucleotide/streptavidin magnetic bead complex by adding 50 microliters of 0.1 N NaOH and incubating at room temperature for 10 mins. Six microliters of 3 M Sodium Acetate was added along with 15 micrograms of glycogen and the solution ethanol precipitated with 120 microliters of 100% ethanol. The DNA was resuspended in 12 microliters of TE (10 mM Tris-HCl, pH 8.0), 1 mM EDTA, pH 8.0). The single stranded cDNA was converted into double strands in a thermal cycler by mixing 5 microliters of the captured DNA with 1.5 microliters 10 micromolar standard SP6 primer (homologous to a sequence on the cDNA cloning vector) and 1.5 microliters of 10× PCR buffer. The mixture was heated to 95° C. for 20 seconds then ramped down to 59° C. At this time 15 microliters of a repair mix, that was preheated to 70° C. (Repair mix contains 4 microliters of 5 mM dNTPs (1.25 mM each), 1.5 microliters of 10×PCR buffer, 9.25 microliters of water, and 0.25 microliters of Taq polymerase). The solution was ramped back to 73° C. and incubated for 23 mins. The repaired DNA was ethanol precipitate and resuspended in 10 microliters of TE. Two microliters were electroporated in *E. coli* DH12S cells and resulting colonies were screen by PCR, using a primer pair designed from the genomic exonic sequence to identify the proper cDNAs.

Oligonucleotides used to identity the cDNA by PCR.

```
AL132708-L1 GCCTCTGTGCTCCAATCTACT  (SEQ ID NO:19)

AL132708-R1 GCTGCAGCTCCTTCTTGAC    (SEQ ID NO:20)
```

Those cDNA clones that were positive by PCR had the inserts sized and two clones were chosen for DNA sequencing. Both clones had identical sequence.

The full-length nucleotide sequence and the encoded polypeptide for LSI-01 is shown in FIGS. 1A–B. The sequence was analyzed and plotted in a hydrophobicity plot showing a putative signal sequence at the $NH_2$ terminal (see FIG. 4).

Example 4

Expression Profiling of the Novel Human LSI-01 Serpin

The same PCR primer pair that was used to identify the novel LSI-01 cDNA clones (SEQ ID NO:18 and 19) was used to measure the steady state levels of mRNA by quantitative PCR. Briefly, first strand cDNA was made from commercially available mRNA. The relative amount of cDNA used in each assay was determined by performing a parallel experiment using a primer pair for a gene expressed in equal amounts in all tissues, cyclophilin. The cyclophilin primer pair detected small variations in the amount of cDNA in each sample and these data were used for normalization of the data obtained with the primer pair for the novel LSI-01. The PCR data was converted into a relative assessment of the difference in transcript abundance amongst the tissues tested and the data is presented in FIG. 5. Transcripts corresponding to LSI-01 were expressed highly in the lymph node, and to a lesser extent in thumus, small intestine, and spleen.

Example 5

Method of Measuring the Serine Protease Inhibitory Activity of LSI-01 Polypeptides Serpin (serine protease inhibitory) activity of the LSI-01 polypeptide may be measured by following the inhibition of proteolytic activity in cells, tissues, and/or in in vitro assays. The LSI-01 serpin may be incubated with one or more proteases (preferably Arg-specific proteases provided below and elsewhere herein) for different times and with varying serpin concentrations. Residual protease activity could then be measured according to any appropriate means known in the art. As discussed elsewhere herein, serpin activity results in the inhibition of protease activity. Likewise, serpin inhibitors or antagonists may be capable of preventing the loss of such protease activity.

In vitro assays for measuring protease activity using synthetic peptide fluorescent, spectrophotometric and fluorescence resonance transfer assays are well described in the art, either through the use of single substrates (see below for examples), or as part of substrate libraries (Backes et al., 2000).

Non-limiting examples of Arg-specific proteases include the coagulation proteases (thrombin, FXa, and TF:FVIIa), the fibrinolytic enzymes (tPA, uPA and plasmin), and the inflammatory enzyme tryptase. Other Arg-specific proteases may be known in the art and are encompassed by the present invention. Assays for thrombin, plasmin, uPA, tPA, and tryptase are well described in the art (Balasubramanian et al., 1993; Combrink et al., 1998).

An example of a spectrophotometric protease assay is the Factor Xa assay. Briefly, human FXa (Calbiochem #233526) enzymatic activity is measured in a buffer containing 0.145 M NaCl, 0.005 M KCl, 1 mg/ml Polyethylene Glycol (PEG-8000), 0.030 M HEPES (pH 7.4) using 96-well microtiter plates (Nunc Immuno #439454). The enzyme is incubated with the serpin at room temperature for varying amounts of time prior to starting the reaction with 100 µM S-2222 (phenyl-Ile-Glu-Gly-Arg-pNA, $K_m$=137 µM). The $K_m$ for this, and other substrates, may be determined experimentally by measuring the enzyme activity at different substrate concentrations and curve fitting the data using Kaleidagraph V. Time-dependent optical density change may be followed at 405 nm using a kinetic microplate reader (Molecular Devices UVmax) at room temperature. Enzyme activity in the presence of serpin (LSI-01) may be expressed as fraction of control and curve fit to pre-incubation time and serpin concentration to determine inhibitory parameters.

An example of a fluorescence assay which may be used for the present invention is the Factor VIIa assay. Briefly, the Factor VIIa assay is measured in the presence of human recombinant tissue factor (INNOVIN from Dade Behring Cat.# B4212-100). Human Factor VIIa may be obtained from Enzyme Research Labs (Cat.# HFVIIA 1640). Enzymatic activity could be measured in a buffer containing 150 mM NaCl, 5 mM $CaCl_2$, 1 mM CHAPS and 1 mg/ml PEG 6000 (pH 7.4) with 1 nM FVIIa and 100 µM D-Ile-Pro-Arg-AFC (Enzyme Systems Products, $K_m$>200 µM) 0.66% DMSO. The assay (302 µl total volume) may be incubated at room temperature for 2 hr prior to reading fluorometric signal (Ex 405/Em 535) using a Victor 2 (Wallac) fluorescent plate reader.

In addition to the methods described above, protease activity (and therefore serpin activity) can be measured using fluorescent resonance energy transfer (FRET with Quencher -$P_n$-P3-P2-$P_1$- -$P_1$'-$P_2$'- Fluorophore), fluorescent peptide bound to beads (Fluorophore -$P_n$-$P_3$-$P_2$-$P_1$- -$P_1$'-$P_2$'- Bead), dye-protein substrates and serpin-protease gel shifts. All of which are well known to those skilled in the art.

Additional assays, in addition to, assay methods are known in the art and are encompassed by the present inventoin. See, for example, Backes B J, Harris J L, Leonetti F, Craik C S, Ellman J A. Synthesis of positional-scanning libraries of fluorogenic peptide substrates to define the extended substrate specificity of plasmin and thrombin. Nat Biotechnol. 18:187–93 (2000); Balasubramanian, N., St. Laurent, D. R., Federici, M. E., Meanwell, N. A., Wright, J. J., Schumacher, W. A., and Seiler, S. M. Active site-directed synthetic thrombin inhibitors: synthesis, in vitro and in vivo activity profile of BMY 44621 and analogs. an examination of the role of the amino group in the D-Phe-Pro-Arg-H series. J. Med. Chem. 36:300–303 (1993); and Combrink, K. D., Gülgeze, H. B., Meanwell, N. A., Pearce, B. C. Zulan, P., Bisacchi, G. S., Roberts, D. G. M., Stanley, P. Seiler, S. M. Novel 1,2-Benzisothiazol-3-one-1,1-dioxide Inhibitors of Human Mast Cell Tryptase. J. Med. Chem. 41:4854–4860 (1998); which are hereby incorporated herein by reference in their entirety.

Additional methods of assessing LSI-01 serpin activity may be in reference to the methods disclosed in any of the publications referenced herein.

Example 6

Method of Screening for Compounds that Interact with the LSI-01 Polypeptide

The following assays are designed to identify compounds that bind to the LSI-01 polypeptide, bind to other cellular proteins that interact with the LSI-01 polypeptide, and to compounds that interfere with the interaction of the LSI-01 polypeptide with other cellular proteins.

Such compounds can include, but are not limited to, other cellular proteins. Specifically, such compounds can include, but are not limited to, peptides, such as, for example, soluble peptides, including, but not limited to Ig-tailed fusion peptides, comprising extracellular portions of LSI-01 polypeptide transmembrane receptors, and members of random peptide libraries (see, e.g., Lam, K. S. et al., 1991, Nature 354:82–84; Houghton, R. et al., 1991, Nature 354:84–86), made of D-and/or L-configuration amino acids, phosphopeptides (including, but not limited to, members of random or partially degenerate phosphopeptide libraries; see, e.g., Songyang, Z., et al., 1993, Cell 72:767–778), antibodies (including, but not limited to, polyclonal, monoclonal, humanized, anti-idiotypic, chimeric or single chain antibodies, and FAb, F(ab').sub.2 and FAb expression libary fragments, and epitope-binding fragments thereof), and small organic or inorganic molecules.

Compounds identified via assays such as those described herein can be useful, for example, in elaborating the biological function of the LSI-01 polypeptide, and for ameliorating symptoms of tumor progression, for example. In instances, for example, whereby a tumor progression state or disorder results from a lower overall level of LSI-01 expression, LSI-01 polypeptide, and/or LSI-01 polypeptide activity in a cell involved in the tumor progression state or disorder, compounds that interact with the LSI-01 polypeptide can include ones which accentuate or amplify the activity of the bound LSI-01 polypeptide. Such compounds would bring about an effective increase in the level of LSI-01 polypeptide activity, thus ameliorating symptoms of the tumor progression disorder or state. In instances whereby mutations within the LSI-01 polypeptide cause aberrant LSI-01 polypeptides to be made which have a deleterious effect that leads to tumor progression, compounds that bind LSI-01 polypeptide can be identified that inhibit the activity of the bound LSI-01 polypeptide. Assays for testing the effectiveness of such compounds are known in the art and discussed, elsewhere herein.

Example 7

Method of Screening, in vitro, Compounds that Bind to the LSI-01 Polypeptide

In vitro systems can be designed to identify compounds capable of binding the LSI-01 polypeptide of the invention. Compounds identified can be useful, for example, in modulating the activity of wild type and/or mutant LSI-01 polypeptide, preferably mutant LSI-01 polypeptide, can be useful in elaborating the biological function of the LSI-01 polypeptide, can be utilized in screens for identifying compounds that disrupt normal LSI-01 polypeptide interactions, or can in themselves disrupt such interactions.

The principle of the assays used to identify compounds that bind to the LSI-01 polypeptide involves preparing a reaction mixture of the LSI-01 polypeptide and the test compound under conditions and for a time sufficient to allow the two components to interact and bind, thus forming a complex which can be removed and/or detected in the reaction mixture. These assays can be conducted in a variety of ways. For example, one method to conduct such an assay would involve anchoring LSI-01 polypeptide or the test substance onto a solid phase and detecting LSI-01 polypeptide/test compound complexes anchored on the solid phase at the end of the reaction. In one embodiment of such a method, the LSI-01 polypeptide can be anchored onto a solid surface, and the test compound, which is not anchored, can be labeled, either directly or indirectly.

In practice, microtitre plates can conveniently be utilized as the solid phase. The anchored component can be immobilized by non-covalent or covalent attachments. Non-covalent attachment can be accomplished by simply coating the solid surface with a solution of the protein and drying. Alternatively, an immobilized antibody, preferably a monoclonal antibody, specific for the protein to be immobilized can be used to anchor the protein to the solid surface. The surfaces can be prepared in advance and stored.

In order to conduct the assay, the nonimmobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously immobilized component is pre-labeled, the detection of label immobilized on the surface indicates that complexes were formed. Where the previously nonimmobilized component is not pre-labeled, an indirect label can be used to detect complexes anchored on the surface; e.g., using a labeled antibody specific for the immobilized component (the antibody, in turn, can be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for LSI-01 polypeptide or the test compound to anchor any complexes formed in solution, and a labeled antibody specific for the other component of the possible complex to detect anchored complexes.

Example 8

Method of Identifying Compounds that Interfere with LSI-01 Polypeptide/Cellular Product Interaction The LSI-01 polypeptide of the invention can, in vivo, interact with one or more cellular or extracellular macromolecules, such as proteins. Such macromolecules include, but are not limited to, nucleic acid molecules and those products identified via methods such as those described, elsewhere herein. For the purposes of this discussion, such cellular and extracellular macromolecules are referred to herein as "binding partner(s)". For the purpose of the present invention, "binding partner" may also encompass small molecule compounds, polysaccharides, lipids, and any other molecule or molecule type referenced herein. Compounds that disrupt such interactions can be useful in regulating the activity of the LSI-01 polypeptide, especially mutant LSI-01 polypeptide. Such compounds can include, but are not limited to molecules such as antibodies, peptides, and the like described in elsewhere herein.

The basic principle of the assay systems used to identify compounds that interfere with the interaction between the LSI-01 polypeptide and its cellular or extracellular binding partner or partners involves preparing a reaction mixture containing the LSI-01 polypeptide, and the binding partner under conditions and for a time sufficient to allow the two products to interact and bind, thus forming a complex. In order to test a compound for inhibitory activity, the reaction mixture is prepared in the presence and absence of the test compound. The test compound can be initially included in the reaction mixture, or can be added at a time subsequent to the addition of LSI-01 polypeptide and its cellular or extracellular binding partner. Control reaction mixtures are incubated without the test compound or with a placebo. The formation of any complexes between the LSI-01 polypeptide and the cellular or extracellular binding partner is then detected. The formation of a complex in the control reaction, but not in the reaction mixture containing the test compound, indicates that the compound interferes with the interaction of the LSI-01 polypeptide and the interactive binding partner. Additionally, complex formation within reaction mixtures containing the test compound and normal LSI-01 polypeptide can also be compared to complex formation within reaction mixtures containing the test compound and mutant LSI-01 polypeptide. This comparison can be important in those cases wherein it is desirable to identify compounds that disrupt interactions of mutant but not normal LSI-01 polypeptide.

The assay for compounds that interfere with the interaction of the LSI-01 polypeptide and binding partners can be conducted in a heterogeneous or homogeneous format. Heterogeneous assays involve anchoring either the LSI-01 polypeptide or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the LSI-01 polypeptide and the binding partners, e.g., by competition, can be identified by conducting the reaction in the presence of the test substance; i.e., by adding the test substance to the reaction mixture prior to or simultaneously with the LSI-01 polypeptide and interactive cellular or extracellular binding partner. Alternatively, test compounds that disrupt preformed complexes, e.g. compounds with higher binding constants that displace one of the components from the complex, can be tested by adding the test compound to the reaction mixture after complexes have been formed. The various formats are described briefly below.

In a heterogeneous assay system, either the LSI-01 polypeptide or the interactive cellular or extracellular binding partner, is anchored onto a solid surface, while the non-anchored species is labeled, either directly or indirectly. In practice, microtitre plates are conveniently utilized. The anchored species can be immobilized by non-covalent or covalent attachments. Non-covalent attachment can be accomplished simply by coating the solid surface with a solution of the LSI-01 polypeptide or binding partner and drying. Alternatively, an immobilized antibody specific for the species to be anchored can be used to anchor the species to the solid surface. The surfaces can be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with a labeled anti-Ig antibody). Depending upon the order of addition of reaction components, test compounds which inhibit complex formation or which disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds which inhibit complex or which disrupt preformed complexes can be identified.

In an alternate embodiment of the invention, a homogeneous assay can be used. In this approach, a preformed complex of the LSI-01 polypeptide and the interactive cellular or extracellular binding partner product is prepared in which either the LSI-01 polypeptide or their binding partners are labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances which disrupt LSI-01 polypeptide -cellular or extracellular binding partner interaction can be identified.

In a particular embodiment, the LSI-01 polypeptide can be prepared for immobilization using recombinant DNA techniques known in the art. For example, the LST-01 polypeptide coding region can be fused to a glutathione-S-transferase (GST) gene using a fusion vector such as pGEX-5X-1, in such a manner that its binding activity is maintained in the resulting fusion product. The interactive cellular or extracellular product can be purified and used to raise a monoclonal antibody, using methods routinely practiced in the art and described above. This antibody can be labeled with the radioactive isotope sup.125 I, for example, by methods routinely practiced in the art. In a heterogeneous assay, e.g., the GST- LSI-01 polypeptide fusion product can be anchored to glutathione-agarose beads. The interactive cellular or extracellular binding partner product can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the LSI-01 polypeptide and the interactive cellular or extracellular binding partner can be detected by measuring the amount of radioactivity that remains associated with the glutathione-agarose beads. A successful inhibition of the interaction by the test compound will result in a decrease in measured radioactivity.

Alternatively, the GST- LSI-01 polypeptide fusion product and the interactive cellular or extracellular binding partner product can be mixed together in liquid in the absence of the solid glutathione-agarose beads. The test compound can be added either during or after the binding partners are allowed to interact. This mixture can then be added to the glutathione-agarose beads and unbound material is washed away. Again the extent of inhibition of the binding partner interaction can be detected by adding the labeled antibody and measuring the radioactivity associated with the beads.

In another embodiment of the invention, these same techniques can be employed using peptide fragments that correspond to the binding domains of the LSI-01 polypeptide product and the interactive cellular or extracellular binding partner (in case where the binding partner is a product), in place of one or both of the full length products.

Any number of methods routinely practiced in the art can be used to identify and isolate the protein's binding site. These methods include, but are not limited to, mutagenesis of one of the genes encoding one of the products and screening for disruption of binding in a co-immunoprecipitation assay. Compensating mutations in the gene encoding the second species in the complex can be selected. Sequence analysis of the genes encoding the respective products will reveal the mutations that correspond to the region of the product involved in interactive binding. Alternatively, one product can be anchored to a solid surface using methods described in this Section above, and allowed to interact with and bind to its labeled binding partner, which has been treated with a proteolytic enzyme, such as trypsin. After washing, a short, labeled peptide comprising the binding domain can remain associated with the solid material, which can be isolated and identified by amino acid sequencing. Also, once the gene coding for the cellular or extracellular binding partner product is obtained, short gene segments can be engineered to express peptide fragments of the product, which can then be tested for binding activity and purified or synthesized.

Example 9

Isolation of a Specific Clone from the Deposited Sample

The deposited material in the sample assigned the ATCC Deposit Number cited in Table I for any given cDNA clone also may contain one or more additional plasmids, each comprising a cDNA clone different from that given clone. Thus, deposits sharing the same ATCC Deposit Number contain at least a plasmid for each cDNA clone identified in Table I. Typically, each ATCC deposit sample cited in Table I comprises a mixture of approximately equal amounts (by weight) of about 1–10 plasmid DNAs, each containing a different cDNA clone and/or partial cDNA clone; but such a deposit sample may include plasmids for more or less than 2 cDNA clones.

Two approaches can be used to isolate a particular clone from the deposited sample of plasmid DNA(s) cited for that clone in Table I. First, a plasmid is directly isolated by screening the clones using a polynucleotide probe corresponding to SEQ ID NO:1.

Particularly, a specific polynucleotide with 30–40 nucleotides is synthesized using an Applied Biosystems DNA synthesizer according to the sequence reported. The oligonucleotide is labeled, for instance, with 32P-(-ATP using T4 polynucleotide kinase and purified according to routine methods. (E.g., Maniatis et al., Molecular Cloning: A Laboratory Manual, Cold Spring Harbor Press, Cold Spring, N.Y. (1982).) The plasmid mixture is transformed into a suitable host, as indicated above (such as XL-1 Blue (Stratagene)) using techniques known to those of skill in the art, such as those provided by the vector supplier or in related publications or patents cited above. The transformants are plated on 1.5% agar plates (containing the appropriate selection agent, e.g., ampicillin) to a density of about 150 transformants (colonies) per plate. These plates are screened using Nylon membranes according to routine methods for bacterial colony screening (e.g., Sambrook et al., Molecular Cloning: A Laboratory Manual, 2nd Edit., (1989), Cold Spring Harbor Laboratory Press, pages 1.93 to 1.104), or other techniques known to those of skill in the art.

Alternatively, two primers of 17–20 nucleotides derived from both ends of the SEQ I) NO: 1 (i.e., within the region of SEQ ID NO:1 bounded by the 5' NT and the 3' NT of the clone defined in Table I) are synthesized and used to amplify the desired cDNA using the deposited cDNA plasmid as a template. The polymerase chain reaction is carried out under routine conditions, for instance, in 25 ul of reaction mixture with 0.5 ug of the above cDNA template. A convenient reaction mixture is 1.5–5 mM MgCl2, 0.01% (w/v) gelatin, 20 uM each of dATP, dCTP, dGTP, dTTP, 25 pmol of each primer and 0.25 Unit of Taq polymerase. Thirty five cycles of PCR (denaturation at 94 degree C. for 1 min; annealing at 55 degree C. for 1 min; elongation at 72 degree C. for 1 min) are performed with a Perkin-Elmer Cetus automated thermal cycler. The amplified product is analyzed by agarose gel electrophoresis and the DNA band with expected molecular weight is excised and purified. The PCR product is verified to be the selected sequence by subcloning and sequencing the DNA product.

The polynucleotide(s) of the present invention, the polynucleotide encoding the polypeptide of the present invention, or the polypeptide encoded by the deposited clone may represent partial, or incomplete versions of the complete coding region (i.e., full-length gene). Several methods are known in the art for the identification of the 5' or 3' non-coding and/or coding portions of a gene which may not be present in the deposited clone. The methods that follow are exemplary and should not be construed as limiting the scope of the invention. These methods include but are not limited to, filter probing, clone enrichment using specific probes, and protocols similar or identical to 5' and 3' "RACE" protocols that are well known in the art. For instance, a method similar to 5' RACE is available for generating the missing 5' end of a desired full-length transcript. (Fromont-Racine et al., Nucleic Acids Res. 21(7): 1683–1684 (1993)).

Briefly, a specific RNA oligonucleotide is ligated to the 5' ends of a population of RNA presumably containing full-length gene RNA transcripts. A primer set containing a primer specific to the ligated RNA oligonucleotide and a primer specific to a known sequence of the gene of interest is used to PCR amplify the 5' portion of the desired full-length gene. This amplified product may then be sequenced and used to generate the full-length gene.

This above method starts with total RNA isolated from the desired source, although poly-A+RNA can be used. The RNA preparation can then be treated with phosphatase if necessary to eliminate 5' phosphate groups on degraded or damaged RNA that may interfere with the later RNA ligase step. The phosphatase should then be inactivated and the RNA treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase.

This modified RNA preparation is used as a template for first strand cDNA synthesis using a gene specific oligonucleotide. The first strand synthesis reaction is used as a template for PCR amplification of the desired 5' end using a primer specific to the ligated RNA oligonucleotide and a primer specific to the known sequence of the gene of interest. The resultant product is then sequenced and analyzed to confirm that the 5' end sequence belongs to the desired gene. Moreover, it may be advantageous to optimize the RACE protocol to increase the probability of isolating additional 5' or 3' coding or non-coding sequences. Various methods of optimizing a RACE protocol are known in the art, though a detailed description summarizing these methods can be found in B. C. Schaefer, Anal. Biochem., 227:255–273, (1995).

An alternative method for carrying out 5' or 3' RACE for the identification of coding or non-coding sequences is provided by Frohman, M. A., et al., Proc.Nat'l.Acad.Sci.USA, 85:8998–9002 (1988). Briefly, a cDNA clone missing either the 5' or 3' end can be reconstructed to include the absent base pairs extending to the translational start or stop codon, respectively. In some cases, cDNAs are missing the start of translation, therefor. The following briefly describes a modification of this original 5' RACE procedure. Poly A+ or total RNAs reverse transcribed with Superscript II (Gibco/BRL) and an antisense or I complementary primer specific to the cDNA sequence. The primer is removed from the reaction with a Microcon Concentrator (Amicon). The first-strand cDNA is then tailed with dATP and terminal deoxynucleotide transferase (Gibco/BRL). Thus, an anchor sequence is produced which is needed for PCR amplification. The second strand is synthesized from the dA-tail in PCR buffer, Taq DNA polymerase (Perkin-Elmer Cetus), an oligo-dT primer containing three adjacent restriction sites (XhoIJ SaiI and ClaI) at the 5' end and a primer containing just these restriction sites. This double-stranded cDNA is PCR amplified for 40 cycles with the same primers as well as a nested cDNA-specific antisense primer. The PCR products are size-separated on an ethidium bromide-agarose gel and the region of gel containing cDNA products the predicted size of missing protein-coding DNA is removed. cDNA is purified from the agarose with the Magic PCR Prep kit (Promega), restriction digested with XhoI or SalI, and ligated to a plasmid such as pBluescript SKII (Stratagene) at XhoI and EcoRV sites. This DNA is transformed into bacteria and the plasmid clones sequenced to identify the correct protein-coding inserts. Correct 5' ends are confirmed by comparing this sequence with the putatively identified homologue and overlap with the partial cDNA clone. Similar methods known in the art and/or commercial kits are used to amplify and recover 3' ends.

Several quality-controlled kits are commercially available for purchase. Similar reagents and methods to those above are supplied in kit form from Gibco/BRL for both 5' and 3' RACE for recovery of full length genes. A second kit is available from Clontech which is a modification of a related technique, SLIC (single-stranded ligation to single-stranded cDNA), developed by Dumas et al., Nucleic Acids Res., 19:5227–32(1991). The major differences in procedure are that the RNA is alkaline hydrolyzed after reverse transcription and RNA ligase is used to join a restriction site-containing anchor primer to the first-strand cDNA. This obviates the necessity for the dA-tailing reaction which results in a polyT stretch that is difficult to sequence past.

An alternative to generating 5' or 3' cDNA from RNA is to use cDNA library double-stranded DNA. An asymmetric PCR-amplified antisense cDNA strand is synthesized with an antisense cDNA-specific primer and a plasmid-anchored primer. These primers are removed and a symmetric PCR reaction is performed with a nested cDNA-specific antisense primer and the plasmid-anchored primer.

RNA Ligase Protocol for Generating The 5' or 3' End Sequences to Obtain Full Length Genes Once a gene of interest is identified, several methods are available for the identification of the 5' or 3' portions of the gene which may not be present in the original cDNA plasmid. These methods include, but are not limited to, filter probing, clone enrichment using specific probes and protocols similar and identical to 5' and 3'RACE. While the full-length gene may be present in the library and can be identified by probing, a useful method for generating the 5' or 3' end is to use the existing sequence information from the original cDNA to generate the missing information. A method similar to 5'RACE is available for generating the missing 5' end of a desired full-length gene. (This method was published by Fromont-Racine et al., Nucleic Acids Res., 21(7): 1683–1684 (1993)). Briefly, a specific RNA oligonucleotide is ligated to the 5' ends of a population of RNA presumably 30 containing full-length gene RNA transcript and a primer set containing a primer specific to the ligated RNA oligonucleotide and a primer specific to a known sequence of the gene of interest, is used to PCR amplify the 5' portion of the desired full length gene which may then be sequenced and used to generate the full length gene. This method starts with total RNA isolated from the desired source, poly A RNA may be used but is not a prerequisite for this procedure. The RNA preparation may then be treated with phosphatase if necessary to eliminate 5' phosphate groups on degraded or damaged RNA which may interfere with the later RNA ligase step. The phosphatase if used is then inactivated and the RNA is treated with tobacco acid pyrophosphatase in order to remove the cap structure present at the 5' ends of messenger RNAs. This reaction leaves a 5' phosphate group at the 5' end of the cap cleaved RNA which can then be ligated to an RNA oligonucleotide using T4 RNA ligase. This modified RNA preparation can then be used as a template for first strand cDNA synthesis using a gene specific oligonucleotide. The first strand synthesis reaction can then be used as a template for PCR amplification of the desired 5' end using a primer specific to the ligated RNA oligonucleotide and a primer specific to the known sequence of the apoptosis related of interest. The resultant product is then sequenced and analyzed to confirm that the 5' end sequence belongs to the relevant apoptosis related.

Example 10

Tissue Distribution of Polypeptide

Tissue distribution of mRNA expression of polynucleotides of the present invention is determined using protocols for Northern blot analysis, described by, among others, Sambrook et al. For example, a cDNA probe produced by the method described in Example 9 is labeled with p32 using the rediprime™ DNA labeling system (Amersham Life Science), according to manufacturer's instructions. After labeling, the probe is purified using CHROMA SPINO-100 column (Clontech Laboratories, Inc.) according to manufacturer's protocol number PT1200-1. The purified labeled probe is then used to examine various tissues for mRNA expression.

Tissue Northern blots containing the bound mRNA of various tissues are examined with the labeled probe using ExpressHybtm hybridization solution (Clonetech according to manufacturers protocol number PT1190-1. Northern blots can be produced using various protocols well known in the art (e.g., Sambrook et al). Following hybridization and washing, the blots are mounted and exposed to film at −70 C. overnight, and the films developed according to standard procedures.

Example 11

Chromosomal Mapping of the Polynucleotides

An oligonucleotide primer set is designed according to the sequence at the 5' end of SEQ ID NO:1. This primer preferably spans about 100 nucleotides. This primer set is then used in a polymerase chain reaction under the following set of conditions: 30 seconds,95 degree C.; 1 minute, 56 degree C.; 1 minute, 70 degree C. This cycle is repeated 32 times followed by one 5 minute cycle at 70 degree C. Mammalian DNA, preferably human DNA, is used as template in addition to a somatic cell hybrid panel containing individual chromosomes or chromosome fragments (Bios, Inc). The reactions are analyzed on either 8% polyacrylamide gels or 3.5% agarose gels. Chromosome mapping is determined by the presence of an approximately 100 bp PCR fragment in the particular somatic cell hybrid.

Example 12

Bacterial Expression of a Polypeptide

A polynucleotide encoding a polypeptide of the present invention is amplified using PCR oligonucleotide primers corresponding to the 5' and 3' ends of the DNA sequence, as outlined in Example 9, to synthesize insertion fragments. The primers used to amplify the cDNA insert should preferably contain restriction sites, such as BamHI and XbaI, at the 5' end of the primers in order to clone the amplified product into the expression vector. For example, BamHI and XbaI correspond to the restriction enzyme sites on the bacterial expression vector pQE-9. (Qiagen, Inc., Chatsworth, Calif.). This plasmid vector encodes antibiotic resistance (Ampr), a bacterial origin of replication (ori), an IPTG-regulatable promoter/operator (P/O), a ribosome binding site (RBS), a 6-histidine tag (6-His), and restriction enzyme cloning sites.

The pQE-9 vector is digested with BamiHI and XbaI and the amplified fragment is ligated into the pQE-9 vector maintaining the reading frame initiated at the bacterial RBS. The ligation mixture is then used to transform the E. coli strain M15/rep4 (Qiagen, Inc.) which contains multiple copies of the plasmid pREP4, that expresses the lacI repressor and also confers kanamycin resistance (Kanr). Transformants are identified by their ability to grow on LB plates and ampicillin/kanamycin resistant colonies are selected. Plasmid DNA is isolated and confirmed by restriction analysis.

Clones containing the desired constructs are grown overnight (O/N) in liquid culture in LB media supplemented with both Amp (100 ug/ml) and Kan (25 ug/ml). The O/N culture is used to inoculate a large culture at a ratio of 1:100 to 1:250. The cells are grown to an optical density 600 (O.D.600) of between 0.4 and 0.6. IPTG (Isopropyl-B-D-thiogalacto pyranoside) is then added to a final concentration of 1 mM. IPTG induces by inactivating the lacI repressor, clearing the P/O leading to increased gene expression.

Cells are grown for an extra 3 to 4 hours. Cells are then harvested by centrifugation (20 mins at 6000×g). The cell pellet is solubilized in the chaotropic agent 6 Molar Guanidine HCl by stirring for 3–4 hours at 4 degree C. The cell debris is removed by centrifugation, and the supernatant containing the polypeptide is loaded onto a nickel-nitrilotri-acetic acid ("Ni-NTA") affinity resin column (available from QIAGEN, Inc., supra). Proteins with a 6×His tag bind to the Ni-NTA resin with high affinity and can be purified in a simple one-step procedure (for details see: The QIAexpressionist (1995) QIAGEN, Inc., supra).

Briefly, the supernatant is loaded onto the column in 6 M guanidine-HCl, pH 8, the column is first washed with 10 volumes of 6 M guanidine-HCl, pH 8, then washed with 10 volumes of 6 M guanidine-HCl pH 6, and finally the polypeptide is eluted with 6 M guanidine-HCl, pH 5.

The purified protein is then renatured by dialyzing it against phosphate-buffered saline (PBS) or 50 mM Na-acetate, pH 6 buffer plus 200 mM NaCl. Alternatively, the protein can be successfully refolded while immobilized on the Ni-NTA column. The recommended conditions are as follows: renature using a linear 6M-1M urea gradient in 500 mM NaCl, 20% glycerol, 20 mM Tris/HCl pH 7.4, containing protease inhibitors. The renaturation should be performed over a period of 1.5 hours or more. After renaturation the proteins are eluted by the addition of 250 mM imidazole. Imidazole is removed by a final dialyzing step against PBS or 50 mM sodium acetate pH 6 buffer plus 200 mM NaCl. The purified protein is stored at 4 degree C. or frozen at −80 degree C.

Example 13

Purification of a Polypeptide from an Inclusion Body

The following alternative method can be used to purify a polypeptide expressed in E coli when it is present in the form of inclusion bodies. Unless otherwise specified, all of the following steps are conducted at 4–10 degree C.

Upon completion of the production phase of the E. coli fermentation, the cell culture is cooled to 4–10 degree C. and the cells harvested by continuous centrifugation at 15,000 rpm (Heraeus Sepatech). On the basis of the expected yield of protein per unit weight of cell paste and the amount of purified protein required, an appropriate amount of cell paste, by weight, is suspended in a buffer solution containing 100 mM Tris, 50 mM EDTA, pH 7.4. The cells are dispersed to a homogeneous suspension using a high shear mixer.

The cells are then lysed by passing the solution through a microfluidizer (Microfluidics, Corp. or APV Gaulin, Inc.) twice at 4000–6000 psi. The homogenate is then mixed with NaCl solution to a final concentration of 0.5 M NaCl, followed by centrifugation at 7000× g for 15 min. The resultant pellet is washed again using 0.5M NaCl, 100 mM Tris, 50 mM EDTA, pH 7.4

The resulting washed inclusion bodies are solubilized with 1.5 M guanidine hydrochloride (GuHCl) for 2–4 hours.

After 7000× g centrifugation for 15 min., the pellet is discarded and the polypeptide containing supernatant is incubated at 4 degree C. overnight to allow further GuHCl extraction.

Following high speed centrifugation (30,000×g) to remove insoluble particles, the GuHCl solubilized protein is refolded by quickly mixing the GuHCl extract with 20 volumes of buffer containing 50 mM sodium, pH 4.5, 150 mM NaCl, 2 mM EDTA by vigorous stirring. The refolded diluted protein solution is kept at 4 degree C. without mixing for 12 hours prior to further purification steps.

To clarify the refolded polypeptide solution, a previously prepared tangential filtration unit equipped with 0.16 um membrane filter with appropriate surface area (e.g., Filtron), equilibrated with 40 mM sodium acetate, pH 6.0 is employed. The filtered sample is loaded onto a cation exchange resin (e.g., Poros HS-50, Perceptive Biosystems). The column is washed with 40 mM sodium acetate, pH 6.0 and eluted with 250 mM, 500 mM, 1000 mM, and 1500 mM NaCl in the same buffer, in a stepwise manner. The absorbance at 280 nm of the effluent is continuously monitored. Fractions are collected and further analyzed by SDS-PAGE.

Fractions containing the polypeptide are then pooled and mixed with 4 volumes of water. The diluted sample is then loaded onto a previously prepared set of tandem columns of strong anion (Poros HQ-50, Perceptive Biosystems) and weak anion (Poros CM-20, Perceptive Biosystems) exchange resins. The columns are equilibrated with 40 mM sodium acetate, pH 6.0. Both columns are washed with 40 mM sodium acetate, pH 6.0, 200 mM NaCl. The CM-20 column is then eluted using a 10 column volume linear gradient ranging from 0.2 M NaCl, 50 mM sodium acetate, pH 6.0 to 1.0 M NaCl, 50 mM sodium acetate, pH 6.5. Fractions are collected under constant A280 monitoring of the effluent. Fractions containing the polypeptide (determined, for instance, by 16% SDS-PAGE) are then pooled.

The resultant polypeptide should exhibit greater than 95% purity after the above refolding and purification steps. No major contaminant bands should be observed from Coomassie blue stained 16% SDS-PAGE gel when 5 ug of purified protein is loaded. The purified protein can also be tested for endotoxin/LPS contamination, and typically the LPS content is less than 0.1 ng/ml according to LAL assays.

Example 14

Cloning and Expression of a Polypeptide in a Baculovirus Expression System

In this example, the plasmid shuttle vector pAc373 is used to insert a polynucleotide into a baculovirus to express a polypeptide. A typical baculovirus expression vector contains the strong polyhedrin promoter of the Autographa califomica nuclear polyhedrosis virus (AcMNPV) followed by convenient restriction sites, which may include, for example BamHI, Xba I and Asp718. The polyadenylation site of the simian virus 40 ("SV40") is often used for efficient polyadenylation. For easy selection of recombinant virus, the plasmid contains the beta-galactosidase gene from E. coli under control of a weak Drosophila promoter in the same orientation, followed by the polyadenylation signal of the polyhedrin gene. The inserted genes are flanked on both sides by viral sequences for cell-mediated homologous recombination with wild-type viral DNA to generate a viable virus that express the cloned polynucleotide.

Many other baculovirus vectors can be used in place of the vector above, such as pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., Virology 170:31–39 (1989).

A polynucleotide encoding a polypeptide of the present invention is amplified using PCR oligonucleotide primers corresponding to the 5' and 3' ends of the DNA sequence, as outlined in Example 9, to synthesize insertion fragments. The primers used to amplify the cDNA insert should preferably contain restriction sites at the 5' end of the primers in order to clone the amplified product into the expression vector. Specifically, the cDNA sequence contained in the deposited clone, including the AUG initiation codon and the naturally associated leader sequence identified elsewhere herein (if applicable), is amplified using the PCR protocol described in Example 9. If the naturally occurring signal sequence is used to produce the protein, the vector used does not need a second signal peptide. Alternatively, the vector can be modified to include a baculovirus leader sequence, using the standard methods described in Summers et al., "A Manual of Methods for Baculovirus Vectors and Insect Cell Culture Procedures," Texas Agricultural Experimental Station Bulletin No. 1555 (1987).

The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The plasmid is digested with the corresponding restriction enzymes and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.).

The fragment and the dephosphorylated plasmid are ligated together with T4 DNA ligase. E. coli HB101 or other suitable E. coli hosts such as XL-1 Blue (Stratagene Cloning Systems, La Jolla, Calif.) cells are transformed with the ligation mixture and spread on culture plates. Bacteria containing the plasmid are identified by digesting DNA from individual colonies and analyzing the digestion product by gel electrophoresis. The sequence of the cloned fragment is confirmed by DNA sequencing.

Five ug of a plasmid containing the polynucleotide is co-transformed with 1.0 ug of a commercially available linearized baculovirus DNA ("BaculoGoldtm baculovirus DNA", Pharmingen, San Diego, Calif.), using the lipofection method described by Felgner et al., Proc. Natl. Acad. Sci. USA 84:7413–7417 (1987). One ug of BaculoGoldtm virus DNA and 5 ug of the plasmid are mixed in a sterile well of a microtiter plate containing 50 ul of serum-free Grace's medium (Life Technologies Inc., Gaithersburg, Md.). Afterwards, 10 ul Lipofectin plus 90 ul Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is then incubated for 5 hours at 27 degrees C. The transfection solution is then removed from the plate and 1 ml of Grace's insect medium supplemented with 10% fetal calf serum is added. Cultivation is then continued at 27 degrees C. for four days.

After four days the supernatant is collected and a plaque assay is performed, as described by Summers and Smith, supra. An agarose gel with "Blue Gal" (Life Technologies Inc., Gaithersburg) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Gaithersburg, page 9–10.) After appropriate incubation, blue stained plaques are picked with the tip of a micropipettor (e.g., Eppendorf). The agar containing the recombinant viruses is then resuspended in a microcentrifuge tube containing 200 ul of Grace's medium and the suspension containing the recombinant baculovirus is used to infect Sf9 cells seeded in 35 mm dishes. Four days later the supernatants of these culture dishes are harvested and then they are stored at 4 degree C.

To verify the expression of the polypeptide, Sf9 cells are grown in Grace's medium supplemented with 10% heat-inactivated FBS. The cells are infected with the recombinant baculovirus containing the polynucleotide at a multiplicity of infection ("MOI") of about 2. If radiolabeled proteins are desired, 6 hours later the medium is removed and is replaced with SF900 II medium minus methionine and cysteine (available from Life Technologies Inc., Rockville, Md.). After 42 hours, 5 uCi of 35S-methionine and 5 uCi 35S-cysteine (available from Amersham) are added. The cells are further incubated for 16 hours and then are harvested by centrifugation. The proteins in the supernatant as well as the intracellular proteins are analyzed by SDS-PAGE followed by autoradiography (if radiolabeled).

Microsequencing of the amino acid sequence of the amino terminus of purified protein may be used to determine the amino terminal sequence of the produced protein.

Example 15

Expression of a Polypeptide in Mammalian Cells

The polypeptide of the present invention can be expressed in a mammalian cell. A typical mammalian expression vector contains a promoter element, which mediates the initiation of transcription of mRNA, a protein coding sequence, and signals required for the termination of transcription and polyadenylation of the transcript. Additional elements include enhancers, Kozak sequences and intervening sequences flanked by donor and acceptor sites for RNA splicing. Highly efficient transcription is achieved with the early and late promoters from SV40, the long terminal repeats (LTRs) from Retroviruses, e.g., RSV, HTLVI, HIVI and the early promoter of the cytomegalovirus (CMV). However, cellular elements can also be used (e.g., the human actin promoter).

Suitable expression vectors for use in practicing the present invention include, for example, vectors such as pSVL and pMSG (Pharmacia, Uppsala, Sweden), pRSVcat (ATCC 37152), pSV2dhfr (ATCC 37146), pBC12MI (ATCC 67109), pCMVSport 2.0, and pCMVSport 3.0. Mammalian host cells that could be used include, human Hela, 293, H9 and Jurkat cells, mouse NIH3T3 and C127 cells, Cos 1, Cos 7 and CV1, quail QC1-3 cells, mouse L cells and Chinese hamster ovary (CHO) cells.

Alternatively, the polypeptide can be expressed in stable cell lines containing the polynucleotide integrated into a chromosome. The co-transformation with a selectable marker such as dhfr, gpt, neomycin, hygromycin allows the identification and isolation of the transformed cells.

The transformed gene can also be amplified to express large amounts of the encoded protein. The DHFR (dihydrofolate reductase) marker is useful in developing cell lines that carry several hundred or even several thousand copies of the gene of interest. (See, e.g., Alt, F. W., et al., J. Biol. Chem . . . 253:1357–1370 (1978); Hamlin, J. L. and Ma, C., Biochem. et Biophys. Acta, 1097:107–143 (1990); Page, M. J. and Sydenham, M. A., Biotechnology 9:64–68 (1991).) Another useful selection marker is the enzyme glutamine synthase (GS) (Murphy et al., Biochem J. 227:277–279 (1991); Bebbington et al., Bio/Technology 10: 169–175 (1992). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

A polynucleotide of the present invention is amplified according to the protocol outlined in herein. If the naturally occurring signal sequence is used to produce the protein, the vector does not need a second signal peptide. Alternatively, if the naturally occurring signal sequence is not used, the vector can be modified to include a heterologous signal sequence. (See, e.g., WO 96/34891.) The amplified fragment is isolated from a 1% agarose gel using a commercially available kit ("Geneclean," BIO 101 Inc., La Jolla, Calif.). The fragment then is digested with appropriate restriction enzymes and again purified on a 1% agarose gel.

The amplified fragment is then digested with the same restriction enzyme and purified on a 1% agarose gel. The isolated fragment and the dephosphorylated vector are then ligated with T4 DNA ligase. E. coli HB101 or XL-1 Blue cells are then transformed and bacteria are identified that contain the fragment inserted into plasmid pC6 using, for instance, restriction enzyme analysis.

Chinese hamster ovary cells lacking an active DHFR gene is used for transformation. Five μg of an expression plasmid is cotransformed with 0.5 ug of the plasmid pSVneo using lipofectin (Felgner et al., supra). The plasmid pSV2-neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10–14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 uM, 2 uM, 5 uM, 10 mM, 20 mM). The same procedure is repeated until clones are obtained which grow at a concentration of 100–200 uM. Expression of the desired gene product is analyzed, for instance, by SDS-PAGE and Western blot or by reversed phase HPLC analysis.

Example 16

Protein Fusions

The polypeptides of the present invention are preferably fused to other proteins. These fusion proteins can be used for a variety of applications. For example, fusion of the present polypeptides to His-tag, HA-tag, protein A, IgG domains, and maltose binding protein facilitates purification. (See Example described herein; see also EP A 394,827; Traunecker, et al., Nature 331:84–86 (1988).) Similarly, fusion to IgG-1, IgG-3, and albumin increases the half-life time in vivo. Nuclear localization signals fused to the polypeptides of the present invention can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made by modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also should have convenient restriction enzyme sites that will facilitate cloning into an expression vector, preferably a mammalian expression vector. Note that the polynucleotide is cloned without a stop codon, otherwise a fusion protein will not be produced.

The naturally occurring signal sequence may be used to produce the protein (if applicable). Alternatively, if the naturally occurring signal sequence is not used, the vector can be modified to include a heterologous signal sequence. (See, e.g., WO 96/34891 and/or U.S. Pat. No. 6,066,781, supra.)

of natural contaminants. Such a preparation is then introduced into an animal in order to produce polyclonal antisera of greater specific activity.

In the most preferred method, the antibodies of the present invention are monoclonal antibodies (or protein binding fragments thereof). Such monoclonal antibodies can be prepared using hybridoma technology. (Köhler et al., Nature 256:495 (1975); Köhler et al., Eur. J. Immunol. 6:511 (1976); Köhler et al., Eur. J. Immunol. 6:292 (1976); Hammerling et al., in: Monoclonal Antibodies and T-Cell Hybridomas, Elsevier, N.Y., pp. 563–681 (1981).) In general, such procedures involve immunizing an animal (preferably a mouse) with polypeptide or, more preferably, with a polypeptide-expressing cell. Such cells may be cultured in any suitable tissue culture medium; however, it is preferable to culture cells in Earle's modified Eagle's medium supplemented with 10% fetal bovine serum (inactivated at about 56 degrees C.), and supplemented with about 10 g/l of nonessential amino acids, about 1,000 U/ml of penicillin, and about 100 ug/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT

```
Human IgG Fc region:
    GGGATCCGGAGCCCAAATCTTCTGACAAAACTCACACATGCCCACC          (SEQ ID NO: 32)

GTGCCCAGCACCTGAATTCGAGGGTGCACCGTCAGTCTTCCTCTTCCCCCC

AAAACCCAAGGACACCCTCATGATCTCCCGGACTCCTGAGGTCACATGCG

TGGTGGTGGACGTAAGCCACGAAGACCCTGAGGTCAAGTTCAACTGGTAC

GTGGACGGCGTGGAGGTGCATAATGCCAAGACAAAGCCGCGGGAGGAGC

AGTACAACAGCACGTACCGTGTGGTCAGCGTCCTCACCGTCCTGCACCAG

GACTGGCTGAATGGCAAGGAGTACAAGTGCAAGGTCTCCAACAAAGCCCT

CCCAACCCCCATCGAGAAAACCATCTCCAAAGCCAAAGGGCAGCCCCGA

GAACCACAGGTGTACACCCTGCCCCCATCCCGGGATGAGCTGACCAAGAA

CCAGGTCAGCCTGACCTGCCTGGTCAAAGGCTTCTATCCAAGCGACATCG

CCGTGGAGTGGGAGAGCAATGGGCAGCCGGAGAACAACTACAAGACCAC

GCCTCCCGTGCTGGACTCCGACGGCTCCTTCTTCCTCTACAGCAAGCTCAC

CGTGGACAAGAGCAGGTGGCAGCAGGGGAACGTCTTCTCATGCTCCGTGA

TGCATGAGGCTCTGCACAACCACTACACGCAGAAGAGCCTCTCCCTGTCT

CCGGGTAAATGAGTGCGACGGCCGCGACTCTAGAGGAT
```

Example 17

Production of an Antibody from a Polypeptide

The antibodies of the present invention can be prepared by a variety of methods. (See, Current Protocols, Chapter 2.) As one example of such methods, cells expressing a polypeptide of the present invention are administered to an animal to induce the production of sera containing polyclonal antibodies. In a preferred method, a preparation of the protein is prepared and purified to render it substantially free medium, and then cloned by limiting dilution as described by Wands et al. (Gastroenterology 80:225–232 (1981).) The hybridoma cells obtained through such a selection are then assayed to identify clones which secrete antibodies capable of binding the polypeptide.

Alternatively, additional antibodies capable of binding to the polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones that produce an antibody whose ability to bind to the protein-specific antibody can be blocked by the polypeptide. Such antibodies comprise antiidiotypic antibodies to the protein-specific antibody and can be used to immunize an animal to induce formation of further protein-specific antibodies.

It will be appreciated that Fab and F(ab')2 and other fragments of the antibodies of the present invention may be used according to the methods disclosed herein. Such fragments are typically produced by proteolytic cleavage, using enzymes such as papain (to produce Fab fragments) or pepsin (to produce F(ab')2 fragments). Alternatively, protein-binding fragments can be produced through the application of recombinant DNA technology or through synthetic chemistry.

For in vivo use of antibodies in humans, it may be preferable to use "humanized" chimeric monoclonal antibodies. Such antibodies can be produced using genetic constructs derived from hybridoma cells producing the monoclonal antibodies described above. Methods for producing chimeric antibodies are known in the art. (See, for review, Morrison, Science 229:1202 (1985); Oi et al., Bio-Techniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Moreover, in another preferred method, the antibodies directed against the polypeptides of the present invention may be produced in plants. Specific methods are disclosed in U.S. Pat. Nos. 5,959,177, and 6,080,560, which are hereby incorporated in their entirety herein. The methods not only describe methods of expressing antibodies, but also the means of assembling foreign multimeric proteins in plants (i.e., antibodies, etc,), and the subsequent secretion of such antibodies from the plant.

Example 18

Method of Creating N- and C-terminal Deletion Mutants Corresponding to the LSI-01 Polypeptide of the Present Invention As described elsewhere herein, the present invention encompasses the creation of N- and C-terminal deletion mutants, in addition to any combination of N- and C-terminal deletions thereof, corresponding to the LSI-01 polypeptide of the present invention. A number of methods are available to one skilled in the art for creating such mutants. Such methods may include a combination of PCR amplification and gene cloning methodology. Although one of skill in the art of molecular biology, through the use of the teachings provided or referenced herein, and/or otherwise known in the art as standard methods, could readily create each deletion mutant of the present invention, exemplary methods are described below.

Briefly, using the isolated cDNA clone encoding the full-length LSI-01 polypeptide sequence (as described in Example 9, for example), appropriate primers of about 15–25 nucleotides derived from the desired 5' and 3' positions of SEQ ID NO:1 may be designed to PCR amplify, and subsequently clone, the intended N- and/or C-terminal deletion mutant. Such primers could comprise, for example, an inititation and stop codon for the 5' and 3' primer, respectively. Such primers may also comprise restriction sites to facilitate cloning of the deletion mutant post amplification. Moreover, the primers may comprise additional sequences, such as, for example, flag-tag sequences, kozac sequences, or other sequences discussed and/or referenced herein.

For example, in the case of the V39 to S435 N-terminal deletion mutant, the following primers could be used to amplify a cDNA fragment corresponding to this deletion mutant:

```
5' Primer 5'-GCAGCA GCGGCCGC GTGTCCCCGGCCAATGCCCCCAGTG-3'   (SEQ ID NO:34)
                    NotI 3' Primer 5'- GCAGCA GTCGAC GGATTTAGTGGGATTTTCCACTTTC-3'    (SEQ ID NO:35)
                     SalI
```

For example, in the case of the M1 to T404 C-terminal deletion mutant, the following primers could be used to amplify a cDNA fragment corresponding to this deletion mutant:

```
5' Primer 5'- GCAGCA GCGGCCGC ATGCAAGGACAGGGCAGGAGAAGAG-3'   (SEQ ID NO:36)
                     NotI 3' Primer 5'- GCAGCA GTCGAC TGACATCCAGCACAGCCTTGTTGGG-3'     (SEQ ID NO:37)
                     SalI
```

Representative PCR amplification conditions are provided below, although the skilled artisan would appreciate that other conditions may be required for efficient amplification. A 100 ul PCR reaction mixture may be prepared using 10 ng of the template DNA (cDNA clone of LSI-01), 200 uM 4dNTPs, 1 uM primers, 0.25U Taq DNA polymerase (PE), and standard Taq DNA polymerase buffer. Typical PCR cycling condition are as follows:

| | |
|---|---|
| 20–25 cycles: | 45 sec, 93 degrees |
| | 2 min, 50 degrees |
| | 2 min, 72 degrees |
| 1 cycle: | 10 min, 72 degrees |

After the final extension step of PCR, 5U Klenow Fragment may be added and incubated for 15 min at 30 degrees.

Upon digestion of the fragment with the NotI and SalI restriction enzymes, the fragment could be cloned into an appropriate expression and/or cloning vector which has been similarly digested (e.g., pSport1, among others). The skilled artisan would appreciate that other plasmids could be equally substituted, and may be desirable in certain circumstances. The digested fragment and vector are then ligated using a DNA ligase, and then used to transform competent *E.coli* cells using methods provided herein and/or otherwise known in the art.

The 5' primer sequence for amplifying any additional N-terminal deletion mutants may be determined by reference to the following formula:

(S+(X*3)) to ((S+(X*3))+25), wherein 'S' is equal to the nucleotide position of the initiating start codon of the LSI-01 gene (SEQ ID NO:1), and 'X' is equal to the most N-terminal amino acid of the intended N-terminal deletion mutant. The first term will provide the start 5' nucleotide position of the 5' primer, while the second term will provide the end 3' nucleotide position of the 5' primer corresponding to sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 5' primer may be desired in certain circumstances (e.g., kozac sequences, etc.).

The 3' primer sequence for amplifying any additional N-terminal deletion mutants may be determined by reference to the following formula:

(S+(X*3)) to ((S+(X*3))−25), wherein 'S' is equal to the nucleotide position of the initiating start codon of the LSI-01 gene (SEQ ID NO:1), and 'X' is equal to the most C-terminal amino acid of the intended N-terminal deletion mutant. The first term will provide the start 5' nucleotide position of the 3' primer, while the second term will provide the end 3' nucleotide position of the 3' primer corresponding to the anti-sense strand of SEQ ID NO:1. Once the corresponding nucleotide positions of the primer are determined, the final nucleotide sequence may be created by the addition of applicable restriction site sequences to the 5' end of the sequence, for example. As referenced herein, the addition of other sequences to the 3' primer may be desired in certain circumstances (e.g., stop codon sequences, etc.). The skilled artisan would appreciate that modifications of the above nucleotide positions may be necessary for optimizing PCR amplification.

The same general formulas provided above may be used in identifying the 5' and 3' primer sequences for amplifying any C-terminal deletion mutant of the present invention. Moreover, the same general formulas provided above may be used in identifying the 5' and 3' primer sequences for amplifying any combination of N-terminal and C-terminal deletion mutant of the present invention. The skilled artisan would appreciate that modifications of the above nucleotide positions may be necessary for optimizing PCR amplification.

Example 19

Regulation of Protein Expression via Controlled Aggregation in the Endoplasmic Reticulum As described more particularly herein, proteins regulate diverse cellular processes in higher organisms, ranging from rapid metabolic changes to growth and differentiation. Increased production of specific proteins could be used to prevent certain diseases and/or disease states. Thus, the ability to modulate the expression of specific proteins in an organism would provide significant benefits.

Numerous methods have been developed to date for introducing foreign genes, either under the control of an inducible, constitutively active, or endogenous promoter, into organisms. Of particular interest are the inducible promoters (see, M. Gossen, et al., Proc. Natl. Acad. Sci. USA., 89:5547 (1992); Y. Wang, et al., Proc. Natl. Acad. Sci. USA, 91:8180 (1994), D. No., et al., Proc. Natl. Acad. Sci. USA, 93:3346 (1996); and V. M. Rivera, et al., Nature Med, 2:1028 (1996); in addition to additional examples disclosed elsewhere herein). In one example, the gene for erthropoietin (Epo) was transferred into mice and primates under the control of a small molecule inducer for expression (e.g., tetracycline or rapamycin) (see, D. Bohl, et al., Blood, 92:1512, (1998); K. G. Rendahl, et al., Nat. Biotech, 16:757, (1998); V. M. Rivera, et al., Proc. Natl. Acad. Sci. USA, 96:8657 (1999); and X. Ye et al., Science, 283:88 (1999). Although such systems enable efficient induction of the gene of interest in the organism upon addition of the inducing agent (i.e., tetracycline, rapamycin, etc,.), the levels of expression tend to peak at 24 hours and trail off to background levels after 4 to 14 days. Thus, controlled transient expression is virtually impossible using these systems, though such control would be desirable.

A new alternative method of controlling gene expression levels of a protein from a transgene (i.e., includes stable and transient transformants) has recently been elucidated (V. M. Rivera., et al., Science, 287:826–830, (2000)). This method does not control gene expression at the level of the mRNA like the aforementioned systems. Rather, the system controls the level of protein in an active secreted form. In the absence of the inducing agent, the protein aggregates in the ER and is not secreted. However, addition of the inducing agent results in dis-aggregation of the protein and the subsequent secretion from the ER. Such a system affords low basal secretion, rapid, high level secretion in the presence of the inducing agent, and rapid cessation of secretion upon removal of the inducing agent. In fact, protein secretion reached a maximum level within 30 minutes of induction, and a rapid cessation of secretion within 1 hour of removing the inducing agent. The method is also applicable for controlling the level of production for membrane proteins.

Detailed methods are presented in V. M. Rivera., et al., Science, 287:826–830, (2000)), briefly:

Fusion protein constructs are created using polynucleotide sequences of the present invention with one or more copies (preferably at least 2, 3, 4, or more) of a conditional aggregation domain (CAD) a domain that interacts with itself in a ligand-reversible manner (i.e., in the presence of an inducing agent) using molecular biology methods known in the art and discussed elsewhere herein. The CAD domain may be the mutant domain isolated from the human FKBP12 (Phe$^{36}$ to Met) protein (as disclosed in V. M. Rivera., et al., Science, 287:826–830, (2000), or alternatively other proteins having domains with similar ligand-reversible, self-aggregation properties. As a principle of design the fusion protein vector would contain a furin cleavage sequence operably linked between the polynucleotides of the present invention and the CAD domains. Such a cleavage site would enable the proteolytic cleavage of the CAD domains from the polypeptide of the present invention subsequent to secretion from the ER and upon entry into the trans-Golgi (J. B. Denault, et al., FEBS Lett., 379:113, (1996)). Alternatively, the skilled artisan would recognize that any proteolytic cleavage sequence could be substituted for the furin sequence provided the substituted sequence is cleavable either endogenously (e.g., the furin sequence) or exogenously (e.g., post secretion, post purification, post production, etc.). The preferred sequence of each feature of the fusion protein construct, from the 5' to 3' direction with each feature being operably linked to the other, would be a promoter, signal sequence, "X" number of (CAD)x domains, the furin sequence (or other proteolytic sequence), and the coding sequence of the polypeptide of the present invention. The artisan would appreciate that the promotor and signal sequence, independent from the other, could be either the endogenous promotor or signal sequence of a polypeptide of the present invention, or alternatively, could be a heterologous signal sequence and promotor.

The specific methods described herein for controlling protein secretion levels through controlled ER aggregation are not meant to be limiting are would be generally applicable to any of the polynucleotides and polypeptides of the present invention, including variants, homologues, orthologs, and fragments therein.

Example 20

Alteration of Protein Glycosylation Sites to Enhance Characteristics of Polypeptides of the Invention Many eukaryotic cell surface and proteins are post-translationally processed to incorporate N-linked and O-linked carbohydrates (Komfeld and Kornfeld (1985) Annu. Rev. Biochem. 54:631–64; Rademacher et al., (1988) Annu. Rev. Biochem. 57:785–838). Protein glycosylation is thought to serve a variety of functions including: augmentation of protein folding, inhibition of protein aggregation, regulation of intracellular trafficking to organelles, increasing resistance to proteolysis, modulation of protein antigenicity, and mediation of intercellular adhesion (Fieldler and Simons (1995) Cell, 81:309–312; Helenius (1994) Mol. Biol. Of the Cell 5:253–265; Olden et al., (1978) Cell, 13:461–473; Caton et al., (1982) Cell, 37:417–427; Alexamnder and Elder (1984), Science, 226:1328–1330; and Flack et al., (1994), J. Biol. Chem . . . , 269:14015–14020). In higher organisms, the nature and extent of glycosylation can markedly affect the circulating half-life and bio-availability of proteins by mechanisms involving receptor mediated uptake and clearance (Ashwell and Morrell, (1974), Adv. Enzymol., 41:99–128; Ashwell and Harford (1982), Ann. Rev. Biochem., 51:531–54). Receptor systems have been identified that are thought to play a major role in the clearance of serum proteins through recognition of various carbohydrate structures on the glycoproteins (Stockert (1995), Physiol. Rev., 75:591–609; Kery et al., (1992), Arch. Biochem. Biophys., 298:49–55). Thus, production strategies resulting in incomplete attachment of terminal sialic acid residues might provide a means of shortening the bioavailability and half-life of glycoproteins. Conversely, expression strategies resulting in saturation of terminal sialic acid attachment sites might lengthen protein bioavailability and half-life.

In the development of recombinant glycoproteins for use as pharmaceutical products, for example, it has been speculated that the pharmacodynamics of recombinant proteins can be modulated by the addition or deletion of glycosylation sites from a glycoproteins primary structure (Berman and Lasky (1985a) Trends in Biotechnol., 3:51–53). However, studies have reported that the deletion of N-linked glycosylation sites often impairs intracellular transport and results in the intracellular accumulation of glycosylation site variants (Machamer and Rose (1988), J. Biol Chem., 263: 5955–5960; Gallagher et al., (1992), J. Virology., 66:7136–7145; Collier et al., (1993), Biochem., 32:7818–7823; Claffey et al., (1995) Biochemica et Biophysica Acta, 1246:1–9; Dube et al., (1988), J. Biol. Chem . . . 263:17516–17521). While glycosylation site variants of proteins can be expressed intracellularly, it has proved difficult to recover useful quantities from growth conditioned cell culture medium.

Moreover, it is unclear to what extent a glycosylation site in one species will be recognized by another species glycosylation machinery. Due to the importance of glycosylation in protein metabolism, particularly the secretion and/or expression of the protein, whether a glycosylation signal is recognized may profoundly determine a proteins ability to be expressed, either endogenously or recombinately, in another organism (i.e., expressing a human protein in E.coli, yeast, or viral organisms; or an E.coli, yeast, or viral protein in human, etc.). Thus, it may be desirable to add, delete, or modify a glycosylation site, and possibly add a glycosylation site of one species to a protein of another species to improve the proteins functional, bioprocess purification, and/or structural characteristics (e.g., a polypeptide of the present invention).

A number of methods may be employed to identify the location of glycosylation sites within a protein. One preferred method is to run the translated protein sequence through the PROSITE computer program (Swiss Institute of Bioinformatics). Once identified, the sites could be systematically deleted, or impaired, at the level of the DNA using mutagenesis methodology known in the art and available to the skilled artisan, Preferably using PCR-directed mutagenesis (See Maniatis, Molecular Cloning: A Laboratory Manual, Cold Spring Harbor Press, Cold Spring, N.Y. (1982)). Similarly, glycosylation sites could be added, or modified at the level of the DNA using similar methods, preferably PCR methods (See, Maniatis, supra). The results of modifying the glycosylation sites for a particular protein (e.g., solubility, secretion potential, activity, aggregation, proteolytic resistance, etc.) could then be analyzed using methods know in the art.

The skilled artisan would acknowledge the existence of other computer algorithms capable of predicting the location of glycosylation sites within a protein. For example, the Motif computer program (Genetics Computer Group suite of programs) provides this function, as well.

Example 21

Method of Enhancing the Biological Activity/Functional Characteristics of Invention through Molecular Evolution Although many of the most biologically active proteins known are highly effective for their specified function in an organism, they often possess characteristics that make them undesirable for transgenic, therapeutic, and/or industrial applications. Among these traits, a short physiological half-life is the most prominent problem, and is present either at the level of the protein, or the level of the proteins mRNA. The ability to extend the half-life, for example, would be particularly important for a proteins use in gene therapy, transgenic animal production, the bioprocess production and purification of the protein, and use of the protein as a chemical modulator among others. Therefore, there is a need to identify novel variants of isolated proteins possessing characteristics which enhance their application as a therapeutic for treating diseases of animal origin, in addition to the proteins applicability to common industrial and pharmaceutical applications.

Thus, one aspect of the present invention relates to the ability to enhance specific characteristics of invention through directed molecular evolution. Such an enhancement may, in a non-limiting example, benefit the inventions utility as an essential component in a kit, the inventions physical attributes such as its solubility, structure, or codon optimization, the inventions specific biological activity, including any associated enzymatic activity, the proteins enzyme kinetics, the proteins Ki, Kcat, Km, Vmax, Kd, protein-protein activity, protein-DNA binding activity, antagonist/inhibitory activity (including direct or indirect interaction), agonist activity (including direct or indirect interaction), the proteins antigenicity (e.g., where it would be desirable to either increase or decrease the antigenic potential of the protein), the immunogenicity of the protein, the ability of the protein to form dimers, trimers, or multimers with either itself or other proteins, the antigenic efficacy of the invention, including its subsequent use a preventative treatment for disease or disease states, or as an effector for targeting diseased genes. Moreover, the ability to enhance specific characteristics of a protein may also be applicable to changing the characterized activity of an enzyme to an activity completely unrelated to its initially characterized activity. Other desirable enhancements of the invention would be specific to each individual protein, and would thus be well known in the art and contemplated by the present invention.

For example, an engineered serpin may have enhanced serine proteasei inhibitory activity. Alternatively, an engineered serpin may be constitutively active in the absence of substrate binding. In yet another example, an engineered serpin may be capable of being activated with less than all of the regulatory factors and/or conditions typically required for serpin activation (e.g., substrate binding, phosphorylation, conformational changes, etc.). In another example, an engineered serpin may have altered substrate specificity. In yet another example, an engineered serpin may be useful as a suicide inhibitor by covalently binding to its substrate and rendering it permanently inactive. Such serpins would also be useful in screens to identify serpin modulators, among other uses described herein.

Directed evolution is comprised of several steps. The first step is to establish a library of variants for the gene or protein of interest. The most important step is to then select for those variants that entail the activity you wish to identify. The design of the screen is essential since your screen should be selective enough to eliminate non-useful variants, but not so stringent as to eliminate all variants. The last step is then to repeat the above steps using the best variant from the previous screen. Each successive cycle, can then be tailored as necessary, such as increasing the stringency of the screen, for example.

Over the years, there have been a number of methods developed to introduce mutations into macromolecules. Some of these methods include, random mutagenesis, "error-prone" PCR, chemical mutagenesis, site-directed mutagenesis, and other methods well known in the art (for a comprehensive listing of current mutagenesis methods, see Maniatis, Molecular Cloning: A Laboratory Manual, Cold Spring Harbor Press, Cold Spring, N.Y. (1982)). Typically, such methods have been used, for example, as tools for identifying the core functional region(s) of a protein or the function of specific domains of a protein (if a multi-domain protein). However, such methods have more recently been applied to the identification of macromolecule variants with specific or enhanced characteristics.

Random mutagenesis has been the most widely recognized method to date. Typically, this has been carried out either through the use of "error-prone" PCR (as described in Moore, J., et al, Nature Biotechnology 14:458, (1996), or through the application of randomized synthetic oligonucleotides corresponding to specific regions of interest (as described by Derbyshire, K. M. et al, Gene, 46:145–152, (1986), and Hill, D E, et al, Methods Enzymol., 55:559–568, (1987). Both approaches have limits to the level of mutagenesis that can be obtained. However, either approach enables the investigator to effectively control the rate of mutagenesis. This is particularly important considering the fact that mutations beneficial to the activity of the enzyme are fairly rare. In fact, using too high a level of mutagenesis may counter or inhibit the desired benefit of a useful mutation.

While both of the aforementioned methods are effective for creating randomized pools of macromolecule variants, a third method, termed "DNA Shuffling", or "sexual PCR" (WPC, Stemmer, PNAS, 91:10747, (1994)) has recently been elucidated. DNA shuffling has also been referred to as "directed molecular evolution", "exon-shuffling", "directed enzyme evolution", "in vitro evolution", and "artificial evolution". Such reference terms are known in the art and are encompassed by the invention. This new, preferred, method apparently overcomes the limitations of the previous methods in that it not only propagates positive traits, but simultaneously eliminates negative traits in the resulting progeny.

DNA shuffling accomplishes this task by combining the principal of in vitro recombination, along with the method of "error-prone" PCR. In effect, you begin with a randomly digested pool of small fragments of your gene, created by Dnase I digestion, and then introduce said random fragments into an "error-prone" PCR assembly reaction. During the PCR reaction, the randomly sized DNA fragments not only hybridize to their cognate strand, but also may hybridize to other DNA fragments corresponding to different regions of the polynucleotide of interest—regions not typically accessible via hybridization of the entire polynucleotide. Moreover, since the PCR assembly reaction utilizes "error-prone" PCR reaction conditions, random mutations are introduced during the DNA synthesis step of the PCR reaction for all of the fragments—further diversifying the potential hybridization sites during the annealing step of the reaction.

A variety of reaction conditions could be utilized to carry-out the DNA shuffling reaction. However, specific reaction conditions for DNA shuffling are provided, for example, in PNAS, 91:10747, (1994). Briefly:

Prepare the DNA substrate to be subjected to the DNA shuffling reaction. Preparation may be in the form of simply purifying the DNA from contaminating cellular material, chemicals, buffers, oligonucleotide primers, deoxynucleotides, RNAs, etc., and may entail the use of DNA purification kits as those provided by Qiagen, Inc., or by the Promega, Corp., for example.

Once the DNA substrate has been purified, it would be subjected to Dnase I digestion. About 2–4 ug of the DNA substrate(s) would be digested with 0.0015 units of Dnase I (Sigma) per ul in 100 ul of 50 mM Tris-HCL, pH 7.4/1 mM MgCl2 for 10–20 min. at room temperature. The resulting fragments of 10–50 bp could then be purified by running them through a 2% low-melting point agarose gel by electrophoresis onto DE81 ion-exchange paper (Whatmann) or could be purified using Microcon concentrators (Amicon) of the appropriate molecular weight cutoff, or could use oligonucleotide purification columns (Qiagen), in addition to other methods known in the art. If using DE81 ion-exchange paper, the 10–50 bp fragments could be eluted from said paper using 1M NaCl, followed by ethanol precipitation.

The resulting purified fragments would then be subjected to a PCR assembly reaction by re-suspension in a PCR mixture containing: 2 mM of each dNTP, 2.2 mM MgCl2, 50 mM KCl, 10 mM Tris.HCL, pH 9.0, and 0.1% Triton X-100, at a final fragment concentration of 10–30 ng/ul. No primers are added at this point. Taq DNA polymerase (Promega) would be used at 2.5 units per 100 ul of reaction mixture. A PCR program of 94 C. for 60 s; 94 C. for 30 s, 50–55 C. for 30 s, and 72 C. for 30 s using 30–45 cycles, followed by 72 C. for 5 min using an MJ Research (Cambridge, Mass.) PTC-150 thermocycler. After the assembly reaction is completed, a 1:40 dilution of the resulting primerless product would then be introduced into a PCR mixture (using the same buffer mixture used for the assembly reaction) containing 0.8 um of each primer and subjecting this mixture to 15 cycles of PCR (using 94 C. for 30 s, 50 C. for 30 s, and 72 C. for 30 s). The referred primers would be primers corresponding to the nucleic acid sequences of the polynucleotide(s) utilized in the shuffling reaction. Said primers could consist of modified nucleic acid base pairs using methods known in the art and referred to else where herein, or could contain additional sequences (i.e., for adding restriction sites, mutating specific base-pairs, etc.).

The resulting shuffled, assembled, and amplified product can be purified using methods well known in the art (e.g., Qiagen PCR purification kits) and then subsequently cloned using appropriate restriction enzymes.

Although a number of variations of DNA shuffling have been published to date, such variations would be obvious to the skilled artisan and are encompassed by the invention. The DNA shuffling method can also be tailored to the desired level of mutagenesis using the methods described by Zhao, et al. (Nucl Acid Res., 25(6): 1307–1308, (1997).

As described above, once the randomized pool has been created, it can then be subjected to a specific screen to identify the variant possessing the desired characteristic(s). Once the variant has been identified, DNA corresponding to the variant could then be used as the DNA substrate for initiating another round of DNA shuffling. This cycle of shuffling, selecting the optimized variant of interest, and then re-shuffling, can be repeated until the ultimate variant is obtained. Examples of model screens applied to identify variants created using DNA shuffling technology may be found in the following publications: J. C., Moore, et al., J. Mol. Biol., 272:336–347, (1997), F. R., Cross, et al., Mol. Cell. Biol., 18:2923–2931, (1998), and A. Crameri., et al., Nat. Biotech., 15:436–438, (1997).

DNA shuffling has several advantages. First, it makes use of beneficial mutations. When combined with screening, DNA shuffling allows the discovery of the best mutational combinations and does not assume that the best combination contains all the mutations in a population. Secondly, recombination occurs simultaneously with point mutagenesis. An effect of forcing DNA polymerase to synthesize full-length genes from the small fragment DNA pool is a background mutagenesis rate. In combination with a stringent selection method, enzymatic activity has been evolved up to 16000 fold increase over the wild-type form of the enzyme. In essence, the background mutagenesis yielded the genetic variability on which recombination acted to enhance the activity.

A third feature of recombination is that it can be used to remove deleterious mutations. As discussed above, during the process of the randomization, for every one beneficial mutation, there may be at least one or more neutral or inhibitory mutations. Such mutations can be removed by including in the assembly reaction an excess of the wild-type random-size fragments, in addition to the random-size fragments of the selected mutant from the previous selection. During the next selection, some of the most active variants of the polynucleotide/polypeptide/enzyme, should have lost the inhibitory mutations.

Finally, recombination enables parallel processing. This represents a significant advantage since there are likely multiple characteristics that would make a protein more desirable (e.g. solubility, activity, etc.). Since it is increasingly difficult to screen for more than one desirable trait at a time, other methods of molecular evolution tend to be inhibitory. However, using recombination, it would be possible to combine the randomized fragments of the best representative variants for the various traits, and then select for multiple properties at once.

DNA shuffling can also be applied to the polynucleotides and polypeptides of the present invention to decrease their immunogenicity in a specified host. For example, a particular variant of the present invention may be created and isolated using DNA shuffling technology. Such a variant may have all of the desired characteristics, though may be highly immunogenic in a host due to its novel intrinsic structure. Specifically, the desired characteristic may cause the polypeptide to have a non-native structure which could no longer be recognized as a "self" molecule, but rather as a "foreign", and thus activate a host immune response directed against the novel variant. Such a limitation can be overcome, for example, by including a copy of the gene sequence for a xenobiotic ortholog of the native protein in with the gene sequence of the novel variant gene in one or more cycles of DNA shuffling. The molar ratio of the ortholog and novel variant DNAs could be varied accordingly. Ideally, the resulting hybrid variant identified would contain at least some of the coding sequence which enabled the xenobiotic protein to evade the host immune system, and additionally, the coding sequence of the original novel variant that provided the desired characteristics.

Likewise, the invention encompasses the application of DNA shuffling technology to the evolution of polynucleotides and polypeptides of the invention, wherein one or more cycles of DNA shuffling include, in addition to the gene template DNA, oligonucleotides coding for known allelic sequences, optimized codon sequences, known variant sequences, known polynucleotide polymorphism sequences, known ortholog sequences, known homologue sequences, additional homologous sequences, additional non-homologous sequences, sequences from another species, and any number and combination of the above.

In addition to the described methods above, there are a number of related methods that may also be applicable, or desirable in certain cases. Representative among these are the methods discussed in PCT applications WO 98/31700, and WO 98/32845, which are hereby incorporated by reference. Furthermore, related methods can also be applied to the polynucleotide sequences of the present invention in order to evolve invention for creating ideal variants for use in gene therapy, protein engineering, evolution of whole cells containing the variant, or in the evolution of entire enzyme pathways containing polynucleotides of the invention as described in PCT applications WO 98/13485, WO 98/13487, WO 98/27230, WO 98/31837, and Crameri, A., et al., Nat. Biotech., 15:436–438, (1997), respectively.

Additional methods of applying "DNA Shuffling" technology to the polynucleotides and polypeptides of the present invention, including their proposed applications, may be found in U.S. Pat. No. 5,605,793; PCT Application No. WO 95/22625; PCT Application No. WO 97/20078; PCT Application No. WO 97/35966; and PCT Application No. WO 98/42832; PCT Application No. WO 00/09727 specifically provides methods for applying DNA shuffling to the identification of herbicide selective crops which could be applied to the polynucleotides and polypeptides of the present invention; additionally, PCT Application No. WO 00/12680 provides methods and compositions for generating, modifying, adapting, and optimizing polynucleotide sequences that confer detectable phenotypic properties on plant species; each of the above are hereby incorporated in their entirety herein for all purposes.

Example 22

Method of Determining Alterations in a Gene Corresponding to a Polynucleotide

RNA isolated from entire families or individual patients presenting with a phenotype of interest (such as a disease) is be isolated. cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95 degrees C. for 30 seconds; 60–120 seconds at 52–58 degrees C.; and 60–120 seconds at 70 degrees C., using buffer solutions described in Sidransky et al., Science 252:706 (1991).

PCR products are then sequenced using primers labeled at their 5' end with T4 polynucleotide kinase, employing SequiTherm Polymerase. (Epicentre Technologies). The intron-exon borders of selected exons is also determined and genomic PCR products analyzed to confirm the results. PCR products harboring suspected mutations is then cloned and sequenced to validate the results of the direct sequencing.

PCR products is cloned into T-tailed vectors as described in Holton et al., Nucleic Acids Research, 19:1156 (1991) and sequenced with T7 polymerase (United States Biochemical). Affected individuals are identified by mutations not present in unaffected individuals.

Genomic rearrangements are also observed as a method of determining alterations in a gene corresponding to a polynucleotide. Genomic clones isolated according to Example 2 are nick-translated with digoxigenindeoxy-uridine 5'-triphosphate (Boehringer Manheim), and FISH performed as described in Johnson et al., Methods Cell Biol. 35:73–99 (1991). Hybridization with the labeled probe is carried out using a vast excess of human cot-1 DNA for specific hybridization to the corresponding genomic locus.

Chromosomes are counterstained with 4,6-diamino-2-phenylidole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region hybridized by the probe are identified as insertions, deletions, and translocations. These alterations are used as a diagnostic marker for an associated disease.

Example 23

Method of Detecting Abnormal Levels of a Polypeptide in a Biological Sample

A polypeptide of the present invention can be detected in a biological sample, and if an increased or decreased level of the polypeptide is detected, this polypeptide is a marker for a particular phenotype. Methods of detection are numerous, and thus, it is understood that one skilled in the art can modify the following assay to fit their particular needs.

For example, antibody-sandwich ELISAs are used to detect polypeptides in a sample, preferably a biological sample. Wells of a microtiter plate are coated with specific antibodies, at a final concentration of 0.2 to 10 ug/ml. The antibodies are either monoclonal or polyclonal and are produced by the method described elsewhere herein. The wells are blocked so that non-specific binding of the polypeptide to the well is reduced.

The coated wells are then incubated for >2 hours at RT with a sample containing the polypeptide. Preferably, serial dilutions of the sample should be used to validate results. The plates are then washed three times with deionized or distilled water to remove unbounded polypeptide.

Next, 50 ul of specific antibody-alkaline phosphatase conjugate, at a concentration of 25–400 ng, is added and incubated for 2 hours at room temperature. The plates are again washed three times with deionized or distilled water to remove unbounded conjugate.

Add 75 ul of 4-methylumbelliferyl phosphate (MUP) or p-nitrophenyl phosphate (NPP) substrate solution to each well and incubate 1 hour at room temperature. Measure the reaction by a microtiter plate reader. Prepare a standard curve, using serial dilutions of a control sample, and plot polypeptide concentration on the X-axis (log scale) and fluorescence or absorbance of the Y-axis (linear scale). Interpolate the concentration of the polypeptide in the sample using the standard curve.

Example 24

Formulation

The invention also provides methods of treatment and/or prevention diseases, disorders, and/or conditions (such as, for example, any one or more of the diseases or disorders disclosed herein) by administration to a subject of an effective amount of a Therapeutic. By therapeutic is meant a polynucleotides or polypeptides of the invention (including fragments and variants), agonists or antagonists thereof, and/or antibodies thereto, in combination with a pharmaceutically acceptable carrier type (e.g., a sterile carrier).

The Therapeutic will be formulated and dosed in a fashion consistent with good medical practice, taking into account the clinical condition of the individual patient (especially the side effects of treatment with the Therapeutic alone), the site of delivery, the method of administration, the scheduling of administration, and other factors known to practitioners. The "effective amount" for purposes herein is thus determined by such considerations.

As a general proposition, the total pharmaceutically effective amount of the Therapeutic administered parenterally per dose will be in the range of about 1 ug/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the Therapeutic is typically administered at a dose rate of about 1 ug/kg/hour to about 50 ug/kg/hour, either by 1–4 injections per day or by continuous subcutaneous infusions, for example, using a mini-pump. An intravenous bag solution may also be employed. The length of treatment needed to observe changes and the interval following treatment for responses to occur appears to vary depending on the desired effect.

Therapeutics can be administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any. The term "parenteral" as used herein refers to modes of administration which include intravenous, intramuscular, intraperitoneal, intrastemal, subcutaneous and intraarticular injection and infusion.

Therapeutics of the invention are also suitably administered by sustained-release systems. Suitable examples of sustained-release Therapeutics are administered orally, rectally, parenterally, intracisternally, intravaginally, intraperitoneally, topically (as by powders, ointments, gels, drops or transdermal patch), bucally, or as an oral or nasal spray. "Pharmaceutically acceptable carrier" refers to a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

Therapeutics of the invention may also be suitably administered by sustained-release systems. Suitable examples of sustained-release Therapeutics include suitable polymeric materials (such as, for example, semi-permeable polymer matrices in the form of shaped articles, e.g., films, or microcapsules), suitable hydrophobic materials (for example as an emulsion in an acceptable oil) or ion exchange resins, and sparingly soluble derivatives (such as, for example, a sparingly soluble salt).

Sustained-release matrices include polylactides (U.S. Pat. No. 3,773,919, EP 58,481), copolymers of L-glutamic acid and gamma-ethyl-L-glutamate (Sidman et al., Biopolymers 22:547–556 (1983)), poly (2-hydroxyethyl methacrylate) (Langer et al., J. Biomed. Mater. Res. 15:167–277 (1981), and Langer, Chem. Tech. 12:98–105 (1982)), ethylene vinyl acetate (Langer et al., Id.) or poly-D-(–)-3-hydroxybutyric acid (EP 133,988).

Sustained-release Therapeutics also include liposomally entrapped Therapeutics of the invention (see, generally, Langer, Science 249:1527–1533 (1990); Treat et al., in Liposomes in the Therapy of Infectious Disease and Cancer, Lopez-Berestein and Fidler (eds.), Liss, New York, pp. 317–327 and 353–365 (1989)). Liposomes containing the Therapeutic are prepared by methods known per se: DE 3,218,121; Epstein et al., Proc. Natl. Acad. Sci. (USA) 82:3688–3692 (1985); Hwang et al., Proc. Natl. Acad. Sci.(USA) 77:4030–4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200–800 Angstroms) unilamellar type in which the lipid content is greater than about 30 mol. percent cholesterol, the selected proportion being adjusted for the optimal Therapeutic.

In yet an additional embodiment, the Therapeutics of the invention are delivered by way of a pump (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)).

Other controlled release systems are discussed in the review by Langer (Science 249:1527–1533 (1990)).

For parenteral administration, in one embodiment, the Therapeutic is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation. For example, the formulation preferably does not include oxidizing agents and other compounds that are known to be deleterious to the Therapeutic.

Generally, the formulations are prepared by contacting the Therapeutic uniformly and intimately with liquid carriers or finely divided solid carriers or both. Then, if necessary, the product is shaped into the desired formulation. Preferably the carrier is a parenteral carrier, more preferably a solution that is isotonic with the blood of the recipient. Examples of such carrier vehicles include water, saline, Ringer's solution, and dextrose solution. Non-aqueous vehicles such as fixed oils and ethyl oleate are also useful herein, as well as liposomes.

The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) polypeptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, mannose, or dextrins; chelating agents such as EDTA; sugar alcohols such as mannitol or sorbitol; counterions such as sodium; and/or nonionic surfactants such as polysorbates, poloxamers, or PEG.

The Therapeutic will typically be formulated in such vehicles at a concentration of about 0.1 mg/ml to 100 mg/ml, preferably 1–10 mg/ml, at a pH of about 3 to 8. It will be understood that the use of certain of the foregoing excipients, carriers, or stabilizers will result in the formation of polypeptide salts.

Any pharmaceutical used for therapeutic administration can be sterile. Sterility is readily accomplished by filtration through sterile filtration membranes (e.g., 0.2 micron membranes). Therapeutics generally are placed into a container having a sterile access port, for example, an intravenous solution bag or vial having a stopper pierceable by a hypodermic injection needle.

Therapeutics ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous Therapeutic solution, and the resulting mixture is lyophilized. The infusion solution is prepared by reconstituting the lyophilized Therapeutic using bacteriostatic Water-for-Injection.

The invention also provides a pharmaceutical pack or kit comprising one or more containers filled with one or more of the ingredients of the Therapeutics of the invention.

Associated with such container(s) can be a notice in the form prescribed by a governmental agency regulating the manufacture, use or sale of pharmaceuticals or biological products, which notice reflects approval by the agency of manufacture, use or sale for human administration. In addition, the Therapeutics may be employed in conjunction with other therapeutic compounds.

The Therapeutics of the invention may be administered alone or in combination with adjuvants. Adjuvants that may be administered with the Therapeutics of the invention include, but are not limited to, alum, alum plus deoxycholate (InmunoAg), MTP-PE (Biocine Corp.), QS21 (Genentech, Inc.), BCG, and MPL. In a specific embodiment, Therapeutics of the invention are administered in combination with alum. In another specific embodiment, Therapeutics of the invention are administered in combination with QS-21. Further adjuvants that may be administered with the Therapeutics of the invention include, but are not limited to, Monophosphoryl lipid immunomodulator, AdjuVax 100a, QS-21, QS-18, CRL1005, Aluminum salts, MF-59, and Virosomal adjuvant technology. Vaccines that may be administered with the Therapeutics of the invention include, but are not limited to, vaccines directed toward protection against MMR (measles, mumps, rubella), polio, varicella, tetanus/diptheria, hepatitis A, hepatitis B, haemophilus influenzae B, whooping cough, pneumonia, influenza, Lyme's Disease, rotavirus, cholera, yellow fever, Japanese encephalitis, poliomyelitis, rabies, typhoid fever, and pertussis. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

The Therapeutics of the invention may be administered alone or in combination with other therapeutic agents. Therapeutic agents that may be administered in combination with the Therapeutics of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the Therapeutics of the invention are administered in combination with members of the TNF family. TNF, TNF-related or TNF-like molecules that may be administered with the Therapeutics of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892),TR10 (International Publication No. WO 98/54202), 312C2 (International Publication No. WO 98/06842), and TR12, and soluble forms CD154, CD70, and CD153.

In certain embodiments, Therapeutics of the invention are administered in combination with antiretroviral agents, nucleoside reverse transcriptase inhibitors, non-nucleoside reverse transcriptase inhibitors, and/or protease inhibitors. Nucleoside reverse transcriptase inhibitors that may be administered in combination with the Therapeutics of the invention, include, but are not limited to, RETROVIR( (zidovudine/AZT), VIDEX((didanosine/ddI), HIVID((zalcitabine/ddC), ZERIT( (stavudine/d4T), EPIVIR((lamivudine/3TC), and COMBIVIR( (zidovudine/lamivudine). Non-nucleoside reverse transcriptase inhibitors that may be administered in combination with the Therapeutics of the invention, include, but are not limited to, VIRAMUNE ((nevirapine), RESCRIPTOR((delavirdine), and SUSTIVA ((efavirenz). Protease inhibitors that may be administered in combination with the Therapeutics of the invention, include, but are not limited to, CRIXIVAN( (indinavir), NORVIR ((ritonavir), INVIRASE((saquinavir), and VIRACEPT( (nelfinavir). In a specific embodiment, antiretroviral agents, nucleoside reverse transcriptase inhibitors, non-nucleoside reverse transcriptase inhibitors, and/or protease inhibitors may be used in any combination with Therapeutics of the invention to treat AIDS and/or to prevent or treat HIV infection.

In other embodiments, Therapeutics of the invention may be administered in combination with anti-opportunistic infection agents. Anti-opportunistic agents that may be administered in combination with the Therapeutics of the invention, include, but are not limited to, TRIMETHOPRIM-SULFAMETHOXAZOLE(, DAPSONE(, PENTAMIDINE(, ATOVAQUONE(, ISONIAZID(, RIFAMPIN(, PYRAZINAMIDE(, ETHAMBUTOL(, RIFABUTIN(, CLARITHROMYCIN(, AZITHROMYCIN(, GANCICLOVIR(, FOSCARNET(, CIDOFOVIR(, FLUCONAZOLE(, ITRACONAZOLE(, KETOCONAZOLE(, ACYCLOVIR(, FAMCICOLVIR(, PYRIMETHAMINE(, LEUCOVORIN(, NEUPOGEN( (filgrastim/G-CSF), and LEUKINE((sargramostim/GM-CSF). In a specific embodiment, Therapeutics of the invention are used in any combination with TRIMETHOPRIM-SULFAMETHOXAZOLE(, DAPSONE(, PENTAMIDINE(, and/or ATOVAQUONE(to prophylactically treat or prevent an opportunistic Pneumocystis carinii pneumonia infection. In another specific embodiment, Therapeutics of the invention are used in any combination with ISONIAZID(, RIFAMPIN(, PYRAZINAMIDE(, and/or ETHAMBUTOL(to prophylactically treat or prevent an opportunistic *Mycobacterium avium* complex infection. In another specific embodiment, Therapeutics of the invention are used in any combination with RIFABUTIN(, CLARITHROMYCIN(, and/or AZITHROMYCIN(to prophylactically treat or prevent an opportunistic *Mycobacterium* tuberculosis infection. In another specific embodiment, Therapeutics of the invention are used in any combination with GANCICLOVIR(, FOSCARNET(, and/or CIDOFOVIR(to prophylactically treat or prevent an opportunistic cytomegalovirus infection. In another specific embodiment, Therapeutics of the invention are used in any combination with FLUCONAZOLE(, ITRACONAZOLE(, and/or KETOCONAZOLE(to prophylactically treat or prevent an opportunistic fungal infection. In another specific embodiment, Therapeutics of the invention are used in any combination with ACYCLOVIR(and/or FAMCICOLVIR( to prophylactically treat or prevent an opportunistic herpes simplex virus type I and/or type II infection. In another specific embodiment, Therapeutics of the invention are used in any combination with PYRIMETHAMINE(and/or LEUCOVORIN(to prophylactically treat or prevent an opportunistic Toxoplasma gondii infection. In another specific embodiment, Therapeutics of the invention are used in any combination with LEUCOVORIN(and/or NEUPOGEN(to prophylactically treat or prevent an opportunistic bacterial infection.

In a further embodiment, the Therapeutics of the invention are administered in combination with an antiviral agent. Antiviral agents that may be administered with the Therapeutics of the invention include, but are not limited to, acyclovir, ribavirin, amantadine, and remantidine.

In a further embodiment, the Therapeutics of the invention are administered in combination with an antibiotic agent. Antibiotic agents that may be administered with the Therapeutics of the invention include, but are not limited to, amoxicillin, beta-lactamases, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the Therapeutics of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In specific embodiments, Therapeutics of the invention are administered in combination with immunosuppressants. Immunosuppressants preparations that may be administered with the Therapeutics of the invention include, but are not limited to, ORTHOCLONE((OKT3), SANDIMMUNE(/NEORAL(/SANGDYA((cyclosporin), PROGRAF((tacrolimus), CELLCEPT((mycophenolate), Azathioprine, glucorticosteroids, and RAPAMUNE((sirolimus). In a specific embodiment, immunosuppressants may be used to prevent rejection of organ or bone marrow transplantation.

In an additional embodiment, Therapeutics of the invention are administered alone or in combination with one or more intravenous immune globulin preparations. Intravenous immune globulin preparations that may be administered with the Therapeutics of the invention include, but not limited to, GAMMAR(, IVEEGAM(, SANDOGLOBULIN(, GAMMAGARD S/D(, and GAMIMUNE(. In a specific embodiment, Therapeutics of the invention are administered in combination with intravenous immune globulin preparations in transplantation therapy (e.g., bone marrow transplant).

In an additional embodiment, the Therapeutics of the invention are administered alone or in combination with an anti-inflammatory agent. Anti-inflammatory agents that may be administered with the Therapeutics of the invention include, but are not limited to, glucocorticoids and the nonsteroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compositions of the invention are administered in combination with a chemotherapeutic agent. Chemotherapeutic agents that may be administered with the Therapeutics of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In a specific embodiment, Therapeutics of the invention are administered in combination with CHOP (cyclophosphamide, doxorubicin, vincristine, and prednisone) or any combination of the components of CHOP. In another embodiment, Therapeutics of the invention are administered in combination with Rituximab. In a further embodiment, Therapeutics of the invention are administered with Rituxmab and CHOP, or Rituxmab and any combination of the components of CHOP.

In an additional embodiment, the Therapeutics of the invention are administered in combination with cytokines. Cytokines that may be administered with the Therapeutics of the invention include, but are not limited to, IL2, IL3, ILA, IL5, IL6, IL7, IL10, IL12, IL13, IL15, anti-CD40, CD40L, IFN-gamma and TNF-alpha. In another embodiment, Therapeutics of the invention may be administered with any interleukin, including, but not limited to, IL-1alpha, IL-1beta, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, and IL-21.

In an additional embodiment, the Therapeutics of the invention are administered in combination with angiogenic proteins. Angiogenic proteins that may be administered with the Therapeutics of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Gorwth Factors, 4:259–268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B (VEGF-3); Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the Therapeutics of the invention are administered in combination with hematopoietic growth factors. Hematopoietic growth factors that may be administered with the Therapeutics of the invention include, but are not limited to, LEUKINE((SARGRAMOSTIM( ) and NEUPOGEN( (FILGRASTIM( ).

In an additional embodiment, the Therapeutics of the invention are administered in combination with Fibroblast Growth Factors. Fibroblast Growth Factors that may be administered with the Therapeutics of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In a specific embodiment, formulations of the present invention may further comprise antagonists of P-glycoprotein (also referred to as the multiresistance protein, or PGP), including antagonists of its encoding polynucleotides (e.g., antisense oligonucleotides, ribozymes, zinc-finger proteins, etc.). P-glycoprotein is well known for decreasing the efficacy of various drug administrations due to its ability to export intracellular levels of absorbed drug to the cell exterior. While this activity has been particularly pronounced in cancer cells in response to the administration of chemotherapy regimens, a variety of other cell types and the administration of other drug classes have been noted (e.g., T-cells and anti-HIV drugs). In fact, certain mutations in the PGP gene significantly reduces PGP function, making it less able to force drugs out of cells. People who have two versions of the mutated gene—one inherited from each parent—have more than four times less PGP than those with two normal versions of the gene. People may also have one normal gene and one mutated one. Certain ethnic populations have increased incidence of such PGP mutations. Among individuals from Ghana, Kenya, the Sudan, as well as African Americans, frequency of the normal gene ranged from 73% to 84%. In contrast, the frequency was 34% to 59% among British whites, Portuguese, Southwest Asian, Chinese, Filipino and Saudi populations. As a result, certain ethnic populations may require increased administration of PGP antagonist in the formulation of the present invention to arrive at the an efficacious dose of the therapeutic (e.g., those from African descent). Conversely, certain ethnic populations, particularly those having increased frequency of the mutated PGP (e.g., of Caucasian descent, or non-African descent) may require less pharmaceutical compositions in the formulation due to an effective increase in efficacy of such compositions as a result of the increased effective absorption (e.g., less PGP activity) of said composition.

Moreover, in another specific embodiment, formulations of the present invention may further comprise antagonists of OATP2 (also referred to as the multiresistance protein, or MRP2), including antagonists of its encoding polynucleotides (e.g., antisense oligonucleotides, ribozymes, zinc-finger proteins, etc.). The invention also further comprises any additional antagonists known to inhibit proteins thought to be attributable to a multidrug resistant phenotype in proliferating cells.

In additional embodiments, the Therapeutics of the invention are administered in combination with other therapeutic or prophylactic regimens, such as, for example, radiation therapy.

Example 25

Method of Treating Decreased Levels of the Polypeptide

The present invention relates to a method for treating an individual in need of an increased level of a polypeptide of the invention in the body comprising administering to such an individual a composition comprising a therapeutically effective amount of an agonist of the invention (including polypeptides of the invention). Moreover, it will be appreciated that conditions caused by a decrease in the standard or normal expression level of a secreted protein in an individual can be treated by administering the polypeptide of the present invention, preferably in the secreted form. Thus, the invention also provides a method of treatment of an individual in need of an increased level of the polypeptide comprising administering to such an individual a Therapeutic comprising an amount of the polypeptide to increase the activity level of the polypeptide in such an individual.

For example, a patient with decreased levels of a polypeptide receives a daily dose 0.1–100 ug/kg of the polypeptide for six consecutive days. Preferably, the polypeptide is in the secreted form. The exact details of the dosing scheme, based on administration and formulation, are provided herein.

Example 26

Method of Treating Increased Levels of the Polypeptide

The present invention also relates to a method of treating an individual in need of a decreased level of a polypeptide of the invention in the body comprising administering to such an individual a composition comprising a therapeutically effective amount of an antagonist of the invention (including polypeptides and antibodies of the invention).

In one example, antisense technology is used to inhibit production of a polypeptide of the present invention. This technology is one example of a method of decreasing levels of a polypeptide, preferably a secreted form, due to a variety of etiologies, such as cancer. For example, a patient diagnosed with abnormally increased levels of a polypeptide is administered intravenously antisense polynucleotides at 0.5, 1.0, 1.5, 2.0 and 3.0 mg/kg day for 21 days. This treatment is repeated after a 7-day rest period if the treatment was well tolerated. The formulation of the antisense polynucleotide is provided herein.

Example 27

Method of Treatment Using Gene Therapy-Ex Vivo

One method of gene therapy transplants fibroblasts, which are capable of expressing a polypeptide, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219–25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention can be amplified using PCR primers which correspond to the 5' and 3' end sequences respectively as set forth in Example 9 using primers and having appropriate restriction sites and initiation/stop codons, if necessary. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform bacteria HB101, which are then plated onto agar containing kanamycin for the purpose of confirming that the vector has the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether protein is produced.

The engineered fibroblasts are then transplanted onto the host, either alone or after having been grown to confluence on cytodex 3 microcarrier beads.

Example 28

Gene Therapy Using Endogenous Genes Corresponding to Polynucleotides of the Invention Another method of gene therapy according to the present invention involves operably associating the endogenous polynucleotide sequence of the invention with a promoter via homologous recombination as described, for example, in U.S. Pat. No. 5,641,670, issued Jun. 24, 1997; International Publication NO: WO 96/29411, published Sep. 26, 1996; International Publication NO: WO 94/12650, published Aug. 4, 1994; Koller et al., Proc. Natl. Acad. Sci. USA, 86:8932–8935 (1989); and Zijlstra et al., Nature, 342:435–438 (1989). This method involves the activation of a gene which is present in the target cells, but which is not expressed in the cells, or is expressed at a lower level than desired.

Polynucleotide constructs are made which contain a promoter and targeting sequences, which are homologous to the 5' non-coding sequence of endogenous polynucleotide sequence, flanking the promoter. The targeting sequence will be sufficiently near the 5' end of the polynucleotide sequence so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous polynucleotide sequence. This results in the expression of polynucleotide corresponding to the polynucleotide in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the locus corresponding to the polynucleotide of the invention, plasmid pUC18 (MBI Fermentas, Amherst, N.Y.) is digested with HindIII. The CMV promoter is amplified by PCR with an XbaI site on the 5' end and a BamHI site on the 3'end. Two non-coding sequences are amplified via PCR: one non-coding sequence (fragment 1) is amplified with a HindIII site at the 5' end and an Xba site at the 3'end; the other non-coding sequence (fragment 2) is amplified with a BamHI site at the 5'end and a HindIII site at the 3'end. The CMV promoter and the fragments (1 and 2) are digested with the appropriate enzymes (CMV promoter—XbaI and BamHI; fragment 1—XbaI; fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5.×106 cells) is then added to the cuvette, and the cell suspension and DNA solutions are gently mixed. Electroporation is performed with a Gene-Pulser apparatus (Bio-Rad). Capacitance and voltage are set at 960 µF and 250–300 V, respectively. As voltage increases, cell survival decreases, but the percentage of surviving cells that stably incorporate the introduced DNA into their genome increases dramatically. Given these parameters, a pulse time of approximately 14–20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37 degree C. The following day, the media is aspirated and replaced with 10 ml of fresh media and incubated for a further 16–24 hours.

The engineered fibroblasts are then injected into the host, either alone or after having been grown to confluence on cytodex 3 microcarrier beads. The fibroblasts now produce the protein product. The fibroblasts can then be introduced into a patient as described above.

Example 29

Method of Treatment Using Gene Therapy—in vivo

Another aspect of the present invention is using in vivo gene therapy methods to treat disorders, diseases and conditions. The gene therapy method relates to the introduction of naked nucleic acid (DNA, RNA, and antisense DNA or RNA) sequences into an animal to increase or decrease the expression of the polypeptide. The polynucleotide of the present invention may be operatively linked to a promoter or any other genetic elements necessary for the expression of the polypeptide by the target tissue. Such gene therapy and delivery techniques and methods are known in the art, see, for example, WO90/11092, WO98/11779; U.S. Patent No. 5,693,622, 5,705,151, 5,580,859; Tabata et al., Cardiovasc. Res. 35(3):470–479 (1997); Chao et al., Pharmacol. Res. 35(6):517–522 (1997); Wolff, Neuromuscul. Disord. 7(5): 314–318 (1997); Schwartz et al., Gene Ther. 3(5):405–411 (1996); Tsurumi et al., Circulation 94(12):3281–3290 (1996) (incorporated herein by reference).

The polynucleotide constructs may be delivered by any method that delivers injectable materials to the cells of an animal, such as, injection into the interstitial space of tissues (heart, muscle, skin, lung, liver, intestine and the like). The polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the polynucleotides of the present invention may also be delivered in liposome formulations (such as those taught in Felgner P. L. et al. (1995) Ann. NY Acad. Sci. 772:126–139 and Abdallah B. et al. (1995) Biol. Cell 85(1):1–7) which can be prepared by methods well known to those skilled in the art.

The polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked polynucleotide constructs can be delivered to arteries during angioplasty by the catheter used in the procedure.

The dose response effects of injected polynucleotide in muscle in vivo is determined as follows. Suitable template DNA for production of mRNA coding for polypeptide of the present invention is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for protein expression. A time course for protein expression may be done in a similar fashion except that quadriceps from different mice are harvested at different times. Persistence of DNA in muscle following injection may be determined by Southern blot analysis after preparing total cellular DNA and HIRT supernatants from injected and control mice. The results of the above experimentation in mice can be use to extrapolate proper dosages and other treatment parameters in humans and other animals using naked DNA.

Example 30

Transgenic Animals

The polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., polynucleotides of the invention) into animals to produce the founder lines of transgenic animals. Such techniques include, but are not limited to, pronuclear microinjection (Paterson et al., Appl. Microbiol. Biotechnol. 40:691–698 (1994); Carver et al., Biotechnology (NY) 11:1263–1270 (1993); Wright et al., Biotechnology (NY) 9:830–834 (1991); and Hoppe et al., U.S. Pat. No. 4,873,191 (1989)); retrovirus mediated gene transfer into germ lines (Van der Putten et al., Proc. Natl. Acad. Sci., USA 82:6148–6152 (1985)), blastocysts or embryos; gene targeting in embryonic stem cells (Thompson et al., Cell 56:313–321 (1989)); electroporation of cells or embryos (Lo, 1983, Mol Cell. Biol. 3:1803–1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717–723 (1989); etc. For a review of such techniques, see Gordon, "Transgenic Animals," Intl. Rev. Cytol. 115:171–229 (1989), which is incorporated by reference herein in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64–66 (1996); Wilmut et al., Nature 385:810–813 (1997)).

The present invention provides for transgenic animals that carry the transgene in all their cells, as well as animals which carry the transgene in some, but not all their cells, i.e., mosaic animals or chimeric. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Lasko et al., Proc. Natl. Acad. Sci. USA 89:6232–6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Gu et al., Science 265:103–106 (1994)). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR(RT-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 31

Knock-Out Animals

Endogenous gene expression can also be reduced by inactivating or "knocking out" the gene and/or its promoter using targeted homologous recombination. (E.g., see Smithies et al., Nature 317:230–234 (1985); Thomas & Capecchi, Cell 51:503–512 (1987); Thompson et al., Cell 5:313–321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art.

In further embodiments of the invention, cells that are genetically engineered to express the polypeptides of the invention, or alternatively, that are genetically engineered not to express the polypeptides of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally.

Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al. U.S. Pat. No. 5,399,349; and Mulligan & Wilson, U.S. Pat. No. 5,460,959 each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

Transgenic and "knock-out" animals of the invention have uses which include, but are not limited to, animal model systems useful in elaborating the biological function of polypeptides of the present invention, studying diseases, disorders, and/or conditions associated with aberrant expression, and in screening for compounds effective in ameliorating such diseases, disorders, and/or conditions.

Example 32

Production of an Antibody a) Hybridoma Technology

The antibodies of the present invention can be prepared by a variety of methods. (See, Current Protocols, Chapter 2.) As one example of such methods, cells expressing LSI-01 are administered to an animal to induce the production of sera containing polyclonal antibodies. In a preferred method, a preparation of LSI-01 protein is prepared and purified to render it substantially free of natural contaminants. Such a preparation is then introduced into an animal in order to produce polyclonal antisera of greater specific activity.

Monoclonal antibodies specific for protein LSI-01 are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell Hybridomas, Elsevier, N.Y., pp. 563–681 (1981)). In general, an animal (preferably a mouse) is immunized with LSI-01 polypeptide or, more preferably, with a secreted LSI-01 polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 µl of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP20), available from the ATCC. After fusion, the resulting hybridoma cells are selectively maintained in HAT medium, and then cloned by limiting dilution as described by Wands et al. (Gastroenterology 80:225–232 (1981)). The hybridoma cells obtained through such a selection are then assayed to identify clones which secrete antibodies capable of binding the LSI-01 polypeptide.

Alternatively, additional antibodies capable of binding to LSI-01 polypeptide can be produced in a two-step procedure using anti-idiotypic antibodies. Such a method makes use of the fact that antibodies are themselves antigens, and therefore, it is possible to obtain an antibody that binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the LSI-01 protein-specific antibody can be blocked by LSI-01. Such antibodies comprise anti-idiotypic antibodies to the LSI-01 protein-specific antibody and are used to immunize an animal to induce formation of further LSI-01 protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

b) Isolation Of Antibody Fragments Directed Against LSI-01 From A Library of scFvs Naturally occurring V-genes isolated from human PBLs are constructed into a library of antibody fragments which contain reactivities against LSI-01 to which the donor may or may not have been exposed (see e.g., U.S. Pat. No. 5,885,793 incorporated herein by reference in its entirety).

Rescue of the Library. A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to inoculate 50 ml of 2×TY-AMP-GLU, 2×108 TU of delta gene 3 helper (M13 delta gene m, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 ug/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library. Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders. Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 33

Assays Detecting Stimulation or Inhibition of B cell Proliferation and Differentiation Generation of functional humoral immune responses requires both soluble and cognate signaling between B-lineage cells and their microenvironment. Signals may impart a positive stimulus that allows a B-lineage cell to continue its programmed development, or a negative stimulus that instructs the cell to arrest its current developmental pathway. To date, numerous stimulatory and inhibitory signals have been found to influence B cell responsiveness including IL-2, IL-4, IL-5, IL-6, IL-7, IL-10, IL-13, IL-14 and IL-15. Interestingly, these signals are by themselves weak effectors but can, in combination with various co-stimulatory proteins, induce activation, proliferation, differentiation, homing, tolerance and death among B cell populations.

One of the best studied classes of B-cell co-stimulatory proteins is the TNF-superfamily. Within this family CD40, CD27, and CD30 along with their respective ligands CD154, CD70, and CD153 have been found to regulate a variety of immune responses. Assays which allow for the detection and/or observation of the proliferation and differentiation of these B-cell populations and their precursors are valuable tools in determining the effects various proteins may have on these B-cell populations in terms of proliferation and differentiation. Listed below are two assays designed to allow for the detection of the differentiation, proliferation, or inhibition of B-cell populations and their precursors.

In Vitro Assay- Purified polypeptides of the invention, or truncated forms thereof, is assessed for its ability to induce activation, proliferation, differentiation or inhibition and/or death in B-cell populations and their precursors. The activity of the polypeptides of the invention on purified human tonsillar B cells, measured qualitatively over the dose range from 0.1 to 10,000 ng/mL, is assessed in a standard B-lymphocyte co-stimulation assay in which purified tonsillar B cells are cultured in the presence of either formalin-fixed Staphylococcus aureus Cowan I (SAC) or immobilized anti-human IgM antibody as the priming agent. Second signals such as IL-2 and IL-15 synergize with SAC and IgM crosslinking to elicit B cell proliferation as measured by tritiated-thymidine incorporation. Novel synergizing agents can be readily identified using this assay. The assay involves isolating human tonsillar B cells by magnetic bead (MACS) depletion of CD3-positive cells. The resulting cell population is greater than 95% B cells as assessed by expression of CD45R(B220).

Various dilutions of each sample are placed into individual wells of a 96-well plate to which are added 105 B-cells suspended in culture medium (RPMI 1640 containing 10% FBS, 5×10-5M 2ME, 100 U/ml penicillin, 10 ug/ml streptomycin, and 10-5 dilution of SAC) in a total volume of 150 ul. Proliferation or inhibition is quantitated by a 20 h pulse (luCi/well) with 3H-thymidine (6.7 Ci/mM) beginning 72 h post factor addition. The positive and negative controls are IL2 and medium respectively.

In Vivo Assay—BALB/c mice are injected (i.p.) twice per day with buffer only, or 2 mg/Kg of a polypeptide of the invention, or truncated forms thereof. Mice receive this treatment for 4 consecutive days, at which time they are sacrificed and various tissues and serum collected for analyses. Comparison of H&E sections from normal spleens and spleens treated with polypeptides of the invention identify the results of the activity of the polypeptides on spleen cells, such as the diffusion of peri-arterial lymphatic sheaths, and/or significant increases in the nucleated cellularity of the red pulp regions, which may indicate the activation of the differentiation and proliferation of B-cell populations. Immunohistochemical studies using a B cell marker, anti-CD45R(B220), are used to determine whether any physiological changes to splenic cells, such as splenic disorganization, are due to increased B-cell representation within loosely defined B-cell zones that infiltrate established T-cell regions.

Flow cytometric analyses of the spleens from mice treated with polypeptide is used to indicate whether the polypeptide specifically increases the proportion of ThB+, CD45R (B220)dull B cells over that which is observed in control mice.

Likewise, a predicted consequence of increased mature B-cell representation in vivo is a relative increase in serum Ig titers. Accordingly, serum IgM and IgA levels are compared between buffer and polypeptide-treated mice.

One skilled in the art could easily modify the exemplified studies to test the activity of polynucleotides of the invention (e.g., gene therapy), agonists, and/or antagonists of polynucleotides or polypeptides of the invention.

Example 34

T Cell Proliferation Assay

A CD3-induced proliferation assay is performed on PBMCs and is measured by the uptake of 3H-thymidine. The assay is performed as follows. Ninety-six well plates are coated with 100 (1/well of mAb to CD3 (HIT3a, Pharmingen) or isotype-matched control mAb (B33.1) overnight at 4 degrees C. (1 (g/ml in 0.05M bicarbonate buffer, pH 9.5), then washed three times with PBS. PBMC are isolated by F/H gradient centrifugation from human peripheral blood and added to quadruplicate wells (5×104/well) of mAb coated plates in RPMI containing 10% FCS and P/S in the presence of varying concentrations of polypeptides of the invention (total volume 200 ul). Relevant protein buffer and medium alone are controls. After 48 hr. culture at 37 degrees C., plates are spun for 2 min. at 1000 rpm and 100 (1 of supernatant is removed and stored −20 degrees C. for measurement of IL-2 (or other cytokines) if effect on proliferation is observed. Wells are supplemented with 100 ul of medium containing 0.5 uCi of 3H-thymidine and cultured at 37 degrees C. for 18–24 hr. Wells are harvested and incorporation of 3H-thymidine used as a measure of proliferation. Anti-CD3 alone is the positive control for proliferation. IL-2 (100 U/ml) is also used as a control which enhances proliferation. Control antibody which does not induce proliferation of T cells is used as the negative controls for the effects of polypeptides of the invention.

One skilled in the art could easily modify the exemplified studies to test the activity of polynucleotides of the invention (e.g., gene therapy), agonists, and/or antagonists of polynucleotides or polypeptides of the invention.

Example 35

Effect of Polypeptides of the Invention on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7–10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-(, causes a rapid change in surface phenotype (increased expression of MHC class I and II, costimulatory and adhesion molecules, downregulation of FC(RII, upregulation of CD83). These changes correlate with increased antigen-presenting capacity and with functional maturation of the dendritic cells.

FACS analysis of surface antigens is performed as follows. Cells are treated 1–3 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Effect on the production of cytokines. Cytokines generated by dendritic cells, in particular L-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells (106/ ml) are treated with increasing concentrations of polypeptides of the invention for 24 hours. LPS (100 ng/ml) is added to the cell culture as positive control. Supernatants from the cell cultures are then collected and analyzed for IL-12 content using commercial ELISA kit(e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fe receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1–5 days with increasing concentrations of polypeptides of the invention or LPS (positive control), washed with PBS containing 1% BSA and 0.02 mM sodium azide, and then incubated with 1:20 dilution of appropriate FITC- or PE-labeled monoclonal antibodies for 30 minutes at 4 degrees C. After an additional wash, the labeled cells are analyzed by flow cytometry on a FACScan (Becton Dickinson).

Monocyte activation and/or increased survival. Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. Polypeptides, agonists, or antagonists of the invention can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 (g/ml, and then incubated at room temperature for 5 minutes before FACScan analysis. PI uptake has been demonstrated to correlate with DNA fragmentation in this experimental paradigm.

Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of 5×15 cells/ml with increasing concentrations of the a polypeptide of the invention and under the same conditions, but in the absence of the polypeptide. For IL-12 production, the cells are primed overnight with IFN (100 U/ml) in presence of a polypeptide of the invention. LPS (10 ng/ml) is then added. Conditioned media are collected after 24 h and kept frozen until use. Measurement of TNF-alpha, IL-10, MCP-1 and IL-8 is then performed using a commercially available ELISA kit(e.g., R & D Systems (Minneapolis, Minn.)) and applying the standard protocols provided with the kit.

Oxidative burst. Purified monocytes are plated in 96-w plate at $2-1\times10^5$ cell/well. Increasing concentrations of polypeptides of the invention are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37(C. for 2 hours and the reaction is stopped by adding 20 μl 1N NaOH per well. The absorbance is read at 610 nm. To calculate the amount of $H_2O_2$ produced by the macrophages, a standard curve of a $H_2O_2$ solution of known molarity is performed for each experiment.

One skilled in the art could easily modify the exemplified studies to test the activity of polynucleotides of the invention (e.g., gene therapy), agonists, and/or antagonists of polynucleotides or polypeptides of the invention.

Example 36

Biological Effects of Polypeptides of the Invention

Astrocyte and Neuronal Assays.

Recombinant polypeptides of the invention, expressed in Escherichia coli and purified as described above, can be tested for activity in promoting the survival, neurite outgrowth, or phenotypic differentiation of cortical neuronal cells and for inducing the proliferation of glial fibrillary acidic protein immunopositive cells, astrocytes. The selection of cortical cells for the bioassay is based on the prevalent expression of FGF-1 and FGF-2 in cortical structures and on the previously reported enhancement of cortical neuronal survival resulting from FGF-2 treatment. A thymidine incorporation assay, for example, can be used to elucidate a polypeptide of the invention's activity on these cells.

Moreover, previous reports describing the biological effects of FGF-2 (basic FGF) on cortical or hippocampal neurons in vitro have demonstrated increases in both neuron survival and neurite outgrowth (Walicke et al., "Fibroblast growth factor promotes survival of dissociated hippocampal neurons and enhances neurite extension." Proc. Natl. Acad. Sci. USA 83:3012–3016. (1986), assay herein incorporated by reference in its entirety). However, reports from experiments done on PC-12 cells suggest that these two responses are not necessarily synonymous and may depend on not only which FGF is being tested but also on which receptor(s) are expressed on the target cells. Using the primary cortical neuronal culture paradigm, the ability of a polypeptide of the invention to induce neurite outgrowth can be compared to the response achieved with FGF-2 using, for example, a thymidine incorporation assay.

Fibroblast and Endothelial Cell Assays

Human lung fibroblasts are obtained from Clonetics (San Diego, Calif.) and maintained in growth media from Clonetics. Dermal microvascular endothelial cells are obtained from Cell Applications (San Diego, Calif.). For proliferation assays, the human lung fibroblasts and dermal microvascular endothelial cells can be cultured at 5,000 cells/well in a 96-well plate for one day in growth medium. The cells are then incubated for one day in 0.1% BSA basal medium. After replacing the medium with fresh 0.1% BSA medium, the cells are incubated with the test proteins for 3 days. Alamar Blue (Alamar Biosciences, Sacramento, Calif.) is added to each well to a final concentration of 10%. The cells are incubated for 4 hr. Cell viability is measured by reading in a CytoFluor fluorescence reader. For the PGE2 assays, the human lung fibroblasts are cultured at 5,000 cells/well in a 96-well plate for one day. After a medium change to 0.1% BSA basal medium, the cells are incubated with FGF-2 or polypeptides of the invention with or without IL-1(for 24 hours. The supernatants are collected and assayed for PGE2 by EIA kit (Cayman, Ann Arbor, Mich.). For the IL-6 assays, the human lung fibroblasts are cultured at 5,000 cells/well in a 96-well plate for one day. After a medium change to 0.1% BSA basal medium, the cells are incubated with FGF-2 or with or without polypeptides of the invention IL-1(for 24 hours. The supernatants are collected and assayed for IL-6 by ELISA kit (Endogen, Cambridge, Mass.).

Human lung fibroblasts are cultured with FGF-2 or polypeptides of the invention for 3 days in basal medium before the addition of Alamar Blue to assess effects on growth of the fibroblasts. FGF-2 should show a stimulation at 10–2500 ng/ml which can be used to compare stimulation with polypeptides of the invention.

Parkinson Models.

The loss of motor function in Parkinson's disease is attributed to a deficiency of striatal dopamine resulting from the degeneration of the nigrostriatal dopaminergic projection neurons. An animal model for Parkinson's that has been extensively characterized involves the systemic administration of 1-methyl-4 phenyl 1,2,3,6-tetrahydropyridine (MPTP). In the CNS, MPTP is taken-up by astrocytes and catabolized by monoamine oxidase B to 1-methyl-4-phenyl pyridine (MPP+) and released. Subsequently, MPP+ is actively accumulated in dopaminergic neurons by the high-affinity reuptake transporter for dopamine. MPP+ is then concentrated in mitochondria by the electrochemical gradient and selectively inhibits nicotidamide adenine disphosphate: ubiquinone oxidoreductionase (complex I), thereby interfering with electron transport and eventually generating oxygen radicals.

It has been demonstrated in tissue culture paradigms that FGF-2 (basic FGF) has trophic activity towards nigral dopaminergic neurons (Ferrari et al., Dev. Biol. 1989). Recently, Dr. Unsicker's group has demonstrated that administering FGF-2 in gel foam implants in the striatum results in the near complete protection of nigral dopaminergic neurons from the toxicity associated with MPTP exposure (Otto and Unsicker, J. Neuroscience, 1990).

Based on the data with FGF-2, polypeptides of the invention can be evaluated to determine whether it has an action similar to that of FGF-2 in enhancing dopaminergic neuronal survival in vitro and it can also be tested in vivo for protection of dopaminergic neurons in the striatum from the damage associated with MPTP treatment. The potential effect of a polypeptide of the invention is first examined in vitro in a dopaminergic neuronal cell culture paradigm. The cultures are prepared by dissecting the midbrain floor plate from gestation day 14 Wistar rat embryos. The tissue is dissociated with trypsin and seeded at a density of 200,000 cells/cm2 on polyorthinine-laminin coated glass coverslips. The cells are maintained in Dulbecco's Modified Eagle's medium and F12 medium containing hormonal supplements (NI). The cultures are fixed with paraformaldehyde after 8 days in vitro and are processed for tyrosine hydroxylase, a specific marker for dopaminergic neurons, immunohistochemical staining. Dissociated cell cultures are prepared from embryonic rats. The culture medium is changed every third day and the factors are also added at that time.

Since the dopaminergic neurons are isolated from animals at gestation day 14, a developmental time which is past the stage when the dopaminergic precursor cells are proliferating, an increase in the number of tyrosine hydroxylase immunopositive neurons would represent an increase in the number of dopaminergic neurons surviving in vitro. Therefore, if a polypeptide of the invention acts to prolong the survival of dopaminergic neurons, it would suggest that the polypeptide may be involved in Parkinson's Disease.

One skilled in the art could easily modify the exemplified studies to test the activity of polynucleotides of the invention (e.g., gene therapy), agonists, and/or antagonists of polynucleotides or polypeptides of the invention.

Example 37

The Effect of Polypeptides of the Invention on the Growth of Vascular Endothelial Cells On day 1, human umbilical vein endothelial cells (HUVEC) are seeded at $2-5 \times 10^4$ cells/35 mm dish density in M199 medium containing 4% fetal bovine serum (FBS), 16 units/ml heparin, and 50 units/ml endothelial cell growth supplements (ECGS, Biotechnique, Inc.). On day 2, the medium is replaced with M199 containing 10% FBS, 8 units/ml heparin. A polypeptide having the amino acid sequence of SEQ ID NO:2, and positive controls, such as VEGF and basic FGF (bFGF) are added, at varying concentrations. On days 4 and 6, the medium is replaced. On day 8, cell number is determined with a Coulter Counter.

An increase in the number of HUVEC cells indicates that the polypeptide of the invention may proliferate vascular endothelial cells.

One skilled in the art could easily modify the exemplified studies to test the activity of polynucleotides of the invention (e.g., gene therapy), agonists, and/or antagonists of polynucleotides or polypeptides of the invention.

Example 38

Stimulatory Effect of Polypeptides of the Invention on the Proliferation of Vascular Endothelial Cells For evaluation of mitogenic activity of growth factors, the calorimetric MTS (3-(4,5-dimethylthiazol-2-yl)-5-(3-carboxymethoxyphenyl)-2-(4-sulfophenyl)2H-tetrazolium) assay with the electron coupling reagent PMS (phenazine methosulfate) was performed (CellTiter 96 AQ, Promega). Cells are seeded in a 96-well plate (5,000 cells/well) in 0.1 mL serum-supplemented medium and are allowed to attach overnight. After serum-starvation for 12 hours in 0.5% FBS, conditions (bFGF, VEGF165 or a polypeptide of the invention in 0.5% FBS) with or without Heparin (8 U/ml) are added to wells for 48 hours. 20 mg of MTS/PMS mixture (1:0.05) are added per well and allowed to incubate for 1 hour at 37° C. before measuring the absorbance at 490 nm in an ELISA plate reader. Background absorbance from control wells (some media, no cells) is subtracted, and seven wells are performed in parallel for each condition. See, Leak et al. In Vitro Cell. Dev. Biol. 30A:512–518 (1994).

One skilled in the art could easily modify the exemplified studies to test the activity of polynucleotides of the invention (e.g., gene therapy), agonists, and/or antagonists of polynucleotides or polypeptides of the invention.

Example 39

Inhibition of PDGF-induced Vascular Smooth Muscle Cell Proliferation Stimulatory Effect HAoSMC proliferation can be measured, for example, by BrdUrd incorporation. Briefly, subconfluent, quiescent cells grown on the 4-chamber slides are transfected with CRP or FITC-labeled AT2-3LP. Then, the cells are pulsed with 10% calf serum and 6 mg/ml BrdUrd. After 24 h, immunocytochemistry is performed by using BrdUrd Staining Kit (Zymed Laboratories). In brief, the cells are incubated with the biotinylated mouse anti-BrdUrd antibody at 4 degrees C. for 2 h after being exposed to denaturing solution and then incubated with the streptavidin-peroxidase and diaminobenzidine. After counterstaining with hematoxylin, the cells are mounted for microscopic examination, and the BrdUrd-positive cells are counted. The BrdUrd index is calculated as a percent of the BrdUrd-positive cells to the total cell number. In addition, the simultaneous detection of the BrdUrd staining (nucleus) and the FITC uptake (cytoplasm) is performed for individual cells by the concomitant use of bright field illumination and dark field-UV fluorescent illumination. See, Hayashida et al., J. Biol. Chem . . . 6:271 (36):21985–21992 (1996).

One skilled in the art could easily modify the exemplified studies to test the activity of polynucleotides of the invention (e.g., gene therapy), agonists, and/or antagonists of polynucleotides or polypeptides of the invention.

Example 40

Stimulation of Endothelial Migration

This example will be used to explore the possibility that a polypeptide of the invention may stimulate lymphatic endothelial cell migration.

Endothelial cell migration assays are performed using a 48 well microchemotaxis chamber (Neuroprobe Inc., Cabin John, M D; Falk, W., et al., J. Immunological Methods 1980;33 :239–247). Polyvinylpyrrolidone-free polycarbonate filters with a pore size of 8 um (Nucleopore Corp. Cambridge, Mass.) are coated with 0.1% gelatin for at least 6 hours at room temperature and dried under sterile air. Test substances are diluted to appropriate concentrations in M199 supplemented with 0.25% bovine serum albumin (BSA), and 25 ul of the final dilution is placed in the lower chamber of the modified Boyden apparatus. Subconfluent, early passage (2–6) HUVEC or BMEC cultures are washed and trypsinized for the minimum time required to achieve cell detachment. After placing the filter between lower and upper chamber, 2.5×105 cells suspended in 50 ul M199 containing 1% FBS are seeded in the upper compartment. The apparatus is then incubated for 5 hours at 37° C. in a humidified chamber with 5% CO2 to allow cell migration. After the incubation period, the filter is removed and the upper side of the filter with the non-migrated cells is scraped with a rubber policeman. The filters are fixed with methanol and stained with a Giemsa solution (Diff-Quick, Baxter, McGraw Park, Ill.). Migration is quantified by counting cells of three random high-power fields (40×) in each well, and all groups are performed in quadruplicate.

One skilled in the art could easily modify the exemplified studies to test the activity of polynucleotides of the invention (e.g., gene therapy), agonists, and/or antagonists of polynucleotides or polypeptides of the invention.

Example 41

Stimulation of Nitric Oxide Production by Endothelial Cells

Nitric oxide released by the vascular endothelium is believed to be a mediator of vascular endothelium relaxation. Thus, activity of a polypeptide of the invention can be assayed by determining nitric oxide production by endothelial cells in response to the polypeptide.

Nitric oxide is measured in 96-well plates of confluent microvascular endothelial cells after 24 hours starvation and a subsequent 4 hr exposure to various levels of a positive control (such as VEGF-1) and the polypeptide of the invention. Nitric oxide in the medium is determined by use of the Griess reagent to measure total nitrite after reduction of nitric oxide-derived nitrate by nitrate reductase. The effect of the polypeptide of the invention on nitric oxide release is examined on HUVEC.

Briefly, NO release from cultured HUVEC monolayer is measured with a NO-specific polarographic electrode connected to a NO meter (Iso-NO, World Precision Instruments Inc.) (1049). Calibration of the NO elements is performed according to the following equation:

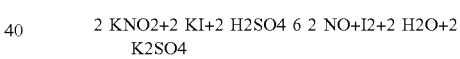

2 KNO2+2 KI+2 H2SO4 6 2 NO+I2+2 H2O+2 K2SO4

The standard calibration curve is obtained by adding graded concentrations of KNO2 (0, 5, 10, 25, 50, 100, 250, and 500 nmol/L) into the calibration solution containing KI and H2SO4. The specificity of the Iso-NO electrode to NO is previously determined by measurement of NO from authentic NO gas (1050). The culture medium is removed and HUVECs are washed twice with Dulbecco's phosphate buffered saline. The cells are then bathed in 5 ml of filtered Krebs-Henseleit solution in 6-well plates, and the cell plates are kept on a slide warmer (Lab Line Instruments Inc.) To maintain the temperature at 37° C. The NO sensor probe is inserted vertically into the wells, keeping the tip of the electrode 2 mm under the surface of the solution, before addition of the different conditions. S-nitroso acetyl penicillamin (SNAP) is used as a positive control. The amount of released NO is expressed as picomoles per 1×106 endothelial cells. All values reported are means of four to six measurements in each group (number of cell culture wells). See, Leak et al. Biochem. and Biophys. Res. Comm. 217: 96–105 (1995).

One skilled in the art could easily modify the exemplified studies to test the activity of polynucleotides of the invention (e.g., gene therapy), agonists, and/or antagonists of polynucleotides or polypeptides of the invention.

Example 42

Effect of Polypepides of the Invention on Cord Formation in Angiogenesis

Another step in angiogenesis is cord formation, marked by differentiation of endothelial cells. This bioassay measures the ability of microvascular endothelial cells to form capillary-like structures (hollow structures) when cultured in vitro.

CADMEC (microvascular endothelial cells) are purchased from Cell Applications, Inc. as proliferating (passage 2) cells and are cultured in Cell Applications' CADMEC Growth Medium and used at passage 5. For the in vitro angiogenesis assay, the wells of a 48-well cell culture plate are coated with Cell Applications' Attachment Factor Medium (200 ml/well) for 30 min. at 37° C. CADMEC are seeded onto the coated wells at 7,500 cells/well and cultured overnight in Growth Medium. The Growth Medium is then replaced with 300 mg Cell Applications' Chord Formation Medium containing control buffer or a polypeptide of the invention (0.1 to 100 ng/ml) and the cells are cultured for an additional 48 hr. The numbers and lengths of the capillary-like chords are quantitated through use of the Boeckeler VIA-170 video image analyzer. All assays are done in triplicate.

Commercial (R&D) VEGF (50 ng/ml) is used as a positive control. b-esteradiol (1 ng/ml) is used as a negative control. The appropriate buffer (without protein) is also utilized as a control.

One skilled in the art could easily modify the exemplified studies to test the activity of polynucleotides of the invention (e.g., gene therapy), agonists, and/or antagonists of polynucleotides or polypeptides of the invention.

Example 43

Angiogenic Effect on Chick Chorioallantoic Membrane

Chick chorioallantoic membrane (CAM) is a well-established system to examine angiogenesis. Blood vessel formation on CAM is easily visible and quantifiable. The ability of polypeptides of the invention to stimulate angiogenesis in CAM can be examined.

Fertilized eggs of the White Leghorn chick (Gallus gallus) and the Japanese qual (Coturnix coturnix) are incubated at 37.8° C. and 80% humidity. Differentiated CAM of 16-day-old chick and 13-day-old qual embryos is studied with the following methods.

On Day 4 of development, a window is made into the egg shell of chick eggs. The embryos are checked for normal development and the eggs sealed with cellotape. They are further incubated until Day 13. Thermanox coverslips (Nunc, Naperville, Ill.) are cut into disks of about 5 mm in diameter. Sterile and salt-free growth factors are dissolved in distilled water and about 3.3 mg/ 5 ml are pipetted on the disks. After air-drying, the inverted disks are applied on CAM. After 3 days, the specimens are fixed in 3% glutaraldehyde and 2% formaldehyde and rinsed in 0.12 M sodium cacodylate buffer. They are photographed with a stereo microscope [Wild M8] and embedded for semi- and ultrathin sectioning as described above. Controls are performed with carrier disks alone.

One skilled in the art could easily modify the exemplified studies to test the activity of polynucleotides of the invention (e.g., gene therapy), agonists, and/or antagonists of polynucleotides or polypeptides of the invention.

Example 44

Angiogenesis Assay Using a Matrigel Implant in Mouse

In vivo angiogenesis assay of a polypeptide of the invention measures the ability of an existing capillary network to form new vessels in an implanted capsule of murine extracellular matrix material (Matrigel). The protein is mixed with the liquid Matrigel at 4 degree C. and the mixture is then injected subcutaneously in mice where it solidifies. After 7 days, the solid "plug" of Matrigel is removed and examined for the presence of new blood vessels. Matrigel is purchased from Becton Dickinson Labware/Collaborative Biomedical Products.

When thawed at 4 degree C. the Matrigel material is a liquid. The Matrigel is mixed with a polypeptide of the invention at 150 ng/ml at 4 degrees C. and drawn into cold 3 ml syringes. Female C57B1/6 mice approximately 8 weeks old are injected with the mixture of Matrigel and experimental protein at 2 sites at the midventral aspect of the abdomen (0.5 ml/site). After 7 days, the mice are sacrificed by cervical dislocation, the Matrigel plugs are removed and cleaned (i.e., all clinging membranes and fibrous tissue is removed). Replicate whole plugs are fixed in neutral buffered 10% formaldehyde, embedded in paraffin and used to produce sections for histological examination after staining with Masson's Trichrome. Cross sections from 3 different regions of each plug are processed. Selected sections are stained for the presence of vWF. The positive control for this assay is bovine basic FGF (150 ng/ml). Matrigel alone is used to determine basal levels of angiogenesis.

One skilled in the art could easily modify the exemplified studies to test the activity of polynucleotides of the invention (e.g., gene therapy), agonists, and/or antagonists of polynucleotides or polypeptides of the invention.

Example 45

Rescue of Ischemia in Rabbit Lower Limb Model

To study the in vivo effects of polynucleotides and polypeptides of the invention on ischemia, a rabbit hindlimb ischemia model is created by surgical removal of one femoral arteries as described previously (Takeshita et al., Am J. Pathol 147:1649–1660 (1995)). The excision of the femoral artery results in retrograde propagation of thrombus and occlusion of the external iliac artery. Consequently, blood flow to the ischemic limb is dependent upon collateral vessels originating from the internal iliac artery (Takeshitaet al. Am J. Pathol 147:1649–1660 (1995)). An interval of 10 days is allowed for post-operative recovery of rabbits and development of endogenous collateral vessels. At 10 day post-operatively (day 0), after performing a baseline angiogram, the internal iliac artery of the ischemic limb is transfected with 500 mg naked expression plasmid containing a polynucleotide of the invention by arterial gene transfer technology using a hydrogel-coated balloon catheter as described (Riessen et al. Hum Gene Ther. 4:749–758 (1993); Leclerc et al. J. Clin. Invest. 90: 936–944 (1992)). When a polypeptide of the invention is used in the treatment, a single bolus of 500 mg polypeptide of the invention or control is delivered into the internal iliac artery of the ischemic limb over a period of 1 min. through an infusion catheter. On day 30, various parameters are measured in these rabbits: (a) BP ratio—The blood pressure ratio of systolic pressure of the ischemic limb to that of normal limb; (b) Blood Flow and Flow Reserve—Resting FL: the blood flow during undilated condition and Max FL: the blood flow during fully dilated condition (also an indirect measure of the blood vessel amount) and Flow Reserve is reflected by the ratio of max FL: resting FL; (c) Angiographic Score - This is measured by the angiogram of collateral vessels. A score is determined by the percentage of circles in an overlaying grid that with crossing opacified arteries divided by the total number m the rabbit thigh; (d) Capillary density—The number of collateral capillaries determined in light microscopic sections taken from hindlimbs.

One skilled in the art could easily modify the exemplified studies to test the activity of polynucleotides of the invention (e.g., gene therapy), agonists, and/or antagonists of polynucleotides or polypeptides of the invention.

Example 46

Effect of Polypeptides of the Invention on Vasodilation

Since dilation of vascular endothelium is important in reducing blood pressure, the ability of polypeptides of the invention to affect the blood pressure in spontaneously hypertensive rats (SHR) is examined. Increasing doses (0, 10, 30, 100, 300, and 900 mg/kg) of the polypeptides of the invention are administered to 13–14 week old spontaneously hypertensive rats (SHR). Data are expressed as the mean +/−SEM. Statistical analysis are performed with a paired t-test and statistical significance is defined as $p<0.05$ vs. the response to buffer alone.

One skilled in the art could easily modify the exemplified studies to test the activity of polynucleotides of the invention (e.g., gene therapy), agonists, and/or antagonists of polynucleotides or polypeptides of the invention.

Example 47

Rat Ischemic Skin Flap Model

The evaluation parameters include skin blood flow, skin temperature, and factor VIII immunohistochemistry or endothelial alkaline phosphatase reaction. Expression of polypeptides of the invention, during the skin ischemia, is studied using in situ hybridization.

The study in this model is divided into three parts as follows:
 a) Ischemic skin
 b) Ischemic skin wounds
 c) Normal wounds The experimental protocol includes:
 a) Raising a 3×4 cm, single pedicle full-thickness random skin flap (myocutaneous flap over the lower back of the animal).
 b) An excisional wounding (4–6 mm in diameter) in the ischemic skin (skin-flap).
 c) Topical treatment with a polypeptide of the invention of the excisional wounds (day 0, 1, 2, 3, 4 post-wounding) at the following various dosage ranges: 1 mg to 100 mg.
 d) Harvesting the wound tissues at day 3, 5, 7, 10, 14 and 21 post-wounding for histological, immunohistochemical, and in situ studies.

One skilled in the art could easily modify the exemplified studies to test the activity of polynucleotides of the invention (e.g., gene therapy), agonists, and/or antagonists of polynucleotides or polypeptides of the invention.

Example 48

Peripheral Arterial Disease Model

Angiogenic therapy using a polypeptide of the invention is a novel therapeutic strategy to obtain restoration of blood flow around the ischemia in case of peripheral arterial diseases. The experimental protocol includes:
 a) One side of the femoral artery is ligated to create ischemic muscle of the hindlimb, the other side of hindlimb serves as a control.
 b) a polypeptide of the invention, in a dosage range of 20 mg–500 mg, is delivered intravenously and/or intramuscularly 3 times (perhaps more) per week for 2–3 weeks.
 c) The ischemic muscle tissue is collected after ligation of the femoral artery at 1, 2, and 3 weeks for the analysis of expression of a polypeptide of the invention and histology. Biopsy is also performed on the other side of normal muscle of the contralateral hindlimb.

One skilled in the art could easily modify the exemplified studies to test the activity of polynucleotides of the invention (e.g., gene therapy), agonists, and/or antagonists of polynucleotides or polypeptides of the invention.

Example 49

Ischemic Myocardial Disease Model

A polypeptide of the invention is evaluated as a potent mitogen capable of stimulating the development of collateral vessels, and restructuring new vessels after coronary artery occlusion. Alteration of expression of the polypeptide is investigated in situ. The experimental protocol includes:
 a) The heart is exposed through a left-side thoracotomy in the rat. Immediately, the left coronary artery is occluded with a thin suture (6-0) and the thorax is closed.
 b) a polypeptide of the invention, in a dosage range of 20 mg–500 mg, is delivered intravenously and/or intramuscularly 3 times (perhaps more) per week for 2–4 weeks.
 c) Thirty days after the surgery, the heart is removed and cross-sectioned for morphometric and in situ analyzes.

One skilled in the art could easily modify the exemplified studies to test the activity of polynucleotides of the invention (e.g., gene therapy), agonists, and/or antagonists of polynucleotides or polypeptides of the invention.

Example 50

Rat Corneal Wound Healing Model

This animal model shows the effect of a polypeptide of the invention on neovascularization. The experimental protocol includes:
 a) Making a 1–1.5 mm long incision from the center of cornea into the stromal layer.
 b) Inserting a spatula below the lip of the incision facing the outer corner of the eye.
 c) Making a pocket (its base is 1–1.5 mm form the edge of the eye).
 d) Positioning a pellet, containing 50 ng–5 ug of a polypeptide of the invention, within the pocket.

e) Treatment with a polypeptide of the invention can also be applied topically to the corneal wounds in a dosage range of 20 mg–500 mg (daily treatment for five days).

One skilled in the art could easily modify the exemplified studies to test the activity of polynucleotides of the invention (e.g., gene therapy), agonists, and/or antagonists of polynucleotides or polypeptides of the invention.

Example 51

Diabetic Mouse and Glucocorticoid-Impaired Wound Healing Models

A. Diabetic db+/db+ Mouse Model.

To demonstrate that a polypeptide of the invention accelerates the healing process, the genetically diabetic mouse model of wound healing is used. The full thickness wound healing model in the db+/db+mouse is a well characterized, clinically relevant and reproducible model of impaired wound healing. Healing of the diabetic wound is dependent on formation of granulation tissue and re-epithelialization rather than contraction (Gartner, M. H. et al., J. Surg. Res. 52:389 (1992); Greenhalgh, D. G. et al., Am. J. Pathol. 136:1235 (1990)).

The diabetic animals have many of the characteristic features observed in Type II diabetes mellitus. Homozygous (db+/db+) mice are obese in comparison to their normal heterozygous (db+/+m) littermates. Mutant diabetic (db+/db+) mice have a single autosomal recessive mutation on chromosome 4 (db+) (Coleman et al. Proc. Natl. Acad. Sci. USA 77:283–293 (1982)). Animals show polyphagia, polydipsia and polyuria. Mutant diabetic mice (db+/db+) have elevated blood glucose, increased or normal insulin levels, and suppressed cell-mediated immunity (Mandel et al., J. Immunol. 120:1375 (1978); Debray-Sachs, M. et al., Clin. Exp. Immunol. 51(1):1–7 (1983); Leiter et al., Am. J. of Pathol. 114:46–55 (1985)). Peripheral neuropathy, myocardial complications, and microvascular lesions, basement membrane thickening and glomerular filtration abnormalities have been described in these animals (Norido, F. et al., Exp. Neurol. 83(2):221–232 (1984); Robertson et al., Diabetes 29(1):60–67 (1980); Giacomelli et al., Lab Invest. 40(4):460–473 (1979); Coleman, D. L., Diabetes 31 (Suppl): 1–6 (1982)). These homozygous diabetic mice develop hyperglycemia that is resistant to insulin analogous to human type II diabetes (Mandel et al., J. Immunol. 120:1375–1377 (1978)).

The characteristics observed in these animals suggests that healing in this model may be similar to the healing observed in human diabetes (Greenhalgh, et al., Am. J. of Pathol. 136:1235–1246 (1990)).

Genetically diabetic female C57BL/KsJ (db+/db+) mice and their non-diabetic (db+/+m) heterozygous littermates are used in this study (Jackson Laboratories). The animals are purchased at 6 weeks of age and are 8 weeks old at the beginning of the study. Animals are individually housed and received food and water ad libitum. All manipulations are performed using aseptic techniques. The experiments are conducted according to the rules and guidelines of Bristol-Myers Squibb Company's Institutional Animal Care and Use Committee and the Guidelines for the Care and Use of Laboratory Animals.

Wounding protocol is performed according to previously reported methods (Tsuboi, R. and Rifkin, D. B., J. Exp. Med. 172:245–251 (1990)). Briefly, on the day of wounding, animals are anesthetized with an intraperitoneal injection of Avertin (0.01 mg/mL), 2,2,2-tribromoethanol and 2-methyl-2-butanol dissolved in deionized water. The dorsal region of the animal is shaved and the skin washed with 70% ethanol solution and iodine. The surgical area is dried with sterile gauze prior to wounding. An 8 mm full-thickness wound is then created using a Keyes tissue punch. Immediately following wounding, the surrounding skin is gently stretched to eliminate wound expansion. The wounds are left open for the duration of the experiment. Application of the treatment is given topically for 5 consecutive days commencing on the day of wounding. Prior to treatment, wounds are gently cleansed with sterile saline and gauze sponges.

Wounds are visually examined and photographed at a fixed distance at the day of surgery and at two day intervals thereafter. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

A polypeptide of the invention is administered using at a range different doses, from 4 mg to 500 mg per wound per day for 8 days in vehicle. Vehicle control groups received 50 mL of vehicle solution.

Animals are euthanized on day 8 with an intraperitoneal injection of sodium pentobarbital (300 mg/kg). The wounds and surrounding skin are then harvested for histology and immunohistochemistry. Tissue specimens are placed in 10% neutral buffered formalin in tissue cassettes between biopsy sponges for further processing.

Three groups of 10 animals each (5 diabetic and 5 non-diabetic controls) are evaluated: 1) Vehicle placebo control, 2) untreated group, and 3) treated group.

Wound closure is analyzed by measuring the area in the vertical and horizontal axis and obtaining the total square area of the wound. Contraction is then estimated by establishing the differences between the initial wound area (day 0) and that of post treatment (day 8). The wound area on day 1 is 64 mm2, the corresponding size of the dermal punch. Calculations are made using the following formula:

[Open area on day 8]−[Open area on day 1]/[Open area on day 1]

Specimens are fixed in 10% buffered formalin and paraffin embedded blocks are sectioned perpendicular to the wound surface (5 mm) and cut using a Reichert-Jung microtome. Routine hematoxylin-eosin (H&E) staining is performed on cross-sections of bisected wounds. Histologic examination of the wounds are used to assess whether the healing process and the morphologic appearance of the repaired skin is altered by treatment with a polypeptide of the invention. This assessment included verification of the presence of cell accumulation, inflammatory cells, capillaries, fibroblasts, re-epithelialization and epidermal maturity (Greenhalgh, D. G. et al., Am. J. Pathol. 136:1235 (1990)). A calibrated lens micrometer is used by a blinded observer.

Tissue sections are also stained immunohistochemically with a polyclonal rabbit anti-human keratin antibody using ABC Elite detection system. Human skin is used as a positive tissue control while non-immune IgG is used as a negative control. Keratinocyte growth is determined by evaluating the extent of reepithelialization of the wound using a calibrated lens micrometer.

Proliferating cell nuclear antigen/cyclin (PCNA) in skin specimens is demonstrated by using anti-PCNA antibody (1:50) with an ABC Elite detection system. Human colon cancer can serve as a positive tissue control and human brain tissue can be used as a negative tissue control. Each specimen includes a section with omission of the primary antibody and substitution with non-immune mouse IgG. Ranking of these sections is based on the extent of proliferation on a scale of 0–8, the lower side of the scale reflecting slight proliferation to the higher side reflecting intense proliferation.

Experimental data are analyzed using an unpaired t test. A p value of <0.05 is considered significant.

B. Steroid Impaired Rat Model

The inhibition of wound healing by steroids has been well documented in various in vitro and in vivo systems (Wahl, Glucocorticoids and Wound healing. In: Anti-Inflammatory Steroid Action: Basic and Clinical Aspects. 280–302 (1989); Wahl et al., J. Immunol. 115: 476–481 (1975); Werb et al., J. Exp. Med. 147:1684–1694 (1978)). Glucocorticoids retard wound healing by inhibiting angiogenesis, decreasing vascular permeability (Ebert et al., An. Intern. Med. 37:701–705 (1952)), fibroblast proliferation, and collagen synthesis (Beck et al., Growth Factors. 5: 295–304 (1991); Haynes et al., J. Clin. Invest. 61: 703–797 (1978)) and producing a transient reduction of circulating monocytes (Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989)). The systemic administration of steroids to impaired wound healing is a well establish phenomenon in rats (Beck et al., Growth Factors. 5: 295–304 (1991); Haynes et al., J. Clin. Invest. 61: 703–797 (1978); Wahl, "Glucocorticoids and wound healing", In: Antiinflammatory Steroid Action: Basic and Clinical Aspects, Academic Press, New York, pp. 280–302 (1989); Pierce et al., Proc. Natl. Acad. Sci. USA 86: 2229–2233 (1989)).

To demonstrate that a polypeptide of the invention can accelerate the healing process, the effects of multiple topical applications of the polypeptide on full thickness excisional skin wounds in rats in which healing has been impaired by the systemic administration of methylprednisolone is assessed.

Young adult male Sprague Dawley rats weighing 250–300 g (Charles River Laboratories) are used in this example. The animals are purchased at 8 weeks of age and are 9 weeks old at the beginning of the study. The healing response of rats is impaired by the systemic administration of methylprednisolone (17 mg/kg/rat intramuscularly) at the time of wounding. Animals are individually housed and received food and water ad libitum. All manipulations are performed using aseptic techniques. This study would be conducted according to the rules and guidelines of Bristol-Myers Squibb Corporations Guidelines for the Care and Use of Laboratory Animals.

The wounding protocol is followed according to section A, above. On the day of wounding, animals are anesthetized with an intramuscular injection of ketamine (50 mg/kg) and xylazine (5 mg/kg). The dorsal region of the animal is shaved and the skin washed with 70% ethanol and iodine solutions. The surgical area is dried with sterile gauze prior to wounding. An 8 mm full-thickness wound is created using a Keyes tissue punch. The wounds are left open for the duration of the experiment. Applications of the testing materials are given topically once a day for 7 consecutive days commencing on the day of wounding and subsequent to methylprednisolone administration. Prior to treatment, wounds are gently cleansed with sterile saline and gauze sponges.

Wounds are visually examined and photographed at a fixed distance at the day of wounding and at the end of treatment. Wound closure is determined by daily measurement on days 1–5 and on day 8. Wounds are measured horizontally and vertically using a calibrated Jameson caliper. Wounds are considered healed if granulation tissue is no longer visible and the wound is covered by a continuous epithelium.

The polypeptide of the invention is administered using at a range different doses, from 4 mg to 500 mg per wound per day for 8 days in vehicle. Vehicle control groups received 50 µL of vehicle solution.

Animals are euthanized on day 8 with an intraperitoneal injection of sodium pentobarbital (300 mg/kg). The wounds and surrounding skin are then harvested for histology. Tissue specimens are placed in 10% neutral buffered formalin in tissue cassettes between biopsy sponges for further processing.

Four groups of 10 animals each (5 with methylprednisolone and 5 without glucocorticoid) are evaluated: 1) Untreated group 2) Vehicle placebo control 3) treated groups.

Wound closure is analyzed by measuring the area in the vertical and horizontal axis and obtaining the total area of the wound. Closure is then estimated by establishing the differences between the initial wound area (day 0) and that of post treatment (day 8). The wound area on day 1 is 64 mm2, the corresponding size of the dermal punch. Calculations are made using the following formula:

[Open area on day 8]–[Open area on day 1]/[Open area on day 1]

Specimens are fixed in 10% buffered formalin and paraffin embedded blocks are sectioned perpendicular to the wound surface (5 mm) and cut using an Olympus microtome. Routine hematoxylin-eosin (H&E) staining is performed on cross-sections of bisected wounds. Histologic examination of the wounds allows assessment of whether the healing process and the morphologic appearance of the repaired skin is improved by treatment with a polypeptide of the invention. A calibrated lens micrometer is used by a blinded observer to determine the distance of the wound gap.

Experimental data are analyzed using an unpaired t test. A p value of <0.05 is considered significant.

One skilled in the art could easily modify the exemplified studies to test the activity of polynucleotides of the invention (e.g., gene therapy), agonists, and/or antagonists of polynucleotides or polypeptides of the invention.

Example 52

Lymphedema Animal Model

The purpose of this experimental approach is to create an appropriate and consistent lymphedema model for testing the therapeutic effects of a polypeptide of the invention in lymphangiogenesis and re-establishment of the lymphatic circulatory system in the rat hind limb. Effectiveness is measured by swelling volume of the affected limb, quantification of the amount of lymphatic vasculature, total blood plasma protein, and histopathology. Acute lymphedema is observed for 7–10 days. Perhaps more importantly, the chronic progress of the edema is followed for up to 3–4 weeks.

Prior to beginning surgery, blood sample is drawn for protein concentration analysis. Male rats weighing approximately ~350 g are dosed with Pentobarbital. Subsequently, the right legs are shaved from knee to hip. The shaved area is swabbed with gauze soaked in 70% EtOH. Blood is drawn for serum total protein testing. Circumference and volumetric measurements are made prior to injecting dye into paws after marking 2 measurement levels (0.5 cm above heel, at mid-pt of dorsal paw). The intradermal dorsum of both right and left paws are injected with 0.05 ml of 1% Evan's Blue. Circumference and volumetric measurements are then made following injection of dye into paws.

Using the knee joint as a landmark, a mid-leg inguinal incision is made circumferentially allowing the femoral vessels to be located. Forceps and hemostats are used to dissect and separate the skin flaps. After locating the femoral vessels, the lymphatic vessel that runs along side and underneath the vessel(s) is located. The main lymphatic vessels in this area are then electrically coagulated suture ligated.

Using a microscope, muscles in back of the leg (near the semitendinosis and adductors) are bluntly dissected. The popliteal lymph node is then located. The 2 proximal and 2 distal lymphatic vessels and distal blood supply of the popliteal node are then and ligated by suturing. The popliteal lymph node, and any accompanying adipose tissue, is then removed by cutting connective tissues.

Care is taken to control any mild bleeding resulting from this procedure. After lymphatics are occluded, the skin flaps are sealed by using liquid skin (Vetbond) (AJ Buck). The separated skin edges are sealed to the underlying muscle tissue while leaving a gap of ~0.5 cm around the leg. Skin also may be anchored by suturing to underlying muscle when necessary.

To avoid infection, animals are housed individually with mesh (no bedding). Recovering animals are checked daily through the optimal edematous peak, which typically occurred by day 5–7. The plateau edematous peak are then observed. To evaluate the intensity of the lymphedema, the circumference and volumes of 2 designated places on each paw before operation and daily for 7 days are measured. The effect plasma proteins on lymphedema is determined and whether protein analysis is a useful testing perimeter is also investigated. The weights of both control and edematous limbs are evaluated at 2 places. Analysis is performed in a blind manner.

Circumference Measurements: Under brief gas anesthetic to prevent limb movement, a cloth tape is used to measure limb circumference. Measurements are done at the ankle bone and dorsal paw by 2 different people then those 2 readings are averaged. Readings are taken from both control and edematous limbs.

Volumetric Measurements: On the day of surgery, animals are anesthetized with Pentobarbital and are tested prior to surgery. For daily volumetrics animals are under brief halothane anesthetic (rapid immobilization and quick recovery), both legs are shaved and equally marked using waterproof marker on legs. Legs are first dipped in water, then dipped into instrument to each marked level then measured by Buxco edema software(Chen/Victor). Data is recorded by one person, while the other is dipping the limb to marked area.

Blood-plasma protein measurements: Blood is drawn, spun, and serum separated prior to surgery and then at conclusion for total protein and Ca2+ comparison.

Limb Weight Comparison: After drawing blood, the animal is prepared for tissue collection. The limbs are amputated using a quillitine, then both experimental and control legs are cut at the ligature and weighed. A second weighing is done as the tibio-cacaneal joint is disarticulated and the foot is weighed.

Histological Preparations: The transverse muscle located behind the knee (popliteal) area is dissected and arranged in a metal mold, filled with freezeGel, dipped into cold methylbutane, placed into labeled sample bags at −80EC until sectioning. Upon sectioning, the muscle is observed under fluorescent microscopy for lymphatics.

One skilled in the art could easily modify the exemplified studies to test the activity of polynucleotides of the invention (e.g., gene therapy), agonists, and/or antagonists of polynucleotides or polypeptides of the invention.

Example 53

Suppression of TNF Alpha-induced Adhesion Molecule Expression by a Polypeptide of the Invention The recruitment of lymphocytes to areas of inflammation and angiogenesis involves specific receptor-ligand interactions between cell surface adhesion molecules (CAMs) on lymphocytes and the vascular endothelium. The adhesion process, in both normal and pathological settings, follows a multi-step cascade that involves intercellular adhesion molecule-1 (ICAM-1), vascular cell adhesion molecule-1 (VCAM-1), and endothelial leukocyte adhesion molecule-1 (E-selectin) expression on endothelial cells (EC). The expression of these molecules and others on the vascular endothelium determines the efficiency with which leukocytes may adhere to the local vasculature and extravasate into the local tissue during the development of an inflammatory response. The local concentration of cytokines and growth factor participate in the modulation of the expression of these CAMs.

Tumor necrosis factor alpha (TNF-a), a potent proinflammatory cytokine, is a stimulator of all three CAMs on endothelial cells and may be involved in a wide variety of inflammatory responses, often resulting in a pathological outcome.

The potential of a polypeptide of the invention to mediate a suppression of TNF-a induced CAM expression can be examined. A modified ELISA assay which uses ECs as a solid phase absorbent is employed to measure the amount of CAM expression on TNF-a treated ECs when co-stimulated with a member of the FGF family of proteins.

To perform the experiment, human umbilical vein endothelial cell (HUVEC) cultures are obtained from pooled cord harvests and maintained in growth medium (EGM-2; Clonetics, San Diego, Calif.) supplemented with 10% FCS and 1% penicillin/streptomycin in a 37 degree C. humidified incubator containing 5% CO2. HUVECs are seeded in 96-well plates at concentrations of 1×104 cells/well in EGM medium at 37 degree C. for 18–24 hrs or until confluent. The monolayers are subsequently washed 3 times with a serum-free solution of RPMI-1640 supplemented with 100 U/ml penicillin and 100 mg/ml streptomycin, and treated with a given cytokine and/or growth factor(s) for 24 h at 37 degree C. Following incubation, the cells are then evaluated for CAM expression.

Human Umbilical Vein Endothelial cells (HUVECs) are grown in a standard 96 well plate to confluence. Growth medium is removed from the cells and replaced with 90 ul of 199 Medium (10% FBS). Samples for testing and positive or negative controls are added to the plate in triplicate (in 10 ul volumes). Plates are incubated at 37 degree C. for either 5 h (selectin and integrin expression) or 24 h (integrin expression only). Plates are aspirated to remove medium and 100 µl of 0.1% paraformaldehyde-PBS(with Ca++ and Mg++) is added to each well. Plates are held at 4° C. for 30 min.

Fixative is then removed from the wells and wells are washed 1× with PBS(+Ca,Mg)+0.5% BSA and drained. Do not allow the wells to dry. Add 10 µl of diluted primary antibody to the test and control wells. Anti-ICAM-1-Biotin, Anti-VCAM-1-Biotin and Anti-E-selectin-Biotin are used at a concentration of 10 µg/ml (1:10 dilution of 0.1 mg/ml stock antibody). Cells are incubated at 37° C. for 30 min. in a humidified environment. Wells are washed X3 with PBS (+Ca,Mg)+0.5% BSA.

Then add 20 µl of diluted ExtrAvidin-Alkaline Phosphatase (1:5,000 dilution) to each well and incubated at 37° C. for 30 min. Wells are washed X3 with PBS(+Ca,Mg)+ 0.5% BSA. 1 tablet of p-Nitrophenol Phosphate pNPP is dissolved in 5 ml of glycine buffer (pH 10.4). 100 µl of pNPP substrate in glycine buffer is added to each test well. Standard wells in triplicate are prepared from the working dilution of the ExtrAvidin-Alkaline Phosphatase in glycine buffer: 1:5,000 (100) >10–0.5>10–1>10–1.5. 5 µl of each dilution is added to triplicate wells and the resulting AP content in each well is 5.50 ng, 1.74 ng, 0.55 ng, 0.18 ng. 100 µl of pNNP reagent must then be added to each of the standard wells. The plate must be incubated at 37° C. for 4 h. A volume of 50 µl of 3M NaOH is added to all wells. The results are quantified on a plate reader at 405 nm. The background subtraction option is used on blank wells filled with glycine buffer only. The template is set up to indicate the concentration of AP-conjugate in each standard well [5.50 ng; 1.74 ng; 0.55 ng; 0.18 ng]. Results are indicated as amount of bound AP-conjugate in each sample.

One skilled in the art could easily modify the exemplified studies to test the activity of polynucleotides of the invention (e.g., gene therapy), agonists, and/or antagonists of polynucleotides or polypeptides of the invention.

Example 54

Method of Chromosomal mapping of Serpin LS-1 in 14q32.1 Among a Cluster of Proteases in a Region Prone to Rearrangement causing Leukemias A chromosomal localization of the Serpin LS-1 gene was performed by using the nucleic acid sequence of the invention (SEQ ID NO:1) in a database search of the recently completed draft of human genome sequence. Using the Basic Local Alignment Search Tool 2 (BLAST2), the first 200 bp of Serpin LS-1 cDNA sequence (SEQ ID NO:1) showed a perfect alignment of nucleotides 12 to 104 and 103 to 200 with Homo sapiens chromosome 14 Bac clones R-262P9 (gi|AL132990) and R-34911 (gi|AL132708), suggesting the presence of two introns. Despite the absence of map data for Bac R-262P9, Bac R-34911 was already registered in the clone database (NCBI), and mapped by the Genoscope center (France), to 14q32.1. AL132708 is part of NCBI contig NT_019573 that already contains 6 serpins (A1-A6) and a protease Z inhibitor. This chromosomal region is commonly involved in chromosomal rearrangements, inversion, or translocations associated with the incidence of T-cell malignancy (T-cell neoplasms, leukemias; Saitou et al,. Identification of the TCL6 genes within the breakpoint cluster region on chromosome 14q32 in T-cell leukemia. Oncogene 19: 2796–2802, 2000.), or B-cell leukemias (i.e. one of the most frequent hematologic malignancies, follicular lymphoma is associated with a reciprocal translocation t(14;18)(q32;q21) and can result in deregulated expression of a chromosome 18 gene, Bcl2, which interferes with normal apoptosis of B lymphocytes; Ngan, B.-Y. et al. Expression in non-Hodgkin's lymphoma of the BCL-2 protein associated with the t(14;18) chromosomal translocation. New Eng. J. Med. 318:1638–1644, 1988). The oncogene activated by these different rearrangements is not always the same, and is dependent upon where the chromosomal breakpoints occur. Several candidate oncogenes responsible for malignant transformation have already been identified in chromosome 14q32 (i.e. TCL1A (T-cell leukemia/lymphoma 1a), TCL1b, TCL6, TRIP11(Thyroid Hormone Receptor Interactor 11)).

Based on its expression profile and genetic map, Serpin LS-1 could be a novel specific biomarker that could pinpoint a subgroup of patients with chronic lymphocytic leukemias (with a distinct prognostic).

It will be clear that the invention may be practiced otherwise than as particularly described in the foregoing description and examples. Numerous modifications and variations of the present invention are possible in light of the above teachings and, therefore, are within the scope of the appended claims.

The entire disclosure of each document cited (including patents, patent applications, journal articles, abstracts, laboratory manuals, books, or other disclosures) in the Background of the Invention, Detailed Description, and Examples is hereby incorporated herein by reference. Further, the hard copy of the sequence listing submitted herewith and the corresponding computer readable form are both incorporated herein by reference in their entireties.

Table III

| | Atom | Atom Type | Residue | | # | X | Y | Z | B | Occ |
|---|---|---|---|---|---|---|---|---|---|---|
| ATOM | 1 | N | MET | A | 1 | 15.398 | 13.285 | -2.442 | 1.00 | 51.19 |
| ATOM | 5 | CA | MET | A | 1 | 14.789 | 12.112 | -3.100 | 1.00 | 50.26 |
| ATOM | 6 | CB | MET | A | 1 | 13.488 | 12.499 | -3.787 | 1.00 | 48.58 |
| ATOM | 7 | CG | MET | A | 1 | 12.513 | 13.187 | -2.840 | 1.00 | 48.82 |
| ATOM | 8 | SD | MET | A | 1 | 10.963 | 13.735 | -3.590 | 1.00 | 48.56 |
| ATOM | 9 | CE | MET | A | 1 | 10.258 | 14.614 | -2.177 | 1.00 | 48.52 |
| ATOM | 10 | C | MET | A | 1 | 15.740 | 11.549 | -4.150 | 1.00 | 49.68 |
| ATOM | 11 | O | MET | A | 1 | 16.289 | 12.312 | -4.954 | 1.00 | 49.45 |
| ATOM | 12 | N | GLN | A | 2 | 15.955 | 10.244 | -4.112 | 1.00 | 49.48 |
| ATOM | 14 | CA | GLN | A | 2 | 16.809 | 9.589 | -5.115 | 1.00 | 48.97 |
| ATOM | 15 | CB | GLN | A | 2 | 18.283 | 9.898 | -4.815 | 1.00 | 48.89 |
| ATOM | 16 | CG | GLN | A | 2 | 19.293 | 9.196 | -5.738 | 1.00 | 48.48 |
| ATOM | 17 | CD | GLN | A | 2 | 19.133 | 9.555 | -7.225 | 1.00 | 47.98 |
| ATOM | 18 | OE1 | GLN | A | 2 | 18.028 | 9.792 | -7.725 | 1.00 | 47.57 |
| ATOM | 19 | NE2 | GLN | A | 2 | 20.227 | 9.435 | -7.952 | 1.00 | 48.08 |
| ATOM | 22 | C | GLN | A | 2 | 16.567 | 8.076 | -5.192 | 1.00 | 48.31 |
| ATOM | 23 | O | GLN | A | 2 | 16.528 | 7.372 | -4.174 | 1.00 | 48.16 |
| ATOM | 24 | N | GLY | A | 3 | 16.442 | 7.592 | -6.417 | 1.00 | 48.01 |
| ATOM | 26 | CA | GLY | A | 3 | 16.245 | 6.173 | -6.683 | 1.00 | 47.41 |
| ATOM | 27 | C | GLY | A | 3 | 17.482 | 5.483 | -7.254 | 1.00 | 46.87 |
| ATOM | 28 | O | GLY | A | 3 | 18.162 | 5.975 | -8.166 | 1.00 | 46.65 |
| ATOM | 29 | N | GLN | A | 4 | 17.791 | 4.349 | -6.657 | 1.00 | 46.75 |
| ATOM | 31 | CA | GLN | A | 4 | 18.825 | 3.454 | -7.179 | 1.00 | 46.31 |
| ATOM | 32 | CB | GLN | A | 4 | 19.438 | 2.741 | -5.984 | 1.00 | 46.49 |
| ATOM | 33 | CG | GLN | A | 4 | 20.569 | 1.810 | -6.385 | 1.00 | 47.05 |
| ATOM | 34 | CD | GLN | A | 4 | 20.529 | 0.605 | -5.459 | 1.00 | 47.56 |
| ATOM | 35 | OE1 | GLN | A | 4 | 21.435 | 0.388 | -4.647 | 1.00 | 48.03 |
| ATOM | 36 | NE2 | GLN | A | 4 | 19.465 | -0.166 | -5.603 | 1.00 | 47.50 |
| ATOM | 39 | C | GLN | A | 4 | 18.192 | 2.419 | -8.114 | 1.00 | 45.37 |
| ATOM | 40 | O | GLN | A | 4 | 17.816 | 1.319 | -7.683 | 1.00 | 45.03 |
| ATOM | 41 | N | GLY | A | 5 | 18.153 | 2.742 | -9.395 | 1.00 | 45.01 |
| ATOM | 43 | CA | GLY | A | 5 | 17.485 | 1.863 | -10.363 | 1.00 | 44.13 |
| ATOM | 44 | C | GLY | A | 5 | 17.931 | 2.078 | -11.807 | 1.00 | 43.80 |
| ATOM | 45 | O | GLY | A | 5 | 17.182 | 2.627 | -12.630 | 1.00 | 43.85 |
| ATOM | 46 | N | ARG | A | 6 | 18.987 | 1.366 | -12.159 | 1.00 | 44.78 |
| ATOM | 48 | CA | ARG | A | 6 | 19.560 | 1.419 | -13.511 | 1.00 | 44.72 |
| ATOM | 49 | CB | ARG | A | 6 | 20.840 | 0.577 | -13.455 | 1.00 | 45.73 |
| ATOM | 50 | CG | ARG | A | 6 | 21.653 | 0.544 | -14.748 | 1.00 | 46.28 |
| ATOM | 51 | CD | ARG | A | 6 | 21.214 | -0.551 | -15.717 | 1.00 | 46.92 |
| ATOM | 52 | NE | ARG | A | 6 | 21.341 | -1.878 | -15.096 | 1.00 | 47.35 |
| ATOM | 53 | CZ | ARG | A | 6 | 21.802 | -2.945 | -15.751 | 1.00 | 47.43 |
| ATOM | 54 | NH1 | ARG | A | 6 | 22.185 | -2.829 | -17.025 | 1.00 | 47.60 |
| ATOM | 55 | NH2 | ARG | A | 6 | 21.883 | -4.125 | - | 1.00 | 47.39 |

| | | | | | | | 15.132 | | |
|---|---|---|---|---|---|---|---|---|---|
| ATOM | 56 | C | ARG | A | 6 | 18.570 | 0.859 | -14.532 | 1.00 | 43.76 |
| ATOM | 57 | O | ARG | A | 6 | 18.222 | 1.569 | -15.490 | 1.00 | 43.44 |
| ATOM | 58 | N | ARG | A | 7 | 17.854 | -0.164 | -14.079 | 1.00 | 43.34 |
| ATOM | 60 | CA | ARG | A | 7 | 16.899 | -0.917 | -14.899 | 1.00 | 42.46 |
| ATOM | 61 | CB | ARG | A | 7 | 16.641 | -2.243 | -14.194 | 1.00 | 43.40 |
| ATOM | 62 | CG | ARG | A | 7 | 17.924 | -2.971 | -13.819 | 1.00 | 43.50 |
| ATOM | 63 | CD | ARG | A | 7 | 17.598 | -4.239 | -13.038 | 1.00 | 43.72 |
| ATOM | 64 | NE | ARG | A | 7 | 18.816 | -4.938 | -12.600 | 1.00 | 43.80 |
| ATOM | 65 | CZ | ARG | A | 7 | 19.090 | -5.179 | -11.316 | 1.00 | 43.65 |
| ATOM | 66 | NH1 | ARG | A | 7 | 18.302 | -4.680 | -10.360 | 1.00 | 43.77 |
| ATOM | 67 | NH2 | ARG | A | 7 | 20.196 | -5.849 | -10.985 | 1.00 | 43.45 |
| ATOM | 68 | C | ARG | A | 7 | 15.539 | -0.239 | -15.071 | 1.00 | 41.88 |
| ATOM | 69 | O | ARG | A | 7 | 14.728 | -0.728 | -15.865 | 1.00 | 42.14 |
| ATOM | 70 | N | ARG | A | 8 | 15.292 | 0.874 | -14.395 | 1.00 | 41.14 |
| ATOM | 72 | CA | ARG | A | 8 | 13.995 | 1.533 | -14.557 | 1.00 | 40.60 |
| ATOM | 73 | CB | ARG | A | 8 | 13.541 | 2.104 | -13.214 | 1.00 | 40.61 |
| ATOM | 74 | CG | ARG | A | 8 | 14.151 | 3.454 | -12.848 | 1.00 | 40.15 |
| ATOM | 75 | CD | ARG | A | 8 | 13.879 | 3.761 | -11.379 | 1.00 | 39.95 |
| ATOM | 76 | NE | ARG | A | 8 | 13.957 | 5.197 | -11.056 | 1.00 | 40.56 |
| ATOM | 77 | CZ | ARG | A | 8 | 15.044 | 5.843 | -10.627 | 1.00 | 41.08 |
| ATOM | 78 | NH1 | ARG | A | 8 | 14.906 | 6.999 | -9.975 | 1.00 | 41.39 |
| ATOM | 79 | NH2 | ARG | A | 8 | 16.212 | 5.210 | -10.572 | 1.00 | 41.34 |
| ATOM | 80 | C | ARG | A | 8 | 14.071 | 2.601 | -15.647 | 1.00 | 39.99 |
| ATOM | 81 | O | ARG | A | 8 | 13.045 | 3.140 | -16.077 | 1.00 | 39.81 |
| ATOM | 82 | N | GLY | A | 9 | 15.272 | 2.814 | -16.163 | 1.00 | 39.73 |
| ATOM | 84 | CA | GLY | A | 9 | 15.471 | 3.775 | -17.243 | 1.00 | 39.19 |
| ATOM | 85 | C | GLY | A | 9 | 16.382 | 4.900 | -16.789 | 1.00 | 38.79 |
| ATOM | 86 | O | GLY | A | 9 | 16.113 | 6.082 | -17.041 | 1.00 | 38.36 |
| ATOM | 87 | N | THR | A | 10 | 17.431 | 4.530 | -16.078 | 1.00 | 39.03 |
| ATOM | 89 | CA | THR | A | 10 | 18.377 | 5.532 | - | 1.00 | 38.73 |

| | | | | | | | | | |
|---|---|---|---|---|---|---|---|---|---|
| | | | | | | | 15.590 | | |
| ATOM | 90 | CB | THR | A | 10 | 18.584 | 5.253 | -14.107 | 1.00 | 39.28 |
| ATOM | 91 | OG1 | THR | A | 10 | 17.312 | 5.377 | -13.488 | 1.00 | 39.82 |
| ATOM | 92 | CG2 | THR | A | 10 | 19.536 | 6.238 | -13.440 | 1.00 | 39.49 |
| ATOM | 93 | C | THR | A | 10 | 19.699 | 5.477 | -16.353 | 1.00 | 38.15 |
| ATOM | 94 | O | THR | A | 10 | 20.441 | 6.463 | -16.406 | 1.00 | 38.33 |
| ATOM | 95 | N | CYS | A | 11 | 19.936 | 4.357 | -17.016 | 1.00 | 37.53 |
| ATOM | 97 | CA | CYS | A | 11 | 21.187 | 4.185 | -17.763 | 1.00 | 36.98 |
| ATOM | 98 | CB | CYS | A | 11 | 21.704 | 2.781 | -17.468 | 1.00 | 37.21 |
| ATOM | 99 | SG | CYS | A | 11 | 23.381 | 2.392 | -18.024 | 1.00 | 37.18 |
| ATOM | 100 | C | CYS | A | 11 | 21.015 | 4.373 | -19.274 | 1.00 | 36.77 |
| ATOM | 101 | O | CYS | A | 11 | 21.989 | 4.257 | -20.025 | 1.00 | 36.52 |
| ATOM | 102 | N | LYS | A | 12 | 19.804 | 4.660 | -19.722 | 1.00 | 37.20 |
| ATOM | 104 | CA | LYS | A | 12 | 19.569 | 4.726 | -21.169 | 1.00 | 37.21 |
| ATOM | 105 | CB | LYS | A | 12 | 18.372 | 3.848 | -21.522 | 1.00 | 37.42 |
| ATOM | 106 | CG | LYS | A | 12 | 17.097 | 4.333 | -20.845 | 1.00 | 37.48 |
| ATOM | 107 | CD | LYS | A | 12 | 15.883 | 3.547 | -21.326 | 1.00 | 38.13 |
| ATOM | 108 | CE | LYS | A | 12 | 14.599 | 4.079 | -20.702 | 1.00 | 38.28 |
| ATOM | 109 | NZ | LYS | A | 12 | 13.424 | 3.339 | -21.186 | 1.00 | 38.36 |
| ATOM | 110 | C | LYS | A | 12 | 19.323 | 6.148 | -21.670 | 1.00 | 36.94 |
| ATOM | 111 | O | LYS | A | 12 | 18.893 | 7.025 | -20.918 | 1.00 | 36.54 |
| ATOM | 112 | N | ASP | A | 13 | 19.566 | 6.316 | -22.963 | 1.00 | 37.27 |
| ATOM | 114 | CA | ASP | A | 13 | 19.263 | 7.542 | -23.737 | 1.00 | 37.15 |
| ATOM | 115 | CB | ASP | A | 13 | 17.796 | 7.492 | -24.158 | 1.00 | 37.99 |
| ATOM | 116 | CG | ASP | A | 13 | 17.537 | 6.285 | -25.053 | 1.00 | 38.69 |
| ATOM | 117 | OD1 | ASP | A | 13 | 17.088 | 5.272 | -24.533 | 1.00 | 39.33 |
| ATOM | 118 | OD2 | ASP | A | 13 | 17.786 | 6.402 | -26.245 | 1.00 | 38.66 |
| ATOM | 119 | C | ASP | A | 13 | 19.536 | 8.871 | -23.028 | 1.00 | 36.89 |
| ATOM | 120 | O | ASP | A | 13 | 20.506 | 8.992 | -22.272 | 1.00 | 37.25 |
| ATOM | 121 | N | ILE | A | 14 | 18.749 | 9.863 | -23.436 | 1.00 | 36.29 |

| | | | | | | | | | |
|---|---|---|---|---|---|---|---|---|---|
| ATOM | 123 | CA | ILE | A | 14 | 18.784 | 11.283 | -23.004 | 1.00 | 36.08 |
| ATOM | 124 | CB | ILE | A | 14 | 17.594 | 11.554 | -22.087 | 1.00 | 36.68 |
| ATOM | 125 | CG2 | ILE | A | 14 | 17.672 | 12.935 | -21.442 | 1.00 | 36.42 |
| ATOM | 126 | CG1 | ILE | A | 14 | 16.300 | 11.424 | -22.883 | 1.00 | 37.41 |
| ATOM | 127 | CD1 | ILE | A | 14 | 15.092 | 11.878 | -22.071 | 1.00 | 38.01 |
| ATOM | 128 | C | ILE | A | 14 | 20.089 | 11.781 | -22.384 | 1.00 | 35.41 |
| ATOM | 129 | O | ILE | A | 14 | 20.477 | 11.412 | -21.270 | 1.00 | 35.11 |
| ATOM | 130 | N | PHE | A | 15 | 20.678 | 12.723 | -23.108 | 1.00 | 35.24 |
| ATOM | 132 | CA | PHE | A | 15 | 21.982 | 13.323 | -22.792 | 1.00 | 34.77 |
| ATOM | 133 | CB | PHE | A | 15 | 22.080 | 14.603 | -23.618 | 1.00 | 35.12 |
| ATOM | 134 | CG | PHE | A | 15 | 23.432 | 15.309 | -23.595 | 1.00 | 35.04 |
| ATOM | 135 | CD1 | PHE | A | 15 | 24.604 | 14.583 | -23.764 | 1.00 | 35.07 |
| ATOM | 136 | CE1 | PHE | A | 15 | 25.832 | 15.232 | -23.748 | 1.00 | 35.04 |
| ATOM | 137 | CZ | PHE | A | 15 | 25.887 | 16.608 | -23.570 | 1.00 | 35.02 |
| ATOM | 138 | CE2 | PHE | A | 15 | 24.715 | 17.336 | -23.410 | 1.00 | 34.98 |
| ATOM | 139 | CD2 | PHE | A | 15 | 23.488 | 16.686 | -23.426 | 1.00 | 34.98 |
| ATOM | 140 | C | PHE | A | 15 | 22.145 | 13.648 | -21.308 | 1.00 | 34.03 |
| ATOM | 141 | O | PHE | A | 15 | 21.313 | 14.340 | -20.704 | 1.00 | 33.59 |
| ATOM | 142 | N | CYS | A | 16 | 23.133 | 12.977 | -20.730 | 1.00 | 33.95 |
| ATOM | 144 | CA | CYS | A | 16 | 23.581 | 13.118 | -19.330 | 1.00 | 33.34 |
| ATOM | 145 | CB | CYS | A | 16 | 23.688 | 14.595 | -18.951 | 1.00 | 33.26 |
| ATOM | 146 | SG | CYS | A | 16 | 24.914 | 15.560 | -19.865 | 1.00 | 33.25 |
| ATOM | 147 | C | CYS | A | 16 | 22.733 | 12.386 | -18.278 | 1.00 | 32.74 |
| ATOM | 148 | O | CYS | A | 16 | 23.314 | 11.677 | -17.447 | 1.00 | 32.44 |
| ATOM | 149 | N | SER | A | 17 | 21.415 | 12.532 | -18.300 | 1.00 | 32.60 |
| ATOM | 151 | CA | SER | A | 17 | 20.591 | 11.978 | -17.211 | 1.00 | 32.03 |
| ATOM | 152 | CB | SER | A | 17 | 20.891 | 12.787 | -15.950 | 1.00 | 32.30 |
| ATOM | 153 | OG | SER | A | 17 | 21.022 | 14.156 | -16.322 | 1.00 | 32.53 |
| ATOM | 154 | C | SER | A | 17 | 19.084 | 11.984 | -17.487 | 1.00 | 32.04 |
| ATOM | 155 | O | SER | A | 17 | 18.593 | 11.378 | - | 1.00 | 32.34 |

|  |  |  |  |  |  |  |  | 18.447 |  |  |
|---|---|---|---|---|---|---|---|---|---|---|
| ATOM | 156 | N | LYS | A | 18 | 18.369 | 12.606 | -16.558 | 1.00 | 33.24 |
| ATOM | 158 | CA | LYS | A | 18 | 16.905 | 12.756 | -16.602 | 1.00 | 32.73 |
| ATOM | 159 | CB | LYS | A | 18 | 16.501 | 13.572 | -17.824 | 1.00 | 33.18 |
| ATOM | 160 | CG | LYS | A | 18 | 17.080 | 14.978 | -17.749 | 1.00 | 33.24 |
| ATOM | 161 | CD | LYS | A | 18 | 16.657 | 15.820 | -18.945 | 1.00 | 33.87 |
| ATOM | 162 | CE | LYS | A | 18 | 17.230 | 17.230 | -18.853 | 1.00 | 34.03 |
| ATOM | 163 | NZ | LYS | A | 18 | 16.800 | 18.049 | -19.998 | 1.00 | 34.59 |
| ATOM | 164 | C | LYS | A | 18 | 16.170 | 11.422 | -16.584 | 1.00 | 32.46 |
| ATOM | 165 | O | LYS | A | 18 | 16.295 | 10.659 | -15.619 | 1.00 | 32.34 |
| ATOM | 166 | N | MET | A | 19 | 15.468 | 11.137 | -17.670 | 1.00 | 32.43 |
| ATOM | 168 | CA | MET | A | 19 | 14.544 | 9.991 | -17.789 | 1.00 | 32.25 |
| ATOM | 169 | CB | MET | A | 19 | 15.269 | 8.820 | -18.433 | 1.00 | 33.06 |
| ATOM | 170 | CG | MET | A | 19 | 15.850 | 9.218 | -19.778 | 1.00 | 33.76 |
| ATOM | 171 | SD | MET | A | 19 | 15.922 | 7.897 | -21.003 | 1.00 | 34.22 |
| ATOM | 172 | CE | MET | A | 19 | 14.148 | 7.643 | -21.234 | 1.00 | 34.73 |
| ATOM | 173 | C | MET | A | 19 | 13.934 | 9.527 | -16.469 | 1.00 | 32.00 |
| ATOM | 174 | O | MET | A | 19 | 13.467 | 10.345 | -15.661 | 1.00 | 32.06 |
| ATOM | 175 | N | ALA | A | 20 | 14.101 | 8.249 | -16.170 | 1.00 | 31.80 |
| ATOM | 177 | CA | ALA | A | 20 | 13.431 | 7.674 | -14.999 | 1.00 | 31.62 |
| ATOM | 178 | CB | ALA | A | 20 | 13.386 | 6.164 | -15.140 | 1.00 | 31.45 |
| ATOM | 179 | C | ALA | A | 20 | 14.059 | 8.048 | -13.658 | 1.00 | 30.71 |
| ATOM | 180 | O | ALA | A | 20 | 13.333 | 8.045 | -12.657 | 1.00 | 30.35 |
| ATOM | 181 | N | SER | A | 21 | 15.235 | 8.662 | -13.683 | 1.00 | 30.45 |
| ATOM | 183 | CA | SER | A | 21 | 15.855 | 9.132 | -12.442 | 1.00 | 29.65 |
| ATOM | 184 | CB | SER | A | 21 | 17.371 | 9.206 | -12.577 | 1.00 | 29.99 |
| ATOM | 185 | OG | SER | A | 21 | 17.709 | 10.386 | -13.291 | 1.00 | 29.93 |
| ATOM | 186 | C | SER | A | 21 | 15.307 | 10.501 | -12.037 | 1.00 | 29.12 |
| ATOM | 187 | O | SER | A | 21 | 15.765 | 11.067 | -11.043 | 1.00 | 28.77 |
| ATOM | 188 | N | TYR | A | 22 | 14.426 | 11.070 | -12.845 | 1.00 | 29.15 |

| ATOM | 190 | CA | TYR | A | 22 | 13.652 | 12.235 | -12.410 | 1.00 | 28.75 |
|------|-----|----|-----|---|----|---------|---------|---------|------|-------|
| ATOM | 191 | CB | TYR | A | 22 | 13.788 | 13.365 | -13.429 | 1.00 | 28.70 |
| ATOM | 192 | CG | TYR | A | 22 | 15.018 | 14.267 | -13.299 | 1.00 | 28.83 |
| ATOM | 193 | CD1 | TYR | A | 22 | 16.292 | 13.734 | -13.147 | 1.00 | 29.48 |
| ATOM | 194 | CE1 | TYR | A | 22 | 17.391 | 14.574 | -13.034 | 1.00 | 29.69 |
| ATOM | 195 | CZ | TYR | A | 22 | 17.213 | 15.950 | -13.077 | 1.00 | 29.26 |
| ATOM | 196 | OH | TYR | A | 22 | 18.302 | 16.786 | -12.968 | 1.00 | 29.57 |
| ATOM | 197 | CE2 | TYR | A | 22 | 15.943 | 16.489 | -13.231 | 1.00 | 28.61 |
| ATOM | 198 | CD2 | TYR | A | 22 | 14.845 | 15.645 | -13.344 | 1.00 | 28.39 |
| ATOM | 199 | C | TYR | A | 22 | 12.181 | 11.853 | -12.280 | 1.00 | 28.19 |
| ATOM | 200 | O | TYR | A | 22 | 11.509 | 12.233 | -11.307 | 1.00 | 27.76 |
| ATOM | 201 | N | LEU | A | 23 | 11.777 | 10.910 | -13.120 | 1.00 | 28.27 |
| ATOM | 203 | CA | LEU | A | 23 | 10.363 | 10.512 | -13.228 | 1.00 | 27.85 |
| ATOM | 204 | CB | LEU | A | 23 | 10.153 | 9.796 | -14.558 | 1.00 | 28.59 |
| ATOM | 205 | CG | LEU | A | 23 | 10.320 | 10.731 | -15.750 | 1.00 | 28.61 |
| ATOM | 206 | CD1 | LEU | A | 23 | 10.253 | 9.952 | -17.061 | 1.00 | 29.14 |
| ATOM | 207 | CD2 | LEU | A | 23 | 9.276 | 11.843 | -15.732 | 1.00 | 28.27 |
| ATOM | 208 | C | LEU | A | 23 | 9.855 | 9.602 | -12.111 | 1.00 | 27.38 |
| ATOM | 209 | O | LEU | A | 23 | 8.636 | 9.458 | -11.966 | 1.00 | 26.72 |
| ATOM | 210 | N | TYR | A | 24 | 10.740 | 9.103 | -11.263 | 1.00 | 27.81 |
| ATOM | 212 | CA | TYR | A | 24 | 10.310 | 8.300 | -10.111 | 1.00 | 27.64 |
| ATOM | 213 | CB | TYR | A | 24 | 11.392 | 7.268 | -9.828 | 1.00 | 28.21 |
| ATOM | 214 | CG | TYR | A | 24 | 10.974 | 6.095 | -8.948 | 1.00 | 28.08 |
| ATOM | 215 | CD1 | TYR | A | 24 | 11.905 | 5.494 | -8.113 | 1.00 | 28.38 |
| ATOM | 216 | CE1 | TYR | A | 24 | 11.531 | 4.421 | -7.316 | 1.00 | 28.36 |
| ATOM | 217 | CZ | TYR | A | 24 | 10.227 | 3.951 | -7.356 | 1.00 | 28.03 |
| ATOM | 218 | OH | TYR | A | 24 | 9.845 | 2.938 | -6.504 | 1.00 | 28.10 |
| ATOM | 219 | CE2 | TYR | A | 24 | 9.296 | 4.543 | -8.197 | 1.00 | 27.70 |
| ATOM | 220 | CD2 | TYR | A | 24 | 9.672 | 5.614 | -8.996 | 1.00 | 27.73 |
| ATOM | 221 | C | TYR | A | 24 | 10.041 | 9.162 | -8.865 | 1.00 | 27.22 |
| ATOM | 222 | O | TYR | A | 24 | 9.989 | 8.641 | -7.745 | 1.00 | 27.04 |
| ATOM | 223 | N | GLY | A | 25 | 9.915 | 10.467 | -9.049 | 1.00 | 27.18 |
| ATOM | 225 | CA | GLY | A | 25 | 9.673 | 11.366 | -7.922 | 1.00 | 26.90 |
| ATOM | 226 | C | GLY | A | 25 | 11.001 | 11.758 | -7.294 | 1.00 | 26.20 |
| ATOM | 227 | O | GLY | A | 25 | 11.223 | 11.567 | -6.092 | 1.00 | 25.81 |
| ATOM | 228 | N | VAL | A | 26 | 11.902 | 12.243 | -8.129 | 1.00 | 26.15 |
| ATOM | 230 | CA | VAL | A | 26 | 13.225 | 12.643 | -7.641 | 1.00 | 25.61 |

| ATOM | 231 | CB | VAL | A | 26 | 14.291 | 11.883 | -8.423 | 1.00 | 26.41 |
| ATOM | 232 | CG1 | VAL | A | 26 | 15.697 | 12.336 | -8.049 | 1.00 | 26.69 |
| ATOM | 233 | CG2 | VAL | A | 26 | 14.147 | 10.379 | -8.231 | 1.00 | 26.42 |
| ATOM | 234 | C | VAL | A | 26 | 13.416 | 14.148 | -7.797 | 1.00 | 25.10 |
| ATOM | 235 | O | VAL | A | 26 | 13.750 | 14.631 | -8.886 | 1.00 | 24.61 |
| ATOM | 236 | N | LEU | A | 27 | 13.141 | 14.875 | -6.724 | 1.00 | 25.30 |
| ATOM | 238 | CA | LEU | A | 27 | 13.296 | 16.339 | -6.721 | 1.00 | 24.97 |
| ATOM | 239 | CB | LEU | A | 27 | 12.039 | 17.034 | -7.237 | 1.00 | 25.66 |
| ATOM | 240 | CG | LEU | A | 27 | 11.990 | 17.123 | -8.758 | 1.00 | 26.01 |
| ATOM | 241 | CD1 | LEU | A | 27 | 10.728 | 17.838 | -9.219 | 1.00 | 26.79 |
| ATOM | 242 | CD2 | LEU | A | 27 | 13.229 | 17.824 | -9.307 | 1.00 | 25.84 |
| ATOM | 243 | C | LEU | A | 27 | 13.601 | 16.894 | -5.334 | 1.00 | 24.45 |
| ATOM | 244 | O | LEU | A | 27 | 13.017 | 16.487 | -4.323 | 1.00 | 24.15 |
| ATOM | 245 | N | PHE | A | 28 | 14.463 | 17.895 | -5.323 | 1.00 | 24.45 |
| ATOM | 247 | CA | PHE | A | 28 | 14.796 | 18.618 | -4.091 | 1.00 | 24.08 |
| ATOM | 248 | CB | PHE | A | 28 | 16.252 | 19.078 | -4.203 | 1.00 | 24.22 |
| ATOM | 249 | CG | PHE | A | 28 | 16.754 | 20.007 | -3.096 | 1.00 | 24.07 |
| ATOM | 250 | CD1 | PHE | A | 28 | 16.812 | 19.571 | -1.779 | 1.00 | 24.31 |
| ATOM | 251 | CE1 | PHE | A | 28 | 17.271 | 20.426 | -0.786 | 1.00 | 24.27 |
| ATOM | 252 | CZ | PHE | A | 28 | 17.677 | 21.714 | -1.110 | 1.00 | 24.01 |
| ATOM | 253 | CE2 | PHE | A | 28 | 17.630 | 22.147 | -2.427 | 1.00 | 23.74 |
| ATOM | 254 | CD2 | PHE | A | 28 | 17.172 | 21.292 | -3.420 | 1.00 | 23.76 |
| ATOM | 255 | C | PHE | A | 28 | 13.853 | 19.809 | -3.923 | 1.00 | 23.38 |
| ATOM | 256 | O | PHE | A | 28 | 14.109 | 20.890 | -4.466 | 1.00 | 22.93 |
| ATOM | 257 | N | ALA | A | 29 | 12.739 | 19.577 | -3.244 | 1.00 | 23.41 |
| ATOM | 259 | CA | ALA | A | 29 | 11.760 | 20.650 | -3.022 | 1.00 | 22.89 |
| ATOM | 260 | CB | ALA | A | 29 | 11.077 | 20.995 | -4.343 | 1.00 | 23.75 |
| ATOM | 261 | C | ALA | A | 29 | 10.686 | 20.270 | -2.009 | 1.00 | 22.80 |
| ATOM | 262 | O | ALA | A | 29 | 10.338 | 19.095 | -1.852 | 1.00 | 22.68 |
| ATOM | 263 | N | VAL | A | 30 | 10.163 | 21.304 | -1.364 | 1.00 | 23.63 |
| ATOM | 265 | CA | VAL | A | 30 | 9.004 | 21.219 | -0.450 | 1.00 | 23.70 |
| ATOM | 266 | CB | VAL | A | 30 | 7.806 | 20.619 | -1.189 | 1.00 | 23.97 |
| ATOM | 267 | CG1 | VAL | A | 30 | 6.649 | 20.312 | -0.241 | 1.00 | 24.62 |
| ATOM | 268 | CG2 | VAL | A | 30 | 7.343 | 21.542 | -2.313 | 1.00 | 23.77 |
| ATOM | 269 | C | VAL | A | 30 | 9.279 | 20.458 | 0.849 | 1.00 | 23.16 |
| ATOM | 270 | O | VAL | A | 30 | 9.463 | 19.235 | 0.863 | 1.00 | 23.04 |
| ATOM | 271 | N | GLY | A | 31 | 9.271 | 21.215 | 1.936 | 1.00 | 22.80 |
| ATOM | 273 | CA | GLY | A | 31 | 9.406 | 20.648 | 3.280 | 1.00 | 22.28 |
| ATOM | 274 | C | GLY | A | 31 | 8.442 | 21.328 | 4.252 | 1.00 | 21.88 |
| ATOM | 275 | O | GLY | A | 31 | 7.225 | 21.116 | 4.214 | 1.00 | 21.64 |
| ATOM | 276 | N | LEU | A | 32 | 9.007 | 22.129 | 5.138 | 1.00 | 21.78 |
| ATOM | 278 | CA | LEU | A | 32 | 8.207 | 22.877 | 6.117 | 1.00 | 21.43 |
| ATOM | 279 | CB | LEU | A | 32 | 8.544 | 22.349 | 7.515 | 1.00 | 22.42 |
| ATOM | 280 | CG | LEU | A | 32 | 7.599 | 22.865 | 8.597 | 1.00 | 22.76 |
| ATOM | 281 | CD1 | LEU | A | 32 | 6.170 | 22.410 | 8.334 | 1.00 | 23.25 |
| ATOM | 282 | CD2 | LEU | A | 32 | 8.060 | 22.407 | 9.976 | 1.00 | 22.89 |
| ATOM | 283 | C | LEU | A | 32 | 8.547 | 24.365 | 6.014 | 1.00 | 20.99 |
| ATOM | 284 | O | LEU | A | 32 | 7.801 | 25.152 | 5.414 | 1.00 | 20.51 |
| ATOM | 285 | N | CYS | A | 33 | 9.712 | 24.716 | 6.533 | 1.00 | 21.11 |
| ATOM | 287 | CA | CYS | A | 33 | 10.181 | 26.103 | 6.497 | 1.00 | 20.83 |
| ATOM | 288 | CB | CYS | A | 33 | 10.731 | 26.453 | 7.873 | 1.00 | 21.69 |
| ATOM | 289 | SG | CYS | A | 33 | 9.540 | 26.401 | 9.225 | 1.00 | 21.95 |
| ATOM | 290 | C | CYS | A | 33 | 11.280 | 26.263 | 5.454 | 1.00 | 20.22 |
| ATOM | 291 | O | CYS | A | 33 | 12.394 | 25.764 | 5.641 | 1.00 | 20.04 |
| ATOM | 292 | N | ALA | A | 34 | 10.950 | 26.901 | 4.340 | 1.00 | 20.02 |
| ATOM | 294 | CA | ALA | A | 34 | 11.963 | 27.127 | 3.294 | 1.00 | 19.55 |
| ATOM | 295 | CB | ALA | A | 34 | 12.020 | 25.927 | 2.347 | 1.00 | 20.28 |
| ATOM | 296 | C | ALA | A | 34 | 11.870 | 28.478 | 2.542 | 1.00 | 19.00 |

| ATOM | 297 | O | ALA | A | 34 | 12.598 | 29.398 | 2.938 | 1.00 | 18.64 |
|------|-----|-----|-----|---|----|--------|--------|--------|------|-------|
| ATOM | 298 | N | PRO | A | 35 | 10.921 | 28.691 | 1.630 | 1.00 | 19.10 |
| ATOM | 299 | CA | PRO | A | 35 | 11.203 | 29.563 | 0.471 | 1.00 | 18.67 |
| ATOM | 300 | CB | PRO | A | 35 | 9.981 | 29.495 | -0.396 | 1.00 | 18.52 |
| ATOM | 301 | CG | PRO | A | 35 | 8.995 | 28.499 | 0.185 | 1.00 | 18.81 |
| ATOM | 302 | CD | PRO | A | 35 | 9.668 | 27.947 | 1.430 | 1.00 | 19.17 |
| ATOM | 303 | C | PRO | A | 35 | 11.525 | 31.010 | 0.840 | 1.00 | 18.54 |
| ATOM | 304 | O | PRO | A | 35 | 12.696 | 31.356 | 1.047 | 1.00 | 18.21 |
| ATOM | 305 | N | ILE | A | 36 | 10.488 | 31.759 | 1.181 | 1.00 | 19.59 |
| ATOM | 307 | CA | ILE | A | 36 | 10.641 | 33.187 | 1.498 | 1.00 | 19.45 |
| ATOM | 308 | CB | ILE | A | 36 | 9.262 | 33.831 | 1.382 | 1.00 | 19.67 |
| ATOM | 309 | CG2 | ILE | A | 36 | 9.274 | 35.299 | 1.805 | 1.00 | 19.81 |
| ATOM | 310 | CG1 | ILE | A | 36 | 8.739 | 33.712 | -0.043 | 1.00 | 20.01 |
| ATOM | 311 | CD1 | ILE | A | 36 | 9.622 | 34.488 | -1.016 | 1.00 | 20.78 |
| ATOM | 312 | C | ILE | A | 36 | 11.232 | 33.429 | 2.891 | 1.00 | 19.16 |
| ATOM | 313 | O | ILE | A | 36 | 11.830 | 34.483 | 3.116 | 1.00 | 19.14 |
| ATOM | 314 | N | TYR | A | 37 | 11.370 | 32.359 | 3.656 | 1.00 | 19.07 |
| ATOM | 316 | CA | TYR | A | 37 | 11.889 | 32.423 | 5.020 | 1.00 | 18.90 |
| ATOM | 317 | CB | TYR | A | 37 | 11.235 | 31.245 | 5.735 | 1.00 | 19.62 |
| ATOM | 318 | CG | TYR | A | 37 | 11.389 | 31.176 | 7.249 | 1.00 | 20.13 |
| ATOM | 319 | CD1 | TYR | A | 37 | 11.392 | 32.330 | 8.019 | 1.00 | 20.53 |
| ATOM | 320 | CE1 | TYR | A | 37 | 11.519 | 32.240 | 9.398 | 1.00 | 21.08 |
| ATOM | 321 | CZ | TYR | A | 37 | 11.632 | 30.996 | 10.000 | 1.00 | 21.23 |
| ATOM | 322 | OH | TYR | A | 37 | 11.783 | 30.899 | 11.364 | 1.00 | 21.89 |
| ATOM | 323 | CE2 | TYR | A | 37 | 11.615 | 29.843 | 9.233 | 1.00 | 20.85 |
| ATOM | 324 | CD2 | TYR | A | 37 | 11.488 | 29.934 | 7.857 | 1.00 | 20.30 |
| ATOM | 325 | C | TYR | A | 37 | 13.418 | 32.291 | 5.031 | 1.00 | 18.56 |
| ATOM | 326 | O | TYR | A | 37 | 14.058 | 32.505 | 6.068 | 1.00 | 18.70 |
| ATOM | 327 | N | CYS | A | 38 | 13.973 | 31.887 | 3.897 | 1.00 | 18.26 |
| ATOM | 329 | CA | CYS | A | 38 | 15.424 | 31.862 | 3.711 | 1.00 | 18.03 |
| ATOM | 330 | CB | CYS | A | 38 | 15.805 | 30.492 | 3.156 | 1.00 | 18.35 |
| ATOM | 331 | SG | CYS | A | 38 | 17.572 | 30.172 | 2.943 | 1.00 | 19.04 |
| ATOM | 332 | C | CYS | A | 38 | 15.860 | 32.949 | 2.731 | 1.00 | 17.59 |
| ATOM | 333 | O | CYS | A | 38 | 17.037 | 33.330 | 2.693 | 1.00 | 17.59 |
| ATOM | 334 | N | VAL | A | 39 | 14.908 | 33.454 | 1.960 | 1.00 | 17.35 |
| ATOM | 336 | CA | VAL | A | 39 | 15.210 | 34.551 | 1.035 | 1.00 | 17.03 |
| ATOM | 337 | CB | VAL | A | 39 | 14.194 | 34.530 | -0.105 | 1.00 | 17.39 |
| ATOM | 338 | CG1 | VAL | A | 39 | 14.333 | 35.745 | -1.018 | 1.00 | 17.82 |
| ATOM | 339 | CG2 | VAL | A | 39 | 14.314 | 33.244 | -0.913 | 1.00 | 17.41 |
| ATOM | 340 | C | VAL | A | 39 | 15.149 | 35.880 | 1.781 | 1.00 | 16.57 |
| ATOM | 341 | O | VAL | A | 39 | 15.960 | 36.786 | 1.549 | 1.00 | 16.13 |
| ATOM | 342 | N | SER | A | 40 | 14.231 | 35.949 | 2.726 | 1.00 | 16.82 |
| ATOM | 344 | CA | SER | A | 40 | 14.179 | 37.070 | 3.654 | 1.00 | 16.58 |
| ATOM | 345 | CB | SER | A | 40 | 12.721 | 37.433 | 3.889 | 1.00 | 17.10 |
| ATOM | 346 | OG | SER | A | 40 | 12.109 | 37.609 | 2.621 | 1.00 | 17.63 |
| ATOM | 347 | C | SER | A | 40 | 14.804 | 36.625 | 4.965 | 1.00 | 16.18 |
| ATOM | 348 | O | SER | A | 40 | 14.580 | 35.489 | 5.400 | 1.00 | 16.02 |
| ATOM | 349 | N | PRO | A | 41 | 15.636 | 37.477 | 5.538 | 1.00 | 16.16 |
| ATOM | 350 | CA | PRO | A | 41 | 16.177 | 37.231 | 6.876 | 1.00 | 15.95 |
| ATOM | 351 | CB | PRO | A | 41 | 17.273 | 38.241 | 7.028 | 1.00 | 16.47 |
| ATOM | 352 | CG | PRO | A | 41 | 17.185 | 39.250 | 5.894 | 1.00 | 16.77 |
| ATOM | 353 | CD | PRO | A | 41 | 16.067 | 38.763 | 4.989 | 1.00 | 16.71 |
| ATOM | 354 | C | PRO | A | 41 | 15.114 | 37.434 | 7.957 | 1.00 | 15.51 |
| ATOM | 355 | O | PRO | A | 41 | 14.924 | 38.547 | 8.457 | 1.00 | 15.39 |
| ATOM | 356 | N | ALA | A | 42 | 14.424 | 36.364 | 8.300 | 1.00 | 15.56 |
| ATOM | 358 | CA | ALA | A | 42 | 13.462 | 36.422 | 9.397 | 1.00 | 15.32 |
| ATOM | 359 | CB | ALA | A | 42 | 12.173 | 35.720 | 8.986 | 1.00 | 15.56 |
| ATOM | 360 | C | ALA | A | 42 | 14.074 | 35.757 | 10.620 | 1.00 | 15.35 |

| ATOM | 361 | O | ALA | A | 42 | 15.113 | 36.201 | 11.123 | 1.00 | 15.57 |
|---|---|---|---|---|---|---|---|---|---|---|
| ATOM | 362 | N | ASN | A | 43 | 13.442 | 34.692 | 11.080 | 1.00 | 15.19 |
| ATOM | 364 | CA | ASN | A | 43 | 13.969 | 33.959 | 12.235 | 1.00 | 15.22 |
| ATOM | 365 | CB | ASN | A | 43 | 12.840 | 33.244 | 12.961 | 1.00 | 15.86 |
| ATOM | 366 | CG | ASN | A | 43 | 11.718 | 34.223 | 13.290 | 1.00 | 15.73 |
| ATOM | 367 | OD1 | ASN | A | 43 | 11.957 | 35.352 | 13.733 | 1.00 | 15.55 |
| ATOM | 368 | ND2 | ASN | A | 43 | 10.500 | 33.783 | 13.031 | 1.00 | 15.89 |
| ATOM | 371 | C | ASN | A | 43 | 15.024 | 32.956 | 11.791 | 1.00 | 15.19 |
| ATOM | 372 | O | ASN | A | 43 | 14.746 | 31.882 | 11.237 | 1.00 | 14.96 |
| ATOM | 373 | N | ALA | A | 44 | 16.258 | 33.361 | 12.016 | 1.00 | 15.41 |
| ATOM | 375 | CA | ALA | A | 44 | 17.414 | 32.551 | 11.648 | 1.00 | 15.49 |
| ATOM | 376 | CB | ALA | A | 44 | 18.618 | 33.479 | 11.534 | 1.00 | 16.78 |
| ATOM | 377 | C | ALA | A | 44 | 17.689 | 31.461 | 12.680 | 1.00 | 14.95 |
| ATOM | 378 | O | ALA | A | 44 | 17.239 | 31.539 | 13.828 | 1.00 | 14.99 |
| ATOM | 379 | N | PRO | A | 45 | 18.323 | 30.397 | 12.217 | 1.00 | 14.51 |
| ATOM | 380 | CA | PRO | A | 45 | 18.417 | 30.065 | 10.794 | 1.00 | 14.09 |
| ATOM | 381 | CB | PRO | A | 45 | 19.749 | 29.386 | 10.732 | 1.00 | 15.04 |
| ATOM | 382 | CG | PRO | A | 45 | 19.991 | 28.754 | 12.102 | 1.00 | 15.75 |
| ATOM | 383 | CD | PRO | A | 45 | 18.914 | 29.328 | 13.016 | 1.00 | 15.56 |
| ATOM | 384 | C | PRO | A | 45 | 17.366 | 29.040 | 10.370 | 1.00 | 13.14 |
| ATOM | 385 | O | PRO | A | 45 | 17.726 | 28.150 | 9.594 | 1.00 | 12.61 |
| ATOM | 386 | N | SER | A | 46 | 16.093 | 29.241 | 10.684 | 1.00 | 12.99 |
| ATOM | 388 | CA | SER | A | 46 | 15.135 | 28.120 | 10.687 | 1.00 | 12.17 |
| ATOM | 389 | CB | SER | A | 46 | 13.896 | 28.570 | 11.446 | 1.00 | 12.36 |
| ATOM | 390 | OG | SER | A | 46 | 14.304 | 29.125 | 12.688 | 1.00 | 13.04 |
| ATOM | 391 | C | SER | A | 46 | 14.710 | 27.579 | 9.315 | 1.00 | 11.42 |
| ATOM | 392 | O | SER | A | 46 | 14.251 | 26.433 | 9.244 | 1.00 | 10.99 |
| ATOM | 393 | N | ALA | A | 47 | 15.008 | 28.290 | 8.241 | 1.00 | 11.41 |
| ATOM | 395 | CA | ALA | A | 47 | 14.719 | 27.767 | 6.902 | 1.00 | 10.80 |
| ATOM | 396 | CB | ALA | A | 47 | 14.344 | 28.923 | 5.995 | 1.00 | 11.50 |
| ATOM | 397 | C | ALA | A | 47 | 15.892 | 26.992 | 6.294 | 1.00 | 10.75 |
| ATOM | 398 | O | ALA | A | 47 | 15.772 | 26.447 | 5.193 | 1.00 | 10.39 |
| ATOM | 399 | N | TYR | A | 48 | 17.013 | 26.957 | 6.995 | 1.00 | 12.04 |
| ATOM | 401 | CA | TYR | A | 48 | 18.177 | 26.175 | 6.553 | 1.00 | 11.89 |
| ATOM | 402 | CB | TYR | A | 48 | 19.448 | 26.926 | 6.935 | 1.00 | 12.88 |
| ATOM | 403 | CG | TYR | A | 48 | 20.719 | 26.229 | 6.463 | 1.00 | 13.41 |
| ATOM | 404 | CD1 | TYR | A | 48 | 20.842 | 25.842 | 5.134 | 1.00 | 13.91 |
| ATOM | 405 | CE1 | TYR | A | 48 | 21.991 | 25.194 | 4.703 | 1.00 | 14.50 |
| ATOM | 406 | CZ | TYR | A | 48 | 23.016 | 24.938 | 5.603 | 1.00 | 14.60 |
| ATOM | 407 | OH | TYR | A | 48 | 24.103 | 24.194 | 5.203 | 1.00 | 15.31 |
| ATOM | 408 | CE2 | TYR | A | 48 | 22.904 | 25.338 | 6.929 | 1.00 | 14.16 |
| ATOM | 409 | CD2 | TYR | A | 48 | 21.753 | 25.985 | 7.359 | 1.00 | 13.55 |
| ATOM | 410 | C | TYR | A | 48 | 18.251 | 24.717 | 7.075 | 1.00 | 11.54 |
| ATOM | 411 | O | TYR | A | 48 | 18.628 | 23.860 | 6.261 | 1.00 | 11.71 |
| ATOM | 412 | N | PRO | A | 49 | 17.912 | 24.374 | 8.323 | 1.00 | 11.19 |
| ATOM | 413 | CA | PRO | A | 49 | 17.932 | 22.951 | 8.679 | 1.00 | 10.95 |
| ATOM | 414 | CB | PRO | A | 49 | 17.660 | 22.880 | 10.145 | 1.00 | 11.17 |
| ATOM | 415 | CG | PRO | A | 49 | 17.388 | 24.271 | 10.678 | 1.00 | 11.31 |
| ATOM | 416 | CD | PRO | A | 49 | 17.545 | 25.195 | 9.489 | 1.00 | 11.40 |
| ATOM | 417 | C | PRO | A | 49 | 16.905 | 22.114 | 7.930 | 1.00 | 10.04 |
| ATOM | 418 | O | PRO | A | 49 | 17.225 | 20.968 | 7.584 | 1.00 | 9.90 |
| ATOM | 419 | N | ARG | A | 50 | 15.827 | 22.740 | 7.482 | 1.00 | 9.55 |
| ATOM | 421 | CA | ARG | A | 50 | 14.794 | 22.014 | 6.748 | 1.00 | 8.74 |
| ATOM | 422 | CB | ARG | A | 50 | 13.594 | 22.910 | 6.472 | 1.00 | 9.11 |
| ATOM | 423 | CG | ARG | A | 50 | 12.455 | 22.038 | 5.975 | 1.00 | 9.19 |
| ATOM | 424 | CD | ARG | A | 50 | 12.107 | 21.007 | 7.043 | 1.00 | 9.81 |
| ATOM | 425 | NE | ARG | A | 50 | 11.247 | 19.944 | 6.506 | 1.00 | 10.42 |
| ATOM | 426 | CZ | ARG | A | 50 | 10.609 | 19.062 | 7.276 | 1.00 | 11.31 |

| ATOM | 427 | NH1 | ARG | A | 50 | 10.725 | 19.129 | 8.604 | 1.00 | 12.00 |
|------|-----|-----|-----|---|----|--------|--------|-------|------|-------|
| ATOM | 428 | NH2 | ARG | A | 50 | 9.837 | 18.127 | 6.718 | 1.00 | 11.69 |
| ATOM | 429 | C | ARG | A | 50 | 15.308 | 21.335 | 5.466 | 1.00 | 8.18 |
| ATOM | 430 | O | ARG | A | 50 | 15.260 | 20.103 | 5.438 | 1.00 | 8.13 |
| ATOM | 431 | N | PRO | A | 51 | 15.873 | 22.027 | 4.482 | 1.00 | 7.98 |
| ATOM | 432 | CA | PRO | A | 51 | 16.236 | 21.311 | 3.255 | 1.00 | 7.63 |
| ATOM | 433 | CB | PRO | A | 51 | 16.414 | 22.386 | 2.227 | 1.00 | 8.38 |
| ATOM | 434 | CG | PRO | A | 51 | 16.443 | 23.742 | 2.908 | 1.00 | 9.01 |
| ATOM | 435 | CD | PRO | A | 51 | 16.118 | 23.472 | 4.362 | 1.00 | 8.97 |
| ATOM | 436 | C | PRO | A | 51 | 17.507 | 20.444 | 3.310 | 1.00 | 7.66 |
| ATOM | 437 | O | PRO | A | 51 | 17.716 | 19.692 | 2.350 | 1.00 | 7.43 |
| ATOM | 438 | N | SER | A | 52 | 18.302 | 20.463 | 4.373 | 1.00 | 8.11 |
| ATOM | 440 | CA | SER | A | 52 | 19.584 | 19.749 | 4.262 | 1.00 | 8.31 |
| ATOM | 441 | CB | SER | A | 52 | 20.475 | 20.588 | 3.351 | 1.00 | 9.41 |
| ATOM | 442 | OG | SER | A | 52 | 20.648 | 21.850 | 3.986 | 1.00 | 10.16 |
| ATOM | 443 | C | SER | A | 52 | 20.376 | 19.533 | 5.550 | 1.00 | 7.49 |
| ATOM | 444 | O | SER | A | 52 | 21.315 | 18.726 | 5.531 | 1.00 | 7.60 |
| ATOM | 445 | N | SER | A | 53 | 20.008 | 20.183 | 6.640 | 1.00 | 6.82 |
| ATOM | 447 | CA | SER | A | 53 | 20.992 | 20.341 | 7.719 | 1.00 | 6.11 |
| ATOM | 448 | CB | SER | A | 53 | 21.021 | 21.802 | 8.132 | 1.00 | 8.00 |
| ATOM | 449 | OG | SER | A | 53 | 21.153 | 22.562 | 6.938 | 1.00 | 8.48 |
| ATOM | 450 | C | SER | A | 53 | 20.803 | 19.469 | 8.954 | 1.00 | 5.80 |
| ATOM | 451 | O | SER | A | 53 | 19.680 | 19.110 | 9.342 | 1.00 | 6.02 |
| ATOM | 452 | N | THR | A | 54 | 21.872 | 19.538 | 9.736 | 1.00 | 6.64 |
| ATOM | 454 | CA | THR | A | 54 | 22.105 | 18.732 | 10.950 | 1.00 | 6.72 |
| ATOM | 455 | CB | THR | A | 54 | 23.588 | 18.765 | 11.298 | 1.00 | 7.78 |
| ATOM | 456 | OG1 | THR | A | 54 | 23.918 | 20.088 | 11.700 | 1.00 | 8.09 |
| ATOM | 457 | CG2 | THR | A | 54 | 24.477 | 18.369 | 10.126 | 1.00 | 8.15 |
| ATOM | 458 | C | THR | A | 54 | 21.346 | 19.183 | 12.197 | 1.00 | 6.30 |
| ATOM | 459 | O | THR | A | 54 | 21.670 | 18.742 | 13.305 | 1.00 | 6.19 |
| ATOM | 460 | N | LYS | A | 55 | 20.346 | 20.027 | 12.031 | 1.00 | 6.22 |
| ATOM | 462 | CA | LYS | A | 55 | 19.660 | 20.554 | 13.200 | 1.00 | 6.00 |
| ATOM | 463 | CB | LYS | A | 55 | 19.417 | 22.045 | 12.977 | 1.00 | 6.38 |
| ATOM | 464 | CG | LYS | A | 55 | 18.813 | 22.772 | 14.181 | 1.00 | 7.21 |
| ATOM | 465 | CD | LYS | A | 55 | 19.856 | 23.354 | 15.142 | 1.00 | 7.56 |
| ATOM | 466 | CE | LYS | A | 55 | 20.675 | 22.295 | 15.874 | 1.00 | 8.08 |
| ATOM | 467 | NZ | LYS | A | 55 | 21.674 | 22.919 | 16.753 | 1.00 | 8.26 |
| ATOM | 468 | C | LYS | A | 55 | 18.341 | 19.833 | 13.484 | 1.00 | 5.00 |
| ATOM | 469 | O | LYS | A | 55 | 17.994 | 19.685 | 14.661 | 1.00 | 5.17 |
| ATOM | 470 | N | SER | A | 56 | 17.660 | 19.312 | 12.470 | 1.00 | 4.28 |
| ATOM | 472 | CA | SER | A | 56 | 16.344 | 18.717 | 12.756 | 1.00 | 3.33 |
| ATOM | 473 | CB | SER | A | 56 | 15.358 | 19.866 | 12.979 | 1.00 | 2.95 |
| ATOM | 474 | OG | SER | A | 56 | 15.435 | 20.755 | 11.867 | 1.00 | 3.03 |
| ATOM | 475 | C | SER | A | 56 | 15.751 | 17.768 | 11.705 | 1.00 | 2.29 |
| ATOM | 476 | O | SER | A | 56 | 15.363 | 16.644 | 12.058 | 1.00 | 2.75 |
| ATOM | 477 | N | THR | A | 57 | 15.867 | 18.108 | 10.433 | 1.00 | 1.18 |
| ATOM | 479 | CA | THR | A | 57 | 14.941 | 17.542 | 9.435 | 1.00 | 0.39 |
| ATOM | 480 | CB | THR | A | 57 | 15.098 | 18.307 | 8.142 | 1.00 | 1.62 |
| ATOM | 481 | OG1 | THR | A | 57 | 14.781 | 19.647 | 8.463 | 1.00 | 2.31 |
| ATOM | 482 | CG2 | THR | A | 57 | 14.113 | 17.803 | 7.097 | 1.00 | 2.10 |
| ATOM | 483 | C | THR | A | 57 | 14.971 | 16.022 | 9.224 | 1.00 | 0.19 |
| ATOM | 484 | O | THR | A | 57 | 13.954 | 15.407 | 9.576 | 1.00 | 0.28 |
| ATOM | 485 | N | PRO | A | 58 | 16.067 | 15.391 | 8.806 | 1.00 | 0.34 |
| ATOM | 486 | CA | PRO | A | 58 | 16.016 | 13.941 | 8.552 | 1.00 | 0.33 |
| ATOM | 487 | CB | PRO | A | 58 | 17.316 | 13.606 | 7.896 | 1.00 | 1.25 |
| ATOM | 488 | CG | PRO | A | 58 | 18.167 | 14.854 | 7.779 | 1.00 | 1.43 |
| ATOM | 489 | CD | PRO | A | 58 | 17.362 | 15.969 | 8.412 | 1.00 | 1.02 |
| ATOM | 490 | C | PRO | A | 58 | 15.748 | 13.029 | 9.760 | 1.00 | 0.16 |

| ATOM | 491 | O | PRO | A | 58 | 15.268 | 11.914 | 9.523 | 1.00 | 0.19 |
|---|---|---|---|---|---|---|---|---|---|---|
| ATOM | 492 | N | ALA | A | 59 | 15.759 | 13.536 | 10.987 | 1.00 | 0.18 |
| ATOM | 494 | CA | ALA | A | 59 | 15.399 | 12.691 | 12.132 | 1.00 | 0.16 |
| ATOM | 495 | CB | ALA | A | 59 | 15.816 | 13.375 | 13.426 | 1.00 | 0.63 |
| ATOM | 496 | C | ALA | A | 59 | 13.893 | 12.442 | 12.176 | 1.00 | 0.16 |
| ATOM | 497 | O | ALA | A | 59 | 13.474 | 11.296 | 12.374 | 1.00 | 0.31 |
| ATOM | 498 | N | SER | A | 60 | 13.125 | 13.402 | 11.685 | 1.00 | 0.01 |
| ATOM | 500 | CA | SER | A | 60 | 11.671 | 13.222 | 11.618 | 1.00 | 0.01 |
| ATOM | 501 | CB | SER | A | 60 | 10.987 | 14.584 | 11.676 | 1.00 | 0.23 |
| ATOM | 502 | OG | SER | A | 60 | 11.286 | 15.282 | 10.474 | 1.00 | 1.03 |
| ATOM | 503 | C | SER | A | 60 | 11.255 | 12.503 | 10.338 | 1.00 | 0.00 |
| ATOM | 504 | O | SER | A | 60 | 10.154 | 11.946 | 10.267 | 1.00 | 0.01 |
| ATOM | 505 | N | GLN | A | 61 | 12.183 | 12.377 | 9.404 | 1.00 | 0.01 |
| ATOM | 507 | CA | GLN | A | 61 | 11.887 | 11.693 | 8.150 | 1.00 | 0.00 |
| ATOM | 508 | CB | GLN | A | 61 | 12.694 | 12.362 | 7.050 | 1.00 | 0.37 |
| ATOM | 509 | CG | GLN | A | 61 | 12.342 | 13.843 | 6.975 | 1.00 | 1.02 |
| ATOM | 510 | CD | GLN | A | 61 | 13.163 | 14.531 | 5.893 | 1.00 | 1.17 |
| ATOM | 511 | OE1 | GLN | A | 61 | 14.396 | 14.598 | 5.976 | 1.00 | 1.88 |
| ATOM | 512 | NE2 | GLN | A | 61 | 12.459 | 15.114 | 4.939 | 1.00 | 1.51 |
| ATOM | 515 | C | GLN | A | 61 | 12.235 | 10.212 | 8.246 | 1.00 | 0.01 |
| ATOM | 516 | O | GLN | A | 61 | 11.542 | 9.376 | 7.652 | 1.00 | 0.01 |
| ATOM | 517 | N | VAL | A | 62 | 13.136 | 9.883 | 9.160 | 1.00 | 0.00 |
| ATOM | 519 | CA | VAL | A | 62 | 13.470 | 8.477 | 9.399 | 1.00 | 0.01 |
| ATOM | 520 | CB | VAL | A | 62 | 14.932 | 8.330 | 9.823 | 1.00 | 0.37 |
| ATOM | 521 | CG1 | VAL | A | 62 | 15.873 | 8.901 | 8.768 | 1.00 | 0.73 |
| ATOM | 522 | CG2 | VAL | A | 62 | 15.210 | 8.953 | 11.185 | 1.00 | 0.81 |
| ATOM | 523 | C | VAL | A | 62 | 12.547 | 7.846 | 10.441 | 1.00 | 0.01 |
| ATOM | 524 | O | VAL | A | 62 | 12.561 | 6.617 | 10.582 | 1.00 | 0.01 |
| ATOM | 525 | N | TYR | A | 63 | 11.609 | 8.627 | 10.964 | 1.00 | 0.00 |
| ATOM | 527 | CA | TYR | A | 63 | 10.620 | 8.144 | 11.940 | 1.00 | 0.01 |
| ATOM | 528 | CB | TYR | A | 63 | 9.681 | 9.308 | 12.252 | 1.00 | 0.95 |
| ATOM | 529 | CG | TYR | A | 63 | 8.348 | 8.934 | 12.904 | 1.00 | 1.26 |
| ATOM | 530 | CD1 | TYR | A | 63 | 7.161 | 9.196 | 12.228 | 1.00 | 1.76 |
| ATOM | 531 | CE1 | TYR | A | 63 | 5.941 | 8.859 | 12.802 | 1.00 | 2.50 |
| ATOM | 532 | CZ | TYR | A | 63 | 5.910 | 8.263 | 14.056 | 1.00 | 2.77 |
| ATOM | 533 | OH | TYR | A | 63 | 4.700 | 7.893 | 14.609 | 1.00 | 3.61 |
| ATOM | 534 | CE2 | TYR | A | 63 | 7.092 | 8.010 | 14.738 | 1.00 | 2.43 |
| ATOM | 535 | CD2 | TYR | A | 63 | 8.311 | 8.346 | 14.163 | 1.00 | 1.69 |
| ATOM | 536 | C | TYR | A | 63 | 9.786 | 6.981 | 11.420 | 1.00 | 0.01 |
| ATOM | 537 | O | TYR | A | 63 | 9.729 | 5.938 | 12.085 | 1.00 | 0.00 |
| ATOM | 538 | N | SER | A | 64 | 9.388 | 7.048 | 10.160 | 1.00 | 0.00 |
| ATOM | 540 | CA | SER | A | 64 | 8.518 | 6.008 | 9.618 | 1.00 | 0.01 |
| ATOM | 541 | CB | SER | A | 64 | 7.937 | 6.501 | 8.301 | 1.00 | 0.07 |
| ATOM | 542 | OG | SER | A | 64 | 7.191 | 7.679 | 8.576 | 1.00 | 0.58 |
| ATOM | 543 | C | SER | A | 64 | 9.271 | 4.708 | 9.388 | 1.00 | 0.00 |
| ATOM | 544 | O | SER | A | 64 | 8.802 | 3.659 | 9.844 | 1.00 | 0.01 |
| ATOM | 545 | N | LEU | A | 65 | 10.541 | 4.814 | 9.043 | 1.00 | 0.01 |
| ATOM | 547 | CA | LEU | A | 65 | 11.302 | 3.606 | 8.729 | 1.00 | 0.00 |
| ATOM | 548 | CB | LEU | A | 65 | 12.391 | 3.989 | 7.736 | 1.00 | 0.19 |
| ATOM | 549 | CG | LEU | A | 65 | 11.769 | 4.693 | 6.527 | 1.00 | 0.31 |
| ATOM | 550 | CD1 | LEU | A | 65 | 12.829 | 5.223 | 5.568 | 1.00 | 0.42 |
| ATOM | 551 | CD2 | LEU | A | 65 | 10.776 | 3.799 | 5.787 | 1.00 | 0.30 |
| ATOM | 552 | C | LEU | A | 65 | 11.868 | 2.975 | 9.999 | 1.00 | 0.00 |
| ATOM | 553 | O | LEU | A | 65 | 11.751 | 1.751 | 10.154 | 1.00 | 0.01 |
| ATOM | 554 | N | ASN | A | 66 | 12.057 | 3.813 | 11.008 | 1.00 | 0.01 |
| ATOM | 556 | CA | ASN | A | 66 | 12.478 | 3.354 | 12.336 | 1.00 | 0.01 |
| ATOM | 557 | CB | ASN | A | 66 | 12.838 | 4.583 | 13.174 | 1.00 | 0.20 |
| ATOM | 558 | CG | ASN | A | 66 | 13.358 | 4.202 | 14.562 | 1.00 | 0.42 |

| ATOM | 559 | OD1 | ASN | A | 66 | 14.527 | 3.832 | 14.714 | 1.00 | 1.44 |
| ATOM | 560 | ND2 | ASN | A | 66 | 12.506 | 4.348 | 15.567 | 1.00 | 0.90 |
| ATOM | 563 | C | ASN | A | 66 | 11.341 | 2.604 | 13.017 | 1.00 | 0.01 |
| ATOM | 564 | O | ASN | A | 66 | 11.543 | 1.472 | 13.473 | 1.00 | 0.01 |
| ATOM | 565 | N | THR | A | 67 | 10.125 | 3.104 | 12.857 | 1.00 | 0.00 |
| ATOM | 567 | CA | THR | A | 67 | 8.970 | 2.428 | 13.458 | 1.00 | 0.00 |
| ATOM | 568 | CB | THR | A | 67 | 7.800 | 3.398 | 13.595 | 1.00 | 0.32 |
| ATOM | 569 | OG1 | THR | A | 67 | 7.469 | 3.918 | 12.315 | 1.00 | 1.02 |
| ATOM | 570 | CG2 | THR | A | 67 | 8.152 | 4.565 | 14.508 | 1.00 | 1.22 |
| ATOM | 571 | C | THR | A | 67 | 8.546 | 1.202 | 12.655 | 1.00 | 0.01 |
| ATOM | 572 | O | THR | A | 67 | 8.146 | 0.206 | 13.268 | 1.00 | 0.00 |
| ATOM | 573 | N | ASP | A | 68 | 8.887 | 1.166 | 11.376 | 1.00 | 0.01 |
| ATOM | 575 | CA | ASP | A | 68 | 8.646 | -0.036 | 10.573 | 1.00 | 0.01 |
| ATOM | 576 | CB | ASP | A | 68 | 8.899 | 0.265 | 9.098 | 1.00 | 0.09 |
| ATOM | 577 | CG | ASP | A | 68 | 7.881 | 1.263 | 8.547 | 1.00 | 0.60 |
| ATOM | 578 | OD1 | ASP | A | 68 | 6.748 | 1.239 | 9.009 | 1.00 | 0.78 |
| ATOM | 579 | OD2 | ASP | A | 68 | 8.223 | 1.944 | 7.587 | 1.00 | 1.02 |
| ATOM | 580 | C | ASP | A | 68 | 9.571 | -1.160 | 11.021 | 1.00 | 0.01 |
| ATOM | 581 | O | ASP | A | 68 | 9.068 | -2.216 | 11.426 | 1.00 | 0.01 |
| ATOM | 582 | N | PHE | A | 69 | 10.832 | -0.827 | 11.256 | 1.00 | 0.00 |
| ATOM | 584 | CA | PHE | A | 69 | 11.808 | -1.808 | 11.748 | 1.00 | 0.01 |
| ATOM | 585 | CB | PHE | A | 69 | 13.193 | -1.172 | 11.652 | 1.00 | 0.01 |
| ATOM | 586 | CG | PHE | A | 69 | 14.294 | -1.923 | 12.397 | 1.00 | 0.01 |
| ATOM | 587 | CD1 | PHE | A | 69 | 14.711 | -3.173 | 11.958 | 1.00 | 0.00 |
| ATOM | 588 | CE1 | PHE | A | 69 | 15.708 | -3.853 | 12.645 | 1.00 | 0.01 |
| ATOM | 589 | CZ | PHE | A | 69 | 16.288 | -3.285 | 13.772 | 1.00 | 0.01 |
| ATOM | 590 | CE2 | PHE | A | 69 | 15.871 | -2.035 | 14.212 | 1.00 | 0.01 |
| ATOM | 591 | CD2 | PHE | A | 69 | 14.874 | -1.355 | 13.525 | 1.00 | 0.01 |
| ATOM | 592 | C | PHE | A | 69 | 11.537 | -2.226 | 13.195 | 1.00 | 0.01 |
| ATOM | 593 | O | PHE | A | 69 | 11.671 | -3.414 | 13.524 | 1.00 | 0.01 |
| ATOM | 594 | N | ALA | A | 70 | 10.940 | -1.334 | 13.966 | 1.00 | 0.01 |
| ATOM | 596 | CA | ALA | A | 70 | 10.573 | -1.645 | 15.346 | 1.00 | 0.01 |
| ATOM | 597 | CB | ALA | A | 70 | 10.227 | -0.336 | 16.042 | 1.00 | 0.01 |
| ATOM | 598 | C | ALA | A | 70 | 9.382 | -2.598 | 15.426 | 1.00 | 0.00 |
| ATOM | 599 | O | ALA | A | 70 | 9.438 | -3.570 | 16.190 | 1.00 | 0.01 |
| ATOM | 600 | N | PHE | A | 71 | 8.457 | -2.481 | 14.485 | 1.00 | 0.01 |
| ATOM | 602 | CA | PHE | A | 71 | 7.313 | -3.398 | 14.453 | 1.00 | 0.01 |
| ATOM | 603 | CB | PHE | A | 71 | 6.218 | -2.830 | 13.556 | 1.00 | 0.00 |
| ATOM | 604 | CG | PHE | A | 71 | 5.568 | -1.540 | 14.048 | 1.00 | 0.01 |
| ATOM | 605 | CD1 | PHE | A | 71 | 5.361 | -1.330 | 15.406 | 1.00 | 0.01 |
| ATOM | 606 | CE1 | PHE | A | 71 | 4.772 | -0.151 | 15.843 | 1.00 | 0.00 |
| ATOM | 607 | CZ | PHE | A | 71 | 4.383 | 0.813 | 14.922 | 1.00 | 0.00 |
| ATOM | 608 | CE2 | PHE | A | 71 | 4.575 | 0.596 | 13.564 | 1.00 | 0.00 |
| ATOM | 609 | CD2 | PHE | A | 71 | 5.163 | -0.583 | 13.127 | 1.00 | 0.00 |
| ATOM | 610 | C | PHE | A | 71 | 7.731 | -4.758 | 13.915 | 1.00 | 0.00 |
| ATOM | 611 | O | PHE | A | 71 | 7.347 | -5.783 | 14.495 | 1.00 | 0.01 |
| ATOM | 612 | N | ARG | A | 72 | 8.702 | -4.756 | 13.016 | 1.00 | 0.00 |
| ATOM | 614 | CA | ARG | A | 72 | 9.225 | -6.011 | 12.474 | 1.00 | 0.01 |
| ATOM | 615 | CB | ARG | A | 72 | 10.216 | -5.697 | 11.365 | 1.00 | 0.20 |
| ATOM | 616 | CG | ARG | A | 72 | 9.590 | -4.923 | 10.217 | 1.00 | 0.96 |
| ATOM | 617 | CD | ARG | A | 72 | 10.667 | -4.523 | 9.219 | 1.00 | 1.05 |
| ATOM | 618 | NE | ARG | A | 72 | 10.152 | -3.580 | 8.218 | 1.00 | 1.27 |
| ATOM | 619 | CZ | ARG | A | 72 | 10.946 | -3.002 | 7.317 | 1.00 | 1.66 |
| ATOM | 620 | NH1 | ARG | A | 72 | 10.449 | -2.099 | 6.470 | 1.00 | 2.10 |
| ATOM | 621 | NH2 | ARG | A | 72 | 12.249 | -3.292 | 7.300 | 1.00 | 2.00 |
| ATOM | 622 | C | ARG | A | 72 | 9.964 | -6.806 | 13.537 | 1.00 | 0.01 |
| ATOM | 623 | O | ARG | A | 72 | 9.629 | -7.974 | 13.760 | 1.00 | 0.00 |
| ATOM | 624 | N | LEU | A | 73 | 10.764 | -6.124 | 14.341 | 1.00 | 0.00 |

| ATOM | 626 | CA  | LEU | A | 73 | 11.537 | -6.823  | 15.365 | 1.00 | 0.01 |
|------|-----|-----|-----|---|----|--------|---------|--------|------|------|
| ATOM | 627 | CB  | LEU | A | 73 | 12.664 | -5.899  | 15.815 | 1.00 | 0.01 |
| ATOM | 628 | CG  | LEU | A | 73 | 13.628 | -6.598  | 16.766 | 1.00 | 0.01 |
| ATOM | 629 | CD1 | LEU | A | 73 | 14.126 | -7.909  | 16.170 | 1.00 | 0.01 |
| ATOM | 630 | CD2 | LEU | A | 73 | 14.801 | -5.690  | 17.118 | 1.00 | 0.01 |
| ATOM | 631 | C   | LEU | A | 73 | 10.670 | -7.237  | 16.555 | 1.00 | 0.01 |
| ATOM | 632 | O   | LEU | A | 73 | 10.824 | -8.367  | 17.037 | 1.00 | 0.01 |
| ATOM | 633 | N   | TYR | A | 74 | 9.610  | -6.490  | 16.824 | 1.00 | 0.01 |
| ATOM | 635 | CA  | TYR | A | 74 | 8.727  | -6.861  | 17.930 | 1.00 | 0.01 |
| ATOM | 636 | CB  | TYR | A | 74 | 7.800  | -5.698  | 18.262 | 1.00 | 0.01 |
| ATOM | 637 | CG  | TYR | A | 74 | 6.878  | -5.984  | 19.444 | 1.00 | 0.01 |
| ATOM | 638 | CD1 | TYR | A | 74 | 7.378  | -5.918  | 20.739 | 1.00 | 0.01 |
| ATOM | 639 | CE1 | TYR | A | 74 | 6.547  | -6.185  | 21.819 | 1.00 | 0.01 |
| ATOM | 640 | CZ  | TYR | A | 74 | 5.217  | -6.518  | 21.600 | 1.00 | 0.00 |
| ATOM | 641 | OH  | TYR | A | 74 | 4.393  | -6.794  | 22.670 | 1.00 | 0.01 |
| ATOM | 642 | CE2 | TYR | A | 74 | 4.714  | -6.584  | 20.307 | 1.00 | 0.01 |
| ATOM | 643 | CD2 | TYR | A | 74 | 5.546  | -6.316  | 19.228 | 1.00 | 0.01 |
| ATOM | 644 | C   | TYR | A | 74 | 7.896  | -8.082  | 17.574 | 1.00 | 0.01 |
| ATOM | 645 | O   | TYR | A | 74 | 7.932  | -9.072  | 18.316 | 1.00 | 0.01 |
| ATOM | 646 | N   | ARG | A | 75 | 7.412  | -8.126  | 16.344 | 1.00 | 0.01 |
| ATOM | 648 | CA  | ARG | A | 75 | 6.597  | -9.263  | 15.920 | 1.00 | 0.00 |
| ATOM | 649 | CB  | ARG | A | 75 | 5.781  | -8.854  | 14.703 | 1.00 | 0.00 |
| ATOM | 650 | CG  | ARG | A | 75 | 4.855  | -7.695  | 15.048 | 1.00 | 0.01 |
| ATOM | 651 | CD  | ARG | A | 75 | 4.096  | -7.205  | 13.823 | 1.00 | 0.00 |
| ATOM | 652 | NE  | ARG | A | 75 | 3.269  | -6.038  | 14.165 | 1.00 | 0.00 |
| ATOM | 653 | CZ  | ARG | A | 75 | 3.021  | -5.040  | 13.315 | 1.00 | 0.01 |
| ATOM | 654 | NH1 | ARG | A | 75 | 3.530  | -5.072  | 12.082 | 1.00 | 0.00 |
| ATOM | 655 | NH2 | ARG | A | 75 | 2.263  | -4.010  | 13.697 | 1.00 | 0.01 |
| ATOM | 656 | C   | ARG | A | 75 | 7.456  | -10.480 | 15.599 | 1.00 | 0.01 |
| ATOM | 657 | O   | ARG | A | 75 | 7.014  | -11.604 | 15.862 | 1.00 | 0.00 |
| ATOM | 658 | N   | ARG | A | 76 | 8.734  | -10.261 | 15.336 | 1.00 | 0.01 |
| ATOM | 660 | CA  | ARG | A | 76 | 9.650  | -11.381 | 15.129 | 1.00 | 0.01 |
| ATOM | 661 | CB  | ARG | A | 76 | 10.935 | -10.852 | 14.504 | 1.00 | 0.28 |
| ATOM | 662 | CG  | ARG | A | 76 | 11.790 | -11.993 | 13.973 | 1.00 | 1.10 |
| ATOM | 663 | CD  | ARG | A | 76 | 11.014 | -12.768 | 12.914 | 1.00 | 1.58 |
| ATOM | 664 | NE  | ARG | A | 76 | 11.815 | -13.856 | 12.336 | 1.00 | 2.21 |
| ATOM | 665 | CZ  | ARG | A | 76 | 11.783 | -14.161 | 11.037 | 1.00 | 2.96 |
| ATOM | 666 | NH1 | ARG | A | 76 | 12.433 | -15.236 | 10.589 | 1.00 | 3.85 |
| ATOM | 667 | NH2 | ARG | A | 76 | 11.019 | -13.449 | 10.206 | 1.00 | 3.23 |
| ATOM | 668 | C   | ARG | A | 76 | 9.975  | -12.057 | 16.456 | 1.00 | 0.01 |
| ATOM | 669 | O   | ARG | A | 76 | 9.903  | -13.288 | 16.537 | 1.00 | 0.01 |
| ATOM | 670 | N   | LEU | A | 77 | 10.031 | -11.279 | 17.525 | 1.00 | 0.01 |
| ATOM | 672 | CA  | LEU | A | 77 | 10.285 | -11.858 | 18.848 | 1.00 | 0.01 |

| | | | | | | | | | |
|---|---|---|---|---|---|---|---|---|---|
| ATOM | 673 | CB | LEU | A | 77 | 10.772 | -10.752 | 19.775 | 1.00 | 0.01 |
| ATOM | 674 | CG | LEU | A | 77 | 12.100 | -10.176 | 19.297 | 1.00 | 0.01 |
| ATOM | 675 | CD1 | LEU | A | 77 | 12.468 | -8.915 | 20.069 | 1.00 | 0.01 |
| ATOM | 676 | CD2 | LEU | A | 77 | 13.216 | -11.213 | 19.375 | 1.00 | 0.01 |
| ATOM | 677 | C | LEU | A | 77 | 9.033 | -12.517 | 19.425 | 1.00 | 0.01 |
| ATOM | 678 | O | LEU | A | 77 | 9.147 | -13.600 | 20.020 | 1.00 | 0.01 |
| ATOM | 679 | N | VAL | A | 78 | 7.869 | -12.043 | 19.002 | 1.00 | 0.01 |
| ATOM | 681 | CA | VAL | A | 78 | 6.603 | -12.672 | 19.402 | 1.00 | 0.01 |
| ATOM | 682 | CB | VAL | A | 78 | 5.447 | -11.736 | 19.045 | 1.00 | 0.11 |
| ATOM | 683 | CG1 | VAL | A | 78 | 4.095 | -12.384 | 19.325 | 1.00 | 0.20 |
| ATOM | 684 | CG2 | VAL | A | 78 | 5.551 | -10.403 | 19.773 | 1.00 | 0.20 |
| ATOM | 685 | C | VAL | A | 78 | 6.398 | -13.999 | 18.675 | 1.00 | 0.01 |
| ATOM | 686 | O | VAL | A | 78 | 6.015 | -14.989 | 19.310 | 1.00 | 0.01 |
| ATOM | 687 | N | LEU | A | 79 | 6.872 | -14.068 | 17.439 | 1.00 | 0.01 |
| ATOM | 689 | CA | LEU | A | 79 | 6.763 | -15.296 | 16.644 | 1.00 | 0.01 |
| ATOM | 690 | CB | LEU | A | 79 | 6.776 | -14.925 | 15.166 | 1.00 | 0.19 |
| ATOM | 691 | CG | LEU | A | 79 | 5.533 | -14.129 | 14.784 | 1.00 | 0.24 |
| ATOM | 692 | CD1 | LEU | A | 79 | 5.635 | -13.603 | 13.357 | 1.00 | 0.38 |
| ATOM | 693 | CD2 | LEU | A | 79 | 4.266 | -14.957 | 14.971 | 1.00 | 0.37 |
| ATOM | 694 | C | LEU | A | 79 | 7.882 | -16.294 | 16.933 | 1.00 | 0.01 |
| ATOM | 695 | O | LEU | A | 79 | 7.786 | -17.458 | 16.528 | 1.00 | 0.01 |
| ATOM | 696 | N | GLU | A | 80 | 8.912 | -15.863 | 17.642 | 1.00 | 0.01 |
| ATOM | 698 | CA | GLU | A | 80 | 9.894 | -16.823 | 18.142 | 1.00 | 0.01 |
| ATOM | 699 | CB | GLU | A | 80 | 11.209 | -16.127 | 18.478 | 1.00 | 0.49 |
| ATOM | 700 | CG | GLU | A | 80 | 11.857 | -15.481 | 17.258 | 1.00 | 1.39 |
| ATOM | 701 | CD | GLU | A | 80 | 12.079 | -16.498 | 16.142 | 1.00 | 1.48 |
| ATOM | 702 | OE1 | GLU | A | 80 | 11.433 | -16.347 | 15.114 | 1.00 | 2.26 |
| ATOM | 703 | OE2 | GLU | A | 80 | 13.034 | -17.252 | 16.255 | 1.00 | 1.23 |
| ATOM | 704 | C | GLU | A | 80 | 9.318 | -17.467 | 19.394 | 1.00 | 0.01 |
| ATOM | 705 | O | GLU | A | 80 | 9.257 | -18.698 | 19.495 | 1.00 | 0.01 |

| ATOM | 706 | N | THR | A | 81 | 8.856 | -16.619 | 20.301 | 1.00 | 0.01 |
|---|---|---|---|---|---|---|---|---|---|---|
| ATOM | 708 | CA | THR | A | 81 | 8.132 | -17.067 | 21.498 | 1.00 | 0.02 |
| ATOM | 709 | CB | THR | A | 81 | 8.969 | -17.980 | 22.395 | 1.00 | 1.52 |
| ATOM | 710 | OG1 | THR | A | 81 | 8.309 | -18.010 | 23.652 | 1.00 | 2.01 |
| ATOM | 711 | CG2 | THR | A | 81 | 10.389 | -17.486 | 22.633 | 1.00 | 2.60 |
| ATOM | 712 | C | THR | A | 81 | 7.596 | -15.897 | 22.316 | 1.00 | 0.01 |
| ATOM | 713 | O | THR | A | 81 | 8.349 | -15.135 | 22.945 | 1.00 | 0.01 |
| ATOM | 714 | N | PRO | A | 82 | 6.281 | -15.924 | 22.474 | 1.00 | 0.01 |
| ATOM | 715 | CA | PRO | A | 82 | 5.547 | -14.945 | 23.285 | 1.00 | 0.01 |
| ATOM | 716 | CB | PRO | A | 82 | 4.116 | -15.121 | 22.876 | 1.00 | 0.18 |
| ATOM | 717 | CG | PRO | A | 82 | 3.983 | -16.396 | 22.058 | 1.00 | 0.19 |
| ATOM | 718 | CD | PRO | A | 82 | 5.392 | -16.932 | 21.889 | 1.00 | 0.14 |
| ATOM | 719 | C | PRO | A | 82 | 5.680 | -15.115 | 24.809 | 1.00 | 0.01 |
| ATOM | 720 | O | PRO | A | 82 | 5.041 | -14.357 | 25.547 | 1.00 | 0.01 |
| ATOM | 721 | N | SER | A | 83 | 6.493 | -16.055 | 25.281 | 1.00 | 0.02 |
| ATOM | 723 | CA | SER | A | 83 | 6.697 | -16.235 | 26.722 | 1.00 | 0.01 |
| ATOM | 724 | CB | SER | A | 83 | 6.985 | -17.702 | 27.015 | 1.00 | 0.01 |
| ATOM | 725 | OG | SER | A | 83 | 8.279 | -18.000 | 26.509 | 1.00 | 0.02 |
| ATOM | 726 | C | SER | A | 83 | 7.868 | -15.393 | 27.232 | 1.00 | 0.01 |
| ATOM | 727 | O | SER | A | 83 | 8.277 | -15.528 | 28.391 | 1.00 | 0.01 |
| ATOM | 728 | N | GLN | A | 84 | 8.492 | -14.651 | 26.334 | 1.00 | 0.02 |
| ATOM | 730 | CA | GLN | A | 84 | 9.553 | -13.730 | 26.735 | 1.00 | 0.01 |
| ATOM | 731 | CB | GLN | A | 84 | 10.513 | -13.545 | 25.567 | 1.00 | 1.11 |
| ATOM | 732 | CG | GLN | A | 84 | 11.173 | -14.843 | 25.130 | 1.00 | 1.61 |
| ATOM | 733 | CD | GLN | A | 84 | 12.060 | -14.558 | 23.922 | 1.00 | 1.93 |
| ATOM | 734 | OE1 | GLN | A | 84 | 13.283 | -14.730 | 23.977 | 1.00 | 2.66 |
| ATOM | 735 | NE2 | GLN | A | 84 | 11.422 | -14.146 | 22.838 | 1.00 | 1.90 |
| ATOM | 738 | C | GLN | A | 84 | 8.991 | -12.358 | 27.076 | 1.00 | 0.00 |
| ATOM | 739 | O | GLN | A | 84 | 8.119 | -11.841 | 26.368 | 1.00 | 0.01 |
| ATOM | 740 | N | ASN | A | 85 | 9.526 | - | 28.132 | 1.00 | 0.01 |

| | | | | | | 11.766 | | | |
|---|---|---|---|---|---|---|---|---|---|
| ATOM | 742 | CA | ASN | A | 85 | 9.314 | -10.334 | 28.379 | 1.00 | 0.01 |
| ATOM | 743 | CB | ASN | A | 85 | 9.736 | -9.974 | 29.798 | 1.00 | 0.01 |
| ATOM | 744 | CG | ASN | A | 85 | 8.816 | -10.618 | 30.824 | 1.00 | 0.02 |
| ATOM | 745 | OD1 | ASN | A | 85 | 7.585 | -10.488 | 30.751 | 1.00 | 0.01 |
| ATOM | 746 | ND2 | ASN | A | 85 | 9.426 | -11.245 | 31.811 | 1.00 | 0.01 |
| ATOM | 749 | C | ASN | A | 85 | 10.170 | -9.542 | 27.399 | 1.00 | 0.01 |
| ATOM | 750 | O | ASN | A | 85 | 11.369 | -9.336 | 27.617 | 1.00 | 0.01 |
| ATOM | 751 | N | ILE | A | 86 | 9.554 | -9.156 | 26.297 | 1.00 | 0.01 |
| ATOM | 753 | CA | ILE | A | 86 | 10.277 | -8.469 | 25.226 | 1.00 | 0.01 |
| ATOM | 754 | CB | ILE | A | 86 | 9.369 | -8.454 | 23.996 | 1.00 | 0.01 |
| ATOM | 755 | CG2 | ILE | A | 86 | 10.021 | -7.781 | 22.792 | 1.00 | 0.00 |
| ATOM | 756 | CG1 | ILE | A | 86 | 8.974 | -9.879 | 23.629 | 1.00 | 0.01 |
| ATOM | 757 | CD1 | ILE | A | 86 | 8.153 | -9.905 | 22.347 | 1.00 | 0.01 |
| ATOM | 758 | C | ILE | A | 86 | 10.661 | -7.064 | 25.671 | 1.00 | 0.00 |
| ATOM | 759 | O | ILE | A | 86 | 9.906 | -6.417 | 26.406 | 1.00 | 0.01 |
| ATOM | 760 | N | PHE | A | 87 | 11.877 | -6.664 | 25.342 | 1.00 | 0.01 |
| ATOM | 762 | CA | PHE | A | 87 | 12.324 | -5.303 | 25.630 | 1.00 | 0.00 |
| ATOM | 763 | CB | PHE | A | 87 | 12.633 | -5.134 | 27.110 | 1.00 | 0.01 |
| ATOM | 764 | CG | PHE | A | 87 | 12.846 | -3.664 | 27.423 | 1.00 | 0.01 |
| ATOM | 765 | CD1 | PHE | A | 87 | 11.782 | -2.784 | 27.282 | 1.00 | 0.00 |
| ATOM | 766 | CE1 | PHE | A | 87 | 11.964 | -1.432 | 27.531 | 1.00 | 0.01 |
| ATOM | 767 | CZ | PHE | A | 87 | 13.213 | -0.964 | 27.912 | 1.00 | 0.01 |
| ATOM | 768 | CE2 | PHE | A | 87 | 14.278 | -1.844 | 28.051 | 1.00 | 0.00 |
| ATOM | 769 | CD2 | PHE | A | 87 | 14.094 | -3.197 | 27.807 | 1.00 | 0.01 |
| ATOM | 770 | C | PHE | A | 87 | 13.559 | -4.950 | 24.810 | 1.00 | 0.01 |
| ATOM | 771 | O | PHE | A | 87 | 14.695 | -5.254 | 25.195 | 1.00 | 0.01 |
| ATOM | 772 | N | PHE | A | 88 | 13.324 | -4.284 | 23.696 | 1.00 | 0.01 |
| ATOM | 774 | CA | PHE | A | 88 | 14.428 | -3.886 | 22.819 | 1.00 | 0.01 |
| ATOM | 775 | CB | PHE | A | 88 | 14.399 | -4.710 | 21.532 | 1.00 | 0.01 |
| ATOM | 776 | CG | PHE | A | 88 | 13.216 | -4.453 | 20.600 | 1.00 | 0.01 |
| ATOM | 777 | CD1 | PHE | A | 88 | 12.037 | -5.171 | 20.752 | 1.00 | 0.01 |
| ATOM | 778 | CE1 | PHE | A | 88 | 10.966 | -4.930 | 19.904 | 1.00 | 0.01 |
| ATOM | 779 | CZ | PHE | A | 88 | 11.076 | -3.979 | 18.898 | 1.00 | 0.01 |
| ATOM | 780 | CE2 | PHE | A | 88 | 12.258 | -3.272 | 18.735 | 1.00 | 0.01 |
| ATOM | 781 | CD2 | PHE | A | 88 | 13.329 | -3.513 | 19.583 | 1.00 | 0.01 |
| ATOM | 782 | C | PHE | A | 88 | 14.369 | -2.404 | 22.477 | 1.00 | 0.00 |
| ATOM | 783 | O | PHE | A | 88 | 13.301 | -1.779 | 22.467 | 1.00 | 0.01 |
| ATOM | 784 | N | SER | A | 89 | 15.537 | -1.856 | 22.202 | 1.00 | 0.01 |
| ATOM | 786 | CA | SER | A | 89 | 15.633 | -0.485 | 21.714 | 1.00 | 0.00 |
| ATOM | 787 | CB | SER | A | 89 | 16.812 | 0.213 | 22.369 | 1.00 | 0.01 |
| ATOM | 788 | OG | SER | A | 89 | 17.000 | 1.443 | 21.675 | 1.00 | 0.01 |
| ATOM | 789 | C | SER | A | 89 | 15.843 | -0.446 | 20.212 | 1.00 | 0.01 |
| ATOM | 790 | O | SER | A | 89 | 16.975 | -0.633 | 19.739 | 1.00 | 0.01 |
| ATOM | 791 | N | PRO | A | 90 | 14.804 | -0.047 | 19.493 | 1.00 | 0.01 |
| ATOM | 792 | CA | PRO | A | 90 | 14.926 | 0.148 | 18.048 | 1.00 | 0.01 |
| ATOM | 793 | CB | PRO | A | 90 | 13.554 | 0.526 | 17.581 | 1.00 | 0.01 |
| ATOM | 794 | CG | PRO | A | 90 | 12.621 | 0.615 | 18.780 | 1.00 | 0.01 |
| ATOM | 795 | CD | PRO | A | 90 | 13.465 | 0.275 | 19.995 | 1.00 | 0.01 |
| ATOM | 796 | C | PRO | A | 90 | 15.947 | 1.233 | 17.718 | 1.00 | 0.01 |
| ATOM | 797 | O | PRO | A | 90 | 16.867 | 0.951 | 16.942 | 1.00 | 0.01 |
| ATOM | 798 | N | VAL | A | 91 | 15.995 | 2.264 | 18.549 | 1.00 | 0.00 |
| ATOM | 800 | CA | VAL | A | 91 | 16.952 | 3.354 | 18.363 | 1.00 | 0.01 |
| ATOM | 801 | CB | VAL | A | 91 | 16.642 | 4.444 | 19.381 | 1.00 | 0.01 |

| ATOM | 802 | CG1 | VAL | A | 91 | 17.798 | 5.427 | 19.540 | 1.00 | 0.01 |
|------|-----|-----|-----|---|----|--------|-------|--------|------|------|
| ATOM | 803 | CG2 | VAL | A | 91 | 15.361 | 5.174 | 19.001 | 1.00 | 0.01 |
| ATOM | 804 | C | VAL | A | 91 | 18.409 | 2.908 | 18.486 | 1.00 | 0.01 |
| ATOM | 805 | O | VAL | A | 91 | 19.147 | 3.108 | 17.515 | 1.00 | 0.00 |
| ATOM | 806 | N | SER | A | 92 | 18.764 | 2.110 | 19.485 | 1.00 | 0.01 |
| ATOM | 808 | CA | SER | A | 92 | 20.179 | 1.744 | 19.608 | 1.00 | 0.01 |
| ATOM | 809 | CB | SER | A | 92 | 20.433 | 1.193 | 21.006 | 1.00 | 0.01 |
| ATOM | 810 | OG | SER | A | 92 | 19.684 | -0.004 | 21.158 | 1.00 | 0.01 |
| ATOM | 811 | C | SER | A | 92 | 20.633 | 0.734 | 18.551 | 1.00 | 0.01 |
| ATOM | 812 | O | SER | A | 92 | 21.717 | 0.937 | 17.981 | 1.00 | 0.01 |
| ATOM | 813 | N | VAL | A | 93 | 19.729 | -0.115 | 18.086 | 1.00 | 0.00 |
| ATOM | 815 | CA | VAL | A | 93 | 20.106 | -1.096 | 17.067 | 1.00 | 0.01 |
| ATOM | 816 | CB | VAL | A | 93 | 19.066 | -2.211 | 17.045 | 1.00 | 0.09 |
| ATOM | 817 | CG1 | VAL | A | 93 | 19.417 | -3.261 | 15.997 | 1.00 | 0.13 |
| ATOM | 818 | CG2 | VAL | A | 93 | 18.926 | -2.862 | 18.413 | 1.00 | 0.17 |
| ATOM | 819 | C | VAL | A | 93 | 20.176 | -0.450 | 15.689 | 1.00 | 0.00 |
| ATOM | 820 | O | VAL | A | 93 | 21.195 | -0.594 | 15.001 | 1.00 | 0.01 |
| ATOM | 821 | N | SER | A | 94 | 19.274 | 0.482 | 15.434 | 1.00 | 0.01 |
| ATOM | 823 | CA | SER | A | 94 | 19.235 | 1.133 | 14.121 | 1.00 | 0.01 |
| ATOM | 824 | CB | SER | A | 94 | 17.859 | 1.765 | 13.922 | 1.00 | 0.17 |
| ATOM | 825 | OG | SER | A | 94 | 17.660 | 2.767 | 14.914 | 1.00 | 0.70 |
| ATOM | 826 | C | SER | A | 94 | 20.327 | 2.189 | 13.969 | 1.00 | 0.01 |
| ATOM | 827 | O | SER | A | 94 | 20.922 | 2.291 | 12.888 | 1.00 | 0.01 |
| ATOM | 828 | N | THR | A | 95 | 20.775 | 2.742 | 15.084 | 1.00 | 0.01 |
| ATOM | 830 | CA | THR | A | 95 | 21.859 | 3.719 | 15.038 | 1.00 | 0.00 |
| ATOM | 831 | CB | THR | A | 95 | 21.807 | 4.547 | 16.318 | 1.00 | 0.01 |
| ATOM | 832 | OG1 | THR | A | 95 | 20.577 | 5.260 | 16.317 | 1.00 | 0.02 |
| ATOM | 833 | CG2 | THR | A | 95 | 22.937 | 5.566 | 16.388 | 1.00 | 0.01 |
| ATOM | 834 | C | THR | A | 95 | 23.211 | 3.027 | 14.903 | 1.00 | 0.01 |
| ATOM | 835 | O | THR | A | 95 | 24.026 | 3.454 | 14.076 | 1.00 | 0.00 |
| ATOM | 836 | N | SER | A | 96 | 23.321 | 1.827 | 15.451 | 1.00 | 0.01 |
| ATOM | 838 | CA | SER | A | 96 | 24.582 | 1.089 | 15.319 | 1.00 | 0.01 |
| ATOM | 839 | CB | SER | A | 96 | 24.727 | 0.089 | 16.462 | 1.00 | 0.15 |
| ATOM | 840 | OG | SER | A | 96 | 23.632 | -0.817 | 16.438 | 1.00 | 0.84 |
| ATOM | 841 | C | SER | A | 96 | 24.688 | 0.379 | 13.970 | 1.00 | 0.01 |
| ATOM | 842 | O | SER | A | 96 | 25.791 | 0.294 | 13.416 | 1.00 | 0.01 |
| ATOM | 843 | N | LEU | A | 97 | 23.559 | 0.119 | 13.333 | 1.00 | 0.01 |
| ATOM | 845 | CA | LEU | A | 97 | 23.607 | -0.467 | 11.994 | 1.00 | 0.01 |
| ATOM | 846 | CB | LEU | A | 97 | 22.315 | -1.224 | 11.738 | 1.00 | 0.13 |
| ATOM | 847 | CG | LEU | A | 97 | 22.233 | -2.463 | 12.617 | 1.00 | 0.13 |
| ATOM | 848 | CD1 | LEU | A | 97 | 20.874 | -3.135 | 12.478 | 1.00 | 0.64 |
| ATOM | 849 | CD2 | LEU | A | 97 | 23.361 | -3.436 | 12.290 | 1.00 | 0.47 |
| ATOM | 850 | C | LEU | A | 97 | 23.828 | 0.591 | 10.918 | 1.00 | 0.00 |
| ATOM | 851 | O | LEU | A | 97 | 24.610 | 0.347 | 9.990 | 1.00 | 0.00 |
| ATOM | 852 | N | ALA | A | 98 | 23.405 | 1.816 | 11.182 | 1.00 | 0.01 |
| ATOM | 854 | CA | ALA | A | 98 | 23.698 | 2.904 | 10.243 | 1.00 | 0.01 |
| ATOM | 855 | CB | ALA | A | 98 | 22.655 | 3.993 | 10.410 | 1.00 | 0.01 |
| ATOM | 856 | C | ALA | A | 98 | 25.103 | 3.470 | 10.455 | 1.00 | 0.00 |
| ATOM | 857 | O | ALA | A | 98 | 25.659 | 4.131 | 9.572 | 1.00 | 0.01 |
| ATOM | 858 | N | MET | A | 99 | 25.702 | 3.114 | 11.577 | 1.00 | 0.01 |
| ATOM | 860 | CA | MET | A | 99 | 27.114 | 3.392 | 11.817 | 1.00 | 0.02 |
| ATOM | 861 | CB | MET | A | 99 | 27.319 | 3.255 | 13.315 | 1.00 | 0.00 |
| ATOM | 862 | CG | MET | A | 99 | 28.783 | 3.315 | 13.704 | 1.00 | 0.01 |
| ATOM | 863 | SD | MET | A | 99 | 29.098 | 2.753 | 15.386 | 1.00 | 0.01 |
| ATOM | 864 | CE | MET | A | 99 | 28.443 | 1.074 | 15.249 | 1.00 | 0.02 |
| ATOM | 865 | C | MET | A | 99 | 27.989 | 2.367 | 11.103 | 1.00 | 0.01 |
| ATOM | 866 | O | MET | A | 99 | 28.949 | 2.735 | 10.412 | 1.00 | 0.01 |
| ATOM | 867 | N | LEU | A | 100 | 27.496 | 1.139 | 11.054 | 1.00 | 0.01 |

| ATOM | 869 | CA | LEU | A | 100 | 28.216 | 0.054 | 10.381 | 1.00 | 0.01 |
|---|---|---|---|---|---|---|---|---|---|---|
| ATOM | 870 | CB | LEU | A | 100 | 27.610 | -1.265 | 10.847 | 1.00 | 0.01 |
| ATOM | 871 | CG | LEU | A | 100 | 28.374 | -2.467 | 10.305 | 1.00 | 0.01 |
| ATOM | 872 | CD1 | LEU | A | 100 | 29.822 | -2.450 | 10.784 | 1.00 | 0.01 |
| ATOM | 873 | CD2 | LEU | A | 100 | 27.691 | -3.768 | 10.714 | 1.00 | 0.01 |
| ATOM | 874 | C | LEU | A | 100 | 28.104 | 0.162 | 8.862 | 1.00 | 0.01 |
| ATOM | 875 | O | LEU | A | 100 | 29.088 | -0.102 | 8.160 | 1.00 | 0.01 |
| ATOM | 876 | N | SER | A | 101 | 27.047 | 0.812 | 8.397 | 1.00 | 0.01 |
| ATOM | 878 | CA | SER | A | 101 | 26.872 | 1.083 | 6.962 | 1.00 | 0.01 |
| ATOM | 879 | CB | SER | A | 101 | 25.395 | 1.301 | 6.668 | 1.00 | 0.00 |
| ATOM | 880 | OG | SER | A | 101 | 24.997 | 2.495 | 7.322 | 1.00 | 0.00 |
| ATOM | 881 | C | SER | A | 101 | 27.673 | 2.295 | 6.469 | 1.00 | 0.01 |
| ATOM | 882 | O | SER | A | 101 | 27.547 | 2.678 | 5.304 | 1.00 | 0.00 |
| ATOM | 883 | N | LEU | A | 102 | 28.450 | 2.909 | 7.350 | 1.00 | 0.01 |
| ATOM | 885 | CA | LEU | A | 102 | 29.438 | 3.915 | 6.944 | 1.00 | 0.01 |
| ATOM | 886 | CB | LEU | A | 102 | 29.500 | 5.012 | 7.994 | 1.00 | 0.00 |
| ATOM | 887 | CG | LEU | A | 102 | 28.356 | 5.997 | 7.809 | 1.00 | 0.01 |
| ATOM | 888 | CD1 | LEU | A | 102 | 28.419 | 7.100 | 8.855 | 1.00 | 0.01 |
| ATOM | 889 | CD2 | LEU | A | 102 | 28.408 | 6.601 | 6.411 | 1.00 | 0.01 |
| ATOM | 890 | C | LEU | A | 102 | 30.833 | 3.318 | 6.730 | 1.00 | 0.00 |
| ATOM | 891 | O | LEU | A | 102 | 31.800 | 4.067 | 6.540 | 1.00 | 0.01 |
| ATOM | 892 | N | GLY | A | 103 | 30.947 | 2.008 | 6.874 | 1.00 | 0.02 |
| ATOM | 894 | CA | GLY | A | 103 | 32.193 | 1.306 | 6.555 | 1.00 | 0.02 |
| ATOM | 895 | C | GLY | A | 103 | 31.876 | 0.155 | 5.611 | 1.00 | 0.01 |
| ATOM | 896 | O | GLY | A | 103 | 32.740 | -0.334 | 4.866 | 1.00 | 0.02 |
| ATOM | 897 | N | ALA | A | 104 | 30.658 | -0.337 | 5.756 | 1.00 | 0.01 |
| ATOM | 899 | CA | ALA | A | 104 | 30.107 | -1.315 | 4.823 | 1.00 | 0.00 |
| ATOM | 900 | CB | ALA | A | 104 | 28.828 | -1.898 | 5.410 | 1.00 | 0.60 |
| ATOM | 901 | C | ALA | A | 104 | 29.798 | -0.648 | 3.494 | 1.00 | 0.01 |
| ATOM | 902 | O | ALA | A | 104 | 29.377 | 0.511 | 3.431 | 1.00 | 0.01 |
| ATOM | 903 | N | HIS | A | 105 | 30.084 | -1.371 | 2.434 | 1.00 | 0.01 |
| ATOM | 905 | CA | HIS | A | 105 | 29.819 | -0.868 | 1.093 | 1.00 | 0.01 |
| ATOM | 906 | CB | HIS | A | 105 | 31.163 | -0.638 | 0.413 | 1.00 | 0.36 |
| ATOM | 907 | CG | HIS | A | 105 | 31.157 | 0.500 | -0.582 | 1.00 | 1.35 |
| ATOM | 908 | ND1 | HIS | A | 105 | 30.544 | 1.685 | -0.417 | 1.00 | 1.70 |
| ATOM | 910 | CE1 | HIS | A | 105 | 30.748 | 2.447 | -1.511 | 1.00 | 2.51 |
| ATOM | 911 | NE2 | HIS | A | 105 | 31.505 | 1.730 | -2.373 | 1.00 | 2.95 |
| ATOM | 912 | CD2 | HIS | A | 105 | 31.767 | 0.527 | -1.813 | 1.00 | 2.35 |
| ATOM | 913 | C | HIS | A | 105 | 28.971 | -1.875 | 0.322 | 1.00 | 0.01 |
| ATOM | 914 | O | HIS | A | 105 | 28.605 | -2.934 | 0.858 | 1.00 | 0.01 |
| ATOM | 915 | N | SER | A | 106 | 28.645 | -1.518 | -0.912 | 1.00 | 0.01 |
| ATOM | 917 | CA | SER | A | 106 | 27.870 | -2.369 | -1.833 | 1.00 | 0.00 |
| ATOM | 918 | CB | SER | A | 106 | 28.789 | -3.466 | -2.358 | 1.00 | 0.30 |
| ATOM | 919 | OG | SER | A | 106 | 29.945 | -2.846 | -2.902 | 1.00 | 0.54 |
| ATOM | 920 | C | SER | A | 106 | 26.661 | -3.026 | -1.177 | 1.00 | 0.01 |
| ATOM | 921 | O | SER | A | 106 | 25.993 | -2.427 | -0.326 | 1.00 | 0.01 |
| ATOM | 922 | N | VAL | A | 107 | 26.547 | -4.326 | -1.403 | 1.00 | 0.01 |
| ATOM | 924 | CA | VAL | A | 107 | 25.393 | -5.106 | -0.926 | 1.00 | 0.01 |
| ATOM | 925 | CB | VAL | A | 107 | 25.402 | -6.429 | -1.689 | 1.00 | 0.37 |
| ATOM | 926 | CG1 | VAL | A | 107 | 24.244 | -7.339 | -1.287 | 1.00 | 0.53 |
| ATOM | 927 | CG2 | VAL | A | 107 | 25.369 | -6.171 | -3.191 | 1.00 | 0.37 |
| ATOM | 928 | C | VAL | A | 107 | 25.391 | -5.361 | 0.589 | 1.00 | 0.01 |
| ATOM | 929 | O | VAL | A | 107 | 24.304 | -5.492 | 1.162 | 1.00 | 0.01 |
| ATOM | 930 | N | THR | A | 108 | 26.506 | -5.109 | 1.255 | 1.00 | 0.02 |
| ATOM | 932 | CA | THR | A | 108 | 26.545 | -5.286 | 2.706 | 1.00 | 0.01 |
| ATOM | 933 | CB | THR | A | 108 | 28.003 | -5.413 | 3.133 | 1.00 | 0.00 |
| ATOM | 934 | OG1 | THR | A | 108 | 28.524 | -6.614 | 2.573 | 1.00 | 0.01 |
| ATOM | 935 | CG2 | THR | A | 108 | 28.144 | -5.507 | 4.645 | 1.00 | 0.01 |

| ATOM | 936 | C | THR | A | 108 | 25.891 | -4.079 | 3.374 | 1.00 | 0.01 |
|------|-----|-----|-----|---|-----|--------|--------|-------|------|------|
| ATOM | 937 | O | THR | A | 108 | 24.945 | -4.252 | 4.154 | 1.00 | 0.00 |
| ATOM | 938 | N | LYS | A | 109 | 26.119 | -2.925 | 2.767 | 1.00 | 0.01 |
| ATOM | 940 | CA | LYS | A | 109 | 25.517 | -1.675 | 3.238 | 1.00 | 0.01 |
| ATOM | 941 | CB | LYS | A | 109 | 26.307 | -0.543 | 2.601 | 1.00 | 0.10 |
| ATOM | 942 | CG | LYS | A | 109 | 25.738 | 0.831 | 2.919 | 1.00 | 0.14 |
| ATOM | 943 | CD | LYS | A | 109 | 26.456 | 1.893 | 2.098 | 1.00 | 0.38 |
| ATOM | 944 | CE | LYS | A | 109 | 26.342 | 1.577 | 0.611 | 1.00 | 1.01 |
| ATOM | 945 | NZ | LYS | A | 109 | 27.041 | 2.585 | -0.201 | 1.00 | 1.35 |
| ATOM | 946 | C | LYS | A | 109 | 24.061 | -1.567 | 2.799 | 1.00 | 0.01 |
| ATOM | 947 | O | LYS | A | 109 | 23.203 | -1.164 | 3.596 | 1.00 | 0.01 |
| ATOM | 948 | N | THR | A | 110 | 23.758 | -2.201 | 1.678 | 1.00 | 0.01 |
| ATOM | 950 | CA | THR | A | 110 | 22.396 | -2.187 | 1.145 | 1.00 | 0.00 |
| ATOM | 951 | CB | THR | A | 110 | 22.447 | -2.650 | -0.307 | 1.00 | 0.09 |
| ATOM | 952 | OG1 | THR | A | 110 | 23.256 | -1.733 | -1.031 | 1.00 | 0.10 |
| ATOM | 953 | CG2 | THR | A | 110 | 21.064 | -2.670 | -0.949 | 1.00 | 0.15 |
| ATOM | 954 | C | THR | A | 110 | 21.466 | -3.093 | 1.945 | 1.00 | 0.01 |
| ATOM | 955 | O | THR | A | 110 | 20.337 | -2.678 | 2.241 | 1.00 | 0.01 |
| ATOM | 956 | N | GLN | A | 111 | 22.002 | -4.168 | 2.504 | 1.00 | 0.01 |
| ATOM | 958 | CA | GLN | A | 111 | 21.181 | -5.033 | 3.350 | 1.00 | 0.00 |
| ATOM | 959 | CB | GLN | A | 111 | 21.872 | -6.371 | 3.549 | 1.00 | 0.18 |
| ATOM | 960 | CG | GLN | A | 111 | 21.854 | -7.232 | 2.297 | 1.00 | 0.37 |
| ATOM | 961 | CD | GLN | A | 111 | 22.526 | -8.554 | 2.636 | 1.00 | 0.89 |
| ATOM | 962 | OE1 | GLN | A | 111 | 23.234 | -8.651 | 3.648 | 1.00 | 1.44 |
| ATOM | 963 | NE2 | GLN | A | 111 | 22.246 | -9.572 | 1.842 | 1.00 | 1.73 |
| ATOM | 966 | C | GLN | A | 111 | 20.952 | -4.409 | 4.714 | 1.00 | 0.01 |
| ATOM | 967 | O | GLN | A | 111 | 19.821 | -4.458 | 5.211 | 1.00 | 0.01 |
| ATOM | 968 | N | ILE | A | 112 | 21.915 | -3.630 | 5.179 | 1.00 | 0.01 |
| ATOM | 970 | CA | ILE | A | 112 | 21.757 | -2.939 | 6.459 | 1.00 | 0.00 |
| ATOM | 971 | CB | ILE | A | 112 | 23.092 | -2.316 | 6.844 | 1.00 | 0.01 |
| ATOM | 972 | CG2 | ILE | A | 112 | 22.932 | -1.466 | 8.094 | 1.00 | 0.01 |
| ATOM | 973 | CG1 | ILE | A | 112 | 24.156 | -3.385 | 7.060 | 1.00 | 0.01 |
| ATOM | 974 | CD1 | ILE | A | 112 | 25.506 | -2.767 | 7.404 | 1.00 | 0.01 |
| ATOM | 975 | C | ILE | A | 112 | 20.698 | -1.846 | 6.371 | 1.00 | 0.00 |
| ATOM | 976 | O | ILE | A | 112 | 19.735 | -1.868 | 7.152 | 1.00 | 0.01 |
| ATOM | 977 | N | LEU | A | 113 | 20.717 | -1.103 | 5.277 | 1.00 | 0.01 |
| ATOM | 979 | CA | LEU | A | 113 | 19.765 | -0.004 | 5.119 | 1.00 | 0.01 |
| ATOM | 980 | CB | LEU | A | 113 | 20.218 | 0.869 | 3.959 | 1.00 | 0.01 |
| ATOM | 981 | CG | LEU | A | 113 | 21.566 | 1.512 | 4.267 | 1.00 | 0.01 |
| ATOM | 982 | CD1 | LEU | A | 113 | 22.129 | 2.218 | 3.041 | 1.00 | 0.01 |
| ATOM | 983 | CD2 | LEU | A | 113 | 21.471 | 2.468 | 5.452 | 1.00 | 0.01 |
| ATOM | 984 | C | LEU | A | 113 | 18.348 | -0.507 | 4.883 | 1.00 | 0.01 |
| ATOM | 985 | O | LEU | A | 113 | 17.476 | -0.187 | 5.702 | 1.00 | 0.01 |
| ATOM | 986 | N | GLN | A | 114 | 18.193 | -1.516 | 4.040 | 1.00 | 0.01 |
| ATOM | 988 | CA | GLN | A | 114 | 16.849 | -2.042 | 3.757 | 1.00 | 0.01 |
| ATOM | 989 | CB | GLN | A | 114 | 16.906 | -2.855 | 2.468 | 1.00 | 0.08 |
| ATOM | 990 | CG | GLN | A | 114 | 17.175 | -1.980 | 1.243 | 1.00 | 0.98 |
| ATOM | 991 | CD | GLN | A | 114 | 15.896 | -1.331 | 0.705 | 1.00 | 1.17 |
| ATOM | 992 | OE1 | GLN | A | 114 | 14.925 | -1.088 | 1.431 | 1.00 | 0.48 |
| ATOM | 993 | NE2 | GLN | A | 114 | 15.902 | -1.091 | -0.596 | 1.00 | 2.23 |
| ATOM | 996 | C | GLN | A | 114 | 16.290 | -2.901 | 4.897 | 1.00 | 0.01 |
| ATOM | 997 | O | GLN | A | 114 | 15.081 | -2.841 | 5.146 | 1.00 | 0.01 |
| ATOM | 998 | N | GLY | A | 115 | 17.167 | -3.418 | 5.744 | 1.00 | 0.01 |
| ATOM | 1000 | CA | GLY | A | 115 | 16.750 | -4.161 | 6.941 | 1.00 | 0.01 |
| ATOM | 1001 | C | GLY | A | 115 | 16.228 | -3.226 | 8.030 | 1.00 | 0.01 |
| ATOM | 1002 | O | GLY | A | 115 | 15.375 | -3.613 | 8.837 | 1.00 | 0.01 |
| ATOM | 1003 | N | LEU | A | 116 | 16.724 | -1.997 | 8.030 | 1.00 | 0.00 |
| ATOM | 1005 | CA | LEU | A | 116 | 16.217 | -0.954 | 8.933 | 1.00 | 0.00 |

| ATOM | 1006 | CB | LEU | A | 116 | 17.330 | 0.055 | 9.176 | 1.00 | 0.01 |
|---|---|---|---|---|---|---|---|---|---|---|
| ATOM | 1007 | CG | LEU | A | 116 | 18.543 | -0.556 | 9.859 | 1.00 | 0.01 |
| ATOM | 1008 | CD1 | LEU | A | 116 | 19.679 | 0.460 | 9.928 | 1.00 | 0.01 |
| ATOM | 1009 | CD2 | LEU | A | 116 | 18.183 | -1.064 | 11.249 | 1.00 | 0.01 |
| ATOM | 1010 | C | LEU | A | 116 | 15.011 | -0.197 | 8.360 | 1.00 | 0.00 |
| ATOM | 1011 | O | LEU | A | 116 | 14.511 | 0.734 | 9.004 | 1.00 | 0.00 |
| ATOM | 1012 | N | GLY | A | 117 | 14.620 | -0.516 | 7.136 | 1.00 | 0.01 |
| ATOM | 1014 | CA | GLY | A | 117 | 13.451 | 0.115 | 6.517 | 1.00 | 0.00 |
| ATOM | 1015 | C | GLY | A | 117 | 13.831 | 1.183 | 5.497 | 1.00 | 0.00 |
| ATOM | 1016 | O | GLY | A | 117 | 12.957 | 1.814 | 4.890 | 1.00 | 0.01 |
| ATOM | 1017 | N | PHE | A | 118 | 15.121 | 1.368 | 5.286 | 1.00 | 0.00 |
| ATOM | 1019 | CA | PHE | A | 118 | 15.586 | 2.450 | 4.416 | 1.00 | 0.00 |
| ATOM | 1020 | CB | PHE | A | 118 | 16.933 | 2.952 | 4.908 | 1.00 | 0.01 |
| ATOM | 1021 | CG | PHE | A | 118 | 16.806 | 3.634 | 6.262 | 1.00 | 0.01 |
| ATOM | 1022 | CD1 | PHE | A | 118 | 16.182 | 4.872 | 6.344 | 1.00 | 0.00 |
| ATOM | 1023 | CE1 | PHE | A | 118 | 16.039 | 5.498 | 7.574 | 1.00 | 0.00 |
| ATOM | 1024 | CZ | PHE | A | 118 | 16.517 | 4.885 | 8.723 | 1.00 | 0.01 |
| ATOM | 1025 | CE2 | PHE | A | 118 | 17.143 | 3.648 | 8.640 | 1.00 | 0.01 |
| ATOM | 1026 | CD2 | PHE | A | 118 | 17.289 | 3.023 | 7.410 | 1.00 | 0.01 |
| ATOM | 1027 | C | PHE | A | 118 | 15.643 | 2.029 | 2.958 | 1.00 | 0.01 |
| ATOM | 1028 | O | PHE | A | 118 | 16.641 | 1.497 | 2.448 | 1.00 | 0.00 |
| ATOM | 1029 | N | ASN | A | 119 | 14.538 | 2.332 | 2.302 | 1.00 | 0.01 |
| ATOM | 1031 | CA | ASN | A | 119 | 14.351 | 2.050 | 0.884 | 1.00 | 0.00 |
| ATOM | 1032 | CB | ASN | A | 119 | 12.865 | 2.195 | 0.593 | 1.00 | 0.01 |
| ATOM | 1033 | CG | ASN | A | 119 | 12.593 | 1.896 | -0.871 | 1.00 | 0.01 |
| ATOM | 1034 | OD1 | ASN | A | 119 | 12.727 | 2.781 | -1.726 | 1.00 | 0.00 |
| ATOM | 1035 | ND2 | ASN | A | 119 | 12.292 | 0.642 | -1.155 | 1.00 | 0.00 |
| ATOM | 1038 | C | ASN | A | 119 | 15.162 | 2.997 | 0.007 | 1.00 | 0.00 |
| ATOM | 1039 | O | ASN | A | 119 | 14.742 | 4.127 | -0.281 | 1.00 | 0.01 |
| ATOM | 1040 | N | LEU | A | 120 | 16.152 | 2.409 | -0.642 | 1.00 | 0.00 |
| ATOM | 1042 | CA | LEU | A | 120 | 17.113 | 3.144 | -1.480 | 1.00 | 0.00 |
| ATOM | 1043 | CB | LEU | A | 120 | 18.373 | 2.294 | -1.585 | 1.00 | 0.01 |
| ATOM | 1044 | CG | LEU | A | 120 | 18.987 | 2.053 | -0.209 | 1.00 | 0.00 |
| ATOM | 1045 | CD1 | LEU | A | 120 | 20.142 | 1.062 | -0.290 | 1.00 | 0.00 |
| ATOM | 1046 | CD2 | LEU | A | 120 | 19.439 | 3.363 | 0.430 | 1.00 | 0.01 |
| ATOM | 1047 | C | LEU | A | 120 | 16.621 | 3.502 | -2.889 | 1.00 | 0.01 |
| ATOM | 1048 | O | LEU | A | 120 | 17.432 | 3.878 | -3.742 | 1.00 | 0.01 |
| ATOM | 1049 | N | THR | A | 121 | 15.343 | 3.312 | -3.176 | 1.00 | 0.01 |
| ATOM | 1051 | CA | THR | A | 121 | 14.820 | 3.787 | -4.454 | 1.00 | 0.00 |
| ATOM | 1052 | CB | THR | A | 121 | 13.901 | 2.756 | -5.098 | 1.00 | 0.00 |
| ATOM | 1053 | OG1 | THR | A | 121 | 12.623 | 2.809 | -4.484 | 1.00 | 0.01 |
| ATOM | 1054 | CG2 | THR | A | 121 | 14.462 | 1.342 | -4.991 | 1.00 | 0.01 |
| ATOM | 1055 | C | THR | A | 121 | 14.079 | 5.104 | -4.233 | 1.00 | 0.01 |
| ATOM | 1056 | O | THR | A | 121 | 13.539 | 5.682 | -5.182 | 1.00 | 0.00 |
| ATOM | 1057 | N | HIS | A | 122 | 13.997 | 5.525 | -2.980 | 1.00 | 0.01 |
| ATOM | 1059 | CA | HIS | A | 122 | 13.428 | 6.835 | -2.669 | 1.00 | 0.01 |
| ATOM | 1060 | CB | HIS | A | 122 | 12.089 | 6.647 | -1.963 | 1.00 | 0.29 |
| ATOM | 1061 | CG | HIS | A | 122 | 11.014 | 5.994 | -2.808 | 1.00 | 0.30 |
| ATOM | 1062 | ND1 | HIS | A | 122 | 10.628 | 4.704 | -2.763 | 1.00 | 1.03 |
| ATOM | 1064 | CE1 | HIS | A | 122 | 9.642 | 4.505 | -3.661 | 1.00 | 0.88 |
| ATOM | 1065 | NE2 | HIS | A | 122 | 9.411 | 5.682 | -4.286 | 1.00 | 0.56 |
| ATOM | 1066 | CD2 | HIS | A | 122 | 10.249 | 6.610 | -3.771 | 1.00 | 0.88 |
| ATOM | 1067 | C | HIS | A | 122 | 14.354 | 7.643 | -1.765 | 1.00 | 0.00 |
| ATOM | 1068 | O | HIS | A | 122 | 14.502 | 8.859 | -1.949 | 1.00 | 0.01 |
| ATOM | 1069 | N | THR | A | 123 | 14.987 | 6.970 | -0.818 | 1.00 | 0.00 |
| ATOM | 1071 | CA | THR | A | 123 | 15.788 | 7.677 | 0.191 | 1.00 | 0.01 |
| ATOM | 1072 | CB | THR | A | 123 | 15.631 | 6.987 | 1.549 | 1.00 | 0.59 |
| ATOM | 1073 | OG1 | THR | A | 123 | 16.236 | 5.700 | 1.515 | 1.00 | 1.04 |

| ATOM | 1074 | CG2 | THR | A | 123 | 14.166 | 6.821 | 1.939 | 1.00 | 0.99 |
|------|------|-----|-----|---|-----|--------|-------|-------|------|------|
| ATOM | 1075 | C | THR | A | 123 | 17.270 | 7.773 | -0.171 | 1.00 | 0.00 |
| ATOM | 1076 | O | THR | A | 123 | 17.948 | 6.768 | -0.415 | 1.00 | 0.00 |
| ATOM | 1077 | N | PRO | A | 124 | 17.754 | 9.003 | -0.197 | 1.00 | 0.01 |
| ATOM | 1078 | CA | PRO | A | 124 | 19.196 | 9.259 | -0.178 | 1.00 | 0.00 |
| ATOM | 1079 | CB | PRO | A | 124 | 19.325 | 10.729 | -0.438 | 1.00 | 0.01 |
| ATOM | 1080 | CG | PRO | A | 124 | 17.953 | 11.375 | -0.308 | 1.00 | 0.01 |
| ATOM | 1081 | CD | PRO | A | 124 | 16.977 | 10.237 | -0.053 | 1.00 | 0.01 |
| ATOM | 1082 | C | PRO | A | 124 | 19.803 | 8.894 | 1.177 | 1.00 | 0.01 |
| ATOM | 1083 | O | PRO | A | 124 | 19.255 | 9.238 | 2.234 | 1.00 | 0.01 |
| ATOM | 1084 | N | GLU | A | 125 | 21.035 | 8.412 | 1.136 | 1.00 | 0.01 |
| ATOM | 1086 | CA | GLU | A | 125 | 21.718 | 7.981 | 2.366 | 1.00 | 0.00 |
| ATOM | 1087 | CB | GLU | A | 125 | 22.887 | 7.071 | 2.009 | 1.00 | 0.00 |
| ATOM | 1088 | CG | GLU | A | 125 | 22.398 | 5.759 | 1.407 | 1.00 | 0.01 |
| ATOM | 1089 | CD | GLU | A | 125 | 23.581 | 4.845 | 1.106 | 1.00 | 0.01 |
| ATOM | 1090 | OE1 | GLU | A | 125 | 24.620 | 5.042 | 1.720 | 1.00 | 0.01 |
| ATOM | 1091 | OE2 | GLU | A | 125 | 23.455 | 4.043 | 0.191 | 1.00 | 0.01 |
| ATOM | 1092 | C | GLU | A | 125 | 22.215 | 9.141 | 3.231 | 1.00 | 0.01 |
| ATOM | 1093 | O | GLU | A | 125 | 22.304 | 8.970 | 4.451 | 1.00 | 0.01 |
| ATOM | 1094 | N | SER | A | 126 | 22.222 | 10.346 | 2.683 | 1.00 | 0.01 |
| ATOM | 1096 | CA | SER | A | 126 | 22.599 | 11.526 | 3.473 | 1.00 | 0.01 |
| ATOM | 1097 | CB | SER | A | 126 | 22.978 | 12.656 | 2.523 | 1.00 | 0.17 |
| ATOM | 1098 | OG | SER | A | 126 | 21.811 | 13.035 | 1.805 | 1.00 | 0.54 |
| ATOM | 1099 | C | SER | A | 126 | 21.460 | 11.996 | 4.384 | 1.00 | 0.01 |
| ATOM | 1100 | O | SER | A | 126 | 21.710 | 12.718 | 5.358 | 1.00 | 0.01 |
| ATOM | 1101 | N | ALA | A | 127 | 20.253 | 11.509 | 4.143 | 1.00 | 0.00 |
| ATOM | 1103 | CA | ALA | A | 127 | 19.143 | 11.802 | 5.044 | 1.00 | 0.01 |
| ATOM | 1104 | CB | ALA | A | 127 | 17.859 | 11.898 | 4.228 | 1.00 | 0.11 |
| ATOM | 1105 | C | ALA | A | 127 | 19.023 | 10.688 | 6.077 | 1.00 | 0.01 |
| ATOM | 1106 | O | ALA | A | 127 | 18.841 | 10.972 | 7.265 | 1.00 | 0.01 |
| ATOM | 1107 | N | ILE | A | 128 | 19.457 | 9.504 | 5.678 | 1.00 | 0.01 |
| ATOM | 1109 | CA | ILE | A | 128 | 19.417 | 8.335 | 6.561 | 1.00 | 0.01 |
| ATOM | 1110 | CB | ILE | A | 128 | 19.720 | 7.113 | 5.701 | 1.00 | 0.01 |
| ATOM | 1111 | CG2 | ILE | A | 128 | 19.813 | 5.854 | 6.554 | 1.00 | 0.01 |
| ATOM | 1112 | CG1 | ILE | A | 128 | 18.673 | 6.954 | 4.605 | 1.00 | 0.01 |
| ATOM | 1113 | CD1 | ILE | A | 128 | 18.998 | 5.776 | 3.693 | 1.00 | 0.01 |
| ATOM | 1114 | C | ILE | A | 128 | 20.457 | 8.442 | 7.670 | 1.00 | 0.00 |
| ATOM | 1115 | O | ILE | A | 128 | 20.121 | 8.299 | 8.854 | 1.00 | 0.01 |
| ATOM | 1116 | N | HIS | A | 129 | 21.625 | 8.948 | 7.311 | 1.00 | 0.00 |
| ATOM | 1118 | CA | HIS | A | 129 | 22.695 | 9.088 | 8.292 | 1.00 | 0.01 |
| ATOM | 1119 | CB | HIS | A | 129 | 24.020 | 9.140 | 7.544 | 1.00 | 0.01 |
| ATOM | 1120 | CG | HIS | A | 129 | 24.348 | 7.770 | 6.990 | 1.00 | 0.00 |
| ATOM | 1121 | ND1 | HIS | A | 129 | 24.406 | 6.646 | 7.719 | 1.00 | 0.01 |
| ATOM | 1123 | CE1 | HIS | A | 129 | 24.704 | 5.605 | 6.914 | 1.00 | 0.01 |
| ATOM | 1124 | NE2 | HIS | A | 129 | 24.842 | 6.088 | 5.659 | 1.00 | 0.01 |
| ATOM | 1125 | CD2 | HIS | A | 129 | 24.631 | 7.425 | 5.690 | 1.00 | 0.00 |
| ATOM | 1126 | C | HIS | A | 129 | 22.490 | 10.286 | 9.208 | 1.00 | 0.01 |
| ATOM | 1127 | O | HIS | A | 129 | 22.551 | 10.086 | 10.429 | 1.00 | 0.01 |
| ATOM | 1128 | N | GLN | A | 130 | 21.884 | 11.347 | 8.692 | 1.00 | 0.00 |
| ATOM | 1130 | CA | GLN | A | 130 | 21.584 | 12.495 | 9.554 | 1.00 | 0.01 |
| ATOM | 1131 | CB | GLN | A | 130 | 21.345 | 13.744 | 8.723 | 1.00 | 0.17 |
| ATOM | 1132 | CG | GLN | A | 130 | 22.630 | 14.305 | 8.135 | 1.00 | 0.98 |
| ATOM | 1133 | CD | GLN | A | 130 | 22.347 | 15.685 | 7.550 | 1.00 | 1.72 |
| ATOM | 1134 | OE1 | GLN | A | 130 | 22.530 | 16.708 | 8.220 | 1.00 | 2.37 |
| ATOM | 1135 | NE2 | GLN | A | 130 | 21.885 | 15.698 | 6.313 | 1.00 | 2.56 |
| ATOM | 1138 | C | GLN | A | 130 | 20.372 | 12.251 | 10.448 | 1.00 | 0.01 |
| ATOM | 1139 | O | GLN | A | 130 | 20.352 | 12.767 | 11.570 | 1.00 | 0.00 |
| ATOM | 1140 | N | GLY | A | 131 | 19.527 | 11.301 | 10.080 | 1.00 | 0.01 |

| ATOM | 1142 | CA | GLY | A | 131 | 18.427 | 10.871 | 10.943 | 1.00 | 0.01 |
|------|------|------|-----|---|-----|--------|--------|--------|------|------|
| ATOM | 1143 | C | GLY | A | 131 | 18.960 | 10.364 | 12.275 | 1.00 | 0.01 |
| ATOM | 1144 | O | GLY | A | 131 | 18.723 | 10.998 | 13.315 | 1.00 | 0.01 |
| ATOM | 1145 | N | PHE | A | 132 | 19.895 | 9.429 | 12.203 | 1.00 | 0.01 |
| ATOM | 1147 | CA | PHE | A | 132 | 20.463 | 8.857 | 13.427 | 1.00 | 0.01 |
| ATOM | 1148 | CB | PHE | A | 132 | 21.059 | 7.497 | 13.110 | 1.00 | 0.01 |
| ATOM | 1149 | CG | PHE | A | 132 | 19.987 | 6.504 | 12.696 | 1.00 | 0.01 |
| ATOM | 1150 | CD1 | PHE | A | 132 | 18.916 | 6.253 | 13.543 | 1.00 | 0.01 |
| ATOM | 1151 | CE1 | PHE | A | 132 | 17.930 | 5.353 | 13.166 | 1.00 | 0.01 |
| ATOM | 1152 | CZ | PHE | A | 132 | 18.018 | 4.704 | 11.942 | 1.00 | 0.01 |
| ATOM | 1153 | CE2 | PHE | A | 132 | 19.088 | 4.957 | 11.095 | 1.00 | 0.01 |
| ATOM | 1154 | CD2 | PHE | A | 132 | 20.071 | 5.861 | 11.470 | 1.00 | 0.01 |
| ATOM | 1155 | C | PHE | A | 132 | 21.504 | 9.756 | 14.083 | 1.00 | 0.01 |
| ATOM | 1156 | O | PHE | A | 132 | 21.634 | 9.705 | 15.310 | 1.00 | 0.01 |
| ATOM | 1157 | N | GLN | A | 133 | 22.021 | 10.734 | 13.358 | 1.00 | 0.00 |
| ATOM | 1159 | CA | GLN | A | 133 | 22.907 | 11.715 | 13.988 | 1.00 | 0.01 |
| ATOM | 1160 | CB | GLN | A | 133 | 23.676 | 12.464 | 12.912 | 1.00 | 0.01 |
| ATOM | 1161 | CG | GLN | A | 133 | 24.601 | 11.545 | 12.125 | 1.00 | 0.01 |
| ATOM | 1162 | CD | GLN | A | 133 | 25.235 | 12.362 | 11.008 | 1.00 | 0.01 |
| ATOM | 1163 | OE1 | GLN | A | 133 | 25.151 | 12.017 | 9.820 | 1.00 | 0.00 |
| ATOM | 1164 | NE2 | GLN | A | 133 | 25.763 | 13.506 | 11.403 | 1.00 | 0.00 |
| ATOM | 1167 | C | GLN | A | 133 | 22.132 | 12.726 | 14.832 | 1.00 | 0.01 |
| ATOM | 1168 | O | GLN | A | 133 | 22.580 | 13.036 | 15.942 | 1.00 | 0.01 |
| ATOM | 1169 | N | HIS | A | 134 | 20.896 | 13.025 | 14.459 | 1.00 | 0.01 |
| ATOM | 1171 | CA | HIS | A | 134 | 20.097 | 13.966 | 15.263 | 1.00 | 0.01 |
| ATOM | 1172 | CB | HIS | A | 134 | 18.982 | 14.624 | 14.460 | 1.00 | 0.18 |
| ATOM | 1173 | CG | HIS | A | 134 | 19.312 | 15.245 | 13.125 | 1.00 | 0.86 |
| ATOM | 1174 | ND1 | HIS | A | 134 | 18.393 | 15.644 | 12.235 | 1.00 | 1.74 |
| ATOM | 1176 | CE1 | HIS | A | 134 | 19.018 | 16.128 | 11.144 | 1.00 | 2.27 |
| ATOM | 1177 | NE2 | HIS | A | 134 | 20.344 | 16.050 | 11.364 | 1.00 | 2.14 |
| ATOM | 1178 | CD2 | HIS | A | 134 | 20.545 | 15.536 | 12.597 | 1.00 | 1.59 |
| ATOM | 1179 | C | HIS | A | 134 | 19.412 | 13.225 | 16.393 | 1.00 | 0.01 |
| ATOM | 1180 | O | HIS | A | 134 | 19.141 | 13.801 | 17.454 | 1.00 | 0.01 |
| ATOM | 1181 | N | LEU | A | 135 | 19.310 | 11.920 | 16.226 | 1.00 | 0.01 |
| ATOM | 1183 | CA | LEU | A | 135 | 18.802 | 11.066 | 17.292 | 1.00 | 0.01 |
| ATOM | 1184 | CB | LEU | A | 135 | 18.447 | 9.732 | 16.655 | 1.00 | 0.01 |
| ATOM | 1185 | CG | LEU | A | 135 | 17.628 | 8.844 | 17.574 | 1.00 | 0.01 |
| ATOM | 1186 | CD1 | LEU | A | 135 | 16.426 | 9.600 | 18.133 | 1.00 | 0.01 |
| ATOM | 1187 | CD2 | LEU | A | 135 | 17.182 | 7.601 | 16.813 | 1.00 | 0.01 |
| ATOM | 1188 | C | LEU | A | 135 | 19.875 | 10.912 | 18.369 | 1.00 | 0.01 |
| ATOM | 1189 | O | LEU | A | 135 | 19.565 | 11.061 | 19.557 | 1.00 | 0.01 |
| ATOM | 1190 | N | VAL | A | 136 | 21.129 | 10.952 | 17.944 | 1.00 | 0.01 |
| ATOM | 1192 | CA | VAL | A | 136 | 22.252 | 11.007 | 18.884 | 1.00 | 0.01 |
| ATOM | 1193 | CB | VAL | A | 136 | 23.538 | 10.706 | 18.115 | 1.00 | 0.27 |
| ATOM | 1194 | CG1 | VAL | A | 136 | 24.779 | 11.158 | 18.874 | 1.00 | 0.79 |
| ATOM | 1195 | CG2 | VAL | A | 136 | 23.631 | 9.230 | 17.746 | 1.00 | 0.30 |
| ATOM | 1196 | C | VAL | A | 136 | 22.357 | 12.377 | 19.558 | 1.00 | 0.00 |
| ATOM | 1197 | O | VAL | A | 136 | 22.491 | 12.418 | 20.786 | 1.00 | 0.01 |
| ATOM | 1198 | N | HIS | A | 137 | 22.011 | 13.439 | 18.844 | 1.00 | 0.01 |
| ATOM | 1200 | CA | HIS | A | 137 | 22.037 | 14.787 | 19.436 | 1.00 | 0.02 |
| ATOM | 1201 | CB | HIS | A | 137 | 21.806 | 15.838 | 18.348 | 1.00 | 0.16 |
| ATOM | 1202 | CG | HIS | A | 137 | 22.837 | 15.906 | 17.234 | 1.00 | 0.20 |
| ATOM | 1203 | ND1 | HIS | A | 137 | 22.648 | 16.421 | 16.003 | 1.00 | 0.23 |
| ATOM | 1205 | CE1 | HIS | A | 137 | 23.784 | 16.303 | 15.288 | 1.00 | 0.21 |
| ATOM | 1206 | NE2 | HIS | A | 137 | 24.709 | 15.722 | 16.085 | 1.00 | 0.23 |
| ATOM | 1207 | CD2 | HIS | A | 137 | 24.145 | 15.483 | 17.290 | 1.00 | 0.25 |
| ATOM | 1208 | C | HIS | A | 137 | 20.950 | 14.950 | 20.499 | 1.00 | 0.01 |
| ATOM | 1209 | O | HIS | A | 137 | 21.257 | 15.358 | 21.627 | 1.00 | 0.01 |

| ATOM | 1210 | N | SER | A | 138 | 19.784 | 14.376 | 20.239 | 1.00 | 0.01 |
|------|------|---|-----|---|-----|--------|--------|--------|------|------|
| ATOM | 1212 | CA | SER | A | 138 | 18.665 | 14.459 | 21.191 | 1.00 | 0.01 |
| ATOM | 1213 | CB | SER | A | 138 | 17.355 | 14.205 | 20.449 | 1.00 | 0.30 |
| ATOM | 1214 | OG | SER | A | 138 | 17.373 | 12.882 | 19.930 | 1.00 | 0.53 |
| ATOM | 1215 | C | SER | A | 138 | 18.799 | 13.466 | 22.348 | 1.00 | 0.01 |
| ATOM | 1216 | O | SER | A | 138 | 18.125 | 13.616 | 23.375 | 1.00 | 0.00 |
| ATOM | 1217 | N | LEU | A | 139 | 19.717 | 12.523 | 22.225 | 1.00 | 0.01 |
| ATOM | 1219 | CA | LEU | A | 139 | 20.031 | 11.612 | 23.325 | 1.00 | 0.01 |
| ATOM | 1220 | CB | LEU | A | 139 | 20.118 | 10.188 | 22.797 | 1.00 | 0.01 |
| ATOM | 1221 | CG | LEU | A | 139 | 18.756 | 9.706 | 22.308 | 1.00 | 0.00 |
| ATOM | 1222 | CD1 | LEU | A | 139 | 18.857 | 8.310 | 21.708 | 1.00 | 0.01 |
| ATOM | 1223 | CD2 | LEU | A | 139 | 17.723 | 9.741 | 23.431 | 1.00 | 0.01 |
| ATOM | 1224 | C | LEU | A | 139 | 21.327 | 11.991 | 24.045 | 1.00 | 0.01 |
| ATOM | 1225 | O | LEU | A | 139 | 21.830 | 11.202 | 24.853 | 1.00 | 0.01 |
| ATOM | 1226 | N | THR | A | 140 | 21.881 | 13.152 | 23.737 | 1.00 | 0.01 |
| ATOM | 1228 | CA | THR | A | 140 | 23.071 | 13.626 | 24.453 | 1.00 | 0.01 |
| ATOM | 1229 | CB | THR | A | 140 | 24.276 | 13.631 | 23.517 | 1.00 | 0.52 |
| ATOM | 1230 | OG1 | THR | A | 140 | 23.934 | 14.391 | 22.365 | 1.00 | 1.05 |
| ATOM | 1231 | CG2 | THR | A | 140 | 24.672 | 12.227 | 23.071 | 1.00 | 0.85 |
| ATOM | 1232 | C | THR | A | 140 | 22.886 | 15.029 | 25.026 | 1.00 | 0.01 |
| ATOM | 1233 | O | THR | A | 140 | 23.881 | 15.742 | 25.199 | 1.00 | 0.01 |
| ATOM | 1234 | N | VAL | A | 141 | 21.650 | 15.419 | 25.304 | 1.00 | 0.02 |
| ATOM | 1236 | CA | VAL | A | 141 | 21.356 | 16.781 | 25.793 | 1.00 | 0.01 |
| ATOM | 1237 | CB | VAL | A | 141 | 19.842 | 16.978 | 25.741 | 1.00 | 0.79 |
| ATOM | 1238 | CG1 | VAL | A | 141 | 19.440 | 18.380 | 26.189 | 1.00 | 1.02 |
| ATOM | 1239 | CG2 | VAL | A | 141 | 19.312 | 16.707 | 24.338 | 1.00 | 0.94 |
| ATOM | 1240 | C | VAL | A | 141 | 21.861 | 17.027 | 27.220 | 1.00 | 0.01 |
| ATOM | 1241 | O | VAL | A | 141 | 21.240 | 16.603 | 28.202 | 1.00 | 0.01 |
| ATOM | 1242 | N | PRO | A | 142 | 22.865 | 17.887 | 27.325 | 1.00 | 0.01 |
| ATOM | 1243 | CA | PRO | A | 142 | 23.559 | 18.090 | 28.603 | 1.00 | 0.02 |
| ATOM | 1244 | CB | PRO | A | 142 | 24.852 | 18.745 | 28.224 | 1.00 | 0.01 |
| ATOM | 1245 | CG | PRO | A | 142 | 24.793 | 19.171 | 26.763 | 1.00 | 0.01 |
| ATOM | 1246 | CD | PRO | A | 142 | 23.476 | 18.639 | 26.223 | 1.00 | 0.02 |
| ATOM | 1247 | C | PRO | A | 142 | 22.794 | 18.975 | 29.594 | 1.00 | 0.01 |
| ATOM | 1248 | O | PRO | A | 142 | 22.973 | 18.832 | 30.808 | 1.00 | 0.02 |
| ATOM | 1249 | N | SER | A | 143 | 21.846 | 19.756 | 29.097 | 1.00 | 0.01 |
| ATOM | 1251 | CA | SER | A | 143 | 21.070 | 20.655 | 29.962 | 1.00 | 0.02 |
| ATOM | 1252 | CB | SER | A | 143 | 20.710 | 21.911 | 29.179 | 1.00 | 1.07 |
| ATOM | 1253 | OG | SER | A | 143 | 19.787 | 21.539 | 28.164 | 1.00 | 1.15 |
| ATOM | 1254 | C | SER | A | 143 | 19.786 | 19.997 | 30.459 | 1.00 | 0.01 |
| ATOM | 1255 | O | SER | A | 143 | 19.067 | 20.572 | 31.283 | 1.00 | 0.02 |
| ATOM | 1256 | N | LYS | A | 144 | 19.510 | 18.806 | 29.956 | 1.00 | 0.01 |
| ATOM | 1258 | CA | LYS | A | 144 | 18.340 | 18.042 | 30.382 | 1.00 | 0.02 |
| ATOM | 1259 | CB | LYS | A | 144 | 17.101 | 18.505 | 29.620 | 1.00 | 0.39 |
| ATOM | 1260 | CG | LYS | A | 144 | 15.850 | 17.808 | 30.147 | 1.00 | 0.73 |
| ATOM | 1261 | CD | LYS | A | 144 | 15.693 | 18.028 | 31.649 | 1.00 | 0.88 |
| ATOM | 1262 | CE | LYS | A | 144 | 14.516 | 17.238 | 32.208 | 1.00 | 1.90 |
| ATOM | 1263 | NZ | LYS | A | 144 | 14.372 | 17.446 | 33.657 | 1.00 | 2.56 |
| ATOM | 1264 | C | LYS | A | 144 | 18.625 | 16.575 | 30.111 | 1.00 | 0.01 |
| ATOM | 1265 | O | LYS | A | 144 | 18.213 | 16.009 | 29.089 | 1.00 | 0.02 |
| ATOM | 1266 | N | ASP | A | 145 | 19.330 | 15.963 | 31.045 | 1.00 | 0.01 |
| ATOM | 1268 | CA | ASP | A | 145 | 19.767 | 14.583 | 30.849 | 1.00 | 0.00 |
| ATOM | 1269 | CB | ASP | A | 145 | 21.057 | 14.363 | 31.629 | 1.00 | 0.63 |
| ATOM | 1270 | CG | ASP | A | 145 | 21.709 | 13.068 | 31.158 | 1.00 | 1.02 |
| ATOM | 1271 | OD1 | ASP | A | 145 | 22.537 | 12.543 | 31.886 | 1.00 | 1.80 |
| ATOM | 1272 | OD2 | ASP | A | 145 | 21.406 | 12.669 | 30.041 | 1.00 | 0.62 |
| ATOM | 1273 | C | ASP | A | 145 | 18.703 | 13.568 | 31.272 | 1.00 | 0.01 |
| ATOM | 1274 | O | ASP | A | 145 | 18.729 | 13.027 | 32.381 | 1.00 | 0.01 |

| ATOM | 1275 | N   | LEU | A | 146 | 17.768 | 13.333 | 30.364 | 1.00 | 0.01 |
|------|------|-----|-----|---|-----|--------|--------|--------|------|------|
| ATOM | 1277 | CA  | LEU | A | 146 | 16.796 | 12.240 | 30.509 | 1.00 | 0.02 |
| ATOM | 1278 | CB  | LEU | A | 146 | 15.424 | 12.731 | 30.037 | 1.00 | 0.01 |
| ATOM | 1279 | CG  | LEU | A | 146 | 14.351 | 11.649 | 30.160 | 1.00 | 0.01 |
| ATOM | 1280 | CD1 | LEU | A | 146 | 14.209 | 11.160 | 31.599 | 1.00 | 0.01 |
| ATOM | 1281 | CD2 | LEU | A | 146 | 13.007 | 12.109 | 29.612 | 1.00 | 0.01 |
| ATOM | 1282 | C   | LEU | A | 146 | 17.253 | 11.058 | 29.650 | 1.00 | 0.02 |
| ATOM | 1283 | O   | LEU | A | 146 | 16.750 | 9.934  | 29.763 | 1.00 | 0.01 |
| ATOM | 1284 | N   | THR | A | 147 | 18.323 | 11.305 | 28.915 | 1.00 | 0.00 |
| ATOM | 1286 | CA  | THR | A | 147 | 18.804 | 10.382 | 27.894 | 1.00 | 0.01 |
| ATOM | 1287 | CB  | THR | A | 147 | 19.914 | 11.089 | 27.153 | 1.00 | 2.66 |
| ATOM | 1288 | OG1 | THR | A | 147 | 21.122 | 10.931 | 27.882 | 1.00 | 3.01 |
| ATOM | 1289 | CG2 | THR | A | 147 | 19.599 | 12.574 | 27.002 | 1.00 | 3.30 |
| ATOM | 1290 | C   | THR | A | 147 | 19.313 | 9.064  | 28.460 | 1.00 | 0.01 |
| ATOM | 1291 | O   | THR | A | 147 | 19.523 | 8.894  | 29.666 | 1.00 | 0.01 |
| ATOM | 1292 | N   | LEU | A | 148 | 19.478 | 8.131  | 27.543 | 1.00 | 0.01 |
| ATOM | 1294 | CA  | LEU | A | 148 | 19.785 | 6.740  | 27.901 | 1.00 | 0.00 |
| ATOM | 1295 | CB  | LEU | A | 148 | 19.422 | 5.797  | 26.747 | 1.00 | 0.01 |
| ATOM | 1296 | CG  | LEU | A | 148 | 17.933 | 5.672  | 26.394 | 1.00 | 0.01 |
| ATOM | 1297 | CD1 | LEU | A | 148 | 17.000 | 6.009  | 27.550 | 1.00 | 0.00 |
| ATOM | 1298 | CD2 | LEU | A | 148 | 17.554 | 6.469  | 25.149 | 1.00 | 0.01 |
| ATOM | 1299 | C   | LEU | A | 148 | 21.263 | 6.540  | 28.222 | 1.00 | 0.01 |
| ATOM | 1300 | O   | LEU | A | 148 | 22.140 | 7.211  | 27.660 | 1.00 | 0.02 |
| ATOM | 1301 | N   | LYS | A | 149 | 21.526 | 5.577  | 29.090 | 1.00 | 0.01 |
| ATOM | 1303 | CA  | LYS | A | 149 | 22.899 | 5.138  | 29.373 | 1.00 | 0.01 |
| ATOM | 1304 | CB  | LYS | A | 149 | 22.989 | 4.568  | 30.784 | 1.00 | 0.59 |
| ATOM | 1305 | CG  | LYS | A | 149 | 22.743 | 5.637  | 31.840 | 1.00 | 0.67 |
| ATOM | 1306 | CD  | LYS | A | 149 | 22.935 | 5.064  | 33.239 | 1.00 | 0.79 |
| ATOM | 1307 | CE  | LYS | A | 149 | 24.323 | 4.451  | 33.397 | 1.00 | 0.79 |
| ATOM | 1308 | NZ  | LYS | A | 149 | 24.486 | 3.849  | 34.730 | 1.00 | 1.03 |
| ATOM | 1309 | C   | LYS | A | 149 | 23.310 | 4.070  | 28.367 | 1.00 | 0.01 |
| ATOM | 1310 | O   | LYS | A | 149 | 23.169 | 2.862  | 28.605 | 1.00 | 0.01 |
| ATOM | 1311 | N   | MET | A | 150 | 23.712 | 4.541  | 27.201 | 1.00 | 0.01 |
| ATOM | 1313 | CA  | MET | A | 150 | 24.103 | 3.652  | 26.110 | 1.00 | 0.02 |
| ATOM | 1314 | CB  | MET | A | 150 | 23.980 | 4.407  | 24.794 | 1.00 | 0.87 |
| ATOM | 1315 | CG  | MET | A | 150 | 22.548 | 4.877  | 24.562 | 1.00 | 1.11 |
| ATOM | 1316 | SD  | MET | A | 150 | 22.254 | 5.732  | 22.997 | 1.00 | 2.15 |
| ATOM | 1317 | CE  | MET | A | 150 | 22.722 | 4.406  | 21.860 | 1.00 | 2.30 |
| ATOM | 1318 | C   | MET | A | 150 | 25.525 | 3.136  | 26.285 | 1.00 | 0.01 |
| ATOM | 1319 | O   | MET | A | 150 | 26.345 | 3.715  | 27.004 | 1.00 | 0.02 |
| ATOM | 1320 | N   | GLY | A | 151 | 25.762 | 1.986  | 25.684 | 1.00 | 0.01 |
| ATOM | 1322 | CA  | GLY | A | 151 | 27.084 | 1.360  | 25.688 | 1.00 | 0.02 |
| ATOM | 1323 | C   | GLY | A | 151 | 27.333 | 0.658  | 24.358 | 1.00 | 0.01 |
| ATOM | 1324 | O   | GLY | A | 151 | 27.128 | -0.558 | 24.235 | 1.00 | 0.01 |
| ATOM | 1325 | N   | SER | A | 152 | 27.756 | 1.424  | 23.366 | 1.00 | 0.02 |
| ATOM | 1327 | CA  | SER | A | 152 | 27.965 | 0.840  | 22.037 | 1.00 | 0.01 |
| ATOM | 1328 | CB  | SER | A | 152 | 27.031 | 1.518  | 21.042 | 1.00 | 0.59 |
| ATOM | 1329 | OG  | SER | A | 152 | 26.747 | 0.584  | 20.003 | 1.00 | 1.14 |
| ATOM | 1330 | C   | SER | A | 152 | 29.430 | 0.954  | 21.604 | 1.00 | 0.01 |
| ATOM | 1331 | O   | SER | A | 152 | 29.998 | 2.051  | 21.483 | 1.00 | 0.01 |
| ATOM | 1332 | N   | ALA | A | 153 | 30.002 | -0.201 | 21.312 | 1.00 | 0.01 |
| ATOM | 1334 | CA  | ALA | A | 153 | 31.434 | -0.285 | 21.014 | 1.00 | 0.01 |
| ATOM | 1335 | CB  | ALA | A | 153 | 32.184 | -0.564 | 22.308 | 1.00 | 0.16 |
| ATOM | 1336 | C   | ALA | A | 153 | 31.785 | -1.353 | 19.982 | 1.00 | 0.01 |
| ATOM | 1337 | O   | ALA | A | 153 | 31.344 | -2.509 | 20.054 | 1.00 | 0.01 |
| ATOM | 1338 | N   | LEU | A | 154 | 32.661 | -0.952 | 19.079 | 1.00 | 0.01 |
| ATOM | 1340 | CA  | LEU | A | 154 | 33.177 | -1.833 | 18.032 | 1.00 | 0.02 |
| ATOM | 1341 | CB  | LEU | A | 154 | 33.318 | -1.043 | 16.738 | 1.00 | 0.02 |

| ATOM | 1342 | CG | LEU | A | 154 | 31.967 | -0.608 | 16.192 | 1.00 | 0.02 |
|---|---|---|---|---|---|---|---|---|---|---|
| ATOM | 1343 | CD1 | LEU | A | 154 | 32.149 | 0.287 | 14.974 | 1.00 | 0.02 |
| ATOM | 1344 | CD2 | LEU | A | 154 | 31.112 | -1.821 | 15.843 | 1.00 | 0.01 |
| ATOM | 1345 | C | LEU | A | 154 | 34.545 | -2.373 | 18.419 | 1.00 | 0.02 |
| ATOM | 1346 | O | LEU | A | 154 | 35.547 | -1.646 | 18.423 | 1.00 | 0.02 |
| ATOM | 1347 | N | PHE | A | 155 | 34.580 | -3.660 | 18.697 | 1.00 | 0.01 |
| ATOM | 1349 | CA | PHE | A | 155 | 35.833 | -4.328 | 19.045 | 1.00 | 0.01 |
| ATOM | 1350 | CB | PHE | A | 155 | 35.588 | -5.319 | 20.177 | 1.00 | 0.02 |
| ATOM | 1351 | CG | PHE | A | 155 | 35.233 | -4.669 | 21.513 | 1.00 | 0.02 |
| ATOM | 1352 | CD1 | PHE | A | 155 | 33.905 | -4.509 | 21.891 | 1.00 | 0.01 |
| ATOM | 1353 | CE1 | PHE | A | 155 | 33.595 | -3.915 | 23.108 | 1.00 | 0.02 |
| ATOM | 1354 | CZ | PHE | A | 155 | 34.612 | -3.487 | 23.951 | 1.00 | 0.02 |
| ATOM | 1355 | CE2 | PHE | A | 155 | 35.938 | -3.656 | 23.579 | 1.00 | 0.02 |
| ATOM | 1356 | CD2 | PHE | A | 155 | 36.248 | -4.248 | 22.362 | 1.00 | 0.01 |
| ATOM | 1357 | C | PHE | A | 155 | 36.396 | -5.020 | 17.811 | 1.00 | 0.01 |
| ATOM | 1358 | O | PHE | A | 155 | 36.004 | -6.140 | 17.456 | 1.00 | 0.01 |
| ATOM | 1359 | N | VAL | A | 156 | 37.292 | -4.305 | 17.155 | 1.00 | 0.01 |
| ATOM | 1361 | CA | VAL | A | 156 | 37.900 | -4.765 | 15.907 | 1.00 | 0.02 |
| ATOM | 1362 | CB | VAL | A | 156 | 38.348 | -3.545 | 15.106 | 1.00 | 0.49 |
| ATOM | 1363 | CG1 | VAL | A | 156 | 37.177 | -2.605 | 14.855 | 1.00 | 0.60 |
| ATOM | 1364 | CG2 | VAL | A | 156 | 39.465 | -2.791 | 15.815 | 1.00 | 0.71 |
| ATOM | 1365 | C | VAL | A | 156 | 39.096 | -5.655 | 16.208 | 1.00 | 0.02 |
| ATOM | 1366 | O | VAL | A | 156 | 39.663 | -5.590 | 17.305 | 1.00 | 0.01 |
| ATOM | 1367 | N | LYS | A | 157 | 39.400 | -6.547 | 15.284 | 1.00 | 0.01 |
| ATOM | 1369 | CA | LYS | A | 157 | 40.561 | -7.422 | 15.450 | 1.00 | 0.01 |
| ATOM | 1370 | CB | LYS | A | 157 | 40.556 | -8.448 | 14.320 | 1.00 | 0.81 |
| ATOM | 1371 | CG | LYS | A | 157 | 41.622 | -9.520 | 14.506 | 1.00 | 0.87 |
| ATOM | 1372 | CD | LYS | A | 157 | 41.619 | -10.513 | 13.352 | 1.00 | 1.04 |
| ATOM | 1373 | CE | LYS | A | 157 | 42.711 | -11.559 | 13.538 | 1.00 | 0.96 |
| ATOM | 1374 | NZ | LYS | A | 157 | 44.032 | -10.918 | 13.638 | 1.00 | 2.10 |
| ATOM | 1375 | C | LYS | A | 157 | 41.862 | -6.621 | 15.450 | 1.00 | 0.02 |
| ATOM | 1376 | O | LYS | A | 157 | 42.037 | -5.658 | 14.691 | 1.00 | 0.02 |
| ATOM | 1377 | N | LYS | A | 158 | 42.687 | -6.932 | 16.434 | 1.00 | 0.01 |
| ATOM | 1379 | CA | LYS | A | 158 | 44.031 | -6.371 | 16.530 | 1.00 | 0.01 |
| ATOM | 1380 | CB | LYS | A | 158 | 44.706 | -7.030 | 17.731 | 1.00 | 0.36 |
| ATOM | 1381 | CG | LYS | A | 158 | 46.081 | -6.452 | 18.039 | 1.00 | 1.34 |
| ATOM | 1382 | CD | LYS | A | 158 | 46.724 | -7.176 | 19.214 | 1.00 | 1.37 |
| ATOM | 1383 | CE | LYS | A | 158 | 48.116 | -6.632 | 19.509 | 1.00 | 2.23 |
| ATOM | 1384 | NZ | LYS | A | 158 | 48.728 | -7.342 | 20.642 | 1.00 | 2.98 |
| ATOM | 1385 | C | LYS | A | 158 | 44.818 | -6.663 | 15.256 | 1.00 | 0.02 |
| ATOM | 1386 | O | LYS | A | 158 | 44.750 | -7.769 | 14.708 | 1.00 | 0.02 |
| ATOM | 1387 | N | GLU | A | 159 | 45.458 | -5.616 | 14.752 | 1.00 | 0.02 |
| ATOM | 1389 | CA | GLU | A | 159 | 46.337 | -5.662 | 13.568 | 1.00 | 0.00 |
| ATOM | 1390 | CB | GLU | A | 159 | 47.312 | -6.837 | 13.652 | 1.00 | 0.97 |
| ATOM | 1391 | CG | GLU | A | 159 | 48.235 | -6.729 | 14.860 | 1.00 | 1.47 |
| ATOM | 1392 | CD | GLU | A | 159 | 49.069 | -7.997 | 14.999 | 1.00 | 1.57 |
| ATOM | 1393 | OE1 | GLU | A | 159 | 49.297 | -8.396 | 16.135 | 1.00 | 2.13 |
| ATOM | 1394 | OE2 | GLU | A | 159 | 49.515 | -8.508 | 13.982 | 1.00 | 1.77 |
| ATOM | 1395 | C | GLU | A | 159 | 45.561 | -5.739 | 12.255 | 1.00 | 0.01 |
| ATOM | 1396 | O | GLU | A | 159 | 45.933 | -6.505 | 11.360 | 1.00 | 0.02 |
| ATOM | 1397 | N | LEU | A | 160 | 44.478 | -4.986 | 12.163 | 1.00 | 0.02 |
| ATOM | 1399 | CA | LEU | A | 160 | 43.803 | -4.808 | 10.872 | 1.00 | 0.02 |
| ATOM | 1400 | CB | LEU | A | 160 | 42.291 | -4.800 | 11.054 | 1.00 | 0.02 |
| ATOM | 1401 | CG | LEU | A | 160 | 41.736 | -6.146 | 11.496 | 1.00 | 0.01 |
| ATOM | 1402 | CD1 | LEU | A | 160 | 40.224 | -6.046 | 11.653 | 1.00 | 0.02 |

| ATOM | 1403 | CD2 | LEU | A | 160 | 42.095 | -7.249 | 10.506 | 1.00 | 0.00 |
|------|------|-----|-----|---|-----|--------|--------|--------|------|------|
| ATOM | 1404 | C   | LEU | A | 160 | 44.218 | -3.479 | 10.256 | 1.00 | 0.00 |
| ATOM | 1405 | O   | LEU | A | 160 | 44.754 | -2.605 | 10.950 | 1.00 | 0.02 |
| ATOM | 1406 | N   | GLN | A | 161 | 43.941 | -3.317 | 8.974  | 1.00 | 0.01 |
| ATOM | 1408 | CA  | GLN | A | 161 | 44.189 | -2.029 | 8.312  | 1.00 | 0.01 |
| ATOM | 1409 | CB  | GLN | A | 161 | 44.562 | -2.265 | 6.857  | 1.00 | 0.92 |
| ATOM | 1410 | CG  | GLN | A | 161 | 46.073 | -2.179 | 6.681  | 1.00 | 1.52 |
| ATOM | 1411 | CD  | GLN | A | 161 | 46.526 | -0.743 | 6.938  | 1.00 | 1.99 |
| ATOM | 1412 | OE1 | GLN | A | 161 | 45.895 | 0.209  | 6.469  | 1.00 | 2.12 |
| ATOM | 1413 | NE2 | GLN | A | 161 | 47.601 | -0.601 | 7.694  | 1.00 | 2.59 |
| ATOM | 1416 | C   | GLN | A | 161 | 42.978 | -1.108 | 8.421  | 1.00 | 0.00 |
| ATOM | 1417 | O   | GLN | A | 161 | 42.227 | -0.902 | 7.459  | 1.00 | 0.00 |
| ATOM | 1418 | N   | LEU | A | 162 | 42.846 | -0.533 | 9.605  | 1.00 | 0.02 |
| ATOM | 1420 | CA  | LEU | A | 162 | 41.713 | 0.327  | 9.948  | 1.00 | 0.00 |
| ATOM | 1421 | CB  | LEU | A | 162 | 41.655 | 0.461  | 11.464 | 1.00 | 0.02 |
| ATOM | 1422 | CG  | LEU | A | 162 | 41.484 | -0.895 | 12.139 | 1.00 | 0.02 |
| ATOM | 1423 | CD1 | LEU | A | 162 | 41.692 | -0.783 | 13.644 | 1.00 | 0.01 |
| ATOM | 1424 | CD2 | LEU | A | 162 | 40.125 | -1.510 | 11.816 | 1.00 | 0.02 |
| ATOM | 1425 | C   | LEU | A | 162 | 41.847 | 1.709  | 9.324  | 1.00 | 0.00 |
| ATOM | 1426 | O   | LEU | A | 162 | 42.798 | 2.456  | 9.587  | 1.00 | 0.02 |
| ATOM | 1427 | N   | GLN | A | 163 | 40.861 | 2.041  | 8.516  | 1.00 | 0.01 |
| ATOM | 1429 | CA  | GLN | A | 163 | 40.834 | 3.337  | 7.847  | 1.00 | 0.00 |
| ATOM | 1430 | CB  | GLN | A | 163 | 39.974 | 3.191  | 6.604  | 1.00 | 0.67 |
| ATOM | 1431 | CG  | GLN | A | 163 | 40.562 | 2.109  | 5.706  | 1.00 | 1.20 |
| ATOM | 1432 | CD  | GLN | A | 163 | 39.575 | 1.724  | 4.613  | 1.00 | 2.06 |
| ATOM | 1433 | OE1 | GLN | A | 163 | 39.212 | 0.548  | 4.484  | 1.00 | 2.42 |
| ATOM | 1434 | NE2 | GLN | A | 163 | 39.127 | 2.710  | 3.859  | 1.00 | 2.92 |
| ATOM | 1437 | C   | GLN | A | 163 | 40.291 | 4.420  | 8.768  | 1.00 | 0.01 |
| ATOM | 1438 | O   | GLN | A | 163 | 39.235 | 4.271  | 9.398  | 1.00 | 0.02 |
| ATOM | 1439 | N   | ALA | A | 164 | 40.912 | 5.584  | 8.666  | 1.00 | 0.00 |
| ATOM | 1441 | CA  | ALA | A | 164 | 40.567 | 6.716  | 9.535  | 1.00 | 0.02 |
| ATOM | 1442 | CB  | ALA | A | 164 | 41.691 | 7.742  | 9.468  | 1.00 | 0.37 |
| ATOM | 1443 | C   | ALA | A | 164 | 39.244 | 7.384  | 9.171  | 1.00 | 0.01 |
| ATOM | 1444 | O   | ALA | A | 164 | 38.627 | 8.022  | 10.030 | 1.00 | 0.00 |
| ATOM | 1445 | N   | ASN | A | 165 | 38.696 | 7.036  | 8.019  | 1.00 | 0.02 |
| ATOM | 1447 | CA  | ASN | A | 165 | 37.393 | 7.564  | 7.624  | 1.00 | 0.02 |
| ATOM | 1448 | CB  | ASN | A | 165 | 37.238 | 7.379  | 6.122  | 1.00 | 0.32 |
| ATOM | 1449 | CG  | ASN | A | 165 | 38.369 | 8.106  | 5.408  | 1.00 | 1.12 |
| ATOM | 1450 | OD1 | ASN | A | 165 | 39.322 | 7.482  | 4.925  | 1.00 | 1.77 |
| ATOM | 1451 | ND2 | ASN | A | 165 | 38.285 | 9.425  | 5.425  | 1.00 | 2.08 |
| ATOM | 1454 | C   | ASN | A | 165 | 36.271 | 6.831  | 8.344  | 1.00 | 0.01 |
| ATOM | 1455 | O   | ASN | A | 165 | 35.347 | 7.484  | 8.842  | 1.00 | 0.02 |
| ATOM | 1456 | N   | PHE | A | 166 | 36.494 | 5.563  | 8.654  | 1.00 | 0.02 |
| ATOM | 1458 | CA  | PHE | A | 166 | 35.481 | 4.817  | 9.395  | 1.00 | 0.01 |
| ATOM | 1459 | CB  | PHE | A | 166 | 35.696 | 3.326  | 9.201  | 1.00 | 0.02 |
| ATOM | 1460 | CG  | PHE | A | 166 | 34.703 | 2.464  | 9.972  | 1.00 | 0.02 |
| ATOM | 1461 | CD1 | PHE | A | 166 | 33.360 | 2.476  | 9.623  | 1.00 | 0.01 |
| ATOM | 1462 | CE1 | PHE | A | 166 | 32.453 | 1.687  | 10.317 | 1.00 | 0.01 |
| ATOM | 1463 | CZ  | PHE | A | 166 | 32.889 | 0.892  | 11.369 | 1.00 | 0.02 |
| ATOM | 1464 | CE2 | PHE | A | 166 | 34.230 | 0.892  | 11.731 | 1.00 | 0.01 |
| ATOM | 1465 | CD2 | PHE | A | 166 | 35.137 | 1.681  | 11.035 | 1.00 | 0.01 |
| ATOM | 1466 | C   | PHE | A | 166 | 35.573 | 5.138  | 10.874 | 1.00 | 0.01 |
| ATOM | 1467 | O   | PHE | A | 166 | 34.534 | 5.303  | 11.524 | 1.00 | 0.02 |
| ATOM | 1468 | N   | LEU | A | 167 | 36.769 | 5.495  | 11.315 | 1.00 | 0.01 |
| ATOM | 1470 | CA  | LEU | A | 167 | 36.960 | 5.888  | 12.712 | 1.00 | 0.02 |
| ATOM | 1471 | CB  | LEU | A | 167 | 38.457 | 5.931  | 13.000 | 1.00 | 0.02 |
| ATOM | 1472 | CG  | LEU | A | 167 | 39.122 | 4.585  | 12.726 | 1.00 | 0.02 |
| ATOM | 1473 | CD1 | LEU | A | 167 | 40.639 | 4.684  | 12.848 | 1.00 | 0.01 |

| ATOM | 1474 | CD2 | LEU | A | 167 | 38.580 | 3.494 | 13.643 | 1.00 | 0.02 |
|------|------|-----|-----|---|-----|--------|-------|--------|------|------|
| ATOM | 1475 | C | LEU | A | 167 | 36.339 | 7.261 | 12.953 | 1.00 | 0.02 |
| ATOM | 1476 | O | LEU | A | 167 | 35.587 | 7.429 | 13.923 | 1.00 | 0.01 |
| ATOM | 1477 | N | GLY | A | 168 | 36.441 | 8.120 | 11.951 | 1.00 | 0.01 |
| ATOM | 1479 | CA | GLY | A | 168 | 35.776 | 9.427 | 11.965 | 1.00 | 0.01 |
| ATOM | 1480 | C | GLY | A | 168 | 34.261 | 9.276 | 12.052 | 1.00 | 0.01 |
| ATOM | 1481 | O | GLY | A | 168 | 33.673 | 9.677 | 13.063 | 1.00 | 0.01 |
| ATOM | 1482 | N | ASN | A | 169 | 33.691 | 8.508 | 11.136 | 1.00 | 0.02 |
| ATOM | 1484 | CA | ASN | A | 169 | 32.238 | 8.294 | 11.107 | 1.00 | 0.01 |
| ATOM | 1485 | CB | ASN | A | 169 | 31.922 | 7.334 | 9.965 | 1.00 | 0.23 |
| ATOM | 1486 | CG | ASN | A | 169 | 32.243 | 7.956 | 8.607 | 1.00 | 0.32 |
| ATOM | 1487 | OD1 | ASN | A | 169 | 32.241 | 9.183 | 8.452 | 1.00 | 1.33 |
| ATOM | 1488 | ND2 | ASN | A | 169 | 32.425 | 7.101 | 7.614 | 1.00 | 0.79 |
| ATOM | 1491 | C | ASN | A | 169 | 31.692 | 7.704 | 12.407 | 1.00 | 0.01 |
| ATOM | 1492 | O | ASN | A | 169 | 30.833 | 8.331 | 13.043 | 1.00 | 0.01 |
| ATOM | 1493 | N | VAL | A | 170 | 32.369 | 6.699 | 12.934 | 1.00 | 0.01 |
| ATOM | 1495 | CA | VAL | A | 170 | 31.893 | 6.039 | 14.149 | 1.00 | 0.01 |
| ATOM | 1496 | CB | VAL | A | 170 | 32.705 | 4.765 | 14.329 | 1.00 | 0.02 |
| ATOM | 1497 | CG1 | VAL | A | 170 | 32.420 | 4.094 | 15.663 | 1.00 | 0.01 |
| ATOM | 1498 | CG2 | VAL | A | 170 | 32.422 | 3.803 | 13.189 | 1.00 | 0.02 |
| ATOM | 1499 | C | VAL | A | 170 | 32.007 | 6.909 | 15.397 | 1.00 | 0.01 |
| ATOM | 1500 | O | VAL | A | 170 | 30.975 | 7.179 | 16.027 | 1.00 | 0.02 |
| ATOM | 1501 | N | LYS | A | 171 | 33.147 | 7.541 | 15.608 | 1.00 | 0.01 |
| ATOM | 1503 | CA | LYS | A | 171 | 33.345 | 8.264 | 16.867 | 1.00 | 0.01 |
| ATOM | 1504 | CB | LYS | A | 171 | 34.843 | 8.333 | 17.125 | 1.00 | 0.00 |
| ATOM | 1505 | CG | LYS | A | 171 | 35.458 | 6.940 | 17.120 | 1.00 | 0.02 |
| ATOM | 1506 | CD | LYS | A | 171 | 36.977 | 7.001 | 17.204 | 1.00 | 0.02 |
| ATOM | 1507 | CE | LYS | A | 171 | 37.580 | 5.606 | 17.105 | 1.00 | 0.02 |
| ATOM | 1508 | NZ | LYS | A | 171 | 39.050 | 5.655 | 17.129 | 1.00 | 0.02 |
| ATOM | 1509 | C | LYS | A | 171 | 32.773 | 9.677 | 16.841 | 1.00 | 0.01 |
| ATOM | 1510 | O | LYS | A | 171 | 32.098 | 10.082 | 17.793 | 1.00 | 0.01 |
| ATOM | 1511 | N | ARG | A | 172 | 32.835 | 10.316 | 15.688 | 1.00 | 0.01 |
| ATOM | 1513 | CA | ARG | A | 172 | 32.435 | 11.720 | 15.585 | 1.00 | 0.00 |
| ATOM | 1514 | CB | ARG | A | 172 | 33.397 | 12.362 | 14.591 | 1.00 | 0.23 |
| ATOM | 1515 | CG | ARG | A | 172 | 32.990 | 13.760 | 14.149 | 1.00 | 1.13 |
| ATOM | 1516 | CD | ARG | A | 172 | 33.933 | 14.237 | 13.052 | 1.00 | 1.10 |
| ATOM | 1517 | NE | ARG | A | 172 | 34.064 | 13.196 | 12.018 | 1.00 | 1.48 |
| ATOM | 1518 | CZ | ARG | A | 172 | 33.587 | 13.311 | 10.777 | 1.00 | 2.53 |
| ATOM | 1519 | NH1 | ARG | A | 172 | 33.721 | 12.299 | 9.917 | 1.00 | 3.39 |
| ATOM | 1520 | NH2 | ARG | A | 172 | 32.953 | 14.425 | 10.404 | 1.00 | 3.21 |
| ATOM | 1521 | C | ARG | A | 172 | 30.992 | 11.912 | 15.124 | 1.00 | 0.01 |
| ATOM | 1522 | O | ARG | A | 172 | 30.331 | 12.858 | 15.567 | 1.00 | 0.01 |
| ATOM | 1523 | N | LEU | A | 173 | 30.467 | 10.983 | 14.344 | 1.00 | 0.01 |
| ATOM | 1525 | CA | LEU | A | 173 | 29.098 | 11.161 | 13.854 | 1.00 | 0.01 |
| ATOM | 1526 | CB | LEU | A | 173 | 29.062 | 10.874 | 12.356 | 1.00 | 0.01 |
| ATOM | 1527 | CG | LEU | A | 173 | 29.977 | 11.809 | 11.572 | 1.00 | 0.02 |
| ATOM | 1528 | CD1 | LEU | A | 173 | 30.030 | 11.409 | 10.102 | 1.00 | 0.01 |
| ATOM | 1529 | CD2 | LEU | A | 173 | 29.540 | 13.263 | 11.717 | 1.00 | 0.01 |
| ATOM | 1530 | C | LEU | A | 173 | 28.103 | 10.255 | 14.571 | 1.00 | 0.01 |
| ATOM | 1531 | O | LEU | A | 173 | 26.901 | 10.546 | 14.576 | 1.00 | 0.02 |
| ATOM | 1532 | N | TYR | A | 174 | 28.592 | 9.176 | 15.160 | 1.00 | 0.01 |
| ATOM | 1534 | CA | TYR | A | 174 | 27.700 | 8.255 | 15.881 | 1.00 | 0.01 |
| ATOM | 1535 | CB | TYR | A | 174 | 27.665 | 6.919 | 15.148 | 1.00 | 0.01 |
| ATOM | 1536 | CG | TYR | A | 174 | 26.771 | 6.904 | 13.912 | 1.00 | 0.01 |
| ATOM | 1537 | CD1 | TYR | A | 174 | 27.282 | 7.217 | 12.659 | 1.00 | 0.01 |
| ATOM | 1538 | CE1 | TYR | A | 174 | 26.452 | 7.192 | 11.547 | 1.00 | 0.00 |
| ATOM | 1539 | CZ | TYR | A | 174 | 25.114 | 6.850 | 11.688 | 1.00 | 0.01 |
| ATOM | 1540 | OH | TYR | A | 174 | 24.338 | 6.654 | 10.568 | 1.00 | 0.01 |

| ATOM | 1541 | CE2 | TYR | A | 174 | 24.599 | 6.548 | 12.940 | 1.00 | 0.01 |
|---|---|---|---|---|---|---|---|---|---|---|
| ATOM | 1542 | CD2 | TYR | A | 174 | 25.429 | 6.576 | 14.052 | 1.00 | 0.01 |
| ATOM | 1543 | C | TYR | A | 174 | 28.088 | 8.028 | 17.342 | 1.00 | 0.01 |
| ATOM | 1544 | O | TYR | A | 174 | 27.429 | 7.233 | 18.025 | 1.00 | 0.01 |
| ATOM | 1545 | N | GLU | A | 175 | 29.085 | 8.764 | 17.816 | 1.00 | 0.02 |
| ATOM | 1547 | CA | GLU | A | 175 | 29.666 | 8.641 | 19.175 | 1.00 | 0.01 |
| ATOM | 1548 | CB | GLU | A | 175 | 28.893 | 9.507 | 20.187 | 1.00 | 2.11 |
| ATOM | 1549 | CG | GLU | A | 175 | 27.387 | 9.247 | 20.319 | 1.00 | 2.81 |
| ATOM | 1550 | CD | GLU | A | 175 | 27.038 | 8.241 | 21.419 | 1.00 | 3.91 |
| ATOM | 1551 | OE1 | GLU | A | 175 | 27.508 | 8.466 | 22.527 | 1.00 | 4.60 |
| ATOM | 1552 | OE2 | GLU | A | 175 | 26.072 | 7.518 | 21.217 | 1.00 | 4.31 |
| ATOM | 1553 | C | GLU | A | 175 | 29.848 | 7.202 | 19.666 | 1.00 | 0.02 |
| ATOM | 1554 | O | GLU | A | 175 | 29.416 | 6.852 | 20.768 | 1.00 | 0.02 |
| ATOM | 1555 | N | ALA | A | 176 | 30.497 | 6.378 | 18.863 | 1.00 | 0.01 |
| ATOM | 1557 | CA | ALA | A | 176 | 30.770 | 5.009 | 19.298 | 1.00 | 0.01 |
| ATOM | 1558 | CB | ALA | A | 176 | 30.085 | 4.021 | 18.371 | 1.00 | 0.31 |
| ATOM | 1559 | C | ALA | A | 176 | 32.265 | 4.741 | 19.371 | 1.00 | 0.02 |
| ATOM | 1560 | O | ALA | A | 176 | 33.063 | 5.261 | 18.581 | 1.00 | 0.01 |
| ATOM | 1561 | N | GLU | A | 177 | 32.630 | 3.913 | 20.331 | 1.00 | 0.01 |
| ATOM | 1563 | CA | GLU | A | 177 | 34.048 | 3.668 | 20.610 | 1.00 | 0.02 |
| ATOM | 1564 | CB | GLU | A | 177 | 34.154 | 3.396 | 22.101 | 1.00 | 0.01 |
| ATOM | 1565 | CG | GLU | A | 177 | 33.567 | 4.556 | 22.894 | 1.00 | 0.02 |
| ATOM | 1566 | CD | GLU | A | 177 | 33.460 | 4.182 | 24.366 | 1.00 | 0.01 |
| ATOM | 1567 | OE1 | GLU | A | 177 | 34.417 | 4.421 | 25.089 | 1.00 | 0.02 |
| ATOM | 1568 | OE2 | GLU | A | 177 | 32.414 | 3.674 | 24.741 | 1.00 | 0.02 |
| ATOM | 1569 | C | GLU | A | 177 | 34.603 | 2.482 | 19.829 | 1.00 | 0.02 |
| ATOM | 1570 | O | GLU | A | 177 | 34.006 | 1.401 | 19.833 | 1.00 | 0.02 |
| ATOM | 1571 | N | VAL | A | 178 | 35.710 | 2.696 | 19.138 | 1.00 | 0.01 |
| ATOM | 1573 | CA | VAL | A | 178 | 36.389 | 1.592 | 18.442 | 1.00 | 0.02 |
| ATOM | 1574 | CB | VAL | A | 178 | 36.763 | 2.034 | 17.029 | 1.00 | 0.21 |
| ATOM | 1575 | CG1 | VAL | A | 178 | 37.555 | 0.962 | 16.287 | 1.00 | 0.34 |
| ATOM | 1576 | CG2 | VAL | A | 178 | 35.525 | 2.417 | 16.230 | 1.00 | 0.34 |
| ATOM | 1577 | C | VAL | A | 178 | 37.641 | 1.164 | 19.208 | 1.00 | 0.02 |
| ATOM | 1578 | O | VAL | A | 178 | 38.536 | 1.975 | 19.474 | 1.00 | 0.01 |
| ATOM | 1579 | N | PHE | A | 179 | 37.673 | -0.103 | 19.582 | 1.00 | 0.02 |
| ATOM | 1581 | CA | PHE | A | 179 | 38.813 | -0.652 | 20.325 | 1.00 | 0.02 |
| ATOM | 1582 | CB | PHE | A | 179 | 38.331 | -1.131 | 21.688 | 1.00 | 0.01 |
| ATOM | 1583 | CG | PHE | A | 179 | 37.785 | -0.030 | 22.590 | 1.00 | 0.02 |
| ATOM | 1584 | CD1 | PHE | A | 179 | 38.610 | 1.013 | 22.989 | 1.00 | 0.01 |
| ATOM | 1585 | CE1 | PHE | A | 179 | 38.114 | 2.014 | 23.814 | 1.00 | 0.02 |
| ATOM | 1586 | CZ | PHE | A | 179 | 36.794 | 1.969 | 24.241 | 1.00 | 0.01 |
| ATOM | 1587 | CE2 | PHE | A | 179 | 35.969 | 0.926 | 23.841 | 1.00 | 0.01 |
| ATOM | 1588 | CD2 | PHE | A | 179 | 36.464 | -0.074 | 23.015 | 1.00 | 0.02 |
| ATOM | 1589 | C | PHE | A | 179 | 39.456 | -1.824 | 19.594 | 1.00 | 0.01 |
| ATOM | 1590 | O | PHE | A | 179 | 38.765 | -2.745 | 19.145 | 1.00 | 0.02 |
| ATOM | 1591 | N | SER | A | 180 | 40.772 | -1.770 | 19.469 | 1.00 | 0.02 |
| ATOM | 1593 | CA | SER | A | 180 | 41.520 | -2.893 | 18.890 | 1.00 | 0.01 |
| ATOM | 1594 | CB | SER | A | 180 | 42.876 | -2.402 | 18.405 | 1.00 | 0.08 |
| ATOM | 1595 | OG | SER | A | 180 | 43.587 | -3.537 | 17.933 | 1.00 | 0.09 |
| ATOM | 1596 | C | SER | A | 180 | 41.713 | -3.982 | 19.938 | 1.00 | 0.01 |
| ATOM | 1597 | O | SER | A | 180 | 42.463 | -3.816 | 20.906 | 1.00 | 0.02 |
| ATOM | 1598 | N | THR | A | 181 | 41.050 | -5.100 | 19.718 | 1.00 | 0.01 |
| ATOM | 1600 | CA | THR | A | 181 | 41.020 | -6.168 | 20.712 | 1.00 | 0.02 |
| ATOM | 1601 | CB | THR | A | 181 | 39.553 | -6.503 | 20.935 | 1.00 | 0.65 |
| ATOM | 1602 | OG1 | THR | A | 181 | 38.817 | -5.290 | 20.839 | 1.00 | 1.46 |
| ATOM | 1603 | CG2 | THR | A | 181 | 39.298 | -7.129 | 22.301 | 1.00 | 0.43 |
| ATOM | 1604 | C | THR | A | 181 | 41.786 | -7.392 | 20.221 | 1.00 | 0.03 |
| ATOM | 1605 | O | THR | A | 181 | 41.690 | -7.780 | 19.049 | 1.00 | 0.01 |

| ATOM | 1606 | N | ASP | A | 182 | 42.579 | -7.975 | 21.104 | 1.00 | 0.02 |
|---|---|---|---|---|---|---|---|---|---|---|
| ATOM | 1608 | CA | ASP | A | 182 | 43.355 | -9.159 | 20.722 | 1.00 | 0.02 |
| ATOM | 1609 | CB | ASP | A | 182 | 44.572 | -9.307 | 21.629 | 1.00 | 0.71 |
| ATOM | 1610 | CG | ASP | A | 182 | 45.377 | -10.519 | 21.174 | 1.00 | 0.75 |
| ATOM | 1611 | OD1 | ASP | A | 182 | 45.596 | -10.586 | 19.972 | 1.00 | 0.69 |
| ATOM | 1612 | OD2 | ASP | A | 182 | 45.339 | -11.498 | 21.906 | 1.00 | 0.90 |
| ATOM | 1613 | C | ASP | A | 182 | 42.503 | -10.426 | 20.768 | 1.00 | 0.00 |
| ATOM | 1614 | O | ASP | A | 182 | 42.490 | -11.169 | 21.756 | 1.00 | 0.02 |
| ATOM | 1615 | N | PHE | A | 183 | 42.021 | -10.785 | 19.589 | 1.00 | 0.02 |
| ATOM | 1617 | CA | PHE | A | 183 | 41.163 | -11.961 | 19.427 | 1.00 | 0.01 |
| ATOM | 1618 | CB | PHE | A | 183 | 40.225 | -11.721 | 18.253 | 1.00 | 0.02 |
| ATOM | 1619 | CG | PHE | A | 183 | 39.191 | -10.636 | 18.536 | 1.00 | 0.01 |
| ATOM | 1620 | CD1 | PHE | A | 183 | 38.500 | -10.639 | 19.740 | 1.00 | 0.01 |
| ATOM | 1621 | CE1 | PHE | A | 183 | 37.560 | -9.652 | 20.004 | 1.00 | 0.01 |
| ATOM | 1622 | CZ | PHE | A | 183 | 37.310 | -8.664 | 19.061 | 1.00 | 0.02 |
| ATOM | 1623 | CE2 | PHE | A | 183 | 37.996 | -8.666 | 17.855 | 1.00 | 0.00 |
| ATOM | 1624 | CD2 | PHE | A | 183 | 38.936 | -9.652 | 17.593 | 1.00 | 0.02 |
| ATOM | 1625 | C | PHE | A | 183 | 41.938 | -13.264 | 19.246 | 1.00 | 0.01 |
| ATOM | 1626 | O | PHE | A | 183 | 41.325 | -14.335 | 19.184 | 1.00 | 0.01 |
| ATOM | 1627 | N | SER | A | 184 | 43.263 | -13.192 | 19.291 | 1.00 | 0.01 |
| ATOM | 1629 | CA | SER | A | 184 | 44.070 | -14.418 | 19.321 | 1.00 | 0.02 |
| ATOM | 1630 | CB | SER | A | 184 | 45.492 | -14.127 | 18.858 | 1.00 | 0.40 |
| ATOM | 1631 | OG | SER | A | 184 | 46.142 | -13.367 | 19.866 | 1.00 | 1.07 |
| ATOM | 1632 | C | SER | A | 184 | 44.093 | -14.982 | 20.744 | 1.00 | 0.02 |
| ATOM | 1633 | O | SER | A | 184 | 44.506 | -16.127 | 20.961 | 1.00 | 0.01 |
| ATOM | 1634 | N | ASN | A | 185 | 43.690 | -14.163 | 21.703 | 1.00 | 0.00 |
| ATOM | 1636 | CA | ASN | A | 185 | 43.336 | -14.670 | 23.023 | 1.00 | 0.02 |
| ATOM | 1637 | CB | ASN | A | 185 | 44.304 | -14.136 | 24.072 | 1.00 | 0.49 |
| ATOM | 1638 | CG | ASN | A | 185 | 44.036 | -14.815 | 25.415 | 1.00 | 1.32 |
| ATOM | 1639 | OD1 | ASN | A | 185 | 42.918 | -14.767 | 25.947 | 1.00 | 1.55 |
| ATOM | 1640 | ND2 | ASN | A | 185 | 45.056 | -15.472 | 25.933 | 1.00 | 2.05 |
| ATOM | 1643 | C | ASN | A | 185 | 41.915 | -14.218 | 23.337 | 1.00 | 0.02 |
| ATOM | 1644 | O | ASN | A | 185 | 41.708 | -13.214 | 24.036 | 1.00 | 0.02 |

| ATOM | 1645 | N | PRO | A | 186 | 40.958 | -15.073 | 23.010 | 1.00 | 0.01 |
|------|------|----|-----|---|-----|--------|---------|--------|------|------|
| ATOM | 1646 | CA | PRO | A | 186 | 39.547 | -14.699 | 23.123 | 1.00 | 0.02 |
| ATOM | 1647 | CB | PRO | A | 186 | 38.808 | -15.742 | 22.343 | 1.00 | 0.14 |
| ATOM | 1648 | CG | PRO | A | 186 | 39.772 | -16.852 | 21.951 | 1.00 | 0.20 |
| ATOM | 1649 | CD | PRO | A | 186 | 41.142 | -16.410 | 22.435 | 1.00 | 0.14 |
| ATOM | 1650 | C | PRO | A | 186 | 39.027 | -14.640 | 24.564 | 1.00 | 0.02 |
| ATOM | 1651 | O | PRO | A | 186 | 38.000 | -13.994 | 24.797 | 1.00 | 0.01 |
| ATOM | 1652 | N | SER | A | 187 | 39.786 | -15.119 | 25.538 | 1.00 | 0.01 |
| ATOM | 1654 | CA | SER | A | 187 | 39.295 | -15.048 | 26.913 | 1.00 | 0.02 |
| ATOM | 1655 | CB | SER | A | 187 | 39.850 | -16.206 | 27.741 | 1.00 | 0.10 |
| ATOM | 1656 | OG | SER | A | 187 | 41.267 | -16.119 | 27.793 | 1.00 | 1.03 |
| ATOM | 1657 | C | SER | A | 187 | 39.656 | -13.702 | 27.533 | 1.00 | 0.02 |
| ATOM | 1658 | O | SER | A | 187 | 38.778 | -13.067 | 28.128 | 1.00 | 0.01 |
| ATOM | 1659 | N | ILE | A | 188 | 40.787 | -13.144 | 27.130 | 1.00 | 0.02 |
| ATOM | 1661 | CA | ILE | A | 188 | 41.173 | -11.823 | 27.627 | 1.00 | 0.02 |
| ATOM | 1662 | CB | ILE | A | 188 | 42.691 | -11.705 | 27.593 | 1.00 | 0.16 |
| ATOM | 1663 | CG2 | ILE | A | 188 | 43.138 | -10.302 | 27.988 | 1.00 | 0.71 |
| ATOM | 1664 | CG1 | ILE | A | 188 | 43.322 | -12.737 | 28.518 | 1.00 | 0.98 |
| ATOM | 1665 | CD1 | ILE | A | 188 | 44.841 | -12.619 | 28.524 | 1.00 | 1.50 |
| ATOM | 1666 | C | ILE | A | 188 | 40.537 | -10.730 | 26.782 | 1.00 | 0.02 |
| ATOM | 1667 | O | ILE | A | 188 | 40.068 | -9.726 | 27.338 | 1.00 | 0.02 |
| ATOM | 1668 | N | ALA | A | 189 | 40.245 | -11.065 | 25.536 | 1.00 | 0.02 |
| ATOM | 1670 | CA | ALA | A | 189 | 39.522 | -10.135 | 24.668 | 1.00 | 0.02 |
| ATOM | 1671 | CB | ALA | A | 189 | 39.525 | -10.700 | 23.255 | 1.00 | 0.02 |
| ATOM | 1672 | C | ALA | A | 189 | 38.085 | -9.964 | 25.141 | 1.00 | 0.02 |
| ATOM | 1673 | O | ALA | A | 189 | 37.648 | -8.831 | 25.380 | 1.00 | 0.02 |
| ATOM | 1674 | N | GLN | A | 190 | 37.508 | -11.065 | 25.592 | 1.00 | 0.01 |
| ATOM | 1676 | CA | GLN | A | 190 | 36.132 | -11.066 | 26.081 | 1.00 | 0.02 |
| ATOM | 1677 | CB | GLN | A | 190 | 35.692 | -12.514 | 26.029 | 1.00 | 0.17 |
| ATOM | 1678 | CG | GLN | A | 190 | 34.203 | -12.707 | 26.211 | 1.00 | 0.67 |
| ATOM | 1679 | CD | GLN | A | 190 | 33.898 | -14.128 | 25.770 | 1.00 | 1.38 |

| ATOM | 1680 | OE1 | GLN | A | 190 | 32.823 | -14.394 | 25.226 | 1.00 | 2.17 |
|---|---|---|---|---|---|---|---|---|---|---|
| ATOM | 1681 | NE2 | GLN | A | 190 | 34.948 | -14.929 | 25.720 | 1.00 | 2.05 |
| ATOM | 1684 | C | GLN | A | 190 | 36.026 | -10.537 | 27.506 | 1.00 | 0.02 |
| ATOM | 1685 | O | GLN | A | 190 | 35.015 | -9.914 | 27.853 | 1.00 | 0.01 |
| ATOM | 1686 | N | ALA | A | 191 | 37.130 | -10.569 | 28.234 | 1.00 | 0.01 |
| ATOM | 1688 | CA | ALA | A | 191 | 37.151 | -9.978 | 29.568 | 1.00 | 0.02 |
| ATOM | 1689 | CB | ALA | A | 191 | 38.387 | -10.467 | 30.312 | 1.00 | 0.09 |
| ATOM | 1690 | C | ALA | A | 191 | 37.178 | -8.460 | 29.464 | 1.00 | 0.02 |
| ATOM | 1691 | O | ALA | A | 191 | 36.374 | -7.803 | 30.135 | 1.00 | 0.01 |
| ATOM | 1692 | N | ARG | A | 192 | 37.836 | -7.949 | 28.435 | 1.00 | 0.01 |
| ATOM | 1694 | CA | ARG | A | 192 | 37.847 | -6.502 | 28.210 | 1.00 | 0.01 |
| ATOM | 1695 | CB | ARG | A | 192 | 38.983 | -6.166 | 27.256 | 1.00 | 0.18 |
| ATOM | 1696 | CG | ARG | A | 192 | 40.332 | -6.317 | 27.948 | 1.00 | 0.97 |
| ATOM | 1697 | CD | ARG | A | 192 | 41.484 | -6.059 | 26.985 | 1.00 | 1.10 |
| ATOM | 1698 | NE | ARG | A | 192 | 41.578 | -7.133 | 25.987 | 1.00 | 1.92 |
| ATOM | 1699 | CZ | ARG | A | 192 | 42.740 | -7.521 | 25.458 | 1.00 | 2.61 |
| ATOM | 1700 | NH1 | ARG | A | 192 | 43.863 | -6.868 | 25.763 | 1.00 | 3.27 |
| ATOM | 1701 | NH2 | ARG | A | 192 | 42.773 | -8.534 | 24.592 | 1.00 | 3.22 |
| ATOM | 1702 | C | ARG | A | 192 | 36.524 | -6.006 | 27.636 | 1.00 | 0.02 |
| ATOM | 1703 | O | ARG | A | 192 | 36.009 | -4.985 | 28.111 | 1.00 | 0.01 |
| ATOM | 1704 | N | ILE | A | 193 | 35.862 | -6.846 | 26.857 | 1.00 | 0.01 |
| ATOM | 1706 | CA | ILE | A | 193 | 34.552 | -6.478 | 26.313 | 1.00 | 0.02 |
| ATOM | 1707 | CB | ILE | A | 193 | 34.160 | -7.505 | 25.258 | 1.00 | 0.01 |
| ATOM | 1708 | CG2 | ILE | A | 193 | 32.765 | -7.216 | 24.719 | 1.00 | 0.02 |
| ATOM | 1709 | CG1 | ILE | A | 193 | 35.172 | -7.510 | 24.121 | 1.00 | 0.02 |
| ATOM | 1710 | CD1 | ILE | A | 193 | 34.843 | -8.578 | 23.087 | 1.00 | 0.02 |
| ATOM | 1711 | C | ILE | A | 193 | 33.486 | -6.430 | 27.406 | 1.00 | 0.00 |
| ATOM | 1712 | O | ILE | A | 193 | 32.863 | -5.376 | 27.594 | 1.00 | 0.02 |
| ATOM | 1713 | N | ASN | A | 194 | 33.515 | -7.409 | 28.296 | 1.00 | 0.02 |
| ATOM | 1715 | CA | ASN | A | 194 | 32.533 | -7.467 | 29.378 | 1.00 | 0.02 |
| ATOM | 1716 | CB | ASN | A | 194 | 32.502 | -8.893 | 29.900 | 1.00 | 0.02 |
| ATOM | 1717 | CG | ASN | A | 194 | 31.780 | -9.764 | 28.883 | 1.00 | 0.02 |
| ATOM | 1718 | OD1 | ASN | A | 194 | 30.787 | -9.320 | 28.289 | 1.00 | 0.02 |
| ATOM | 1719 | ND2 | ASN | A | 194 | 32.154 | -11.028 | 28.844 | 1.00 | 0.02 |
| ATOM | 1722 | C | ASN | A | 194 | 32.821 | -6.502 | 30.521 | 1.00 | 0.02 |
| ATOM | 1723 | O | ASN | A | 194 | 31.865 | -6.020 | 31.147 | 1.00 | 0.02 |
| ATOM | 1724 | N | SER | A | 195 | 34.059 | -6.057 | 30.644 | 1.00 | 0.02 |
| ATOM | 1726 | CA | SER | A | 195 | 34.377 | -5.051 | 31.654 | 1.00 | 0.02 |
| ATOM | 1727 | CB | SER | A | 195 | 35.849 | -5.156 | 32.027 | 1.00 | 0.14 |
| ATOM | 1728 | OG | SER | A | 195 | 36.057 | -6.438 | 32.601 | 1.00 | 0.40 |
| ATOM | 1729 | C | SER | A | 195 | 34.074 | -3.648 | 31.148 | 1.00 | 0.01 |
| ATOM | 1730 | O | SER | A | 195 | 33.677 | -2.794 | 31.947 | 1.00 | 0.02 |
| ATOM | 1731 | N | HIS | A | 196 | 34.015 | -3.488 | 29.836 | 1.00 | 0.02 |
| ATOM | 1733 | CA | HIS | A | 196 | 33.628 | -2.201 | 29.258 | 1.00 | 0.02 |
| ATOM | 1734 | CB | HIS | A | 196 | 34.143 | -2.145 | 27.826 | 1.00 | 0.17 |
| ATOM | 1735 | CG | HIS | A | 196 | 33.764 | -0.873 | 27.099 | 1.00 | 1.00 |
| ATOM | 1736 | ND1 | HIS | A | 196 | 32.882 | -0.755 | 26.088 | 1.00 | 2.01 |
| ATOM | 1738 | CE1 | HIS | A | 196 | 32.814 | 0.536 | 25.706 | 1.00 | 2.59 |
| ATOM | 1739 | NE2 | HIS | A | 196 | 33.661 | 1.240 | 26.490 | 1.00 | 2.37 |
| ATOM | 1740 | CD2 | HIS | A | 196 | 34.254 | 0.385 | 27.353 | 1.00 | 1.67 |
| ATOM | 1741 | C | HIS | A | 196 | 32.111 | -2.043 | 29.265 | 1.00 | 0.03 |
| ATOM | 1742 | O | HIS | A | 196 | 31.601 | -0.956 | 29.572 | 1.00 | 0.02 |

| ATOM | 1743 | N | VAL | A | 197 | 31.420 | -3.169 | 29.187 | 1.00 | 0.01 |
|------|------|----|-----|---|-----|--------|--------|--------|------|------|
| ATOM | 1745 | CA | VAL | A | 197 | 29.958 | -3.169 | 29.286 | 1.00 | 0.02 |
| ATOM | 1746 | CB | VAL | A | 197 | 29.467 | -4.552 | 28.875 | 1.00 | 0.01 |
| ATOM | 1747 | CG1 | VAL | A | 197 | 27.989 | -4.721 | 29.171 | 1.00 | 0.01 |
| ATOM | 1748 | CG2 | VAL | A | 197 | 29.752 | -4.831 | 27.404 | 1.00 | 0.01 |
| ATOM | 1749 | C | VAL | A | 197 | 29.518 | -2.860 | 30.716 | 1.00 | 0.01 |
| ATOM | 1750 | O | VAL | A | 197 | 28.743 | -1.915 | 30.935 | 1.00 | 0.01 |
| ATOM | 1751 | N | LYS | A | 198 | 30.263 | -3.415 | 31.658 | 1.00 | 0.01 |
| ATOM | 1753 | CA | LYS | A | 198 | 30.030 | -3.139 | 33.072 | 1.00 | 0.01 |
| ATOM | 1754 | CB | LYS | A | 198 | 30.907 | -4.106 | 33.854 | 1.00 | 0.11 |
| ATOM | 1755 | CG | LYS | A | 198 | 30.931 | -3.796 | 35.343 | 1.00 | 0.81 |
| ATOM | 1756 | CD | LYS | A | 198 | 31.958 | -4.676 | 36.041 | 1.00 | 0.83 |
| ATOM | 1757 | CE | LYS | A | 198 | 33.334 | -4.491 | 35.411 | 1.00 | 1.41 |
| ATOM | 1758 | NZ | LYS | A | 198 | 34.329 | -5.373 | 36.041 | 1.00 | 2.32 |
| ATOM | 1759 | C | LYS | A | 198 | 30.403 | -1.705 | 33.439 | 1.00 | 0.01 |
| ATOM | 1760 | O | LYS | A | 198 | 29.614 | -1.038 | 34.119 | 1.00 | 0.01 |
| ATOM | 1761 | N | LYS | A | 199 | 31.413 | -1.162 | 32.779 | 1.00 | 0.01 |
| ATOM | 1763 | CA | LYS | A | 199 | 31.881 | 0.196 | 33.062 | 1.00 | 0.02 |
| ATOM | 1764 | CB | LYS | A | 199 | 33.240 | 0.367 | 32.391 | 1.00 | 0.02 |
| ATOM | 1765 | CG | LYS | A | 199 | 33.799 | 1.771 | 32.582 | 1.00 | 0.02 |
| ATOM | 1766 | CD | LYS | A | 199 | 35.105 | 1.951 | 31.818 | 1.00 | 0.01 |
| ATOM | 1767 | CE | LYS | A | 199 | 35.636 | 3.373 | 31.955 | 1.00 | 0.02 |
| ATOM | 1768 | NZ | LYS | A | 199 | 36.877 | 3.548 | 31.184 | 1.00 | 0.01 |
| ATOM | 1769 | C | LYS | A | 199 | 30.935 | 1.281 | 32.553 | 1.00 | 0.02 |
| ATOM | 1770 | O | LYS | A | 199 | 30.631 | 2.207 | 33.317 | 1.00 | 0.02 |
| ATOM | 1771 | N | LYS | A | 200 | 30.300 | 1.076 | 31.409 | 1.00 | 0.01 |
| ATOM | 1773 | CA | LYS | A | 200 | 29.396 | 2.122 | 30.913 | 1.00 | 0.00 |
| ATOM | 1774 | CB | LYS | A | 200 | 29.241 | 2.021 | 29.403 | 1.00 | 0.54 |
| ATOM | 1775 | CG | LYS | A | 200 | 30.566 | 2.268 | 28.696 | 1.00 | 0.77 |
| ATOM | 1776 | CD | LYS | A | 200 | 30.344 | 2.585 | 27.223 | 1.00 | 1.41 |
| ATOM | 1777 | CE | LYS | A | 200 | 29.590 | 3.900 | 27.054 | 1.00 | 2.57 |
| ATOM | 1778 | NZ | LYS | A | 200 | 29.363 | 4.207 | 25.632 | 1.00 | 3.36 |
| ATOM | 1779 | C | LYS | A | 200 | 28.025 | 2.062 | 31.577 | 1.00 | 0.02 |
| ATOM | 1780 | O | LYS | A | 200 | 27.350 | 3.091 | 31.696 | 1.00 | 0.01 |
| ATOM | 1781 | N | THR | A | 201 | 27.706 | 0.918 | 32.158 | 1.00 | 0.01 |
| ATOM | 1783 | CA | THR | A | 201 | 26.471 | 0.794 | 32.935 | 1.00 | 0.02 |
| ATOM | 1784 | CB | THR | A | 201 | 25.869 | -0.573 | 32.675 | 1.00 | 0.02 |
| ATOM | 1785 | OG1 | THR | A | 201 | 26.737 | -1.537 | 33.256 | 1.00 | 0.01 |
| ATOM | 1786 | CG2 | THR | A | 201 | 25.729 | -0.843 | 31.182 | 1.00 | 0.02 |
| ATOM | 1787 | C | THR | A | 201 | 26.710 | 0.937 | 34.436 | 1.00 | 0.01 |
| ATOM | 1788 | O | THR | A | 201 | 25.821 | 0.578 | 35.217 | 1.00 | 0.02 |
| ATOM | 1789 | N | GLN | A | 202 | 27.929 | 1.298 | 34.815 | 1.00 | 0.01 |
| ATOM | 1791 | CA | GLN | A | 202 | 28.342 | 1.444 | 36.222 | 1.00 | 0.01 |
| ATOM | 1792 | CB | GLN | A | 202 | 27.749 | 2.737 | 36.767 | 1.00 | 0.01 |
| ATOM | 1793 | CG | GLN | A | 202 | 28.390 | 3.955 | 36.107 | 1.00 | 0.02 |
| ATOM | 1794 | CD | GLN | A | 202 | 29.832 | 4.128 | 36.586 | 1.00 | 0.02 |
| ATOM | 1795 | OE1 | GLN | A | 202 | 30.071 | 4.474 | 37.748 | 1.00 | 0.02 |
| ATOM | 1796 | NE2 | GLN | A | 202 | 30.781 | 3.868 | 35.702 | 1.00 | 0.02 |
| ATOM | 1799 | C | GLN | A | 202 | 27.944 | 0.258 | 37.096 | 1.00 | 0.02 |
| ATOM | 1800 | O | GLN | A | 202 | 27.133 | 0.391 | 38.017 | 1.00 | 0.02 |
| ATOM | 1801 | N | GLY | A | 203 | 28.388 | -0.919 | 36.684 | 1.00 | 0.01 |
| ATOM | 1803 | CA | GLY | A | 203 | 28.146 | -2.150 | 37.443 | 1.00 | 0.02 |
| ATOM | 1804 | C | GLY | A | 203 | 26.858 | -2.892 | 37.073 | 1.00 | 0.01 |
| ATOM | 1805 | O | GLY | A | 203 | 26.715 | -4.067 | 37.432 | 1.00 | 0.02 |
| ATOM | 1806 | N | LYS | A | 204 | 25.948 | -2.241 | 36.365 | 1.00 | 0.02 |
| ATOM | 1808 | CA | LYS | A | 204 | 24.640 | -2.848 | 36.097 | 1.00 | 0.02 |
| ATOM | 1809 | CB | LYS | A | 204 | 23.717 | -1.784 | 35.509 | 1.00 | 0.02 |
| ATOM | 1810 | CG | LYS | A | 204 | 22.306 | -2.319 | 35.295 | 1.00 | 0.02 |

| ATOM | 1811 | CD | LYS | A | 204 | 21.668 | -2.736 | 36.615 | 1.00 | 0.01 |
|---|---|---|---|---|---|---|---|---|---|---|
| ATOM | 1812 | CE | LYS | A | 204 | 20.310 | -3.385 | 36.387 | 1.00 | 0.02 |
| ATOM | 1813 | NZ | LYS | A | 204 | 20.448 | -4.592 | 35.555 | 1.00 | 0.01 |
| ATOM | 1814 | C | LYS | A | 204 | 24.714 | -4.046 | 35.154 | 1.00 | 0.02 |
| ATOM | 1815 | O | LYS | A | 204 | 24.300 | -5.148 | 35.535 | 1.00 | 0.01 |
| ATOM | 1816 | N | VAL | A | 205 | 25.316 | -3.888 | 33.988 | 1.00 | 0.02 |
| ATOM | 1818 | CA | VAL | A | 205 | 25.328 | -5.002 | 33.046 | 1.00 | 0.02 |
| ATOM | 1819 | CB | VAL | A | 205 | 24.963 | -4.480 | 31.663 | 1.00 | 1.75 |
| ATOM | 1820 | CG1 | VAL | A | 205 | 24.930 | -5.618 | 30.660 | 1.00 | 2.29 |
| ATOM | 1821 | CG2 | VAL | A | 205 | 23.609 | -3.781 | 31.690 | 1.00 | 1.90 |
| ATOM | 1822 | C | VAL | A | 205 | 26.693 | -5.678 | 33.049 | 1.00 | 0.02 |
| ATOM | 1823 | O | VAL | A | 205 | 27.606 | -5.332 | 32.287 | 1.00 | 0.02 |
| ATOM | 1824 | N | VAL | A | 206 | 26.830 | -6.623 | 33.959 | 1.00 | 0.02 |
| ATOM | 1826 | CA | VAL | A | 206 | 28.087 | -7.359 | 34.091 | 1.00 | 0.02 |
| ATOM | 1827 | CB | VAL | A | 206 | 28.282 | -7.714 | 35.564 | 1.00 | 0.02 |
| ATOM | 1828 | CG1 | VAL | A | 206 | 28.669 | -6.487 | 36.378 | 1.00 | 0.02 |
| ATOM | 1829 | CG2 | VAL | A | 206 | 27.044 | -8.374 | 36.164 | 1.00 | 0.02 |
| ATOM | 1830 | C | VAL | A | 206 | 28.135 | -8.619 | 33.226 | 1.00 | 0.02 |
| ATOM | 1831 | O | VAL | A | 206 | 27.325 | -9.541 | 33.380 | 1.00 | 0.02 |
| ATOM | 1832 | N | ASP | A | 207 | 29.094 | -8.621 | 32.311 | 1.00 | 0.01 |
| ATOM | 1834 | CA | ASP | A | 207 | 29.461 | -9.822 | 31.538 | 1.00 | 0.01 |
| ATOM | 1835 | CB | ASP | A | 207 | 29.973 | -10.855 | 32.545 | 1.00 | 0.01 |
| ATOM | 1836 | CG | ASP | A | 207 | 30.574 | -12.075 | 31.861 | 1.00 | 0.02 |
| ATOM | 1837 | OD1 | ASP | A | 207 | 31.781 | -12.066 | 31.656 | 1.00 | 0.02 |
| ATOM | 1838 | OD2 | ASP | A | 207 | 29.828 | -13.006 | 31.589 | 1.00 | 0.01 |
| ATOM | 1839 | C | ASP | A | 207 | 28.307 | -10.405 | 30.715 | 1.00 | 0.02 |
| ATOM | 1840 | O | ASP | A | 207 | 27.567 | -11.272 | 31.197 | 1.00 | 0.01 |
| ATOM | 1841 | N | ILE | A | 208 | 28.194 | -9.988 | 29.464 | 1.00 | 0.02 |
| ATOM | 1843 | CA | ILE | A | 208 | 27.103 | -10.495 | 28.619 | 1.00 | 0.02 |
| ATOM | 1844 | CB | ILE | A | 208 | 26.250 | -9.320 | 28.151 | 1.00 | 2.45 |
| ATOM | 1845 | CG2 | ILE | A | 208 | 25.292 | -9.714 | 27.031 | 1.00 | 3.34 |
| ATOM | 1846 | CG1 | ILE | A | 208 | 25.463 | -8.770 | 29.330 | 1.00 | 3.29 |
| ATOM | 1847 | CD1 | ILE | A | 208 | 24.554 | -9.843 | 29.922 | 1.00 | 4.19 |
| ATOM | 1848 | C | ILE | A | 208 | 27.613 | -11.320 | 27.438 | 1.00 | 0.01 |
| ATOM | 1849 | O | ILE | A | 208 | 26.952 | -12.280 | 27.023 | 1.00 | 0.00 |
| ATOM | 1850 | N | ILE | A | 209 | 28.838 | -11.054 | 27.020 | 1.00 | 0.02 |
| ATOM | 1852 | CA | ILE | A | 209 | 29.452 | -11.827 | 25.933 | 1.00 | 0.02 |
| ATOM | 1853 | CB | ILE | A | 209 | 30.602 | -10.999 | 25.362 | 1.00 | 1.56 |
| ATOM | 1854 | CG2 | ILE | A | 209 | 31.305 | -11.731 | 24.229 | 1.00 | 2.38 |
| ATOM | 1855 | CG1 | ILE | A | 209 | 30.097 | -9.651 | 24.861 | 1.00 | 2.02 |
| ATOM | 1856 | CD1 | ILE | A | 209 | 29.197 | -9.802 | 23.639 | 1.00 | 2.14 |
| ATOM | 1857 | C | ILE | A | 209 | 29.949 | -13.157 | 26.494 | 1.00 | 0.02 |
| ATOM | 1858 | O | ILE | A | 209 | 30.876 | -13.182 | 27.314 | 1.00 | 0.02 |

| ATOM | 1859 | N | GLN | A | 210 | 29.245 | -14.223 | 26.140 | 1.00 | 0.02 |
|------|------|---|-----|---|-----|--------|---------|--------|------|------|
| ATOM | 1861 | CA | GLN | A | 210 | 29.515 | -15.557 | 26.698 | 1.00 | 0.01 |
| ATOM | 1862 | CB | GLN | A | 210 | 28.181 | -16.245 | 26.979 | 1.00 | 1.43 |
| ATOM | 1863 | CG | GLN | A | 210 | 27.267 | -15.429 | 27.887 | 1.00 | 2.09 |
| ATOM | 1864 | CD | GLN | A | 210 | 27.915 | -15.196 | 29.247 | 1.00 | 2.72 |
| ATOM | 1865 | OE1 | GLN | A | 210 | 28.581 | -16.080 | 29.799 | 1.00 | 2.94 |
| ATOM | 1866 | NE2 | GLN | A | 210 | 27.649 | -14.026 | 29.797 | 1.00 | 3.33 |
| ATOM | 1869 | C | GLN | A | 210 | 30.311 | -16.465 | 25.763 | 1.00 | 0.02 |
| ATOM | 1870 | O | GLN | A | 210 | 30.722 | -17.560 | 26.167 | 1.00 | 0.02 |
| ATOM | 1871 | N | GLY | A | 211 | 30.544 | -16.021 | 24.542 | 1.00 | 0.01 |
| ATOM | 1873 | CA | GLY | A | 211 | 31.234 | -16.887 | 23.587 | 1.00 | 0.02 |
| ATOM | 1874 | C | GLY | A | 211 | 31.664 | -16.167 | 22.315 | 1.00 | 0.01 |
| ATOM | 1875 | O | GLY | A | 211 | 30.924 | -16.144 | 21.323 | 1.00 | 0.01 |
| ATOM | 1876 | N | LEU | A | 212 | 32.829 | -15.544 | 22.365 | 1.00 | 0.02 |
| ATOM | 1878 | CA | LEU | A | 212 | 33.429 | -15.021 | 21.131 | 1.00 | 0.02 |
| ATOM | 1879 | CB | LEU | A | 212 | 34.730 | -14.291 | 21.442 | 1.00 | 0.02 |
| ATOM | 1880 | CG | LEU | A | 212 | 34.509 | -12.973 | 22.166 | 1.00 | 0.03 |
| ATOM | 1881 | CD1 | LEU | A | 212 | 35.848 | -12.284 | 22.399 | 1.00 | 0.02 |
| ATOM | 1882 | CD2 | LEU | A | 212 | 33.589 | -12.070 | 21.357 | 1.00 | 0.02 |
| ATOM | 1883 | C | LEU | A | 212 | 33.764 | -16.166 | 20.184 | 1.00 | 0.02 |
| ATOM | 1884 | O | LEU | A | 212 | 34.391 | -17.152 | 20.586 | 1.00 | 0.02 |
| ATOM | 1885 | N | ASP | A | 213 | 33.348 | -16.028 | 18.937 | 1.00 | 0.02 |
| ATOM | 1887 | CA | ASP | A | 213 | 33.725 | -17.009 | 17.915 | 1.00 | 0.02 |
| ATOM | 1888 | CB | ASP | A | 213 | 33.025 | -16.663 | 16.602 | 1.00 | 0.02 |
| ATOM | 1889 | CG | ASP | A | 213 | 31.513 | -16.871 | 16.720 | 1.00 | 0.02 |
| ATOM | 1890 | OD1 | ASP | A | 213 | 31.146 | -17.786 | 17.446 | 1.00 | 0.02 |
| ATOM | 1891 | OD2 | ASP | A | 213 | 30.814 | -16.339 | 15.873 | 1.00 | 0.01 |
| ATOM | 1892 | C | ASP | A | 213 | 35.243 | -17.007 | 17.735 | 1.00 | 0.01 |
| ATOM | 1893 | O | ASP | A | 213 | 35.895 | -15.971 | 17.900 | 1.00 | 0.02 |
| ATOM | 1894 | N | LEU | A | 214 | 35.801 | - | 17.333 | 1.00 | 0.02 |

| | | | | | | 18.139 | | | |
|---|---|---|---|---|---|---|---|---|---|
| ATOM | 1896 | CA | LEU | A | 214 | 37.269 | -18.245 | 17.212 | 1.00 | 0.02 |
| ATOM | 1897 | CB | LEU | A | 214 | 37.656 | -19.719 | 17.218 | 1.00 | 0.71 |
| ATOM | 1898 | CG | LEU | A | 214 | 37.303 | -20.384 | 18.545 | 1.00 | 1.18 |
| ATOM | 1899 | CD1 | LEU | A | 214 | 37.561 | -21.886 | 18.490 | 1.00 | 2.00 |
| ATOM | 1900 | CD2 | LEU | A | 214 | 38.070 | -19.749 | 19.702 | 1.00 | 0.70 |
| ATOM | 1901 | C | LEU | A | 214 | 37.834 | -17.570 | 15.958 | 1.00 | 0.02 |
| ATOM | 1902 | O | LEU | A | 214 | 39.046 | -17.360 | 15.853 | 1.00 | 0.01 |
| ATOM | 1903 | N | LEU | A | 215 | 36.952 | -17.175 | 15.054 | 1.00 | 0.02 |
| ATOM | 1905 | CA | LEU | A | 215 | 37.337 | -16.379 | 13.885 | 1.00 | 0.01 |
| ATOM | 1906 | CB | LEU | A | 215 | 36.730 | -17.010 | 12.636 | 1.00 | 0.36 |
| ATOM | 1907 | CG | LEU | A | 215 | 37.280 | -18.410 | 12.386 | 1.00 | 0.58 |
| ATOM | 1908 | CD1 | LEU | A | 215 | 36.543 | -19.089 | 11.238 | 1.00 | 0.90 |
| ATOM | 1909 | CD2 | LEU | A | 215 | 38.782 | -18.375 | 12.118 | 1.00 | 0.75 |
| ATOM | 1910 | C | LEU | A | 215 | 36.851 | -14.934 | 14.019 | 1.00 | 0.02 |
| ATOM | 1911 | O | LEU | A | 215 | 36.600 | -14.274 | 13.002 | 1.00 | 0.02 |
| ATOM | 1912 | N | THR | A | 216 | 36.624 | -14.491 | 15.248 | 1.00 | 0.02 |
| ATOM | 1914 | CA | THR | A | 216 | 36.066 | -13.154 | 15.478 | 1.00 | 0.01 |
| ATOM | 1915 | CB | THR | A | 216 | 35.668 | -13.016 | 16.948 | 1.00 | 0.02 |
| ATOM | 1916 | OG1 | THR | A | 216 | 34.418 | -13.675 | 17.093 | 1.00 | 0.02 |
| ATOM | 1917 | CG2 | THR | A | 216 | 35.435 | -11.568 | 17.361 | 1.00 | 0.02 |
| ATOM | 1918 | C | THR | A | 216 | 36.995 | -12.024 | 15.054 | 1.00 | 0.01 |
| ATOM | 1919 | O | THR | A | 216 | 38.106 | -11.858 | 15.566 | 1.00 | 0.02 |
| ATOM | 1920 | N | ALA | A | 217 | 36.546 | -11.310 | 14.035 | 1.00 | 0.02 |
| ATOM | 1922 | CA | ALA | A | 217 | 37.233 | -10.105 | 13.595 | 1.00 | 0.01 |
| ATOM | 1923 | CB | ALA | A | 217 | 37.410 | -10.187 | 12.085 | 1.00 | 0.41 |
| ATOM | 1924 | C | ALA | A | 217 | 36.467 | -8.837 | 13.977 | 1.00 | 0.02 |
| ATOM | 1925 | O | ALA | A | 217 | 37.029 | -7.735 | 13.887 | 1.00 | 0.02 |
| ATOM | 1926 | N | MET | A | 218 | 35.230 | -8.988 | 14.433 | 1.00 | 0.02 |
| ATOM | 1928 | CA | MET | A | 218 | 34.427 | -7.813 | 14.799 | 1.00 | 0.02 |
| ATOM | 1929 | CB | MET | A | 218 | 33.769 | -7.272 | 13.532 | 1.00 | 0.89 |
| ATOM | 1930 | CG | MET | A | 218 | 32.877 | -6.070 | 13.823 | 1.00 | 1.03 |
| ATOM | 1931 | SD | MET | A | 218 | 33.726 | -4.594 | 14.425 | 1.00 | 1.41 |
| ATOM | 1932 | CE | MET | A | 218 | 34.664 | -4.210 | 12.930 | 1.00 | 1.60 |

| ATOM | 1933 | C | MET | A | 218 | 33.340 | -8.122 | 15.832 | 1.00 | 0.01 |
|---|---|---|---|---|---|---|---|---|---|---|
| ATOM | 1934 | O | MET | A | 218 | 32.415 | -8.910 | 15.578 | 1.00 | 0.01 |
| ATOM | 1935 | N | VAL | A | 219 | 33.482 | -7.517 | 16.999 | 1.00 | 0.02 |
| ATOM | 1937 | CA | VAL | A | 219 | 32.422 | -7.542 | 18.017 | 1.00 | 0.02 |
| ATOM | 1938 | CB | VAL | A | 219 | 33.068 | -7.764 | 19.381 | 1.00 | 0.06 |
| ATOM | 1939 | CG1 | VAL | A | 219 | 32.055 | -7.782 | 20.521 | 1.00 | 0.12 |
| ATOM | 1940 | CG2 | VAL | A | 219 | 33.866 | -9.056 | 19.379 | 1.00 | 0.07 |
| ATOM | 1941 | C | VAL | A | 219 | 31.650 | -6.220 | 17.995 | 1.00 | 0.01 |
| ATOM | 1942 | O | VAL | A | 219 | 32.250 | -5.139 | 17.968 | 1.00 | 0.02 |
| ATOM | 1943 | N | LEU | A | 220 | 30.333 | -6.315 | 18.009 | 1.00 | 0.01 |
| ATOM | 1945 | CA | LEU | A | 220 | 29.482 | -5.123 | 17.957 | 1.00 | 0.01 |
| ATOM | 1946 | CB | LEU | A | 220 | 28.642 | -5.205 | 16.680 | 1.00 | 0.01 |
| ATOM | 1947 | CG | LEU | A | 220 | 28.089 | -3.862 | 16.191 | 1.00 | 0.01 |
| ATOM | 1948 | CD1 | LEU | A | 220 | 27.668 | -3.953 | 14.729 | 1.00 | 0.01 |
| ATOM | 1949 | CD2 | LEU | A | 220 | 26.946 | -3.313 | 17.041 | 1.00 | 0.01 |
| ATOM | 1950 | C | LEU | A | 220 | 28.594 | -5.077 | 19.200 | 1.00 | 0.01 |
| ATOM | 1951 | O | LEU | A | 220 | 27.497 | -5.650 | 19.218 | 1.00 | 0.01 |
| ATOM | 1952 | N | VAL | A | 221 | 29.073 | -4.388 | 20.221 | 1.00 | 0.01 |
| ATOM | 1954 | CA | VAL | A | 221 | 28.305 | -4.223 | 21.462 | 1.00 | 0.01 |
| ATOM | 1955 | CB | VAL | A | 221 | 29.305 | -4.000 | 22.595 | 1.00 | 0.02 |
| ATOM | 1956 | CG1 | VAL | A | 221 | 28.634 | -3.684 | 23.928 | 1.00 | 0.01 |
| ATOM | 1957 | CG2 | VAL | A | 221 | 30.216 | -5.211 | 22.736 | 1.00 | 0.02 |
| ATOM | 1958 | C | VAL | A | 221 | 27.345 | -3.041 | 21.336 | 1.00 | 0.01 |
| ATOM | 1959 | O | VAL | A | 221 | 27.729 | -1.976 | 20.839 | 1.00 | 0.02 |
| ATOM | 1960 | N | ASN | A | 222 | 26.090 | -3.262 | 21.689 | 1.00 | 0.01 |
| ATOM | 1962 | CA | ASN | A | 222 | 25.084 | -2.195 | 21.631 | 1.00 | 0.01 |
| ATOM | 1963 | CB | ASN | A | 222 | 24.364 | -2.314 | 20.295 | 1.00 | 0.01 |
| ATOM | 1964 | CG | ASN | A | 222 | 23.343 | -1.197 | 20.131 | 1.00 | 0.01 |
| ATOM | 1965 | OD1 | ASN | A | 222 | 22.132 | -1.435 | 20.262 | 1.00 | 0.01 |
| ATOM | 1966 | ND2 | ASN | A | 222 | 23.834 | 0.015 | 19.928 | 1.00 | 0.01 |
| ATOM | 1969 | C | ASN | A | 222 | 24.095 | -2.302 | 22.795 | 1.00 | 0.01 |
| ATOM | 1970 | O | ASN | A | 222 | 22.975 | -2.808 | 22.661 | 1.00 | 0.02 |
| ATOM | 1971 | N | HIS | A | 223 | 24.526 | -1.833 | 23.950 | 1.00 | 0.01 |
| ATOM | 1973 | CA | HIS | A | 223 | 23.697 | -1.944 | 25.158 | 1.00 | 0.02 |
| ATOM | 1974 | CB | HIS | A | 223 | 24.551 | -2.496 | 26.298 | 1.00 | 0.87 |
| ATOM | 1975 | CG | HIS | A | 223 | 24.966 | -3.960 | 26.176 | 1.00 | 1.28 |
| ATOM | 1976 | ND1 | HIS | A | 223 | 25.150 | -4.803 | 27.206 | 1.00 | 1.65 |
| ATOM | 1978 | CE1 | HIS | A | 223 | 25.513 | -6.015 | 26.741 | 1.00 | 2.67 |
| ATOM | 1979 | NE2 | HIS | A | 223 | 25.558 | -5.941 | 25.393 | 1.00 | 3.07 |
| ATOM | 1980 | CD2 | HIS | A | 223 | 25.223 | -4.684 | 25.032 | 1.00 | 2.44 |
| ATOM | 1981 | C | HIS | A | 223 | 23.079 | -0.594 | 25.527 | 1.00 | 0.01 |
| ATOM | 1982 | O | HIS | A | 223 | 23.507 | 0.440 | 24.998 | 1.00 | 0.01 |
| ATOM | 1983 | N | ILE | A | 224 | 22.034 | -0.619 | 26.344 | 1.00 | 0.01 |
| ATOM | 1985 | CA | ILE | A | 224 | 21.324 | 0.625 | 26.704 | 1.00 | 0.02 |
| ATOM | 1986 | CB | ILE | A | 224 | 20.522 | 1.038 | 25.466 | 1.00 | 0.01 |
| ATOM | 1987 | CG2 | ILE | A | 224 | 19.655 | -0.104 | 24.944 | 1.00 | 0.01 |
| ATOM | 1988 | CG1 | ILE | A | 224 | 19.686 | 2.287 | 25.693 | 1.00 | 0.01 |
| ATOM | 1989 | CD1 | ILE | A | 224 | 18.973 | 2.688 | 24.405 | 1.00 | 0.00 |
| ATOM | 1990 | C | ILE | A | 224 | 20.434 | 0.501 | 27.963 | 1.00 | 0.01 |
| ATOM | 1991 | O | ILE | A | 224 | 19.450 | -0.251 | 27.990 | 1.00 | 0.02 |
| ATOM | 1992 | N | PHE | A | 225 | 20.793 | 1.254 | 28.996 | 1.00 | 0.02 |
| ATOM | 1994 | CA | PHE | A | 225 | 20.052 | 1.255 | 30.279 | 1.00 | 0.01 |
| ATOM | 1995 | CB | PHE | A | 225 | 21.077 | 1.048 | 31.398 | 1.00 | 0.01 |
| ATOM | 1996 | CG | PHE | A | 225 | 20.524 | 1.137 | 32.821 | 1.00 | 0.02 |
| ATOM | 1997 | CD1 | PHE | A | 225 | 19.720 | 0.121 | 33.320 | 1.00 | 0.00 |
| ATOM | 1998 | CE1 | PHE | A | 225 | 19.207 | 0.206 | 34.608 | 1.00 | 0.01 |
| ATOM | 1999 | CZ | PHE | A | 225 | 19.500 | 1.309 | 35.400 | 1.00 | 0.01 |
| ATOM | 2000 | CE2 | PHE | A | 225 | 20.306 | 2.324 | 34.903 | 1.00 | 0.02 |

| ATOM | 2001 | CD2 | PHE | A | 225 | 20.817 | 2.238 | 33.615 | 1.00 | 0.01 |
|------|------|-----|-----|---|-----|--------|-------|--------|------|------|
| ATOM | 2002 | C   | PHE | A | 225 | 19.257 | 2.550 | 30.534 | 1.00 | 0.02 |
| ATOM | 2003 | O   | PHE | A | 225 | 19.752 | 3.660 | 30.299 | 1.00 | 0.02 |
| ATOM | 2004 | N   | PHE | A | 226 | 18.034 | 2.401 | 31.023 | 1.00 | 0.01 |
| ATOM | 2006 | CA  | PHE | A | 226 | 17.212 | 3.560 | 31.412 | 1.00 | 0.01 |
| ATOM | 2007 | CB  | PHE | A | 226 | 16.186 | 3.802 | 30.308 | 1.00 | 0.01 |
| ATOM | 2008 | CG  | PHE | A | 226 | 15.325 | 5.054 | 30.479 | 1.00 | 0.01 |
| ATOM | 2009 | CD1 | PHE | A | 226 | 15.909 | 6.259 | 30.851 | 1.00 | 0.01 |
| ATOM | 2010 | CE1 | PHE | A | 226 | 15.124 | 7.394 | 31.007 | 1.00 | 0.01 |
| ATOM | 2011 | CZ  | PHE | A | 226 | 13.756 | 7.327 | 30.783 | 1.00 | 0.01 |
| ATOM | 2012 | CE2 | PHE | A | 226 | 13.174 | 6.126 | 30.399 | 1.00 | 0.01 |
| ATOM | 2013 | CD2 | PHE | A | 226 | 13.959 | 4.992 | 30.243 | 1.00 | 0.01 |
| ATOM | 2014 | C   | PHE | A | 226 | 16.482 | 3.348 | 32.748 | 1.00 | 0.02 |
| ATOM | 2015 | O   | PHE | A | 226 | 15.952 | 2.263 | 33.022 | 1.00 | 0.02 |
| ATOM | 2016 | N   | LYS | A | 227 | 16.510 | 4.367 | 33.594 | 1.00 | 0.01 |
| ATOM | 2018 | CA  | LYS | A | 227 | 15.692 | 4.371 | 34.819 | 1.00 | 0.01 |
| ATOM | 2019 | CB  | LYS | A | 227 | 16.587 | 4.677 | 36.016 | 1.00 | 0.01 |
| ATOM | 2020 | CG  | LYS | A | 227 | 15.844 | 4.470 | 37.332 | 1.00 | 0.02 |
| ATOM | 2021 | CD  | LYS | A | 227 | 16.766 | 4.616 | 38.535 | 1.00 | 0.00 |
| ATOM | 2022 | CE  | LYS | A | 227 | 16.032 | 4.290 | 39.831 | 1.00 | 0.02 |
| ATOM | 2023 | NZ  | LYS | A | 227 | 16.933 | 4.396 | 40.990 | 1.00 | 0.01 |
| ATOM | 2024 | C   | LYS | A | 227 | 14.570 | 5.412 | 34.690 | 1.00 | 0.01 |
| ATOM | 2025 | O   | LYS | A | 227 | 14.826 | 6.574 | 34.352 | 1.00 | 0.00 |
| ATOM | 2026 | N   | ALA | A | 228 | 13.343 | 4.984 | 34.942 | 1.00 | 0.02 |
| ATOM | 2028 | CA  | ALA | A | 228 | 12.164 | 5.833 | 34.703 | 1.00 | 0.00 |
| ATOM | 2029 | CB  | ALA | A | 228 | 10.949 | 4.915 | 34.631 | 1.00 | 2.74 |
| ATOM | 2030 | C   | ALA | A | 228 | 11.903 | 6.930 | 35.745 | 1.00 | 0.02 |
| ATOM | 2031 | O   | ALA | A | 228 | 11.520 | 6.656 | 36.890 | 1.00 | 0.01 |
| ATOM | 2032 | N   | LYS | A | 229 | 12.091 | 8.173 | 35.323 | 1.00 | 0.02 |
| ATOM | 2034 | CA  | LYS | A | 229 | 11.680 | 9.329 | 36.140 | 1.00 | 0.01 |
| ATOM | 2035 | CB  | LYS | A | 229 | 12.712 | 10.446 | 36.047 | 1.00 | 0.01 |
| ATOM | 2036 | CG  | LYS | A | 229 | 14.112 | 10.023 | 36.464 | 1.00 | 0.02 |
| ATOM | 2037 | CD  | LYS | A | 229 | 15.020 | 11.247 | 36.501 | 1.00 | 0.01 |
| ATOM | 2038 | CE  | LYS | A | 229 | 14.956 | 12.014 | 35.184 | 1.00 | 0.02 |
| ATOM | 2039 | NZ  | LYS | A | 229 | 15.754 | 13.250 | 35.241 | 1.00 | 0.02 |
| ATOM | 2040 | C   | LYS | A | 229 | 10.359 | 9.894 | 35.625 | 1.00 | 0.02 |
| ATOM | 2041 | O   | LYS | A | 229 | 10.340 | 10.602 | 34.614 | 1.00 | 0.01 |
| ATOM | 2042 | N   | TRP | A | 230 | 9.288  | 9.641 | 36.355 | 1.00 | 0.01 |
| ATOM | 2044 | CA  | TRP | A | 230 | 7.947  | 10.079 | 35.942 | 1.00 | 0.00 |
| ATOM | 2045 | CB  | TRP | A | 230 | 6.928  | 9.244 | 36.711 | 1.00 | 0.01 |
| ATOM | 2046 | CG  | TRP | A | 230 | 7.132  | 7.747 | 36.623 | 1.00 | 0.02 |
| ATOM | 2047 | CD1 | TRP | A | 230 | 7.766  | 6.944 | 37.544 | 1.00 | 0.02 |
| ATOM | 2048 | NE1 | TRP | A | 230 | 7.738  | 5.666 | 37.093 | 1.00 | 0.02 |
| ATOM | 2050 | CE2 | TRP | A | 230 | 7.105  | 5.583 | 35.910 | 1.00 | 0.02 |
| ATOM | 2051 | CZ2 | TRP | A | 230 | 6.833  | 4.520 | 35.061 | 1.00 | 0.02 |
| ATOM | 2052 | CH2 | TRP | A | 230 | 6.138  | 4.745 | 33.880 | 1.00 | 0.02 |
| ATOM | 2053 | CZ3 | TRP | A | 230 | 5.714  | 6.027 | 33.543 | 1.00 | 0.02 |
| ATOM | 2054 | CE3 | TRP | A | 230 | 5.985  | 7.098 | 34.386 | 1.00 | 0.01 |
| ATOM | 2055 | CD2 | TRP | A | 230 | 6.681  | 6.878 | 35.563 | 1.00 | 0.01 |
| ATOM | 2056 | C   | TRP | A | 230 | 7.682  | 11.542 | 36.280 | 1.00 | 0.01 |
| ATOM | 2057 | O   | TRP | A | 230 | 8.238  | 12.071 | 37.246 | 1.00 | 0.02 |
| ATOM | 2058 | N   | GLU | A | 231 | 6.838  | 12.187 | 35.486 | 1.00 | 0.00 |
| ATOM | 2060 | CA  | GLU | A | 231 | 6.317  | 13.505 | 35.880 | 1.00 | 0.02 |
| ATOM | 2061 | CB  | GLU | A | 231 | 5.940  | 14.317 | 34.648 | 1.00 | 0.01 |
| ATOM | 2062 | CG  | GLU | A | 231 | 7.167  | 14.820 | 33.909 | 1.00 | 0.02 |
| ATOM | 2063 | CD  | GLU | A | 231 | 6.748  | 15.520 | 32.625 | 1.00 | 0.01 |
| ATOM | 2064 | OE1 | GLU | A | 231 | 5.717  | 15.135 | 32.085 | 1.00 | 0.02 |
| ATOM | 2065 | OE2 | GLU | A | 231 | 7.483  | 16.398 | 32.189 | 1.00 | 0.01 |

| ATOM | 2066 | C | GLU | A | 231 | 5.075 | 13.325 | 36.743 | 1.00 | 0.01 |
|---|---|---|---|---|---|---|---|---|---|---|
| ATOM | 2067 | O | GLU | A | 231 | 4.708 | 14.204 | 37.531 | 1.00 | 0.02 |
| ATOM | 2068 | N | LYS | A | 232 | 4.469 | 12.157 | 36.611 | 1.00 | 0.01 |
| ATOM | 2070 | CA | LYS | A | 232 | 3.346 | 11.766 | 37.468 | 1.00 | 0.00 |
| ATOM | 2071 | CB | LYS | A | 232 | 2.213 | 11.333 | 36.545 | 1.00 | 0.65 |
| ATOM | 2072 | CG | LYS | A | 232 | 1.961 | 12.369 | 35.451 | 1.00 | 1.25 |
| ATOM | 2073 | CD | LYS | A | 232 | 0.943 | 11.872 | 34.432 | 1.00 | 1.89 |
| ATOM | 2074 | CE | LYS | A | 232 | 0.755 | 12.859 | 33.286 | 1.00 | 2.53 |
| ATOM | 2075 | NZ | LYS | A | 232 | -0.202 | 12.335 | 32.300 | 1.00 | 3.06 |
| ATOM | 2076 | C | LYS | A | 232 | 3.774 | 10.593 | 38.356 | 1.00 | 0.02 |
| ATOM | 2077 | O | LYS | A | 232 | 3.609 | 9.431 | 37.968 | 1.00 | 0.02 |
| ATOM | 2078 | N | PRO | A | 233 | 4.328 | 10.898 | 39.522 | 1.00 | 0.01 |
| ATOM | 2079 | CA | PRO | A | 233 | 5.023 | 9.884 | 40.325 | 1.00 | 0.02 |
| ATOM | 2080 | CB | PRO | A | 233 | 5.778 | 10.650 | 41.368 | 1.00 | 0.02 |
| ATOM | 2081 | CG | PRO | A | 233 | 5.390 | 12.117 | 41.289 | 1.00 | 0.02 |
| ATOM | 2082 | CD | PRO | A | 233 | 4.451 | 12.240 | 40.101 | 1.00 | 0.01 |
| ATOM | 2083 | C | PRO | A | 233 | 4.059 | 8.901 | 40.978 | 1.00 | 0.02 |
| ATOM | 2084 | O | PRO | A | 233 | 2.893 | 9.225 | 41.240 | 1.00 | 0.02 |
| ATOM | 2085 | N | PHE | A | 234 | 4.542 | 7.694 | 41.205 | 1.00 | 0.01 |
| ATOM | 2087 | CA | PHE | A | 234 | 3.728 | 6.687 | 41.895 | 1.00 | 0.02 |
| ATOM | 2088 | CB | PHE | A | 234 | 3.968 | 5.325 | 41.258 | 1.00 | 0.02 |
| ATOM | 2089 | CG | PHE | A | 234 | 3.429 | 5.190 | 39.837 | 1.00 | 0.00 |
| ATOM | 2090 | CD1 | PHE | A | 234 | 2.096 | 4.850 | 39.647 | 1.00 | 0.01 |
| ATOM | 2091 | CE1 | PHE | A | 234 | 1.587 | 4.724 | 38.363 | 1.00 | 0.00 |
| ATOM | 2092 | CZ | PHE | A | 234 | 2.411 | 4.934 | 37.266 | 1.00 | 0.01 |
| ATOM | 2093 | CE2 | PHE | A | 234 | 3.746 | 5.268 | 37.454 | 1.00 | 0.01 |
| ATOM | 2094 | CD2 | PHE | A | 234 | 4.256 | 5.393 | 38.739 | 1.00 | 0.02 |
| ATOM | 2095 | C | PHE | A | 234 | 4.066 | 6.647 | 43.381 | 1.00 | 0.00 |
| ATOM | 2096 | O | PHE | A | 234 | 5.224 | 6.848 | 43.770 | 1.00 | 0.01 |
| ATOM | 2097 | N | HIS | A | 235 | 3.063 | 6.405 | 44.207 | 1.00 | 0.02 |
| ATOM | 2099 | CA | HIS | A | 235 | 3.314 | 6.361 | 45.648 | 1.00 | 0.02 |
| ATOM | 2100 | CB | HIS | A | 235 | 2.013 | 6.519 | 46.415 | 1.00 | 1.04 |
| ATOM | 2101 | CG | HIS | A | 235 | 1.497 | 7.939 | 46.502 | 1.00 | 1.51 |
| ATOM | 2102 | ND1 | HIS | A | 235 | 1.991 | 8.923 | 47.275 | 1.00 | 1.88 |
| ATOM | 2104 | CE1 | HIS | A | 235 | 1.267 | 10.045 | 47.085 | 1.00 | 2.58 |
| ATOM | 2105 | NE2 | HIS | A | 235 | 0.298 | 9.759 | 46.186 | 1.00 | 2.75 |
| ATOM | 2106 | CD2 | HIS | A | 235 | 0.426 | 8.463 | 45.820 | 1.00 | 2.28 |
| ATOM | 2107 | C | HIS | A | 235 | 3.982 | 5.068 | 46.083 | 1.00 | 0.00 |
| ATOM | 2108 | O | HIS | A | 235 | 3.392 | 3.983 | 46.015 | 1.00 | 0.02 |
| ATOM | 2109 | N | LEU | A | 236 | 5.091 | 5.250 | 46.781 | 1.00 | 0.02 |
| ATOM | 2111 | CA | LEU | A | 236 | 5.863 | 4.124 | 47.320 | 1.00 | 0.02 |
| ATOM | 2112 | CB | LEU | A | 236 | 7.182 | 4.676 | 47.855 | 1.00 | 0.19 |
| ATOM | 2113 | CG | LEU | A | 236 | 8.000 | 3.629 | 48.609 | 1.00 | 1.21 |
| ATOM | 2114 | CD1 | LEU | A | 236 | 8.409 | 2.469 | 47.707 | 1.00 | 1.76 |
| ATOM | 2115 | CD2 | LEU | A | 236 | 9.232 | 4.263 | 49.244 | 1.00 | 2.24 |
| ATOM | 2116 | C | LEU | A | 236 | 5.112 | 3.425 | 48.449 | 1.00 | 0.03 |
| ATOM | 2117 | O | LEU | A | 236 | 4.952 | 2.202 | 48.397 | 1.00 | 0.00 |
| ATOM | 2118 | N | GLU | A | 237 | 4.351 | 4.205 | 49.203 | 1.00 | 0.02 |
| ATOM | 2120 | CA | GLU | A | 237 | 3.569 | 3.650 | 50.314 | 1.00 | 0.02 |
| ATOM | 2121 | CB | GLU | A | 237 | 3.304 | 4.726 | 51.378 | 1.00 | 0.45 |
| ATOM | 2122 | CG | GLU | A | 237 | 2.108 | 5.650 | 51.104 | 1.00 | 1.07 |
| ATOM | 2123 | CD | GLU | A | 237 | 2.452 | 6.916 | 50.324 | 1.00 | 1.99 |
| ATOM | 2124 | OE1 | GLU | A | 237 | 3.332 | 6.858 | 49.468 | 1.00 | 2.71 |
| ATOM | 2125 | OE2 | GLU | A | 237 | 1.787 | 7.917 | 50.546 | 1.00 | 2.42 |
| ATOM | 2126 | C | GLU | A | 237 | 2.244 | 3.028 | 49.856 | 1.00 | 0.02 |
| ATOM | 2127 | O | GLU | A | 237 | 1.503 | 2.497 | 50.688 | 1.00 | 0.02 |
| ATOM | 2128 | N | TYR | A | 238 | 1.938 | 3.109 | 48.569 | 1.00 | 0.00 |
| ATOM | 2130 | CA | TYR | A | 238 | 0.737 | 2.466 | 48.039 | 1.00 | 0.02 |

| | | | | | | | | | |
|---|---|---|---|---|---|---|---|---|---|
| ATOM | 2131 | CB | TYR | A | 238 | -0.174 | 3.500 | 47.384 | 1.00 | 0.46 |
| ATOM | 2132 | CG | TYR | A | 238 | -0.787 | 4.495 | 48.369 | 1.00 | 0.77 |
| ATOM | 2133 | CD1 | TYR | A | 238 | -0.917 | 5.831 | 48.014 | 1.00 | 1.12 |
| ATOM | 2134 | CE1 | TYR | A | 238 | -1.456 | 6.742 | 48.912 | 1.00 | 1.60 |
| ATOM | 2135 | CZ | TYR | A | 238 | -1.873 | 6.310 | 50.164 | 1.00 | 1.80 |
| ATOM | 2136 | OH | TYR | A | 238 | -2.344 | 7.224 | 51.080 | 1.00 | 2.33 |
| ATOM | 2137 | CE2 | TYR | A | 238 | -1.765 | 4.971 | 50.517 | 1.00 | 1.57 |
| ATOM | 2138 | CD2 | TYR | A | 238 | -1.225 | 4.062 | 49.616 | 1.00 | 1.05 |
| ATOM | 2139 | C | TYR | A | 238 | 1.119 | 1.366 | 47.054 | 1.00 | 0.00 |
| ATOM | 2140 | O | TYR | A | 238 | 0.241 | 0.775 | 46.413 | 1.00 | 0.02 |
| ATOM | 2141 | N | THR | A | 239 | 2.411 | 1.101 | 46.939 | 1.00 | 0.02 |
| ATOM | 2143 | CA | THR | A | 239 | 2.892 | 0.016 | 46.077 | 1.00 | 0.00 |
| ATOM | 2144 | CB | THR | A | 239 | 4.306 | 0.340 | 45.605 | 1.00 | 0.02 |
| ATOM | 2145 | OG1 | THR | A | 239 | 4.256 | 1.575 | 44.907 | 1.00 | 0.02 |
| ATOM | 2146 | CG2 | THR | A | 239 | 4.853 | -0.712 | 44.644 | 1.00 | 0.02 |
| ATOM | 2147 | C | THR | A | 239 | 2.869 | -1.310 | 46.835 | 1.00 | 0.02 |
| ATOM | 2148 | O | THR | A | 239 | 3.879 | -1.773 | 47.378 | 1.00 | 0.02 |
| ATOM | 2149 | N | ARG | A | 240 | 1.701 | -1.926 | 46.830 | 1.00 | 0.02 |
| ATOM | 2151 | CA | ARG | A | 240 | 1.484 | -3.175 | 47.567 | 1.00 | 0.00 |
| ATOM | 2152 | CB | ARG | A | 240 | 0.013 | -3.242 | 47.963 | 1.00 | 0.53 |
| ATOM | 2153 | CG | ARG | A | 240 | -0.451 | -1.955 | 48.637 | 1.00 | 0.68 |
| ATOM | 2154 | CD | ARG | A | 240 | 0.259 | -1.704 | 49.964 | 1.00 | 1.22 |
| ATOM | 2155 | NE | ARG | A | 240 | -0.136 | -0.396 | 50.506 | 1.00 | 1.14 |
| ATOM | 2156 | CZ | ARG | A | 240 | -0.871 | -0.252 | 51.611 | 1.00 | 1.24 |
| ATOM | 2157 | NH1 | ARG | A | 240 | -1.252 | -1.327 | 52.305 | 1.00 | 1.79 |
| ATOM | 2158 | NH2 | ARG | A | 240 | -1.204 | 0.969 | 52.035 | 1.00 | 1.15 |
| ATOM | 2159 | C | ARG | A | 240 | 1.806 | -4.367 | 46.681 | 1.00 | 0.00 |
| ATOM | 2160 | O | ARG | A | 240 | 2.199 | -4.194 | 45.524 | 1.00 | 0.00 |
| ATOM | 2161 | N | LYS | A | 241 | 1.732 | -5.561 | 47.238 | 1.00 | 0.02 |
| ATOM | 2163 | CA | LYS | A | 241 | 1.793 | -6.760 | 46.396 | 1.00 | 0.02 |
| ATOM | 2164 | CB | LYS | A | 241 | 2.509 | -7.886 | 47.126 | 1.00 | 0.27 |
| ATOM | 2165 | CG | LYS | A | 241 | 3.960 | -7.513 | 47.403 | 1.00 | 0.53 |
| ATOM | 2166 | CD | LYS | A | 241 | 4.703 | -8.662 | 48.071 | 1.00 | 0.54 |
| ATOM | 2167 | CE | LYS | A | 241 | 4.032 | -9.067 | 49.378 | 1.00 | 1.44 |
| ATOM | 2168 | NZ | LYS | A | 241 | 4.749 | -10.187 | 50.010 | 1.00 | 1.70 |
| ATOM | 2169 | C | LYS | A | 241 | 0.367 | -7.161 | 46.039 | 1.00 | 0.02 |
| ATOM | 2170 | O | LYS | A | 241 | -0.196 | -8.108 | 46.602 | 1.00 | 0.02 |
| ATOM | 2171 | N | ASN | A | 242 | -0.136 | -6.506 | 45.008 | 1.00 | 0.02 |
| ATOM | 2173 | CA | ASN | A | 242 | -1.561 | -6.535 | 44.658 | 1.00 | 0.02 |
| ATOM | 2174 | CB | ASN | A | 242 | -1.762 | -5.487 | 43.562 | 1.00 | 1.70 |
| ATOM | 2175 | CG | ASN | A | 242 | -3.225 | -5.103 | 43.344 | 1.00 | 2.00 |
| ATOM | 2176 | OD1 | ASN | A | 242 | -3.967 | -4.883 | 44.308 | 1.00 | 2.32 |
| ATOM | 2177 | ND2 | ASN | A | 242 | -3.654 | -5.174 | 42.095 | 1.00 | 2.72 |
| ATOM | 2180 | C | ASN | A | 242 | -2.005 | -7.912 | 44.173 | 1.00 | 0.01 |
| ATOM | 2181 | O | ASN | A | 242 | -1.179 | -8.820 | 43.981 | 1.00 | 0.01 |
| ATOM | 2182 | N | PHE | A | 243 | -3.317 | -8.093 | 44.170 | 1.00 | 1.09 |
| ATOM | 2184 | CA | PHE | A | 243 | -3.948 | -9.270 | 43.575 | 1.00 | 1.45 |
| ATOM | 2185 | CB | PHE | A | 243 | -5.448 | -9.023 | 43.445 | 1.00 | 1.44 |
| ATOM | 2186 | CG | PHE | A | 243 | -6.191 | -9.068 | 44.777 | 1.00 | 2.03 |
| ATOM | 2187 | CD1 | PHE | A | 243 | -6.608 | -7.895 | 45.395 | 1.00 | 2.31 |
| ATOM | 2188 | CE1 | PHE | A | 243 | -7.282 | -7.952 | 46.608 | 1.00 | 3.15 |
| ATOM | 2189 | CZ | PHE | A | 243 | -7.543 | -9.181 | 47.201 | 1.00 | 3.65 |
| ATOM | 2190 | CE2 | PHE | A | 243 | -7.132 | -10.353 | 46.581 | 1.00 | 3.50 |
| ATOM | 2191 | CD2 | PHE | A | 243 | -6.457 | -10.296 | 45.368 | 1.00 | 2.79 |
| ATOM | 2192 | C | PHE | A | 243 | -3.329 | -9.557 | 42.216 | 1.00 | 0.50 |

| ATOM | 2193 | O | PHE | A | 243 | -3.162 | -8.676 | 41.360 | 1.00 | 1.04 |
|------|------|------|------|---|-----|--------|---------|--------|------|------|
| ATOM | 2194 | N | PRO | A | 244 | -2.972 | -10.818 | 42.071 | 1.00 | 0.02 |
| ATOM | 2195 | CA | PRO | A | 244 | -1.824 | -11.208 | 41.251 | 1.00 | 0.02 |
| ATOM | 2196 | CB | PRO | A | 244 | -1.664 | -12.670 | 41.499 | 1.00 | 2.44 |
| ATOM | 2197 | CG | PRO | A | 244 | -2.608 | -13.120 | 42.597 | 1.00 | 2.19 |
| ATOM | 2198 | CD | PRO | A | 244 | -3.365 | -11.877 | 43.005 | 1.00 | 1.42 |
| ATOM | 2199 | C | PRO | A | 244 | -1.952 | -10.906 | 39.761 | 1.00 | 0.02 |
| ATOM | 2200 | O | PRO | A | 244 | -3.037 | -10.632 | 39.229 | 1.00 | 0.02 |
| ATOM | 2201 | N | PHE | A | 245 | -0.795 | -10.898 | 39.123 | 1.00 | 0.02 |
| ATOM | 2203 | CA | PHE | A | 245 | -0.678 | -10.695 | 37.682 | 1.00 | 0.02 |
| ATOM | 2204 | CB | PHE | A | 245 | 0.806 | -10.487 | 37.372 | 1.00 | 0.02 |
| ATOM | 2205 | CG | PHE | A | 245 | 1.133 | -9.809 | 36.043 | 1.00 | 0.01 |
| ATOM | 2206 | CD1 | PHE | A | 245 | 1.229 | -10.552 | 34.874 | 1.00 | 0.02 |
| ATOM | 2207 | CE1 | PHE | A | 245 | 1.524 | -9.922 | 33.672 | 1.00 | 0.01 |
| ATOM | 2208 | CZ | PHE | A | 245 | 1.728 | -8.549 | 33.638 | 1.00 | 0.02 |
| ATOM | 2209 | CE2 | PHE | A | 245 | 1.637 | -7.806 | 34.807 | 1.00 | 0.01 |
| ATOM | 2210 | CD2 | PHE | A | 245 | 1.342 | -8.436 | 36.009 | 1.00 | 0.01 |
| ATOM | 2211 | C | PHE | A | 245 | -1.194 | -11.935 | 36.960 | 1.00 | 0.02 |
| ATOM | 2212 | O | PHE | A | 245 | -0.890 | -13.073 | 37.344 | 1.00 | 0.00 |
| ATOM | 2213 | N | LEU | A | 246 | -1.993 | -11.701 | 35.938 | 1.00 | 0.01 |
| ATOM | 2215 | CA | LEU | A | 246 | -2.559 | -12.782 | 35.137 | 1.00 | 0.02 |
| ATOM | 2216 | CB | LEU | A | 246 | -3.901 | -12.339 | 34.565 | 1.00 | 0.69 |
| ATOM | 2217 | CG | LEU | A | 246 | -4.970 | -12.241 | 35.646 | 1.00 | 1.13 |
| ATOM | 2218 | CD1 | LEU | A | 246 | -6.254 | -11.634 | 35.093 | 1.00 | 1.59 |
| ATOM | 2219 | CD2 | LEU | A | 246 | -5.247 | -13.611 | 36.252 | 1.00 | 1.37 |
| ATOM | 2220 | C | LEU | A | 246 | -1.623 | -13.147 | 33.996 | 1.00 | 0.02 |
| ATOM | 2221 | O | LEU | A | 246 | -1.581 | -12.479 | 32.953 | 1.00 | 0.01 |
| ATOM | 2222 | N | VAL | A | 247 | -0.891 | -14.228 | 34.206 | 1.00 | 0.01 |
| ATOM | 2224 | CA | VAL | A | 247 | -0.023 | -14.756 | 33.151 | 1.00 | 0.02 |
| ATOM | 2225 | CB | VAL | A | 247 | 1.315 | -15.191 | 33.749 | 1.00 | 0.02 |
| ATOM | 2226 | CG1 | VAL | A | 247 | 1.981 | -14.005 | 34.430 | 1.00 | 0.01 |
| ATOM | 2227 | CG2 | VAL | A | 247 | 1.180 | -16.337 | 34.742 | 1.00 | 0.01 |
| ATOM | 2228 | C | VAL | A | 247 | -0.762 | - | 32.457 | 1.00 | 0.01 |

| | | | | | | 15.897 | | | |
|---|---|---|---|---|---|---|---|---|---|
| ATOM | 2229 | O | VAL | A | 247 | -0.391 | -16.365 | 31.374 | 1.00 | 0.00 |
| ATOM | 2230 | N | GLY | A | 248 | -1.841 | -16.299 | 33.106 | 1.00 | 0.01 |
| ATOM | 2232 | CA | GLY | A | 248 | -2.850 | -17.181 | 32.524 | 1.00 | 0.02 |
| ATOM | 2233 | C | GLY | A | 248 | -4.164 | -16.776 | 33.173 | 1.00 | 0.01 |
| ATOM | 2234 | O | GLY | A | 248 | -4.136 | -16.141 | 34.233 | 1.00 | 0.02 |
| ATOM | 2235 | N | GLU | A | 249 | -5.279 | -17.290 | 32.682 | 1.00 | 0.02 |
| ATOM | 2237 | CA | GLU | A | 249 | -6.581 | -16.870 | 33.231 | 1.00 | 0.02 |
| ATOM | 2238 | CB | GLU | A | 249 | -7.684 | -17.300 | 32.272 | 1.00 | 0.71 |
| ATOM | 2239 | CG | GLU | A | 249 | -7.580 | -16.561 | 30.942 | 1.00 | 1.41 |
| ATOM | 2240 | CD | GLU | A | 249 | -8.624 | -17.099 | 29.972 | 1.00 | 1.73 |
| ATOM | 2241 | OE1 | GLU | A | 249 | -9.040 | -16.345 | 29.104 | 1.00 | 2.08 |
| ATOM | 2242 | OE2 | GLU | A | 249 | -8.886 | -18.292 | 30.041 | 1.00 | 2.14 |
| ATOM | 2243 | C | GLU | A | 249 | -6.854 | -17.455 | 34.619 | 1.00 | 0.02 |
| ATOM | 2244 | O | GLU | A | 249 | -7.601 | -16.869 | 35.408 | 1.00 | 0.02 |
| ATOM | 2245 | N | GLN | A | 250 | -6.197 | -18.560 | 34.932 | 1.00 | 0.01 |
| ATOM | 2247 | CA | GLN | A | 250 | -6.243 | -19.117 | 36.285 | 1.00 | 0.02 |
| ATOM | 2248 | CB | GLN | A | 250 | -6.843 | -20.516 | 36.228 | 1.00 | 0.06 |
| ATOM | 2249 | CG | GLN | A | 250 | -8.295 | -20.469 | 35.763 | 1.00 | 0.43 |
| ATOM | 2250 | CD | GLN | A | 250 | -8.850 | -21.881 | 35.628 | 1.00 | 0.27 |
| ATOM | 2251 | OE1 | GLN | A | 250 | -10.050 | -22.080 | 35.409 | 1.00 | 0.98 |
| ATOM | 2252 | NE2 | GLN | A | 250 | -7.959 | -22.849 | 35.739 | 1.00 | 1.30 |
| ATOM | 2255 | C | GLN | A | 250 | -4.843 | -19.169 | 36.893 | 1.00 | 0.01 |
| ATOM | 2256 | O | GLN | A | 250 | -4.630 | -19.809 | 37.928 | 1.00 | 0.01 |
| ATOM | 2257 | N | VAL | A | 251 | -3.893 | -18.537 | 36.222 | 1.00 | 0.01 |
| ATOM | 2259 | CA | VAL | A | 251 | -2.492 | -18.612 | 36.650 | 1.00 | 0.00 |
| ATOM | 2260 | CB | VAL | A | 251 | -1.642 | -19.165 | 35.509 | 1.00 | 0.50 |
| ATOM | 2261 | CG1 | VAL | A | 251 | -0.215 | -19.426 | 35.978 | 1.00 | 0.57 |
| ATOM | 2262 | CG2 | VAL | A | 251 | -2.244 | -20.448 | 34.946 | 1.00 | 0.85 |
| ATOM | 2263 | C | VAL | A | 251 | -2.006 | -17.224 | 37.055 | 1.00 | 0.01 |

| ATOM | 2264 | O | VAL | A | 251 | -1.695 | -16.371 | 36.209 | 1.00 | 0.01 |
|------|------|-----|-----|---|-----|--------|---------|--------|------|------|
| ATOM | 2265 | N | THR | A | 252 | -1.927 | -17.035 | 38.360 | 1.00 | 0.02 |
| ATOM | 2267 | CA | THR | A | 252 | -1.641 | -15.716 | 38.930 | 1.00 | 0.01 |
| ATOM | 2268 | CB | THR | A | 252 | -2.806 | -15.364 | 39.849 | 1.00 | 0.02 |
| ATOM | 2269 | OG1 | THR | A | 252 | -2.848 | -16.297 | 40.921 | 1.00 | 0.01 |
| ATOM | 2270 | CG2 | THR | A | 252 | -4.150 | -15.403 | 39.133 | 1.00 | 0.01 |
| ATOM | 2271 | C | THR | A | 252 | -0.323 | -15.655 | 39.714 | 1.00 | 0.02 |
| ATOM | 2272 | O | THR | A | 252 | -0.042 | -16.495 | 40.577 | 1.00 | 0.01 |
| ATOM | 2273 | N | VAL | A | 253 | 0.467 | -14.638 | 39.408 | 1.00 | 0.02 |
| ATOM | 2275 | CA | VAL | A | 253 | 1.739 | -14.387 | 40.116 | 1.00 | 0.00 |
| ATOM | 2276 | CB | VAL | A | 253 | 2.866 | -14.411 | 39.084 | 1.00 | 0.01 |
| ATOM | 2277 | CG1 | VAL | A | 253 | 4.217 | -14.060 | 39.701 | 1.00 | 0.03 |
| ATOM | 2278 | CG2 | VAL | A | 253 | 2.941 | -15.761 | 38.378 | 1.00 | 0.02 |
| ATOM | 2279 | C | VAL | A | 253 | 1.714 | -13.024 | 40.816 | 1.00 | 0.01 |
| ATOM | 2280 | O | VAL | A | 253 | 1.586 | -11.997 | 40.144 | 1.00 | 0.02 |
| ATOM | 2281 | N | GLN | A | 254 | 1.809 | -12.998 | 42.138 | 1.00 | 0.03 |
| ATOM | 2283 | CA | GLN | A | 254 | 1.732 | -11.706 | 42.847 | 1.00 | 0.02 |
| ATOM | 2284 | CB | GLN | A | 254 | 1.677 | -11.901 | 44.354 | 1.00 | 0.41 |
| ATOM | 2285 | CG | GLN | A | 254 | 0.309 | -12.401 | 44.789 | 1.00 | 0.84 |
| ATOM | 2286 | CD | GLN | A | 254 | 0.199 | -12.319 | 46.305 | 1.00 | 0.68 |
| ATOM | 2287 | OE1 | GLN | A | 254 | 0.343 | -13.328 | 47.005 | 1.00 | 0.68 |
| ATOM | 2288 | NE2 | GLN | A | 254 | -0.051 | -11.115 | 46.791 | 1.00 | 1.21 |
| ATOM | 2291 | C | GLN | A | 254 | 2.892 | -10.780 | 42.504 | 1.00 | 0.02 |
| ATOM | 2292 | O | GLN | A | 254 | 4.053 | -11.191 | 42.424 | 1.00 | 0.03 |
| ATOM | 2293 | N | VAL | A | 255 | 2.537 | -9.531 | 42.253 | 1.00 | 0.02 |
| ATOM | 2295 | CA | VAL | A | 255 | 3.523 | -8.525 | 41.852 | 1.00 | 0.02 |
| ATOM | 2296 | CB | VAL | A | 255 | 3.330 | -8.225 | 40.364 | 1.00 | 0.02 |
| ATOM | 2297 | CG1 | VAL | A | 255 | 3.834 | -9.361 | 39.482 | 1.00 | 0.02 |
| ATOM | 2298 | CG2 | VAL | A | 255 | 1.877 | -7.899 | 40.047 | 1.00 | 0.00 |
| ATOM | 2299 | C | VAL | A | 255 | 3.387 | -7.241 | 42.668 | 1.00 | 0.02 |
| ATOM | 2300 | O | VAL | A | 255 | 2.295 | -6.890 | 43.135 | 1.00 | 0.02 |
| ATOM | 2301 | N | PRO | A | 256 | 4.516 | -6.581 | 42.876 | 1.00 | 0.02 |
| ATOM | 2302 | CA | PRO | A | 256 | 4.504 | -5.197 | 43.353 | 1.00 | 0.02 |
| ATOM | 2303 | CB | PRO | A | 256 | 5.943 | -4.796 | 43.459 | 1.00 | 0.02 |
| ATOM | 2304 | CG | PRO | A | 256 | 6.815 | -5.925 | 42.928 | 1.00 | 0.00 |

| ATOM | 2305 | CD | PRO | A | 256 | 5.862 | -7.035 | 42.515 | 1.00 | 0.02 |
|---|---|---|---|---|---|---|---|---|---|---|
| ATOM | 2306 | C | PRO | A | 256 | 3.748 | -4.321 | 42.364 | 1.00 | 0.01 |
| ATOM | 2307 | O | PRO | A | 256 | 3.983 | -4.375 | 41.151 | 1.00 | 0.01 |
| ATOM | 2308 | N | MET | A | 257 | 2.817 | -3.551 | 42.888 | 1.00 | 0.02 |
| ATOM | 2310 | CA | MET | A | 257 | 1.925 | -2.748 | 42.055 | 1.00 | 0.02 |
| ATOM | 2311 | CB | MET | A | 257 | 0.534 | -3.335 | 42.232 | 1.00 | 0.01 |
| ATOM | 2312 | CG | MET | A | 257 | -0.443 | -2.884 | 41.158 | 1.00 | 0.02 |
| ATOM | 2313 | SD | MET | A | 257 | -0.238 | -3.681 | 39.550 | 1.00 | 0.02 |
| ATOM | 2314 | CE | MET | A | 257 | -0.635 | -5.384 | 39.996 | 1.00 | 0.02 |
| ATOM | 2315 | C | MET | A | 257 | 1.902 | -1.296 | 42.515 | 1.00 | 0.00 |
| ATOM | 2316 | O | MET | A | 257 | 1.417 | -0.989 | 43.610 | 1.00 | 0.02 |
| ATOM | 2317 | N | MET | A | 258 | 2.382 | -0.413 | 41.659 | 1.00 | 0.01 |
| ATOM | 2319 | CA | MET | A | 258 | 2.388 | 1.020 | 41.954 | 1.00 | 0.02 |
| ATOM | 2320 | CB | MET | A | 258 | 3.323 | 1.701 | 40.968 | 1.00 | 0.01 |
| ATOM | 2321 | CG | MET | A | 258 | 4.699 | 1.054 | 40.968 | 1.00 | 0.01 |
| ATOM | 2322 | SD | MET | A | 258 | 5.891 | 1.774 | 39.818 | 1.00 | 0.01 |
| ATOM | 2323 | CE | MET | A | 258 | 4.983 | 1.573 | 38.271 | 1.00 | 0.00 |
| ATOM | 2324 | C | MET | A | 258 | 0.990 | 1.600 | 41.788 | 1.00 | 0.02 |
| ATOM | 2325 | O | MET | A | 258 | 0.451 | 1.661 | 40.674 | 1.00 | 0.02 |
| ATOM | 2326 | N | HIS | A | 259 | 0.397 | 1.948 | 42.917 | 1.00 | 0.01 |
| ATOM | 2328 | CA | HIS | A | 259 | -0.940 | 2.541 | 42.928 | 1.00 | 0.01 |
| ATOM | 2329 | CB | HIS | A | 259 | -1.625 | 2.053 | 44.202 | 1.00 | 0.78 |
| ATOM | 2330 | CG | HIS | A | 259 | -3.078 | 2.437 | 44.412 | 1.00 | 1.36 |
| ATOM | 2331 | ND1 | HIS | A | 259 | -3.735 | 2.391 | 45.585 | 1.00 | 2.20 |
| ATOM | 2333 | CE1 | HIS | A | 259 | -5.007 | 2.802 | 45.401 | 1.00 | 2.85 |
| ATOM | 2334 | NE2 | HIS | A | 259 | -5.158 | 3.092 | 44.089 | 1.00 | 2.78 |
| ATOM | 2335 | CD2 | HIS | A | 259 | -3.981 | 2.861 | 43.465 | 1.00 | 2.13 |
| ATOM | 2336 | C | HIS | A | 259 | -0.868 | 4.069 | 42.871 | 1.00 | 0.02 |
| ATOM | 2337 | O | HIS | A | 259 | -0.052 | 4.713 | 43.548 | 1.00 | 0.02 |
| ATOM | 2338 | N | GLN | A | 260 | -1.628 | 4.609 | 41.932 | 1.00 | 0.02 |
| ATOM | 2340 | CA | GLN | A | 260 | -1.776 | 6.062 | 41.789 | 1.00 | 0.01 |
| ATOM | 2341 | CB | GLN | A | 260 | -0.553 | 6.614 | 41.061 | 1.00 | 1.24 |
| ATOM | 2342 | CG | GLN | A | 260 | -0.607 | 8.123 | 40.842 | 1.00 | 1.25 |
| ATOM | 2343 | CD | GLN | A | 260 | -0.738 | 8.894 | 42.150 | 1.00 | 2.10 |
| ATOM | 2344 | OE1 | GLN | A | 260 | -1.835 | 8.996 | 42.716 | 1.00 | 2.67 |
| ATOM | 2345 | NE2 | GLN | A | 260 | 0.355 | 9.512 | 42.553 | 1.00 | 2.69 |
| ATOM | 2348 | C | GLN | A | 260 | -3.068 | 6.411 | 41.041 | 1.00 | 0.00 |
| ATOM | 2349 | O | GLN | A | 260 | -3.191 | 6.194 | 39.829 | 1.00 | 0.01 |
| ATOM | 2350 | N | LYS | A | 261 | -4.002 | 7.002 | 41.764 | 1.00 | 0.02 |
| ATOM | 2352 | CA | LYS | A | 261 | -5.294 | 7.379 | 41.178 | 1.00 | 0.02 |
| ATOM | 2353 | CB | LYS | A | 261 | -6.387 | 7.054 | 42.190 | 1.00 | 0.88 |
| ATOM | 2354 | CG | LYS | A | 261 | -7.778 | 7.356 | 41.645 | 1.00 | 1.64 |
| ATOM | 2355 | CD | LYS | A | 261 | -8.854 | 6.981 | 42.655 | 1.00 | 1.70 |
| ATOM | 2356 | CE | LYS | A | 261 | -8.691 | 7.763 | 43.953 | 1.00 | 2.39 |
| ATOM | 2357 | NZ | LYS | A | 261 | -9.741 | 7.398 | 44.917 | 1.00 | 2.92 |
| ATOM | 2358 | C | LYS | A | 261 | -5.314 | 8.869 | 40.840 | 1.00 | 0.01 |
| ATOM | 2359 | O | LYS | A | 261 | -5.677 | 9.699 | 41.681 | 1.00 | 0.01 |
| ATOM | 2360 | N | GLU | A | 262 | -4.938 | 9.203 | 39.614 | 1.00 | 0.01 |
| ATOM | 2362 | CA | GLU | A | 262 | -4.815 | 10.622 | 39.243 | 1.00 | 0.02 |
| ATOM | 2363 | CB | GLU | A | 262 | -3.393 | 11.113 | 39.505 | 1.00 | 2.06 |
| ATOM | 2364 | CG | GLU | A | 262 | -3.157 | 11.543 | 40.951 | 1.00 | 2.79 |
| ATOM | 2365 | CD | GLU | A | 262 | -1.797 | 12.217 | 41.042 | 1.00 | 3.90 |
| ATOM | 2366 | OE1 | GLU | A | 262 | -1.315 | 12.623 | 39.987 | 1.00 | 4.49 |
| ATOM | 2367 | OE2 | GLU | A | 262 | -1.267 | 12.349 | 42.137 | 1.00 | 4.34 |
| ATOM | 2368 | C | GLU | A | 262 | -5.178 | 10.992 | 37.802 | 1.00 | 0.02 |
| ATOM | 2369 | O | GLU | A | 262 | -6.034 | 10.391 | 37.145 | 1.00 | 0.00 |
| ATOM | 2370 | N | GLN | A | 263 | -4.375 | 11.934 | 37.326 | 1.00 | 0.01 |
| ATOM | 2372 | CA | GLN | A | 263 | -4.570 | 12.772 | 36.122 | 1.00 | 0.00 |

| ATOM | 2373 | CB | GLN | A | 263 | -3.615 | 13.938 | 36.349 | 1.00 | 1.50 |
|------|------|-----|-----|---|-----|--------|--------|--------|------|------|
| ATOM | 2374 | CG | GLN | A | 263 | -2.219 | 13.357 | 36.596 | 1.00 | 2.17 |
| ATOM | 2375 | CD | GLN | A | 263 | -1.135 | 14.425 | 36.683 | 1.00 | 3.16 |
| ATOM | 2376 | OE1 | GLN | A | 263 | -0.815 | 15.081 | 35.688 | 1.00 | 3.64 |
| ATOM | 2377 | NE2 | GLN | A | 263 | -0.508 | 14.507 | 37.845 | 1.00 | 3.93 |
| ATOM | 2380 | C | GLN | A | 263 | -4.159 | 12.182 | 34.770 | 1.00 | 0.02 |
| ATOM | 2381 | O | GLN | A | 263 | -3.864 | 12.951 | 33.851 | 1.00 | 0.01 |
| ATOM | 2382 | N | PHE | A | 264 | -4.137 | 10.874 | 34.627 | 1.00 | 0.02 |
| ATOM | 2384 | CA | PHE | A | 264 | -3.383 | 10.288 | 33.515 | 1.00 | 0.01 |
| ATOM | 2385 | CB | PHE | A | 264 | -3.114 | 8.840 | 33.871 | 1.00 | 0.00 |
| ATOM | 2386 | CG | PHE | A | 264 | -2.376 | 8.716 | 35.193 | 1.00 | 0.02 |
| ATOM | 2387 | CD1 | PHE | A | 264 | -1.090 | 9.220 | 35.307 | 1.00 | 0.00 |
| ATOM | 2388 | CE1 | PHE | A | 264 | -0.408 | 9.118 | 36.509 | 1.00 | 0.01 |
| ATOM | 2389 | CZ | PHE | A | 264 | -1.017 | 8.520 | 37.601 | 1.00 | 0.00 |
| ATOM | 2390 | CE2 | PHE | A | 264 | -2.311 | 8.034 | 37.494 | 1.00 | 0.01 |
| ATOM | 2391 | CD2 | PHE | A | 264 | -2.995 | 8.137 | 36.292 | 1.00 | 0.02 |
| ATOM | 2392 | C | PHE | A | 264 | -4.063 | 10.395 | 32.156 | 1.00 | 0.02 |
| ATOM | 2393 | O | PHE | A | 264 | -5.282 | 10.242 | 32.023 | 1.00 | 0.00 |
| ATOM | 2394 | N | ALA | A | 265 | -3.256 | 10.726 | 31.160 | 1.00 | 0.02 |
| ATOM | 2396 | CA | ALA | A | 265 | -3.737 | 10.764 | 29.778 | 1.00 | 0.01 |
| ATOM | 2397 | CB | ALA | A | 265 | -2.667 | 11.385 | 28.888 | 1.00 | 0.49 |
| ATOM | 2398 | C | ALA | A | 265 | -4.049 | 9.342 | 29.339 | 1.00 | 0.01 |
| ATOM | 2399 | O | ALA | A | 265 | -3.198 | 8.446 | 29.443 | 1.00 | 0.01 |
| ATOM | 2400 | N | PHE | A | 266 | -5.265 | 9.141 | 28.868 | 1.00 | 0.01 |
| ATOM | 2402 | CA | PHE | A | 266 | -5.734 | 7.775 | 28.640 | 1.00 | 0.01 |
| ATOM | 2403 | CB | PHE | A | 266 | -6.156 | 7.234 | 30.003 | 1.00 | 1.51 |
| ATOM | 2404 | CG | PHE | A | 266 | -6.592 | 5.776 | 30.027 | 1.00 | 1.98 |
| ATOM | 2405 | CD1 | PHE | A | 266 | -5.645 | 4.769 | 29.916 | 1.00 | 2.64 |
| ATOM | 2406 | CE1 | PHE | A | 266 | -6.042 | 3.441 | 29.929 | 1.00 | 3.43 |
| ATOM | 2407 | CZ | PHE | A | 266 | -7.386 | 3.122 | 30.058 | 1.00 | 3.64 |
| ATOM | 2408 | CE2 | PHE | A | 266 | -8.332 | 4.128 | 30.183 | 1.00 | 3.15 |
| ATOM | 2409 | CD2 | PHE | A | 266 | -7.933 | 5.455 | 30.172 | 1.00 | 2.32 |
| ATOM | 2410 | C | PHE | A | 266 | -6.904 | 7.704 | 27.665 | 1.00 | 0.01 |
| ATOM | 2411 | O | PHE | A | 266 | -7.866 | 8.475 | 27.754 | 1.00 | 0.01 |
| ATOM | 2412 | N | GLY | A | 267 | -6.821 | 6.749 | 26.755 | 1.00 | 0.01 |
| ATOM | 2414 | CA | GLY | A | 267 | -7.928 | 6.507 | 25.824 | 1.00 | 0.00 |
| ATOM | 2415 | C | GLY | A | 267 | -8.132 | 5.019 | 25.554 | 1.00 | 0.01 |
| ATOM | 2416 | O | GLY | A | 267 | -7.181 | 4.231 | 25.560 | 1.00 | 0.01 |
| ATOM | 2417 | N | VAL | A | 268 | -9.381 | 4.625 | 25.392 | 1.00 | 0.00 |
| ATOM | 2419 | CA | VAL | A | 268 | -9.668 | 3.233 | 25.027 | 1.00 | 0.01 |
| ATOM | 2420 | CB | VAL | A | 268 | -10.971 | 2.778 | 25.676 | 1.00 | 0.65 |
| ATOM | 2421 | CG1 | VAL | A | 268 | -11.318 | 1.348 | 25.270 | 1.00 | 0.75 |
| ATOM | 2422 | CG2 | VAL | A | 268 | -10.887 | 2.887 | 27.194 | 1.00 | 0.82 |
| ATOM | 2423 | C | VAL | A | 268 | -9.748 | 3.112 | 23.508 | 1.00 | 0.01 |
| ATOM | 2424 | O | VAL | A | 268 | -10.726 | 3.521 | 22.871 | 1.00 | 0.01 |
| ATOM | 2425 | N | ASP | A | 269 | -8.692 | 2.563 | 22.940 | 1.00 | 0.01 |
| ATOM | 2427 | CA | ASP | A | 269 | -8.605 | 2.409 | 21.493 | 1.00 | 0.00 |
| ATOM | 2428 | CB | ASP | A | 269 | -7.123 | 2.419 | 21.123 | 1.00 | 0.44 |
| ATOM | 2429 | CG | ASP | A | 269 | -6.905 | 2.536 | 19.616 | 1.00 | 0.29 |
| ATOM | 2430 | OD1 | ASP | A | 269 | -6.024 | 3.277 | 19.222 | 1.00 | 0.56 |
| ATOM | 2431 | OD2 | ASP | A | 269 | -7.593 | 1.833 | 18.883 | 1.00 | 0.37 |
| ATOM | 2432 | C | ASP | A | 269 | -9.270 | 1.096 | 21.091 | 1.00 | 0.01 |
| ATOM | 2433 | O | ASP | A | 269 | -8.686 | 0.017 | 21.240 | 1.00 | 0.01 |
| ATOM | 2434 | N | THR | A | 270 | - | 1.211 | 20.369 | 1.00 | 0.00 |

| | | | | | 10.371 | | | | |
|---|---|---|---|---|---|---|---|---|---|
| ATOM | 2436 | CA | THR | A | 270 | -11.141 | 0.021 | 19.977 | 1.00 | 0.01 |
| ATOM | 2437 | CB | THR | A | 270 | -12.550 | 0.481 | 19.617 | 1.00 | 0.50 |
| ATOM | 2438 | OG1 | THR | A | 270 | -13.085 | 1.154 | 20.750 | 1.00 | 0.86 |
| ATOM | 2439 | CG2 | THR | A | 270 | -13.474 | -0.684 | 19.282 | 1.00 | 1.61 |
| ATOM | 2440 | C | THR | A | 270 | -10.521 | -0.760 | 18.810 | 1.00 | 0.00 |
| ATOM | 2441 | O | THR | A | 270 | -10.683 | -1.983 | 18.756 | 1.00 | 0.01 |
| ATOM | 2442 | N | GLU | A | 271 | -9.583 | -0.147 | 18.105 | 1.00 | 0.01 |
| ATOM | 2444 | CA | GLU | A | 271 | -8.892 | -0.832 | 17.005 | 1.00 | 0.00 |
| ATOM | 2445 | CB | GLU | A | 271 | -8.414 | 0.220 | 16.012 | 1.00 | 0.34 |
| ATOM | 2446 | CG | GLU | A | 271 | -9.585 | 1.034 | 15.473 | 1.00 | 0.93 |
| ATOM | 2447 | CD | GLU | A | 271 | -9.085 | 2.127 | 14.536 | 1.00 | 0.82 |
| ATOM | 2448 | OE1 | GLU | A | 271 | -8.023 | 1.944 | 13.958 | 1.00 | 0.84 |
| ATOM | 2449 | OE2 | GLU | A | 271 | -9.733 | 3.165 | 14.488 | 1.00 | 1.00 |
| ATOM | 2450 | C | GLU | A | 271 | -7.696 | -1.638 | 17.517 | 1.00 | 0.01 |
| ATOM | 2451 | O | GLU | A | 271 | -7.262 | -2.594 | 16.869 | 1.00 | 0.01 |
| ATOM | 2452 | N | LEU | A | 272 | -7.251 | -1.310 | 18.721 | 1.00 | 0.00 |
| ATOM | 2454 | CA | LEU | A | 272 | -6.228 | -2.101 | 19.418 | 1.00 | 0.01 |
| ATOM | 2455 | CB | LEU | A | 272 | -5.293 | -1.154 | 20.163 | 1.00 | 0.01 |
| ATOM | 2456 | CG | LEU | A | 272 | -4.450 | -0.309 | 19.215 | 1.00 | 0.00 |
| ATOM | 2457 | CD1 | LEU | A | 272 | -3.644 | 0.734 | 19.982 | 1.00 | 0.00 |
| ATOM | 2458 | CD2 | LEU | A | 272 | -3.523 | -1.188 | 18.386 | 1.00 | 0.01 |
| ATOM | 2459 | C | LEU | A | 272 | -6.896 | -3.040 | 20.418 | 1.00 | 0.01 |
| ATOM | 2460 | O | LEU | A | 272 | -6.260 | -3.935 | 20.987 | 1.00 | 0.00 |
| ATOM | 2461 | N | ASN | A | 273 | -8.204 | -2.877 | 20.518 | 1.00 | 0.01 |
| ATOM | 2463 | CA | ASN | A | 273 | -9.056 | -3.573 | 21.475 | 1.00 | 0.01 |
| ATOM | 2464 | CB | ASN | A | 273 | -9.106 | -5.052 | 21.124 | 1.00 | 0.59 |
| ATOM | 2465 | CG | ASN | A | 273 | -10.529 | -5.554 | 21.328 | 1.00 | 1.61 |
| ATOM | 2466 | OD1 | ASN | A | 273 | -11.218 | -5.159 | 22.278 | 1.00 | 2.19 |
| ATOM | 2467 | ND2 | ASN | A | 273 | -10.962 | -6.398 | 20.411 | 1.00 | 2.30 |
| ATOM | 2470 | C | ASN | A | 273 | -8.580 | -3.367 | 22.908 | 1.00 | 0.01 |
| ATOM | 2471 | O | ASN | A | 273 | -7.951 | -4.275 | 23.470 | 1.00 | 0.01 |
| ATOM | 2472 | N | CYS | A | 274 | -8.633 | -2.102 | 23.321 | 1.00 | 0.01 |
| ATOM | 2474 | CA | CYS | A | 274 | -8.541 | -1.636 | 24.728 | 1.00 | 0.00 |
| ATOM | 2475 | CB | CYS | A | 274 | -8.367 | -2.729 | 25.774 | 1.00 | 0.97 |
| ATOM | 2476 | SG | CYS | A | 274 | -9.906 | -3.343 | 26.496 | 1.00 | 2.23 |
| ATOM | 2477 | C | CYS | A | 274 | -7.560 | -0.496 | 25.011 | 1.00 | 0.01 |
| ATOM | 2478 | O | CYS | A | 274 | -7.305 | 0.404 | 24.202 | 1.00 | 0.01 |
| ATOM | 2479 | N | PHE | A | 275 | -7.079 | -0.543 | 26.240 | 1.00 | 0.01 |
| ATOM | 2481 | CA | PHE | A | 275 | -6.541 | 0.622 | 26.959 | 1.00 | 0.01 |
| ATOM | 2482 | CB | PHE | A | 275 | -6.426 | 0.196 | 28.420 | 1.00 | 0.85 |
| ATOM | 2483 | CG | PHE | A | 275 | -7.696 | -0.445 | 28.981 | 1.00 | 1.11 |
| ATOM | 2484 | CD1 | PHE | A | 275 | -8.913 | 0.223 | 28.910 | 1.00 | 1.88 |
| ATOM | 2485 | CE1 | PHE | A | 275 | -10.064 | -0.374 | 29.406 | 1.00 | 2.82 |
| ATOM | 2486 | CZ | PHE | A | 275 | -9.999 | -1.637 | 29.980 | 1.00 | 2.95 |
| ATOM | 2487 | CE2 | PHE | A | 275 | -8.782 | -2.300 | 30.062 | 1.00 | 2.21 |
| ATOM | 2488 | CD2 | PHE | A | 275 | -7.631 | -1.703 | 29.565 | 1.00 | 1.32 |
| ATOM | 2489 | C | PHE | A | 275 | -5.181 | 1.126 | 26.485 | 1.00 | 0.01 |

| ATOM | 2490 | O | PHE | A | 275 | -4.230 | 0.355 | 26.329 | 1.00 | 0.01 |
|------|------|------|-----|---|-----|--------|--------|--------|------|------|
| ATOM | 2491 | N | VAL | A | 276 | -5.105 | 2.430 | 26.274 | 1.00 | 0.01 |
| ATOM | 2493 | CA | VAL | A | 276 | -3.837 | 3.106 | 25.971 | 1.00 | 0.00 |
| ATOM | 2494 | CB | VAL | A | 276 | -3.917 | 3.722 | 24.575 | 1.00 | 0.00 |
| ATOM | 2495 | CG1 | VAL | A | 276 | -2.630 | 4.465 | 24.228 | 1.00 | 0.00 |
| ATOM | 2496 | CG2 | VAL | A | 276 | -4.222 | 2.669 | 23.515 | 1.00 | 0.01 |
| ATOM | 2497 | C | VAL | A | 276 | -3.557 | 4.212 | 26.993 | 1.00 | 0.01 |
| ATOM | 2498 | O | VAL | A | 276 | -4.204 | 5.270 | 26.990 | 1.00 | 0.01 |
| ATOM | 2499 | N | LEU | A | 277 | -2.644 | 3.919 | 27.905 | 1.00 | 0.00 |
| ATOM | 2501 | CA | LEU | A | 277 | -2.197 | 4.899 | 28.908 | 1.00 | 0.00 |
| ATOM | 2502 | CB | LEU | A | 277 | -1.933 | 4.135 | 30.206 | 1.00 | 0.01 |
| ATOM | 2503 | CG | LEU | A | 277 | -1.598 | 5.042 | 31.386 | 1.00 | 0.01 |
| ATOM | 2504 | CD1 | LEU | A | 277 | -2.724 | 6.031 | 31.654 | 1.00 | 0.01 |
| ATOM | 2505 | CD2 | LEU | A | 277 | -1.310 | 4.224 | 32.638 | 1.00 | 0.02 |
| ATOM | 2506 | C | LEU | A | 277 | -0.921 | 5.591 | 28.423 | 1.00 | 0.01 |
| ATOM | 2507 | O | LEU | A | 277 | -0.067 | 4.944 | 27.808 | 1.00 | 0.01 |
| ATOM | 2508 | N | GLN | A | 278 | -0.822 | 6.894 | 28.624 | 1.00 | 0.01 |
| ATOM | 2510 | CA | GLN | A | 278 | 0.382 | 7.618 | 28.196 | 1.00 | 0.02 |
| ATOM | 2511 | CB | GLN | A | 278 | 0.085 | 8.219 | 26.831 | 1.00 | 0.54 |
| ATOM | 2512 | CG | GLN | A | 278 | -1.353 | 8.713 | 26.749 | 1.00 | 0.92 |
| ATOM | 2513 | CD | GLN | A | 278 | -1.695 | 9.059 | 25.309 | 1.00 | 0.81 |
| ATOM | 2514 | OE1 | GLN | A | 278 | -1.901 | 8.168 | 24.475 | 1.00 | 1.23 |
| ATOM | 2515 | NE2 | GLN | A | 278 | -1.791 | 10.347 | 25.047 | 1.00 | 1.11 |
| ATOM | 2518 | C | GLN | A | 278 | 0.855 | 8.675 | 29.201 | 1.00 | 0.01 |
| ATOM | 2519 | O | GLN | A | 278 | 0.274 | 9.761 | 29.337 | 1.00 | 0.00 |
| ATOM | 2520 | N | MET | A | 279 | 1.957 | 8.353 | 29.860 | 1.00 | 0.01 |
| ATOM | 2522 | CA | MET | A | 279 | 2.542 | 9.250 | 30.873 | 1.00 | 0.00 |
| ATOM | 2523 | CB | MET | A | 279 | 2.636 | 8.492 | 32.190 | 1.00 | 0.02 |
| ATOM | 2524 | CG | MET | A | 279 | 1.261 | 8.070 | 32.692 | 1.00 | 0.02 |
| ATOM | 2525 | SD | MET | A | 279 | 1.280 | 7.035 | 34.170 | 1.00 | 0.02 |
| ATOM | 2526 | CE | MET | A | 279 | 2.174 | 5.622 | 33.495 | 1.00 | 0.01 |
| ATOM | 2527 | C | MET | A | 279 | 3.937 | 9.737 | 30.481 | 1.00 | 0.01 |
| ATOM | 2528 | O | MET | A | 279 | 4.822 | 8.939 | 30.155 | 1.00 | 0.01 |
| ATOM | 2529 | N | ASP | A | 280 | 4.143 | 11.040 | 30.555 | 1.00 | 0.02 |
| ATOM | 2531 | CA | ASP | A | 280 | 5.448 | 11.608 | 30.190 | 1.00 | 0.01 |
| ATOM | 2532 | CB | ASP | A | 280 | 5.233 | 13.052 | 29.725 | 1.00 | 0.60 |
| ATOM | 2533 | CG | ASP | A | 280 | 6.513 | 13.690 | 29.173 | 1.00 | 1.52 |
| ATOM | 2534 | OD1 | ASP | A | 280 | 7.222 | 13.007 | 28.441 | 1.00 | 2.18 |
| ATOM | 2535 | OD2 | ASP | A | 280 | 6.670 | 14.888 | 29.350 | 1.00 | 1.96 |
| ATOM | 2536 | C | ASP | A | 280 | 6.442 | 11.557 | 31.355 | 1.00 | 0.01 |
| ATOM | 2537 | O | ASP | A | 280 | 6.096 | 11.768 | 32.529 | 1.00 | 0.00 |
| ATOM | 2538 | N | TYR | A | 281 | 7.657 | 11.163 | 31.014 | 1.00 | 0.01 |
| ATOM | 2540 | CA | TYR | A | 281 | 8.799 | 11.244 | 31.924 | 1.00 | 0.01 |
| ATOM | 2541 | CB | TYR | A | 281 | 9.948 | 10.412 | 31.369 | 1.00 | 0.01 |
| ATOM | 2542 | CG | TYR | A | 281 | 9.693 | 8.913 | 31.359 | 1.00 | 0.01 |
| ATOM | 2543 | CD1 | TYR | A | 281 | 9.194 | 8.289 | 32.494 | 1.00 | 0.00 |
| ATOM | 2544 | CE1 | TYR | A | 281 | 8.969 | 6.921 | 32.489 | 1.00 | 0.02 |
| ATOM | 2545 | CZ | TYR | A | 281 | 9.245 | 6.179 | 31.350 | 1.00 | 0.01 |
| ATOM | 2546 | OH | TYR | A | 281 | 9.043 | 4.816 | 31.357 | 1.00 | 0.00 |
| ATOM | 2547 | CE2 | TYR | A | 281 | 9.745 | 6.799 | 30.214 | 1.00 | 0.01 |
| ATOM | 2548 | CD2 | TYR | A | 281 | 9.972 | 8.168 | 30.220 | 1.00 | 0.00 |
| ATOM | 2549 | C | TYR | A | 281 | 9.255 | 12.687 | 32.035 | 1.00 | 0.01 |
| ATOM | 2550 | O | TYR | A | 281 | 8.700 | 13.569 | 31.367 | 1.00 | 0.02 |
| ATOM | 2551 | N | LYS | A | 282 | 10.160 | 12.940 | 32.962 | 1.00 | 0.02 |
| ATOM | 2553 | CA | LYS | A | 282 | 10.701 | 14.291 | 33.131 | 1.00 | 0.01 |
| ATOM | 2554 | CB | LYS | A | 282 | 11.492 | 14.351 | 34.433 | 1.00 | 0.41 |
| ATOM | 2555 | CG | LYS | A | 282 | 10.586 | 14.149 | 35.641 | 1.00 | 0.84 |
| ATOM | 2556 | CD | LYS | A | 282 | 11.364 | 14.264 | 36.948 | 1.00 | 1.00 |

| ATOM | 2557 | CE | LYS | A | 282 | 10.439 | 14.165 | 38.157 | 1.00 | 1.86 |
|------|------|-----|-----|---|-----|--------|--------|--------|------|------|
| ATOM | 2558 | NZ | LYS | A | 282 | 11.195 | 14.269 | 39.415 | 1.00 | 2.31 |
| ATOM | 2559 | C | LYS | A | 282 | 11.602 | 14.667 | 31.963 | 1.00 | 0.01 |
| ATOM | 2560 | O | LYS | A | 282 | 12.704 | 14.130 | 31.821 | 1.00 | 0.01 |
| ATOM | 2561 | N | GLY | A | 283 | 11.108 | 15.543 | 31.106 | 1.00 | 0.01 |
| ATOM | 2563 | CA | GLY | A | 283 | 11.923 | 16.019 | 29.986 | 1.00 | 0.01 |
| ATOM | 2564 | C | GLY | A | 283 | 11.242 | 15.903 | 28.625 | 1.00 | 0.01 |
| ATOM | 2565 | O | GLY | A | 283 | 10.740 | 16.897 | 28.090 | 1.00 | 0.01 |
| ATOM | 2566 | N | ASP | A | 284 | 11.319 | 14.720 | 28.034 | 1.00 | 0.02 |
| ATOM | 2568 | CA | ASP | A | 284 | 10.847 | 14.535 | 26.654 | 1.00 | 0.01 |
| ATOM | 2569 | CB | ASP | A | 284 | 11.811 | 15.258 | 25.704 | 1.00 | 0.72 |
| ATOM | 2570 | CG | ASP | A | 284 | 13.267 | 14.827 | 25.890 | 1.00 | 0.83 |
| ATOM | 2571 | OD1 | ASP | A | 284 | 13.687 | 13.930 | 25.169 | 1.00 | 1.50 |
| ATOM | 2572 | OD2 | ASP | A | 284 | 13.942 | 15.402 | 26.734 | 1.00 | 1.34 |
| ATOM | 2573 | C | ASP | A | 284 | 10.690 | 13.068 | 26.243 | 1.00 | 0.01 |
| ATOM | 2574 | O | ASP | A | 284 | 11.207 | 12.656 | 25.195 | 1.00 | 0.01 |
| ATOM | 2575 | N | ALA | A | 285 | 9.862 | 12.330 | 26.963 | 1.00 | 0.01 |
| ATOM | 2577 | CA | ALA | A | 285 | 9.665 | 10.911 | 26.629 | 1.00 | 0.00 |
| ATOM | 2578 | CB | ALA | A | 285 | 10.844 | 10.098 | 27.153 | 1.00 | 0.02 |
| ATOM | 2579 | C | ALA | A | 285 | 8.362 | 10.354 | 27.198 | 1.00 | 0.01 |
| ATOM | 2580 | O | ALA | A | 285 | 8.231 | 10.161 | 28.413 | 1.00 | 0.00 |
| ATOM | 2581 | N | VAL | A | 286 | 7.444 | 10.020 | 26.310 | 1.00 | 0.01 |
| ATOM | 2583 | CA | VAL | A | 286 | 6.142 | 9.503 | 26.737 | 1.00 | 0.01 |
| ATOM | 2584 | CB | VAL | A | 286 | 5.077 | 9.989 | 25.761 | 1.00 | 0.25 |
| ATOM | 2585 | CG1 | VAL | A | 286 | 3.682 | 9.553 | 26.198 | 1.00 | 0.48 |
| ATOM | 2586 | CG2 | VAL | A | 286 | 5.129 | 11.505 | 25.621 | 1.00 | 0.75 |
| ATOM | 2587 | C | VAL | A | 286 | 6.148 | 7.978 | 26.791 | 1.00 | 0.01 |
| ATOM | 2588 | O | VAL | A | 286 | 6.418 | 7.298 | 25.793 | 1.00 | 0.00 |
| ATOM | 2589 | N | ALA | A | 287 | 5.878 | 7.456 | 27.974 | 1.00 | 0.01 |
| ATOM | 2591 | CA | ALA | A | 287 | 5.757 | 6.012 | 28.160 | 1.00 | 0.01 |
| ATOM | 2592 | CB | ALA | A | 287 | 6.195 | 5.658 | 29.573 | 1.00 | 0.00 |
| ATOM | 2593 | C | ALA | A | 287 | 4.316 | 5.565 | 27.945 | 1.00 | 0.01 |
| ATOM | 2594 | O | ALA | A | 287 | 3.404 | 5.909 | 28.713 | 1.00 | 0.00 |
| ATOM | 2595 | N | PHE | A | 288 | 4.123 | 4.857 | 26.849 | 1.00 | 0.01 |
| ATOM | 2597 | CA | PHE | A | 288 | 2.825 | 4.271 | 26.525 | 1.00 | 0.01 |
| ATOM | 2598 | CB | PHE | A | 288 | 2.663 | 4.190 | 25.010 | 1.00 | 0.48 |
| ATOM | 2599 | CG | PHE | A | 288 | 2.617 | 5.528 | 24.268 | 1.00 | 0.62 |
| ATOM | 2600 | CD1 | PHE | A | 288 | 1.409 | 6.199 | 24.136 | 1.00 | 1.03 |
| ATOM | 2601 | CE1 | PHE | A | 288 | 1.355 | 7.409 | 23.454 | 1.00 | 1.26 |
| ATOM | 2602 | CZ | PHE | A | 288 | 2.509 | 7.946 | 22.898 | 1.00 | 1.09 |
| ATOM | 2603 | CE2 | PHE | A | 288 | 3.716 | 7.272 | 23.024 | 1.00 | 0.95 |
| ATOM | 2604 | CD2 | PHE | A | 288 | 3.769 | 6.064 | 23.705 | 1.00 | 0.77 |
| ATOM | 2605 | C | PHE | A | 288 | 2.695 | 2.876 | 27.131 | 1.00 | 0.01 |
| ATOM | 2606 | O | PHE | A | 288 | 3.632 | 2.066 | 27.116 | 1.00 | 0.01 |
| ATOM | 2607 | N | PHE | A | 289 | 1.533 | 2.653 | 27.717 | 1.00 | 0.00 |
| ATOM | 2609 | CA | PHE | A | 289 | 1.172 | 1.371 | 28.329 | 1.00 | 0.02 |
| ATOM | 2610 | CB | PHE | A | 289 | 1.036 | 1.550 | 29.837 | 1.00 | 0.02 |
| ATOM | 2611 | CG | PHE | A | 289 | 2.351 | 1.838 | 30.553 | 1.00 | 0.02 |
| ATOM | 2612 | CD1 | PHE | A | 289 | 3.146 | 0.780 | 30.970 | 1.00 | 0.01 |
| ATOM | 2613 | CE1 | PHE | A | 289 | 4.347 | 1.026 | 31.621 | 1.00 | 0.01 |
| ATOM | 2614 | CZ | PHE | A | 289 | 4.754 | 2.331 | 31.853 | 1.00 | 0.00 |
| ATOM | 2615 | CE2 | PHE | A | 289 | 3.958 | 3.391 | 31.439 | 1.00 | 0.02 |
| ATOM | 2616 | CD2 | PHE | A | 289 | 2.755 | 3.145 | 30.793 | 1.00 | 0.01 |
| ATOM | 2617 | C | PHE | A | 289 | -0.146 | 0.882 | 27.747 | 1.00 | 0.01 |
| ATOM | 2618 | O | PHE | A | 289 | -1.234 | 1.344 | 28.121 | 1.00 | 0.00 |
| ATOM | 2619 | N | VAL | A | 290 | -0.030 | -0.050 | 26.819 | 1.00 | 0.01 |
| ATOM | 2621 | CA | VAL | A | 290 | -1.199 | -0.530 | 26.087 | 1.00 | 0.01 |
| ATOM | 2622 | CB | VAL | A | 290 | -0.838 | -0.588 | 24.608 | 1.00 | 0.18 |

| ATOM | 2623 | CG1 | VAL | A | 290 | -2.103 | -0.578 | 23.760 | 1.00 | 0.27 |
|------|------|-----|-----|---|-----|--------|--------|--------|------|------|
| ATOM | 2624 | CG2 | VAL | A | 290 | 0.031 | 0.603 | 24.221 | 1.00 | 0.21 |
| ATOM | 2625 | C | VAL | A | 290 | -1.639 | -1.905 | 26.591 | 1.00 | 0.01 |
| ATOM | 2626 | O | VAL | A | 290 | -0.972 | -2.922 | 26.362 | 1.00 | 0.01 |
| ATOM | 2627 | N | LEU | A | 291 | -2.783 | -1.917 | 27.250 | 1.00 | 0.00 |
| ATOM | 2629 | CA | LEU | A | 291 | -3.341 | -3.146 | 27.826 | 1.00 | 0.01 |
| ATOM | 2630 | CB | LEU | A | 291 | -3.874 | -2.824 | 29.219 | 1.00 | 0.01 |
| ATOM | 2631 | CG | LEU | A | 291 | -4.424 | -4.056 | 29.932 | 1.00 | 0.01 |
| ATOM | 2632 | CD1 | LEU | A | 291 | -3.342 | -5.113 | 30.113 | 1.00 | 0.02 |
| ATOM | 2633 | CD2 | LEU | A | 291 | -5.021 | -3.677 | 31.281 | 1.00 | 0.01 |
| ATOM | 2634 | C | LEU | A | 291 | -4.474 | -3.678 | 26.953 | 1.00 | 0.01 |
| ATOM | 2635 | O | LEU | A | 291 | -5.575 | -3.111 | 26.930 | 1.00 | 0.00 |
| ATOM | 2636 | N | PRO | A | 292 | -4.194 | -4.771 | 26.261 | 1.00 | 0.01 |
| ATOM | 2637 | CA | PRO | A | 292 | -5.169 | -5.403 | 25.370 | 1.00 | 0.01 |
| ATOM | 2638 | CB | PRO | A | 292 | -4.388 | -6.418 | 24.595 | 1.00 | 0.01 |
| ATOM | 2639 | CG | PRO | A | 292 | -2.992 | -6.534 | 25.186 | 1.00 | 0.01 |
| ATOM | 2640 | CD | PRO | A | 292 | -2.916 | -5.489 | 26.284 | 1.00 | 0.01 |
| ATOM | 2641 | C | PRO | A | 292 | -6.287 | -6.090 | 26.139 | 1.00 | 0.01 |
| ATOM | 2642 | O | PRO | A | 292 | -6.165 | -6.362 | 27.340 | 1.00 | 0.02 |
| ATOM | 2643 | N | SER | A | 293 | -7.386 | -6.324 | 25.445 | 1.00 | 0.01 |
| ATOM | 2645 | CA | SER | A | 293 | -8.472 | -7.139 | 26.000 | 1.00 | 0.01 |
| ATOM | 2646 | CB | SER | A | 293 | -9.636 | -7.190 | 25.017 | 1.00 | 1.05 |
| ATOM | 2647 | OG | SER | A | 293 | -10.092 | -5.868 | 24.781 | 1.00 | 1.03 |
| ATOM | 2648 | C | SER | A | 293 | -7.975 | -8.559 | 26.229 | 1.00 | 0.01 |
| ATOM | 2649 | O | SER | A | 293 | -7.012 | -8.999 | 25.587 | 1.00 | 0.01 |
| ATOM | 2650 | N | LYS | A | 294 | -8.613 | -9.258 | 27.152 | 1.00 | 0.00 |
| ATOM | 2652 | CA | LYS | A | 294 | -8.253 | -10.655 | 27.434 | 1.00 | 0.01 |
| ATOM | 2653 | CB | LYS | A | 294 | -9.124 | -11.140 | 28.587 | 1.00 | 0.54 |
| ATOM | 2654 | CG | LYS | A | 294 | -8.797 | -12.572 | 28.996 | 1.00 | 1.54 |
| ATOM | 2655 | CD | LYS | A | 294 | -9.634 | -12.990 | 30.198 | 1.00 | 2.50 |
| ATOM | 2656 | CE | LYS | A | 294 | -9.385 | -12.059 | 31.380 | 1.00 | 3.48 |
| ATOM | 2657 | NZ | LYS | A | 294 | -10.205 | -12.443 | 32.539 | 1.00 | 4.07 |
| ATOM | 2658 | C | LYS | A | 294 | -8.468 | -11.533 | 26.199 | 1.00 | 0.01 |
| ATOM | 2659 | O | LYS | A | 294 | -9.591 | -11.681 | 25.707 | 1.00 | 0.01 |
| ATOM | 2660 | N | GLY | A | 295 | -7.360 | -11.997 | 25.639 | 1.00 | 0.01 |
| ATOM | 2662 | CA | GLY | A | 295 | -7.391 | -12.817 | 24.421 | 1.00 | 0.01 |
| ATOM | 2663 | C | GLY | A | 295 | -6.939 | -12.038 | 23.182 | 1.00 | 0.01 |
| ATOM | 2664 | O | GLY | A | 295 | -6.305 | -12.600 | 22.281 | 1.00 | 0.01 |
| ATOM | 2665 | N | LYS | A | 296 | -7.107 | -10.726 | 23.232 | 1.00 | 0.01 |
| ATOM | 2667 | CA | LYS | A | 296 | -6.846 | -9.849 | 22.085 | 1.00 | 0.01 |
| ATOM | 2668 | CB | LYS | A | 296 | -7.853 | -8.710 | 22.110 | 1.00 | 0.01 |
| ATOM | 2669 | CG | LYS | A | 296 | -9.257 | -9.233 | 21.840 | 1.00 | 0.01 |
| ATOM | 2670 | CD | LYS | A | 296 | -9.341 | -9.847 | 20.447 | 1.00 | 0.01 |
| ATOM | 2671 | CE | LYS | A | 296 | - | - | 20.138 | 1.00 | 0.00 |

| | | | | | 10.746 | 10.345 | | | |
|---|---|---|---|---|---|---|---|---|---|
| ATOM | 2672 | NZ | LYS | A | 296 | -10.815 | -10.887 | 18.773 | 1.00 | 0.01 |
| ATOM | 2673 | C | LYS | A | 296 | -5.433 | -9.279 | 22.051 | 1.00 | 0.01 |
| ATOM | 2674 | O | LYS | A | 296 | -5.175 | -8.337 | 21.290 | 1.00 | 0.01 |
| ATOM | 2675 | N | MET | A | 297 | -4.504 | -9.942 | 22.720 | 1.00 | 0.01 |
| ATOM | 2677 | CA | MET | A | 297 | -3.123 | -9.456 | 22.805 | 1.00 | 0.00 |
| ATOM | 2678 | CB | MET | A | 297 | -2.353 | -10.395 | 23.722 | 1.00 | 0.99 |
| ATOM | 2679 | CG | MET | A | 297 | -0.922 | -9.920 | 23.947 | 1.00 | 1.52 |
| ATOM | 2680 | SD | MET | A | 297 | 0.150 | -11.110 | 24.780 | 1.00 | 1.96 |
| ATOM | 2681 | CE | MET | A | 297 | -0.977 | -11.607 | 26.104 | 1.00 | 1.91 |
| ATOM | 2682 | C | MET | A | 297 | -2.448 | -9.451 | 21.439 | 1.00 | 0.01 |
| ATOM | 2683 | O | MET | A | 297 | -1.946 | -8.402 | 21.013 | 1.00 | 0.01 |
| ATOM | 2684 | N | ARG | A | 298 | -2.725 | -10.481 | 20.655 | 1.00 | 0.01 |
| ATOM | 2686 | CA | ARG | A | 298 | -2.131 | -10.573 | 19.323 | 1.00 | 0.01 |
| ATOM | 2687 | CB | ARG | A | 298 | -2.184 | -12.028 | 18.874 | 1.00 | 0.22 |
| ATOM | 2688 | CG | ARG | A | 298 | -1.429 | -12.245 | 17.567 | 1.00 | 0.84 |
| ATOM | 2689 | CD | ARG | A | 298 | 0.040 | -11.853 | 17.695 | 1.00 | 1.21 |
| ATOM | 2690 | NE | ARG | A | 298 | 0.759 | -12.104 | 16.436 | 1.00 | 1.81 |
| ATOM | 2691 | CZ | ARG | A | 298 | 1.716 | -11.304 | 15.959 | 1.00 | 2.42 |
| ATOM | 2692 | NH1 | ARG | A | 298 | 2.319 | -11.599 | 14.805 | 1.00 | 3.43 |
| ATOM | 2693 | NH2 | ARG | A | 298 | 2.068 | -10.206 | 16.632 | 1.00 | 2.42 |
| ATOM | 2694 | C | ARG | A | 298 | -2.852 | -9.676 | 18.318 | 1.00 | 0.01 |
| ATOM | 2695 | O | ARG | A | 298 | -2.171 | -9.052 | 17.497 | 1.00 | 0.01 |
| ATOM | 2696 | N | GLN | A | 299 | -4.099 | -9.330 | 18.599 | 1.00 | 0.01 |
| ATOM | 2698 | CA | GLN | A | 299 | -4.825 | -8.428 | 17.700 | 1.00 | 0.01 |
| ATOM | 2699 | CB | GLN | A | 299 | -6.322 | -8.497 | 17.984 | 1.00 | 0.22 |
| ATOM | 2700 | CG | GLN | A | 299 | -7.083 | -7.552 | 17.056 | 1.00 | 1.14 |
| ATOM | 2701 | CD | GLN | A | 299 | -8.588 | -7.630 | 17.297 | 1.00 | 1.84 |
| ATOM | 2702 | OE1 | GLN | A | 299 | -9.099 | -7.198 | 18.338 | 1.00 | 2.37 |
| ATOM | 2703 | NE2 | GLN | A | 299 | -9.284 | -8.196 | 16.326 | 1.00 | 2.56 |
| ATOM | 2706 | C | GLN | A | 299 | -4.333 | -6.997 | 17.881 | 1.00 | 0.01 |
| ATOM | 2707 | O | GLN | A | 299 | -4.008 | -6.348 | 16.877 | 1.00 | 0.01 |
| ATOM | 2708 | N | LEU | A | 300 | -3.960 | -6.671 | 19.110 | 1.00 | 0.01 |
| ATOM | 2710 | CA | LEU | A | 300 | -3.388 | -5.360 | 19.417 | 1.00 | 0.01 |
| ATOM | 2711 | CB | LEU | A | 300 | -3.364 | -5.224 | 20.941 | 1.00 | 0.01 |
| ATOM | 2712 | CG | LEU | A | 300 | -2.876 | -3.865 | 21.444 | 1.00 | 0.01 |
| ATOM | 2713 | CD1 | LEU | A | 300 | -3.619 | -3.466 | 22.711 | 1.00 | 0.01 |
| ATOM | 2714 | CD2 | LEU | A | 300 | -1.366 | -3.814 | 21.673 | 1.00 | 0.01 |
| ATOM | 2715 | C | LEU | A | 300 | -1.979 | -5.241 | 18.852 | 1.00 | 0.01 |
| ATOM | 2716 | O | LEU | A | 300 | -1.670 | -4.242 | 18.188 | 1.00 | 0.00 |
| ATOM | 2717 | N | GLU | A | 301 | -1.244 | -6.342 | 18.871 | 1.00 | 0.01 |
| ATOM | 2719 | CA | GLU | A | 301 | 0.128 | -6.330 | 18.360 | 1.00 | 0.01 |
| ATOM | 2720 | CB | GLU | A | 301 | 0.833 | -7.573 | 18.881 | 1.00 | 0.00 |
| ATOM | 2721 | CG | GLU | A | 301 | 0.969 | -7.496 | 20.397 | 1.00 | 0.01 |
| ATOM | 2722 | CD | GLU | A | 301 | 1.457 | -8.820 | 20.975 | 1.00 | 0.01 |

| ATOM | 2723 | OE1 | GLU | A | 301 | 0.861 | -9.838 | 20.645 | 1.00 | 0.01 |
|------|------|-----|-----|---|-----|-------|--------|--------|------|------|
| ATOM | 2724 | OE2 | GLU | A | 301 | 2.301 | -8.771 | 21.857 | 1.00 | 0.01 |
| ATOM | 2725 | C | GLU | A | 301 | 0.183 | -6.273 | 16.835 | 1.00 | 0.00 |
| ATOM | 2726 | O | GLU | A | 301 | 1.031 | -5.554 | 16.300 | 1.00 | 0.01 |
| ATOM | 2727 | N | GLN | A | 302 | -0.854 | -6.767 | 16.178 | 1.00 | 0.00 |
| ATOM | 2729 | CA | GLN | A | 302 | -0.954 | -6.664 | 14.717 | 1.00 | 0.01 |
| ATOM | 2730 | CB | GLN | A | 302 | -1.851 | -7.793 | 14.233 | 1.00 | 0.25 |
| ATOM | 2731 | CG | GLN | A | 302 | -1.306 | -9.172 | 14.574 | 1.00 | 0.93 |
| ATOM | 2732 | CD | GLN | A | 302 | -2.446 | -10.171 | 14.418 | 1.00 | 1.50 |
| ATOM | 2733 | OE1 | GLN | A | 302 | -2.265 | -11.388 | 14.534 | 1.00 | 2.23 |
| ATOM | 2734 | NE2 | GLN | A | 302 | -3.632 | -9.625 | 14.210 | 1.00 | 1.68 |
| ATOM | 2737 | C | GLN | A | 302 | -1.588 | -5.351 | 14.249 | 1.00 | 0.01 |
| ATOM | 2738 | O | GLN | A | 302 | -1.615 | -5.082 | 13.043 | 1.00 | 0.00 |
| ATOM | 2739 | N | ALA | A | 303 | -2.109 | -4.560 | 15.174 | 1.00 | 0.00 |
| ATOM | 2741 | CA | ALA | A | 303 | -2.790 | -3.316 | 14.808 | 1.00 | 0.00 |
| ATOM | 2742 | CB | ALA | A | 303 | -4.138 | -3.269 | 15.518 | 1.00 | 0.26 |
| ATOM | 2743 | C | ALA | A | 303 | -1.975 | -2.063 | 15.131 | 1.00 | 0.00 |
| ATOM | 2744 | O | ALA | A | 303 | -2.486 | -0.941 | 15.004 | 1.00 | 0.00 |
| ATOM | 2745 | N | LEU | A | 304 | -0.737 | -2.251 | 15.561 | 1.00 | 0.01 |
| ATOM | 2747 | CA | LEU | A | 304 | 0.133 | -1.114 | 15.905 | 1.00 | 0.01 |
| ATOM | 2748 | CB | LEU | A | 304 | 1.343 | -1.654 | 16.656 | 1.00 | 0.01 |
| ATOM | 2749 | CG | LEU | A | 304 | 0.954 | -2.357 | 17.949 | 1.00 | 0.01 |
| ATOM | 2750 | CD1 | LEU | A | 304 | 2.151 | -3.094 | 18.536 | 1.00 | 0.00 |
| ATOM | 2751 | CD2 | LEU | A | 304 | 0.366 | -1.376 | 18.959 | 1.00 | 0.01 |
| ATOM | 2752 | C | LEU | A | 304 | 0.640 | -0.360 | 14.674 | 1.00 | 0.01 |
| ATOM | 2753 | O | LEU | A | 304 | 1.621 | -0.768 | 14.045 | 1.00 | 0.00 |
| ATOM | 2754 | N | SER | A | 305 | -0.014 | 0.741 | 14.349 | 1.00 | 0.00 |
| ATOM | 2756 | CA | SER | A | 305 | 0.463 | 1.577 | 13.243 | 1.00 | 0.01 |
| ATOM | 2757 | CB | SER | A | 305 | -0.707 | 2.019 | 12.371 | 1.00 | 0.42 |
| ATOM | 2758 | OG | SER | A | 305 | -1.347 | 3.114 | 13.014 | 1.00 | 0.47 |
| ATOM | 2759 | C | SER | A | 305 | 1.161 | 2.818 | 13.779 | 1.00 | 0.00 |
| ATOM | 2760 | O | SER | A | 305 | 0.774 | 3.360 | 14.821 | 1.00 | 0.01 |
| ATOM | 2761 | N | ALA | A | 306 | 2.015 | 3.393 | 12.949 | 1.00 | 0.00 |
| ATOM | 2763 | CA | ALA | A | 306 | 2.696 | 4.636 | 13.326 | 1.00 | 0.01 |
| ATOM | 2764 | CB | ALA | A | 306 | 3.900 | 4.838 | 12.412 | 1.00 | 0.26 |
| ATOM | 2765 | C | ALA | A | 306 | 1.768 | 5.852 | 13.243 | 1.00 | 0.00 |
| ATOM | 2766 | O | ALA | A | 306 | 1.963 | 6.820 | 13.988 | 1.00 | 0.00 |
| ATOM | 2767 | N | ARG | A | 307 | 0.647 | 5.696 | 12.554 | 1.00 | 0.00 |
| ATOM | 2769 | CA | ARG | A | 307 | -0.332 | 6.779 | 12.479 | 1.00 | 0.01 |
| ATOM | 2770 | CB | ARG | A | 307 | -1.239 | 6.557 | 11.278 | 1.00 | 0.19 |
| ATOM | 2771 | CG | ARG | A | 307 | -1.769 | 7.885 | 10.745 | 1.00 | 1.11 |
| ATOM | 2772 | CD | ARG | A | 307 | -3.277 | 7.865 | 10.521 | 1.00 | 1.47 |
| ATOM | 2773 | NE | ARG | A | 307 | -3.994 | 7.930 | 11.805 | 1.00 | 2.53 |
| ATOM | 2774 | CZ | ARG | A | 307 | -4.809 | 6.974 | 12.255 | 1.00 | 3.45 |
| ATOM | 2775 | NH1 | ARG | A | 307 | -4.995 | 5.862 | 11.541 | 1.00 | 4.09 |
| ATOM | 2776 | NH2 | ARG | A | 307 | -5.419 | 7.122 | 13.432 | 1.00 | 4.06 |
| ATOM | 2777 | C | ARG | A | 307 | -1.176 | 6.837 | 13.753 | 1.00 | 0.01 |
| ATOM | 2778 | O | ARG | A | 307 | -1.359 | 7.931 | 14.297 | 1.00 | 0.00 |
| ATOM | 2779 | N | THR | A | 308 | -1.485 | 5.692 | 14.349 | 1.00 | 0.01 |
| ATOM | 2781 | CA | THR | A | 308 | -2.165 | 5.723 | 15.652 | 1.00 | 0.00 |
| ATOM | 2782 | CB | THR | A | 308 | -2.832 | 4.376 | 15.929 | 1.00 | 0.18 |
| ATOM | 2783 | OG1 | THR | A | 308 | -1.837 | 3.361 | 15.955 | 1.00 | 0.24 |
| ATOM | 2784 | CG2 | THR | A | 308 | -3.858 | 4.012 | 14.863 | 1.00 | 0.45 |
| ATOM | 2785 | C | THR | A | 308 | -1.187 | 6.045 | 16.780 | 1.00 | 0.01 |
| ATOM | 2786 | O | THR | A | 308 | -1.579 | 6.676 | 17.767 | 1.00 | 0.00 |
| ATOM | 2787 | N | LEU | A | 309 | 0.093 | 5.852 | 16.514 | 1.00 | 0.01 |

| ATOM | 2789 | CA | LEU | A | 309 | 1.135 | 6.202 | 17.481 | 1.00 | 0.01 |
|------|------|-----|-----|---|-----|-------|-------|--------|------|------|
| ATOM | 2790 | CB | LEU | A | 309 | 2.444 | 5.577 | 17.012 | 1.00 | 0.17 |
| ATOM | 2791 | CG | LEU | A | 309 | 2.809 | 4.260 | 17.697 | 1.00 | 0.39 |
| ATOM | 2792 | CD1 | LEU | A | 309 | 1.665 | 3.253 | 17.805 | 1.00 | 0.43 |
| ATOM | 2793 | CD2 | LEU | A | 309 | 4.007 | 3.630 | 17.001 | 1.00 | 0.47 |
| ATOM | 2794 | C | LEU | A | 309 | 1.304 | 7.714 | 17.567 | 1.00 | 0.01 |
| ATOM | 2795 | O | LEU | A | 309 | 1.259 | 8.269 | 18.673 | 1.00 | 0.01 |
| ATOM | 2796 | N | ILE | A | 310 | 1.224 | 8.387 | 16.428 | 1.00 | 0.01 |
| ATOM | 2798 | CA | ILE | A | 310 | 1.309 | 9.849 | 16.443 | 1.00 | 0.01 |
| ATOM | 2799 | CB | ILE | A | 310 | 1.872 | 10.353 | 15.112 | 1.00 | 0.24 |
| ATOM | 2800 | CG2 | ILE | A | 310 | 0.948 | 10.046 | 13.940 | 1.00 | 0.79 |
| ATOM | 2801 | CG1 | ILE | A | 310 | 2.160 | 11.849 | 15.168 | 1.00 | 1.18 |
| ATOM | 2802 | CD1 | ILE | A | 310 | 2.720 | 12.350 | 13.842 | 1.00 | 1.93 |
| ATOM | 2803 | C | ILE | A | 310 | -0.043 | 10.487 | 16.783 | 1.00 | 0.01 |
| ATOM | 2804 | O | ILE | A | 310 | -0.070 | 11.594 | 17.336 | 1.00 | 0.01 |
| ATOM | 2805 | N | LYS | A | 311 | -1.107 | 9.702 | 16.703 | 1.00 | 0.01 |
| ATOM | 2807 | CA | LYS | A | 311 | -2.419 | 10.150 | 17.164 | 1.00 | 0.01 |
| ATOM | 2808 | CB | LYS | A | 311 | -3.464 | 9.156 | 16.677 | 1.00 | 0.01 |
| ATOM | 2809 | CG | LYS | A | 311 | -4.850 | 9.489 | 17.209 | 1.00 | 0.01 |
| ATOM | 2810 | CD | LYS | A | 311 | -5.842 | 8.389 | 16.858 | 1.00 | 0.01 |
| ATOM | 2811 | CE | LYS | A | 311 | -7.228 | 8.691 | 17.414 | 1.00 | 0.00 |
| ATOM | 2812 | NZ | LYS | A | 311 | -8.166 | 7.606 | 17.087 | 1.00 | 0.01 |
| ATOM | 2813 | C | LYS | A | 311 | -2.452 | 10.227 | 18.686 | 1.00 | 0.01 |
| ATOM | 2814 | O | LYS | A | 311 | -2.705 | 11.305 | 19.242 | 1.00 | 0.01 |
| ATOM | 2815 | N | TRP | A | 312 | -1.911 | 9.206 | 19.329 | 1.00 | 0.01 |
| ATOM | 2817 | CA | TRP | A | 312 | -1.874 | 9.211 | 20.789 | 1.00 | 0.01 |
| ATOM | 2818 | CB | TRP | A | 312 | -1.702 | 7.784 | 21.291 | 1.00 | 0.26 |
| ATOM | 2819 | CG | TRP | A | 312 | -2.941 | 6.939 | 21.080 | 1.00 | 0.93 |
| ATOM | 2820 | CD1 | TRP | A | 312 | -3.058 | 5.824 | 20.281 | 1.00 | 2.03 |
| ATOM | 2821 | NE1 | TRP | A | 312 | -4.334 | 5.374 | 20.351 | 1.00 | 2.63 |
| ATOM | 2823 | CE2 | TRP | A | 312 | -5.073 | 6.138 | 21.177 | 1.00 | 1.99 |
| ATOM | 2824 | CZ2 | TRP | A | 312 | -6.399 | 6.090 | 21.558 | 1.00 | 2.30 |
| ATOM | 2825 | CH2 | TRP | A | 312 | -6.898 | 7.040 | 22.452 | 1.00 | 1.63 |
| ATOM | 2826 | CZ3 | TRP | A | 312 | -6.068 | 8.027 | 22.958 | 1.00 | 0.98 |
| ATOM | 2827 | CE3 | TRP | A | 312 | -4.730 | 8.082 | 22.576 | 1.00 | 0.71 |
| ATOM | 2828 | CD2 | TRP | A | 312 | -4.230 | 7.143 | 21.684 | 1.00 | 0.94 |
| ATOM | 2829 | C | TRP | A | 312 | -0.777 | 10.113 | 21.338 | 1.00 | 0.00 |
| ATOM | 2830 | O | TRP | A | 312 | -1.025 | 10.794 | 22.338 | 1.00 | 0.01 |
| ATOM | 2831 | N | SER | A | 313 | 0.236 | 10.390 | 20.534 | 1.00 | 0.00 |
| ATOM | 2833 | CA | SER | A | 313 | 1.279 | 11.321 | 20.976 | 1.00 | 0.00 |
| ATOM | 2834 | CB | SER | A | 313 | 2.560 | 11.069 | 20.190 | 1.00 | 0.24 |
| ATOM | 2835 | OG | SER | A | 313 | 2.342 | 11.501 | 18.857 | 1.00 | 0.20 |
| ATOM | 2836 | C | SER | A | 313 | 0.882 | 12.796 | 20.830 | 1.00 | 0.01 |
| ATOM | 2837 | O | SER | A | 313 | 1.640 | 13.656 | 21.290 | 1.00 | 0.00 |
| ATOM | 2838 | N | HIS | A | 314 | -0.245 | 13.105 | 20.200 | 1.00 | 0.01 |
| ATOM | 2840 | CA | HIS | A | 314 | -0.728 | 14.488 | 20.258 | 1.00 | 0.01 |
| ATOM | 2841 | CB | HIS | A | 314 | -1.012 | 15.063 | 18.869 | 1.00 | 0.13 |
| ATOM | 2842 | CG | HIS | A | 314 | -2.195 | 14.499 | 18.103 | 1.00 | 0.18 |
| ATOM | 2843 | ND1 | HIS | A | 314 | -2.128 | 13.688 | 17.033 | 1.00 | 0.25 |
| ATOM | 2845 | CE1 | HIS | A | 314 | -3.375 | 13.404 | 16.607 | 1.00 | 0.30 |
| ATOM | 2846 | NE2 | HIS | A | 314 | -4.242 | 14.049 | 17.420 | 1.00 | 0.28 |
| ATOM | 2847 | CD2 | HIS | A | 314 | -3.530 | 14.737 | 18.340 | 1.00 | 0.22 |
| ATOM | 2848 | C | HIS | A | 314 | -1.958 | 14.594 | 21.154 | 1.00 | 0.01 |
| ATOM | 2849 | O | HIS | A | 314 | -2.450 | 15.700 | 21.411 | 1.00 | 0.01 |
| ATOM | 2850 | N | SER | A | 315 | -2.462 | 13.456 | 21.603 | 1.00 | 0.01 |
| ATOM | 2852 | CA | SER | A | 315 | -3.602 | 13.466 | 22.521 | 1.00 | 0.00 |
| ATOM | 2853 | CB | SER | A | 315 | -4.209 | 12.075 | 22.626 | 1.00 | 1.14 |
| ATOM | 2854 | OG | SER | A | 315 | -5.144 | 12.131 | 23.697 | 1.00 | 0.90 |

| ATOM | 2855 | C | SER | A | 315 | -3.187 | 13.914 | 23.912 | 1.00 | 0.01 |
|---|---|---|---|---|---|---|---|---|---|---|
| ATOM | 2856 | O | SER | A | 315 | -2.451 | 13.230 | 24.629 | 1.00 | 0.01 |
| ATOM | 2857 | N | LEU | A | 316 | -3.759 | 15.029 | 24.321 | 1.00 | 0.00 |
| ATOM | 2859 | CA | LEU | A | 316 | -3.489 | 15.563 | 25.654 | 1.00 | 0.01 |
| ATOM | 2860 | CB | LEU | A | 316 | -3.311 | 17.071 | 25.509 | 1.00 | 0.88 |
| ATOM | 2861 | CG | LEU | A | 316 | -2.537 | 17.664 | 26.682 | 1.00 | 2.18 |
| ATOM | 2862 | CD1 | LEU | A | 316 | -1.203 | 16.939 | 26.876 | 1.00 | 2.44 |
| ATOM | 2863 | CD2 | LEU | A | 316 | -2.336 | 19.167 | 26.493 | 1.00 | 3.16 |
| ATOM | 2864 | C | LEU | A | 316 | -4.621 | 15.225 | 26.633 | 1.00 | 0.01 |
| ATOM | 2865 | O | LEU | A | 316 | -4.649 | 15.755 | 27.750 | 1.00 | 0.01 |
| ATOM | 2866 | N | GLN | A | 317 | -5.507 | 14.318 | 26.241 | 1.00 | 0.01 |
| ATOM | 2868 | CA | GLN | A | 317 | -6.718 | 14.058 | 27.030 | 1.00 | 0.00 |
| ATOM | 2869 | CB | GLN | A | 317 | -7.740 | 13.326 | 26.166 | 1.00 | 0.55 |
| ATOM | 2870 | CG | GLN | A | 317 | -9.095 | 13.217 | 26.866 | 1.00 | 1.06 |
| ATOM | 2871 | CD | GLN | A | 317 | -9.686 | 14.609 | 27.104 | 1.00 | 1.59 |
| ATOM | 2872 | OE1 | GLN | A | 317 | -9.231 | 15.360 | 27.973 | 1.00 | 2.10 |
| ATOM | 2873 | NE2 | GLN | A | 317 | -10.682 | 14.947 | 26.304 | 1.00 | 2.07 |
| ATOM | 2876 | C | GLN | A | 317 | -6.428 | 13.248 | 28.288 | 1.00 | 0.01 |
| ATOM | 2877 | O | GLN | A | 317 | -6.204 | 12.030 | 28.245 | 1.00 | 0.01 |
| ATOM | 2878 | N | LYS | A | 318 | -6.423 | 13.963 | 29.397 | 1.00 | 0.01 |
| ATOM | 2880 | CA | LYS | A | 318 | -6.161 | 13.376 | 30.708 | 1.00 | 0.00 |
| ATOM | 2881 | CB | LYS | A | 318 | -5.293 | 14.346 | 31.495 | 1.00 | 0.64 |
| ATOM | 2882 | CG | LYS | A | 318 | -3.944 | 14.570 | 30.825 | 1.00 | 1.38 |
| ATOM | 2883 | CD | LYS | A | 318 | -3.065 | 15.477 | 31.674 | 1.00 | 1.55 |
| ATOM | 2884 | CE | LYS | A | 318 | -1.700 | 15.689 | 31.033 | 1.00 | 2.51 |
| ATOM | 2885 | NZ | LYS | A | 318 | -0.837 | 16.502 | 31.905 | 1.00 | 3.10 |
| ATOM | 2886 | C | LYS | A | 318 | -7.452 | 13.143 | 31.474 | 1.00 | 0.02 |
| ATOM | 2887 | O | LYS | A | 318 | -8.345 | 13.997 | 31.492 | 1.00 | 0.01 |
| ATOM | 2888 | N | ARG | A | 319 | -7.552 | 11.986 | 32.098 | 1.00 | 0.02 |
| ATOM | 2890 | CA | ARG | A | 319 | -8.712 | 11.728 | 32.945 | 1.00 | 0.01 |
| ATOM | 2891 | CB | ARG | A | 319 | -9.810 | 11.008 | 32.171 | 1.00 | 0.01 |
| ATOM | 2892 | CG | ARG | A | 319 | -9.397 | 9.697 | 31.517 | 1.00 | 0.00 |
| ATOM | 2893 | CD | ARG | A | 319 | -10.610 | 9.150 | 30.774 | 1.00 | 0.00 |
| ATOM | 2894 | NE | ARG | A | 319 | -10.350 | 7.878 | 30.088 | 1.00 | 0.02 |
| ATOM | 2895 | CZ | ARG | A | 319 | -10.965 | 7.547 | 28.950 | 1.00 | 0.01 |
| ATOM | 2896 | NH1 | ARG | A | 319 | -11.774 | 8.423 | 28.352 | 1.00 | 0.01 |
| ATOM | 2897 | NH2 | ARG | A | 319 | -10.727 | 6.365 | 28.378 | 1.00 | 0.01 |
| ATOM | 2898 | C | ARG | A | 319 | -8.346 | 10.999 | 34.231 | 1.00 | 0.02 |
| ATOM | 2899 | O | ARG | A | 319 | -7.237 | 10.488 | 34.422 | 1.00 | 0.01 |
| ATOM | 2900 | N | TRP | A | 320 | -9.294 | 11.068 | 35.145 | 1.00 | 0.02 |
| ATOM | 2902 | CA | TRP | A | 320 | -9.134 | 10.543 | 36.499 | 1.00 | 0.01 |
| ATOM | 2903 | CB | TRP | A | 320 | -10.232 | 11.177 | 37.346 | 1.00 | 2.46 |
| ATOM | 2904 | CG | TRP | A | 320 | -10.407 | 12.649 | 37.031 | 1.00 | 3.22 |
| ATOM | 2905 | CD1 | TRP | A | 320 | -9.571 | 13.677 | 37.406 | 1.00 | 4.15 |
| ATOM | 2906 | NE1 | TRP | A | 320 | -10.048 | 14.835 | 36.887 | 1.00 | 4.95 |
| ATOM | 2908 | CE2 | TRP | A | 320 | -11.170 | 14.620 | 36.167 | 1.00 | 4.71 |
| ATOM | 2909 | CZ2 | TRP | A | 320 | -11.968 | 15.453 | 35.399 | 1.00 | 5.57 |

| ATOM | 2910 | CH2 | TRP | A | 320 | -13.083 | 14.932 | 34.750 | 1.00 | 5.51 |
|------|------|-----|-----|---|-----|---------|--------|--------|------|------|
| ATOM | 2911 | CZ3 | TRP | A | 320 | -13.393 | 13.580 | 34.861 | 1.00 | 4.74 |
| ATOM | 2912 | CE3 | TRP | A | 320 | -12.587 | 12.736 | 35.613 | 1.00 | 3.74 |
| ATOM | 2913 | CD2 | TRP | A | 320 | -11.471 | 13.253 | 36.260 | 1.00 | 3.68 |
| ATOM | 2914 | C | TRP | A | 320 | -9.278 | 9.032 | 36.489 | 1.00 | 0.00 |
| ATOM | 2915 | O | TRP | A | 320 | -10.354 | 8.506 | 36.190 | 1.00 | 0.00 |
| ATOM | 2916 | N | ILE | A | 321 | -8.172 | 8.350 | 36.720 | 1.00 | 0.01 |
| ATOM | 2918 | CA | ILE | A | 321 | -8.166 | 6.881 | 36.726 | 1.00 | 0.00 |
| ATOM | 2919 | CB | ILE | A | 321 | -7.656 | 6.390 | 35.378 | 1.00 | 0.72 |
| ATOM | 2920 | CG2 | ILE | A | 321 | -8.752 | 6.400 | 34.315 | 1.00 | 1.67 |
| ATOM | 2921 | CG1 | ILE | A | 321 | -6.452 | 7.206 | 34.930 | 1.00 | 1.15 |
| ATOM | 2922 | CD1 | ILE | A | 321 | -5.986 | 6.773 | 33.549 | 1.00 | 1.60 |
| ATOM | 2923 | C | ILE | A | 321 | -7.317 | 6.306 | 37.857 | 1.00 | 0.02 |
| ATOM | 2924 | O | ILE | A | 321 | -6.287 | 6.869 | 38.249 | 1.00 | 0.00 |
| ATOM | 2925 | N | GLU | A | 322 | -7.732 | 5.140 | 38.323 | 1.00 | 0.01 |
| ATOM | 2927 | CA | GLU | A | 322 | -7.086 | 4.466 | 39.461 | 1.00 | 0.02 |
| ATOM | 2928 | CB | GLU | A | 322 | -8.198 | 3.733 | 40.205 | 1.00 | 0.75 |
| ATOM | 2929 | CG | GLU | A | 322 | -7.735 | 3.098 | 41.508 | 1.00 | 1.32 |
| ATOM | 2930 | CD | GLU | A | 322 | -8.891 | 2.309 | 42.108 | 1.00 | 1.58 |
| ATOM | 2931 | OE1 | GLU | A | 322 | -8.813 | 1.994 | 43.287 | 1.00 | 1.93 |
| ATOM | 2932 | OE2 | GLU | A | 322 | -9.859 | 2.086 | 41.392 | 1.00 | 1.79 |
| ATOM | 2933 | C | GLU | A | 322 | -6.012 | 3.474 | 38.997 | 1.00 | 0.02 |
| ATOM | 2934 | O | GLU | A | 322 | -6.201 | 2.254 | 39.077 | 1.00 | 0.02 |
| ATOM | 2935 | N | VAL | A | 323 | -4.871 | 4.007 | 38.597 | 1.00 | 0.00 |
| ATOM | 2937 | CA | VAL | A | 323 | -3.819 | 3.209 | 37.952 | 1.00 | 0.00 |
| ATOM | 2938 | CB | VAL | A | 323 | -2.852 | 4.200 | 37.307 | 1.00 | 0.58 |
| ATOM | 2939 | CG1 | VAL | A | 323 | -1.511 | 3.597 | 36.913 | 1.00 | 1.12 |
| ATOM | 2940 | CG2 | VAL | A | 323 | -3.507 | 4.860 | 36.104 | 1.00 | 1.30 |
| ATOM | 2941 | C | VAL | A | 323 | -3.095 | 2.236 | 38.885 | 1.00 | 0.02 |
| ATOM | 2942 | O | VAL | A | 323 | -2.768 | 2.554 | 40.038 | 1.00 | 0.00 |
| ATOM | 2943 | N | PHE | A | 324 | -2.997 | 1.007 | 38.396 | 1.00 | 0.02 |
| ATOM | 2945 | CA | PHE | A | 324 | -2.221 | -0.061 | 39.037 | 1.00 | 0.02 |
| ATOM | 2946 | CB | PHE | A | 324 | -3.167 | -1.200 | 39.409 | 1.00 | 0.70 |
| ATOM | 2947 | CG | PHE | A | 324 | -4.225 | -0.894 | 40.461 | 1.00 | 0.66 |
| ATOM | 2948 | CD1 | PHE | A | 324 | -3.850 | -0.696 | 41.783 | 1.00 | 1.33 |
| ATOM | 2949 | CE1 | PHE | A | 324 | -4.815 | -0.432 | 42.745 | 1.00 | 2.10 |
| ATOM | 2950 | CZ | PHE | A | 324 | -6.155 | -0.369 | 42.387 | 1.00 | 2.27 |
| ATOM | 2951 | CE2 | PHE | A | 324 | -6.531 | -0.571 | 41.065 | 1.00 | 1.95 |
| ATOM | 2952 | CD2 | PHE | A | 324 | -5.566 | -0.837 | 40.103 | 1.00 | 1.28 |
| ATOM | 2953 | C | PHE | A | 324 | -1.190 | -0.636 | 38.063 | 1.00 | 0.01 |
| ATOM | 2954 | O | PHE | A | 324 | -1.516 | -1.572 | 37.320 | 1.00 | 0.00 |
| ATOM | 2955 | N | ILE | A | 325 | 0.034 | -0.128 | 38.092 | 1.00 | 0.01 |
| ATOM | 2957 | CA | ILE | A | 325 | 1.088 | -0.642 | 37.188 | 1.00 | 0.02 |
| ATOM | 2958 | CB | ILE | A | 325 | 1.659 | 0.527 | 36.379 | 1.00 | 0.42 |
| ATOM | 2959 | CG2 | ILE | A | 325 | 2.869 | 0.119 | 35.543 | 1.00 | 0.61 |
| ATOM | 2960 | CG1 | ILE | A | 325 | 0.598 | 1.123 | 35.468 | 1.00 | 0.74 |
| ATOM | 2961 | CD1 | ILE | A | 325 | 1.195 | 2.203 | 34.575 | 1.00 | 1.12 |
| ATOM | 2962 | C | ILE | A | 325 | 2.209 | -1.345 | 37.961 | 1.00 | 0.02 |
| ATOM | 2963 | O | ILE | A | 325 | 2.764 | -0.770 | 38.901 | 1.00 | 0.01 |
| ATOM | 2964 | N | PRO | A | 326 | 2.521 | -2.577 | 37.588 | 1.00 | 0.00 |
| ATOM | 2965 | CA | PRO | A | 326 | 3.556 | -3.351 | 38.287 | 1.00 | 0.02 |
| ATOM | 2966 | CB | PRO | A | 326 | 3.580 | -4.687 | 37.615 | 1.00 | 0.02 |
| ATOM | 2967 | CG | PRO | A | 326 | 2.546 | -4.703 | 36.502 | 1.00 | 0.00 |

| ATOM | 2968 | CD | PRO | A | 326 | 1.890 | -3.333 | 36.507 | 1.00 | 0.02 |
|---|---|---|---|---|---|---|---|---|---|---|
| ATOM | 2969 | C | PRO | A | 326 | 4.932 | -2.683 | 38.260 | 1.00 | 0.00 |
| ATOM | 2970 | O | PRO | A | 326 | 5.296 | -1.981 | 37.309 | 1.00 | 0.02 |
| ATOM | 2971 | N | ARG | A | 327 | 5.646 | -2.858 | 39.358 | 1.00 | 0.01 |
| ATOM | 2973 | CA | ARG | A | 327 | 6.977 | -2.267 | 39.528 | 1.00 | 0.02 |
| ATOM | 2974 | CB | ARG | A | 327 | 7.056 | -1.674 | 40.929 | 1.00 | 0.43 |
| ATOM | 2975 | CG | ARG | A | 327 | 8.383 | -0.959 | 41.131 | 1.00 | 1.22 |
| ATOM | 2976 | CD | ARG | A | 327 | 8.580 | -0.486 | 42.561 | 1.00 | 1.09 |
| ATOM | 2977 | NE | ARG | A | 327 | 9.842 | 0.261 | 42.668 | 1.00 | 2.19 |
| ATOM | 2978 | CZ | ARG | A | 327 | 10.975 | -0.253 | 43.151 | 1.00 | 2.68 |
| ATOM | 2979 | NH1 | ARG | A | 327 | 12.079 | 0.495 | 43.192 | 1.00 | 3.44 |
| ATOM | 2980 | NH2 | ARG | A | 327 | 11.008 | -1.517 | 43.581 | 1.00 | 2.85 |
| ATOM | 2981 | C | ARG | A | 327 | 8.077 | -3.316 | 39.398 | 1.00 | 0.02 |
| ATOM | 2982 | O | ARG | A | 327 | 8.186 | -4.202 | 40.256 | 1.00 | 0.02 |
| ATOM | 2983 | N | PHE | A | 328 | 8.933 | -3.157 | 38.399 | 1.00 | 0.02 |
| ATOM | 2985 | CA | PHE | A | 328 | 10.045 | -4.102 | 38.206 | 1.00 | 0.01 |
| ATOM | 2986 | CB | PHE | A | 328 | 9.496 | -5.484 | 37.861 | 1.00 | 1.21 |
| ATOM | 2987 | CG | PHE | A | 328 | 10.160 | -6.623 | 38.635 | 1.00 | 2.16 |
| ATOM | 2988 | CD1 | PHE | A | 328 | 9.523 | -7.158 | 39.747 | 1.00 | 3.00 |
| ATOM | 2989 | CE1 | PHE | A | 328 | 10.117 | -8.194 | 40.457 | 1.00 | 3.93 |
| ATOM | 2990 | CZ | PHE | A | 328 | 11.348 | -8.696 | 40.054 | 1.00 | 4.19 |
| ATOM | 2991 | CE2 | PHE | A | 328 | 11.984 | -8.161 | 38.942 | 1.00 | 3.65 |
| ATOM | 2992 | CD2 | PHE | A | 328 | 11.390 | -7.126 | 38.233 | 1.00 | 2.61 |
| ATOM | 2993 | C | PHE | A | 328 | 10.986 | -3.651 | 37.091 | 1.00 | 0.01 |
| ATOM | 2994 | O | PHE | A | 328 | 10.583 | -2.979 | 36.135 | 1.00 | 0.00 |
| ATOM | 2995 | N | SER | A | 329 | 12.254 | -3.988 | 37.242 | 1.00 | 0.01 |
| ATOM | 2997 | CA | SER | A | 329 | 13.218 | -3.718 | 36.176 | 1.00 | 0.01 |
| ATOM | 2998 | CB | SER | A | 329 | 14.586 | -3.439 | 36.775 | 1.00 | 0.00 |
| ATOM | 2999 | OG | SER | A | 329 | 15.460 | -3.178 | 35.685 | 1.00 | 0.01 |
| ATOM | 3000 | C | SER | A | 329 | 13.324 | -4.900 | 35.215 | 1.00 | 0.02 |
| ATOM | 3001 | O | SER | A | 329 | 13.844 | -5.964 | 35.567 | 1.00 | 0.02 |
| ATOM | 3002 | N | ILE | A | 330 | 12.857 | -4.688 | 33.998 | 1.00 | 0.01 |
| ATOM | 3004 | CA | ILE | A | 330 | 12.930 | -5.723 | 32.962 | 1.00 | 0.00 |
| ATOM | 3005 | CB | ILE | A | 330 | 11.662 | -5.673 | 32.114 | 1.00 | 0.01 |
| ATOM | 3006 | CG2 | ILE | A | 330 | 10.451 | -6.083 | 32.946 | 1.00 | 0.01 |
| ATOM | 3007 | CG1 | ILE | A | 330 | 11.456 | -4.287 | 31.511 | 1.00 | 0.02 |
| ATOM | 3008 | CD1 | ILE | A | 330 | 10.201 | -4.238 | 30.646 | 1.00 | 0.00 |
| ATOM | 3009 | C | ILE | A | 330 | 14.170 | -5.524 | 32.092 | 1.00 | 0.01 |
| ATOM | 3010 | O | ILE | A | 330 | 14.637 | -4.397 | 31.897 | 1.00 | 0.01 |
| ATOM | 3011 | N | SER | A | 331 | 14.740 | -6.622 | 31.631 | 1.00 | 0.01 |
| ATOM | 3013 | CA | SER | A | 331 | 15.937 | -6.517 | 30.790 | 1.00 | 0.00 |
| ATOM | 3014 | CB | SER | A | 331 | 17.164 | -6.528 | 31.687 | 1.00 | 0.38 |
| ATOM | 3015 | OG | SER | A | 331 | 18.286 | -6.315 | 30.846 | 1.00 | 0.92 |
| ATOM | 3016 | C | SER | A | 331 | 16.031 | -7.657 | 29.782 | 1.00 | 0.00 |
| ATOM | 3017 | O | SER | A | 331 | 15.846 | -8.829 | 30.131 | 1.00 | 0.01 |
| ATOM | 3018 | N | ALA | A | 332 | 16.368 | -7.307 | 28.552 | 1.00 | 0.02 |
| ATOM | 3020 | CA | ALA | A | 332 | 16.466 | -8.314 | 27.494 | 1.00 | 0.01 |
| ATOM | 3021 | CB | ALA | A | 332 | 15.182 | -8.277 | 26.679 | 1.00 | 0.17 |
| ATOM | 3022 | C | ALA | A | 332 | 17.683 | -8.130 | 26.585 | 1.00 | 0.01 |
| ATOM | 3023 | O | ALA | A | 332 | 17.896 | -7.074 | 25.973 | 1.00 | 0.02 |
| ATOM | 3024 | N | SER | A | 333 | 18.492 | -9.175 | 26.538 | 1.00 | 0.02 |
| ATOM | 3026 | CA | SER | A | 333 | 19.650 | -9.212 | 25.635 | 1.00 | 0.02 |
| ATOM | 3027 | CB | SER | A | 333 | 20.804 | -9.957 | 26.298 | 1.00 | 0.36 |
| ATOM | 3028 | OG | SER | A | 333 | 20.418 | -11.313 | 26.472 | 1.00 | 1.04 |
| ATOM | 3029 | C | SER | A | 333 | 19.281 | -9.904 | 24.325 | 1.00 | 0.02 |
| ATOM | 3030 | O | SER | A | 333 | 18.520 | -10.878 | 24.311 | 1.00 | 0.01 |

| ATOM | 3031 | N | TYR | A | 334 | 19.810 | -9.379 | 23.234 | 1.00 | 0.00 |
|------|------|-----|-----|---|-----|--------|---------|--------|------|------|
| ATOM | 3033 | CA | TYR | A | 334 | 19.513 | -9.914 | 21.898 | 1.00 | 0.01 |
| ATOM | 3034 | CB | TYR | A | 334 | 18.510 | -9.005 | 21.194 | 1.00 | 0.01 |
| ATOM | 3035 | CG | TYR | A | 334 | 17.169 | -8.855 | 21.903 | 1.00 | 0.01 |
| ATOM | 3036 | CD1 | TYR | A | 334 | 16.270 | -9.915 | 21.930 | 1.00 | 0.01 |
| ATOM | 3037 | CE1 | TYR | A | 334 | 15.052 | -9.775 | 22.583 | 1.00 | 0.01 |
| ATOM | 3038 | CZ | TYR | A | 334 | 14.740 | -8.574 | 23.205 | 1.00 | 0.00 |
| ATOM | 3039 | OH | TYR | A | 334 | 13.541 | -8.429 | 23.867 | 1.00 | 0.01 |
| ATOM | 3040 | CE2 | TYR | A | 334 | 15.636 | -7.516 | 23.178 | 1.00 | 0.01 |
| ATOM | 3041 | CD2 | TYR | A | 334 | 16.851 | -7.657 | 22.527 | 1.00 | 0.01 |
| ATOM | 3042 | C | TYR | A | 334 | 20.767 | -10.002 | 21.036 | 1.00 | 0.01 |
| ATOM | 3043 | O | TYR | A | 334 | 21.439 | -8.995 | 20.779 | 1.00 | 0.01 |
| ATOM | 3044 | N | ASN | A | 335 | 21.063 | -11.202 | 20.573 | 1.00 | 0.01 |
| ATOM | 3046 | CA | ASN | A | 335 | 22.186 | -11.373 | 19.652 | 1.00 | 0.01 |
| ATOM | 3047 | CB | ASN | A | 335 | 22.629 | -12.831 | 19.652 | 1.00 | 0.26 |
| ATOM | 3048 | CG | ASN | A | 335 | 23.835 | -13.005 | 18.736 | 1.00 | 0.35 |
| ATOM | 3049 | OD1 | ASN | A | 335 | 23.683 | -13.139 | 17.515 | 1.00 | 0.52 |
| ATOM | 3050 | ND2 | ASN | A | 335 | 25.016 | -12.899 | 19.318 | 1.00 | 0.87 |
| ATOM | 3053 | C | ASN | A | 335 | 21.755 | -10.940 | 18.254 | 1.00 | 0.01 |
| ATOM | 3054 | O | ASN | A | 335 | 21.077 | -11.684 | 17.532 | 1.00 | 0.01 |
| ATOM | 3055 | N | LEU | A | 336 | 22.375 | -9.868 | 17.792 | 1.00 | 0.01 |
| ATOM | 3057 | CA | LEU | A | 336 | 21.956 | -9.223 | 16.544 | 1.00 | 0.01 |
| ATOM | 3058 | CB | LEU | A | 336 | 22.514 | -7.805 | 16.520 | 1.00 | 0.01 |
| ATOM | 3059 | CG | LEU | A | 336 | 21.987 | -6.958 | 17.671 | 1.00 | 0.01 |
| ATOM | 3060 | CD1 | LEU | A | 336 | 22.678 | -5.599 | 17.697 | 1.00 | 0.01 |
| ATOM | 3061 | CD2 | LEU | A | 336 | 20.472 | -6.796 | 17.582 | 1.00 | 0.01 |
| ATOM | 3062 | C | LEU | A | 336 | 22.463 | -9.964 | 15.317 | 1.00 | 0.01 |
| ATOM | 3063 | O | LEU | A | 336 | 21.785 | -9.955 | 14.284 | 1.00 | 0.01 |
| ATOM | 3064 | N | GLU | A | 337 | 23.419 | -10.849 | 15.532 | 1.00 | 0.01 |
| ATOM | 3066 | CA | GLU | A | 337 | 24.019 | -11.609 | 14.439 | 1.00 | 0.01 |
| ATOM | 3067 | CB | GLU | A | 337 | 25.387 | -12.045 | 14.937 | 1.00 | 0.13 |
| ATOM | 3068 | CG | GLU | A | 337 | 26.202 | -12.823 | 13.918 | 1.00 | 1.05 |
| ATOM | 3069 | CD | GLU | A | 337 | 27.589 | -12.964 | 14.512 | 1.00 | 0.89 |
| ATOM | 3070 | OE1 | GLU | A | 337 | 28.180 | -14.022 | 14.372 | 1.00 | 1.40 |
| ATOM | 3071 | OE2 | GLU | A | 337 | 27.896 | -12.098 | 15.329 | 1.00 | 0.86 |
| ATOM | 3072 | C | GLU | A | 337 | 23.167 | -12.815 | 14.048 | 1.00 | 0.01 |
| ATOM | 3073 | O | GLU | A | 337 | 23.318 | -13.346 | 12.942 | 1.00 | 0.01 |
| ATOM | 3074 | N | THR | A | 338 | 22.229 | -13.179 | 14.906 | 1.00 | 0.01 |
| ATOM | 3076 | CA | THR | A | 338 | 21.265 | - | 14.568 | 1.00 | 0.01 |

| | | | | | | 14.229 | | | |
|------|------|-----|-----|---|-----|--------|---------|------|------|
| ATOM | 3077 | CB  | THR | A | 338 | 21.139 | -15.195 | 15.741 | 1.00 | 0.22 |
| ATOM | 3078 | OG1 | THR | A | 338 | 20.704 | -14.465 | 16.881 | 1.00 | 0.83 |
| ATOM | 3079 | CG2 | THR | A | 338 | 22.473 | -15.854 | 16.073 | 1.00 | 0.78 |
| ATOM | 3080 | C   | THR | A | 338 | 19.892 | -13.646 | 14.238 | 1.00 | 0.01 |
| ATOM | 3081 | O   | THR | A | 338 | 19.056 | -14.333 | 13.639 | 1.00 | 0.01 |
| ATOM | 3082 | N   | ILE | A | 339 | 19.695 | -12.372 | 14.539 | 1.00 | 0.01 |
| ATOM | 3084 | CA  | ILE | A | 339 | 18.391 | -11.748 | 14.284 | 1.00 | 0.01 |
| ATOM | 3085 | CB  | ILE | A | 339 | 18.102 | -10.748 | 15.398 | 1.00 | 0.19 |
| ATOM | 3086 | CG2 | ILE | A | 339 | 16.796 | -10.018 | 15.118 | 1.00 | 0.33 |
| ATOM | 3087 | CG1 | ILE | A | 339 | 18.042 | -11.425 | 16.765 | 1.00 | 0.43 |
| ATOM | 3088 | CD1 | ILE | A | 339 | 16.880 | -12.407 | 16.865 | 1.00 | 0.67 |
| ATOM | 3089 | C   | ILE | A | 339 | 18.363 | -11.030 | 12.938 | 1.00 | 0.01 |
| ATOM | 3090 | O   | ILE | A | 339 | 17.499 | -11.303 | 12.093 | 1.00 | 0.01 |
| ATOM | 3091 | N   | LEU | A | 340 | 19.419 | -10.289 | 12.665 | 1.00 | 0.01 |
| ATOM | 3093 | CA  | LEU | A | 340 | 19.487 | -9.512  | 11.426 | 1.00 | 0.01 |
| ATOM | 3094 | CB  | LEU | A | 340 | 20.616 | -8.504  | 11.556 | 1.00 | 0.01 |
| ATOM | 3095 | CG  | LEU | A | 340 | 20.352 | -7.548  | 12.713 | 1.00 | 0.01 |
| ATOM | 3096 | CD1 | LEU | A | 340 | 21.572 | -6.681  | 12.990 | 1.00 | 0.01 |
| ATOM | 3097 | CD2 | LEU | A | 340 | 19.114 | -6.693  | 12.457 | 1.00 | 0.01 |
| ATOM | 3098 | C   | LEU | A | 340 | 19.624 | -10.296 | 10.102 | 1.00 | 0.01 |
| ATOM | 3099 | O   | LEU | A | 340 | 19.003 | -9.791  | 9.156  | 1.00 | 0.01 |
| ATOM | 3100 | N   | PRO | A | 341 | 20.199 | -11.500 | 9.987  | 1.00 | 0.01 |
| ATOM | 3101 | CA  | PRO | A | 341 | 20.074 | -12.210 | 8.702  | 1.00 | 0.01 |
| ATOM | 3102 | CB  | PRO | A | 341 | 20.942 | -13.425 | 8.813  | 1.00 | 0.39 |
| ATOM | 3103 | CG  | PRO | A | 341 | 21.497 | -13.522 | 10.219 | 1.00 | 0.63 |
| ATOM | 3104 | CD  | PRO | A | 341 | 20.982 | -12.297 | 10.948 | 1.00 | 0.66 |
| ATOM | 3105 | C   | PRO | A | 341 | 18.642 | -12.616 | 8.337  | 1.00 | 0.01 |
| ATOM | 3106 | O   | PRO | A | 341 | 18.306 | -12.529 | 7.150  | 1.00 | 0.01 |
| ATOM | 3107 | N   | LYS | A | 342 | 17.752 | -12.711 | 9.318  | 1.00 | 0.01 |
| ATOM | 3109 | CA  | LYS | A | 342 | 16.348 | -13.035 | 9.039  | 1.00 | 0.01 |
| ATOM | 3110 | CB  | LYS | A | 342 | 15.712 | -13.544 | 10.325 | 1.00 | 0.97 |
| ATOM | 3111 | CG  | LYS | A | 342 | 16.524 | -14.662 | 10.964 | 1.00 | 1.75 |

| ATOM | 3112 | CD | LYS | A | 342 | 15.847 | -15.142 | 12.241 | 1.00 | 2.93 |
|------|------|------|-----|---|-----|--------|---------|--------|------|------|
| ATOM | 3113 | CE | LYS | A | 342 | 15.599 | -13.977 | 13.193 | 1.00 | 3.48 |
| ATOM | 3114 | NZ | LYS | A | 342 | 14.897 | -14.426 | 14.405 | 1.00 | 3.77 |
| ATOM | 3115 | C | LYS | A | 342 | 15.574 | -11.796 | 8.584 | 1.00 | 0.01 |
| ATOM | 3116 | O | LYS | A | 342 | 14.480 | -11.904 | 8.018 | 1.00 | 0.01 |
| ATOM | 3117 | N | MET | A | 343 | 16.172 | -10.634 | 8.797 | 1.00 | 0.01 |
| ATOM | 3119 | CA | MET | A | 343 | 15.594 | -9.369 | 8.350 | 1.00 | 0.01 |
| ATOM | 3120 | CB | MET | A | 343 | 15.740 | -8.343 | 9.469 | 1.00 | 1.42 |
| ATOM | 3121 | CG | MET | A | 343 | 15.088 | -8.823 | 10.762 | 1.00 | 2.03 |
| ATOM | 3122 | SD | MET | A | 343 | 13.348 | -9.309 | 10.639 | 1.00 | 1.82 |
| ATOM | 3123 | CE | MET | A | 343 | 12.684 | -7.810 | 9.878 | 1.00 | 2.49 |
| ATOM | 3124 | C | MET | A | 343 | 16.269 | -8.851 | 7.079 | 1.00 | 0.01 |
| ATOM | 3125 | O | MET | A | 343 | 15.957 | -7.746 | 6.620 | 1.00 | 0.00 |
| ATOM | 3126 | N | GLY | A | 344 | 17.237 | -9.591 | 6.563 | 1.00 | 0.01 |
| ATOM | 3128 | CA | GLY | A | 344 | 17.883 | -9.196 | 5.306 | 1.00 | 0.01 |
| ATOM | 3129 | C | GLY | A | 344 | 19.370 | -8.887 | 5.460 | 1.00 | 0.01 |
| ATOM | 3130 | O | GLY | A | 344 | 20.141 | -9.041 | 4.504 | 1.00 | 0.01 |
| ATOM | 3131 | N | ILE | A | 345 | 19.760 | -8.444 | 6.644 | 1.00 | 0.01 |
| ATOM | 3133 | CA | ILE | A | 345 | 21.156 | -8.078 | 6.921 | 1.00 | 0.01 |
| ATOM | 3134 | CB | ILE | A | 345 | 21.159 | -7.123 | 8.109 | 1.00 | 0.01 |
| ATOM | 3135 | CG2 | ILE | A | 345 | 22.529 | -6.475 | 8.275 | 1.00 | 0.00 |
| ATOM | 3136 | CG1 | ILE | A | 345 | 20.086 | -6.054 | 7.943 | 1.00 | 0.01 |
| ATOM | 3137 | CD1 | ILE | A | 345 | 20.083 | -5.075 | 9.111 | 1.00 | 0.00 |
| ATOM | 3138 | C | ILE | A | 345 | 21.976 | -9.320 | 7.271 | 1.00 | 0.00 |
| ATOM | 3139 | O | ILE | A | 345 | 22.186 | -9.637 | 8.447 | 1.00 | 0.01 |
| ATOM | 3140 | N | GLN | A | 346 | 22.471 | -9.992 | 6.247 | 1.00 | 0.00 |
| ATOM | 3142 | CA | GLN | A | 346 | 23.161 | -11.269 | 6.443 | 1.00 | 0.01 |
| ATOM | 3143 | CB | GLN | A | 346 | 22.500 | -12.262 | 5.500 | 1.00 | 1.21 |
| ATOM | 3144 | CG | GLN | A | 346 | 23.176 | -13.625 | 5.548 | 1.00 | 1.87 |
| ATOM | 3145 | CD | GLN | A | 346 | 22.735 | -14.438 | 4.339 | 1.00 | 2.20 |
| ATOM | 3146 | OE1 | GLN | A | 346 | 21.841 | -15.289 | 4.431 | 1.00 | 2.70 |
| ATOM | 3147 | NE2 | GLN | A | 346 | 23.345 | -14.135 | 3.205 | 1.00 | 2.46 |
| ATOM | 3150 | C | GLN | A | 346 | 24.640 | -11.201 | 6.090 | 1.00 | 0.00 |
| ATOM | 3151 | O | GLN | A | 346 | 25.502 | -11.688 | 6.842 | 1.00 | 0.01 |
| ATOM | 3152 | N | ASN | A | 347 | 24.938 | -10.392 | 5.088 | 1.00 | 0.01 |
| ATOM | 3154 | CA | ASN | A | 347 | 26.273 | -10.397 | 4.483 | 1.00 | 0.00 |
| ATOM | 3155 | CB | ASN | A | 347 | 26.212 | -9.732 | 3.113 | 1.00 | 0.63 |
| ATOM | 3156 | CG | ASN | A | 347 | 25.547 | -10.625 | 2.064 | 1.00 | 1.00 |
| ATOM | 3157 | OD1 | ASN | A | 347 | 24.760 | -11.536 | 2.362 | 1.00 | 1.77 |
| ATOM | 3158 | ND2 | ASN | A | 347 | 25.894 | - | 0.820 | 1.00 | 1.70 |

| | | | | | | 10.349 | | | |
|---|---|---|---|---|---|---|---|---|---|
| ATOM | 3161 | C | ASN | A | 347 | 27.327 | -9.696 | 5.322 | 1.00 | 0.01 |
| ATOM | 3162 | O | ASN | A | 347 | 28.491 | -10.091 | 5.227 | 1.00 | 0.01 |
| ATOM | 3163 | N | ALA | A | 348 | 26.896 | -8.925 | 6.309 | 1.00 | 0.01 |
| ATOM | 3165 | CA | ALA | A | 348 | 27.825 | -8.229 | 7.205 | 1.00 | 0.01 |
| ATOM | 3166 | CB | ALA | A | 348 | 27.092 | -7.043 | 7.822 | 1.00 | 0.19 |
| ATOM | 3167 | C | ALA | A | 348 | 28.345 | -9.130 | 8.324 | 1.00 | 0.01 |
| ATOM | 3168 | O | ALA | A | 348 | 29.375 | -8.827 | 8.939 | 1.00 | 0.00 |
| ATOM | 3169 | N | PHE | A | 349 | 27.681 | -10.253 | 8.543 | 1.00 | 0.01 |
| ATOM | 3171 | CA | PHE | A | 349 | 28.155 | -11.202 | 9.548 | 1.00 | 0.02 |
| ATOM | 3172 | CB | PHE | A | 349 | 26.947 | -11.846 | 10.218 | 1.00 | 0.01 |
| ATOM | 3173 | CG | PHE | A | 349 | 25.980 | -10.840 | 10.834 | 1.00 | 0.02 |
| ATOM | 3174 | CD1 | PHE | A | 349 | 26.446 | -9.880 | 11.723 | 1.00 | 0.01 |
| ATOM | 3175 | CE1 | PHE | A | 349 | 25.569 | -8.957 | 12.275 | 1.00 | 0.01 |
| ATOM | 3176 | CZ | PHE | A | 349 | 24.223 | -8.998 | 11.944 | 1.00 | 0.00 |
| ATOM | 3177 | CE2 | PHE | A | 349 | 23.755 | -9.966 | 11.065 | 1.00 | 0.01 |
| ATOM | 3178 | CD2 | PHE | A | 349 | 24.631 | -10.888 | 10.511 | 1.00 | 0.00 |
| ATOM | 3179 | C | PHE | A | 349 | 28.996 | -12.263 | 8.859 | 1.00 | 0.00 |
| ATOM | 3180 | O | PHE | A | 349 | 29.996 | -12.742 | 9.402 | 1.00 | 0.02 |
| ATOM | 3181 | N | ASP | A | 350 | 28.658 | -12.488 | 7.599 | 1.00 | 0.01 |
| ATOM | 3183 | CA | ASP | A | 350 | 29.393 | -13.425 | 6.745 | 1.00 | 0.00 |
| ATOM | 3184 | CB | ASP | A | 350 | 28.670 | -13.529 | 5.406 | 1.00 | 1.52 |
| ATOM | 3185 | CG | ASP | A | 350 | 27.237 | -14.027 | 5.533 | 1.00 | 2.27 |
| ATOM | 3186 | OD1 | ASP | A | 350 | 26.987 | -14.857 | 6.399 | 1.00 | 2.78 |
| ATOM | 3187 | OD2 | ASP | A | 350 | 26.428 | -13.632 | 4.696 | 1.00 | 2.74 |
| ATOM | 3188 | C | ASP | A | 350 | 30.820 | -12.944 | 6.481 | 1.00 | 0.01 |
| ATOM | 3189 | O | ASP | A | 350 | 31.122 | -11.751 | 6.581 | 1.00 | 0.02 |
| ATOM | 3190 | N | LYS | A | 351 | 31.646 | -13.860 | 5.996 | 1.00 | 0.02 |
| ATOM | 3192 | CA | LYS | A | 351 | 33.055 | -13.558 | 5.674 | 1.00 | 0.01 |
| ATOM | 3193 | CB | LYS | A | 351 | 33.795 | -14.881 | 5.543 | 1.00 | 0.65 |
| ATOM | 3194 | CG | LYS | A | 351 | 33.604 | -15.760 | 6.772 | 1.00 | 1.13 |
| ATOM | 3195 | CD | LYS | A | 351 | 34.251 | -17.123 | 6.564 | 1.00 | 1.37 |
| ATOM | 3196 | CE | LYS | A | 351 | 33.628 | -17.836 | 5.368 | 1.00 | 2.60 |
| ATOM | 3197 | NZ | LYS | A | 351 | 34.266 | -19.142 | 5.136 | 1.00 | 3.15 |
| ATOM | 3198 | C | LYS | A | 351 | 33.213 | -12.806 | 4.350 | 1.00 | 0.02 |

| ATOM | 3199 | O | LYS | A | 351 | 34.297 | -12.309 | 4.023 | 1.00 | 0.01 |
|------|------|------|------|---|-----|--------|---------|-------|------|------|
| ATOM | 3200 | N | ASN | A | 352 | 32.114 | -12.692 | 3.627 | 1.00 | 0.02 |
| ATOM | 3202 | CA | ASN | A | 352 | 32.049 | -11.964 | 2.361 | 1.00 | 0.00 |
| ATOM | 3203 | CB | ASN | A | 352 | 31.173 | -12.759 | 1.390 | 1.00 | 0.51 |
| ATOM | 3204 | CG | ASN | A | 352 | 29.869 | -13.231 | 2.040 | 1.00 | 1.28 |
| ATOM | 3205 | OD1 | ASN | A | 352 | 29.796 | -14.333 | 2.595 | 1.00 | 1.84 |
| ATOM | 3206 | ND2 | ASN | A | 352 | 28.858 | -12.381 | 1.990 | 1.00 | 2.06 |
| ATOM | 3209 | C | ASN | A | 352 | 31.522 | -10.537 | 2.541 | 1.00 | 0.00 |
| ATOM | 3210 | O | ASN | A | 352 | 30.997 | -9.951 | 1.581 | 1.00 | 0.01 |
| ATOM | 3211 | N | ALA | A | 353 | 31.494 | -10.066 | 3.777 | 1.00 | 0.01 |
| ATOM | 3213 | CA | ALA | A | 353 | 31.074 | -8.692 | 4.047 | 1.00 | 0.01 |
| ATOM | 3214 | CB | ALA | A | 353 | 31.097 | -8.473 | 5.551 | 1.00 | 0.01 |
| ATOM | 3215 | C | ALA | A | 353 | 31.997 | -7.683 | 3.379 | 1.00 | 0.01 |
| ATOM | 3216 | O | ALA | A | 353 | 33.229 | -7.781 | 3.429 | 1.00 | 0.02 |
| ATOM | 3217 | N | ASP | A | 354 | 31.385 | -6.708 | 2.728 | 1.00 | 0.01 |
| ATOM | 3219 | CA | ASP | A | 354 | 32.164 | -5.651 | 2.088 | 1.00 | 0.01 |
| ATOM | 3220 | CB | ASP | A | 354 | 31.396 | -5.129 | 0.870 | 1.00 | 0.01 |
| ATOM | 3221 | CG | ASP | A | 354 | 32.212 | -4.138 | 0.030 | 1.00 | 0.00 |
| ATOM | 3222 | OD1 | ASP | A | 354 | 32.848 | -3.267 | 0.615 | 1.00 | 0.01 |
| ATOM | 3223 | OD2 | ASP | A | 354 | 32.008 | -4.141 | -1.174 | 1.00 | 0.00 |
| ATOM | 3224 | C | ASP | A | 354 | 32.385 | -4.542 | 3.103 | 1.00 | 0.00 |
| ATOM | 3225 | O | ASP | A | 354 | 31.565 | -3.630 | 3.230 | 1.00 | 0.01 |
| ATOM | 3226 | N | PHE | A | 355 | 33.507 | -4.604 | 3.793 | 1.00 | 0.02 |
| ATOM | 3228 | CA | PHE | A | 355 | 33.843 | -3.552 | 4.751 | 1.00 | 0.02 |
| ATOM | 3229 | CB | PHE | A | 355 | 34.107 | -4.179 | 6.113 | 1.00 | 1.78 |
| ATOM | 3230 | CG | PHE | A | 355 | 32.846 | -4.653 | 6.834 | 1.00 | 2.43 |
| ATOM | 3231 | CD1 | PHE | A | 355 | 32.859 | -5.839 | 7.555 | 1.00 | 3.08 |
| ATOM | 3232 | CE1 | PHE | A | 355 | 31.718 | -6.265 | 8.221 | 1.00 | 3.90 |
| ATOM | 3233 | CZ | PHE | A | 355 | 30.559 | -5.504 | 8.164 | 1.00 | 4.07 |
| ATOM | 3234 | CE2 | PHE | A | 355 | 30.542 | -4.318 | 7.443 | 1.00 | 3.51 |
| ATOM | 3235 | CD2 | PHE | A | 355 | 31.686 | -3.893 | 6.779 | 1.00 | 2.73 |
| ATOM | 3236 | C | PHE | A | 355 | 35.046 | -2.749 | 4.275 | 1.00 | 0.02 |
| ATOM | 3237 | O | PHE | A | 355 | 35.975 | -2.488 | 5.052 | 1.00 | 0.02 |
| ATOM | 3238 | N | SER | A | 356 | 34.885 | -2.144 | 3.107 | 1.00 | 0.02 |
| ATOM | 3240 | CA | SER | A | 356 | 35.978 | -1.419 | 2.434 | 1.00 | 0.00 |
| ATOM | 3241 | CB | SER | A | 356 | 35.684 | -1.364 | 0.940 | 1.00 | 0.01 |
| ATOM | 3242 | OG | SER | A | 356 | 34.507 | -0.591 | 0.750 | 1.00 | 0.01 |
| ATOM | 3243 | C | SER | A | 356 | 36.196 | 0.009 | 2.949 | 1.00 | 0.02 |
| ATOM | 3244 | O | SER | A | 356 | 37.063 | 0.728 | 2.438 | 1.00 | 0.01 |
| ATOM | 3245 | N | GLY | A | 357 | 35.391 | 0.425 | 3.912 | 1.00 | 0.00 |
| ATOM | 3247 | CA | GLY | A | 357 | 35.604 | 1.702 | 4.590 | 1.00 | 0.01 |
| ATOM | 3248 | C | GLY | A | 357 | 36.279 | 1.465 | 5.937 | 1.00 | 0.02 |
| ATOM | 3249 | O | GLY | A | 357 | 36.934 | 2.363 | 6.484 | 1.00 | 0.02 |
| ATOM | 3250 | N | ILE | A | 358 | 36.160 | 0.241 | 6.429 | 1.00 | 0.00 |
| ATOM | 3252 | CA | ILE | A | 358 | 36.753 | -0.120 | 7.716 | 1.00 | 0.01 |
| ATOM | 3253 | CB | ILE | A | 358 | 35.915 | -1.222 | 8.354 | 1.00 | 1.15 |
| ATOM | 3254 | CG2 | ILE | A | 358 | 36.415 | -1.521 | 9.764 | 1.00 | 1.49 |
| ATOM | 3255 | CG1 | ILE | A | 358 | 34.440 | -0.854 | 8.382 | 1.00 | 1.60 |
| ATOM | 3256 | CD1 | ILE | A | 358 | 33.617 | -1.909 | 9.109 | 1.00 | 2.08 |

| ATOM | 3257 | C | ILE | A | 358 | 38.158 | -0.666 | 7.519 | 1.00 | 0.02 |
|------|------|------|-----|---|-----|--------|--------|-------|------|------|
| ATOM | 3258 | O | ILE | A | 358 | 39.102 | -0.216 | 8.178 | 1.00 | 0.02 |
| ATOM | 3259 | N | ALA | A | 359 | 38.280 | -1.586 | 6.576 | 1.00 | 0.02 |
| ATOM | 3261 | CA | ALA | A | 359 | 39.550 | -2.261 | 6.296 | 1.00 | 0.00 |
| ATOM | 3262 | CB | ALA | A | 359 | 39.821 | -3.283 | 7.395 | 1.00 | 0.83 |
| ATOM | 3263 | C | ALA | A | 359 | 39.467 | -2.976 | 4.953 | 1.00 | 0.02 |
| ATOM | 3264 | O | ALA | A | 359 | 39.356 | -4.210 | 4.917 | 1.00 | 0.01 |
| ATOM | 3265 | N | LYS | A | 360 | 39.799 | -2.242 | 3.903 | 1.00 | 0.00 |
| ATOM | 3267 | CA | LYS | A | 360 | 39.608 | -2.681 | 2.507 | 1.00 | 0.00 |
| ATOM | 3268 | CB | LYS | A | 360 | 39.945 | -1.487 | 1.618 | 1.00 | 1.13 |
| ATOM | 3269 | CG | LYS | A | 360 | 41.351 | -0.963 | 1.906 | 1.00 | 1.56 |
| ATOM | 3270 | CD | LYS | A | 360 | 41.759 | 0.129 | 0.926 | 1.00 | 2.17 |
| ATOM | 3271 | CE | LYS | A | 360 | 40.773 | 1.289 | 0.948 | 1.00 | 3.04 |
| ATOM | 3272 | NZ | LYS | A | 360 | 41.170 | 2.337 | -0.004 | 1.00 | 3.66 |
| ATOM | 3273 | C | LYS | A | 360 | 40.437 | -3.877 | 2.012 | 1.00 | 0.02 |
| ATOM | 3274 | O | LYS | A | 360 | 40.140 | -4.394 | 0.930 | 1.00 | 0.02 |
| ATOM | 3275 | N | ARG | A | 361 | 41.421 | -4.340 | 2.765 | 1.00 | 0.02 |
| ATOM | 3277 | CA | ARG | A | 361 | 42.187 | -5.507 | 2.324 | 1.00 | 0.00 |
| ATOM | 3278 | CB | ARG | A | 361 | 43.662 | -5.131 | 2.299 | 1.00 | 1.38 |
| ATOM | 3279 | CG | ARG | A | 361 | 44.165 | -4.694 | 3.668 | 1.00 | 1.86 |
| ATOM | 3280 | CD | ARG | A | 361 | 45.493 | -3.965 | 3.534 | 1.00 | 2.43 |
| ATOM | 3281 | NE | ARG | A | 361 | 45.300 | -2.722 | 2.770 | 1.00 | 3.31 |
| ATOM | 3282 | CZ | ARG | A | 361 | 46.256 | -1.808 | 2.594 | 1.00 | 4.21 |
| ATOM | 3283 | NH1 | ARG | A | 361 | 45.992 | -0.690 | 1.914 | 1.00 | 5.21 |
| ATOM | 3284 | NH2 | ARG | A | 361 | 47.469 | -2.001 | 3.118 | 1.00 | 4.31 |
| ATOM | 3285 | C | ARG | A | 361 | 41.939 | -6.728 | 3.211 | 1.00 | 0.02 |
| ATOM | 3286 | O | ARG | A | 361 | 42.483 | -7.809 | 2.956 | 1.00 | 0.00 |
| ATOM | 3287 | N | ASP | A | 362 | 41.107 | -6.562 | 4.227 | 1.00 | 0.02 |
| ATOM | 3289 | CA | ASP | A | 362 | 40.847 | -7.655 | 5.171 | 1.00 | 0.01 |
| ATOM | 3290 | CB | ASP | A | 362 | 41.005 | -7.113 | 6.592 | 1.00 | 0.80 |
| ATOM | 3291 | CG | ASP | A | 362 | 42.408 | -6.547 | 6.824 | 1.00 | 0.66 |
| ATOM | 3292 | OD1 | ASP | A | 362 | 43.357 | -7.142 | 6.338 | 1.00 | 0.78 |
| ATOM | 3293 | OD2 | ASP | A | 362 | 42.506 | -5.501 | 7.457 | 1.00 | 1.43 |
| ATOM | 3294 | C | ASP | A | 362 | 39.432 | -8.207 | 4.989 | 1.00 | 0.02 |
| ATOM | 3295 | O | ASP | A | 362 | 38.485 | -7.445 | 4.769 | 1.00 | 0.02 |
| ATOM | 3296 | N | SER | A | 363 | 39.293 | -9.522 | 5.072 | 1.00 | 0.01 |
| ATOM | 3298 | CA | SER | A | 363 | 37.955 | -10.144 | 5.029 | 1.00 | 0.02 |
| ATOM | 3299 | CB | SER | A | 363 | 38.077 | -11.595 | 4.580 | 1.00 | 0.34 |
| ATOM | 3300 | OG | SER | A | 363 | 38.580 | -11.595 | 3.250 | 1.00 | 0.54 |
| ATOM | 3301 | C | SER | A | 363 | 37.296 | -10.070 | 6.407 | 1.00 | 0.02 |
| ATOM | 3302 | O | SER | A | 363 | 37.486 | -10.940 | 7.268 | 1.00 | 0.00 |
| ATOM | 3303 | N | LEU | A | 364 | 36.566 | -8.987 | 6.610 | 1.00 | 0.01 |
| ATOM | 3305 | CA | LEU | A | 364 | 36.018 | -8.664 | 7.926 | 1.00 | 0.01 |
| ATOM | 3306 | CB | LEU | A | 364 | 36.083 | -7.147 | 8.066 | 1.00 | 0.00 |
| ATOM | 3307 | CG | LEU | A | 364 | 35.857 | -6.672 | 9.495 | 1.00 | 0.02 |
| ATOM | 3308 | CD1 | LEU | A | 364 | 36.971 | -7.164 | 10.406 | 1.00 | 0.01 |
| ATOM | 3309 | CD2 | LEU | A | 364 | 35.790 | -5.153 | 9.540 | 1.00 | 0.01 |
| ATOM | 3310 | C | LEU | A | 364 | 34.586 | -9.173 | 8.085 | 1.00 | 0.00 |
| ATOM | 3311 | O | LEU | A | 364 | 33.715 | -8.941 | 7.243 | 1.00 | 0.00 |
| ATOM | 3312 | N | GLN | A | 365 | 34.374 | -9.874 | 9.186 | 1.00 | 0.01 |
| ATOM | 3314 | CA | GLN | A | 365 | 33.063 | -10.445 | 9.512 | 1.00 | 0.02 |
| ATOM | 3315 | CB | GLN | A | 365 | 33.195 | - | 9.376 | 1.00 | 0.93 |

| | | | | | | 11.960 | | | |
|---|---|---|---|---|---|---|---|---|---|
| ATOM | 3316 | CG | GLN | A | 365 | 34.513 | -12.447 | 9.973 | 1.00 | 0.96 |
| ATOM | 3317 | CD | GLN | A | 365 | 34.684 | -13.954 | 9.795 | 1.00 | 1.26 |
| ATOM | 3318 | OE1 | GLN | A | 365 | 33.725 | -14.728 | 9.900 | 1.00 | 1.74 |
| ATOM | 3319 | NE2 | GLN | A | 365 | 35.906 | -14.343 | 9.476 | 1.00 | 1.77 |
| ATOM | 3322 | C | GLN | A | 365 | 32.612 | -10.062 | 10.924 | 1.00 | 0.01 |
| ATOM | 3323 | O | GLN | A | 365 | 33.414 | -10.108 | 11.873 | 1.00 | 0.02 |
| ATOM | 3324 | N | VAL | A | 366 | 31.372 | -9.605 | 11.042 | 1.00 | 0.02 |
| ATOM | 3326 | CA | VAL | A | 366 | 30.808 | -9.330 | 12.373 | 1.00 | 0.02 |
| ATOM | 3327 | CB | VAL | A | 366 | 29.611 | -8.391 | 12.278 | 1.00 | 0.05 |
| ATOM | 3328 | CG1 | VAL | A | 366 | 29.051 | -8.088 | 13.665 | 1.00 | 0.07 |
| ATOM | 3329 | CG2 | VAL | A | 366 | 29.998 | -7.092 | 11.582 | 1.00 | 0.09 |
| ATOM | 3330 | C | VAL | A | 366 | 30.427 | -10.653 | 13.030 | 1.00 | 0.01 |
| ATOM | 3331 | O | VAL | A | 366 | 29.388 | -11.264 | 12.747 | 1.00 | 0.01 |
| ATOM | 3332 | N | SER | A | 367 | 31.218 | -10.967 | 14.038 | 1.00 | 0.01 |
| ATOM | 3334 | CA | SER | A | 367 | 31.284 | -12.311 | 14.608 | 1.00 | 0.01 |
| ATOM | 3335 | CB | SER | A | 367 | 32.695 | -12.811 | 14.376 | 1.00 | 0.02 |
| ATOM | 3336 | OG | SER | A | 367 | 33.550 | -11.755 | 14.784 | 1.00 | 0.02 |
| ATOM | 3337 | C | SER | A | 367 | 30.928 | -12.353 | 16.091 | 1.00 | 0.00 |
| ATOM | 3338 | O | SER | A | 367 | 31.261 | -13.332 | 16.778 | 1.00 | 0.01 |
| ATOM | 3339 | N | LYS | A | 368 | 30.497 | -11.208 | 16.600 | 1.00 | 0.01 |
| ATOM | 3341 | CA | LYS | A | 368 | 29.771 | -11.178 | 17.877 | 1.00 | 0.01 |
| ATOM | 3342 | CB | LYS | A | 368 | 30.719 | -11.360 | 19.055 | 1.00 | 0.01 |
| ATOM | 3343 | CG | LYS | A | 368 | 29.919 | -11.731 | 20.299 | 1.00 | 0.01 |
| ATOM | 3344 | CD | LYS | A | 368 | 29.108 | -12.999 | 20.048 | 1.00 | 0.01 |
| ATOM | 3345 | CE | LYS | A | 368 | 28.171 | -13.322 | 21.206 | 1.00 | 0.01 |
| ATOM | 3346 | NZ | LYS | A | 368 | 28.916 | -13.569 | 22.447 | 1.00 | 0.02 |
| ATOM | 3347 | C | LYS | A | 368 | 28.985 | -9.875 | 18.041 | 1.00 | 0.02 |
| ATOM | 3348 | O | LYS | A | 368 | 29.441 | -8.950 | 18.725 | 1.00 | 0.01 |
| ATOM | 3349 | N | ALA | A | 369 | 27.850 | -9.782 | 17.369 | 1.00 | 0.01 |
| ATOM | 3351 | CA | ALA | A | 369 | 26.963 | -8.618 | 17.546 | 1.00 | 0.01 |
| ATOM | 3352 | CB | ALA | A | 369 | 26.238 | -8.345 | 16.235 | 1.00 | 0.01 |
| ATOM | 3353 | C | ALA | A | 369 | 25.949 | -8.864 | 18.664 | 1.00 | 0.01 |
| ATOM | 3354 | O | ALA | A | 369 | 25.158 | -9.812 | 18.592 | 1.00 | 0.02 |
| ATOM | 3355 | N | THR | A | 370 | 25.939 | -7.993 | 19.662 | 1.00 | 0.01 |
| ATOM | 3357 | CA | THR | A | 370 | 25.101 | -8.219 | 20.852 | 1.00 | 0.01 |
| ATOM | 3358 | CB | THR | A | 370 | 25.947 | -8.954 | 21.890 | 1.00 | 0.48 |

| ATOM | 3359 | OG1 | THR | A | 370 | 26.430 | -10.157 | 21.304 | 1.00 | 1.35 |
|---|---|---|---|---|---|---|---|---|---|---|
| ATOM | 3360 | CG2 | THR | A | 370 | 25.143 | -9.328 | 23.131 | 1.00 | 1.19 |
| ATOM | 3361 | C | THR | A | 370 | 24.538 | -6.927 | 21.465 | 1.00 | 0.01 |
| ATOM | 3362 | O | THR | A | 370 | 25.275 | -6.052 | 21.941 | 1.00 | 0.01 |
| ATOM | 3363 | N | HIS | A | 371 | 23.217 | -6.866 | 21.486 | 1.00 | 0.01 |
| ATOM | 3365 | CA | HIS | A | 371 | 22.455 | -5.767 | 22.092 | 1.00 | 0.01 |
| ATOM | 3366 | CB | HIS | A | 371 | 21.330 | -5.439 | 21.104 | 1.00 | 0.01 |
| ATOM | 3367 | CG | HIS | A | 371 | 20.200 | -4.573 | 21.621 | 1.00 | 0.01 |
| ATOM | 3368 | ND1 | HIS | A | 371 | 20.198 | -3.234 | 21.750 | 1.00 | 0.01 |
| ATOM | 3370 | CE1 | HIS | A | 371 | 19.017 | -2.838 | 22.261 | 1.00 | 0.01 |
| ATOM | 3371 | NE2 | HIS | A | 371 | 18.262 | -3.943 | 22.450 | 1.00 | 0.01 |
| ATOM | 3372 | CD2 | HIS | A | 371 | 18.976 | -5.020 | 22.056 | 1.00 | 0.01 |
| ATOM | 3373 | C | HIS | A | 371 | 21.887 | -6.179 | 23.457 | 1.00 | 0.01 |
| ATOM | 3374 | O | HIS | A | 371 | 21.726 | -7.377 | 23.718 | 1.00 | 0.01 |
| ATOM | 3375 | N | LYS | A | 372 | 21.692 | -5.220 | 24.351 | 1.00 | 0.01 |
| ATOM | 3377 | CA | LYS | A | 372 | 20.961 | -5.502 | 25.600 | 1.00 | 0.01 |
| ATOM | 3378 | CB | LYS | A | 372 | 21.890 | -6.097 | 26.651 | 1.00 | 0.01 |
| ATOM | 3379 | CG | LYS | A | 372 | 21.111 | -6.441 | 27.917 | 1.00 | 0.01 |
| ATOM | 3380 | CD | LYS | A | 372 | 22.006 | -6.977 | 29.023 | 1.00 | 0.01 |
| ATOM | 3381 | CE | LYS | A | 372 | 21.187 | -7.286 | 30.270 | 1.00 | 0.01 |
| ATOM | 3382 | NZ | LYS | A | 372 | 22.038 | -7.707 | 31.393 | 1.00 | 0.00 |
| ATOM | 3383 | C | LYS | A | 372 | 20.295 | -4.252 | 26.174 | 1.00 | 0.01 |
| ATOM | 3384 | O | LYS | A | 372 | 20.979 | -3.322 | 26.625 | 1.00 | 0.01 |
| ATOM | 3385 | N | ALA | A | 373 | 18.972 | -4.272 | 26.212 | 1.00 | 0.02 |
| ATOM | 3387 | CA | ALA | A | 373 | 18.209 | -3.152 | 26.778 | 1.00 | 0.01 |
| ATOM | 3388 | CB | ALA | A | 373 | 17.019 | -2.865 | 25.872 | 1.00 | 0.01 |
| ATOM | 3389 | C | ALA | A | 373 | 17.735 | -3.444 | 28.206 | 1.00 | 0.01 |
| ATOM | 3390 | O | ALA | A | 373 | 17.267 | -4.549 | 28.512 | 1.00 | 0.01 |
| ATOM | 3391 | N | VAL | A | 374 | 17.925 | -2.470 | 29.083 | 1.00 | 0.01 |
| ATOM | 3393 | CA | VAL | A | 374 | 17.524 | -2.612 | 30.496 | 1.00 | 0.01 |
| ATOM | 3394 | CB | VAL | A | 374 | 18.783 | -2.646 | 31.364 | 1.00 | 0.01 |
| ATOM | 3395 | CG1 | VAL | A | 374 | 18.454 | -3.123 | 32.775 | 1.00 | 0.01 |
| ATOM | 3396 | CG2 | VAL | A | 374 | 19.876 | -3.526 | 30.769 | 1.00 | 0.01 |
| ATOM | 3397 | C | VAL | A | 374 | 16.649 | -1.435 | 30.951 | 1.00 | 0.01 |
| ATOM | 3398 | O | VAL | A | 374 | 17.059 | -0.273 | 30.841 | 1.00 | 0.01 |
| ATOM | 3399 | N | LEU | A | 375 | 15.489 | -1.738 | 31.512 | 1.00 | 0.02 |
| ATOM | 3401 | CA | LEU | A | 375 | 14.565 | -0.695 | 31.983 | 1.00 | 0.01 |
| ATOM | 3402 | CB | LEU | A | 375 | 13.288 | -0.778 | 31.165 | 1.00 | 0.01 |
| ATOM | 3403 | CG | LEU | A | 375 | 12.297 | 0.324 | 31.521 | 1.00 | 0.01 |
| ATOM | 3404 | CD1 | LEU | A | 375 | 12.882 | 1.700 | 31.229 | 1.00 | 0.01 |
| ATOM | 3405 | CD2 | LEU | A | 375 | 10.991 | 0.130 | 30.767 | 1.00 | 0.00 |
| ATOM | 3406 | C | LEU | A | 375 | 14.170 | -0.871 | 33.443 | 1.00 | 0.01 |
| ATOM | 3407 | O | LEU | A | 375 | 13.437 | -1.802 | 33.796 | 1.00 | 0.02 |
| ATOM | 3408 | N | ASP | A | 376 | 14.540 | 0.096 | 34.262 | 1.00 | 0.02 |
| ATOM | 3410 | CA | ASP | A | 376 | 14.090 | 0.092 | 35.653 | 1.00 | 0.02 |
| ATOM | 3411 | CB | ASP | A | 376 | 15.157 | 0.722 | 36.539 | 1.00 | 0.48 |
| ATOM | 3412 | CG | ASP | A | 376 | 14.646 | 0.786 | 37.978 | 1.00 | 1.01 |
| ATOM | 3413 | OD1 | ASP | A | 376 | 14.721 | -0.232 | 38.650 | 1.00 | 1.53 |
| ATOM | 3414 | OD2 | ASP | A | 376 | 14.109 | 1.826 | 38.344 | 1.00 | 1.55 |
| ATOM | 3415 | C | ASP | A | 376 | 12.779 | 0.859 | 35.806 | 1.00 | 0.01 |
| ATOM | 3416 | O | ASP | A | 376 | 12.756 | 2.099 | 35.767 | 1.00 | 0.02 |
| ATOM | 3417 | N | VAL | A | 377 | 11.702 | 0.116 | 36.010 | 1.00 | 0.01 |
| ATOM | 3419 | CA | VAL | A | 377 | 10.405 | 0.746 | 36.276 | 1.00 | 0.01 |
| ATOM | 3420 | CB | VAL | A | 377 | 9.297 | -0.111 | 35.676 | 1.00 | 0.54 |
| ATOM | 3421 | CG1 | VAL | A | 377 | 7.930 | 0.537 | 35.872 | 1.00 | 0.52 |
| ATOM | 3422 | CG2 | VAL | A | 377 | 9.551 | -0.371 | 34.197 | 1.00 | 0.68 |
| ATOM | 3423 | C | VAL | A | 377 | 10.184 | 0.903 | 37.779 | 1.00 | 0.02 |

| ATOM | 3424 | O | VAL | A | 377 | 9.720 | -0.020 | 38.459 | 1.00 | 0.00 |
|------|------|------|-----|---|-----|-------|--------|--------|------|------|
| ATOM | 3425 | N | SER | A | 378 | 10.590 | 2.055 | 38.282 | 1.00 | 0.01 |
| ATOM | 3427 | CA | SER | A | 378 | 10.411 | 2.405 | 39.699 | 1.00 | 0.02 |
| ATOM | 3428 | CB | SER | A | 378 | 11.661 | 3.126 | 40.188 | 1.00 | 0.91 |
| ATOM | 3429 | OG | SER | A | 378 | 11.816 | 4.305 | 39.406 | 1.00 | 1.28 |
| ATOM | 3430 | C | SER | A | 378 | 9.200 | 3.317 | 39.861 | 1.00 | 0.00 |
| ATOM | 3431 | O | SER | A | 378 | 8.473 | 3.549 | 38.890 | 1.00 | 0.01 |
| ATOM | 3432 | N | GLU | A | 379 | 8.933 | 3.762 | 41.081 | 1.00 | 0.02 |
| ATOM | 3434 | CA | GLU | A | 379 | 7.850 | 4.742 | 41.287 | 1.00 | 0.02 |
| ATOM | 3435 | CB | GLU | A | 379 | 7.299 | 4.673 | 42.710 | 1.00 | 0.02 |
| ATOM | 3436 | CG | GLU | A | 379 | 6.699 | 3.326 | 43.083 | 1.00 | 0.02 |
| ATOM | 3437 | CD | GLU | A | 379 | 7.621 | 2.653 | 44.083 | 1.00 | 0.02 |
| ATOM | 3438 | OE1 | GLU | A | 379 | 8.796 | 3.005 | 44.070 | 1.00 | 0.02 |
| ATOM | 3439 | OE2 | GLU | A | 379 | 7.165 | 1.780 | 44.802 | 1.00 | 0.02 |
| ATOM | 3440 | C | GLU | A | 379 | 8.405 | 6.144 | 41.093 | 1.00 | 0.00 |
| ATOM | 3441 | O | GLU | A | 379 | 7.702 | 7.072 | 40.671 | 1.00 | 0.02 |
| ATOM | 3442 | N | GLU | A | 380 | 9.660 | 6.274 | 41.489 | 1.00 | 0.01 |
| ATOM | 3444 | CA | GLU | A | 380 | 10.451 | 7.489 | 41.291 | 1.00 | 0.00 |
| ATOM | 3445 | CB | GLU | A | 380 | 10.535 | 8.262 | 42.607 | 1.00 | 1.77 |
| ATOM | 3446 | CG | GLU | A | 380 | 9.195 | 8.834 | 43.055 | 1.00 | 2.64 |
| ATOM | 3447 | CD | GLU | A | 380 | 9.342 | 9.500 | 44.420 | 1.00 | 3.00 |
| ATOM | 3448 | OE1 | GLU | A | 380 | 9.953 | 8.886 | 45.286 | 1.00 | 3.53 |
| ATOM | 3449 | OE2 | GLU | A | 380 | 8.737 | 10.548 | 44.608 | 1.00 | 3.27 |
| ATOM | 3450 | C | GLU | A | 380 | 11.858 | 7.081 | 40.876 | 1.00 | 0.02 |
| ATOM | 3451 | O | GLU | A | 380 | 12.452 | 6.198 | 41.508 | 1.00 | 0.02 |
| ATOM | 3452 | N | GLY | A | 381 | 12.322 | 7.613 | 39.759 | 1.00 | 0.02 |
| ATOM | 3454 | CA | GLY | A | 381 | 13.704 | 7.367 | 39.336 | 1.00 | 0.02 |
| ATOM | 3455 | C | GLY | A | 381 | 14.645 | 8.022 | 40.337 | 1.00 | 0.01 |
| ATOM | 3456 | O | GLY | A | 381 | 15.354 | 7.349 | 41.094 | 1.00 | 0.02 |
| ATOM | 3457 | N | THR | A | 382 | 14.639 | 9.342 | 40.330 | 1.00 | 0.01 |
| ATOM | 3459 | CA | THR | A | 382 | 15.374 | 10.092 | 41.346 | 1.00 | 0.01 |
| ATOM | 3460 | CB | THR | A | 382 | 15.537 | 11.538 | 40.880 | 1.00 | 0.02 |
| ATOM | 3461 | OG1 | THR | A | 382 | 16.095 | 12.288 | 41.953 | 1.00 | 0.01 |
| ATOM | 3462 | CG2 | THR | A | 382 | 14.199 | 12.173 | 40.517 | 1.00 | 0.02 |
| ATOM | 3463 | C | THR | A | 382 | 14.621 | 10.051 | 42.671 | 1.00 | 0.00 |
| ATOM | 3464 | O | THR | A | 382 | 13.390 | 9.952 | 42.703 | 1.00 | 0.02 |
| ATOM | 3465 | N | GLU | A | 383 | 15.377 | 10.089 | 43.756 | 1.00 | 0.01 |
| ATOM | 3467 | CA | GLU | A | 383 | 14.787 | 10.186 | 45.091 | 1.00 | 0.01 |
| ATOM | 3468 | CB | GLU | A | 383 | 15.725 | 9.519 | 46.089 | 1.00 | 0.02 |
| ATOM | 3469 | CG | GLU | A | 383 | 15.867 | 8.028 | 45.806 | 1.00 | 0.00 |
| ATOM | 3470 | CD | GLU | A | 383 | 16.883 | 7.415 | 46.763 | 1.00 | 0.01 |
| ATOM | 3471 | OE1 | GLU | A | 383 | 18.064 | 7.506 | 46.455 | 1.00 | 0.02 |
| ATOM | 3472 | OE2 | GLU | A | 383 | 16.468 | 6.881 | 47.781 | 1.00 | 0.01 |
| ATOM | 3473 | C | GLU | A | 383 | 14.521 | 11.633 | 45.523 | 1.00 | 0.01 |
| ATOM | 3474 | O | GLU | A | 383 | 14.041 | 11.842 | 46.642 | 1.00 | 0.01 |
| ATOM | 3475 | N | ALA | A | 384 | 14.842 | 12.614 | 44.689 | 1.00 | 0.01 |
| ATOM | 3477 | CA | ALA | A | 384 | 14.536 | 14.000 | 45.044 | 1.00 | 0.01 |
| ATOM | 3478 | CB | ALA | A | 384 | 15.301 | 14.930 | 44.110 | 1.00 | 0.01 |
| ATOM | 3479 | C | ALA | A | 384 | 13.039 | 14.246 | 44.909 | 1.00 | 0.01 |
| ATOM | 3480 | O | ALA | A | 384 | 12.393 | 13.719 | 43.996 | 1.00 | 0.02 |
| ATOM | 3481 | N | THR | A | 385 | 12.506 | 15.026 | 45.832 | 1.00 | 0.01 |
| ATOM | 3483 | CA | THR | A | 385 | 11.069 | 15.321 | 45.844 | 1.00 | 0.01 |
| ATOM | 3484 | CB | THR | A | 385 | 10.739 | 16.039 | 47.151 | 1.00 | 0.38 |
| ATOM | 3485 | OG1 | THR | A | 385 | 11.064 | 15.161 | 48.221 | 1.00 | 1.48 |
| ATOM | 3486 | CG2 | THR | A | 385 | 9.258 | 16.388 | 47.268 | 1.00 | 1.35 |
| ATOM | 3487 | C | THR | A | 385 | 10.675 | 16.184 | 44.648 | 1.00 | 0.02 |
| ATOM | 3488 | O | THR | A | 385 | 11.220 | 17.273 | 44.436 | 1.00 | 0.01 |
| ATOM | 3489 | N | ALA | A | 386 | 9.765 | 15.650 | 43.850 | 1.00 | 0.00 |

| ATOM | 3491 | CA | ALA | A | 386 | 9.233 | 16.371 | 42.691 | 1.00 | 0.02 |
|------|------|-----|-----|---|-----|-------|--------|--------|------|------|
| ATOM | 3492 | CB | ALA | A | 386 | 8.398 | 15.407 | 41.855 | 1.00 | 0.42 |
| ATOM | 3493 | C | ALA | A | 386 | 8.369 | 17.551 | 43.126 | 1.00 | 0.03 |
| ATOM | 3494 | O | ALA | A | 386 | 7.949 | 17.640 | 44.287 | 1.00 | 0.02 |
| ATOM | 3495 | N | ALA | A | 387 | 8.167 | 18.475 | 42.201 | 1.00 | 0.01 |
| ATOM | 3497 | CA | ALA | A | 387 | 7.315 | 19.643 | 42.456 | 1.00 | 0.01 |
| ATOM | 3498 | CB | ALA | A | 387 | 7.267 | 20.502 | 41.198 | 1.00 | 0.02 |
| ATOM | 3499 | C | ALA | A | 387 | 5.903 | 19.213 | 42.841 | 1.00 | 0.01 |
| ATOM | 3500 | O | ALA | A | 387 | 5.370 | 18.228 | 42.314 | 1.00 | 0.02 |
| ATOM | 3501 | N | THR | A | 388 | 5.314 | 19.953 | 43.764 | 1.00 | 0.02 |
| ATOM | 3503 | CA | THR | A | 388 | 3.986 | 19.603 | 44.282 | 1.00 | 0.01 |
| ATOM | 3504 | CB | THR | A | 388 | 3.830 | 20.215 | 45.670 | 1.00 | 0.52 |
| ATOM | 3505 | OG1 | THR | A | 388 | 4.892 | 19.727 | 46.479 | 1.00 | 0.64 |
| ATOM | 3506 | CG2 | THR | A | 388 | 2.511 | 19.810 | 46.324 | 1.00 | 0.69 |
| ATOM | 3507 | C | THR | A | 388 | 2.866 | 20.085 | 43.362 | 1.00 | 0.02 |
| ATOM | 3508 | O | THR | A | 388 | 2.391 | 21.223 | 43.457 | 1.00 | 0.01 |
| ATOM | 3509 | N | THR | A | 389 | 2.504 | 19.221 | 42.431 | 1.00 | 0.01 |
| ATOM | 3511 | CA | THR | A | 389 | 1.383 | 19.495 | 41.527 | 1.00 | 0.02 |
| ATOM | 3512 | CB | THR | A | 389 | 1.577 | 18.714 | 40.233 | 1.00 | 0.16 |
| ATOM | 3513 | OG1 | THR | A | 389 | 1.515 | 17.323 | 40.528 | 1.00 | 0.18 |
| ATOM | 3514 | CG2 | THR | A | 389 | 2.927 | 19.015 | 39.592 | 1.00 | 0.12 |
| ATOM | 3515 | C | THR | A | 389 | 0.072 | 19.085 | 42.186 | 1.00 | 0.02 |
| ATOM | 3516 | O | THR | A | 389 | 0.004 | 18.073 | 42.891 | 1.00 | 0.02 |
| ATOM | 3517 | N | THR | A | 390 | -0.958 | 19.883 | 41.971 | 1.00 | 0.01 |
| ATOM | 3519 | CA | THR | A | 390 | -2.260 | 19.577 | 42.572 | 1.00 | 0.02 |
| ATOM | 3520 | CB | THR | A | 390 | -2.500 | 20.548 | 43.722 | 1.00 | 0.38 |
| ATOM | 3521 | OG1 | THR | A | 390 | -1.396 | 20.444 | 44.612 | 1.00 | 1.27 |
| ATOM | 3522 | CG2 | THR | A | 390 | -3.772 | 20.210 | 44.494 | 1.00 | 1.29 |
| ATOM | 3523 | C | THR | A | 390 | -3.383 | 19.680 | 41.545 | 1.00 | 0.01 |
| ATOM | 3524 | O | THR | A | 390 | -3.969 | 20.749 | 41.338 | 1.00 | 0.02 |
| ATOM | 3525 | N | LYS | A | 391 | -3.640 | 18.572 | 40.874 | 1.00 | 0.02 |
| ATOM | 3527 | CA | LYS | A | 391 | -4.725 | 18.537 | 39.890 | 1.00 | 0.01 |
| ATOM | 3528 | CB | LYS | A | 391 | -4.297 | 17.698 | 38.695 | 1.00 | 0.84 |
| ATOM | 3529 | CG | LYS | A | 391 | -3.093 | 18.351 | 38.027 | 1.00 | 1.32 |
| ATOM | 3530 | CD | LYS | A | 391 | -2.706 | 17.653 | 36.732 | 1.00 | 2.13 |
| ATOM | 3531 | CE | LYS | A | 391 | -1.480 | 18.312 | 36.110 | 1.00 | 2.60 |
| ATOM | 3532 | NZ | LYS | A | 391 | -0.340 | 18.271 | 37.038 | 1.00 | 3.28 |
| ATOM | 3533 | C | LYS | A | 391 | -6.011 | 18.011 | 40.516 | 1.00 | 0.02 |
| ATOM | 3534 | O | LYS | A | 391 | -6.000 | 17.074 | 41.322 | 1.00 | 0.01 |
| ATOM | 3535 | N | PHE | A | 392 | -7.107 | 18.653 | 40.155 | 1.00 | 0.01 |
| ATOM | 3537 | CA | PHE | A | 392 | -8.408 | 18.332 | 40.749 | 1.00 | 0.01 |
| ATOM | 3538 | CB | PHE | A | 392 | -9.331 | 19.528 | 40.552 | 1.00 | 0.12 |
| ATOM | 3539 | CG | PHE | A | 392 | -8.787 | 20.807 | 41.183 | 1.00 | 0.14 |
| ATOM | 3540 | CD1 | PHE | A | 392 | -8.513 | 21.914 | 40.390 | 1.00 | 0.22 |
| ATOM | 3541 | CE1 | PHE | A | 392 | -8.010 | 23.074 | 40.966 | 1.00 | 0.31 |
| ATOM | 3542 | CZ | PHE | A | 392 | -7.782 | 23.126 | 42.336 | 1.00 | 0.36 |
| ATOM | 3543 | CE2 | PHE | A | 392 | -8.058 | 22.020 | 43.128 | 1.00 | 0.33 |
| ATOM | 3544 | CD2 | PHE | A | 392 | -8.560 | 20.861 | 42.552 | 1.00 | 0.20 |
| ATOM | 3545 | C | PHE | A | 392 | -9.025 | 17.075 | 40.146 | 1.00 | 0.02 |
| ATOM | 3546 | O | PHE | A | 392 | -9.271 | 16.983 | 38.937 | 1.00 | 0.02 |
| ATOM | 3547 | N | ILE | A | 393 | -9.234 | 16.102 | 41.016 | 1.00 | 0.02 |
| ATOM | 3549 | CA | ILE | A | 393 | -9.840 | 14.829 | 40.625 | 1.00 | 0.02 |
| ATOM | 3550 | CB | ILE | A | 393 | -9.109 | 13.720 | 41.379 | 1.00 | 0.02 |
| ATOM | 3551 | CG2 | ILE | A | 393 | -9.669 | 12.341 | 41.044 | 1.00 | 0.00 |
| ATOM | 3552 | CG1 | ILE | A | 393 | -7.618 | 13.771 | 41.066 | 1.00 | 0.02 |
| ATOM | 3553 | CD1 | ILE | A | 393 | -6.851 | 12.724 | 41.862 | 1.00 | 0.00 |
| ATOM | 3554 | C | ILE | A | 393 | -11.330 | 14.807 | 40.954 | 1.00 | 0.02 |

| ATOM | 3555 | O | ILE | A | 393 | -11.736 | 15.082 | 42.089 | 1.00 | 0.02 |
|------|------|-----|-----|---|-----|---------|--------|--------|------|------|
| ATOM | 3556 | N | VAL | A | 394 | -12.137 | 14.553 | 39.937 | 1.00 | 0.02 |
| ATOM | 3558 | CA | VAL | A | 394 | -13.579 | 14.400 | 40.147 | 1.00 | 0.02 |
| ATOM | 3559 | CB | VAL | A | 394 | -14.274 | 14.489 | 38.787 | 1.00 | 1.05 |
| ATOM | 3560 | CG1 | VAL | A | 394 | -15.768 | 14.192 | 38.854 | 1.00 | 1.37 |
| ATOM | 3561 | CG2 | VAL | A | 394 | -14.052 | 15.872 | 38.188 | 1.00 | 1.35 |
| ATOM | 3562 | C | VAL | A | 394 | -13.848 | 13.075 | 40.863 | 1.00 | 0.02 |
| ATOM | 3563 | O | VAL | A | 394 | -13.339 | 12.021 | 40.472 | 1.00 | 0.00 |
| ATOM | 3564 | N | ARG | A | 395 | -14.678 | 13.150 | 41.893 | 1.00 | 0.02 |
| ATOM | 3566 | CA | ARG | A | 395 | -14.955 | 12.017 | 42.792 | 1.00 | 0.02 |
| ATOM | 3567 | CB | ARG | A | 395 | -15.414 | 12.644 | 44.108 | 1.00 | 1.17 |
| ATOM | 3568 | CG | ARG | A | 395 | -15.493 | 11.662 | 45.273 | 1.00 | 1.69 |
| ATOM | 3569 | CD | ARG | A | 395 | -16.026 | 12.350 | 46.524 | 1.00 | 2.28 |
| ATOM | 3570 | NE | ARG | A | 395 | -17.365 | 12.912 | 46.275 | 1.00 | 2.83 |
| ATOM | 3571 | CZ | ARG | A | 395 | -17.679 | 14.191 | 46.492 | 1.00 | 3.34 |
| ATOM | 3572 | NH1 | ARG | A | 395 | -16.753 | 15.040 | 46.945 | 1.00 | 3.83 |
| ATOM | 3573 | NH2 | ARG | A | 395 | -18.915 | 14.626 | 46.237 | 1.00 | 3.68 |
| ATOM | 3574 | C | ARG | A | 395 | -16.021 | 11.035 | 42.266 | 1.00 | 0.02 |
| ATOM | 3575 | O | ARG | A | 395 | -16.340 | 10.047 | 42.939 | 1.00 | 0.02 |
| ATOM | 3576 | N | SER | A | 396 | -16.547 | 11.286 | 41.077 | 1.00 | 0.01 |
| ATOM | 3578 | CA | SER | A | 396 | -17.573 | 10.408 | 40.497 | 1.00 | 0.01 |
| ATOM | 3579 | CB | SER | A | 396 | -18.008 | 10.956 | 39.140 | 1.00 | 0.02 |
| ATOM | 3580 | OG | SER | A | 396 | -16.889 | 10.942 | 38.261 | 1.00 | 0.00 |
| ATOM | 3581 | C | SER | A | 396 | -17.044 | 8.988 | 40.324 | 1.00 | 0.02 |
| ATOM | 3582 | O | SER | A | 396 | -15.959 | 8.777 | 39.774 | 1.00 | 0.01 |
| ATOM | 3583 | N | LYS | A | 397 | -17.903 | 8.025 | 40.616 | 1.00 | 0.01 |
| ATOM | 3585 | CA | LYS | A | 397 | -17.504 | 6.608 | 40.597 | 1.00 | 0.01 |
| ATOM | 3586 | CB | LYS | A | 397 | -18.483 | 5.845 | 41.476 | 1.00 | 0.53 |
| ATOM | 3587 | CG | LYS | A | 397 | -18.443 | 6.404 | 42.894 | 1.00 | 0.99 |
| ATOM | 3588 | CD | LYS | A | 397 | - | 5.717 | 43.811 | 1.00 | 1.27 |

| | | | | | 19.445 | | | |
|---|---|---|---|---|---|---|---|---|
| ATOM | 3589 | CE | LYS | A | 397 | -19.381 | 6.301 | 45.218 | 1.00 | 1.17 |
| ATOM | 3590 | NZ | LYS | A | 397 | -19.656 | 7.748 | 45.199 | 1.00 | 1.92 |
| ATOM | 3591 | C | LYS | A | 397 | -17.456 | 5.995 | 39.195 | 1.00 | 0.02 |
| ATOM | 3592 | O | LYS | A | 397 | -17.020 | 4.854 | 39.020 | 1.00 | 0.02 |
| ATOM | 3593 | N | ASP | A | 398 | -17.852 | 6.773 | 38.200 | 1.00 | 0.53 |
| ATOM | 3595 | CA | ASP | A | 398 | -17.694 | 6.369 | 36.803 | 1.00 | 1.04 |
| ATOM | 3596 | CB | ASP | A | 398 | -18.868 | 6.954 | 36.019 | 1.00 | 1.51 |
| ATOM | 3597 | CG | ASP | A | 398 | -18.826 | 6.533 | 34.554 | 1.00 | 1.90 |
| ATOM | 3598 | OD1 | ASP | A | 398 | -18.447 | 7.362 | 33.738 | 1.00 | 2.32 |
| ATOM | 3599 | OD2 | ASP | A | 398 | -19.301 | 5.443 | 34.265 | 1.00 | 2.30 |
| ATOM | 3600 | C | ASP | A | 398 | -16.367 | 6.900 | 36.246 | 1.00 | 1.10 |
| ATOM | 3601 | O | ASP | A | 398 | -15.881 | 6.413 | 35.218 | 1.00 | 1.33 |
| ATOM | 3602 | N | GLY | A | 399 | -15.729 | 7.791 | 36.992 | 1.00 | 0.35 |
| ATOM | 3604 | CA | GLY | A | 399 | -14.472 | 8.400 | 36.545 | 1.00 | 0.43 |
| ATOM | 3605 | C | GLY | A | 399 | -13.299 | 7.483 | 36.865 | 1.00 | 0.38 |
| ATOM | 3606 | O | GLY | A | 399 | -12.968 | 6.607 | 36.055 | 1.00 | 0.43 |
| ATOM | 3607 | N | PRO | A | 400 | -12.657 | 7.729 | 38.000 | 1.00 | 0.02 |
| ATOM | 3608 | CA | PRO | A | 400 | -11.593 | 6.852 | 38.509 | 1.00 | 0.00 |
| ATOM | 3609 | CB | PRO | A | 400 | -11.054 | 7.548 | 39.717 | 1.00 | 0.02 |
| ATOM | 3610 | CG | PRO | A | 400 | -11.911 | 8.768 | 40.023 | 1.00 | 0.03 |
| ATOM | 3611 | CD | PRO | A | 400 | -12.932 | 8.851 | 38.902 | 1.00 | 0.03 |
| ATOM | 3612 | C | PRO | A | 400 | -12.127 | 5.475 | 38.879 | 1.00 | 0.01 |
| ATOM | 3613 | O | PRO | A | 400 | -12.521 | 5.237 | 40.026 | 1.00 | 0.00 |
| ATOM | 3614 | N | SER | A | 401 | -12.080 | 4.568 | 37.919 | 1.00 | 0.02 |
| ATOM | 3616 | CA | SER | A | 401 | -12.717 | 3.268 | 38.096 | 1.00 | 0.01 |
| ATOM | 3617 | CB | SER | A | 401 | -13.842 | 3.213 | 37.071 | 1.00 | 2.33 |
| ATOM | 3618 | OG | SER | A | 401 | -14.658 | 4.361 | 37.292 | 1.00 | 3.03 |
| ATOM | 3619 | C | SER | A | 401 | -11.770 | 2.090 | 37.914 | 1.00 | 0.02 |
| ATOM | 3620 | O | SER | A | 401 | -10.675 | 2.214 | 37.356 | 1.00 | 0.01 |

| ATOM | 3621 | N | TYR | A | 402 | -12.326 | 0.933 | 38.231 | 1.00 | 1.42 |
|------|------|-----|-----|---|-----|---------|--------|--------|------|------|
| ATOM | 3623 | CA | TYR | A | 402 | -11.639 | -0.367 | 38.268 | 1.00 | 1.57 |
| ATOM | 3624 | CB | TYR | A | 402 | -12.601 | -1.427 | 38.863 | 1.00 | 1.62 |
| ATOM | 3625 | CG | TYR | A | 402 | -14.106 | -1.543 | 38.474 | 1.00 | 2.37 |
| ATOM | 3626 | CD1 | TYR | A | 402 | -14.922 | -2.337 | 39.277 | 1.00 | 3.23 |
| ATOM | 3627 | CE1 | TYR | A | 402 | -16.272 | -2.486 | 38.985 | 1.00 | 4.33 |
| ATOM | 3628 | CZ | TYR | A | 402 | -16.815 | -1.847 | 37.882 | 1.00 | 4.54 |
| ATOM | 3629 | OH | TYR | A | 402 | -18.149 | -2.013 | 37.577 | 1.00 | 5.70 |
| ATOM | 3630 | CE2 | TYR | A | 402 | -16.013 | -1.065 | 37.065 | 1.00 | 3.73 |
| ATOM | 3631 | CD2 | TYR | A | 402 | -14.663 | -0.922 | 37.358 | 1.00 | 2.65 |
| ATOM | 3632 | C | TYR | A | 402 | -10.998 | -0.872 | 36.963 | 1.00 | 1.61 |
| ATOM | 3633 | O | TYR | A | 402 | -9.774 | -0.749 | 36.800 | 1.00 | 2.21 |
| ATOM | 3634 | N | PHE | A | 403 | -11.818 | -1.232 | 35.982 | 1.00 | 1.32 |
| ATOM | 3636 | CA | PHE | A | 403 | -11.365 | -2.043 | 34.842 | 1.00 | 1.54 |
| ATOM | 3637 | CB | PHE | A | 403 | -12.592 | -2.504 | 34.059 | 1.00 | 1.10 |
| ATOM | 3638 | CG | PHE | A | 403 | -13.556 | -3.460 | 34.757 | 1.00 | 1.20 |
| ATOM | 3639 | CD1 | PHE | A | 403 | -14.908 | -3.425 | 34.434 | 1.00 | 1.54 |
| ATOM | 3640 | CE1 | PHE | A | 403 | -15.794 | -4.301 | 35.048 | 1.00 | 2.04 |
| ATOM | 3641 | CZ | PHE | A | 403 | -15.324 | -5.218 | 35.978 | 1.00 | 2.06 |
| ATOM | 3642 | CE2 | PHE | A | 403 | -13.972 | -5.270 | 36.291 | 1.00 | 1.68 |
| ATOM | 3643 | CD2 | PHE | A | 403 | -13.086 | -4.394 | 35.674 | 1.00 | 1.35 |
| ATOM | 3644 | C | PHE | A | 403 | -10.458 | -1.342 | 33.840 | 1.00 | 1.40 |
| ATOM | 3645 | O | PHE | A | 403 | -9.673 | -2.022 | 33.171 | 1.00 | 2.11 |
| ATOM | 3646 | N | THR | A | 404 | -10.380 | -0.022 | 33.889 | 1.00 | 1.47 |
| ATOM | 3648 | CA | THR | A | 404 | -9.645 | 0.688 | 32.838 | 1.00 | 1.83 |
| ATOM | 3649 | CB | THR | A | 404 | -10.219 | 2.093 | 32.686 | 1.00 | 1.26 |
| ATOM | 3650 | OG1 | THR | A | 404 | -9.975 | 2.812 | 33.891 | 1.00 | 1.46 |
| ATOM | 3651 | CG2 | THR | A | 404 | -11.724 | 2.058 | 32.432 | 1.00 | 2.05 |
| ATOM | 3652 | C | THR | A | 404 | -8.152 | 0.792 | 33.122 | 1.00 | 1.32 |
| ATOM | 3653 | O | THR | A | 404 | -7.371 | 1.044 | 32.200 | 1.00 | 1.45 |
| ATOM | 3654 | N | VAL | A | 405 | -7.747 | 0.528 | 34.352 | 1.00 | 0.00 |
| ATOM | 3656 | CA | VAL | A | 405 | -6.363 | 0.806 | 34.721 | 1.00 | 0.02 |
| ATOM | 3657 | CB | VAL | A | 405 | -6.383 | 2.110 | 35.488 | 1.00 | 0.02 |
| ATOM | 3658 | CG1 | VAL | A | 405 | -6.272 | 3.287 | 34.531 | 1.00 | 0.02 |
| ATOM | 3659 | CG2 | VAL | A | 405 | -7.660 | 2.182 | 36.311 | 1.00 | 0.02 |

| ATOM | 3660 | C | VAL | A | 405 | -5.687 | -0.287 | 35.537 | 1.00 | 0.01 |
|------|------|---|-----|---|-----|--------|--------|--------|------|------|
| ATOM | 3661 | O | VAL | A | 405 | -4.657 | -0.029 | 36.177 | 1.00 | 0.00 |
| ATOM | 3662 | N | SER | A | 406 | -6.268 | -1.473 | 35.546 | 1.00 | 0.02 |
| ATOM | 3664 | CA | SER | A | 406 | -5.611 | -2.602 | 36.206 | 1.00 | 0.02 |
| ATOM | 3665 | CB | SER | A | 406 | -6.655 | -3.585 | 36.743 | 1.00 | 2.03 |
| ATOM | 3666 | OG | SER | A | 406 | -7.513 | -3.997 | 35.685 | 1.00 | 2.68 |
| ATOM | 3667 | C | SER | A | 406 | -4.638 | -3.287 | 35.242 | 1.00 | 0.02 |
| ATOM | 3668 | O | SER | A | 406 | -5.017 | -4.174 | 34.471 | 1.00 | 0.01 |
| ATOM | 3669 | N | PHE | A | 407 | -3.364 | -2.958 | 35.384 | 1.00 | 0.02 |
| ATOM | 3671 | CA | PHE | A | 407 | -2.322 | -3.488 | 34.494 | 1.00 | 0.02 |
| ATOM | 3672 | CB | PHE | A | 407 | -1.268 | -2.413 | 34.235 | 1.00 | 0.01 |
| ATOM | 3673 | CG | PHE | A | 407 | -1.739 | -1.291 | 33.311 | 1.00 | 0.02 |
| ATOM | 3674 | CD1 | PHE | A | 407 | -2.349 | -0.155 | 33.828 | 1.00 | 0.02 |
| ATOM | 3675 | CE1 | PHE | A | 407 | -2.782 | 0.851 | 32.974 | 1.00 | 0.02 |
| ATOM | 3676 | CZ | PHE | A | 407 | -2.598 | 0.725 | 31.603 | 1.00 | 0.02 |
| ATOM | 3677 | CE2 | PHE | A | 407 | -1.977 | -0.405 | 31.087 | 1.00 | 0.00 |
| ATOM | 3678 | CD2 | PHE | A | 407 | -1.548 | -1.412 | 31.941 | 1.00 | 0.01 |
| ATOM | 3679 | C | PHE | A | 407 | -1.682 | -4.760 | 35.045 | 1.00 | 0.02 |
| ATOM | 3680 | O | PHE | A | 407 | -0.462 | -4.949 | 34.979 | 1.00 | 0.02 |
| ATOM | 3681 | N | ASN | A | 408 | -2.517 | -5.611 | 35.619 | 1.00 | 0.02 |
| ATOM | 3683 | CA | ASN | A | 408 | -2.054 | -6.901 | 36.120 | 1.00 | 0.02 |
| ATOM | 3684 | CB | ASN | A | 408 | -2.829 | -7.317 | 37.375 | 1.00 | 0.02 |
| ATOM | 3685 | CG | ASN | A | 408 | -4.294 | -7.673 | 37.106 | 1.00 | 0.01 |
| ATOM | 3686 | OD1 | ASN | A | 408 | -5.030 | -6.943 | 36.432 | 1.00 | 0.01 |
| ATOM | 3687 | ND2 | ASN | A | 408 | -4.709 | -8.787 | 37.681 | 1.00 | 0.02 |
| ATOM | 3690 | C | ASN | A | 408 | -2.170 | -7.944 | 35.014 | 1.00 | 0.02 |
| ATOM | 3691 | O | ASN | A | 408 | -1.639 | -9.047 | 35.153 | 1.00 | 0.00 |
| ATOM | 3692 | N | ARG | A | 409 | -2.855 | -7.619 | 33.932 | 1.00 | 0.00 |
| ATOM | 3694 | CA | ARG | A | 409 | -2.766 | -8.471 | 32.743 | 1.00 | 0.01 |
| ATOM | 3695 | CB | ARG | A | 409 | -4.057 | -8.395 | 31.946 | 1.00 | 1.08 |
| ATOM | 3696 | CG | ARG | A | 409 | -5.240 | -8.876 | 32.774 | 1.00 | 1.16 |
| ATOM | 3697 | CD | ARG | A | 409 | -6.500 | -8.955 | 31.924 | 1.00 | 1.61 |
| ATOM | 3698 | NE | ARG | A | 409 | -6.792 | -7.655 | 31.304 | 1.00 | 1.42 |
| ATOM | 3699 | CZ | ARG | A | 409 | -8.026 | -7.155 | 31.217 | 1.00 | 1.93 |
| ATOM | 3700 | NH1 | ARG | A | 409 | -9.060 | -7.845 | 31.703 | 1.00 | 2.76 |
| ATOM | 3701 | NH2 | ARG | A | 409 | -8.225 | -5.967 | 30.641 | 1.00 | 2.23 |
| ATOM | 3702 | C | ARG | A | 409 | -1.585 | -8.014 | 31.893 | 1.00 | 0.00 |
| ATOM | 3703 | O | ARG | A | 409 | -1.125 | -6.876 | 32.038 | 1.00 | 0.01 |
| ATOM | 3704 | N | THR | A | 410 | -1.078 | -8.921 | 31.074 | 1.00 | 0.01 |
| ATOM | 3706 | CA | THR | A | 410 | 0.062 | -8.630 | 30.187 | 1.00 | 0.01 |
| ATOM | 3707 | CB | THR | A | 410 | 0.301 | -9.867 | 29.326 | 1.00 | 0.83 |
| ATOM | 3708 | OG1 | THR | A | 410 | 0.808 | -10.886 | 30.181 | 1.00 | 1.17 |
| ATOM | 3709 | CG2 | THR | A | 410 | 1.328 | -9.629 | 28.222 | 1.00 | 1.37 |
| ATOM | 3710 | C | THR | A | 410 | -0.176 | -7.399 | 29.309 | 1.00 | 0.01 |
| ATOM | 3711 | O | THR | A | 410 | -1.183 | -7.305 | 28.596 | 1.00 | 0.01 |
| ATOM | 3712 | N | PHE | A | 411 | 0.744 | -6.451 | 29.403 | 1.00 | 0.01 |
| ATOM | 3714 | CA | PHE | A | 411 | 0.617 | -5.191 | 28.656 | 1.00 | 0.01 |
| ATOM | 3715 | CB | PHE | A | 411 | 0.284 | -4.049 | 29.619 | 1.00 | 0.01 |
| ATOM | 3716 | CG | PHE | A | 411 | 1.295 | -3.780 | 30.733 | 1.00 | 0.01 |
| ATOM | 3717 | CD1 | PHE | A | 411 | 2.346 | -2.897 | 30.519 | 1.00 | 0.01 |
| ATOM | 3718 | CE1 | PHE | A | 411 | 3.263 | -2.650 | 31.531 | 1.00 | 0.00 |
| ATOM | 3719 | CZ | PHE | A | 411 | 3.126 | -3.277 | 32.761 | 1.00 | 0.01 |
| ATOM | 3720 | CE2 | PHE | A | 411 | 2.068 | -4.147 | 32.981 | 1.00 | 0.01 |
| ATOM | 3721 | CD2 | PHE | A | 411 | 1.150 | -4.394 | 31.970 | 1.00 | 0.00 |
| ATOM | 3722 | C | PHE | A | 411 | 1.860 | -4.851 | 27.829 | 1.00 | 0.00 |
| ATOM | 3723 | O | PHE | A | 411 | 2.999 | -5.206 | 28.160 | 1.00 | 0.02 |
| ATOM | 3724 | N | LEU | A | 412 | 1.605 | -4.136 | 26.747 | 1.00 | 0.00 |

| ATOM | 3726 | CA | LEU | A | 412 | 2.650 | -3.710 | 25.810 | 1.00 | 0.01 |
|------|------|------|-----|---|-----|--------|--------|--------|------|------|
| ATOM | 3727 | CB | LEU | A | 412 | 1.984 | -3.656 | 24.432 | 1.00 | 0.51 |
| ATOM | 3728 | CG | LEU | A | 412 | 2.939 | -3.528 | 23.245 | 1.00 | 0.86 |
| ATOM | 3729 | CD1 | LEU | A | 412 | 2.345 | -4.205 | 22.018 | 1.00 | 1.15 |
| ATOM | 3730 | CD2 | LEU | A | 412 | 3.308 | -2.081 | 22.925 | 1.00 | 0.92 |
| ATOM | 3731 | C | LEU | A | 412 | 3.213 | -2.348 | 26.222 | 1.00 | 0.01 |
| ATOM | 3732 | O | LEU | A | 412 | 2.461 | -1.415 | 26.530 | 1.00 | 0.01 |
| ATOM | 3733 | N | MET | A | 413 | 4.531 | -2.250 | 26.239 | 1.00 | 0.01 |
| ATOM | 3735 | CA | MET | A | 413 | 5.195 | -0.983 | 26.574 | 1.00 | 0.01 |
| ATOM | 3736 | CB | MET | A | 413 | 6.310 | -1.226 | 27.579 | 1.00 | 1.42 |
| ATOM | 3737 | CG | MET | A | 413 | 5.775 | -1.694 | 28.923 | 1.00 | 0.91 |
| ATOM | 3738 | SD | MET | A | 413 | 7.002 | -1.688 | 30.246 | 1.00 | 1.58 |
| ATOM | 3739 | CE | MET | A | 413 | 7.448 | 0.062 | 30.175 | 1.00 | 1.14 |
| ATOM | 3740 | C | MET | A | 413 | 5.794 | -0.307 | 25.345 | 1.00 | 0.01 |
| ATOM | 3741 | O | MET | A | 413 | 6.388 | -0.960 | 24.477 | 1.00 | 0.01 |
| ATOM | 3742 | N | MET | A | 414 | 5.672 | 1.008 | 25.312 | 1.00 | 0.00 |
| ATOM | 3744 | CA | MET | A | 414 | 6.255 | 1.792 | 24.217 | 1.00 | 0.01 |
| ATOM | 3745 | CB | MET | A | 414 | 5.197 | 1.954 | 23.136 | 1.00 | 0.42 |
| ATOM | 3746 | CG | MET | A | 414 | 5.704 | 2.789 | 21.970 | 1.00 | 1.17 |
| ATOM | 3747 | SD | MET | A | 414 | 4.608 | 2.810 | 20.538 | 1.00 | 1.20 |
| ATOM | 3748 | CE | MET | A | 414 | 3.065 | 3.254 | 21.366 | 1.00 | 1.92 |
| ATOM | 3749 | C | MET | A | 414 | 6.756 | 3.160 | 24.681 | 1.00 | 0.01 |
| ATOM | 3750 | O | MET | A | 414 | 5.983 | 4.113 | 24.830 | 1.00 | 0.00 |
| ATOM | 3751 | N | ILE | A | 415 | 8.056 | 3.254 | 24.884 | 1.00 | 0.01 |
| ATOM | 3753 | CA | ILE | A | 415 | 8.657 | 4.526 | 25.303 | 1.00 | 0.01 |
| ATOM | 3754 | CB | ILE | A | 415 | 9.842 | 4.231 | 26.216 | 1.00 | 0.24 |
| ATOM | 3755 | CG2 | ILE | A | 415 | 10.545 | 5.519 | 26.637 | 1.00 | 0.37 |
| ATOM | 3756 | CG1 | ILE | A | 415 | 9.380 | 3.452 | 27.440 | 1.00 | 0.21 |
| ATOM | 3757 | CD1 | ILE | A | 415 | 10.537 | 3.177 | 28.391 | 1.00 | 0.15 |
| ATOM | 3758 | C | ILE | A | 415 | 9.107 | 5.320 | 24.080 | 1.00 | 0.01 |
| ATOM | 3759 | O | ILE | A | 415 | 10.024 | 4.907 | 23.359 | 1.00 | 0.01 |
| ATOM | 3760 | N | THR | A | 416 | 8.448 | 6.441 | 23.843 | 1.00 | 0.01 |
| ATOM | 3762 | CA | THR | A | 416 | 8.748 | 7.254 | 22.658 | 1.00 | 0.01 |
| ATOM | 3763 | CB | THR | A | 416 | 7.446 | 7.408 | 21.881 | 1.00 | 0.52 |
| ATOM | 3764 | OG1 | THR | A | 416 | 6.945 | 6.101 | 21.629 | 1.00 | 1.01 |
| ATOM | 3765 | CG2 | THR | A | 416 | 7.639 | 8.117 | 20.543 | 1.00 | 1.12 |
| ATOM | 3766 | C | THR | A | 416 | 9.325 | 8.625 | 23.019 | 1.00 | 0.01 |
| ATOM | 3767 | O | THR | A | 416 | 8.744 | 9.378 | 23.811 | 1.00 | 0.01 |
| ATOM | 3768 | N | ASN | A | 417 | 10.471 | 8.931 | 22.433 | 1.00 | 0.01 |
| ATOM | 3770 | CA | ASN | A | 417 | 11.125 | 10.229 | 22.628 | 1.00 | 0.00 |
| ATOM | 3771 | CB | ASN | A | 417 | 12.543 | 10.132 | 22.075 | 1.00 | 0.31 |
| ATOM | 3772 | CG | ASN | A | 417 | 13.254 | 11.475 | 22.170 | 1.00 | 0.35 |
| ATOM | 3773 | OD1 | ASN | A | 417 | 13.106 | 12.332 | 21.287 | 1.00 | 0.53 |
| ATOM | 3774 | ND2 | ASN | A | 417 | 13.993 | 11.651 | 23.247 | 1.00 | 0.80 |
| ATOM | 3777 | C | ASN | A | 417 | 10.368 | 11.324 | 21.886 | 1.00 | 0.01 |
| ATOM | 3778 | O | ASN | A | 417 | 10.458 | 11.428 | 20.654 | 1.00 | 0.01 |
| ATOM | 3779 | N | LYS | A | 418 | 9.838 | 12.264 | 22.652 | 1.00 | 0.01 |
| ATOM | 3781 | CA | LYS | A | 418 | 8.989 | 13.311 | 22.075 | 1.00 | 0.01 |
| ATOM | 3782 | CB | LYS | A | 418 | 7.784 | 13.572 | 22.980 | 1.00 | 0.76 |
| ATOM | 3783 | CG | LYS | A | 418 | 8.047 | 14.546 | 24.124 | 1.00 | 1.20 |
| ATOM | 3784 | CD | LYS | A | 418 | 6.753 | 14.809 | 24.889 | 1.00 | 1.77 |
| ATOM | 3785 | CE | LYS | A | 418 | 6.773 | 16.139 | 25.636 | 1.00 | 2.20 |
| ATOM | 3786 | NZ | LYS | A | 418 | 7.850 | 16.191 | 26.631 | 1.00 | 2.37 |
| ATOM | 3787 | C | LYS | A | 418 | 9.760 | 14.602 | 21.778 | 1.00 | 0.01 |
| ATOM | 3788 | O | LYS | A | 418 | 9.154 | 15.632 | 21.459 | 1.00 | 0.02 |
| ATOM | 3789 | N | ALA | A | 419 | 11.081 | 14.546 | 21.869 | 1.00 | 0.01 |
| ATOM | 3791 | CA | ALA | A | 419 | 11.903 | 15.688 | 21.458 | 1.00 | 0.00 |
| ATOM | 3792 | CB | ALA | A | 419 | 13.230 | 15.650 | 22.207 | 1.00 | 0.15 |

| ATOM | 3793 | C | ALA | A | 419 | 12.154 | 15.589 | 19.955 | 1.00 | 0.00 |
|------|------|---|-----|---|-----|--------|--------|--------|------|------|
| ATOM | 3794 | O | ALA | A | 419 | 12.447 | 16.585 | 19.283 | 1.00 | 0.01 |
| ATOM | 3795 | N | THR | A | 420 | 12.051 | 14.367 | 19.461 | 1.00 | 0.01 |
| ATOM | 3797 | CA | THR | A | 420 | 11.991 | 14.108 | 18.023 | 1.00 | 0.01 |
| ATOM | 3798 | CB | THR | A | 420 | 13.262 | 13.400 | 17.537 | 1.00 | 0.00 |
| ATOM | 3799 | OG1 | THR | A | 420 | 13.774 | 12.554 | 18.563 | 1.00 | 0.01 |
| ATOM | 3800 | CG2 | THR | A | 420 | 14.365 | 14.406 | 17.226 | 1.00 | 0.01 |
| ATOM | 3801 | C | THR | A | 420 | 10.714 | 13.325 | 17.713 | 1.00 | 0.01 |
| ATOM | 3802 | O | THR | A | 420 | 9.651 | 13.924 | 17.516 | 1.00 | 0.01 |
| ATOM | 3803 | N | ASP | A | 421 | 10.836 | 12.009 | 17.632 | 1.00 | 0.01 |
| ATOM | 3805 | CA | ASP | A | 421 | 9.695 | 11.108 | 17.393 | 1.00 | 0.01 |
| ATOM | 3806 | CB | ASP | A | 421 | 9.064 | 11.381 | 16.023 | 1.00 | 2.55 |
| ATOM | 3807 | CG | ASP | A | 421 | 10.108 | 11.518 | 14.905 | 1.00 | 2.84 |
| ATOM | 3808 | OD1 | ASP | A | 421 | 11.024 | 10.706 | 14.858 | 1.00 | 3.45 |
| ATOM | 3809 | OD2 | ASP | A | 421 | 10.035 | 12.509 | 14.201 | 1.00 | 2.99 |
| ATOM | 3810 | C | ASP | A | 421 | 10.143 | 9.649 | 17.489 | 1.00 | 0.01 |
| ATOM | 3811 | O | ASP | A | 421 | 9.368 | 8.722 | 17.223 | 1.00 | 0.01 |
| ATOM | 3812 | N | GLY | A | 422 | 11.387 | 9.459 | 17.893 | 1.00 | 0.01 |
| ATOM | 3814 | CA | GLY | A | 422 | 11.985 | 8.120 | 17.874 | 1.00 | 0.01 |
| ATOM | 3815 | C | GLY | A | 422 | 11.553 | 7.251 | 19.047 | 1.00 | 0.00 |
| ATOM | 3816 | O | GLY | A | 422 | 11.748 | 7.617 | 20.212 | 1.00 | 0.00 |
| ATOM | 3817 | N | ILE | A | 423 | 10.880 | 6.158 | 18.733 | 1.00 | 0.01 |
| ATOM | 3819 | CA | ILE | A | 423 | 10.570 | 5.162 | 19.763 | 1.00 | 0.00 |
| ATOM | 3820 | CB | ILE | A | 423 | 9.661 | 4.089 | 19.179 | 1.00 | 0.37 |
| ATOM | 3821 | CG2 | ILE | A | 423 | 9.305 | 3.046 | 20.234 | 1.00 | 0.32 |
| ATOM | 3822 | CG1 | ILE | A | 423 | 8.393 | 4.706 | 18.609 | 1.00 | 0.51 |
| ATOM | 3823 | CD1 | ILE | A | 423 | 7.475 | 3.623 | 18.059 | 1.00 | 0.70 |
| ATOM | 3824 | C | ILE | A | 423 | 11.871 | 4.534 | 20.242 | 1.00 | 0.01 |
| ATOM | 3825 | O | ILE | A | 423 | 12.566 | 3.841 | 19.486 | 1.00 | 0.01 |
| ATOM | 3826 | N | LEU | A | 424 | 12.153 | 4.741 | 21.515 | 1.00 | 0.01 |
| ATOM | 3828 | CA | LEU | A | 424 | 13.420 | 4.322 | 22.094 | 1.00 | 0.01 |
| ATOM | 3829 | CB | LEU | A | 424 | 13.697 | 5.172 | 23.330 | 1.00 | 0.01 |
| ATOM | 3830 | CG | LEU | A | 424 | 13.710 | 6.667 | 23.041 | 1.00 | 0.01 |
| ATOM | 3831 | CD1 | LEU | A | 424 | 13.732 | 7.462 | 24.342 | 1.00 | 0.01 |
| ATOM | 3832 | CD2 | LEU | A | 424 | 14.884 | 7.057 | 22.149 | 1.00 | 0.01 |
| ATOM | 3833 | C | LEU | A | 424 | 13.331 | 2.880 | 22.544 | 1.00 | 0.01 |
| ATOM | 3834 | O | LEU | A | 424 | 14.291 | 2.125 | 22.369 | 1.00 | 0.01 |
| ATOM | 3835 | N | PHE | A | 425 | 12.153 | 2.486 | 23.003 | 1.00 | 0.01 |
| ATOM | 3837 | CA | PHE | A | 425 | 11.976 | 1.137 | 23.557 | 1.00 | 0.01 |
| ATOM | 3838 | CB | PHE | A | 425 | 12.132 | 1.207 | 25.071 | 1.00 | 0.01 |
| ATOM | 3839 | CG | PHE | A | 425 | 13.530 | 1.519 | 25.595 | 1.00 | 0.01 |
| ATOM | 3840 | CD1 | PHE | A | 425 | 14.590 | 0.672 | 25.298 | 1.00 | 0.01 |
| ATOM | 3841 | CE1 | PHE | A | 425 | 15.858 | 0.949 | 25.792 | 1.00 | 0.01 |
| ATOM | 3842 | CZ | PHE | A | 425 | 16.065 | 2.071 | 26.583 | 1.00 | 0.01 |
| ATOM | 3843 | CE2 | PHE | A | 425 | 15.004 | 2.917 | 26.879 | 1.00 | 0.01 |
| ATOM | 3844 | CD2 | PHE | A | 425 | 13.737 | 2.640 | 26.387 | 1.00 | 0.01 |
| ATOM | 3845 | C | PHE | A | 425 | 10.607 | 0.524 | 23.279 | 1.00 | 0.00 |
| ATOM | 3846 | O | PHE | A | 425 | 9.567 | 1.094 | 23.639 | 1.00 | 0.01 |
| ATOM | 3847 | N | LEU | A | 426 | 10.635 | -0.688 | 22.751 | 1.00 | 0.00 |
| ATOM | 3849 | CA | LEU | A | 426 | 9.418 | -1.500 | 22.604 | 1.00 | 0.01 |
| ATOM | 3850 | CB | LEU | A | 426 | 9.215 | -1.912 | 21.153 | 1.00 | 0.28 |
| ATOM | 3851 | CG | LEU | A | 426 | 8.600 | -0.791 | 20.330 | 1.00 | 0.43 |
| ATOM | 3852 | CD1 | LEU | A | 426 | 8.368 | -1.251 | 18.898 | 1.00 | 0.63 |
| ATOM | 3853 | CD2 | LEU | A | 426 | 7.281 | -0.350 | 20.949 | 1.00 | 1.00 |
| ATOM | 3854 | C | LEU | A | 426 | 9.490 | -2.750 | 23.477 | 1.00 | 0.01 |
| ATOM | 3855 | O | LEU | A | 426 | 10.476 | -3.502 | 23.442 | 1.00 | 0.01 |
| ATOM | 3856 | N | GLY | A | 427 | 8.422 | -2.987 | 24.219 | 1.00 | 0.01 |
| ATOM | 3858 | CA | GLY | A | 427 | 8.407 | -4.123 | 25.141 | 1.00 | 0.01 |

| ATOM | 3859 | C | GLY | A | 427 | 7.051 | -4.798 | 25.346 | 1.00 | 0.00 |
|------|------|----|------|---|-----|-------|--------|--------|------|------|
| ATOM | 3860 | O | GLY | A | 427 | 5.997 | -4.354 | 24.873 | 1.00 | 0.01 |
| ATOM | 3861 | N | LYS | A | 428 | 7.120 | -5.898 | 26.072 | 1.00 | 0.00 |
| ATOM | 3863 | CA | LYS | A | 428 | 5.944 | -6.689 | 26.445 | 1.00 | 0.01 |
| ATOM | 3864 | CB | LYS | A | 428 | 5.789 | -7.862 | 25.484 | 1.00 | 0.01 |
| ATOM | 3865 | CG | LYS | A | 428 | 4.595 | -8.725 | 25.884 | 1.00 | 0.01 |
| ATOM | 3866 | CD | LYS | A | 428 | 4.667 | -10.117 | 25.270 | 1.00 | 0.00 |
| ATOM | 3867 | CE | LYS | A | 428 | 4.692 | -10.060 | 23.750 | 1.00 | 0.00 |
| ATOM | 3868 | NZ | LYS | A | 428 | 4.758 | -11.416 | 23.186 | 1.00 | 0.01 |
| ATOM | 3869 | C | LYS | A | 428 | 6.127 | -7.261 | 27.844 | 1.00 | 0.01 |
| ATOM | 3870 | O | LYS | A | 428 | 6.958 | -8.157 | 28.051 | 1.00 | 0.01 |
| ATOM | 3871 | N | VAL | A | 429 | 5.333 | -6.782 | 28.784 | 1.00 | 0.00 |
| ATOM | 3873 | CA | VAL | A | 429 | 5.387 | -7.325 | 30.142 | 1.00 | 0.01 |
| ATOM | 3874 | CB | VAL | A | 429 | 5.105 | -6.215 | 31.144 | 1.00 | 0.01 |
| ATOM | 3875 | CG1 | VAL | A | 429 | 5.108 | -6.750 | 32.572 | 1.00 | 0.00 |
| ATOM | 3876 | CG2 | VAL | A | 429 | 6.132 | -5.101 | 30.998 | 1.00 | 0.01 |
| ATOM | 3877 | C | VAL | A | 429 | 4.368 | -8.447 | 30.294 | 1.00 | 0.00 |
| ATOM | 3878 | O | VAL | A | 429 | 3.173 | -8.211 | 30.519 | 1.00 | 0.01 |
| ATOM | 3879 | N | GLU | A | 430 | 4.857 | -9.666 | 30.153 | 1.00 | 0.02 |
| ATOM | 3881 | CA | GLU | A | 430 | 4.000 | -10.843 | 30.270 | 1.00 | 0.01 |
| ATOM | 3882 | CB | GLU | A | 430 | 4.477 | -11.877 | 29.261 | 1.00 | 0.30 |
| ATOM | 3883 | CG | GLU | A | 430 | 3.550 | -13.085 | 29.206 | 1.00 | 0.57 |
| ATOM | 3884 | CD | GLU | A | 430 | 4.321 | -14.244 | 28.598 | 1.00 | 0.25 |
| ATOM | 3885 | OE1 | GLU | A | 430 | 3.692 | -15.219 | 28.209 | 1.00 | 0.58 |
| ATOM | 3886 | OE2 | GLU | A | 430 | 5.534 | -14.216 | 28.754 | 1.00 | 0.26 |
| ATOM | 3887 | C | GLU | A | 430 | 4.096 | -11.422 | 31.675 | 1.00 | 0.02 |
| ATOM | 3888 | O | GLU | A | 430 | 3.177 | -12.097 | 32.153 | 1.00 | 0.01 |
| ATOM | 3889 | N | ASN | A | 431 | 5.220 | -11.149 | 32.313 | 1.00 | 0.00 |
| ATOM | 3891 | CA | ASN | A | 431 | 5.443 | -11.521 | 33.713 | 1.00 | 0.00 |
| ATOM | 3892 | CB | ASN | A | 431 | 5.740 | -13.018 | 33.801 | 1.00 | 0.00 |
| ATOM | 3893 | CG | ASN | A | 431 | 5.920 | -13.475 | 35.253 | 1.00 | 0.01 |
| ATOM | 3894 | OD1 | ASN | A | 431 | 6.693 | -12.891 | 36.026 | 1.00 | 0.02 |
| ATOM | 3895 | ND2 | ASN | A | 431 | 5.257 | -14.566 | 35.584 | 1.00 | 0.02 |
| ATOM | 3898 | C | ASN | A | 431 | 6.632 | -10.736 | 34.246 | 1.00 | 0.02 |
| ATOM | 3899 | O | ASN | A | 431 | 7.777 | -11.192 | 34.119 | 1.00 | 0.01 |
| ATOM | 3900 | N | PRO | A | 432 | 6.349 | -9.732 | 35.060 | 1.00 | 0.00 |
| ATOM | 3901 | CA | PRO | A | 432 | 7.387 | -8.783 | 35.483 | 1.00 | 0.02 |
| ATOM | 3902 | CB | PRO | A | 432 | 6.637 | -7.649 | 36.110 | 1.00 | 0.02 |
| ATOM | 3903 | CG | PRO | A | 432 | 5.164 | -8.012 | 36.211 | 1.00 | 0.01 |

| ATOM | 3904 | CD | PRO | A | 432 | 5.016 | -9.365 | 35.537 | 1.00 | 0.02 |
|---|---|---|---|---|---|---|---|---|---|---|
| ATOM | 3905 | C | PRO | A | 432 | 8.408 | -9.346 | 36.479 | 1.00 | 0.01 |
| ATOM | 3906 | O | PRO | A | 432 | 9.515 | -8.805 | 36.553 | 1.00 | 0.00 |
| ATOM | 3907 | N | THR | A | 433 | 8.145 | -10.500 | 37.076 | 1.00 | 0.02 |
| ATOM | 3909 | CA | THR | A | 433 | 9.086 | -11.048 | 38.054 | 1.00 | 0.01 |
| ATOM | 3910 | CB | THR | A | 433 | 8.340 | -11.865 | 39.104 | 1.00 | 0.02 |
| ATOM | 3911 | OG1 | THR | A | 433 | 7.900 | -13.083 | 38.520 | 1.00 | 0.01 |
| ATOM | 3912 | CG2 | THR | A | 433 | 7.136 | -11.114 | 39.660 | 1.00 | 0.01 |
| ATOM | 3913 | C | THR | A | 433 | 10.127 | -11.927 | 37.369 | 1.00 | 0.02 |
| ATOM | 3914 | O | THR | A | 433 | 11.161 | -12.247 | 37.969 | 1.00 | 0.02 |
| ATOM | 3915 | N | LYS | A | 434 | 9.910 | -12.226 | 36.098 | 1.00 | 0.01 |
| ATOM | 3917 | CA | LYS | A | 434 | 10.908 | -12.974 | 35.324 | 1.00 | 0.02 |
| ATOM | 3918 | CB | LYS | A | 434 | 10.202 | -13.816 | 34.268 | 1.00 | 2.22 |
| ATOM | 3919 | CG | LYS | A | 434 | 9.202 | -14.782 | 34.891 | 1.00 | 2.65 |
| ATOM | 3920 | CD | LYS | A | 434 | 9.867 | -15.756 | 35.857 | 1.00 | 2.62 |
| ATOM | 3921 | CE | LYS | A | 434 | 8.831 | -16.644 | 36.534 | 1.00 | 3.30 |
| ATOM | 3922 | NZ | LYS | A | 434 | 9.470 | -17.570 | 37.481 | 1.00 | 3.61 |
| ATOM | 3923 | C | LYS | A | 434 | 11.891 | -12.016 | 34.651 | 1.00 | 0.02 |
| ATOM | 3924 | O | LYS | A | 434 | 11.859 | -11.817 | 33.430 | 1.00 | 0.00 |
| ATOM | 3925 | N | SER | A | 435 | 12.761 | -11.438 | 35.460 | 1.00 | 0.02 |
| ATOM | 3927 | CA | SER | A | 435 | 13.747 | -10.479 | 34.960 | 1.00 | 0.02 |
| ATOM | 3928 | CB | SER | A | 435 | 13.389 | -9.101 | 35.503 | 1.00 | 1.31 |
| ATOM | 3929 | OG | SER | A | 435 | 12.076 | -8.780 | 35.062 | 1.00 | 1.94 |
| ATOM | 3930 | C | SER | A | 435 | 15.152 | -10.861 | 35.411 | 1.00 | 0.02 |
| ATOM | 3931 | O | SER | A | 435 | 15.582 | -10.351 | 36.435 | 1.00 | 0.01 |
| ATOM | 3932 | OXT | SER | A | 435 | 15.790 | -11.618 | 34.691 | 1.00 | 0.01 |

What is claimed is:

1. An isolated nucleic acid molecule consisting of a polynucleotide sequence selected from the group consisting of:
   (a) an isolated polynucleotide encoding a polypeptide consisting of amino acids 1 to 435 of SEQ ID NO:2;
   (b) an isolated polynucleotide encoding a polypeptide consisting of amino acids 2 to 435 of SEQ ID NO:2; and
   (c) an isolated polynucleotide encoding a mature polypeptide consisting of amino acids 39 to 435 of SEQ ID NO:2.

2. The isolated nucleic acid molecule of claim 1, wherein said polynucleotide is (a).

3. The isolated nucleic acid molecule of claim 2, wherein said polynucleotide consists of nucleotides 68 to 1372 of SEQ ID NO:1.

4. The isolated nucleic acid molecule of claim 1, wherein said polynucleotide is (b).

5. The isolated nucleic acid molecule of claim 4, wherein said polynucleotide consists of nucleotides 71 to 1372 of SEQ ID NO:1.

6. The isolated nucleic acid molecule of claim 1, wherein said polynucleotide is (c).

7. The isolated nucleic acid molecule of claim 6, wherein said polynucleotide consists of nucleotides 182 to 1372 of SEQ ID NO:1.

8. The isolated polynucleotide of claim 1 wherein said nucleic acid sequence further comprises a heterologous nucleic acid sequence.

9. The isolated polynucleotide of claim 8 wherein said heterologous nucleic acid sequence encodes a heterologous polypeptide.

10. The isolated polynucleotide of claim 9 wherein said heterologous polypeptide is the Fc domain of immunoglobulin.

11. An isolated polynucleotide which represents the complementary sequence of a member of the group consisting of: (a), (b) and (c) of claim 1.

12. An isolated polynucleotide consisting of the polynucleotide encoding the LSI-01 polypeptide as encoded by the cDNA clone contained in ATCC Deposit No: PTA-2766.

13. A recombinant vector comprising the isolated nucleic acid molecule of claim 1.

14. A recombinant host cell comprising the vector sequence of claim 13.

15. A method of making an isolated polypeptide comprising:
   (a) culturing the recombinant host cell of claim 14 under conditions such that said polypeptide is expressed; and
   (b) recovering said polypeptide.

* * * * *